(12) United States Patent
Mevellec et al.

(10) Patent No.: US 10,280,170 B2
(45) Date of Patent: May 7, 2019

(54) SUBSTITUTED 4,5,6,7-TETRAHYDRO-PYRAZOLO[1,5-A]PYRAZINE DERIVATIVES AND 5,6,7,8-TETRAHYDRO-4H-PYRAZOLO[1,5-A][1,4]DIAZEPINE DERIVATIVES AS ROS1 INHIBITORS

(71) Applicant: Janssen Pharmaceutica NV, Beerse (BE)

(72) Inventors: Laurence Anne Mevellec, Louviers (FR); Elisabeth Therese Jeanne Pasquier, Val de Reuil (FR); Sophie Descamps, Belbeuf (FR); Guillaume Jean Maurice Mercey, Montaure (FR); Berthold Wroblowski, Vosselaar (BE); Jorge Eduardo Vialard, Brussels (BE); Lieven Meerpoel, Beerse (BE); Matthieu Ludovic Jeanty, Louviers (FR); Thierry Francois Alain Jean Jousseaume, Beringen (CH)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 15/129,582

(22) PCT Filed: Mar. 26, 2015

(86) PCT No.: PCT/EP2015/056498
§ 371 (c)(1),
(2) Date: Sep. 27, 2016

(87) PCT Pub. No.: WO2015/144799
PCT Pub. Date: Oct. 1, 2015

(65) Prior Publication Data
US 2017/0174690 A1 Jun. 22, 2017

(30) Foreign Application Priority Data
Mar. 27, 2014 (EP) .................................... 14161950

(51) Int. Cl.
| | |
|---|---|
| *C07D 487/04* | (2006.01) |
| *A61K 31/519* | (2006.01) |
| *A61P 35/00* | (2006.01) |
| *C07B 59/00* | (2006.01) |
| *C07D 487/10* | (2006.01) |
| *C07D 487/20* | (2006.01) |
| *C07D 519/00* | (2006.01) |
| *C07F 9/6561* | (2006.01) |

(52) U.S. Cl.
CPC .......... *C07D 487/04* (2013.01); *A61K 31/519* (2013.01); *A61P 35/00* (2018.01); *C07B 59/002* (2013.01); *C07D 487/10* (2013.01); *C07D 487/20* (2013.01); *C07D 519/00* (2013.01); *C07F 9/6561* (2013.01); *C07B 2200/05* (2013.01)

(58) Field of Classification Search
CPC .. C07D 487/04; C07D 401/04; C07D 401/14; A61K 31/519
USPC .......... 544/350; 540/523, 524; 514/221, 249
See application file for complete search history.

(56) References Cited

U.S. PATENT DOCUMENTS

| | | | |
|---|---|---|---|
| 5,624,931 A | 4/1997 | Oku et al. | |
| 9,187,489 B2 | 11/2015 | Takeda et al. | |
| 2006/0079536 A1 | 4/2006 | Yasuma et al. | |

FOREIGN PATENT DOCUMENTS

| | | |
|---|---|---|
| CN | 102083835 | 6/2011 |
| EP | 1505068 A1 | 2/2005 |
| JP | 2005343889 | 12/2005 |
| WO | WO 2004/058176 A2 | 7/2004 |

(Continued)

OTHER PUBLICATIONS

Freshney et al.,Culture of Animal Cells, A Manual of Basic Technique, Alan R. Liss, Inc., 1983, New York, p. 4.*

(Continued)

*Primary Examiner* — Venkataraman Balasubramanian

(57) ABSTRACT

The present invention relates to substituted 4,5,6,7-tetrahydro-pyrazolo[1,5-a]pyrazine derivatives and 5,6,7,8-tetrahydro-4H-pyrazolo[1,5-a][1,4]diazepine derivatives of formula (I)

wherein the variables have the meaning defined in the claims. The compounds according to the present invention are useful as ROS1 inhibitors. The invention further relates to processes for preparing such novel compounds, pharmaceutical compositions comprising said compounds as an active ingredient as well as the use of said compounds as a medicament.

13 Claims, No Drawings

(56) References Cited

FOREIGN PATENT DOCUMENTS

| WO | 2009076440 | 6/2009 |
| WO | WO 2009/086129 A1 | 7/2009 |
| WO | WO 2009/108838 A1 | 9/2009 |
| WO | 2009126515 | 10/2009 |
| WO | WO 2009/140128 A2 | 11/2009 |
| WO | 2010138579 | 12/2010 |
| WO | WO 2011/153553 A2 | 12/2011 |
| WO | 2013017989 | 2/2013 |

OTHER PUBLICATIONS

Dermeret al., Bio/Technology, 1994, 12:320.*
Golub et al., Science, 286, 531-537, 1999.*
Cecil Textbook of Medicine, edited by Bennet, J.C., and Plum F., 20th edition,vol. 1, 1004-1010, 1996.*
Cohen et al., Current Opinion in Chemical Biology, 3,459-465, 1999.*
Griffin et al. Ochsner Journal 17:388-392, 2017.*
Andres et al., "Synthesis, In Vivo Occupancy, and Radiolabeling of Potent Phosphodiesterase Subtype-10 Inhibitors as Candidates for Positron Emission Tomography Imaging.", J. Med. Chem., 2011, 54, pp. 5820-5835.
Davies et al., "Identifying and Targeting ROS1 Gene Fusions in Non-Small Cell Lung Cancer.",Clin Cancer Res., 2012,18(17), pp. 4570-4579.
Davies et al., "Molecular Pathways: ROS1 Fusion Proteins in Cancer.",Clin Cancer Res., 2013,19(15), pp. 4040-4045.
Gu et al., "Survey of Tyrosine Kinase Signaling Reveals ROS Kinase Fusions in Human Cholangiocarcinoma.", PLoS One, 2011, 6(1):e15640.
Horig et al.,"From bench to clinic and back: Perspective on the 1st IQPC Translational Research conference.", Journal of Translational Medicine, 2004, 2(44), pp. 1-8.
Kim et al., "Clinical and prognostic implications of ALK and ROS1 rearrangements in never-smokers with surgically resected lung adenocarcinoma.", Lung Cancer, 2014, 83, pp. 389-395.
Li et al., "Spectrum of Oncogenic Driver Mutations in Lung Adenocarcinomas from East Asian Never Smokers.", PLoS One, 2011, 6, pp. 28204.
Rimkunas et al., "Analysis of Receptor Tyrosine Kinase ROS1-Positive Tumors in Non-Small Cell Lung Cancer: Identification of a FIG-ROS1 Fusion.", Clin Cancer Res., 2012, 18, pp. 4449-4457.
Schafer et al., "Failure is an option: learning from unsuccessful proof-of-concept trials.", Drug Discovery Today, 13(21/22), pp. 913-916.
Takeuchi et al., "RET, ROS1 and ALK fusions in lung cancer.", Nature Medicine, Mar. 2012, 18(3), pp. 378-381.
Wiesner et al., "Kinase fusions are frequent in Spitz tumours and spitzoid melanomas.", Nat Commun., 2014, 5, pp. 3116.
International Search Report of the International Searching Authority relating to corresponding International Patent Application No. PCT/EP2015/056498, filed Mar. 26, 2015, dated May 19, 2015.
Written Opinion of the International Searching Authority relating to corresponding International Patent Application No. PCT/EP2015/056498, filed Mar. 26, 2015, dated May 19, 2015.

* cited by examiner

SUBSTITUTED 4,5,6,7-TETRAHYDRO-PYRAZOLO[1,5-A]PYRAZINE DERIVATIVES AND 5,6,7,8-TETRAHYDRO-4H-PYRAZOLO[1,5-A][1,4]DIAZEPINE DERIVATIVES AS ROS1 INHIBITORS

CROSS REFERENCE TO RELATED APPLICATIONS

This application is a national stage application of International Patent Application No. PCT/EP2015/056498, filed 26 Mar. 2015, which claims priority from EPO Patent Application No. 14161950.2 filed 27 Mar. 2014. The complete disclosures of the aforementioned related patent applications are hereby incorporated herein by reference for all purposes.

FIELD OF THE INVENTION

The present invention relates to substituted 4,5,6,7-tetrahydro-pyrazolo[1,5-a]pyrazine derivatives and 5,6,7,8-tetrahydro-4H-pyrazolo[1,5-a][1,4]diazepine derivatives useful as ROS1 inhibitors. The invention further relates to processes for preparing such compounds, pharmaceutical compositions comprising said compounds as an active ingredient as well as the use of said compounds as a medicament.

BACKGROUND OF THE INVENTION

Ros1 is a receptor tyrosine kinase closely related to the ALK and LTK kinases based on sequence similarity of their kinase domains. The Ros1 protein is composed of an extracellular domain containing several fibronectin-like repeats and a cytoplasmic kinase domain. The function of Ros1 has not been fully elucidated, but the presence of fibronectin domains suggests a role in cell adhesion or interactions with the extracellular matrix. However, endogenous Ros1 ligands have not yet been identified. Its expression in adult humans has been detected in several tissues, such as the kidney, cerebellum, and gastrointestinal tract, but appears to be low or absent in other tissues. Its expression in the developing kidney and intestine suggests that it may have a role in epithelial-mesenchymal transition. ROS1 deficient mice are healthy and viable, but males are infertile due to defects in the epididymis that result in incomplete spermatocyte maturation.

Several distinct genomic rearrangements involving ROS1 have been detected in a variety of cancers including non-small cell lung cancer (NSCLC), glioblastoma, cholangiocarcinoma, colorectal cancer, gastric adenocarcinoma, ovarian cancer, angiosarcoma, epithelioid hemangioendothelioma, melanoma, and inflammatory myofibroblastic tumors. These rearrangements result in proteins that contain the C-terminal kinase domain of Ros1 fused to the N-terminal domains of a number of different unrelated proteins. Several of these fusion proteins have been shown to be oncogenic. Expression in fibroblasts promotes their proliferation, growth in soft agar, and ability to form tumors in mice. Expression in murine Ba/F3 cells renders them independent of IL-3 for growth and promotes their ability to form tumors in mice (Takeuchi K, et al., Nat Med. 2012, 18:378-81; Gu T L, et al., PLoS One 2011, 6:e15640). The rate of oncogenic Ros1 fusions is generally low, ranging from 1-2% in NSCLC (Kim M H, et al., Lung Cancer 2014, 83:389-95; Takeuchi K, et al., Nat Med. 2012, 18:378-81; Davies K D, et al., Clin Cancer Res. 2012, 18:4570-9; Li C, et al., PLoS One 2011, 6:e28204; Rimkunas V M, et al., Clin Cancer Res. 2012, 18:4449-57), but may be relatively high in other cancers, up to 9% in cholangiocarcinoma (Gu TL, et al., PLoS One 2011, 6(1):e15640) and 17% in spitzoid (melanoma) tumors (Wiesner T, et al., Nat Commun. 2014, 5:3116).

Because of the similarity between ALK and Ros1 kinase domains, many ALK inhibitors also inhibit Ros1. Ros1 inhibition negatively affects proliferation of engineered Ba/F3 cells expressing Ros1 fusion proteins as well as the proliferation of NSCLC patient derived HCC78 cells that harbor a SLC34A2-ROS1 fusion. Ros1 inhibition also negatively affects growth of engineered Ba/F3 and HEK293 tumors containing Ros1 fusion proteins in mice.

Recently, a number of inhibitors described to have activity on Ros1 have entered clinical testing. The first, crizotinib (Xalkori®), has been shown to reduce tumors and significantly prolong survival in patients with ROS1 rearrangements. However, following an initial response, resistance is seen and in one report this has been linked to a G2032R mutation in the Ros1 kinase domain that is expected to affect crizotinib binding.

WO-2004/058176 discloses acyclic pyrazole compounds for the inhibition of mitogen activated protein kinase-activated protein kinase-2.

J. Med. Chem., 2011, 54, 5820-5835 discloses pyrazolo derivatives as phosphodiesterase subtype-10 inhibitors.

There is thus a strong need for novel Ros1 kinase inhibitors thereby opening new avenues for the treatment or prevention of cancer, in particular non-small cell lung cancer (specifically adenocarcinoma), cholangiocarcinoma, glioblastoma, colorectal cancer, gastric adenocarcinoma, ovarian cancer, angiosarcoma, epithelioid hemangioendothelioma, inflammatory myofibroblastic tumors, breast cancer and chronic myelogenous leukemia. In a particular embodiment, there is a need for Ros1 kinase inhibitors that are not affected by mutations that abrogate inhibition of the first wave of Ros1 inhibitors.

It is accordingly an object of the present invention to provide such compounds.

SUMMARY OF THE INVENTION

It has been found that the compounds of the present invention are useful as ROS1 inhibitors. The compounds according to the invention and compositions thereof, may be useful for the treatment or prevention, in particular for the treatment, of cancer, in particular non-small cell lung cancer (specifically adenocarcinoma), cholangiocarcinoma, glioblastoma, colorectal cancer, gastric adenocarcinoma, ovarian cancer, angiosarcoma, epithelioid hemangioendothelioma, inflammatory myofibroblastic tumors, breast cancer and chronic myelogenous leukemia, and the like.

This invention concerns compounds of formula (I)

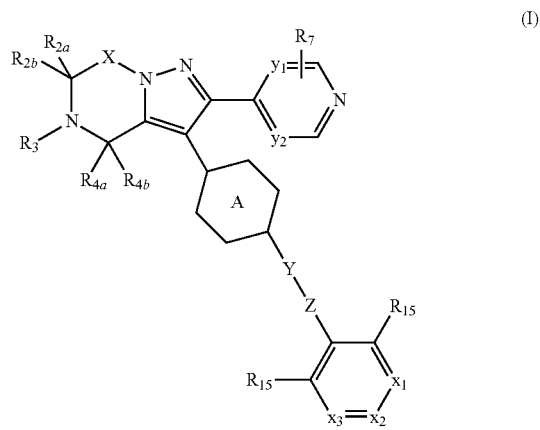

tautomers and stereoisomeric forms thereof, wherein
$y_1$ is $CR_{7a}$ or N;
$y_2$ is CH or N;

$R_{7a}$ is hydrogen, halo, trifluoromethyl or cyano;

$R_7$ is hydrogen, —$NH_2$, —$NHCH_3$, —$NH(CH_2CH_3)$, methyl, —$CH_2OH$, halo or cyano;

or when $y_1$ represents $CR_{7a}$, this $R_{7a}$ can be taken together with a $R_7$ on an adjacent carbon atom to form —CH=CH—NH— or —N=CH—NH—;

X is —$CR_1R_{1a}$—, —$CH_2$—$CHR_1$—;

$R_1$ is hydrogen or $C_{1-6}$alkyl;

$R_{1a}$ is hydrogen; $C_{1-6}$alkyl; mono- or polyhalo$C_{1-6}$alkyl; $C_{1-6}$alkyl substituted with one or two hydroxyl groups; $C_{1-6}$alkyl substituted with one —$NR_{9a}R_{9b}$; or —C(=O)—$NR_{9a}R_{9b}$;

$R_{2a}$ is hydrogen; $C_{1-6}$alkyl; mono- or polyhalo$C_{1-6}$alkyl; $C_{1-6}$alkyl substituted with one or two hydroxyl groups; or $C_{1-6}$alkyl substituted with one substituent selected from the group consisting of —$NR_{9a}R_{9b}$, cyano and $C_{1-4}$alkyloxy;

$R_{2b}$ is hydrogen or $C_{1-6}$alkyl; or $R_{2a}$ and $R_{2b}$ are taken together to form —$CH_2$—$CH_2$—, —$CH_2$—$NR_{2c}$—$CH_2$—, —$CH_2$—$CH_2$—$CH_2$—, —$CH_2$—O—$CH_2$—, —$CH_2$—$CH_2$—$CH_2$—$CH_2$—, —$CH_2$—$CH_2$—$NR_{2c}$—$CH_2$— or =O;

$R_{2c}$ is hydrogen; $C_{1-4}$alkyl optionally substituted with one or two hydroxyl groups; mono- or polyhalo$C_{1-6}$alkyl; $C_{1-6}$alkyloxy; $C_{1-6}$alkyl substituted with one cyano group; or $C_{1-6}$alkyl substituted with one —$NR_{9a}R_{9b}$;

$R_3$ is hydrogen; $C_{1-6}$alkyl; mono- or polyhalo$C_{1-6}$alkyl; $C_{1-6}$alkyl substituted with one or two hydroxyl groups; $C_{1-6}$alkyl substituted with one or two hydroxyl groups and one $C_{1-6}$alkyloxy; $C_{1-6}$alkylcarbonyl- optionally substituted with one or two hydroxyl groups; mono- or polyhalo $C_{1-6}$alkylcarbonyl-; $R_{10a}R_{10b}N$—$C_{1-6}$alkylcarbonyl-; $C_{1-6}$alkyl-O-carbonyl-; $C_{1-6}$alkylcarbonyloxy-; $C_{1-6}$alkyl substituted with one $R_{11}$; $C_{1-6}$alkyloxy optionally substituted with one —$NR_{10a}R_{10b}$; $C_{2-6}$alkenyl; $C_{2-6}$alkynyl; hydroxy$C_{2-6}$alkenyl; hydroxy$C_{2-6}$alkynyl; $C_{1-6}$alkyloxy $C_{2-6}$alkenyl; $C_{1-6}$alkyloxy$C_{2-6}$alkynyl; $C_{2-6}$alkenyl substituted with one —$NR_{10a}R_{10b}$; $C_{2-6}$alkynyl substituted with one —$NR_{10a}R_{10b}$; $C_{1-6}$-alkyl substituted with one or two hydroxyl groups and one —$NR_{10}R_{10b}$; —$C_{1-6}$alkyl-C($R_{13}$)=N—O—$R_{13}$; —S(=O)$_2$—$C_{1-6}$alkyl; —S(=O)$_2$—$NR_{9a}R_{9b}$; $C_{1-6}$-alkyl substituted with one —(C=O)—$R_{14}$; $C_{1-6}$alkyl substituted with one or two hydroxyl groups and one $R_{14}$; $C_{1-6}$alkyl substituted with one $R_{14}$; $C_{2-6}$alkenyl substituted with one $R_{14}$; $C_{2-6}$alkynyl substituted with one $R_{14}$; or $R_{14}$:

$R_{4a}$ is hydrogen;

$R_{4b}$ is hydrogen; or $R_{4a}$ and $R_{4b}$ are taken together to form =O;

Y is —O— or —C(=O)—;

Z is —$CHR_6$— or —$CH_2$—C≡C—;

$R_6$ is hydrogen; $C_{1-4}$alkyl-O-carbonyl-; $C_{1-4}$alkyl; $C_{1-4}$alkyl substituted with one or two hydroxyl groups; $C_{1-4}$alkyl substituted with one —$NR_{9a}R_{9b}$; or —C(=O)—$NR_{9a}R_{9b}$;

Ring A is phenyl or a 6-membered saturated, partially saturated or aromatic heterocyclyl, said heterocyclyl containing one or two nitrogen atoms; wherein the phenyl or the heterocyclyl is optionally substituted with one or two $R_8$ substituents;

each $R_8$ is independently hydrogen; $C_{1-4}$alkyloxy; hydroxyl; cyano; $C_{1-4}$alkyl or halo;

or a $R_8$ substituent on an atom adjacent to the atom carrying the Y—Z substituent may be taken together with the $R_6$ substituent of Z, by which ring A together with Y—Z forms a bicycle of formula (a-1), (a-2), (a-3) or (a-4):

(a-1)

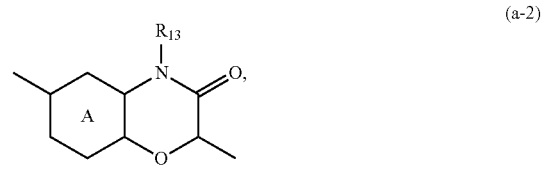

(a-2)

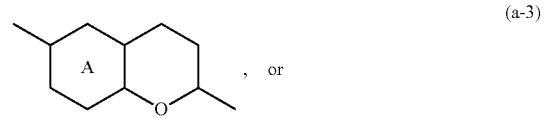

, or (a-3)

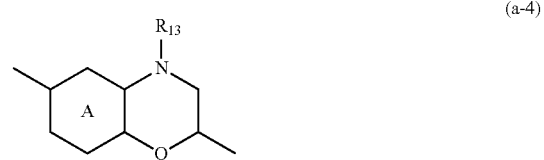

(a-4)

$R_{9a}$ and $R_{9b}$ each independently represent hydrogen; mono- or polyhalo$C_{1-4}$alkyl; $C_{1-4}$alkylcarbonyl-; $C_{1-4}$alkyl-O-carbonyl-; $C_{1-4}$alkyl substituted with one or two hydroxyl groups; or $C_{1-4}$alkyl optionally substituted with one substituent selected from the group consisting of $C_{1-4}$alkyloxy, cyano, amino and mono- or di($C_{1-4}$alkyl)amino;

$R_{10a}$ and $R_{10b}$ each independently represent hydrogen; $C_{1-4}$alkyl; cyano$C_{1-6}$alkyl; $C_{1-6}$alkyl substituted with one $NR_{9a}R_{9b}$; $C_{1-6}$alkyl substituted with one —C(=O)—$NR_{9a}R_{9b}$; $C_{1-6}$alkyloxy optionally substituted with one or two hydroxyl groups; $C_{1-6}$alkyloxy$C_{1-6}$alkyl wherein each $C_{1-6}$alkyl is optionally substituted with one or two hydroxyl groups; $R_{14}$; $C_{1-6}$alkyl substituted with one $R_{14}$; —(C=O)—$R_{14}$; $C_{1-6}$alkylcarbonyl-; $C_{1-6}$alkyl-O-carbonyl-; mono- or polyhalo$C_{1-6}$alkylcarbonyl-substituted with one or two hydroxyl groups; mono- or polyhalo$C_{1-6}$alkyl substituted with one or two hydroxyl groups; mono- or polyhalo$C_{1-6}$alkylcarbonyl-; $C_{1-6}$alkyl substituted with one —Si(CH$_3$)$_3$; —S(=O)$_2$—$C_{1-6}$alkyl optionally substituted with one or more halo substituents; —S(=O)$_2$—$NR_{9a}R_{9b}$; $C_{1-6}$alkyl substituted with one —S(=O)$_2$—$C_{1-6}$alkyl wherein —S(=O)$_2$—$C_{1-6}$alkyl is optionally substituted with one or more halo substituents;

$C_{1-6}$alkyl substituted with one —S(=O)$_2$—$NR_{9a}R_{9b}$;

$C_{1-6}$alkyl substituted with one —NH—S(=O)$_2$—$C_{1-4}$alkyl wherein —NH—S(=O)$_2$—$C_{1-6}$alkyl is optionally substituted on a carbon atom with one or more halo substituents;

$C_{1-6}$alkyl substituted with one —NH—S(=O)$_2$—$NR_{9a}R_{9b}$;

mono- or polyhalo$C_{1-4}$alkyl; or $C_{1-4}$alkyl substituted with one or two hydroxyl groups;

$R_{11}$ is cyano; —$NR_{10a}R_{10b}$; $C_{1-6}$alkyloxy optionally substituted with one or two hydroxyl groups; —S(=O)$_2$—$C_{1-6}$alkyl; —S(=O)$_2$—$NR_{9a}R_{9b}$; —$NR_{13}$—S(=O)$_2$—$C_{1-6}$alkyl; —$NR_{13}$—S(=O)$_2$—$NR_{9a}R_{9b}$; $C_{1-6}$alkylcarbonyloxy-; —C(=O)—$NR_{10a}R_{10b}$; —O—C(=O)—$NR_{10a}R_{10b}$; —COOH; —P(=O)OH)$_2$; or —P(=O)(O—$C_{1-4}$alkyl)$_2$;

$R_{12}$ is —$NR_{9a}R_{9b}$, $C_{1-6}$alkyloxy, or cyano;

$R_{13}$ is hydrogen or $C_{1-4}$alkyl;

$R_{14}$ is a $C_{3-8}$cycloalkyl; or a 4, 5 or 6 membered saturated heterocyclyl which is optionally substituted with one, two or three substituents selected from the group consisting of oxo, $C_{1-4}$alkyl, halogen, cyano, hydroxyl, $C_{1-6}$alkyloxy and $NR_{9a}R_{9b}$;

$x_1$ is $CR_{5a}$ or N;
$x_2$ is $CR_{5b}$ or N;
$x_3$ is $CR_{5c}$ or N;

each $R_{15}$ is independently selected from the group consisting of hydrogen, methyl, halo, $C_{1-4}$alkyloxy and hydroxyl;

$R_{5a}$ and $R_{5c}$ each independently are selected from the group consisting of hydrogen;

hydroxyl; cyano; halo; $C_{1-6}$alkyl; $C_{1-6}$alkyl substituted with one or two hydroxyl groups;

mono- or polyhalo$C_{1-6}$alkyl; mono- or polyhalo$C_{1-6}$alkyloxy; $C_{1-6}$alkyl substituted with one —$NR_{9a}R_{9b}$; $C_{1-6}$alkyl substituted with one cyano; $C_{1-6}$alkyloxy$C_{1-6}$alkyl wherein each of the $C_{1-6}$alkyl groups are optionally substituted with one or two hydroxyl groups; $C_{2-6}$alkenyl; $C_{1-6}$alkyl-O-carbonyl-; $C_{1-6}$alkyloxy; $C_{1-6}$alkyloxy substituted with one or two hydroxyl groups; $C_{1-6}$alkyloxy$C_{1-6}$alkyloxy wherein each of the $C_{1-6}$alkyl groups are optionally substituted with one or two hydroxyl groups; $C_{1-6}$alkyloxy substituted with one cyano; and $C_{1-6}$alkyloxy substituted with one —$NR_{9a}R_{9b}$;

$R_{5b}$ is hydrogen; $C_{1-6}$alkyl; $C_{3-6}$cycloalkyl optionally substituted with one cyano; hydroxyl; cyano; mono- or polyhalo$C_{1-6}$alkyloxy; mono- or polyhalo$C_{1-6}$alkyl; $C_{1-4}$alkyl substituted with one or two hydroxyl groups; $C_{2-6}$alkenyl; $C_{1-4}$alkyloxy; —$Si(CH_3)_3$; $C_{1-6}$alkyl substituted with one $R_{12}$; $C_{1-6}$alkyl-O-carbonyl-; or $C_{1-6}$alkyloxy substituted with one $R_2$;

and the N-oxides, the pharmaceutically acceptable addition salts, and the solvates thereof.

The present invention also concerns methods for the preparation of compounds of the present invention and pharmaceutical compositions comprising them.

The compounds of the present invention were found to inhibit ROS1, and therefore may be useful in the treatment or prevention, in particular in the treatment, of cancer, in particular non-small cell lung cancer (specifically adenocarcinoma), cholangiocarcinoma, glioblastoma, colorectal cancer, gastric adenocarcinoma, ovarian cancer, angiosarcoma, epithelioid hemangioendothelioma, inflammatory myofibroblastic tumors, breast cancer and chronic myelogenous leukemia, and the like. The compounds of the present invention may also have utility in male contraception.

In view of the aforementioned pharmacology of the compounds of Formula (I) and N-oxides, pharmaceutically acceptable addition salts, and solvates thereof, it follows that they may be suitable for use as a medicament.

In particular the compounds of Formula (I) and N-oxides, pharmaceutically acceptable addition salts, and solvates thereof, may be suitable in the treatment or prevention, in particular in the treatment, of cancer.

The present invention also concerns the use of compounds of Formula (I) and N-oxides, pharmaceutically acceptable addition salts, and solvates thereof, for the manufacture of a medicament for the inhibition of ROS1, for the treatment or prevention of cancer.

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

DETAILED DESCRIPTION

When describing the compounds of the invention, the terms used are to be construed in accordance with the following definitions, unless a context dictates otherwise.

When any variable occurs more than one time in any constituent or in any formula (e.g. formula (I)), its definition in each occurence is independent of its definition at every other occurrence.

Whenever the term "substituted" is used in the present invention, it is meant, unless otherwise is indicated or is clear from the context, to indicate that one or more hydrogens, in particular from 1 to 3 hydrogens, preferably 1 or 2 hydrogens, more preferably 1 hydrogen, on the atom or radical indicated in the expression using "substituted" are replaced with a selection from the indicated group, provided that the normal valency is not exceeded, and that the substitution results in a chemically stable compound, i.e. a compound that is sufficiently robust to survive isolation to a useful degree of purity from a reaction mixture, and formulation into a therapeutic agent.

Whenever a radical or group is defined as "optionally substituted" in the present invention, it is meant that said radical or group is unsubstituted or is substituted.

Lines drawn from substituents into ring systems indicate that the bond may be attached to any of the suitable ring atoms.

The prefix "$C_{x-y}$" (where x and y are integers) as used herein refers to the number of carbon atoms in a given group. Thus, a $C_{1-6}$alkyl group contains from 1 to 6 carbon atoms, a $C_{3-6}$cycloalkyl group contains from 3 to 6 carbon atoms, a $C_{1-4}$alkoxy group contains from 1 to 4 carbon atoms, and so on.

The term "halo" as a group or part of a group is generic for fluoro, chloro, bromo, iodo unless otherwise is indicated or is clear from the context.

The term 'mono- or polyhalo$C_{1-4}$alkyl' or 'mono- or polyhalo$C_{1-6}$alkyl' as used herein as a group or part of a group refers to a $C_{1-4}$alkyl or $C_{1-6}$-alkyl group as defined herein wherein one or more than one hydrogen atom is replaced with a halogen. There may be one, two, three or more hydrogen atoms replaced with a halogen, so the 'mono- or polyhalo$C_{1-4}$alkyl' or 'mono- or polyhalo $C_{1-6}$alkyl' may have one, two, three or more halogens. Examples of such groups include fluoroethyl, fluoromethyl, trifluoromethyl or trifluoroethyl and the like.

The term "$C_{1-6}$-alkyl" as a group or part of a group refers to a hydrocarbyl radical of Formula $C_nH_{2n+1}$ wherein n is a number ranging from 1 to 6. $C_{1-6}$alkyl groups comprise from 1 to 6 carbon atoms, preferably from 1 to 4 carbon atoms, more preferably from 1 to 3 carbon atoms, still more preferably 1 to 2 carbon atoms. Alkyl groups may be linear or branched and may be substituted as indicated herein. When a subscript is used herein following a carbon atom, the subscript refers to the number of carbon atoms that the named group may contain. Thus, for example, $C_{1-6}$alkyl includes all linear, or branched alkyl groups with between 1 and 6 carbon atoms, and thus includes such as for example methyl, ethyl, n-propyl, i-propyl, 2-methyl-ethyl, butyl and its isomers (e.g. n-butyl, isobutyl and tert-butyl), pentyl and its isomers, hexyl and its isomers, and the like.

The term "$C_{1-4}$alkyl" as a group or part of a group refers to a hydrocarbyl radical of Formula $C_nH_{2n+1}$ wherein n is a number ranging from 1 to 4. $C_{1-4}$alkyl groups comprise from 1 to 4 carbon atoms, preferably from 1 to 3 carbon atoms, more preferably 1 to 2 carbon atoms. $C_{1-4}$alkyl groups may be linear or branched and may be substituted as indicated herein. When a subscript is used herein following a carbon atom, the subscript refers to the number of carbon atoms that the named group may contain. $C_{1-4}$alkyl includes all linear, or branched alkyl groups with between 1 and 4 carbon atoms, and thus includes methyl, ethyl, n-propyl, i-propyl, 2-methyl-ethyl, butyl and its isomers (e.g. n-butyl, isobutyl and tert-butyl), and the like.

The term "$C_{1-6}$alkyloxy" as a group or part of a group refers to a radical having the Formula —$OR^b$ wherein $R^b$ is $C_{1-6}$alkyl. Non-limiting examples of suitable alkyloxy include methyloxy, ethyloxy, propyloxy, isopropyloxy, butyloxy, isobutyloxy, sec-butyloxy, tert-butyloxy, pentyloxy, and hexyloxy.

The term "$C_{1-4}$alkyloxy" as a group or part of a group refers to a radical having the Formula —$OR^c$ wherein $R^c$ is $C_{1-4}$alkyl. Non-limiting examples of suitable $C_{1-4}$alkyloxy include methyloxy (also methoxy), ethyloxy (also ethoxy), propyloxy, isopropyloxy, butyloxy, isobutyloxy, sec-butyloxy and tert-butyloxy.

The term "$C_{1-6}$alkylcarbonyl" as a group or part of a group refers to a radical —C(=O)—$C_{1-6}$alkyl. The term "$C_{1-4}$alkylcarbonyl" as a group or part of a group refers to a radical —C(=O)—$C_{1-4}$alkyl.

The term "$C_{3-8}$cycloalkyl" alone or in combination, refers to a cyclic saturated hydrocarbon radical having from 3 to 8 carbon atoms. Non-limiting examples of suitable $C_{3-8}$cycloalkyl include cyclopropyl, cyclobutyl, cyclopentyl, cyclohexyl, cycloheptyl and cyclooctyl.

The term "$C_{3-6}$cycloalkyl" alone or in combination, refers to a cyclic saturated hydrocarbon radical having from 3 to 6 carbon atoms. Non-limiting examples of suitable $C_{3-6}$cycloalkyl include cyclopropyl, cyclobutyl, cyclopentyl and cyclohexyl.

The term "$C_{2-4}$alkenyl" or "$C_{2-6}$alkenyl" as used herein as a group or part of a group refers to a linear or branched hydrocarbon group containing from 2 to 4 or 2 to 6 carbon atoms and containing a carbon carbon double bond such as, but not limited to, ethenyl, propenyl, butenyl, pentenyl, 1-propen-2-yl, hexenyl and the like.

The term "$C_{2-4}$alkynyl" or "$C_{2-6}$alkynyl" as used herein as a group or part of a group refers to a linear or branched hydrocarbon group having from 2 to 4 or 2 to 6 carbon atoms and containing a carbon carbon triple bond.

The term "cyano$C_{1-6}$alkyl" means $C_{1-6}$alkyl substituted with one cyano.

The term "hydroxy$C_{2-6}$alkenyl" means $C_{2-6}$alkenyl substituted with one hydroxy.

The term "hydroxy$C_{2-6}$alkynyl" means $C_{2-6}$alkynyl substituted with one hydroxy.

In particular, the 4, 5 or 6 membered saturated heterocyclyls (e.g. in the definition of $R_{14}$), contain 1, 2 or 3 heteroatoms selected from O, S and N, in particular 1 or 2 heteroatoms, in particular selected from O and N.

Examples of 4, 5 or 6 membered saturated heterocyclyls include, but are not limited to, pyrrolidinyl, dioxolanyl, oxazolidinyl, oxetanyl, tetrahydrofuranyl, and the like.

Examples of 6-membered aromatic heterocyclyls containing one or two nitrogen atoms (e.g. in the definition of ring A), include, but are not limited to, pyrimidinyl, pyridinyl, pyrazinyl and the like.

Examples of 6-membered partially saturated heterocyclyls containing one or two nitrogen atoms (e.g. in the definition of ring A), include, but are not limited to, 1,2,3,6-tetrahydro-pyridinyl and the like. In a particular embodiment, the 1,2,3,6-tetrahydro-pyridinyl is attached with its nitrogen atom to variable Y.

Examples of 6-membered saturated heterocyclyls containing one or two nitrogen atoms (e.g. in the definition of ring A), include, but are not limited to, piperidinyl and the like. In a particular embodiment, the piperidinyl is attached with its nitrogen atom to the pyrazolyl ring.

In case $R_{7a}$ is taken together with a $R_7$ on an adjacent carbon atom to form —CH=CH—NH—, it is intended that the CH in position alpha

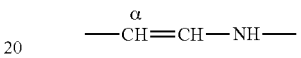

is attached to the carbon atom in the position of y1 as clearly shown below:

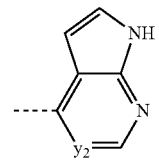

In case $R_{7a}$ is taken together with a $R_7$ on an adjacent carbon atom to form —N=CH—NH—, it is intended that the nitrogen in position alpha

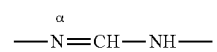

is attached to the carbon atom in the position of y1 as clearly shown below:

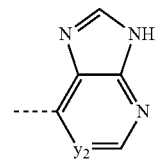

In case X is —$CH_2$—$CHR_1$—, it is intended that the carbon atom with the $R_1$ substituent is attached to the nitrogen atom of the pyrazole ring.

In case Z is —$CH_2$—C≡C—, it is intended that the $CH_2$ group is attached to variable Y.

It will be clear that when a $R_8$ substituent on an atom adjacent to the atom carrying the Y—Z substituent is taken together with the $R_6$ substituent of Z, compounds of formula (I-a-1), (I-a-2), (I-a-3) and (I-a-4) are formed:

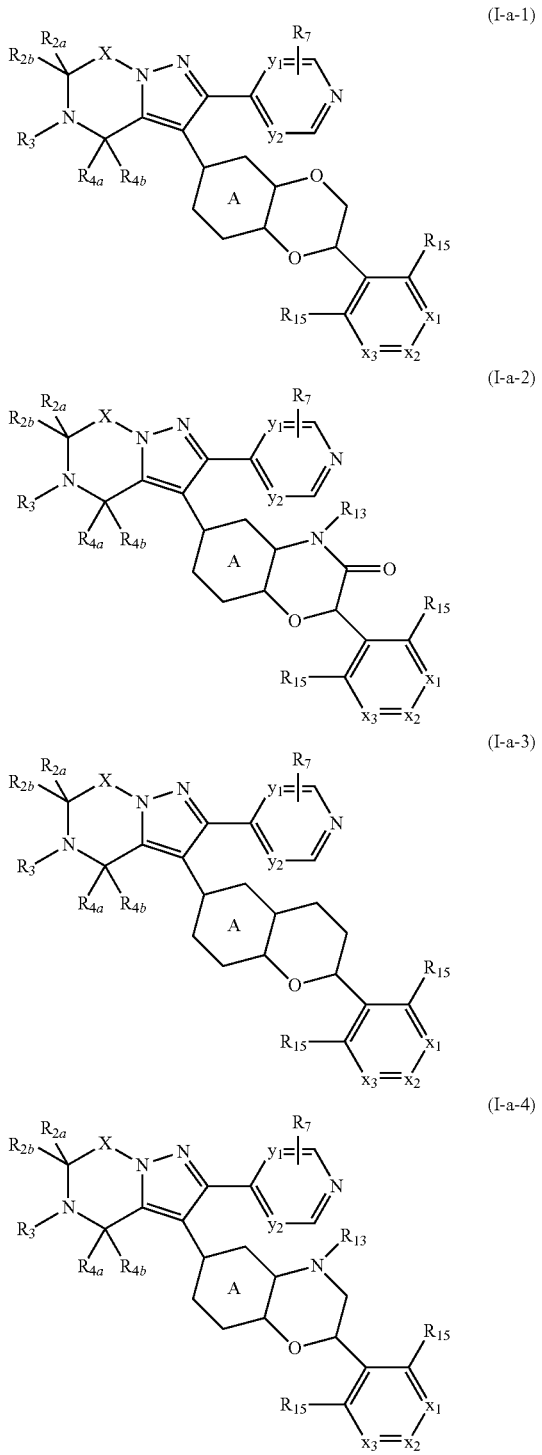

(I-a-1)

(I-a-2)

(I-a-3)

(I-a-4)

The term "subject" as used herein, refers to an animal, preferably a mammal (e.g. cat, dog, primate or human), more preferably a human, who is or has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medicinal doctor or other clinician, which includes alleviation or reversal of the symptoms of the disease or disorder being treated.

The term "composition" is intended to encompass a product comprising the specified ingredients in the specified amounts, as well as any product which results, directly or indirectly, from combinations of the specified ingredients in the specified amounts.

The term "treatment", as used herein, is intended to refer to all processes wherein there may be a slowing, interrupting, arresting or stopping of the progression of a disease, but does not necessarily indicate a total elimination of all symptoms.

The term "compounds of the invention" as used herein, is meant to include the compounds of Formula (I) and N-oxides, pharmaceutically acceptable addition salts, and solvates thereof.

As used herein, any chemical formula with bonds shown only as solid lines and not as solid wedged or hashed wedged bonds, or otherwise indicated as having a particular configuration (e.g. R, S) around one or more atoms, contemplates each possible stereoisomer, or mixture of two or more stereoisomers.

Whenever one of the ring systems, is substituted with one or more substituents, those substituents may replace any hydrogen atom bound to a carbon or nitrogen atom of the ring system.

Hereinbefore and hereinafter, the term "compound of Formula (I)" is meant to include the stereoisomers thereof and the tautomeric forms thereof.

The terms "stereoisomers", "stereoisomeric forms" or "stereochemically isomeric forms" hereinbefore or hereinafter are used interchangeably.

The invention includes all stereoisomers of the compounds of the invention either as a pure stereoisomer or as a mixture of two or more stereoisomers.

Enantiomers are stereoisomers that are non-superimposable mirror images of each other. A 1:1 mixture of a pair of enantiomers is a racemate or racemic mixture.

Diastereomers (or diastereoisomers) are stereoisomers that are not enantiomers, i.e. they are not related as mirror images. If a compound contains a double bond, the substituents may be in the E or the Z configuration. Substituents on bivalent cyclic (partially) saturated radicals may have either the cis- or trans-configuration; for example if a compound contains a disubstituted cycloalkyl group, the substituents may be in the cis or trans configuration. Therefore, the invention includes enantiomers, diastereomers, racemates, E isomers, Z isomers, cis isomers, trans isomers and mixtures thereof, whenever chemically possible.

The meaning of all those terms, i.e. enantiomers, diastereomers, racemates, E isomers, Z isomers, cis isomers, trans isomers and mixtures thereof are known to the skilled person.

The absolute configuration is specified according to the Cahn-Ingold-Prelog system. The configuration at an asymmetric atom is specified by either R or S. Resolved stereoisomers whose absolute configuration is not known can be designated by (+) or (−) depending on the direction in which they rotate plane polarized light. For instance, resolved enantiomers whose absolute configuration is not known can be designated by (+) or (−) depending on the direction in which they rotate plane polarized light.

When a specific stereoisomer is identified, this means that said stereoisomer is substantially free, i.e. associated with less than 50%, preferably less than 20%, more preferably less than 10%, even more preferably less than 5%, in particular less than 2% and most preferably less than 1%, of the other stereoisomers. Thus, when a compound of Formula (I) is for instance specified as (R), this means that the compound is substantially free of the (S) isomer; when a compound of Formula (I) is for instance specified as E, this means that the compound is substantially free of the Z isomer; when a compound of Formula (I) is for instance specified as cis, this means that the compound is substantially free of the trans isomer.

Some of the compounds of Formula (I) may also exist in their tautomeric form. Such forms in so far as they may exist, are intended to be included within the scope of the present invention.

It follows that a single compound may exist in both stereoisomeric and tautomeric form.

For therapeutic use, salts of the compounds of Formula (I), N-oxides and solvates thereof, are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable addition salts as mentioned hereinabove or hereinafter are meant to comprise the therapeutically active non-toxic acid and base addition salt forms which the compounds of Formula (I), N-oxides and solvates thereof, are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds of Formula (I), N-oxides and solvates thereof containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline; the benzathine, N-methyl-D-glucamine, hydrabamine salts, and salts with amino acids such as, for example, arginine, lysine and the like. Conversely the salt form can be converted by treatment with acid into the free acid form.

The term solvate comprises the hydrates and solvent addition forms which the compounds of Formula (I) are able to form, as well as N-oxides and pharmaceutically acceptable addition salts thereof. Examples of such forms are e.g. hydrates, alcoholates and the like.

The compounds of the invention as prepared in the processes described below may be synthesized in the form of mixtures of enantiomers, in particular racemic mixtures of enantiomers, that can be separated from one another following art-known resolution procedures. A manner of separating the enantiomeric forms of the compounds of Formula (I), and N-oxides, pharmaceutically acceptable addition salts, and solvates thereof, involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound would be synthesized by stereospecific methods of preparation. These methods will advantageously employ enantiomerically pure starting materials.

In the framework of this application, an element, in particular when mentioned in relation to a compound of Formula (I), comprises all isotopes and isotopic mixtures of this element, either naturally occurring or synthetically produced, either with natural abundance or in an isotopically enriched form. Radiolabelled compounds of Formula (I) may comprise a radioactive isotope selected from the group of $^{2}H$, $^{3}H$, $^{11}C$, $^{18}F$, $^{122}I$, $^{123}I$, $^{125}I$, $^{131}I$, $^{75}Br$, $^{76}Br$, $^{77}Br$ and $^{82}Br$. Preferably, the radioactive isotope is selected from the group of $^{2}H$, $^{3}H$, $^{11}C$ and $^{18}F$. More preferably, the radioactive isotope is $^{2}H$. In particular, deuterated compounds are intended to be included within the scope of the present invention As used in the specification and the appended claims, the singular forms "a", "an," and "the" also include plural referents unless the context clearly dictates otherwise. For example, "a compound" means 1 compound or more than 1 compound.

In an embodiment, the present invention concerns novel compounds of Formula (I), tautomers and stereoisomeric forms thereof, wherein $y_1$ is $CR_{7a}$ or N;
$y_2$ is CH;
$R_{7a}$ is hydrogen;
$R_7$ is hydrogen, —$NH_2$, —$NHCH_3$, —$NH(CH_2CH_3)$, methyl, —$CH_2OH$, halo or cyano; or when $y_1$ represents $CR_{7a}$, this $R_{7a}$ can be taken together with a $R_7$ on an adjacent carbon atom to form —CH=CH—NH— or —N=CH—NH—;
X is —$CR_1R_{1a}$—, —$CH_2$—$CHR_1$—;
$R_1$ is hydrogen or $C_{1-6}$alkyl;
$R_{1a}$ is hydrogen;
$R_{2a}$ is hydrogen; $C_{1-6}$alkyl; mono- or polyhalo$C_{1-6}$alkyl; $C_{1-6}$alkyl substituted with one or two hydroxyl groups; or $C_{1-6}$alkyl substituted with one substituent selected from the group consisting of —$NR_{9a}R_{9b}$, cyano and $C_{1-4}$alkyloxy;
$R_{2b}$ is hydrogen; or
$R_{2a}$ and $R_{2b}$ are taken together to form —$CH_2$—$CH_2$—, —$CH_2$—$NR_{2c}$—$CH_2$—, —$CH_2$—$CH_2$—$CH_2$—, —$CH_2$—O—$CH_2$—, —$CH_2$—$CH_2$—$CH_2$—$CH_2$—, —$CH_2$—$CH_2$—$NR_{2c}$—$CH_2$— or =O;
$R_{2c}$ is hydrogen; $C_{1-4}$alkyl optionally substituted with one or two hydroxyl groups; mono- or polyhalo$C_{1-6}$alkyl; $C_{1-6}$alkyloxy; $C_{1-6}$alkyl substituted with one cyano group; or $C_{1-6}$alkyl substituted with one —$NR_{9a}R_{9b}$;
$R_3$ is hydrogen; $C_{1-6}$alkyl; mono- or polyhalo$C_{1-6}$alkyl; $C_{1-6}$alkyl substituted with one or two hydroxyl groups; $C_{1-6}$alkyl substituted with one or two hydroxyl groups and one $C_{1-6}$alkyloxy; $C_{1-6}$alkylcarbonyl- optionally substituted with one or two hydroxyl groups; mono- or polyhalo$C_{1-6}$alkylcarbonyl-; $R_{10a}R_{10b}N$—$C_{1-6}$alkylcarbonyl-; $C_{1-6}$alkyl-O-carbonyl-; $C_{1-6}$alkylcarbonyloxy-; $C_{1-6}$alkyl substituted with one $R_{11}$; $C_{1-6}$alkyloxy optionally substituted with one —$NR_{10a}R_{10b}$; $C_{1-6}$alkyl substituted with one or two hydroxyl groups and one —$NR_{10}R_{10b}$; —$S(=O)_2$—$C_{1-6}$alkyl; —$S(=O)_2$—$NR_{9a}R_{9b}$; $C_{1-6}$alkyl substituted with one —(C=O)—$R_{14}$; $C_{1-6}$alkyl substituted with one or two hydroxyl groups and one $R_{14}$; $C_{1-6}$alkyl substituted with one $R_{14}$; or $R_{14}$;

$R_{4a}$ is hydrogen;
$R_{4b}$ is hydrogen; or
$R_{4a}$ and $R_{4b}$ are taken together to form =O;
Y is —O— or —C(=O)—; in particular Y is —O—;
Z is —$CHR_6$— or —$CH_2$—C≡C—;
$R_6$ is hydrogen; $C_{1-4}$alkyl-O-carbonyl-; $C_{1-4}$alkyl; $C_{1-4}$alkyl substituted with one or two hydroxyl groups; $C_{1-4}$alkyl substituted with one —$NR_{9a}R_{9b}$; or —C(=O)—$NR_{9a}R_{9b}$;

Ring A is phenyl or a 6-membered saturated, partially saturated or aromatic heterocyclyl, in particular phenyl or a 6-membered aromatic heterocyclyl, said heterocyclyl containing one or two nitrogen atoms; wherein the phenyl or the heterocyclyl is optionally substituted with one or two $R_8$ substituents;

each $R_8$ is independently hydrogen; $C_{1-4}$alkyloxy; hydroxyl; cyano; $C_{1-4}$alkyl or halo; or a $R_8$ substituent on an atom adjacent to the atom carrying the Y—Z substituent may be taken together with the $R_6$ substituent of Z, by which ring A together with Y—Z forms a bicycle of formula (a-1), (a-2), (a-3) or (a-4);

$R_{9a}$ and $R_{9b}$ each independently represent hydrogen; mono- or polyhalo$C_{1-4}$alkyl; $C_{1-4}$alkylcarbonyl-; $C_{1-4}$alkyl-O-carbonyl-; $C_{1-4}$alkyl substituted with one or two hydroxyl groups; or $C_{1-4}$alkyl optionally substituted with one substituent selected from the group consisting of $C_{1-4}$alkyloxy, cyano, amino and mono- or di($C_{1-4}$alkyl)amino;

$R_{10a}$ and $R_{10b}$ each independently represent hydrogen; $C_{1-4}$alkyl; cyano$C_{1-6}$alkyl; $C_{1-6}$alkyl substituted with one $NR_{9a}R_{9b}$; $C_{1-6}$alkyl substituted with one —C(=O)—$NR_{9a}R_{9b}$; $C_{1-6}$alkyloxy optionally substituted with one or two hydroxyl groups; $C_{1-6}$alkyloxy$C_{1-6}$alkyl wherein each $C_{1-6}$alkyl is optionally substituted with one or two hydroxyl groups; $C_{1-6}$alkylcarbonyl-; $C_{1-6}$alkyl-O-carbonyl-;

mono- or polyhalo$C_{1-6}$alkylcarbonyl- substituted with one or two hydroxyl groups;

mono- or polyhalo$C_{1-6}$alkyl substituted with one or two hydroxyl groups;

mono- or polyhalo$C_{1-6}$alkylcarbonyl-; mono- or polyhalo$C_{1-4}$alkyl; or $C_{1-4}$alkyl substituted with one or two hydroxyl groups;

$R_{11}$ is cyano; —$NR_{10a}R_{10b}$; $C_{1-6}$alkyloxy optionally substituted with one or two hydroxyl groups; —$S(=O)_2$—$C_{1-6}$alkyl; —$S(=O)_2$—$NR_{9a}R_{9b}$; —$NR_{13}$—$S(=O)_2$—$C_{1-6}$alkyl; —$NR_{13}$—$S(=O)_2$—$NR_{9a}R_{9b}$; $C_{1-6}$alkylcarbonyloxy-; —C(=O)—$NR_{10a}R_{10b}$; —COOH; —O—C(=O)—$NR_{10a}R_{10b}$; —COOH; —P(=O)(OH)$_2$; or —P(=O)(O—$C_{1-4}$alkyl)$_2$;

$R_{12}$ is —$NR_{9a}R_{9b}$, $C_{1-6}$alkyloxy, or cyano;
$R_{13}$ is hydrogen or $C_{1-4}$alkyl;
$R_{14}$ is a 4, 5 or 6 membered saturated heterocyclyl which is optionally substituted with one, two or three substituents selected from the group consisting of oxo, $C_{1-4}$alkyl, halogen, cyano, hydroxyl, $C_{1-6}$alkyloxy and $NR_{9a}R_{9b}$;
$x_1$ is $CR_{5a}$ or N;
$x_2$ is $CR_{5b}$;
$x_3$ is $CR_{5c}$ or N;
each $R_{15}$ is independently selected from the group consisting of hydrogen, methyl, halo, $C_{1-4}$alkyloxy and hydroxyl;

$R_{5a}$ and $R_{5c}$ each independently are selected from the group consisting of hydrogen; hydroxyl; cyano; halo; $C_{1-6}$alkyl; $C_{1-6}$alkyl substituted with one or two hydroxyl groups;

mono- or polyhalo$C_{1-6}$alkyl; mono- or polyhalo$C_{1-6}$alkyloxy; $C_{1-6}$alkyl substituted with one —$NR_{9a}R_{9b}$; $C_{1-6}$alkyl substituted with one cyano; $C_{1-6}$alkyloxy$C_{1-6}$alkyl wherein each of the $C_{1-6}$alkyl groups are optionally substituted with one or two hydroxyl groups; $C_{2-6}$alkenyl; $C_{1-6}$alkyl-O-carbonyl-; $C_{1-6}$alkyloxy; $C_{1-6}$alkyloxy substituted with one or two hydroxyl groups; $C_{1-6}$-alkyloxy$C_{1-6}$alkyloxy wherein each of the $C_{1-6}$alkyl groups are optionally substituted with one or two hydroxyl groups; $C_{1-6}$alkyloxy substituted with one cyano; and $C_{1-6}$alkyloxy substituted with one —$NR_{9a}R_{9b}$;

$R_{5b}$ is hydrogen; $C_{1-6}$-alkyl; $C_{3-6}$cycloalkyl optionally substituted with one cyano; hydroxyl; cyano; mono- or polyhalo$C_{1-6}$alkyloxy; mono- or polyhalo$C_{1-6}$alkyl; $C_{1-4}$alkyl substituted with one or two hydroxyl groups; $C_{2-6}$alkenyl; $C_{1-4}$alkyloxy; —Si(CH$_3$)$_3$; $C_{1-6}$alkyl substituted with one $R_{12}$; $C_{1-6}$alkyl-O-carbonyl-; or $C_{1-6}$alkyloxy substituted with one $R_{12}$;

and the N-oxides, the pharmaceutically acceptable addition salts, and the solvates thereof.

In an embodiment, the present invention concerns novel compounds of Formula (I), tautomers and stereoisomeric forms thereof, wherein $y_1$ is $CR_{7a}$ or N;
$y_2$ is CH;
$R_{7a}$ is hydrogen;
$R_7$ is hydrogen, —NH$_2$, —NHCH$_3$, —NH(CH$_2$CH$_3$), methyl, —CH$_2$OH, halo or cyano; or when $y_1$ represents $CR_{7a}$, this $R_{7a}$ can be taken together with a $R_7$ on an adjacent carbon atom to form —CH=CH—NH— or —N=CH—NH—;

X is —$CR_1R_{1a}$—, —$CH_2$—$CHR_1$—;
$R_1$ is hydrogen or $C_{1-6}$alkyl;
$R_{1a}$ is hydrogen;
$R_{2a}$ is hydrogen; $C_{1-6}$alkyl; mono- or polyhalo$C_{1-6}$alkyl; $C_{1-6}$alkyl substituted with one or two hydroxyl groups; or $C_{1-6}$alkyl substituted with one substituent selected from the group consisting of —$NR_{9a}R_{9b}$, cyano and $C_{1-4}$alkyloxy;
$R_{2b}$ is hydrogen; or
$R_{2a}$ and $R_{2b}$ are taken together to form —$CH_2$—$CH_2$—, —$CH_2$—$NR_{2c}$—$CH_2$—, —$CH_2$—$CH_2$—$CH_2$—, —$CH_2$—O—$CH_2$—, —$CH_2$—$CH_2$—$CH_2$—$CH_2$—, —$CH_2$—$CH_2$—$NR_{2c}$—$CH_2$— or =O;
$R_{2c}$ is hydrogen; $C_{1-4}$alkyl optionally substituted with one or two hydroxyl groups; mono- or polyhalo$C_{1-6}$alkyl; $C_{1-6}$alkyloxy; $C_{1-6}$alkyl substituted with one cyano group; or $C_{1-6}$alkyl substituted with one —$NR_{9a}R_{9b}$;
$R_3$ is hydrogen; $C_{1-6}$alkyl; mono- or polyhalo$C_{1-6}$alkyl; $C_{1-6}$alkyl substituted with one or two hydroxyl groups; $C_{1-6}$alkyl substituted with one or two hydroxyl groups and one $C_{1-6}$alkyloxy; $C_{1-6}$alkylcarbonyl- optionally substituted with one or two hydroxyl groups; mono- or polyhalo $C_{1-6}$alkylcarbonyl-; $R_{10a}R_{10b}N$—$C_{1-6}$alkylcarbonyl-; $C_{1-6}$alkyl-O-carbonyl-; $C_{1-6}$alkylcarbonyloxy-; $C_{1-6}$alkyl substituted with one $R_{11}$; $C_{1-6}$alkyloxy optionally substituted with one —$NR_{10a}R_{10b}$; $C_{1-6}$alkyl substituted with one or two hydroxyl groups and one —$NR_{10}R_{10b}$; —$S(=O)_2$—$C_{1-6}$alkyl; —$S(=O)_2$—$NR_{9a}R_{9b}$; $C_{1-6}$alkyl substituted with one —(C=O)—$R_{14}$; $C_{1-6}$alkyl substituted with one or two hydroxyl groups and one $R_{14}$; $C_{1-6}$alkyl substituted with one $R_{14}$; or $R_{14}$;

$R_{4a}$ is hydrogen;
$R_{4b}$ is hydrogen; or
$R_{4a}$ and $R_{4b}$ are taken together to form =O;
Y is —O— or —C(=O)—; in particular Y is —O—;
Z is —$CHR_6$— or —$CH_2$—C≡C—;

$R_6$ is hydrogen; $C_{1-4}$alkyl-O-carbonyl-; $C_{1-4}$alkyl; $C_{1-4}$alkyl substituted with one or two hydroxyl groups; $C_{1-4}$alkyl substituted with one —$NR_{9a}R_{9b}$; or —C(=O)—$NR_{9a}R_{9b}$;

Ring A is phenyl or a 6-membered aromatic heterocyclyl, said heterocyclyl containing one or two nitrogen atoms; wherein the phenyl or the heterocyclyl is optionally substituted with one or two $R_8$ substituents;

each $R_8$ is independently hydrogen; $C_{1-4}$alkyloxy; hydroxyl; cyano; or halo; or a $R_8$ substituent on an atom adjacent to the atom carrying the Y—Z substituent may be taken together with the $R_6$ substituent of Z, by which ring A together with Y—Z forms a bicycle of formula (a-1), (a-2), (a-3) or (a-4);

$R_{9a}$ and $R_{9b}$ each independently represent hydrogen; mono- or polyhalo$C_{1-4}$alkyl; $C_{1-4}$alkylcarbonyl-; $C_{1-4}$alkyl-O-carbonyl-; $C_{1-4}$alkyl substituted with one or two hydroxyl groups; or $C_{1-4}$alkyl optionally substituted with one substituent selected from the group consisting of $C_{1-4}$alkyloxy, cyano, amino and mono- or di($C_{1-4}$alkyl)amino;

$R_{10a}$ and $R_{10b}$ each independently represent hydrogen; $C_{1-6}$alkyl; cyano$C_{1-6}$alkyl; $C_{1-6}$alkyl substituted with one $NR_{9a}R_{9b}$; $C_{1-6}$alkyl substituted with one —C(=O)—$NR_{9a}R_{9b}$; $C_{1-6}$alkyloxy optionally substituted with one or two hydroxyl groups; $C_{1-6}$alkyloxy$C_{1-6}$alkyl wherein each $C_{1-6}$alkyl is optionally substituted with one or two hydroxyl groups; $C_{1-6}$alkylcarbonyl-; $C_{1-6}$alkyl-O-carbonyl-;

mono- or polyhalo$C_{1-6}$alkylcarbonyl- substituted with one or two hydroxyl groups;

mono- or polyhalo$C_{1-6}$alkyl substituted with one or two hydroxyl groups;

mono- or polyhalo$C_{1-6}$alkylcarbonyl-; mono- or polyhalo$C_{1-4}$alkyl; or $C_{1-4}$alkyl substituted with one or two hydroxyl groups;

$R_{11}$ is cyano; —$NR_{10a}R_{10b}$; $C_{1-6}$alkyloxy optionally substituted with one or two hydroxyl groups; —S(=O)$_2$—$C_{1-6}$alkyl; —S(=O)$_2$—$NR_{9a}R_{9b}$; —$NR_{13}$—S(=O)$_2$—$C_{1-6}$alkyl; —$NR_{13}$—S(=O)$_2$—$NR_{9a}R_{9b}$; $C_{1-6}$alkylcarbonyloxy-; —C(=O)—$NR_{10a}R_{10b}$; —O—C(=O)—$NR_{10a}R_{10b}$; —COOH; —P(=O)(OH)$_2$; or —P(=O)(O—$C_{1-4}$alkyl)$_2$;

$R_{12}$ is —$NR_{9a}R_{9b}$, $C_{1-6}$alkyloxy, or cyano;

$R_{13}$ is hydrogen or $C_{1-4}$alkyl;

$R_{14}$ is a 4, 5 or 6 membered saturated heterocyclyl which is optionally substituted with one, two or three substituents selected from the group consisting of oxo, $C_{1-4}$alkyl, halogen, cyano, hydroxyl, $C_{1-6}$alkyloxy and $NR_{9a}R_{9b}$;

$x_1$ is $CR_{5a}$ or N;

$x_2$ is $CR_{5b}$;

$x_3$ is $CR_{5c}$ or N;

each $R_{15}$ is independently selected from the group consisting of hydrogen, methyl, halo, $C_{1-4}$alkyloxy and hydroxyl;

$R_{5a}$ and $R_{5c}$ each independently are selected from the group consisting of hydrogen; hydroxyl; cyano; halo; $C_{1-6}$alkyl; $C_{1-6}$alkyl substituted with one or two hydroxyl groups;

mono- or polyhalo$C_{1-6}$alkyl; mono- or polyhalo$C_{1-6}$alkyloxy; $C_{1-6}$alkyl substituted with one —$NR_{9a}R_{9b}$; $C_{1-6}$alkyl substituted with one cyano; $C_{1-6}$alkyloxy$C_{1-6}$alkyl wherein each of the $C_{1-6}$alkyl groups are optionally substituted with one or two hydroxyl groups; $C_{2-6}$alkenyl; $C_{1-6}$alkyl-O-carbonyl-; $C_{1-6}$alkyloxy; $C_{1-6}$alkyloxy substituted with one or two hydroxyl groups; $C_{1-6}$alkyloxy$C_{1-6}$alkyloxy wherein each of the $C_{1-6}$alkyl groups are optionally substituted with one or two hydroxyl groups; $C_{1-6}$alkyloxy substituted with one cyano; and $C_{1-6}$alkyloxy substituted with one —$NR_{9a}R_{9b}$;

$R_{5b}$ is $C_{1-6}$alkyl; $C_{3-6}$cycloalkyl optionally substituted with one cyano; mono- or polyhalo$C_{1-6}$alkyloxy; mono- or polyhalo$C_{1-6}$alkyl; $C_{1-4}$alkyl substituted with one hydroxyl group; $C_{2-6}$alkenyl; —Si(CH$_3$)$_3$; $C_{1-6}$alkyl substituted with one $R_{12}$; or $C_{1-6}$alkyl-O-carbonyl-;

and the N-oxides, the pharmaceutically acceptable addition salts, and the solvates thereof.

In an embodiment, the present invention concerns novel compounds of Formula (I), tautomers and stereoisomeric forms thereof, wherein $y_1$ is $CR_{7a}$ or N;

$y_2$ is CH or N;

$R_{7a}$ is hydrogen, halo, trifluoromethyl or cyano;

$R_7$ is hydrogen, —NH$_2$, —NHCH$_3$, —NH(CH$_2$CH$_3$), methyl, —CH$_2$OH, halo or cyano; or when $y_1$ represents $CR_{7a}$, this $R_{7a}$ can be taken together with a $R_7$ on an adjacent carbon atom to form —CH=CH—NH— or —N=CH—NH—;

X is —$CR_1R_{1a}$—, —CH$_2$—CHR$_1$—;

$R_1$ is hydrogen or $C_{1-6}$alkyl;

$R_{1a}$ is hydrogen; $C_{1-6}$alkyl; mono- or polyhalo$C_{1-6}$alkyl; $C_{1-6}$alkyl substituted with one or two hydroxyl groups; $C_{1-6}$alkyl substituted with one —$NR_{9a}R_{9b}$; or —C(=O)—$NR_{9a}R_{9b}$;

$R_{2a}$ is hydrogen; $C_{1-6}$alkyl; mono- or polyhalo$C_{1-6}$alkyl; $C_{1-6}$alkyl substituted with one or two hydroxyl groups; or $C_{1-6}$alkyl substituted with one substituent selected from the group consisting of —$NR_{9a}R_{9b}$, cyano and $C_{1-4}$alkyloxy;

$R_{2b}$ is hydrogen or $C_{1-6}$alkyl; or $R_{2a}$ and $R_{2b}$ are taken together to form —CH$_2$—CH$_2$—, —CH$_2$—$NR_{2c}$—CH$_2$—, —CH$_2$—CH$_2$—CH$_2$—, —CH$_2$—O—CH$_2$—, —CH$_2$—CH$_2$—CH$_2$—CH$_2$—, —CH$_2$—CH$_2$—$NR_{2c}$—CH$_2$— or =O;

$R_{2c}$ is hydrogen; $C_{1-4}$alkyl optionally substituted with one or two hydroxyl groups; mono- or polyhalo$C_{1-6}$alkyl; $C_{1-6}$alkyloxy; $C_{1-6}$alkyl substituted with one cyano group; or $C_{1-6}$alkyl substituted with one —$NR_{9a}R_{9b}$;

$R_3$ is hydrogen; $C_{1-6}$alkyl; mono- or polyhalo$C_{1-6}$alkyl; $C_{1-6}$alkyl substituted with one or two hydroxyl groups; $C_{1-6}$alkyl substituted with one or two hydroxyl groups and one $C_{1-6}$alkyloxy; $C_{1-6}$alkylcarbonyl- optionally substituted with one or two hydroxyl groups; mono- or polyhaloC ialkylcarbonyl-; $R_{10a}R_{10b}N$—$C_{1-6}$alkylcarbonyl-; $C_{1-6}$alkyl-O-carbonyl-; $C_{1-6}$alkylcarbonyloxy-; $C_{1-6}$alkyl substituted with one $R_{11}$; $C_{1-6}$alkyloxy optionally substituted with one —$NR_{10a}R_{10b}$; $C_{2-6}$alkenyl; $C_{2-6}$alkynyl; hydroxy$C_{2-6}$alkenyl; hydroxy$C_{2-6}$alkynyl; $C_{1-6}$alkyloxy$C_{2-6}$alkenyl; $C_{1-6}$alkyloxy$C_{2-6}$alkynyl; $C_{2-6}$alkenyl substituted with one —$NR_{10a}R_{10b}$; $C_{2-6}$alkynyl substituted with one —$NR_{10a}R_{10b}$; $C_{1-6}$-alkyl substituted with one or two hydroxyl groups and one —$NR_{10a}R_{10b}$; —$C_{1-6}$alkyl-C(R$_{13}$)=N—O—$R_{13}$; —S(=O)$_2$—$C_{1-6}$alkyl; —S(=O)$_2$—$NR_{9a}R_{9b}$; $C_{1-6}$alkyl substituted with one —(C=O)—$R_{14}$; $C_{1-6}$alkyl substituted with one or two hydroxyl groups and one $R_{14}$; $C_{1-6}$alkyl substituted with one $R_{14}$; $C_{2-6}$alkenyl substituted with one $R_{14}$; $C_{2-6}$alkynyl substituted with one $R_{14}$; or $R_{14}$:

$R_{4a}$ is hydrogen;

$R_{4b}$ is hydrogen; or $R_{4a}$ and $R_{4b}$ are taken together to form =O;

Y is —O— or —C(=O)—; in particular Y is —O—;

Z is —CHR$_6$— or —CH$_2$—C≡C—;

$R_6$ is hydrogen; $C_{1-4}$alkyl-O-carbonyl-; $C_{1-4}$alkyl; $C_{1-4}$alkyl substituted with one or two hydroxyl groups; $C_{1-4}$alkyl substituted with one —$NR_{9a}R_{9b}$; or —C(=O)—$NR_{9a}R_{9b}$;

Ring A is phenyl or a 6-membered saturated, partially saturated or aromatic heterocyclyl, said heterocyclyl containing one or two nitrogen atoms; wherein the phenyl or the heterocyclyl is optionally substituted with one or two $R_8$ substituents; in particular ring A is phenyl or a 6-membered aromatic heterocyclyl, said heterocyclyl containing one or two nitrogen atoms; wherein the phenyl or the heterocyclyl is optionally substituted with one or two $R_8$ substituents;

each $R_8$ is independently hydrogen; $C_{1-4}$alkyloxy; hydroxyl; cyano; or halo;

$R_{9a}$ and $R_{9b}$ each independently represent hydrogen; mono- or polyhalo$C_{1-4}$alkyl; $C_{1-4}$alkylcarbonyl-; $C_{1-4}$alkyl-O-carbonyl-; $C_{1-4}$alkyl substituted with one or two hydroxyl groups; or $C_{1-4}$alkyl optionally substituted with one substituent selected from the group consisting of $C_{1-4}$alkyloxy, cyano, amino and mono- or di($C_{1-4}$alkyl)amino;

$R_{10a}$ and $R_{10b}$ each independently represent hydrogen; $C_{1-4}$alkyl; cyano$C_{1-6}$alkyl; $C_{1-6}$alkyl substituted with one $NR_{9a}R_{9b}$; $C_{1-6}$alkyl substituted with one —C(=O)—$NR_{9a}R_{9b}$; $C_{1-6}$alkyloxy optionally substituted with one or two hydroxyl groups; $C_{1-6}$alkyloxy$C_{1-6}$alkyl wherein each $C_{1-6}$alkyl is optionally substituted with one or two hydroxyl groups; $R_{14}$; $C_{1-6}$alkyl substituted with one $R_{14}$; —(C=O)—$R_{14}$; $C_{1-6}$alkylcarbonyl-; $C_{1-6}$alkyl-O-carbonyl-; mono- or polyhalo$C_{1-6}$alkylcarbonyl-substituted with one or two hydroxyl groups; mono- or polyhalo$C_{1-6}$alkyl substituted with one or two hydroxyl groups; mono- or polyhalo$C_{1-6}$alkylcarbonyl-; $C_{1-6}$alkyl substituted with one —Si(CH$_3$)$_3$; —S(=O)$_2$—$C_{1-6}$alkyl optionally substituted with one or more halo substituents; —S(=O)$_2$—$NR_{9a}R_{9b}$; $C_{1-6}$alkyl substituted with one —S(=O)$_2$—$C_{1-6}$alkyl wherein —S(=O)$_2$—$C_{1-6}$alkyl is optionally substituted with one or more halo substituents;

$C_{1-6}$alkyl substituted with one —S(=O)$_2$—$NR_{9a}R_{9b}$;

$C_{1-6}$alkyl substituted with one —NH—S(=O)$_2$—$C_{1-6}$alkyl wherein —NH—S(=O)$_2$—$C_{1-6}$alkyl is optionally substituted on a carbon atom with one or more halo substituents;

$C_{1-6}$alkyl substituted with one —NH—S(=O)$_2$—$NR_{9a}R_{9b}$;

mono- or polyhalo$C_{1-4}$alkyl; or $C_{1-4}$alkyl substituted with one or two hydroxyl groups;

$R_{11}$ is cyano; —$NR_{10a}R_{10b}$; $C_{1-6}$alkyloxy optionally substituted with one or two hydroxyl groups; —S(=O)$_2$—$C_{1-6}$alkyl; —S(=O)$_2$—$NR_{9a}R_{9b}$; —$NR_{13}$—S(=O)$_2$—$C_{1-6}$alkyl; —$NR_{13}$—S(=O)$_2$—$NR_{9a}R_{9b}$; $C_{1-6}$alkylcarbonyloxy-; —C(=O)—$NR_{10a}R_{10b}$; —O—C(=O)—$NR_{10a}R_{10b}$; —COOH; —P(=O)OH)$_2$; or —P(=O)(O—$C_{1-4}$alkyl)$_2$;

$R_{12}$ is —$NR_{9a}R_{9b}$, $C_{1-6}$alkyloxy, or cyano;

$R_{13}$ is hydrogen or $C_{1-4}$alkyl;

$R_{14}$ is a $C_{3-8}$cycloalkyl; or a 4, 5 or 6 membered saturated heterocyclyl which is optionally substituted with one, two or three substituents selected from the group consisting of oxo, $C_{1-4}$alkyl, halogen, cyano, hydroxyl, $C_{1-6}$alkyloxy and $NR_{9a}R_{9b}$;

$x_1$ is $CR_{5a}$ or N;
$x_2$ is $CR_{5b}$ or N;
$x_3$ is $CR_{5c}$ or N;

each $R_{15}$ is independently selected from the group consisting of hydrogen, methyl, halo, $C_{1-4}$alkyloxy and hydroxyl;

$R_{5a}$ and $R_{5c}$ each independently are selected from the group consisting of hydrogen; hydroxyl; cyano; halo; $C_{1-6}$alkyl; $C_{1-6}$alkyl substituted with one or two hydroxyl groups;

mono- or polyhalo$C_{1-6}$alkyl; mono- or polyhalo$C_{1-6}$alkyloxy; $C_{1-6}$alkyl substituted with one —$NR_{9a}R_{9b}$; $C_{1-6}$alkyl substituted with one cyano; $C_{1-6}$alkyloxy$C_{1-6}$alkyl wherein each of the $C_{1-6}$alkyl groups are optionally substituted with one or two hydroxyl groups; $C_{2-6}$alkenyl; $C_{1-6}$alkyl-O-carbonyl-; $C_{1-6}$alkyloxy; $C_{1-6}$alkyloxy substituted with one or two hydroxyl groups; $C_{1-6}$-alkyloxy$C_{1-6}$alkyloxy wherein each of the $C_{1-6}$alkyl groups are optionally substituted with one or two hydroxyl groups; $C_{1-6}$alkyloxy substituted with one cyano; and $C_{1-6}$alkyloxy substituted with one —$NR_{9a}R_{9b}$;

$R_{5b}$ is hydrogen; $C_{1-6}$alkyl; $C_{3-6}$cycloalkyl optionally substituted with one cyano; hydroxyl; cyano; mono- or polyhalo$C_{1-6}$alkyloxy; mono- or polyhalo$C_{1-6}$alkyl; $C_{1-4}$alkyl substituted with one or two hydroxyl groups; $C_{2-6}$alkenyl; $C_{1-4}$alkyloxy; —Si(CH$_3$)$_3$; $C_{1-6}$alkyl substituted with one $R_{12}$; $C_{1-6}$alkyl-O-carbonyl-; or $C_{1-6}$alkyloxy substituted with one $R_{12}$;

and the N-oxides, the pharmaceutically acceptable addition salts, and the solvates thereof.

Another embodiment of the present invention relates to those compounds of formula (I) and the N-oxides, the pharmaceutically acceptable addition salts, and the solvates thereof, or any subgroup thereof as mentioned in any of the other embodiments wherein the bicycles of formula (a-1), (a-2), (a-3) and (a-4) are limited to bicycles of formula (a-1a), (a-2a), (a-3a), (a-4a) and (a-4b) having the following structures:

(a-1a)

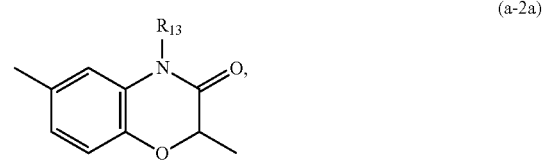
(a-2a)

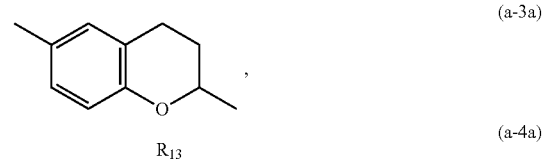
(a-3a)

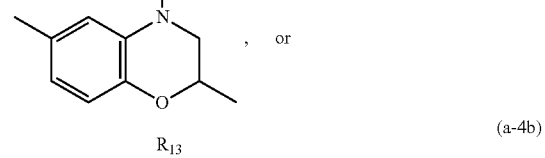
(a-4a), or

(a-4b).

In an embodiment, the present invention concerns novel compounds of Formula (I), tautomers and stereoisomeric forms thereof, wherein $y_1$ is $CR_{7a}$ or N;
$y_2$ is CH;
$R_{7a}$ is hydrogen;
$R_7$ is hydrogen, —$NH_2$, —$CH_2OH$, halo or cyano;
or when $y_1$ represents $CR_{7a}$, this $R_{7a}$ can be taken together with a $R_7$ on an adjacent carbon atom to form —CH=CH—NH—;
X is —$CR_1R_{1a}$—, —$CH_2$—$CHR_1$—;
$R_1$ is hydrogen or $C_{1-6}$alkyl;
$R_{1a}$ is hydrogen;
$R_{2a}$ is hydrogen; $C_{1-6}$alkyl; $C_{1-6}$alkyl substituted with one hydroxyl group; or $C_{1-6}$alkyl substituted with one —$NR_{9a}R_{9b}$ substituent;
$R_{2b}$ is hydrogen; or
$R_{2a}$ and $R_{2b}$ are taken together to form —$CH_2$—$CH_2$—, —$CH_2$—$NR_{2c}$—$CH_2$— or =O;
$R_{2c}$ is hydrogen; or $C_{1-6}$alkyl substituted with one —$NR_9R_{9b}$;
$R_3$ is hydrogen; $C_{1-6}$alkyl; $C_{1-6}$alkyl substituted with one or two hydroxyl groups; $C_{1-6}$alkyl substituted with one or two hydroxyl groups and one $C_{1-6}$alkyloxy; $R_{10a}R_{10b}N$—$C_{1-6}$alkylcarbonyl-; $C_{1-6}$alkyl-O-carbonyl-; $C_{1-6}$alkyl substituted with one $R_{11}$; $C_{1-6}$alkyl substituted with one —(C=O)—$R_{14}$; or $C_{1-6}$alkyl substituted with one $R_{14}$;
$R_{4a}$ is hydrogen;
$R_{4b}$ is hydrogen; or
$R_{4a}$ and $R_{4b}$ are taken together to form =O;
Y is —O— or —C(=O)—;
Z is —$CHR_6$— or —$CH_2$—C≡C—;
$R_6$ is hydrogen; $C_{1-4}$alkyl-O-carbonyl-; $C_{1-4}$alkyl; $C_{1-4}$alkyl substituted with one hydroxyl group; $C_{1-4}$alkyl substituted with one —$NR_{9a}R_{9b}$; or —C(=O)—$NR_{9a}R_{9b}$;
Ring A is phenyl or a 6-membered saturated, partially saturated or aromatic heterocyclyl, said heterocyclyl containing one or two nitrogen atoms; wherein the phenyl or the heterocyclyl is optionally substituted with one or two $R_8$ substituents;
each $R_8$ is independently hydrogen; $C_{1-4}$alkyloxy; cyano; $C_{1-4}$alkyl or halo; or a $R_8$ substituent on an atom adjacent to the atom carrying the Y—Z substituent may be taken together with the $R_6$ substituent of Z, by which ring A together with Y—Z forms a bicycle of formula (a-1a), (a-2a), (a-3a), (a-4a) or (a-4b):

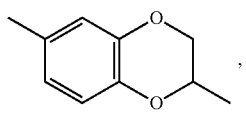
(a-1a)

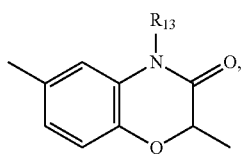
(a-2a)

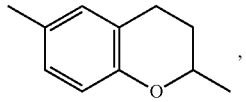
(a-3a)

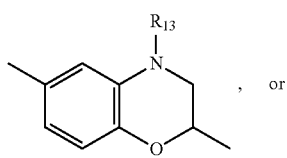
(a-4a)

-continued

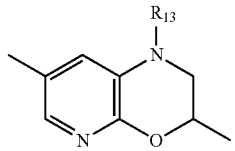
(a-4b)

$R_{9a}$ and $R_{9b}$ each independently represent hydrogen; $C_{1-4}$alkyl substituted with one hydroxyl group; or $C_{1-4}$alkyl;
$R_{10a}$ and $R_{10b}$ each independently represent hydrogen; $C_{1-4}$alkyl; $C_{1-6}$alkyl-O-carbonyl-; mono- or polyhalo $C_{1-4}$alkyl; or $C_{1-4}$alkyl substituted with one hydroxyl group;
$R_{11}$ is cyano; —$NR_{10a}R_{10b}$; $C_{1-6}$alkyloxy optionally substituted with one hydroxyl group; —S(=O)$_2$—$C_{1-4}$alkyl; $C_{1-6}$alkylcarbonyloxy-; —C(=O)—$NR_{10a}R_{10b}$; —COOH; or —P(=O)O—$C_{1-4}$alkyl)$_2$;
$R_{12}$ is —$NR_{9a}R_{9b}$, $C_{1-6}$alkyloxy, or cyano;
$R_{13}$ is hydrogen or $C_{1-4}$alkyl;
$R_{14}$ is a 5 membered saturated heterocyclyl which is optionally substituted with one, two or three substituents selected from the group consisting of oxo and $C_{1-4}$alkyl;
$x_1$ is $CR_{5a}$ or N;
$x_2$ is $CR_{5b}$;
$x_3$ is $CR_{5c}$ or N;
each $R_{15}$ is independently selected from the group consisting of hydrogen, methyl, halo, and $C_{1-4}$alkyloxy;
$R_{5a}$ and $R_{5c}$ each independently are selected from the group consisting of hydrogen; hydroxyl; cyano; halo; $C_{1-6}$alkyl substituted with one or two hydroxyl groups; $C_{1-6}$alkyl substituted with one —$NR_{9a}R_{9b}$; $C_{1-6}$alkyloxy $C_{1-6}$alkyl; $C_{1-6}$alkyloxy; $C_{1-6}$alkyloxy substituted with one hydroxyl group; $C_{1-6}$alkyloxy$C_{1-6}$alkyloxy;
$R_{5b}$ is hydrogen; $C_{1-6}$alkyl; $C_{3-6}$cycloalkyl optionally substituted with one cyano; cyano; mono- or polyhalo$C_{1-6}$alkyloxy; mono- or polyhalo$C_{1-6}$alkyl; $C_{1-4}$alkyl substituted with one hydroxyl group; $C_{2-6}$alkenyl; $C_{1-4}$alkyloxy; —Si($CH_3$)$_3$; $C_{1-6}$alkyl substituted with one $R_{12}$; or $C_{1-6}$alkyl-O-carbonyl-;
and the N-oxides, the pharmaceutically acceptable addition salts, and the solvates thereof.

In an embodiment, the present invention concerns novel compounds of Formula (I), tautomers and stereoisomeric forms thereof, wherein
$y_1$ is CH or N;
$y_2$ is CH;
$R_7$ is hydrogen or —$NH_2$;
X is $CH_2$;
$R_{2a}$ is hydrogen;
$R_{2b}$ is hydrogen; or
$R_{2a}$ and $R_{2b}$ are taken together to form —$CH_2$—$CH_2$— or —$CH_2$—NH—$CH_2$—;
$R_3$ is hydrogen; $C_{1-6}$alkyl; $C_{1-6}$alkyl substituted with one or two hydroxyl groups; $C_{1-6}$alkyl substituted with one $R_{11}$; or $C_{1-6}$alkyl substituted with one $R_{14}$;
$R_{4a}$ is hydrogen;
$R_{4b}$ is hydrogen; or
$R_{4a}$ and $R_{4b}$ are taken together to form =O;
Y is —O—;
Z is —$CHR_6$—;
$R_6$ is hydrogen;
Ring A is phenyl or pyridinyl; wherein the phenyl or pyridinyl is optionally substituted with one or two $R_8$ substituents;
each $R_8$ is independently hydrogen; $C_{1-4}$alkyloxy; cyano; or halo; or a $R_8$ substituent on an atom adjacent to the atom carrying the Y—Z substituent may be taken together with the $R_6$ substituent of Z, by which ring A together with Y—Z forms a bicycle of formula (a-3a);

$R_{11}$ is $C_{1-6}$alkyloxy optionally substituted with one hydroxyl group; or —C(=O)—$NR_{10a}R_{10b}$;

$R_{10a}$ and $R_{10b}$ each independently represent hydrogen or $C_{1-4}$alkyl;

$R_{14}$ is a 5 membered saturated heterocyclyl which is optionally substituted with one, two or three substituents selected from the group consisting of $C_{1-4}$alkyl;

$x_1$ is $CR_{5a}$ or N;
$x_2$ is $CR_{5b}$;
$x_3$ is $CR_{5c}$;
each $R_{15}$ is hydrogen;
$R_{5a}$ is hydrogen or $C_{1-6}$alkyloxy$C_{1-6}$alkyl;
$R_{5b}$ is $C_{1-6}$alkyl; $C_{3-6}$cycloalkyl; mono- or polyhalo $C_{1-6}$alkyloxy; $C_{2-6}$alkenyl; $C_{1-6}$alkyl substituted with one cyano; $C_{1-4}$alkyloxy; or $C_{1-6}$alkyl-O-carbonyl-;
$R_{5c}$ is hydrogen;
and the N-oxides, the pharmaceutically acceptable addition salts, and the solvates thereof.

In an embodiment, the present invention concerns novel compounds of Formula (I), tautomers and stereoisomeric forms thereof, wherein
$y_1$ is CH;
$y_2$ is CH;
$R_7$ is hydrogen;
X is $CH_2$;
$R_{2a}$ is hydrogen;
$R_{2b}$ is hydrogen;
$R_3$ is hydrogen; or $C_{1-6}$alkyl substituted with one or two hydroxyl groups;
$R_{4a}$ and $R_{4b}$ are taken together to form =O;
Y is —O—;
Z is —$CH_2$—;
Ring A is phenyl optionally substituted with one or two $R_8$ substituents;
each $R_8$ is independently hydrogen; $C_{1-4}$alkyloxy; cyano; or F;
$x_1$ is CH;
$x_2$ is $CR_{5b}$;
$x_3$ is CH;
each $R_{15}$ is hydrogen;
$R_{5b}$ is $C_{1-6}$alkyl; $C_{3-6}$cycloalkyl; mono- or polyhalo $C_{1-6}$alkyloxy; $C_{2-6}$alkenyl; $C_{1-6}$alkyl substituted with one cyano; or $C_{1-6}$alkyl-O-carbonyl-; in particular $R_{5b}$ is isopropyl or cyclopropyl;
and the N-oxides, the pharmaceutically acceptable addition salts, and the solvates thereof.

Another embodiment of the present invention relates to those compounds of formula (I) and the N-oxides, the pharmaceutically acceptable addition salts, and the solvates thereof, or any subgroup thereof as mentioned in any of the other embodiments wherein one or more of the following restrictions apply:

(i) $y_2$ is CH;
(ii) $R_{7a}$ is hydrogen;
(iii) $R_7$ is hydrogen, —$NH_2$, —$CH_2OH$, halo or cyano; or when $y_1$ represents $CR_{7a}$, this $R_{7a}$ can be taken together with a $R_7$ on an adjacent carbon atom to form —CH=CH—NH—;
(iv) $R_{1a}$ is hydrogen;
(v) $R_{2a}$ is hydrogen; $C_{1-6}$alkyl; $C_{1-6}$alkyl substituted with one hydroxyl group; or $C_{1-6}$alkyl substituted with one —$NR_{9a}R_{9b}$ substituent;

$R_{2b}$ is hydrogen; or
$R_{2a}$ and $R_{2b}$ are taken together to form —CH—$CH_2$—, —$CH_2$—$NR_{2c}$—$CH_2$— or =O;
(vi) $R_{2c}$ is hydrogen; or $C_{1-6}$alkyl substituted with one —$NR_{9a}R_{9b}$;
(vii) $R_3$ is hydrogen; $C_{1-6}$alkyl; $C_{1-6}$alkyl substituted with one or two hydroxyl groups; $C_{1-6}$alkyl substituted with one or two hydroxyl groups and one $C_{1-6}$alkyloxy; $R_{10a}R_{10b}N$—$C_{1-6}$alkylcarbonyl-; $C_{1-6}$alkyl-O-carbonyl-; $C_{1-6}$alkyl substituted with one $R_{11}$; $C_{1-6}$alkyl substituted with one —(C=O)—$R_{14}$; or $C_{1-6}$alkyl substituted with one $R_{14}$;
(viii) Y is —O— or —C(=O)—;
Z is —$CHR_6$— or —$CH_2$—C≡C—;
$R_6$ is hydrogen; $C_{1-4}$alkyl-O-carbonyl-; $C_{1-4}$alkyl; $C_{1-4}$alkyl substituted with one hydroxyl group; $C_{1-4}$alkyl substituted with one —$NR_{9a}R_{9b}$; or —C(=O)—$NR_{9a}R_{9b}$;
each $R_8$ is independently hydrogen; $C_{1-4}$alkyloxy; cyano; $C_{1-4}$alkyl or halo; or a $R_8$ substituent on an atom adjacent to the atom carrying the Y—Z substituent may be taken together with the $R_6$ substituent of Z, by which ring A together with Y—Z forms a bicycle of formula (a-1a), (a-2a), (a-3a), (a-4a) or (a-4b):

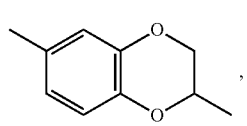

(a-1a)

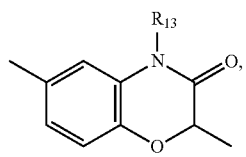

(a-2a)

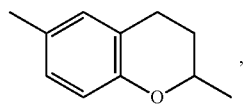

(a-3a)

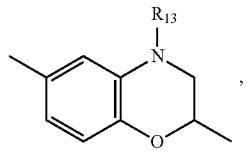

(a-4a)

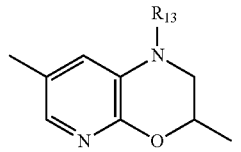

(a-4b)

or (ix) $R_{9a}$ and $R_{9b}$ each independently represent hydrogen; $C_{1-4}$alkyl substituted with one hydroxyl group; or $C_{1-4}$alkyl;
(x) $R_{10a}$ and $R_{10b}$ each independently represent hydrogen; $C_{1-4}$alkyl; $C_{1-6}$alkyl-O-carbonyl-; mono- or polyhalo $C_{1-4}$alkyl; or $C_{1-4}$alkyl substituted with one hydroxyl group;
(xi) $R_{11}$ is cyano; —$NR_{10a}R_{10b}$; $C_{1-6}$alkyloxy optionally substituted with one hydroxyl group; —S(=O)$_2$—$C_{1-6}$alkyl; $C_{1-6}$alkylcarbonyloxy-; —C(=O)—$NR_{10a}R_{10b}$; —COOH; or —P(=O)O—$C_{1-4}$alkyl)$_2$;
(xii) $R_{14}$ is a 5 membered saturated heterocyclyl which is optionally substituted with one, two or three substituents selected from the group consisting of oxo and $C_{1-4}$alkyl;
(xiii) $R_6$ is hydrogen; $C_{1-4}$alkyl-O-carbonyl-; $C_{1-4}$alkyl; $C_{1-4}$alkyl substituted with one hydroxyl group; $C_{1-4}$alkyl substituted with one —$NR_{9a}R_{9b}$; or —C(=O)—$NR_{9a}R_{9b}$;

(xiv) $x_2$ is $CR_{5b}$;
(xv) each $R_{15}$ is independently selected from the group consisting of hydrogen, methyl, halo, and $C_{1-4}$alkyloxy;
(xvi) $R_{5a}$ and $R_{5c}$ each independently are selected from the group consisting of hydrogen; hydroxyl; cyano; halo; $C_{1-6}$alkyl substituted with one or two hydroxyl groups; $C_{1-6}$alkyl substituted with one —$NR_{9a}R_{9b}$; $C_{1-6}$alkyloxy $C_{1-6}$alkyl; $C_{1-6}$alkyloxy; $C_{1-6}$alkyloxy substituted with one hydroxyl group; $C_{1-6}$alkyloxy$C_{1-6}$alkyloxy;
(xvii) $R_{5b}$ is hydrogen; $C_{1-6}$alkyl; $C_{3-6}$cycloalkyl optionally substituted with one cyano; cyano; mono- or polyhalo$C_{1-6}$alkyloxy; mono- or polyhalo$C_{1-6}$alkyl; $C_{1-4}$alkyl substituted with one hydroxyl group; $C_{2-6}$alkenyl; $C_{1-4}$alkyloxy; —Si(CH$_3$)$_3$; $C_{1-6}$alkyl substituted with one $R_{12}$; or $C_{1-6}$alkyl-O-carbonyl-.

Another embodiment of the present invention relates to those compounds of formula (I) and the N-oxides, the pharmaceutically acceptable addition salts, and the solvates thereof, or any subgroup thereof as mentioned in any of the other embodiments wherein one or more of the following restrictions apply:
(i) $y_1$ is CH or N;
(ii) $y_2$ is CH;
(iii) $R_7$ is hydrogen or —NH$_2$;
(iv) X is CH$_2$;
(v) $R_{2a}$ is hydrogen;
$R_{2b}$ is hydrogen; or
$R_{2a}$ and $R_{2b}$ are taken together to form —CH$_2$—CH$_2$— or —CH$_2$—NH—CH$_2$—;
(vi) $R_3$ is hydrogen; $C_{1-6}$ alkyl; $C_{1-6}$ alkyl substituted with one or two hydroxyl groups; $C_{1-6}$alkyl substituted with one $R_{11}$; or $C_{1-6}$alkyl substituted with one $R_{14}$:
(vii) $R_{4a}$ is hydrogen;
$R_{4b}$ is hydrogen; or
$R_{4a}$ and $R_{4b}$ are taken together to form =O;
(viii) Y is —O—;
Z is —CHR$_6$—;
$R_6$ is hydrogen;
Ring A is phenyl or pyridinyl; wherein the phenyl or pyridinyl is optionally substituted with one or two $R_8$ substituents;
each $R_8$ is independently hydrogen; $C_{1-4}$alkyloxy; cyano; or halo; or a $R_8$ substituent on an atom adjacent to the atom carrying the Y—Z substituent may be taken together with the $R_6$ substituent of Z, by which ring A together with Y—Z forms a bicycle of formula (a-3a);
(ix) $R_{11}$ is $C_{1-6}$alkyloxy optionally substituted with one hydroxyl group; or —C(=O)—$NR_{10a}R_{10b}$;
$R_{10a}$ and $R_{10b}$ each independently represent hydrogen or $C_{1-4}$alkyl;
(x) $R_{14}$ is a 5 membered saturated heterocyclyl which is optionally substituted with one, two or three substituents selected from the group consisting of $C_{1-4}$alkyl;
(xi) $x_1$ is $CR_{5a}$ or N;
$x_2$ is $CR_{5b}$;
$x_3$ is $CR_{5c}$;
(xiii) each $R_{15}$ is hydrogen;
(xiv) $R_{5a}$ is hydrogen or $C_{1-6}$alkyloxy$C_{1-6}$alkyl;
(xv) $R_{5b}$ is $C_{1-6}$alkyl; $C_{3-6}$cycloalkyl; mono- or polyhalo$C_{1-6}$alkyloxy; $C_{2-6}$alkenyl; $C_{1-6}$alkyl substituted with one cyano; $C_{1-4}$alkyloxy; or $C_{1-6}$alkyl-O-carbonyl-;
(xvi) $R_{5c}$ is hydrogen.

Another embodiment of the present invention relates to those compounds of formula (I) and the N-oxides, the pharmaceutically acceptable addition salts, and the solvates thereof, or any subgroup thereof as mentioned in any of the other embodiments wherein one or more of the following restrictions apply:
(i) $y_1$ is CH;
(ii) $y_2$ is CH;
(iii) $R_7$ is hydrogen;
(iv) X is CH$_2$;
(v) $R_{2a}$ is hydrogen;
(vi) $R_{2b}$ is hydrogen;
(vii) $R_3$ is hydrogen; or $C_{1-6}$alkyl substituted with one or two hydroxyl groups;
(viii) $R_{4a}$ and $R_{4b}$ are taken together to form =O;
(ix) Ring A is phenyl optionally substituted with one or two $R_8$ substituents;
each $R_8$ is independently hydrogen; $C_{1-4}$alkyloxy; cyano; or F;
(x) Y is —O—;
(xi) Z is —CH$_2$—;
(xii) $x_1$ is CH;
$x_2$ is $CR_{5b}$;
$x_3$ is CH;
(xiii) each $R_{15}$ is hydrogen;
(xiv) $R_{5b}$ is $C_{1-6}$alkyl; $C_{3-6}$cycloalkyl; mono- or polyhalo$C_{1-6}$alkyloxy; $C_{2-6}$alkenyl; $C_{1-6}$alkyl substituted with one cyano; or $C_{1-6}$-alkyl-O-carbonyl-; in particular $R_{5b}$ is isopropyl or cyclopropyl.

In an embodiment, the present invention relates to those compounds of formula (I) and the N-oxides, the pharmaceutically acceptable addition salts, and the solvates thereof, or any subgroup thereof as mentioned in any of the other embodiments, wherein Y is O.

In an embodiment, the present invention relates to those compounds of formula (I) and the N-oxides, the pharmaceutically acceptable addition salts, and the solvates thereof, or any subgroup thereof as mentioned in any of the other embodiments, wherein each $R_8$ is independently hydrogen; $C_{1-4}$alkyloxy; hydroxyl; cyano; or halo; or a $R_8$ substituent on an atom adjacent to the atom carrying the Y—Z substituent may be taken together with the $R_6$ substituent of Z, by which ring A together with Y—Z forms a bicycle of formula (a-1), (a-2), (a-3) or (a-4).

In an embodiment, the present invention relates to those compounds of formula (I) and the N-oxides, the pharmaceutically acceptable addition salts, and the solvates thereof, or any subgroup thereof as mentioned in any of the other embodiments, wherein ring A is phenyl or a 6-membered saturated, partially saturated or aromatic heterocyclyl, in particular phenyl or a 6-membered aromatic heterocyclyl, said heterocyclyl containing one or two nitrogen atoms; wherein the phenyl or the heterocyclyl is optionally substituted with one or two $R_8$ substituents;
each $R_8$ is independently hydrogen; $C_{1-4}$alkyloxy; hydroxyl; cyano; $C_{1-4}$alkyl or halo.

In an embodiment, the present invention relates to those compounds of formula (I) and the N-oxides, the pharmaceutically acceptable addition salts, and the solvates thereof, or any subgroup thereof as mentioned in any of the other embodiments, wherein ring A is phenyl or a 6-membered saturated, partially saturated or aromatic heterocyclyl, in particular phenyl or a 6-membered aromatic heterocyclyl, said heterocyclyl containing one or two nitrogen atoms; wherein the phenyl or the heterocyclyl is optionally substituted with one or two $R_8$ substituents;
each $R_8$ is independently hydrogen; $C_{1-4}$alkyloxy; hydroxyl; cyano; or halo.

In an embodiment, the present invention relates to those compounds of formula (I) and the N-oxides, the pharmaceutically acceptable addition salts, and the solvates thereof, or any subgroup thereof as mentioned in any of the other embodiments, wherein ring A is phenyl or a 6-membered saturated, partially saturated or aromatic heterocyclyl, said heterocyclyl containing one or two nitrogen atoms; wherein the phenyl or the heterocyclyl is substituted with one $R_8$ substituent on an atom adjacent to the atom carrying the Y—Z substituent, and said $R_8$ substituent is taken together with the $R_8$ substituent of Z (Z is —CHR$_6$—), by which ring A together with Y—Z forms a bicycle of formula (a-1), (a-2), (a-3) or (a-4).

In an embodiment, the present invention relates to those compounds of formula (I) and the N-oxides, the pharmaceutically acceptable addition salts, and the solvates thereof, or any subgroup thereof as mentioned in any of the other embodiments, wherein ring A is phenyl or a 6-membered aromatic heterocyclyl, said heterocyclyl containing one or two nitrogen atoms; wherein the phenyl or the heterocyclyl is substituted with one $R_8$ substituent on an atom adjacent to the atom carrying the Y—Z substituent, and said $R_8$ substituent is taken together with the $R_6$ substituent of Z (Z is —CHR$_6$—), by which ring A together with Y—Z forms a bicycle of formula (a-1a), (a-2a), (a-3a), (a-4a) or (a-4b).

In an embodiment, the present invention relates to those compounds of formula (I) and the N-oxides, the pharmaceutically acceptable addition salts, and the solvates thereof, or any subgroup thereof as mentioned in any of the other embodiments, wherein ring A is phenyl or a 6-membered aromatic heterocyclyl, said heterocyclyl containing one or two nitrogen atoms, in particular ring A is phenyl; wherein the phenyl or the heterocyclyl is optionally substituted with one or two $R_8$ substituents.

In an embodiment, the present invention relates to those compounds of formula (I) and the N-oxides, the pharmaceutically acceptable addition salts, and the solvates thereof, or any subgroup thereof as mentioned in any of the other embodiments, wherein ring A is phenyl or a 6-membered aromatic heterocyclyl, said heterocyclyl containing one or two nitrogen atoms.

In an embodiment, the present invention relates to those compounds of formula (I) and the N-oxides, the pharmaceutically acceptable addition salts, and the solvates thereof, or any subgroup thereof as mentioned in any of the other embodiments, wherein ring A is phenyl.

In an embodiment, the present invention relates to those compounds of formula (I) and the N-oxides, the pharmaceutically acceptable addition salts, and the solvates thereof, or any subgroup thereof as mentioned in any of the other embodiments, wherein each $R_8$ is independently hydrogen; $C_{1-4}$alkyloxy; hydroxyl; cyano; or halo.

In an embodiment, the present invention relates to those compounds of formula (I) and the N-oxides, the pharmaceutically acceptable addition salts, and the solvates thereof, or any subgroup thereof as mentioned in any of the other embodiments, wherein each $R_8$ is independently hydrogen; $C_{1-4}$alkyloxy; hydroxyl; cyano; or halo; or a $R_8$ substituent on an atom adjacent to the atom carrying the Y—Z substituent may be taken together with the $R_6$ substituent of Z, by which ring A together with Y—Z forms a bicycle of formula (a-1a), (a-2a), (a-3a), (a-4a), or (a-4b).

In an embodiment, the present invention relates to those compounds of formula (I) and the N-oxides, the pharmaceutically acceptable addition salts, and the solvates thereof, or any subgroup thereof as mentioned in any of the other embodiments, wherein Z is —CHR$_6$— and Y is O.

In an embodiment, the present invention relates to those compounds of formula (I) and the N-oxides, the pharmaceutically acceptable addition salts, and the solvates thereof, or any subgroup thereof as mentioned in any of the other embodiments, wherein $R_8$ is other than $C_{1-4}$alkyl.

In an embodiment, the present invention relates to those compounds of formula (I) and the N-oxides, the pharmaceutically acceptable addition salts, and the solvates thereof, or any subgroup thereof as mentioned in any of the other embodiments, wherein ring A is phenyl or a 6-membered aromatic heterocyclyl, said heterocyclyl containing one or two nitrogen atoms; wherein the phenyl or the heterocyclyl is optionally substituted with one or two $R_8$ substituents;

each $R_8$ is independently hydrogen; $C_{1-4}$alkyloxy; hydroxyl; cyano; or halo; or a $R_8$ substituent on an atom adjacent to the atom carrying the Y—Z substituent may be taken together with the $R_6$ substituent of Z, by which ring A together with Y—Z forms a bicycle of formula (a-1), (a-2), (a-3) or (a-4); and Y is —O—.

In an embodiment, the present invention relates to those compounds of formula (I) and the N-oxides, the pharmaceutically acceptable addition salts, and the solvates thereof, or any subgroup thereof as mentioned in any of the other embodiments, wherein when ring A together with Y—Z forms a bicycle, this bicycle is of formula (a-1), (a-2), (a-3) or (a-4); in particular (a-1a), (a-2a), (a-3a), (a-4a), or (a-4b).

In an embodiment, the present invention relates to those compounds of formula (I) and the N-oxides, the pharmaceutically acceptable addition salts, and the solvates thereof, or any subgroup thereof as mentioned in any of the other embodiments, wherein $R_{14}$ is a 5-membered saturated heterocycle which is optionally substituted with one, two or three substituents selected from the group consisting of oxo, $C_{1-4}$alkyl, halogen, cyano, hydroxyl, $C_{1-6}$alkyloxy and $NR_{9a}R_{9b}$; in particular wherein $R_{14}$ is a 5-membered saturated heterocycle which is substituted with one or two substituents selected from the group consisting of oxo or $C_{1-4}$alkyl.

In an embodiment, the present invention relates to those compounds of formula (I) and the N-oxides, the pharmaceutically acceptable addition salts, and the solvates thereof, or any subgroup thereof as mentioned in any of the other embodiments, wherein $R_{14}$ is a 5-membered saturated heterocycle selected from 1-pyrolidinyl, 1,3-dioxolan-4-yl, 5-oxazolidinyl, 3-oxetanyl and tetrahydro-2-furanyl, each optionally substituted with one, two or three substituents selected from the group consisting of oxo, $C_{1-4}$alkyl, halogen, cyano, hydroxyl, $C_{1-6}$alkyloxy and $NR_{9a}R_{9b}$; in particular wherein $R_{14}$ is a 5-membered saturated heterocycle selected from 1-pyrolidinyl, 1,3-dioxolan-4-yl, 5-oxazolidinyl, 3-oxetanyl and tetrahydro-2-furanyl, each substituted with one or two substituents selected from the group consisting of oxo and $C_{1-4}$alkyl.

In an embodiment, the present invention relates to those compounds of formula (I) and the N-oxides, the pharmaceutically acceptable addition salts, and the solvates thereof, or any subgroup thereof as mentioned in any of the other embodiments, wherein $R_{1a}$ is hydrogen; $C_{1-6}$alkyl; mono- or polyhalo$C_{1-6}$alkyl; $C_{1-6}$alkyl substituted with one or two hydroxyl groups; or $C_{1-6}$alkyl substituted with one —NR$_9$R$_{9b}$.

In an embodiment, the present invention relates to those compounds of formula (I) and the N-oxides, the pharmaceutically acceptable addition salts, and the solvates thereof, or any subgroup thereof as mentioned in any of the other embodiments, wherein $R_{2a}$ is hydrogen; $C_{1-6}$alkyl; mono- or polyhalo$C_{1-6}$alkyl; $C_{1-6}$alkyl substituted with one or two hydroxyl groups; or $C_{1-6}$alkyl substituted with one substituent selected from the group consisting of —$NR_{9a}R_{9b}$, cyano and $C_{1-4}$alkyloxy;

$R_{2b}$ is hydrogen or $C_{1-6}$alkyl; or $R_{2a}$ and $R_{2b}$ are taken together to form —$CH_2$—$CH_2$—, —$CH_2$—$NR_{2c}$—$CH_2$—, —$CH_2$—$CH_2$—$CH_2$—, —$CH_2$—O—$CH_2$—, —$CH_2$—$CH_2$—$CH_2$—$CH_2$—, —$CH_2$—$CH_2$—$NR_{2c}$—$CH_2$—.

In an embodiment, the present invention relates to those compounds of formula (I) and the N-oxides, the pharmaceutically acceptable addition salts, and the solvates thereof, or any subgroup thereof as mentioned in any of the other embodiments, wherein $R_{5b}$ is hydrogen; $C_{1-6}$alkyl; $C_{3-6}$cycloalkyl optionally substituted with one cyano; hydroxyl; cyano; mono- or polyhalo$C_{1-6}$alkyloxy; mono- or polyhalo$C_{1-6}$alkyl; $C_{1-4}$alkyl substituted with one or two hydroxyl groups; $C_{2-6}$alkenyl; $C_{1-4}$alkyloxy; —$Si(CH_3)_3$; $C_{1-6}$alkyl substituted with one $R_{12}$; or $C_{1-6}$alkyloxy substituted with one $R_{12}$.

In an embodiment, the present invention relates to those compounds of formula (I) and the N-oxides, the pharmaceutically acceptable addition salts, and the solvates thereof, or any subgroup thereof as mentioned in any of the other embodiments, wherein $R_{5b}$ is $C_{1-6}$alkyl; $C_{3-6}$cycloalkyl optionally substituted with one cyano; mono- or polyhalo $C_{1-6}$alkyloxy; mono- or polyhalo$C_{1-6}$alkyl; $C_{1-4}$alkyl substituted with one hydroxyl group; $C_{2-6}$alkenyl; —$Si(CH_3)_3$; $C_{1-6}$alkyl substituted with one $R_{12}$; or $C_{1-6}$alkyl-O-carbonyl-.

In an embodiment, the present invention relates to those compounds of formula (I) and the N-oxides, the pharmaceutically acceptable addition salts, and the solvates thereof, or any subgroup thereof as mentioned in any of the other embodiments, wherein $R_{5b}$ is $C_{1-6}$alkyl; $C_{3-6}$cycloalkyl optionally substituted with one cyano; mono- or polyhalo $C_{1-6}$alkyloxy; mono- or polyhalo$C_{1-6}$alkyl; $C_{1-4}$alkyl substituted with one hydroxyl group; $C_{2-6}$alkenyl; —$Si(CH_3)_3$; $C_{1-6}$alkyl substituted with one $R_{12}$; or $C_{1-6}$alkyl-O-carbonyl-; and wherein $R_8$ is other than $C_{1-4}$alkyl.

In an embodiment, the present invention relates to those compounds of formula (I) and the N-oxides, the pharmaceutically acceptable addition salts, and the solvates thereof, or any subgroup thereof as mentioned in any of the other embodiments, wherein ring A is phenyl or a 6-membered aromatic heterocyclyl, said heterocyclyl containing one or two nitrogen atoms; wherein the phenyl or the heterocyclyl is optionally substituted with one or two $R_8$ substituents;

each $R_8$ is independently hydrogen; $C_{1-4}$alkyloxy; hydroxyl; cyano; or halo; or a $R_8$ substituent on an atom adjacent to the atom carrying the Y—Z substituent may be taken together with the $R_6$ substituent of Z, by which ring A together with Y—Z forms a bicycle of formula (a-1), (a-2), (a-3) or (a-4);

$x_2$ is $CR_{5b}$; $R_{5b}$ is $C_{1-6}$alkyl; $C_{3-6}$cycloalkyl optionally substituted with one cyano; mono- or polyhalo$C_{1-6}$alkyloxy; mono- or polyhalo$C_{1-6}$alkyl; $C_{1-4}$alkyl substituted with one hydroxyl group; $C_{2-6}$alkenyl; —$Si(CH_3)_3$; $C_{1-6}$alkyl substituted with one $R_{12}$; or $C_{1-6}$alkyl-O-carbonyl-.

In an embodiment, the present invention relates to those compounds of formula (I) and the N-oxides, the pharmaceutically acceptable addition salts, and the solvates thereof, or any subgroup thereof as mentioned in any of the other embodiments, wherein ring A is phenyl or a 6-membered aromatic heterocyclyl, said heterocyclyl containing one or two nitrogen atoms; wherein the phenyl or the heterocyclyl is optionally substituted with one or two $R_8$ substituents;

each $R_8$ is independently hydrogen; $C_{1-4}$alkyloxy; cyano; or halo; or a $R_8$ substituent on an atom adjacent to the atom carrying the Y—Z substituent may be taken together with the $R_6$ substituent of Z, by which ring A together with Y—Z forms a bicycle of formula (a-1a), (a-2a), (a-3a), (a-4a) or (a-4b);

$x_2$ is $CR_{5b}$; $R_{5b}$ is $C_{1-6}$alkyl; $C_{3-6}$cycloalkyl optionally substituted with one cyano; mono- or polyhalo$C_{1-6}$alkyloxy; mono- or polyhalo$C_{1-6}$alkyl; $C_{1-6}$alkyl substituted with one hydroxyl group; $C_{2-6}$alkenyl; —$Si(CH_3)_3$; $C_{1-6}$alkyl substituted with one $R_{12}$; or $C_{1-6}$alkyl-O-carbonyl-.

In an embodiment, the present invention relates to those compounds of formula (I) and the N-oxides, the pharmaceutically acceptable addition salts, and the solvates thereof, or any subgroup thereof as mentioned in any of the other embodiments, wherein ring A is phenyl or a 6-membered aromatic heterocyclyl, said heterocyclyl containing one or two nitrogen atoms; wherein the phenyl or the heterocyclyl is optionally substituted with one or two $R_8$ substituents;

each $R_8$ is independently hydrogen; $C_{1-4}$alkyloxy; hydroxyl; cyano; or halo; in particular each $R_8$ is independently hydrogen; $C_{1-4}$alkyloxy; cyano; or halo;

$x_2$ is $CR_{5b}$; $R_{5b}$ is $C_{1-6}$alkyl; $C_{3-6}$cycloalkyl optionally substituted with one cyano; mono- or polyhalo$C_{1-6}$alkyloxy; mono- or polyhalo$C_{1-6}$alkyl; $C_{1-4}$alkyl substituted with one hydroxyl group; $C_{2-6}$alkenyl; —$Si(CH_3)_3$; $C_{1-6}$alkyl substituted with one $R_{12}$; or $C_{1-6}$alkyl-O-carbonyl-.

In an embodiment, the present invention relates to those compounds of formula (I) and the N-oxides, the pharmaceutically acceptable addition salts, and the solvates thereof, or any subgroup thereof as mentioned in any of the other embodiments, wherein X is —$CR_1R_{1a}$—; in particular $CH_2$.

In an embodiment, the present invention relates to those compounds of formula (I) and the N-oxides, the pharmaceutically acceptable addition salts, and the solvates thereof, or any subgroup thereof as mentioned in any of the other embodiments, wherein $R_1$ and $R_{1a}$ are hydrogen.

In an embodiment, the present invention relates to those compounds of formula (I) and the N-oxides, the pharmaceutically acceptable addition salts, and the solvates thereof, or any subgroup thereof as mentioned in any of the other embodiments, wherein —Y—Z— is —O—$CH_2$—.

In an embodiment, the present invention relates to those compounds of formula (I) and the N-oxides, the pharmaceutically acceptable addition salts, and the solvates thereof, or any subgroup thereof as mentioned in any of the other embodiments, wherein Z is $CHR_6$, in particular $CH_2$.

In an embodiment, the present invention relates to those compounds of formula (I) and the N-oxides, the pharmaceutically acceptable addition salts, and the solvates thereof, or any subgroup thereof as mentioned in any of the other embodiments, wherein $R_6$ is H.

In an embodiment, the present invention relates to those compounds of formula (I) and the N-oxides, the pharmaceutically acceptable addition salts, and the solvates thereof, or any subgroup thereof as mentioned in any of the other embodiments, wherein $R_3$ is hydrogen or $C_{1-6}$alkyl substituted with one or two, in particular one, hydroxyl groups.

In an embodiment, the present invention relates to those compounds of formula (I) and the N-oxides, the pharmaceutically acceptable addition salts, and the solvates thereof, or any subgroup thereof as mentioned in any of the other embodiments, wherein $R_{2a}$ and $R_{2b}$ are hydrogen.

In an embodiment, the present invention relates to those compounds of formula (I) and the N-oxides, the pharmaceutically acceptable addition salts, and the solvates thereof, or any subgroup thereof as mentioned in any of the other embodiments, wherein $R_{4a}$ is hydrogen; $R_4$ is hydrogen; or $R_{4a}$ and $R_4$ are taken together to form =O.

In an embodiment, the present invention relates to those compounds of formula (I) and the N-oxides, the pharmaceutically acceptable addition salts, and the solvates thereof, or any subgroup thereof as mentioned in any of the other embodiments, wherein $R_{4a}$ and $R_{4b}$ are hydrogen.

In an embodiment, the present invention relates to those compounds of formula (I) and the N-oxides, the pharmaceutically acceptable addition salts, and the solvates thereof, or any subgroup thereof as mentioned in any of the other embodiments, wherein $R_{4a}$ and $R_{4b}$ are taken together to form =O.

In an embodiment, the present invention relates to those compounds of formula (I) and the N-oxides, the pharmaceutically acceptable addition salts, and the solvates thereof, or any subgroup thereof as mentioned in any of the other embodiments, wherein $x_1$ and $x_3$ are CH; and $x_2$ is $CR_{5b}$.

In an embodiment, the present invention relates to those compounds of formula (I) and the N-oxides, the pharmaceutically acceptable addition salts, and the solvates thereof, or any subgroup thereof as mentioned in any of the other embodiments, wherein $x_2$ is $CR_{5b}$; $R_{5b}$ is $C_{1-6}$alkyl; $C_{3-6}$cycloalkyl optionally substituted with one cyano; hydroxyl; mono- or polyhalo$C_{1-6}$alkyloxy; mono- or polyhalo$C_{1-6}$alkyl; $C_{1-4}$alkyl substituted with one or two hydroxyl groups; $C_{2-6}$alkenyl; —Si(CH$_3$)$_3$; $C_{1-6}$alkyl substituted with one $R_{12}$; $C_{1-6}$alkyl-O-carbonyl-; $C_{1-6}$alkyloxy substituted with one $R_{12}$.

In an embodiment, the present invention relates to those compounds of formula (I) and the N-oxides, the pharmaceutically acceptable addition salts, and the solvates thereof, or any subgroup thereof as mentioned in any of the other embodiments, wherein $R_{5b}$ is $C_{1-6}$alkyl; $C_{3-6}$cycloalkyl optionally substituted with one cyano; hydroxyl; mono- or polyhalo$C_{1-6}$alkyloxy; mono- or polyhalo$C_{1-6}$alkyl; $C_{1-4}$alkyl substituted with one or two hydroxyl groups; $C_{2-6}$alkenyl; —Si(CH$_3$)$_3$; $C_{1-6}$alkyl substituted with one $R_{12}$; $C_{1-6}$alkyl-O-carbonyl-; $C_{1-6}$alkyloxy substituted with one $R_{12}$.

In an embodiment, the present invention relates to those compounds of formula (I) and the N-oxides, the pharmaceutically acceptable addition salts, and the solvates thereof, or any subgroup thereof as mentioned in any of the other embodiments, wherein $R_{5a}$ and $R_{5c}$ each independently are selected from the group consisting of hydrogen; hydroxyl; cyano; halo; $C_{1-6}$alkyl; $C_{1-6}$alkyl substituted with one or two hydroxyl groups; mono- or polyhalo$C_{1-6}$alkyl; mono- or polyhalo$C_{1-6}$alkyloxy; $C_{1-6}$alkyloxy$C_{1-6}$alkyl wherein each of the $C_{1-6}$alkyl groups are optionally substituted with one or two hydroxyl groups; $C_{2-6}$alkenyl; $C_{1-6}$alkyloxy; $C_{1-6}$alkyloxy substituted with one or two hydroxyl groups; $C_{1-6}$alkyloxy$C_{1-6}$alkyloxy wherein each of the $C_{1-6}$alkyl groups are optionally substituted with one or two hydroxyl groups.

In an embodiment, the present invention relates to those compounds of formula (I) and the N-oxides, the pharmaceutically acceptable addition salts, and the solvates thereof, or any subgroup thereof as mentioned in any of the other embodiments, wherein $R_3$ is hydrogen; $C_{1-6}$alkyl; mono- or polyhalo$C_{1-6}$alkyl; $C_{1-6}$alkyl substituted with one or two hydroxyl groups; $C_{1-6}$alkyl substituted with one or two hydroxyl groups and one $C_{1-6}$alkyloxy; $C_{1-6}$alkylcarbonyloxy-; $C_{1-6}$alkyl substituted with one $R_{11}$; $C_{1-6}$alkyloxy optionally substituted with one —NR$_{10a}$R$_{10b}$; $C_{2-6}$alkenyl; $C_{2-6}$alkynyl; hydroxy$C_{2-6}$alkenyl; hydroxy$C_{2-6}$alkynyl; $C_{1-6}$alkyloxy$C_{2-6}$alkenyl; $C_{1-6}$alkyloxy$C_{2-6}$alkynyl; $C_{2-6}$alkenyl substituted with one —NR$_{10a}$R$_{10b}$; $C_{2-6}$alkynyl substituted with one —NR$_{10a}$R$_{10b}$; $C_{1-6}$alkyl substituted with one or two hydroxyl groups and one —NR$_{10a}$R$_{10b}$; —$C_{1-6}$alkyl-C(R$_{13}$)=N—O—R$_{13}$; —S(=O)$_2$—C$_{1-6}$alkyl; —S(=O)$_2$—NR$_{9a}$R$_{9b}$; $C_{1-6}$alkyl substituted with one —(C=O)—R$_{14}$; $C_{1-6}$alkyl substituted with one or two hydroxyl groups and one R$_{14}$; $C_{1-6}$alkyl substituted with one R$_{14}$; $C_{2-6}$alkenyl substituted with one R$_{14}$; $C_{2-6}$alkynyl substituted with one R$_{14}$; or R$_{14}$.

In an embodiment, the present invention relates to those compounds of formula (I) and the N-oxides, the pharmaceutically acceptable addition salts, and the solvates thereof, or any subgroup thereof as mentioned in any of the other embodiments, wherein $R_{15}$ is hydrogen.

In an embodiment, the present invention relates to those compounds of formula (I) and the N-oxides, the pharmaceutically acceptable addition salts, and the solvates thereof, or any subgroup thereof as mentioned in any of the other embodiments, wherein $R_{15}$ is hydrogen or F, in particular F.

In an embodiment, the present invention relates to those compounds of formula (I) and the N-oxides, the pharmaceutically acceptable addition salts, and the solvates thereof, or any subgroup thereof as mentioned in any of the other embodiments, wherein $R_{7a}$ is hydrogen, halo, trifluoromethyl or cyano;
$R_7$ is hydrogen, —NH$_2$, —NHCH$_3$, —NH(CH$_2$CH$_3$), methyl, —CH$_2$OH, halo or cyano.

In an embodiment, the present invention relates to those compounds of formula (I) and the N-oxides, the pharmaceutically acceptable addition salts, and the solvates thereof, or any subgroup thereof as mentioned in any of the other embodiments, wherein $R_{7a}$ is hydrogen; $R_7$ is hydrogen, —NH$_2$, —CH$_2$OH, halo or cyano.

In an embodiment, the present invention relates to those compounds of formula (I) and the N-oxides, the pharmaceutically acceptable addition salts, and the solvates thereof, or any subgroup thereof as mentioned in any of the other embodiments, wherein ring A is phenyl optionally substituted with one or two R$_8$ substituents;

each R$_8$ is independently hydrogen; $C_{1-4}$alkyloxy; cyano; or halo;

Y is —O—; Z is —CH$_2$—; R$_{15}$ is H; $x_1$ and $x_3$ are CH; $x_2$ is CR$_{5b}$; R$_{5b}$ is isopropyl.

In an embodiment, the present invention relates to those compounds of formula (I) and the N-oxides, the pharmaceutically acceptable addition salts, and the solvates thereof, or any subgroup thereof as mentioned in any of the other embodiments, wherein $y_1$ and $y_2$ are CH; R$_7$ is H; X is CH$_2$; R$_{2a}$ and R$_{2b}$ are H; R$_{4a}$ and R$_4$ are taken together to form =O;

ring A is phenyl optionally substituted with one or two R$_8$ substituents;

each R$_8$ is independently hydrogen; $C_{1-4}$alkyloxy; cyano; or halo;

Y is —O—; Z is —CH$_2$—; R$_{15}$ is H; $x_1$ and $x_3$ are CH; $x_2$ is CR$_{5b}$; R$_{5b}$ is isopropyl.

In an embodiment, the present invention relates to those compounds of formula (I) and the N-oxides, the pharmaceutically acceptable addition salts, and the solvates thereof, or any subgroup thereof as mentioned in any of the other embodiments, wherein $y_1$ and $y_2$ are CH; R$_7$ is H; X is CH$_2$; R$_{2a}$ and R$_{2b}$ are H; R$_{4a}$ and R$_{4b}$ are taken together to form =O;

ring A is phenyl; Y is —O—; Z is —CH$_2$—; R$_{15}$ is H; $x_1$ and $x_3$ are CH; $x_2$ is CR$_{5b}$; R$_{5b}$ is isopropyl.

In an embodiment, the present invention relates to those compounds of formula (I) and the N-oxides, the pharmaceutically acceptable addition salts, and the solvates thereof, or any subgroup thereof as mentioned in any of the other embodiments, wherein $x_1$ and $x_3$ are CH; $x_2$ is $CR_{5b}$; $R_{5b}$ is isopropyl.

In an embodiment, the present invention relates to those compounds of formula (I) and the N-oxides, the pharmaceutically acceptable addition salts, and the solvates thereof, or any subgroup thereof as mentioned in any of the other embodiments, wherein $y_1$ and $y_2$ are CH.

Another embodiment of the present invention relates to those compounds of formula (I) and the N-oxides, the pharmaceutically acceptable addition salts, and the solvates thereof, or any subgroup thereof as mentioned in any of the other embodiments wherein one or more of the following restrictions apply:
(i) $y_1$ and $y_2$ are CH;
(ii) $R_7$ is H;
(iii) X is $CH_2$;
(iv) $R_{2a}$ and $R_{2b}$ are H;
(v) $R_{4a}$ and $R_{4b}$ are taken together to form =O;
(vi) ring A is phenyl optionally substituted with one or two $R_8$ substituents;
each $R_8$ is independently hydrogen; $C_{1-4}$alkyloxy; cyano; or halo;
(vii) Y is —O—;
(viii) Z is —$CH_2$—;
(ix) $R_{15}$ is H;
(x) $x_1$ and $x_3$ are CH;
(xi) $x_2$ is $CR_{5b}$; $R_{5b}$ is isopropyl.

In an embodiment, the present invention relates to those compounds of formula (I) and the N-oxides, the pharmaceutically acceptable addition salts, and the solvates thereof, or any subgroup thereof as mentioned in any of the other embodiments, wherein $x_2$ is $CR_{5b}$; $R_{5b}$ is isopropyl.

In an embodiment, the present invention relates to those compounds of formula (I) and the N-oxides, the pharmaceutically acceptable addition salts, and the solvates thereof, or any subgroup thereof as mentioned in any of the other embodiments, wherein $C_{1-6}$alkyl is limited to $C_{1-4}$alkyl.

In an embodiment, the present invention relates to those compounds of formula (I) and the N-oxides, the pharmaceutically acceptable addition salts, and the solvates thereof, or any subgroup thereof as mentioned in any of the other embodiments, wherein $R_{7a}$ is hydrogen, halo, trifluoromethyl or cyano;
$R_7$ is hydrogen, —$NH_2$, —$NHCH_3$, —$NH(CH_2CH_3)$, methyl, —$CH_2OH$, halo or cyano.

In an embodiment, the present invention relates to those compounds of formula (I) and the N-oxides, the pharmaceutically acceptable addition salts, and the solvates thereof, or any subgroup thereof as mentioned in any of the other embodiments, wherein $R_8$ is not taken together with the $R_6$ substituent of Z to form a bicycle.

In an embodiment, the present invention relates to those compounds of formula (I) and the N-oxides, the pharmaceutically acceptable addition salts, and the solvates thereof, or any subgroup thereof as mentioned in any of the other embodiments, wherein $R_{14}$ is a 4, 5 or 6 membered saturated heterocyclyl which is optionally substituted with one, two or three substituents selected from the group consisting of oxo, $C_{1-4}$alkyl, halogen, cyano, hydroxyl, $C_{1-6}$alkyloxy and $NR_{9a}R_{9b}$.

In an embodiment, the present invention relates to a subgroup of formula (I) and the N-oxides, the pharmaceutically acceptable addition salts, and the solvates thereof, as defined in the general reaction schemes.

In an embodiment the compound of Formula (I) is selected from the group consisting of

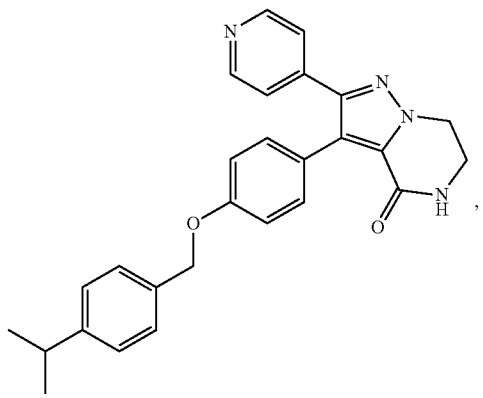

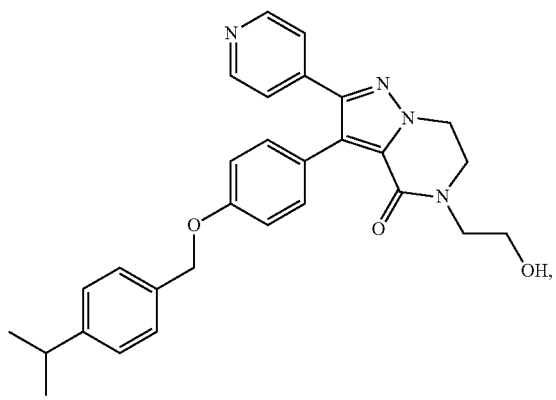

tautomers and stereoisomeric forms thereof, and the N-oxides, the pharmaceutically acceptable addition salts, and the solvates thereof.

In an embodiment the compound of Formula (I) is

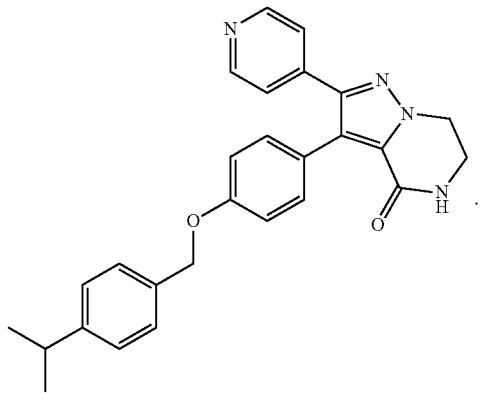 [SMILES: CC(C)c1ccc(COc2ccc(-c3c(-c4ccncc4)nn4c3C(=O)NCC4)cc2)cc1]

In an embodiment the compound of Formula (I) is

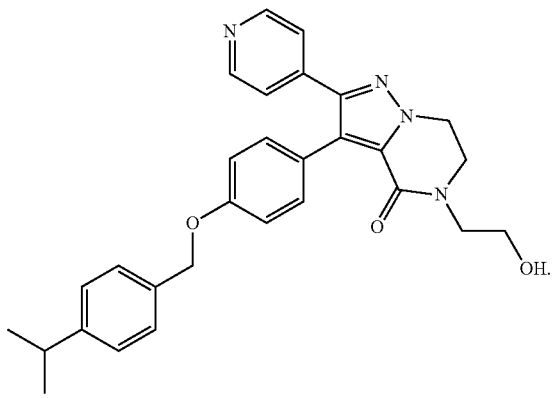 [SMILES: CC(C)c1ccc(COc2ccc(-c3c(-c4ccncc4)nn4c3C(=O)N(CCO)CC4)cc2)cc1]

All possible combinations of the above-indicated embodiments are considered to be embraced within the scope of this invention.

Methods for the Preparation of Compounds of Formula (I)

In this section, as in all other sections unless the context indicates otherwise, references to formula (I) also include all other sub-groups and examples thereof as defined herein.

The general preparation of some typical examples of the compounds of Formula (I) is described hereunder and in the specific examples, and are generally prepared from starting materials which are either commercially available or prepared by standard synthetic processes commonly used by those skilled in the art. The following schemes are only meant to represent examples of the invention and are in no way meant to be a limit of the invention.

Alternatively, compounds of the present invention may also be prepared by analogous reaction protocols as described in the general schemes below, combined with standard synthetic processes commonly used by those skilled in the art of organic chemistry.

The skilled person will realize that in the reactions described in the Schemes, it may be necessary to protect reactive functional groups, for example hydroxy, amino, or carboxy groups, where these are desired in the final product, to avoid their unwanted participation in the reactions. Conventional protecting groups can be used in accordance with standard practice.

The skilled person will realize that in the reactions described in the Schemes, it may be advisable or necessary to perform the reaction under an inert atmosphere, such as for example under $N_2$-gas atmosphere, for example when NaH is used in the reaction.

It will be apparent for the skilled person that it may be necessary to cool the reaction mixture before reaction work-up (refers to the series of manipulations required to isolate and purify the product(s) of a chemical reaction such as for example quenching, column chromatography, extraction).

The skilled person will realize that heating the reaction mixture under stirring may enhance the reaction outcome. In some reactions microwave heating may be used instead of conventional heating to shorten the overall reaction time.

The skilled person will realize that intermediates and final compounds shown in the schemes below may be further functionalized according to methods well-known by the person skilled in the art.

All variables are defined as mentioned hereabove unless otherwise is indicated or is clear from the context.

1) Scheme 1:

In general, compounds of formula (Ia1), (Ia), (Ib), (Ic), (Id), (Ie) (If) and (Ig) can be prepared according to reaction Scheme 1. In scheme 1 the following definitions apply:

$Y_x$ is defined as O;

ring A1 is phenyl or a 6-membered aromatic heterocyclyl containing one or two nitrogen atoms; wherein the phenyl or the heterocyclyl is optionally substituted with one or two $R_8$ substituents;

each $R_8$ is independently hydrogen; $C_{1-4}$alkyloxy; hydroxyl; cyano; $C_{1-4}$alkyl or halo; or a $R_8$ substituent of ring A1 on an atom adjacent to the atom carrying the $Y_x$—Z substituent is taken together with the $R_6$ substituent of Z, by which ring A1 together with $Y_x$—Z forms a bicycle;

R, R' and R" are functional groups within the limits of the scope;

and all other variables in Scheme 1 are defined according to the scope of the present invention.

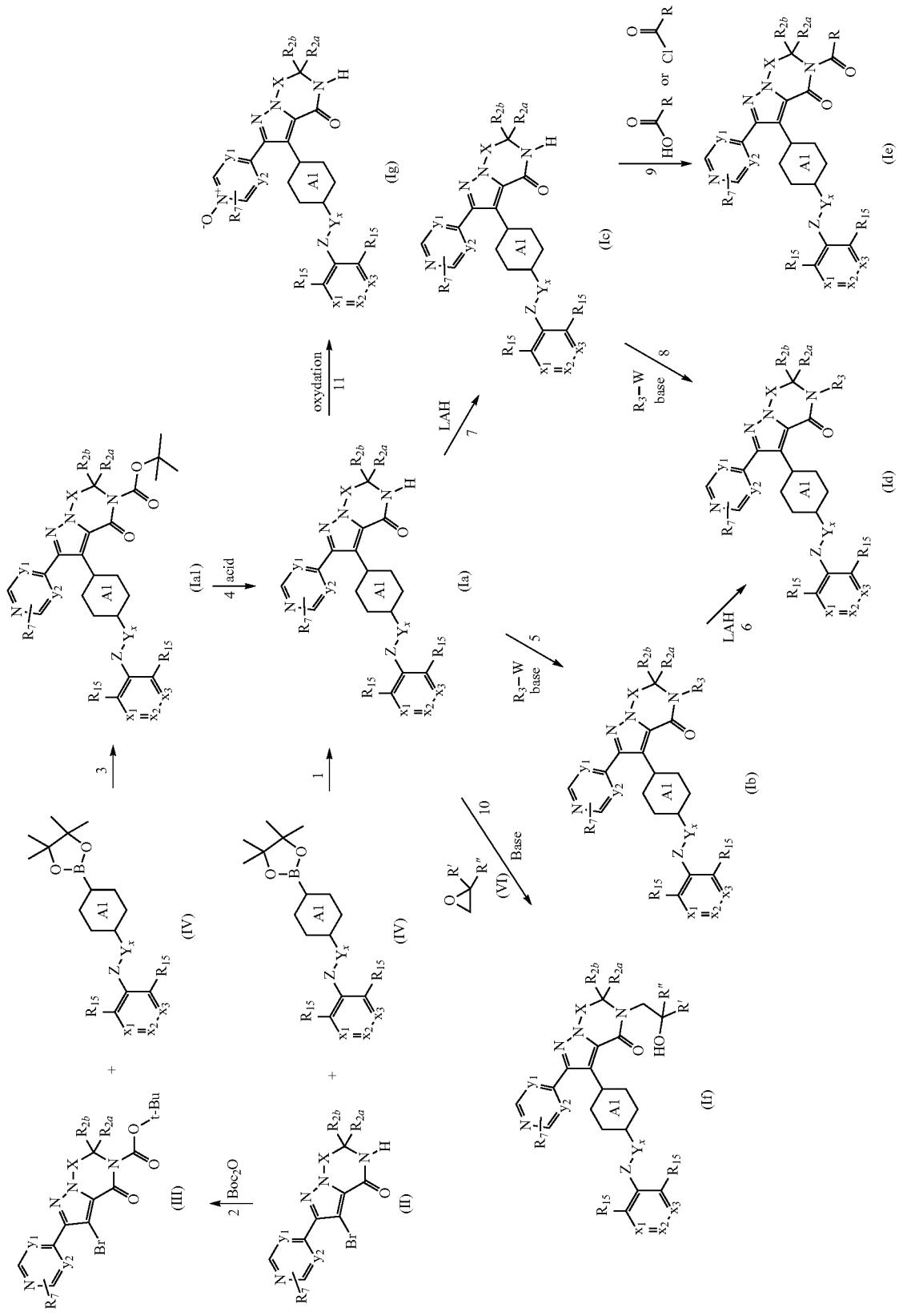

1: an intermediate of formula (II) can be reacted with an intermediate of formula (IV) in the presence of suitable catalyst, such as for example palladium (II) acetate or [1,1'-bis(diphenylphosphino-kP)ferrocene]dichloropalladium (PdCl$_2$dppf), a suitable base, such as for example potassium phosphate (K$_3$PO$_4$) or cesium carbonate (Cs$_2$CO$_3$), and a suitable solvent or solvent mixture, such as for example dimethylformamide or dioxane and water, resulting in a compound of formula (Ia). This type of reaction can also be performed in the presence of a suitable ligand, such as for example tricyclohexylphosphine.

2: an intermediate of formula (II) can be reacted with tert-butoxycarbonyl anhydride (Boc$_2$O) in the presence of a suitable base, such as for example triethylamine (Et$_3$N), a suitable catalyst, such as for example 4-dimethylaminopyridine (DMAP) and a suitable solvent, such as for example tetrahydrofuran, resulting in an intermediate of formula (III).

3: an intermediate of formula (III) can be reacted with an intermediate of formula (IV) in the presence of suitable catalyst, such as for example [1,1'-bis(diphenylphosphino-kP)ferrocene]dichloropalladium (PdCl$_2$dppf), a suitable base, such as potassium phosphate (K$_3$PO$_4$), and a suitable solvent or solvent mixture, such as for example dioxane and water, resulting in a compound of formula (Ia1).

4: a compound of formula (Ia1) can be deprotected to a compound of formula (Ia) with a suitable acid, such as for example HCl and a suitable solvent, such as for example acetonitrile or an alcohol, e.g. methanol.

5: a compound of formula (Ia) can be reacted with an intermediate of formula R$_3$—W, wherein W represents a suitable leaving group, such as for example iodide, bromide, chloride or tosylate, in the presence of suitable base, such as for example sodium hydride, and a suitable solvent, such as for example N,N-dimethylformamide or dimethylsulfoxide, resulting in a compound of formula (Ib).

6: a compound of formula (Ib) can be converted into a compound of formula (Id) by reaction with lithiumaluminiumhydride in the presence of a suitable solvent, such as for example tetrahydrofuran.

7: a compound of formula (Ia) can be converted into a compound of formula (Ic) by reaction with lithiumaluminiumhydride in the presence of a suitable solvent, such as for example tetrahydrofuran.

8: a compound of formula (Ic) can be reacted with an intermediate of formula R$_3$—W, wherein W represents a suitable leaving group, such as for example iodide, bromide, chloride or tosylate, in the presence of suitable base, such as for example sodium hydride, Et$_3$N or K$_2$CO$_3$, and a suitable solvent, such as for example N,N-dimethylformamide or dimethylsulfoxide, resulting in a compound of formula (Id).

9: a compound of formula (Ic) can be reacted with an intermediate of formula R—COOH, in the presence of a suitable peptide coupling agent, such as for example 2-(7-aza-1H-benzotriazole-1-yl)-1,1,3,3-tetramethyluronium hexafluorophosphate (HATU) or carbonyldiimidazole (CDI), a suitable base, such as for example, diisopropylethylamine (DIPEA), and a suitable solvent, such as for example dichloromethane or tetrahydrofuran, resulting in a compound of formula (Ie).

Or alternatively a compound of formula (Ic) can be reacted with an intermediate of formula R—CO—Cl, in the presence of a suitable base, such as for example DIPEA, and a suitable solvent, such as for example dichloromethane.

10: a compound of formula (If) can be prepared by reacting a compound of formula (Ia) and an intermediate of formula (V) in the presence of a suitable base, such as for example sodium hydride, and a suitable solvent, such as for example dimethylformamide.

11: a compound of formula (Ia) can be converted into a compound of formula (Ig) in the presence of a suitable oxidizing agent, such as for example meta-chloroperbenzoic acid (mCpBA), and a suitable solvent, such as for example dichloromethane.

2) Scheme 1a: Second Way Final Compounds (Ia)

Compounds of formula (Ia), wherein all variables are as defined before, can also be prepared according to the following reaction scheme 1a.

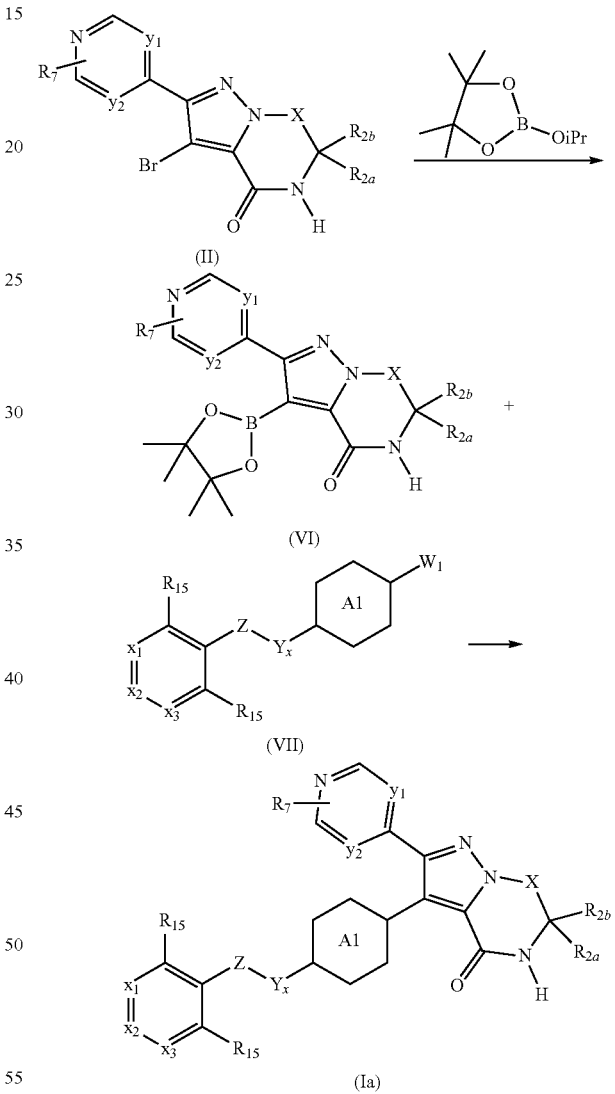

In Scheme 1a, an intermediate of formula (II) can be reacted with 2-isopropoxy-4,4,5,5-tetramethyl-1,3,2-dioxoborolane in the presence of isopropylmagnesium chloride and a suitable solvent, such as for example tetrahydrofuran (THF), resulting in an intermediate of formula (VI).

An intermediate of formula (VI) can be reacted with an intermediate of formula (VII), wherein W1 represents a suitable halogen, such as for example bromide, in the presence of suitable pre-catalyst, such as for example (SP-4-4)-[2'-(amino-κN)[1,1'-biphenyl]-2-yl-κC]chloro[dicyclohexyl[2',4',6'-tris(1-methylethyl)[1,1'-biphenyl]-2-yl]phosphine]-palladium (X-Phos aminobiphenyl palladium chloride precatalyst; X-Phos Pd G2), a suitable base, such as potassium phosphate (K$_3$PO$_4$), and a suitable solvent or solvent mixture, such as for example THF and water, resulting in a compound of formula (Ia).

3) Scheme 1b: Intermediate (II)

Intermediates of formula (II), wherein all variables are as defined before, can be prepared according to the following reaction scheme 1b.

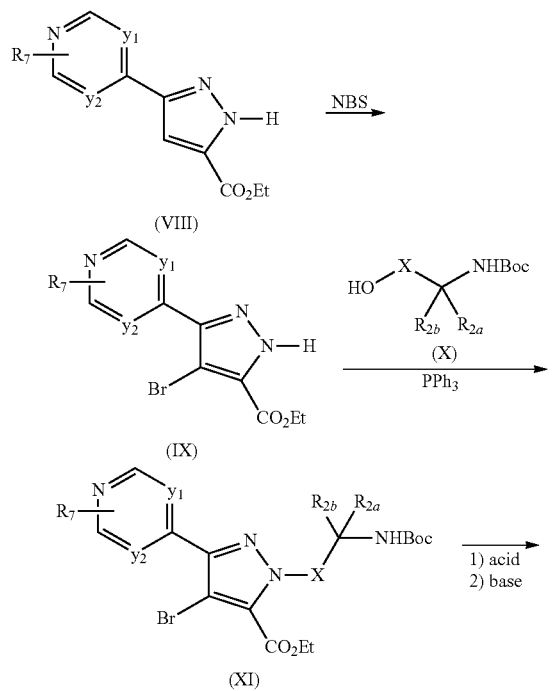

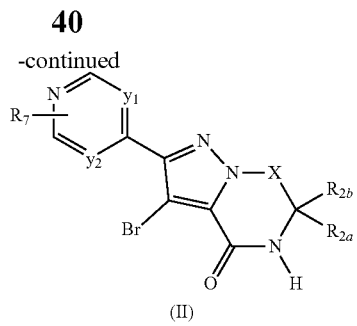

In Scheme 1b, an intermediate of formula (VIII) can be reacted with N-Bromosuccinimide (NBS) in the presence of a suitable solvent, such as for example DCM or DMF, resulting in an intermediate of formula (IX) which can be reacted in a next step with an intermediate of formula (X) in the presence of Triphenylphosphine (PPh$_3$), a suitable Mitsunobu reagent, such as for example Di-tert-butylazodicarboxylate (DBAD) and a suitable solvent, such as for example THF, resulting in an intermediate of formula (XI).

An intermediate of formula (XI) can then be deprotected in the presence of a suitable acid, such as for example Trifluoroacetic acid (TFA) and a suitable solvent, such as for example DCM. The resulting intermediate can be converted into an intermediate of formula (II) in the presence of a suitable base, such as for example cesium carbonate (Cs$_2$CO$_3$) or sodium bicarbonate (NaHCO$_3$) and a suitable solvent, such as for example MeOH or water.

4) Scheme 1c: Intermediate (IVa)

Intermediates of formula (IV), wherein ring A1 is limited to A1' (no bicycles formed with Y$_x$—Z), hereby named an intermediate of formula (IVa), can be prepared according to the following reaction scheme 1c. Ring A1' is optionally substituted phenyl or an optionally substituted 6-membered aromatic heterocyclyl containing one or two nitrogen atoms (thus does not form a bicyclic ring with Y$_x$—Z), and all other variables are as defined before.

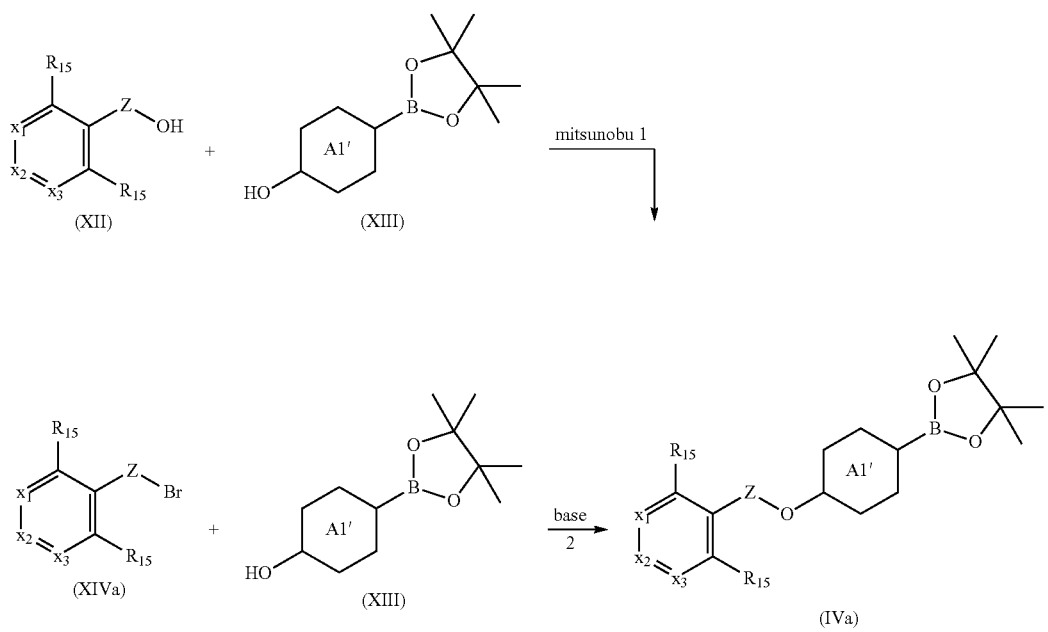

-continued

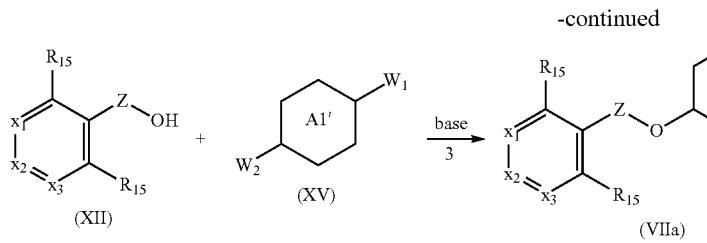

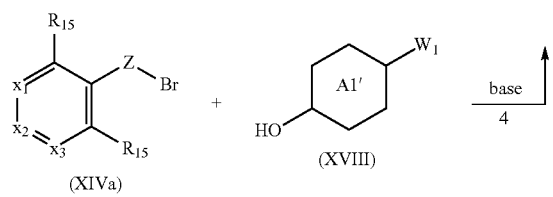

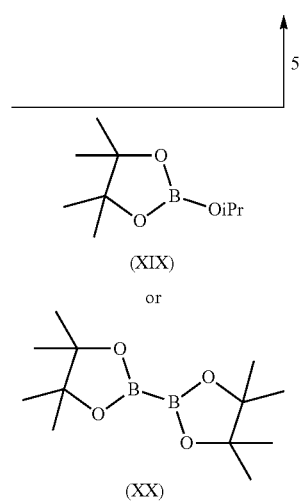

1: an intermediate of formula (XII) can be reacted with an intermediate of formula (XIII) in the presence of triphenylphosphine (PPh₃), a suitable Mitsunobu reagent, such as for example DBAD and a suitable solvent, such as for example Dichloromethane (DCM) or THF, resulting in an intermediate of formula (IV).

2: an intermediate of formula (XIVa) can be reacted with an intermediate of formula (XIII) in the presence of a suitable base, such as for example K₂CO₃ or Ag₂CO₃, and a suitable solvent, such as for example CH₃CN or DMF, resulting in an intermediate of formula (IVa)

3: an intermediate of formula (XII) can be reacted with an intermediate of formula (XV), wherein W1 represents a suitable halogen, such as for example iodide or bromide, and wherein W2 represents a suitable leaving group, such as for example chloride, fluoride or bromide, in the presence of a suitable base, such as for example Sodium hydride (NaH) and a suitable solvent, such as for example DMF, resulting in an intermediate of formula (VIIa).

4: an intermediate of formula (XIVa) can be reacted with an intermediate of formula (XVIII), wherein W1 represents a suitable halogen, such as for example iodide or bromide, in the presence of a suitable base, such as for example K₂CO₃ or Ag₂CO₃, and a suitable solvent, such as for example CH₃CN or DMF, resulting in an intermediate of formula (VIIa).

5: an intermediate of formula (VIIa) can be reacted with intermediates of formula (XIX) or (XX) in the presence of a suitable base, such as for example nBuLi or Potassium acetate (AcOK), and a suitable solvent, such as for example THF or dioxane resulting in an intermediate of formula (IVa).

5) Scheme 1d: Intermediates of Formula (IV) (Bicycles)
Intermediates of formula (IV) wherein $Y_x$—Z forms a bicycle with ring A1 as shown in intermediates of formula (IVb), (IVc) and (IVd), can be prepared according to the following reaction scheme 1d-1. In scheme 1d-1, all variables are as defined before:

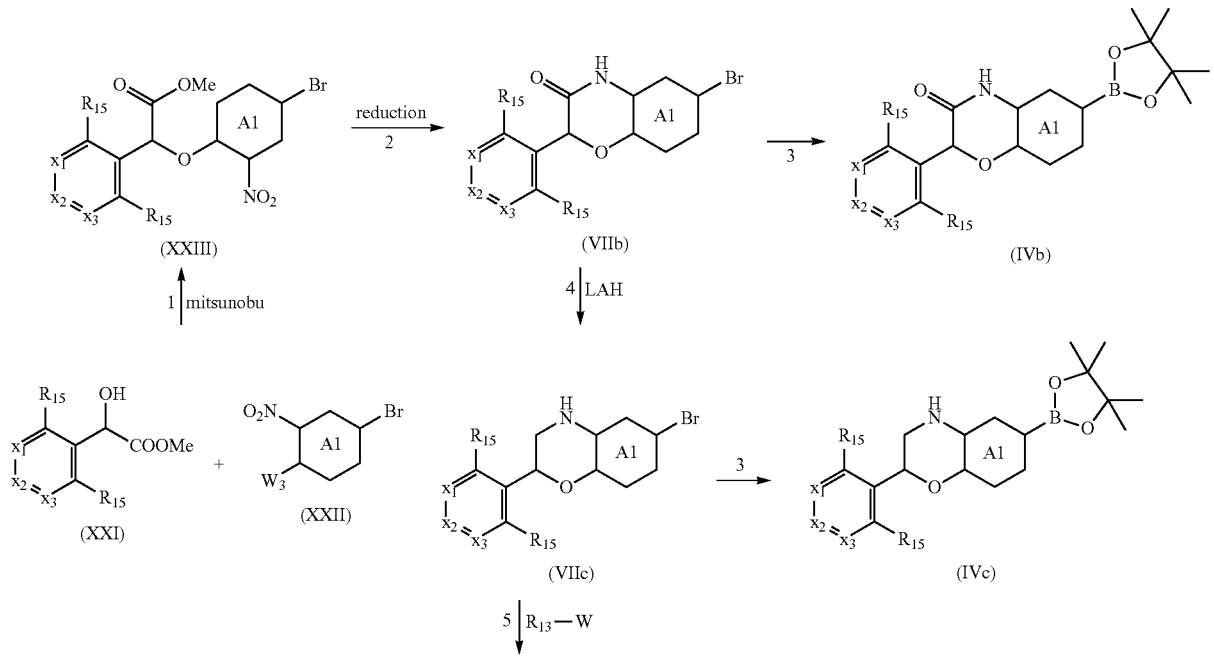

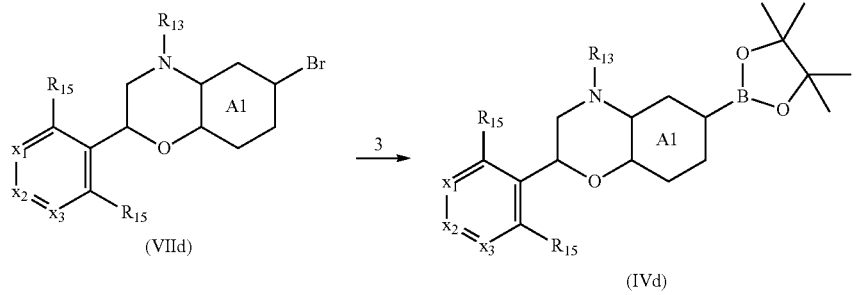

1: an intermediate of formula (XXI) can be reacted with an intermediate of formula (XXII), wherein $W_3$ represents an hydroxyl, in the presence of $PPh_3$, a suitable Mitsunobu reagent, such as for example DBAD and a suitable solvent, such as for example THF resulting in an intermediate of formula (XXIII).

An intermediate of formula (XXI) can also be reacted with an intermediate of formula (XXII), wherein $W_3$ represents a bromide, in the presence of a suitable base, such as for example NaH and a suitable solvent, such as for example THF resulting in an intermediate of formula (XXIII).

2: An intermediate of formula (XXIII) can be converted into an intermediate of formula (VIIb) by reaction with Fe in the presence of a suitable solvent, such as for example acetic acid (AcOH).

3: An intermediate of formula (VIIb), (VIIc) or (VIId) can be reacted with Bis(pinacolato)diboron in the presence of a suitable base, such as for example potassium acetate (AcOK), a suitable catalyst, such as for example $PdCl_2$ (dppf) and a suitable solvent, such as for example 1,2-dimethoxyethane (DME) resulting in an intermediate of formula (IVb), (IVc) or (IVd) respectively.

4: an intermediate of formula (VIIb) can be reduced in an intermediate of formula (VIIc) by reaction with LAH in the presence of a suitable solvent, such as for example THF.

5: an intermediate of formula (VIIc) can be reacted with an intermediate of formula $R_{13}$—W, wherein W represents a suitable leaving group, such as for example iodide, in the presence of a suitable base, such as for example $K_2CO_3$ and a suitable solvent, such as for example DMF, resulting in an intermediate of formula (VIId).

Intermediates of formula (IV) wherein $Y_x$—Z forms a bicycle with ring A1 as shown in intermediate (IVf), can be prepared according to the following reaction scheme 1d-2. In scheme 1d-2, all variables are as defined before:

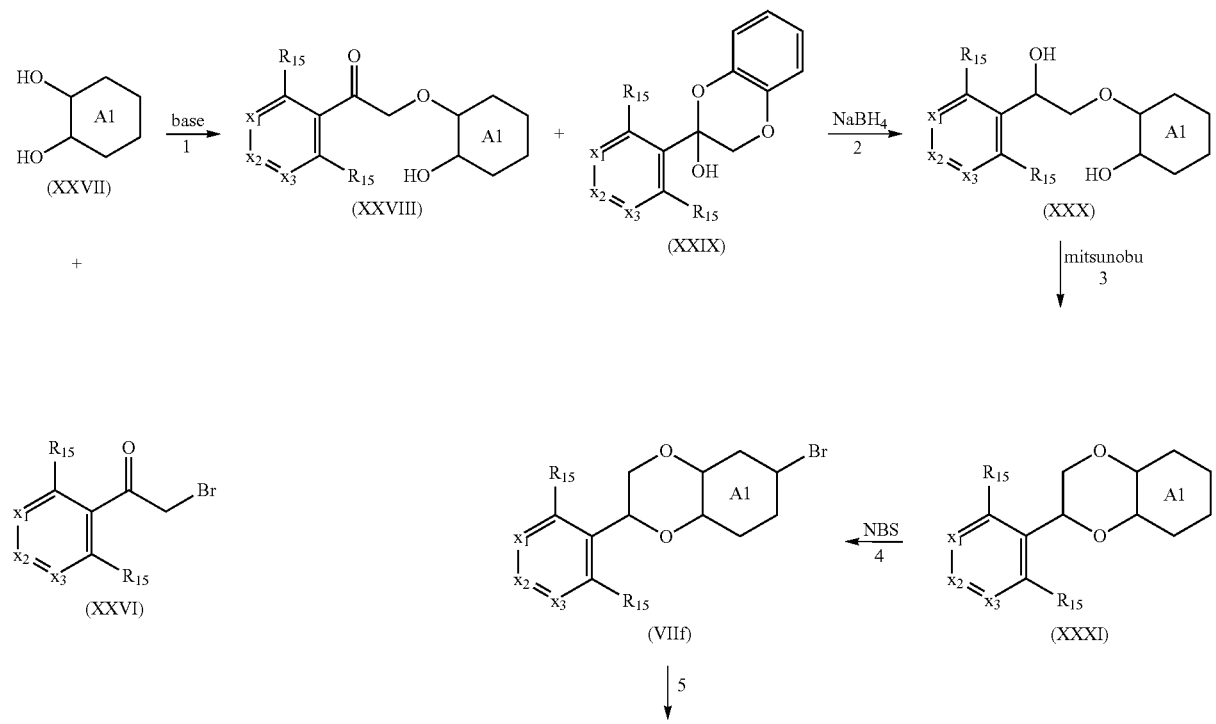

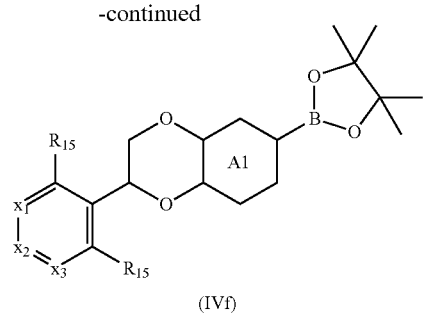

(IVf)

1: an intermediate of formula (XXVI) can be reacted with an intermediate of formula (XXVII) in the presence of a suitable base, such as for example Et$_3$N, and a suitable solvent, such as for example 2-propanol (iPrOH), resulting in a mixture of intermediate of formula (XXVIII) and intermediate of formula (XXIX).

example PdCl$_2$(dppf) and a suitable solvent, such as for example DME resulting in an intermediate of formula (IVf).

Intermediates of formula (IV) wherein Y$_x$—Z forms a bicycle with ring A1, as shown in an intermediate of formula (IVg), can be prepared according to the following reaction scheme 1d-3. In scheme 1d-3, all variables are as defined before:

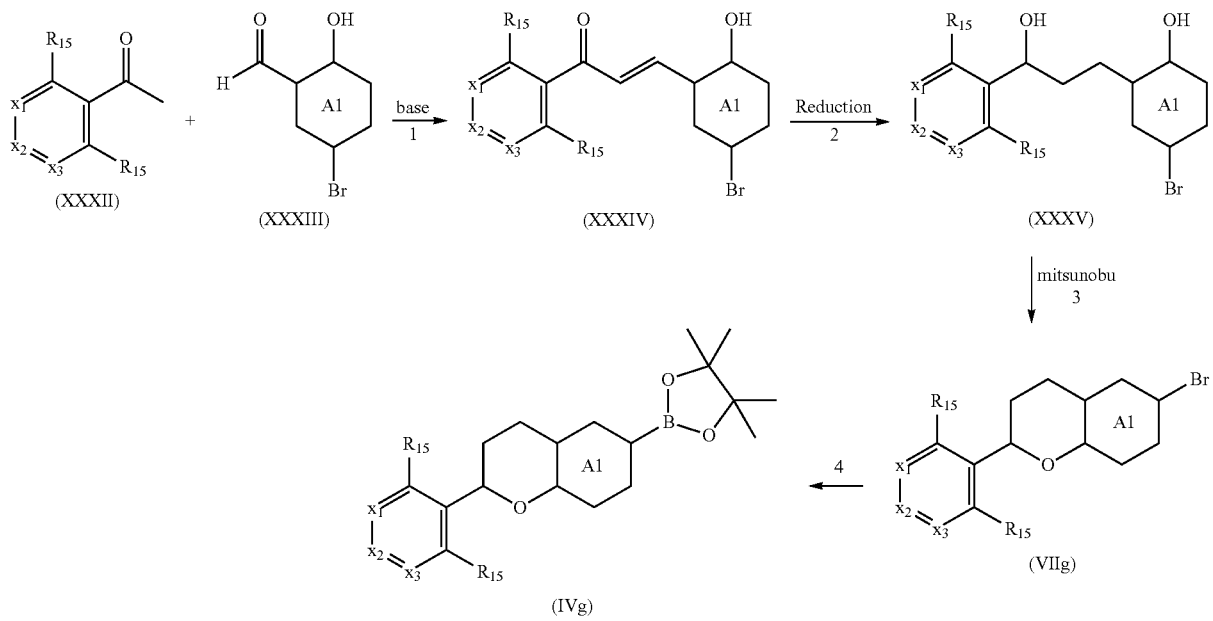

2: a mixture of intermediate of formula (XXVIII) and an intermediate of formula (XXIX) can be converted into an intermediate of formula (XXX) by reaction with NaBH$_4$ in the presence of a suitable solvent or solvent mixture, such as for example THF and MeOH.

3: an intermediate of formula (XXX) can be converted into an intermediate of formula (XXXI) by reaction with PPh$_3$, a suitable Mitsunobu reagent, such as for example DBAD and a suitable solvent, such as for example DCM.

4: an intermediate of formula (XXXI) can be reacted with NBS in the presence of a suitable solvent, such as for example AcOH, resulting in an intermediate of formula (VIIf).

5: An intermediate of formula (VIIf) can be reacted with Bis(pinacolato)diboron in the presence of a suitable base, such as for example AcOK, a suitable catalyst, such as for 1: an intermediate of formula (XXXII) can be reacted with an intermediate of formula (XXXIII) in the presence of a suitable base, such as for example KOH, and a suitable solvent, such as for example EtOH, resulting in an intermediate of formula (XXXIV).

2: an intermediate of formula (XXXIV) can be converted into an intermediate of formula (XXXV) by reaction with NaBH$_4$ in the presence of Indium Chloride and a suitable solvent, such as for example acetonitrile.

3: an intermediate of formula (XXXV) can be converted into an intermediate of formula (VIIg) by reaction with PPh$_3$, a suitable Mitsunobu reagent, such as for example DBAD and a suitable solvent, such as for example DCM.

4: An intermediate of formula (VIIg) can be reacted with Bis(pinacolato)diboron in the presence of a suitable base, such as for example AcOK, a suitable catalyst, such as for example PdCl$_2$(dppf) and a suitable solvent, such as for example DME resulting in an intermediate of formula (IVg).

6) Scheme 1e: Intermediates of Formula (IVh) (Y is Carbonyl)

By preparing derivatives of intermediates of formula (IV) wherein the general Y definition is carbonyl and wherein Z is CHR$_6$, hereby named an intermediate of formula (IVh), more compounds of formula (I) can be prepared by using analogous reaction protocols as described above or below and/or reaction protocols known by the skilled person.

Such an intermediate of formula (IVh) can be prepared according to the following reaction scheme 1e, wherein ring A1' is optionally substituted phenyl or an optionally substituted 6-membered aromatic heterocyclyl containing one or two nitrogen atoms, and wherein all other variables are as defined before:

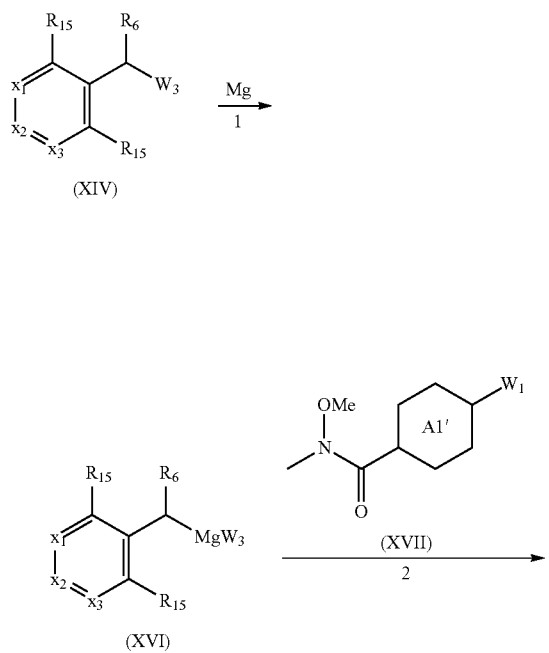

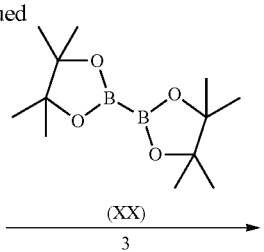

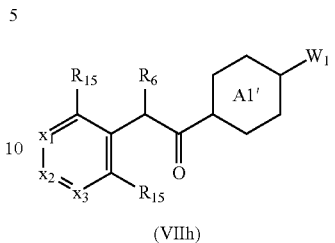

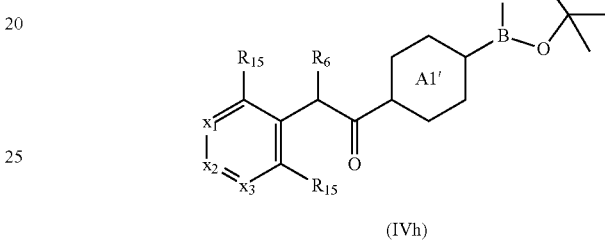

1: an intermediate of formula (XIV) can be converted into an intermediate of formula (XVI) by reaction with magnesium and a suitable solvent, such as for example THF or diethyl ether (Et$_2$O). This type of reaction can also be performed in the presence of a suitable reagent, such as for example 1,2-dibromoethane.

2: an intermediate of formula (XVI) can be reacted with an intermediate of formula (XVII) in the presence of a suitable solvent, such as for example methyltetrahydrofuran (Methyl-THF) or THF, resulting in an intermediate of formula (VIIh)

3: an intermediate of formula (VIIh) can be reacted with an intermediate of formula (XX) in the presence of a suitable base, such as for example AcOK, and a suitable solvent, such as for example dioxane resulting in an intermediate of formula (IVh).

7) Scheme 2: Alternative for a Compound of Formula (Ic)

Compounds of formula (Ic) and (Ic1), wherein all variables are as defined before, can also be prepared according to the following reaction scheme 2.

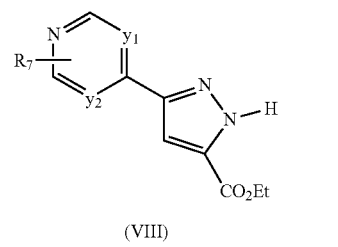

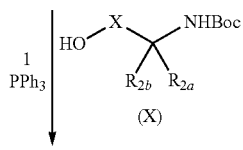

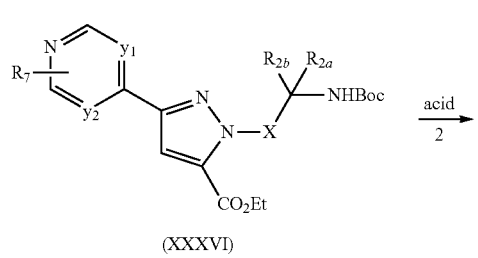 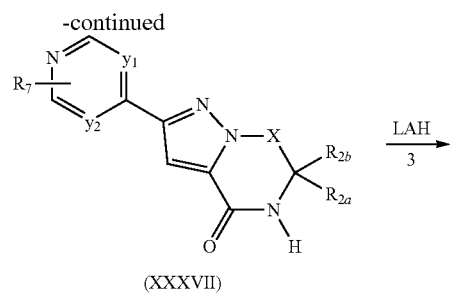

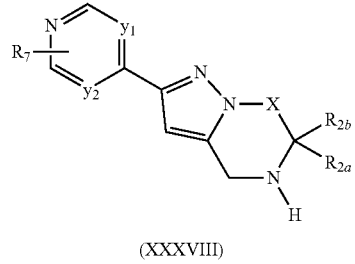

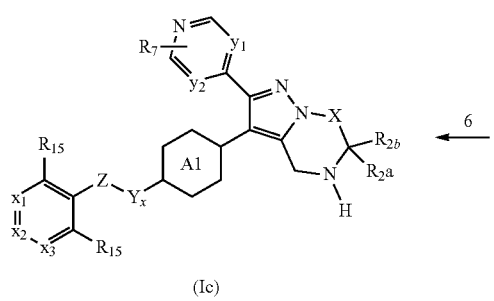 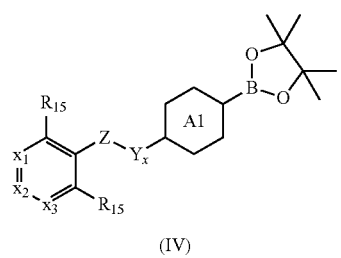 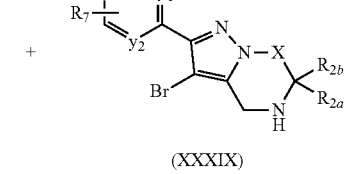

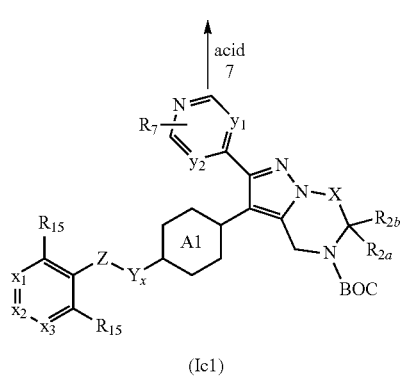 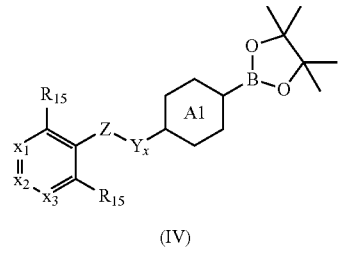 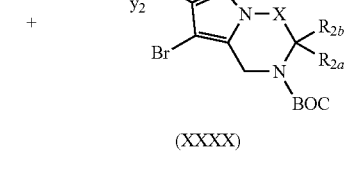

1: an intermediate of formula (VIII) can be reacted with an intermediate of formula (X), in the presence of PPh$_3$, a suitable Mitsunobu reagent, such as for example DBAD and a suitable solvent, such as for example THF resulting in an intermediate of formula (XXXVI).

2: an intermediate of formula (XXXVI) or (II) can be converted into an intermediate of formula (XXXVII) in the presence of a suitable acid, such as for example TFA, and a suitable solvent, such as for example DCM.

3: an intermediate of formula (XXXVII) can be converted into an intermediate of formula (XXXVIII) by reaction with lithium aluminium hydride in the presence of a suitable solvent, such as for example THF.

4: an intermediate of formula (XXXVIII) can be reacted with NBS in the presence of a suitable solvent or solvent mixture, such as for example AcOH or AcOH and DCM, resulting in an intermediate of formula (XXXIX).

5: an intermediate of formula (XXXIX) can be reacted with Boc$_2$O in the presence of a suitable base, such as for example Et$_3$N, and a suitable solvent, such as for example DCM, resulting in an intermediate of formula (XXXX).

6: an intermediate of formula (IV) can be reacted with an intermediate of formula (XXXVIII) or (XXXIX) in the presence of suitable catalyst, such as for example [1,1'-bis(diphenylphosphino-kP)ferrocene]dichloropalladium (PdCl$_2$dppf), a suitable base, such as for example potassium phosphate (K$_3$PO$_4$) and a suitable solvent or solvent mixture, such as for example dioxane and water, resulting in a compound of formula (Ic).

7: a compound of formula (Ic1) can be converted in a compound of formula (Ic) in a presence of a suitable acid, such as for example HCl, and a suitable solvent, such as for example MeOH.

8) Scheme 3a: Third Way Final Compound

Compounds of formula (Ia) and (Ic) wherein ring A1 is limited to A1' (no bicycles) hereby named compounds of formula (Ia-a) and (Ic-a), can also be prepared by the synthesis protocol described in Scheme 3a wherein ring A1' and all other variables are as defined before,

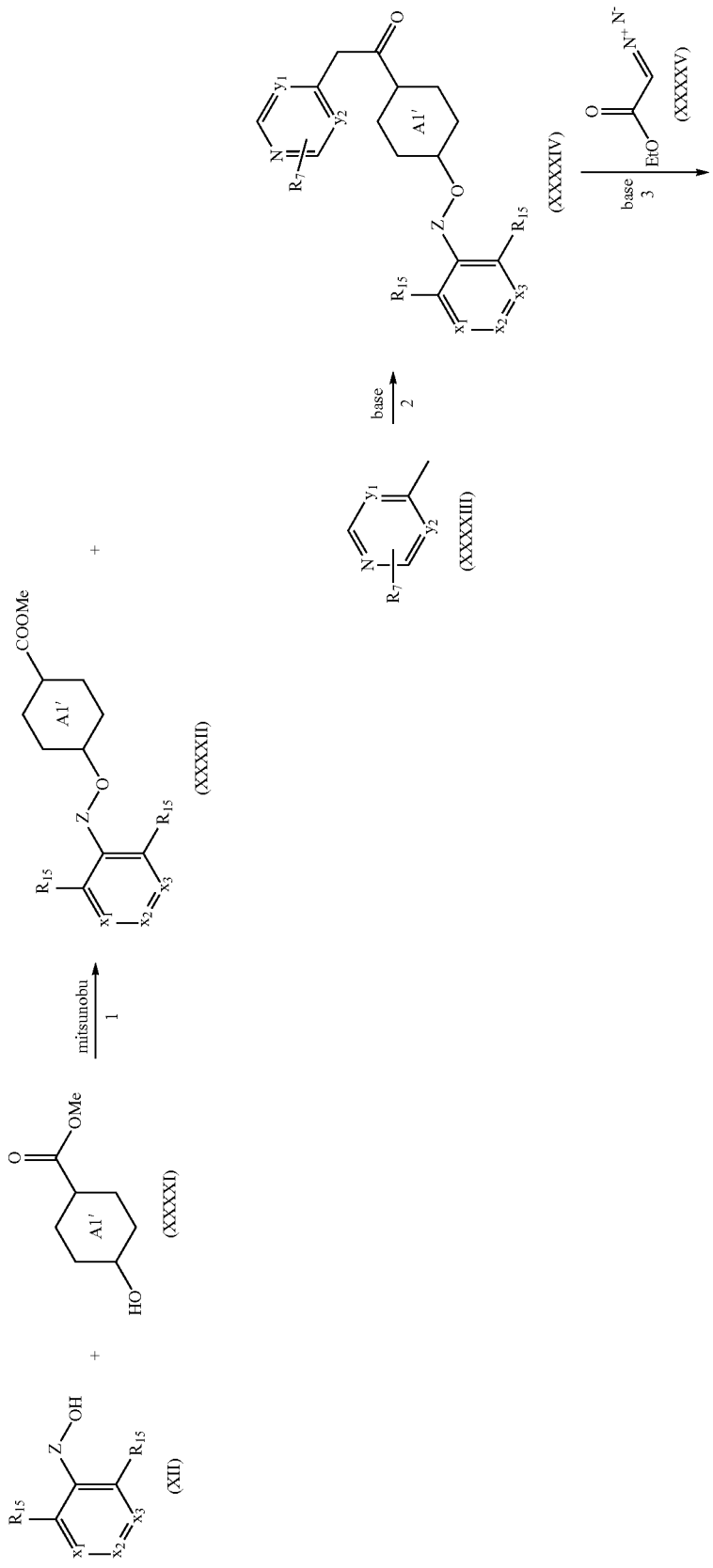

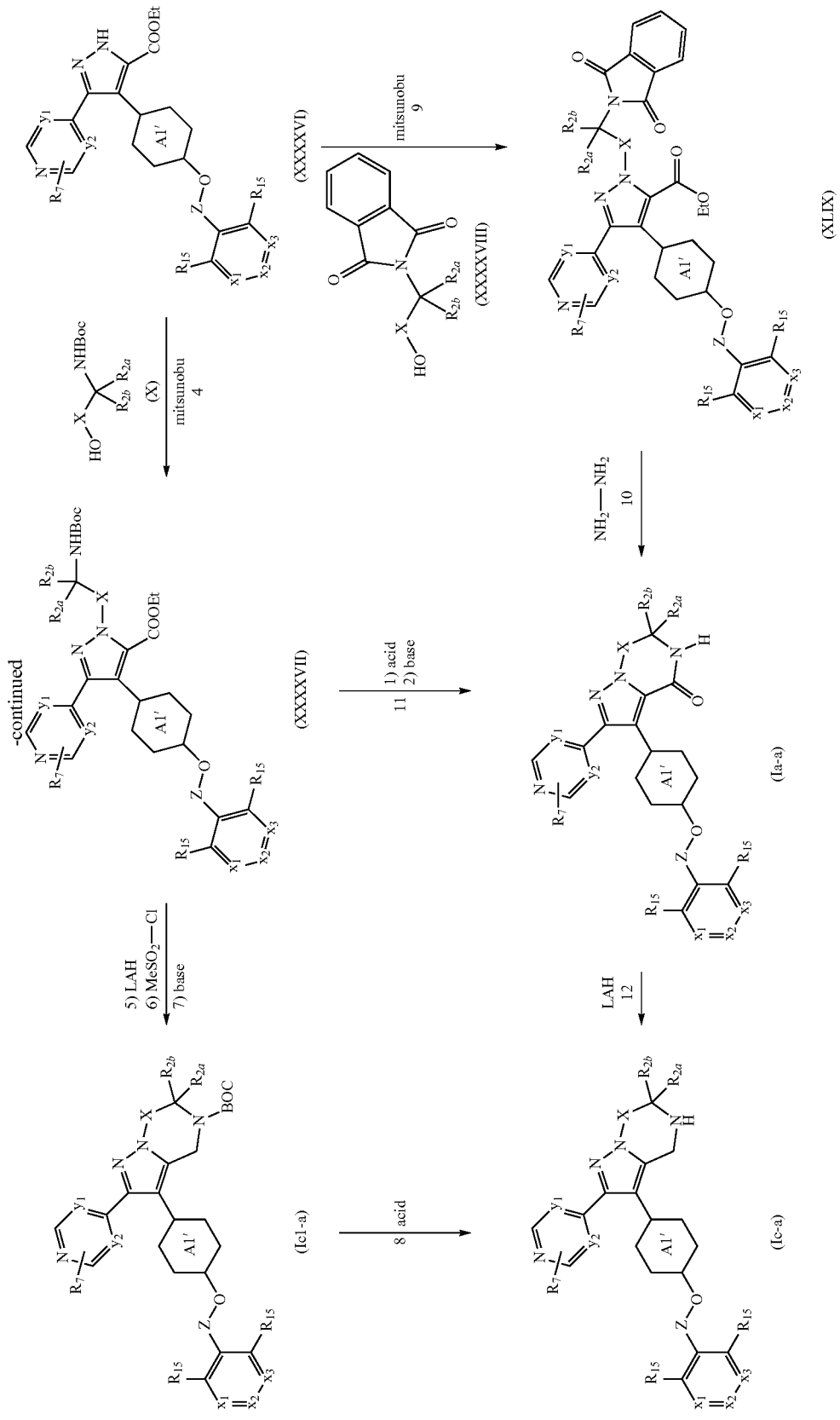

1: an intermediate of formula (XII) can be reacted with an intermediate of formula (XXXXI), in the presence of PPh₃, a suitable Mitsunobu reagent, such as for example DBAD and a suitable solvent, such as for example THF resulting in an intermediate of formula (XXXXII).

2: an intermediate of formula (XXXXII) can be reacted with an intermediate of formula (XXXXIII), in the presence of a suitable base, such as for example LiHMDS, and a suitable solvent, such as for example THF, resulting in an intermediate of formula (XXXXIV).

3: an intermediate of formula (XXXXIV) can be reacted with an intermediate of formula (XXXXV), in the presence of a suitable base, such as for example DBU, and a suitable solvent, such as for example CH₃CN, resulting in an intermediate of formula (XXXXVI).

4: an intermediate of formula (XXXXVI) can be reacted with an intermediate of formula (X), in the presence of PPh₃, a suitable Mitsunobu reagent, such as for example DBAD and a suitable solvent, such as for example THF or DCE resulting in an intermediate of formula (XXXXVII).

5-6-7: an intermediate of formula (XXXXVII) can be reacted with lithium aluminium hydride in the presence of a suitable solvent, such as for example THF. The resulting intermediate can be reacted with methanesulfonyl chloride in the presence of a suitable base, such as for example Et₃N, and a suitable solvent, such as for example DCM. The resulting intermediate can be reacted with a suitable base, such as for example NaH, and a suitable solvent, such as for example DMF, resulting in a compound of formula (Ic1-a).

8: a compound of formula (Ic1-a) can be reacted into a compound of formula (Ic-a) in the presence of a suitable acid, such as for example HCl, an d a suitable solvent, such as for example CH₃CN.

9: an intermediate of formula (XXXXVI) can be reacted with an intermediate of formula (XXXXVIII), in the presence of PPh₃, a suitable Mitsunobu reagent, such as for example DBAD and a suitable solvent, such as for example THF, resulting in an intermediate of formula (XLIX).

10: an intermediate of formula (XLIX) can be deprotected to a compound of formula (Ia-a) with hydrazine hydrate and a suitable solvent, such as for example EtOH.

11: an intermediate of formula (XXXXVII) can be deprotected with a suitable acid, such as for example HCl, and a suitable solvent, such as for example dioxane or ACN. The resulting intermediate can be converted into a compound of formula (Ia) in the presence of a suitable base, such as for example Cs₂CO₃ or K₂CO₃, and a suitable solvent, such as for example DCM or MeOH.

12: a compound of formula (Ia-a) can be converted into a compound of formula (Ic-a) by reaction with lithiumaluminiumhydride in the presence of a suitable solvent, such as for example tetrahydrofuran or DME.

9) Scheme 3b: Alternative Method Alkylated Final Compound

A compound of formula (Ib-a) wherein ring A1' is as defined before (no bicycles), and wherein all other variables are as defined before, can be prepared by the synthesis protocol described in Scheme 3b:

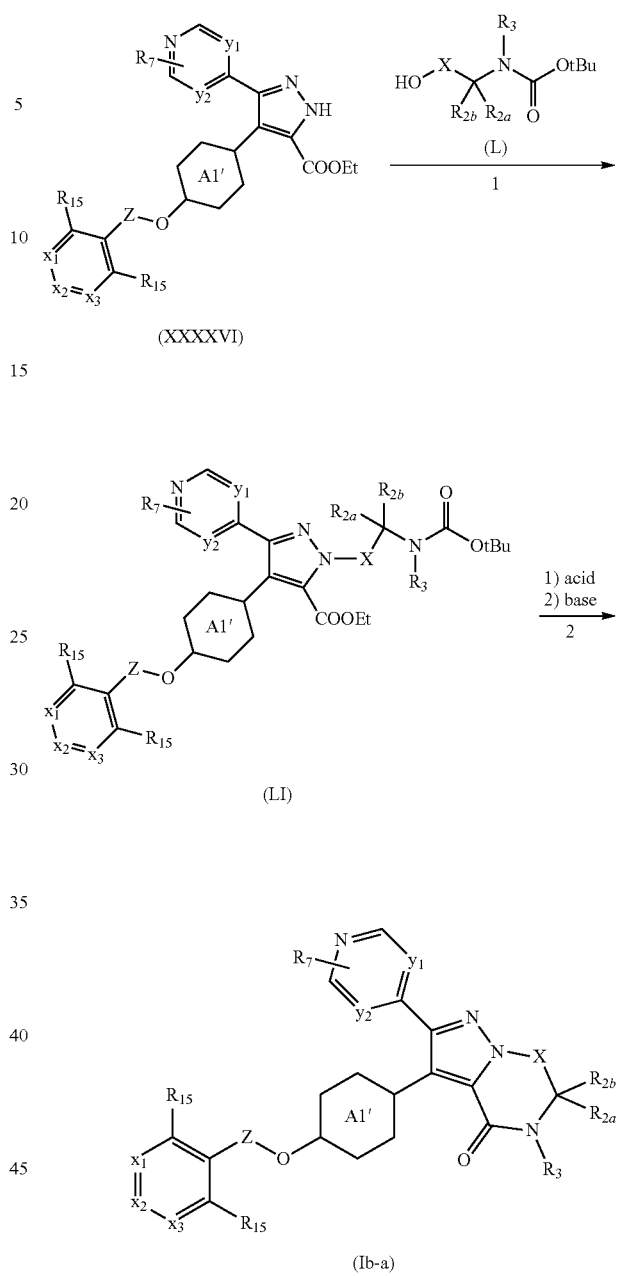

1: an intermediate of formula (XXXXVI) can be reacted with an intermediate of formula (L) (tBu is tert-butyl), in the presence of PPh₃, a suitable Mitsunobu reagent, such as for example DBAD and a suitable solvent, such as for example THF resulting in an intermediate of formula (LI).

2: an intermediate of formula (LI) can be deprotected with a suitable acid, such as for example HCl, and a suitable solvent, such as for example dioxane or ACN. The resulting intermediate can be converted into a compound of formula (Ib-a) in the presence of a suitable base, such as for example Cs₂CO₃, and a suitable solvent, such as for example DCM or MeOH.

10) Scheme 4:

Compounds of formula (Ib), wherein R₄ₐ and R₄ᵦ are taken together to form =O, and (Id), wherein R₄ₐ and R₄ᵦ are hydrogen, can also be prepared according to the following reaction scheme 4.

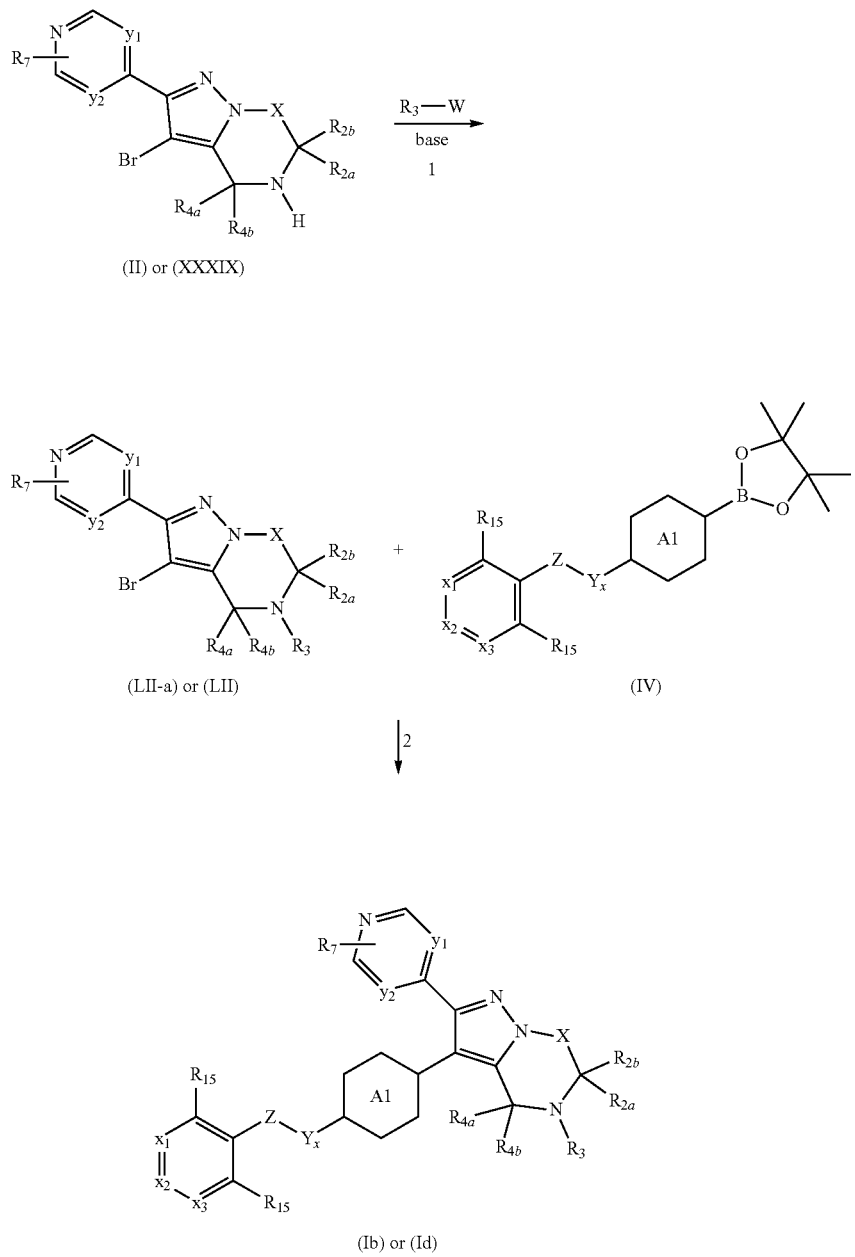

1: an intermediate of formula (II), wherein $R_{4a}$ and $R_{4b}$ are taken together to form =O, or (XXXIX), wherein $R_{4a}$ and $R_{4b}$ are hydrogen, can be reacted with an intermediate of formula $R_3$—W, wherein W represents a suitable leaving group, such as for example iodide, bromide, chloride or tosylate, in the presence of suitable base, such as for example sodium hydride, $Et_3N$ or $K_2CO_3$, and a suitable solvent, such as for example N,N-dimethylformamide or dimethylsulfoxide, resulting in an intermediate of formula (LII-a), wherein $R_{4a}$ and $R_{4b}$ are taken together to form =O or (LII), wherein $R_{4a}$ and $R_{4b}$ are hydrogen.

2: an intermediate of formula (LII-a) or (LII) can be reacted with an intermediate of formula (IV) in the presence of suitable catalyst, such as for example [1,1'-bis(diphenylphosphino-kP)ferrocene]dichloropalladium ($PdCl_2dppf$), a suitable base, such as potassium phosphate ($K_3PO_4$), and a suitable solvent or solvent mixture, such as for example dioxane and water, resulting in a compound of formula (Ib), wherein $R_{4a}$ and $R_{4b}$ are taken together to form =O or (Id), wherein $R_{4a}$ and $R_{4b}$ are hydrogen.

11) Scheme 5: Alternative Synthesis Pyrazole-ester

Intermediates of formula (LI) wherein all variables are as defined before (Et means ethyl) can also be prepared according to the following reaction scheme 5:

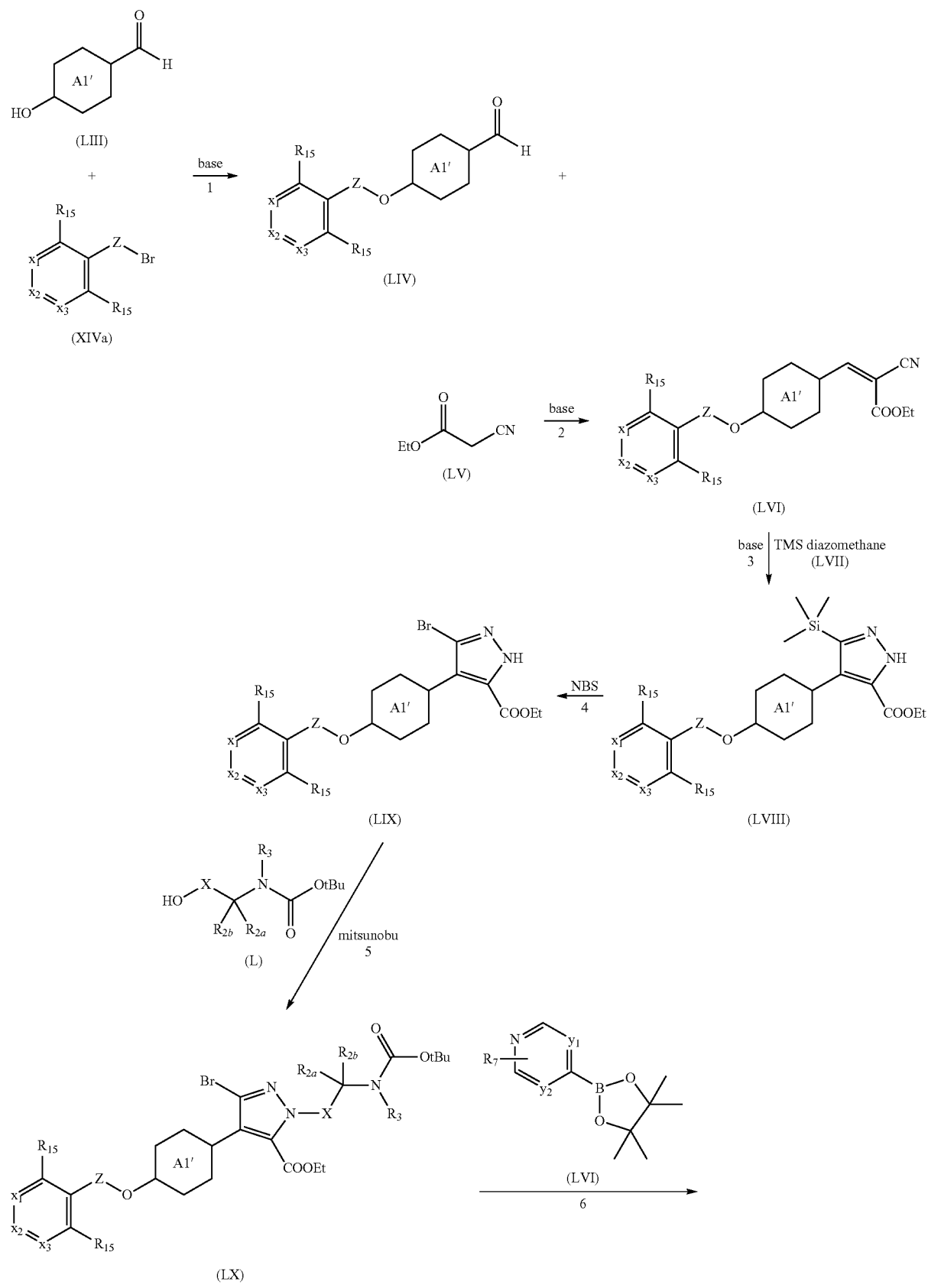

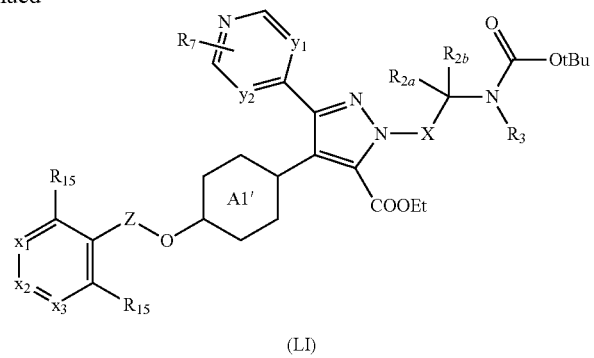

(LI)

1: an intermediate of formula (XIVa) can be reacted with an intermediate of formula (LIII) in the presence of a suitable base, such as for example K₂CO₃, and a suitable solvent, such as for example CH₃CN, resulting in an intermediate of formula (LIV).

2: an intermediate of formula ((LIV) can be reacted with an intermediate of formula (LV) in the presence of a suitable base, such as for example piperidine, and a suitable solvent, such as for example EtOH, resulting in an intermediate of formula (LVI).

3: an intermediate of formula (LVI) can be converted into an intermediate of formula (LVIII) by reaction with an intermediate of formula (LVII) (=trimethylsilyldiazomethane) in the presence of a suitable base, such as for example nBuLi and a suitable solvent, such as for example THF.

4: an intermediate of formula (LVIII)) can be reacted with NBS in the presence of a suitable solvent, such as for example ACN, resulting in an intermediate of formula (LIX).

5: an intermediate of formula (LIX) can be reacted with an intermediate of formula (L) in the presence of PPh₃, a suitable Mitsunobu reagent, such as for example DBAD and a suitable solvent, such as for example THF, resulting in an intermediate of formula (LX).

6: an intermediate of formula (LX) can be reacted with an intermediate of formula (LXI) in the presence of suitable catalyst, such as for example Palladium acetate (Pd(OAc)₂), a suitable ligand, such as for example PCy₃ a suitable base, such as potassium phosphate (K₃PO₄), and a suitable solvent or solvent mixture, such as for example dioxane and water, resulting in an intermediate of formula (LI).

12) Scheme 5a: Alternative II Synthesis Pyrazole-ester

Intermediates of formula (LI) can also be prepared according to the following reaction scheme 5a:

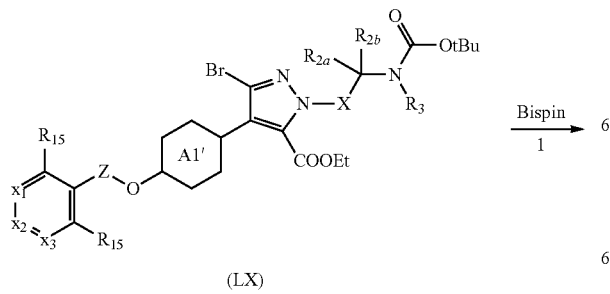

(LX)

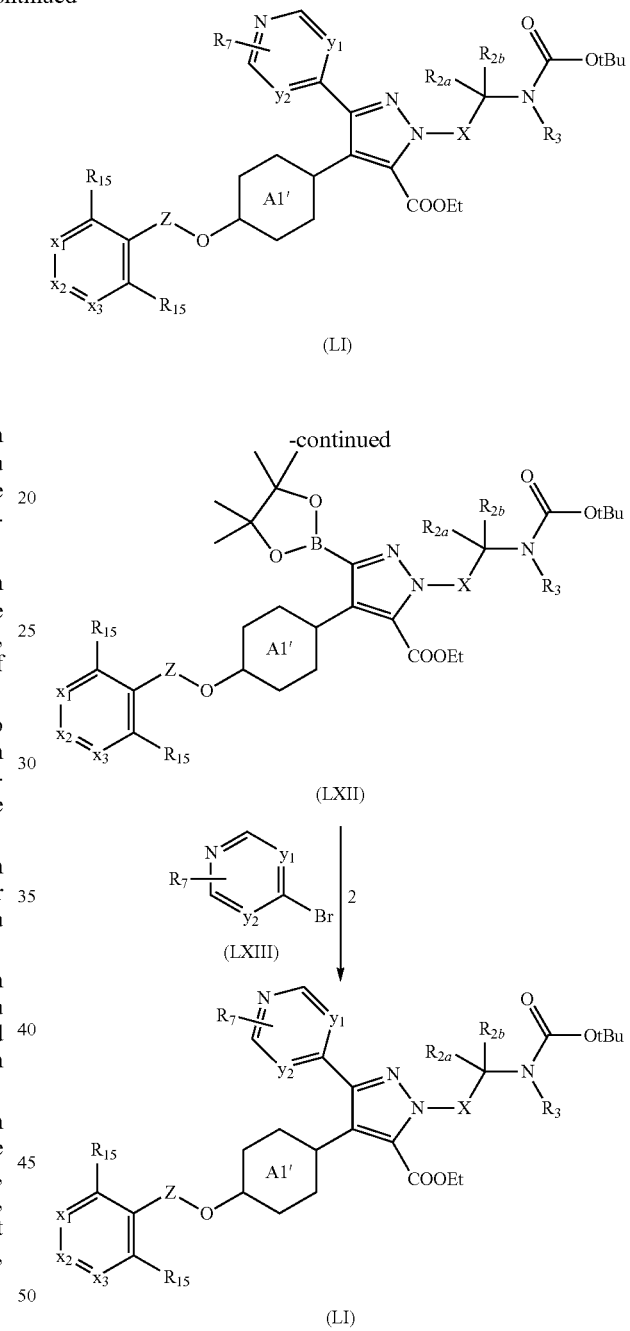

1: an intermediate of formula (LX) can be reacted with bis(pinacolato)diboron (Bispin) in the presence of a suitable catalyst, such as for example PdCl₂(dppf), a suitable base, such as for example AcOK and a suitable solvent, such as for example DME, resulting in an intermediate of formula (LXII).

2: an intermediate of formula (LXII) can be reacted with an intermediate of formula (LXIII) in the presence of suitable catalyst, such as for example Palladium acetate (Pd(OAc)₂), a suitable ligand, such as for example tricyclohexylphosphine (PCy₃) a suitable base, such as potassium phosphate (K₃PO₄), and a suitable solvent or solvent mixture, such as for example dioxane and water, resulting in an intermediate of formula (LI).

13) Scheme 5b: Alternative III Synthesis Pyrazoleester

Intermediates of formula (LI) can also be prepared according to the following reaction scheme 5b.

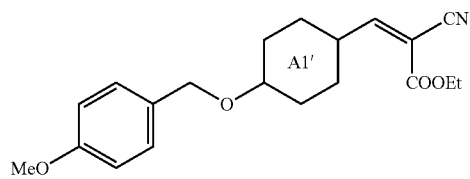
(LVIa)
TMS diazomethane (LVII) | base  1 ↓
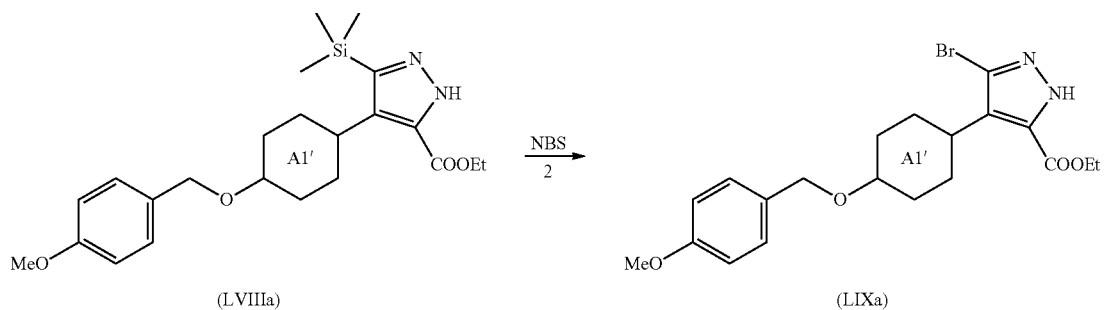
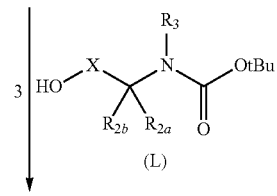
(L)
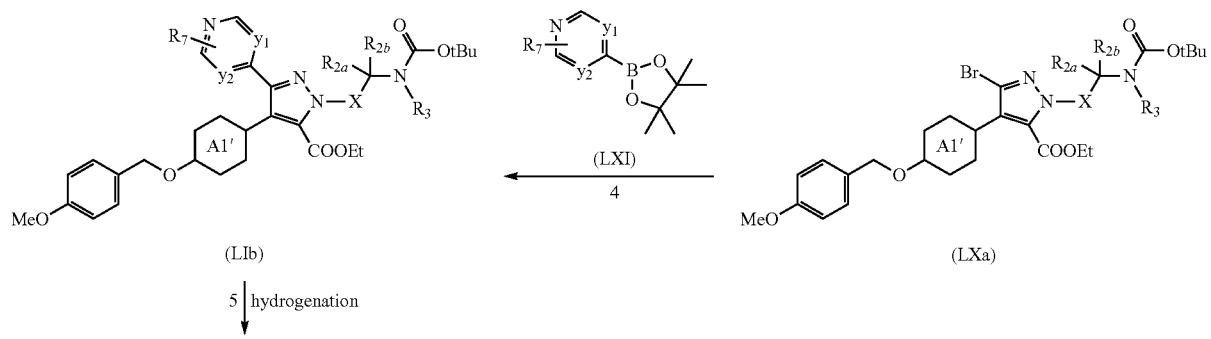
5 | hydrogenation ↓
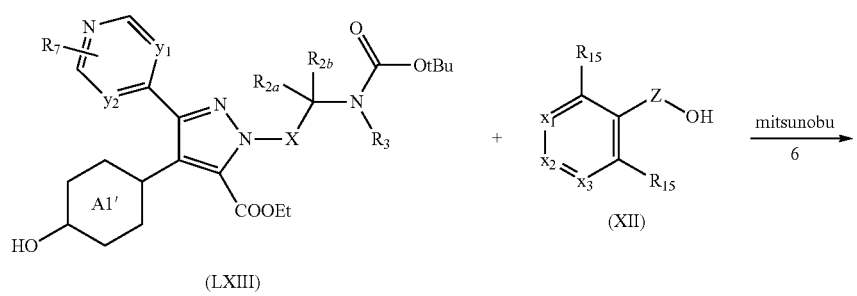

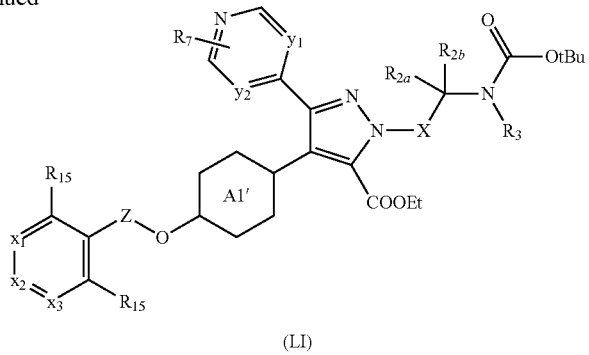

(LI)

1: an intermediate of formula (LVIa) can be converted into an intermediate of formula (LVIIIa) by reaction with an intermediate of formula (LVII) in the presence of a suitable base, such as for example nBuLi and a suitable solvent, such as for example THF 2: an intermediate of formula (LVIIIa) can be reacted with NBS in the presence of a suitable solvent, such as for example ACN, resulting in an intermediate of formula (LIXa).

3: an intermediate of formula (LIXa) can be reacted with an intermediate of formula (L) in the presence of PPh₃, a suitable Mitsunobu reagent, such as for example DBAD and a suitable solvent, such as for example THF, resulting in an intermediate of formula (LXa).

4: an intermediate of formula (LXa) can be reacted with an intermediate of formula (LXI) in the presence of suitable catalyst, such as for example Palladium acetate (Pd(OAc)₂), a suitable ligand, such as for example PCy₃ a suitable base, such as potassium phosphate (K₃PO₄), and a suitable solvent or solvent mixture, such as for example dioxane and water, resulting in an intermediate of formula (LIb).

5: an intermediate of formula (LIb) can be converted into a compound of formula (LXIII) by hydrogenation in the presence of a suitable catalyst, such as for example Pd/C 10%, and a suitable solvent, such as for example EtOH.

6: an intermediate of formula (LXIII) can be reacted with an intermediate of formula (XII) in the presence of PPh₃, a suitable Mitsunobu reagent, such as for example DBAD and a suitable solvent, such as for example THF, resulting in an intermediate of formula (LI).

14) Scheme 5c: Alternative IV Synthesis Pyrazole-Ester

With the synthesis method in Scheme 5c, intermediates of formula (LI-x) can be prepared, which also includes the possibility that ring A1 forms a bicyclic ring with Z—Y$_x$. All variables in Scheme 5c are defined as mentioned before.

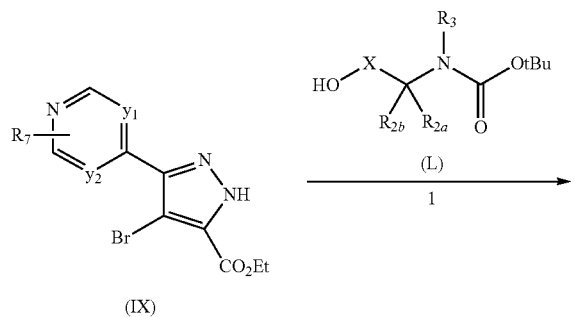

(IX)

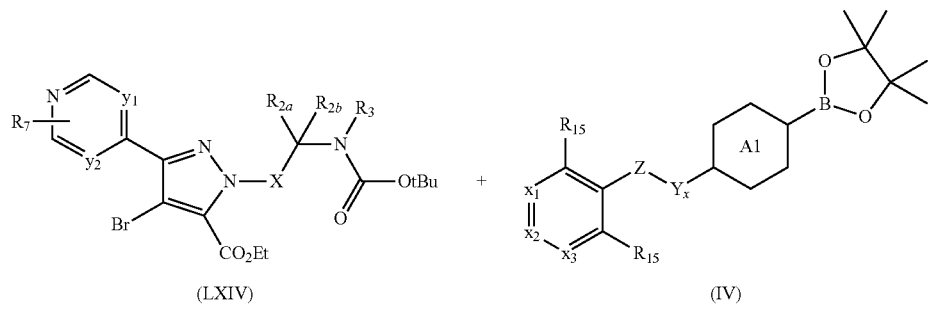

(LXIV)    (IV)

↓ 2

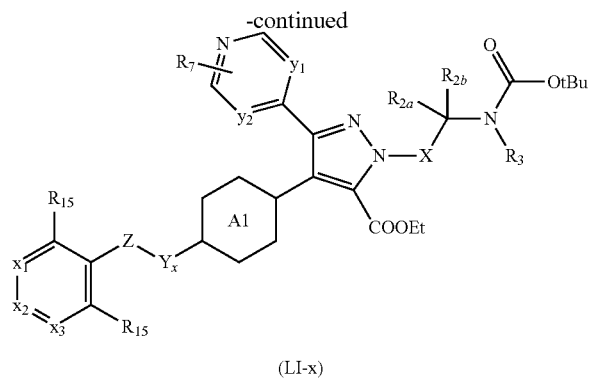

(LI-x)

1: an intermediate of formula (IX) can be reacted with an intermediate of formula (L), in the presence of PPh$_3$, a suitable Mitsunobu reagent, such as for example DBAD and a suitable solvent, such as for example THF resulting in an intermediate of formula (LXIV).

2: an intermediate of formula (IV) can be reacted with an intermediate of formula (LXIV) in the presence of a suitable catalyst, such as for example PdCl$_2$dppf, a suitable base, such as for example potassium phosphate (K$_3$PO$_4$) and a suitable solvent or solvent mixture, such as for example dioxane and water, resulting in an intermediate of formula (LI-x).

15) Scheme 6: Fourth Way Final Compound

Compounds of formula (Ib-a) and (Ib-b) wherein all variables are defined as before, can be prepared according to the following reaction scheme 6.

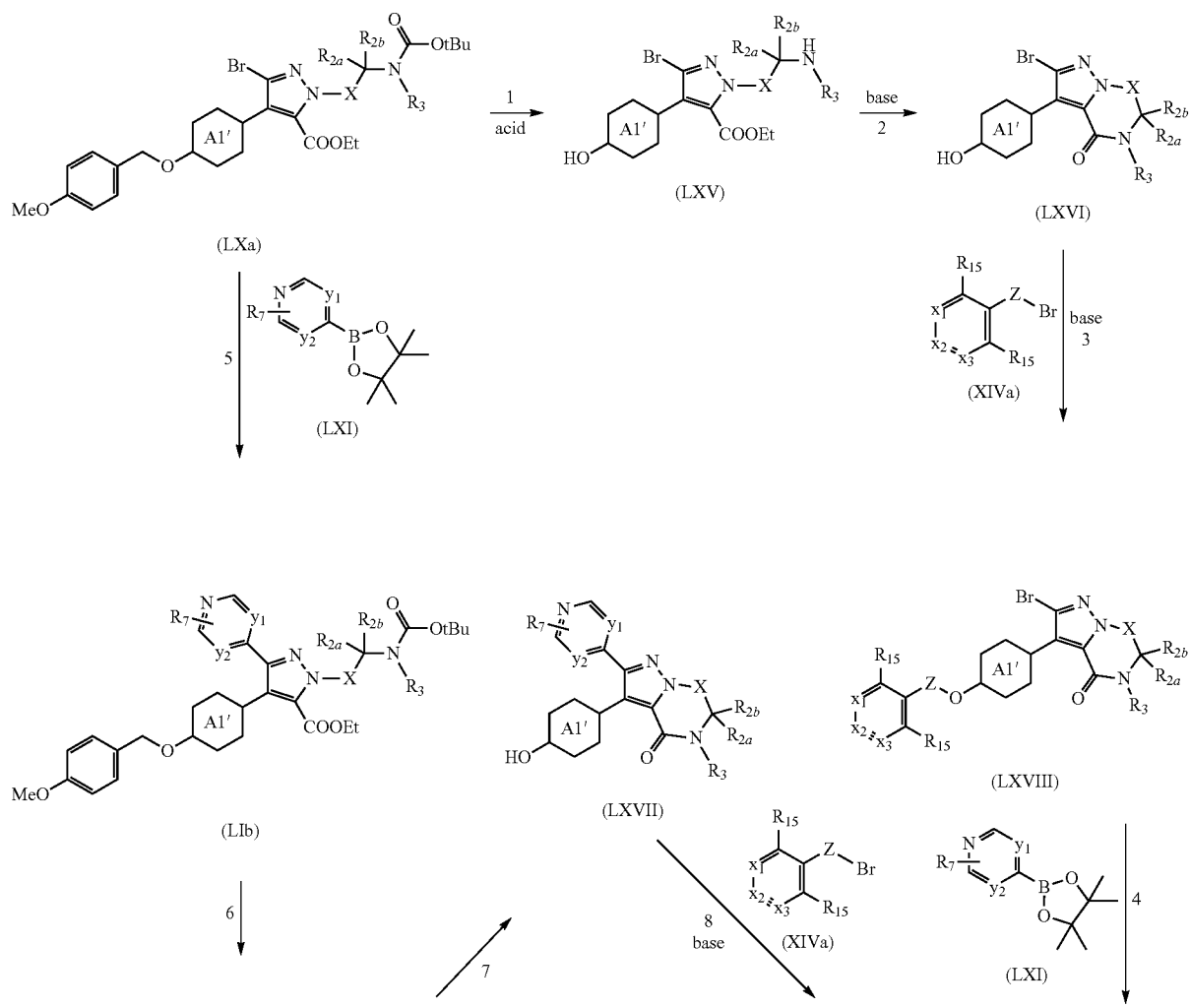

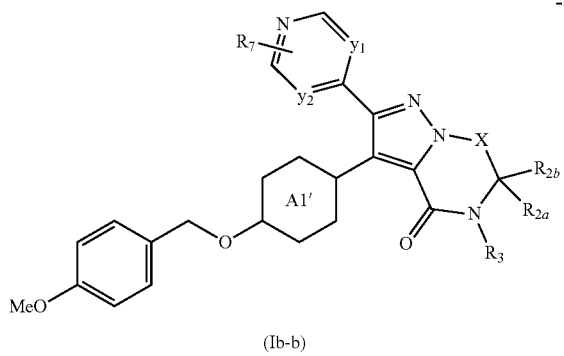

(Ib-b)

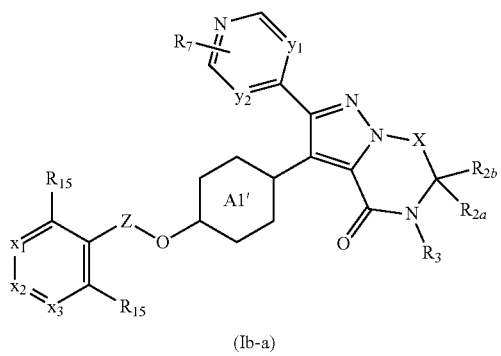

(Ib-a)

1: an intermediate of formula (LXa) can be converted into an intermediate of formula (LXV) by reaction with a suitable acid, such as for example HCl, and a suitable solvent, such as for example dioxane.

2: an intermediate of formula (LXV) can be converted into an intermediate of formula (LXVI) by reaction with a suitable base, such as for example $Cs_2CO_3$, and a suitable solvent, such as for example MeOH.

3: an intermediate of formula (LXVI) can be reacted with an intermediate of formula (XIVa) in the presence of a suitable base, such as for example $K_2CO_3$, and a suitable solvent, such as for example DMF, resulting in an intermediate of formula (LXVIII). This type of reaction can also be performed in the presence of a suitable reagent, such as for example NaI.

4: an intermediate of formula (LXVIII) can be reacted with an intermediate of formula (LXI) in the presence of suitable catalyst, such as for example Palladium acetate $(Pd(OAc)_2)$, a suitable ligand, such as for example $PCy_3$ a suitable base, such as potassium phosphate $(K_3PO_4)$, and a suitable solvent or solvent mixture, such as for example dioxane and water, resulting in a compound of formula (Ib-a).

5: an intermediate of formula (LXa) can be reacted with an intermediate of formula (LXI) in the presence of suitable catalyst, such as for example Palladium acetate $(Pd(OAc)_2)$, a suitable ligand, such as for example $PCy_3$ a suitable base, such as potassium phosphate $(K_3PO_4)$, and a suitable solvent or solvent mixture, such as for example dioxane and water, resulting in an intermediate of formula (LIb).

6: an intermediate of formula (LIb) can be deprotected with a suitable acid, such as for example HCl, and a suitable solvent, such as for example dioxane or ACN. The resulting intermediate can be converted into a compound of formula (Ib-b) in the presence of a suitable base, such as for example $Cs_2CO_3$ or $K_2CO_3$, and a suitable solvent, such as for example DCM or MeOH.

7: a compound of formula (Ib-b) can be converted into an intermediate of formula (LXVII) by reaction with a suitable acid, such as for example TFA, and a suitable solvent, such as for example toluene.

8: an intermediate of formula (LXVII) can be reacted with an intermediate of formula (XIVa) in the presence of a suitable base, such as for example $K_2CO_3$, and a suitable solvent, such as for example DMF, resulting in a compound of formula (Ib-a).

16) Scheme 7: Fifth Way Final Compound

A compound of formula (Ia) wherein ring A1 is limited to A1' (no bicycles), wherein $R_{2b}$ is hydrogen and X is $CH_2$, hereby named a compound of formula (Ia2) can also be prepared according to the following reaction scheme 7.

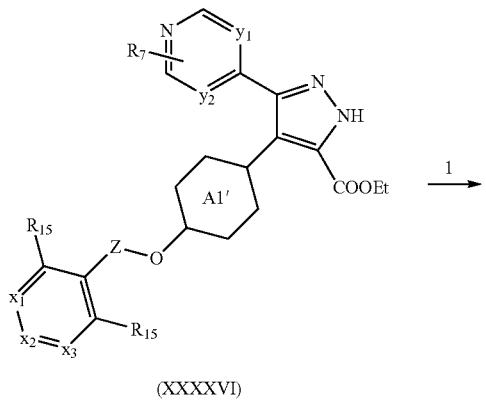

(XXXXVI)

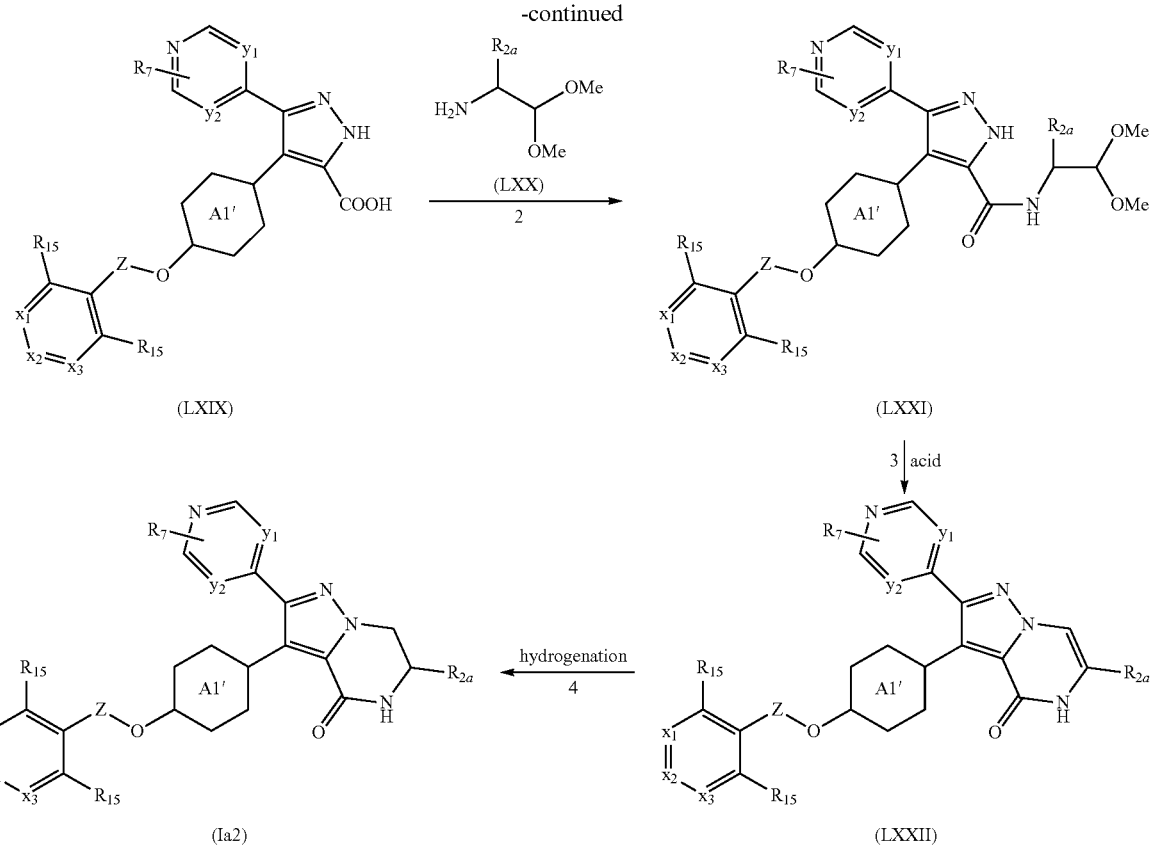

1: an intermediate of formula (XXXXVI) can be converted into an intermediate of formula (LXIX) by reaction with a suitable base, such as for example KOH, and a suitable solvent or solvent mixture, such as for example EtOH and water.

2: an intermediate of formula (LXIX) can be reacted with an intermediate of formula (LXX) in the presence of a suitable peptide coupling agent, such as for example HATU, a suitable base, such as for example, DIPEA, and a suitable solvent, such as for example DMF, resulting in an intermediate of formula (LXXI).

3: an intermediate of formula (LXXI) can be converted into an intermediate of formula (LXXII) by reaction with a suitable acid, such as for example methanesulfonic acid, HCl or TFA, and a suitable solvent, such as for example acetone or DCM.

4: an intermediate of formula (LXXII) can be converted into a compound of formula (Ia2) by hydrogenation in the presence of a suitable catalyst, such as for example Pd/C 10% or PtO$_2$, and a suitable solvent, such as for example EtOH or MeOH.

17) Scheme 8: Another Alternative

Compounds of formula (Ia3), wherein all variables are defined as described before, can also be prepared according to the following reaction scheme 8.

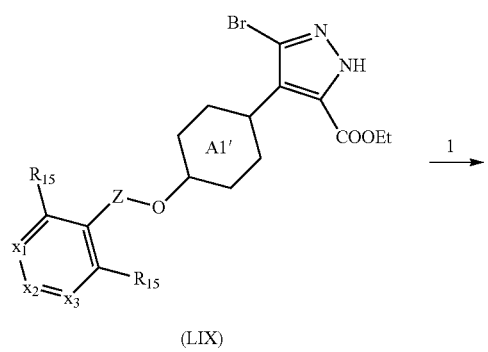

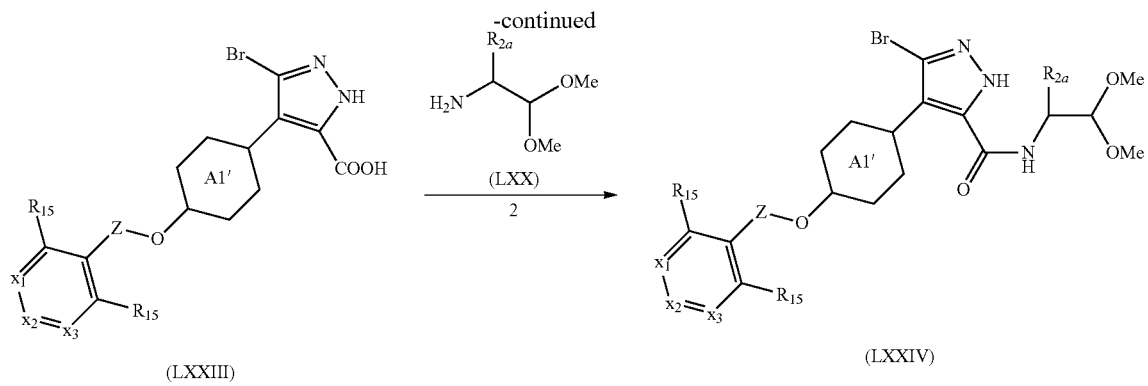

(LXXIII)

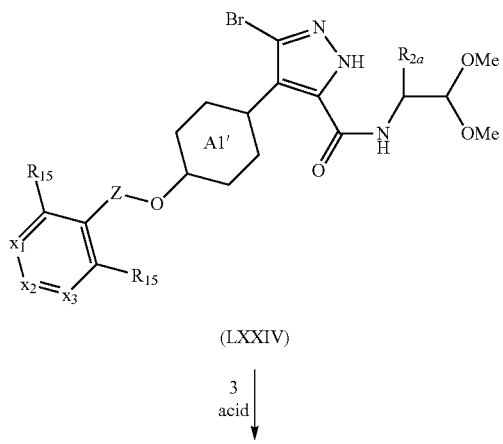

(LXXIV)

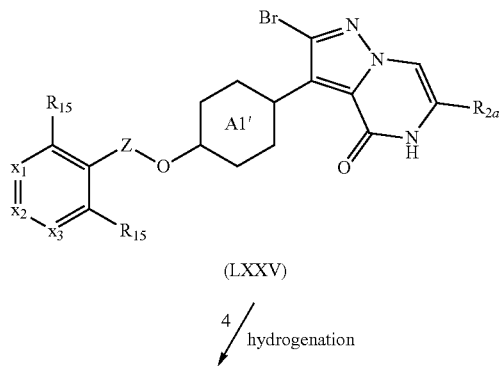

(LXXV)

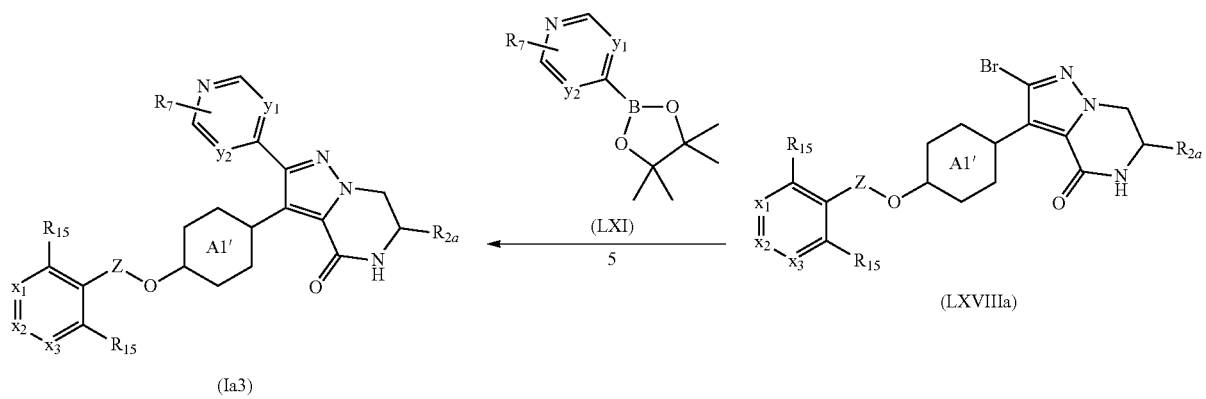

(Ia3)          (LXVIIIa)

1: an intermediate of formula (LIX) can be converted into an intermediate of formula (LXXIII) by reaction with a suitable base, such as for example KOH, and a suitable solvent or solvent mixture, such as for example EtOH and water.

2: an intermediate of formula (LXXIII) can be reacted with an intermediate of formula (LXX) in the presence of a suitable peptide coupling agent, such as for example HATU, a suitable base, such as for example, DIPEA, and a suitable solvent, such as for example DMF, resulting in an intermediate of formula (LXXIV).

3: an intermediate of formula (LXXIV) can be converted into an intermediate of formula (LXXV) by reaction with a suitable acid, such as for example methanesulfonic acid, HCl or TFA, and a suitable solvent, such as for example acetone or DCM.

4: an intermediate of formula (LXXV) can be converted into a compound of formula (LXVIIIa) by hydrogenation in the presence of a suitable catalyst, such as for example Pd/C 10% or PtO$_2$, and a suitable solvent, such as for example EtOH or MeOH.

5: an intermediate of formula (LXVIII) can be reacted with an intermediate of formula (LXI) in the presence of suitable catalyst, such as for example Palladium acetate (Pd(OAc)$_2$), a suitable ligand, such as for example PCy$_3$ a suitable base, such as potassium phosphate (K$_3$PO$_4$), and a suitable solvent or solvent mixture, such as for example dioxane and water, resulting in a compound of formula (Ia3).

18) Scheme 9: Synthesis of Final Compounds when Ring A is Partially Saturated:

A compound of formula (I), wherein Y is C=O and Ring A is partially saturated, and wherein all other variables are as defined before, hereby named a compound of formula (I-j) or (I-k), can be prepared according to the following reaction scheme 9:

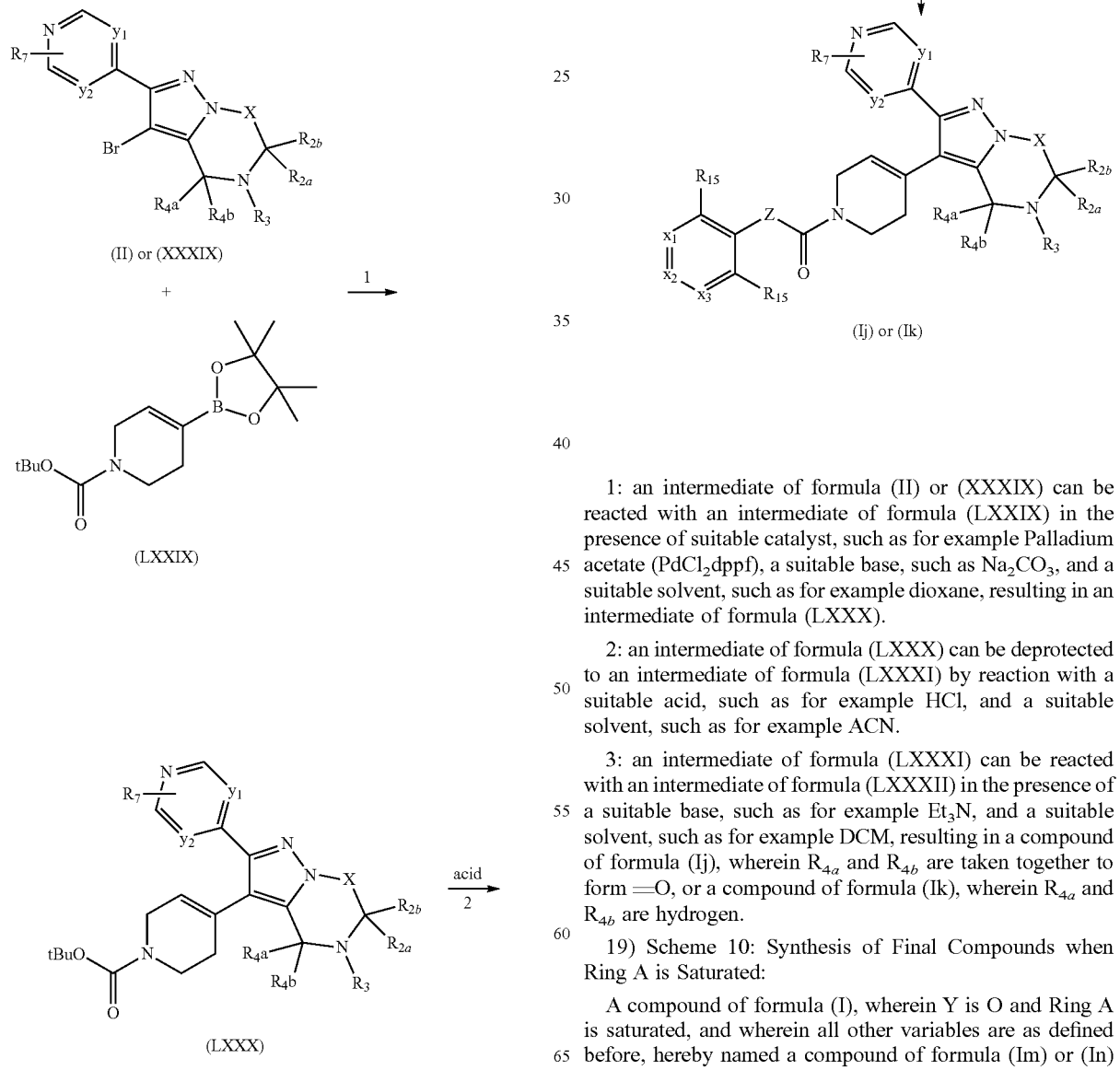

1: an intermediate of formula (II) or (XXXIX) can be reacted with an intermediate of formula (LXXIX) in the presence of suitable catalyst, such as for example Palladium acetate (PdCl$_2$dppf), a suitable base, such as Na$_2$CO$_3$, and a suitable solvent, such as for example dioxane, resulting in an intermediate of formula (LXXX).

2: an intermediate of formula (LXXX) can be deprotected to an intermediate of formula (LXXXI) by reaction with a suitable acid, such as for example HCl, and a suitable solvent, such as for example ACN.

3: an intermediate of formula (LXXXI) can be reacted with an intermediate of formula (LXXXII) in the presence of a suitable base, such as for example Et$_3$N, and a suitable solvent, such as for example DCM, resulting in a compound of formula (Ij), wherein R$_{4a}$ and R$_{4b}$ are taken together to form =O, or a compound of formula (Ik), wherein R$_{4a}$ and R$_{4b}$ are hydrogen.

19) Scheme 10: Synthesis of Final Compounds when Ring A is Saturated:

A compound of formula (I), wherein Y is O and Ring A is saturated, and wherein all other variables are as defined before, hereby named a compound of formula (Im) or (In) can be prepared according to the following reaction scheme 10:

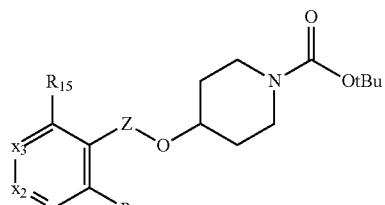
(LXXXIII)
1↓
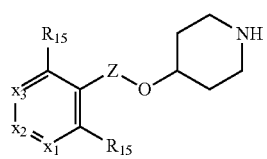
(LXXXIV)
+
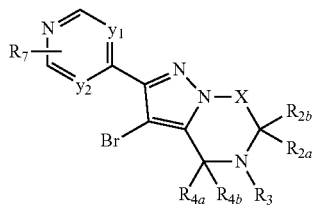
(II) or (XXXIX)
2→
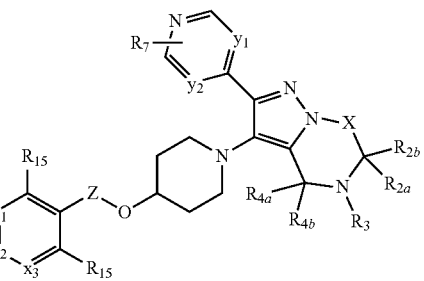
(Im) or (In)
3↓
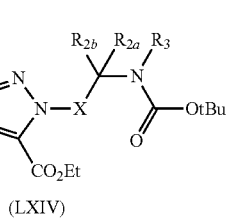
(LXIV)
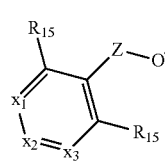
(LXXXV)
1) acid
2) peptidic coupling
4 →
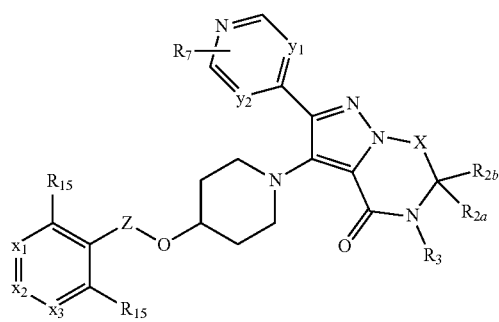
(Im)
1: an intermediate of formula (LXXXIII) can be deprotected to an intermediate of formula (LXXXIV) by reaction with a suitable acid, such as for example HCl, in the presence of a suitable solvent, such as for example ACN.

2: an intermediate of formula (II) or (XXXIX) can be reacted with an intermediate of formula (LXXXIV) in the presence of suitable catalyst, such as for example (SP-4-4)-[2-[2-(amino-κN)ethyl]phenyl-κC]chloro[dicyclohexyl[3,6-dimethoxy-2',4',6'-tris(1-methylethyl)[1,1'-biphenyl]-2-yl]phosphine-κP]-palladium (BrettPhos Palladacycle), a suitable base, such as NaOtBu, and a suitable solvent, such as for example toluene, resulting in a compound of formula (Im), wherein $R_{4a}$ and $R_{4b}$ are taken together to form =O, and a compound of formula (In), wherein $R_{4a}$ and $R_{4b}$ are hydrogen.

3: an intermediate of formula (LXXXIV) can be reacted with an intermediate of formula (LXIV) in the presence of a suitable base, such as for example $Cs_2CO_3$, suitable catalysts, such as for example CuI and 2-acetylcyclohexanone, and a suitable solvent, such as for example DMF, resulting in an intermediate of formula (LXXXV).

4: an intermediate of formula (LXXXV) can be deprotected by reaction with a suitable acid, such as for example HCl, in the presence of a suitable solvent, such as for example ACN. The resulting intermediate can be converted into a compound of formula (Im), wherein $R_{4a}$ and $R_{4b}$ are taken together to form =O, by reaction with suitable peptide coupling reagents, such as for example 1-hydroxy-benzotriazole and 1-(3-dimethylaminopropyl)-3-ethylcarbodiimide HCl, a suitable base, such as for example, $Et_3N$, and a suitable solvent, such as for example DCM.

Scheme 11: A Compound of Formula (Ih), Wherein all Variables are as Defined Before, can be Prepared According to the Following Reaction Scheme 11:

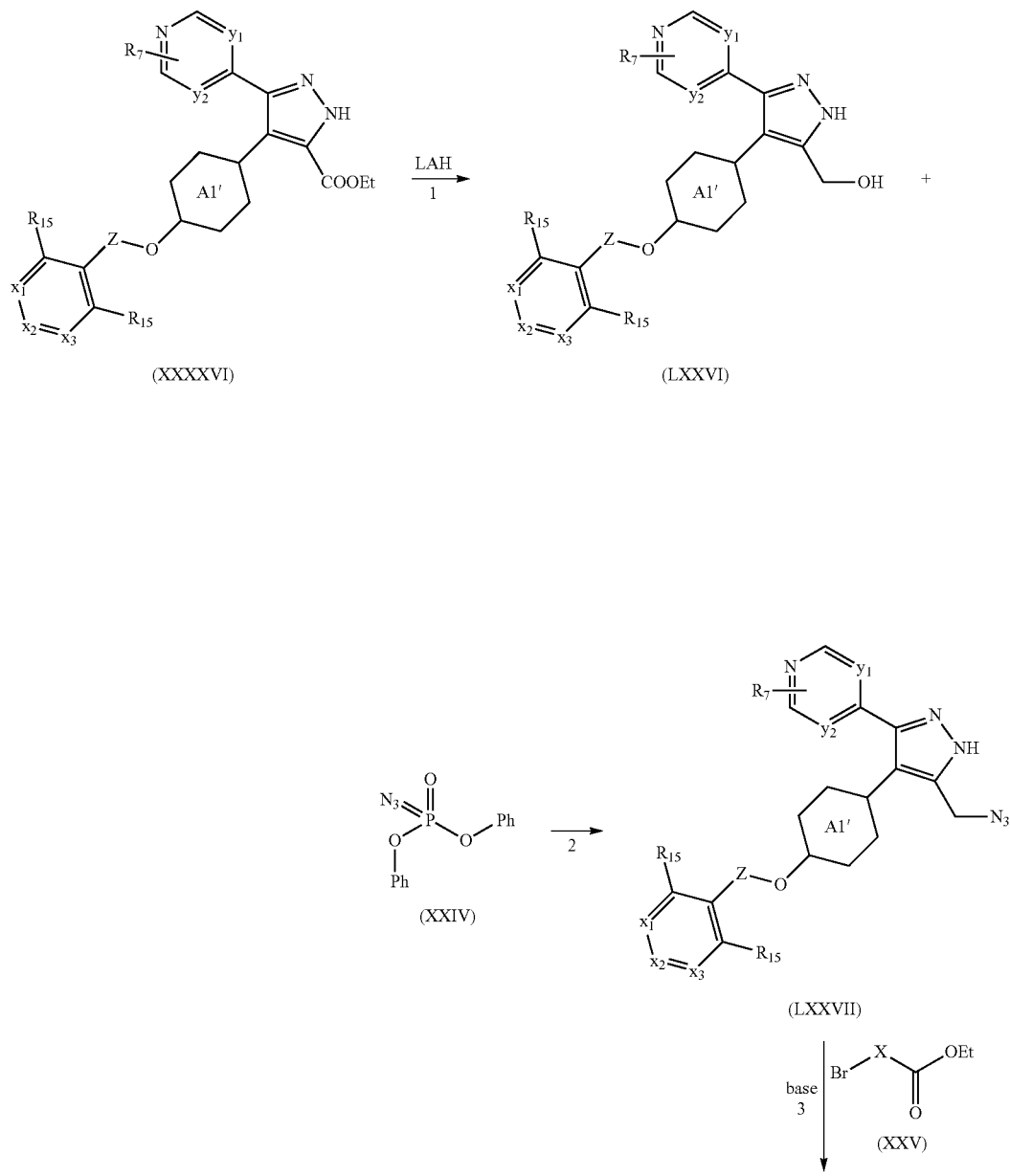

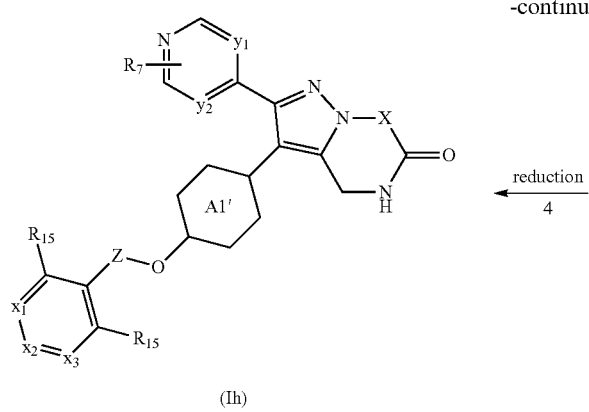

(Ih)

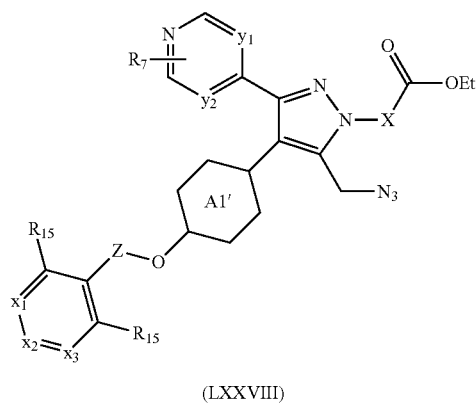

(LXXVIII)

1: an intermediate of formula (XXXXVI) can be converted into an intermediate of formula (LXXVI) by reaction with LAH in the presence of a suitable solvent, such as for example THF.

2: an intermediate of formula (LXXVI) can be reacted with an intermediate of formula (XXIV) in the presence of a suitable base, such as for example DBU, and a suitable solvent, such as for example THF, resulting in an intermediate of formula (LXXVII).

3: an intermediate of formula (LXXVII) can be reacted with an intermediate of formula (XXV) in the presence of a suitable base, such as for example $K_2CO_3$, and a suitable solvent, such as for example DMF, resulting in an intermediate of formula (LXXVIII).

4: an intermediate of formula (LXXVIII) can be converted into a compound of formula (Ih) by hydrogenation in the presence of a suitable catalyst, such as for example Nickel of Raney, and a suitable solvent, such as for example EtOH.

In all these preparations, the reaction products may be isolated from the reaction medium and, if necessary, further purified according to methodologies generally known in the art such as, for example, extraction, crystallization, trituration and chromatography. In particular, stereoisomers can be isolated chromatographically by Supercritical fluid chromatography using polysaccharide-based chiral stationary.

The chirally pure forms of the compounds of Formula (I) form a preferred group of compounds. It is therefore that the chirally pure forms of the intermediates and their salt forms are particularly useful in the preparation of chirally pure compounds of Formula (I). Also enantiomeric mixtures of the intermediates are useful in the preparation of compounds of Formula (I) with the corresponding configuration.

Pharmacology

It has been found that the compounds of the present invention inhibit ROS1 kinase activity. In particular, the compounds of the present invention are potent and selective Ros1 inhibitors.

As a consequence of their activity in inhibiting ROS kinases, the compounds and compositions thereof will be useful in providing a means of preventing the growth or inducing apoptosis of neoplasias. It is therefore anticipated that the compounds or compositions thereof will prove useful in treating or preventing, in particular treating, proliferative disorders such as cancers. In addition, the compounds of the invention could be useful in the treatment of diseases in which there is a disorder of proliferation, apoptosis or differentiation.

Examples of cancers which may be treated (or inhibited) include, but are not limited to, a carcinoma, for example a carcinoma of the bladder, breast, colon (e.g. colorectal carcinomas such as colon adenocarcinoma and colon adenoma), kidney, urothelial, uterus, epidermis, liver, lung (for example adenocarcinoma, small cell lung cancer and non-small cell lung carcinomas, squamous lung cancer), oesophagus, head and neck, gall bladder, ovary, pancreas (e.g. exocrine pancreatic carcinoma), stomach, gastrointestinal (also known as gastric) cancer (e.g. gastrointestinal stromal tumours), cervix, endometrium, thyroid, prostate, or skin (for example squamous cell carcinoma or dermatofibrosarcoma protuberans); pituitary cancer, a hematopoietic tumour of lymphoid lineage, for example leukemia, acute lymphocytic leukemia, chronic lymphocytic leukemia, B-cell lymphoma (e.g. diffuse large B-cell lymphoma), T-cell lymphoma, Hodgkin's lymphoma, non-Hodgkin's lymphoma, hairy cell lymphoma, or Burkett's lymphoma; a hematopoietic tumour of myeloid lineage, for example leukemias, acute and chronic myelogenous leukemias, chronic myelomonocytic leukemia (CMML), myeloproliferative disorder, myeloproliferative syndrome, myelodysplastic syndrome, or promyelocytic leukemia; multiple myeloma, thyroid follicular cancer; hepatocellular cancer, a tumour of mesenchymal origin (e.g. Ewing's sarcoma), for example fibrosarcoma or rhabdomyosarcoma; a tumour of the central or peripheral nervous system, for example astrocytoma, neuroblastoma, glioma (such as glioblastoma multiforme) or schwannoma; melanoma; seminoma; teratocarcinoma; osteosarcoma; xeroderma pigmentosum; keratoctanthoma; thyroid follicular cancer; or Kaposi's sarcoma.

In particular examples of cancers which may be treated (or inhibited) include non-small cell lung cancer (specifically adenocarcinoma), cholangiocarcinoma, glioblastoma, colorectal cancer, gastric adenocarcinoma, ovarian cancer, angiosarcoma, epithelioid hemangioendothelioma, inflammatory myofibroblastic tumors, breast cancer and chronic myelogenous leukemia.

In an embodiment, the compounds of the invention and compositions thereof may be useful for use in the treatment or prevention, in particular in the treatment, of non-small-cell lung cancer, cholangiocarcinoma, and glioblastoma multiforme.

In an embodiment, all or some of the compounds of the invention and compositions thereof may be useful for use in reducing tumors or prolonging survival in patients with a G2032R mutation in the Ros1 kinase domain.

In an embodiment, all or some the compounds of the invention and compositions thereof may be useful for use in reducing tumors or prolonging survival in patients with a L2026M mutation in the Ros1 kinase domain.

The compounds of the invention can also be used in the treatment of hematopoetic diseases of abnormal cell proliferation whether pre-malignant or stable such as myeloproliferative diseases. Myeloproliferative diseases ("MPD"s) are a group of diseases of the bone marrow in which excess cells are produced. They are related to, and may evolve into, myelodysplastic syndrome. Myeloproliferative diseases include polycythemia vera, essential thrombocythemia and primary myelofibrosis. A further haematological disorder is hypereosinophilic syndrome. T-cell lymphoproliferative diseases include those derived from natural Killer cells.

Thus, in the pharmaceutical compositions, uses or methods of this invention for treating a disease or condition comprising abnormal cell growth, the disease or condition comprising abnormal cell growth in one embodiment is a cancer.

The compounds of the invention and compositions thereof may be useful in treating other conditions which result from disorders in proliferation such as type II or non-insulin dependent diabetes mellitus, autoimmune diseases, head trauma, stroke, epilepsy, neurodegenerative diseases such as Alzheimer's, motor neurone disease, progressive supranuclear palsy, corticobasal degeneration and Pick's disease for example autoimmune diseases and neurodegenerative diseases.

ROS is also known to play a role in apoptosis, proliferation, differentiation and transcription and therefore the compounds of the invention could also be useful in the treatment of the following diseases other than cancer; chronic inflammatory diseases, for example systemic lupus erythematosus, autoimmune mediated glomerulonephritis, rheumatoid arthritis, psoriasis, inflammatory bowel disease, autoimmune diabetes mellitus, Eczema hypersensitivity reactions, asthma, COPD, rhinitis, and upper respiratory tract disease; cardiovascular diseases for example cardiac hypertrophy, restenosis, atherosclerosis; neurodegenerative disorders, for example Alzheimer's disease, AIDS-related dementia, Parkinson's disease, amyotropic lateral sclerosis, retinitis pigmentosa, spinal muscular atropy and cerebellar degeneration; glomerulonephritis; myelodysplastic syndromes, ischemic injury associated myocardial infarctions, stroke and reperfusion injury, arrhythmia, atherosclerosis, toxin-induced or alcohol related liver diseases, haematological diseases, for example, chronic anemia and aplastic anemia; degenerative diseases of the musculoskeletal system, for example, osteoporosis and arthritis, aspirin-sensitive rhinosinusitis, cystic fibrosis, multiple sclerosis, kidney diseases and cancer pain.

The compounds of the present invention and compositions thereof may also have utility in male contraception.

The compounds of the present invention may also have therapeutic applications in sensitising tumour cells for radiotherapy and chemotherapy.

Hence the compounds of the present invention may be used as "radiosensitizer" and/or "chemosensitizer" or can be given in combination with another "radiosensitizer" and/or "chemosensitizer".

The term "radiosensitizer", as used herein, is defined as a molecule, preferably a low molecular weight molecule, administered to animals in therapeutically effective amounts to increase the sensitivity of the cells to ionizing radiation and/or to promote the treatment of diseases which are treatable with ionizing radiation.

The term "chemosensitizer", as used herein, is defined as a molecule, preferably a low molecular weight molecule, administered to animals in therapeutically effective amounts to increase the sensitivity of cells to chemotherapy and/or promote the treatment of diseases which are treatable with chemotherapeutics.

Several mechanisms for the mode of action of radiosensitizers have been suggested in the literature including: hypoxic cell radiosensitizers (e.g., 2-nitroimidazole compounds, and benzotriazine dioxide compounds) mimicking oxygen or alternatively behave like bioreductive agents under hypoxia; non-hypoxic cell radiosensitizers (e.g., halogenated pyrimidines) can be analogues of DNA bases and preferentially incorporate into the DNA of cancer cells and thereby promote the radiation-induced breaking of DNA molecules and/or prevent the normal DNA repair mechanisms; and various other potential mechanisms of action have been hypothesized for radiosensitizers in the treatment of disease.

Many cancer treatment protocols currently employ radiosensitizers in conjunction with radiation of x-rays. Examples of x-ray activated radiosensitizers include, but are not limited to, the following: metronidazole, misonidazole, desmethylmisonidazole, pimonidazole, etanidazole, nimorazole, mitomycin C, RSU 1069, SR 4233, EO9, RB 6145, nicotinamide, 5-bromodeoxyuridine (BUdR), 5-iododeoxyuridine (IUdR), bromodeoxycytidine, fluorodeoxyuridine (FudR), hydroxyurea, cisplatin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, Photofrin, benzoporphyrin derivatives, tin etioporphyrin, pheoborbide-a, bacteriochlorophyll-a, naphthalocyanines, phthalocyanines, zinc phthalocyanine, and therapeutically effective analogs and derivatives of the same.

Radiosensitizers may be administered in conjunction with a therapeutically effective amount of one or more other compounds, including but not limited to: compounds which promote the incorporation of radiosensitizers to the target cells; compounds which control the flow of therapeutics, nutrients, and/or oxygen to the target cells; chemotherapeutic agents which act on the tumour with or without additional radiation; or other therapeutically effective compounds for treating cancer or other diseases.

Chemosensitizers may be administered in conjunction with a therapeutically effective amount of one or more other compounds, including but not limited to: compounds which promote the incorporation of chemosensitizers to the target cells; compounds which control the flow of therapeutics, nutrients, and/or oxygen to the target cells; chemotherapeutic agents which act on the tumour or other therapeutically effective compounds for treating cancer or other disease. Calcium antagonists, for example verapamil, are found useful in combination with antineoplastic agents to establish chemosensitivity in tumor cells resistant to accepted chemotherapeutic agents and to potentiate the efficacy of such compounds in drug-sensitive malignancies.

The invention relates to compounds of Formula (I) and N-oxides, pharmaceutically acceptable addition salts, and solvates thereof, for use as a medicament.

The invention also relates to compounds of Formula (I) and N-oxides, pharmaceutically acceptable addition salts, and solvates thereof, for use in the inhibition of ROS, in particular ROS1, kinase activity.

The compounds of the present invention can be "anti-cancer agents", which term also encompasses "anti-tumor cell growth agents" and "anti-neoplastic agents".

The invention also relates to compounds of Formula (I) and N-oxides, pharmaceutically acceptable addition salts, and solvates thereof, for use in the treatment of diseases mentioned above.

The invention also relates to compounds of Formula (I) and N-oxides, pharmaceutically acceptable addition salts, and solvates thereof, for the treatment or prevention, in particular for the treatment, of said diseases.

The invention also relates to compounds of Formula (I) and N-oxides, pharmaceutically acceptable addition salts, and solvates thereof, for the treatment or prevention, in particular in the treatment, of ROS, in particular ROS1, mediated diseases or conditions.

The invention also relates to the use of compounds of Formula (I) and N-oxides, pharmaceutically acceptable addition salts, and solvates thereof, for the manufacture of a medicament.

The invention also relates to the use of compounds of Formula (I) and N-oxides, pharmaceutically acceptable addition salts, and solvates thereof, for the manufacture of a medicament for the inhibition of ROS, in particular ROS1.

The invention also relates to the use of compounds of Formula (I) and N-oxides, pharmaceutically acceptable addition salts, and solvates thereof, for the manufacture of a medicament for the treatment or prevention, in particular for the treatment, of any one of the disease conditions mentioned hereinbefore.

The invention also relates to the use of compounds of Formula (I) and N-oxides, pharmaceutically acceptable addition salts, and solvates thereof, for the manufacture of a medicament for the treatment of any one of the disease conditions mentioned hereinbefore.

The compounds of Formula (I) and N-oxides, pharmaceutically acceptable addition salts, and solvates thereof, can be administered to mammals, preferably humans for the treatment or prevention of any one of the diseases mentioned hereinbefore.

In view of the utility of the compounds of Formula (I) and N-oxides, pharmaceutically acceptable addition salts, and solvates thereof, there is provided a method of treating warm-blooded animals, including humans, suffering from or a method of preventing warm-blooded animals, including humans, to suffer from any one of the diseases mentioned hereinbefore.

Said methods comprise the administration, i.e. the systemic or topical administration, preferably oral administration, of an effective amount of a compound of Formula (I) or a N-oxide, a pharmaceutically acceptable addition salt, or a solvate thereof, to warm-blooded animals, including humans.

Those of skill in the treatment of such diseases could determine the effective therapeutic daily amount from the test results presented hereinafter. An effective therapeutic daily amount would be from about 0.005 mg/kg to 50 mg/kg, in particular 0.01 mg/kg to 50 mg/kg body weight, more in particular from 0.01 mg/kg to 25 mg/kg body weight, preferably from about 0.01 mg/kg to about 15 mg/kg, more preferably from about 0.01 mg/kg to about 10 mg/kg, even more preferably from about 0.01 mg/kg to about 1 mg/kg, most preferably from about 0.05 mg/kg to about 1 mg/kg body weight. The amount of a compound according to the present invention, also referred to here as the active ingredient, which is required to achieve a therapeutically effect will of course, vary on case-by-case basis, for example with the particular compound, the route of administration, the age and condition of the recipient, and the particular disorder or disease being treated.

A method of treatment may also include administering the active ingredient on a regimen of between one and four intakes per day. In these methods of treatment the compounds according to the invention are preferably formulated prior to administration. As described herein below, suitable pharmaceutical formulations are prepared by known procedures using well known and readily available ingredients.

The compounds of the present invention, that can be suitable to treat or prevent cancer or cancer-related conditions, may be administered alone or in combination with one or more additional therapeutic agents. Combination therapy includes administration of a single pharmaceutical dosage formulation which contains a compound of Formula (I), a N-oxide, a pharmaceutically acceptable addition salt, or a solvate thereof, and one or more additional therapeutic agents, as well as administration of the compound of Formula (I), a N-oxide, a pharmaceutically acceptable addition salt, or a solvate thereof, and each additional therapeutic agents in its own separate pharmaceutical dosage formulation. For example, a compound of Formula (I), a N-oxide, a pharmaceutically acceptable addition salt, or a solvate thereof, and a therapeutic agent may be administered to the patient together in a single oral dosage composition such as a tablet or capsule, or each agent may be administered in separate oral dosage formulations.

While it is possible for the active ingredient to be administered alone, it is preferable to present it as a pharmaceutical composition.

Accordingly, the present invention further provides a pharmaceutical composition comprising a pharmaceutically acceptable carrier and, as active ingredient, a therapeutically effective amount of a compound of Formula (I), a N-oxide, a pharmaceutically acceptable addition salt, or a solvate thereof.

The carrier or diluent must be "acceptable" in the sense of being compatible with the other ingredients of the composition and not deleterious to the recipients thereof.

For ease of administration, the subject compounds may be formulated into various pharmaceutical forms for administration purposes. The compounds according to the invention, in particular the compounds of Formula (I) and N-oxides, pharmaceutically acceptable addition salts, and solvates thereof, or any subgroup or combination thereof may be formulated into various pharmaceutical forms for administration purposes. As appropriate compositions there may be cited all compositions usually employed for systemically administering drugs.

To prepare the pharmaceutical compositions of this invention, an effective amount of the particular compound as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, in particular, for administration orally, rectally, percutaneously, by parenteral injection or by inhalation. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules and tablets. Because of their ease in administration, tablets and capsules represent the most advantageous oral dosage unit forms in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable solutions, for example, may be prepared in which the carrier comprises saline solution, glucose solution or a mixture of saline and glucose solution. Injectable solutions containing a compound of Formula (I), a N-oxide, a pharmaceutically acceptable addition salt, or a solvate thereof, may be formulated in an oil for prolonged action. Appropriate oils for this purpose are, for example, peanut oil, sesame oil, cottonseed oil, corn oil, soybean oil, synthetic glycerol esters of long chain fatty acids and mixtures of these and other oils. Injectable suspensions may also be prepared in which case appropriate liquid carriers, suspending agents and the like may be employed. Also included are solid form preparations that are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. Acid or base addition salts of compounds of Formula (I) due to their increased water solubility over the corresponding base or acid form, are more suitable in the preparation of aqueous compositions.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

In order to enhance the solubility and/or the stability of the compounds of Formula (I) and N-oxides, pharmaceutically acceptable addition salts, and solvates thereof, in pharmaceutical compositions, it can be advantageous to employ α-, β- or γ-cyclodextrins or their derivatives, in particular hydroxyalkyl substituted cyclodextrins, e.g. 2-hydroxypropyl-β-cyclodextrin or sulfobutyl-β-cyclodextrin. Also co-solvents such as alcohols may improve the solubility and/or the stability of the compounds according to the invention in pharmaceutical compositions.

Depending on the mode of administration, the pharmaceutical composition will preferably comprise from 0.05 to 99% by weight, more preferably from 0.1 to 70% by weight, even more preferably from 0.1 to 50% by weight of the compound of Formula (I), a N-oxide, a pharmaceutically acceptable addition salt, or a solvate thereof, and from 1 to 99.95% by weight, more preferably from 30 to 99.9% by weight, even more preferably from 50 to 99.9% by weight of a pharmaceutically acceptable carrier, all percentages being based on the total weight of the composition.

As another aspect of the present invention, a combination of a compound of the present invention with another anti-cancer agent is envisaged, especially for use as a medicine, more specifically for use in the treatment of cancer or related diseases.

For the treatment of the above conditions, the compounds of the invention may be advantageously employed in combination with one or more other medicinal agents, more particularly, with other anti-cancer agents or adjuvants in cancer therapy. Examples of anti-cancer agents or adjuvants (supporting agents in the therapy) include but are not limited to:

platinum coordination compounds for example cisplatin optionally combined with amifostine, carboplatin or oxaliplatin;

taxane compounds for example paclitaxel, paclitaxel protein bound particles (Abraxane™) or docetaxel;

topoisomerase I inhibitors such as camptothecin compounds for example irinotecan, SN-38, topotecan, topotecan hcl;

topoisomerase II inhibitors such as anti-tumour epipodophyllotoxins or podophyllotoxin derivatives for example etoposide, etoposide phosphate or teniposide;

anti-tumour vinca alkaloids for example vinblastine, vincristine or vinorelbine;

anti-tumour nucleoside derivatives for example 5-fluorouracil, leucovorin, gemcitabine, gemcitabine hcl, capecitabine, cladribine, fludarabine, nelarabine;

alkylating agents such as nitrogen mustard or nitrosourea for example cyclophosphamide, chlorambucil, carmustine, thiotepa, mephalan (melphalan), lomustine, altretamine, busulfan, dacarbazine, estramustine, ifosfamide optionally in combination with mesna, pipobroman, procarbazine, streptozocin, temozolomide, uracil;

anti-tumour anthracycline derivatives for example daunorubicin, doxorubicin optionally in combination with dexrazoxane, doxil, idarubicin, mitoxantrone, epirubicin, epirubicin hcl, valrubicin;

molecules that target the IGF-1 receptor for example picropodophilin;

tetracarcin derivatives for example tetrocarcin A;

glucocorticoids for example prednisone;

antibodies for example trastuzumab (HER2 antibody), rituximab (CD20 antibody), gemtuzumab, gemtuzumab ozogamicin, cetuximab, pertuzumab, bevacizumab, alemtuzumab, eculizumab, ibritumomab tiuxetan, nofetumomab, panitumumab, tositumomab, CNTO 328;

estrogen receptor antagonists or selective estrogen receptor modulators or inhibitors of estrogen synthesis for example tamoxifen, fulvestrant, toremifene, droloxifene, faslodex, raloxifene or letrozole;

aromatase inhibitors such as exemestane, anastrozole, letrazole, testolactone and vorozole;

differentiating agents such as retinoids, vitamin D or retinoic acid and retinoic acid metabolism blocking agents (RAMBA) for example accutane;

DNA methyl transferase inhibitors for example azacytidine or decitabine;

antifolates for example premetrexed disodium;

antibiotics for example antinomycin D, bleomycin, mitomycin C, dactinomycin, carminomycin, daunomycin, levamisole, plicamycin, mithramycin;

antimetabolites for example clofarabine, aminopterin, cytosine arabinoside or methotrexate, azacitidine, cytarabine, floxuridine, pentostatin, thioguanine;

apoptosis inducing agents and antiangiogenic agents such as Bcl-2 inhibitors for example YC 137, BH 312, ABT 737, gossypol, HA 14-1, TW 37 or decanoic acid;

tubuline-binding agents for example combrestatin, colchicines or nocodazole;

kinase inhibitors (e.g. EGFR (epithelial growth factor receptor) inhibitors, MTKI (multi target kinase inhibitors), mTOR inhibitors) for example flavoperidol, imatinib mesylate, erlotinib, gefitinib, dasatinib, lapatinib, lapatinib ditosylate, sorafenib, sunitinib, sunitinib maleate, temsirolimus;

farnesyltransferase inhibitors for example tipifarnib;

histone deacetylase (HDAC) inhibitors for example sodium butyrate, suberoylanilide hydroxamic acid (SAHA), depsipeptide (FR 901228), NVP-LAQ824, R306465, JNJ-26481585, trichostatin A, vorinostat;

Inhibitors of the ubiquitin-proteasome pathway for example PS-341, MLN 0.41 or bortezomib;

Yondelis;

Telomerase inhibitors for example telomestatin;

Matrix metalloproteinase inhibitors for example batimastat, marimastat, prinostat or metastat;

Recombinant interleukins for example aldesleukin, denileukin diftitox, interferon alfa 2a, interferon alfa 2b, peginterferon alfa 2b;

MAPK inhibitors;

Retinoids for example alitretinoin, bexarotene, tretinoin;

Arsenic trioxide;

Asparaginase;

Steroids for example dromostanolone propionate, megestrol acetate, nandrolone (decanoate, phenpropionate), dexamethasone;

Gonadotropin releasing hormone agonists or antagonists for example abarelix, goserelin acetate, histrelin acetate, leuprolide acetate;

Thalidomide, lenalidomide;

Mercaptopurine, mitotane, pamidronate, pegademase, pegaspargase, rasburicase

BH3 mimetics for example ABT-737;

MEK inhibitors for example PD98059, AZD6244, CI-1040;

colony-stimulating factor analogs for example filgrastim, pegfilgrastim, sargramostim; erythropoietin or analogues thereof (e.g. darbepoetin alfa); interleukin 11; oprelvekin; zoledronate, zoledronic acid; fentanyl; bisphosphonate; palifermin;

a steroidal cytochrome P450 17alpha-hydroxylase-17,20-lyase inhibitor (CYP 17), e.g. abiraterone, abiraterone acetate;

Glycolysis inhibitors, such as 2-deoxyglucose;

mTOR inhibitors such as rapamycins and rapalogs, and mTOR kinase inhibitors

PI3K inhibitors and dual mTOR/PI3K inhibitors;

autophagy inhibitors, such as chloroquine and hydroxychloroquine;

androgen receptor antagonist drugs, e.g. enzalutamide or ARN-509;

antibodies that re-activate the immune response to tumors, for example nivolumab (anti-PD-1), lambrolizumab (anti-PD-1), ipilimumab (anti-CTLA4), and MPDL3280A (anti-PD-L1).

The present invention further relates to a product containing as first active ingredient a compound according to the invention and as further active ingredient one or more anticancer agents, as a combined preparation for simultaneous, separate or sequential use in the treatment of patients suffering from cancer.

The one or more other medicinal agents and the compound according to the present invention may be administered simultaneously (e.g. in separate or unitary compositions) or sequentially in either order. In the latter case, the two or more compounds will be administered within a period and in an amount and manner that is sufficient to ensure that an advantageous or synergistic effect is achieved. It will be appreciated that the preferred method and order of administration and the respective dosage amounts and regimes for each component of the combination will depend on the particular other medicinal agent and compound of the present invention being administered, their route of administration, the particular tumour being treated and the particular host being treated. The optimum method and order of administration and the dosage amounts and regime can be readily determined by those skilled in the art using conventional methods and in view of the information set out herein.

The weight ratio of the compound according to the present invention and the one or more other anticancer agent(s) when given as a combination may be determined by the person skilled in the art. Said ratio and the exact dosage and frequency of administration depends on the particular compound according to the invention and the other anticancer agent(s) used, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the compounds of the instant invention. A particular weight ratio for the present compound of Formula (I) and another anticancer agent may range from 1/10 to 10/1, more in particular from 1/5 to 5/1, even more in particular from 1/3 to 3/1.

The platinum coordination compound is advantageously administered in a dosage of 1 to 500 mg per square meter $(mg/m^2)$ of body surface area, for example 50 to 400 $mg/m^2$, particularly for cisplatin in a dosage of about 75 $mg/m^2$ and for carboplatin in about 300 $mg/m^2$ per course of treatment.

The taxane compound is advantageously administered in a dosage of 50 to 400 mg per square meter $(mg/m^2)$ of body surface area, for example 75 to 250 $mg/m^2$, particularly for paclitaxel in a dosage of about 175 to 250 $mg/m^2$ and for docetaxel in about 75 to 150 $mg/m^2$ per course of treatment.

The camptothecin compound is advantageously administered in a dosage of 0.1 to 400 mg per square meter $(mg/m^2)$ of body surface area, for example 1 to 300 $mg/m^2$, particularly for irinotecan in a dosage of about 100 to 350 $mg/m^2$ and for topotecan in about 1 to 2 $mg/m^2$ per course of treatment.

The anti-tumour podophyllotoxin derivative is advantageously administered in a dosage of 30 to 300 mg per square meter $(mg/m^2)$ of body surface area, for example 50 to 250 $mg/m^2$, particularly for etoposide in a dosage of about 35 to 100 $mg/m^2$ and for teniposide in about 50 to 250 $mg/m^2$ per course of treatment.

The anti-tumour vinca alkaloid is advantageously administered in a dosage of 2 to 30 mg per square meter $(mg/m^2)$ of body surface area, particularly for vinblastine in a dosage of about 3 to 12 $mg/m^2$, for vincristine in a dosage of about 1 to 2 $mg/m^2$, and for vinorelbine in dosage of about 10 to 30 $mg/m^2$ per course of treatment.

The anti-tumour nucleoside derivative is advantageously administered in a dosage of 200 to 2500 mg per square meter (mg/m²) of body surface area, for example 700 to 1500 mg/m², particularly for 5-FU in a dosage of 200 to 500 mg/m², for gemcitabine in a dosage of about 800 to 1200 mg/m² and for capecitabine in about 1000 to 2500 mg/m² per course of treatment.

The alkylating agents such as nitrogen mustard or nitrosourea is advantageously administered in a dosage of 100 to 500 mg per square meter (mg/m²) of body surface area, for example 120 to 200 mg/m², particularly for cyclophosphamide in a dosage of about 100 to 500 mg/m², for chlorambucil in a dosage of about 0.1 to 0.2 mg/kg, for carmustine in a dosage of about 150 to 200 mg/m², and for lomustine in a dosage of about 100 to 150 mg/m² per course of treatment.

The anti-tumour anthracycline derivative is advantageously administered in a dosage of 10 to 75 mg per square meter (mg/m²) of body surface area, for example 15 to 60 mg/m², particularly for doxorubicin in a dosage of about 40 to 75 mg/m², for daunorubicin in a dosage of about 25 to 45 mg/m², and for idarubicin in a dosage of about 10 to 15 mg/m² per course of treatment.

The antiestrogen agent is advantageously administered in a dosage of about 1 to 100 mg daily depending on the particular agent and the condition being treated. Tamoxifen is advantageously administered orally in a dosage of 5 to 50 mg, preferably 10 to 20 mg twice a day, continuing the therapy for sufficient time to achieve and maintain a therapeutic effect. Toremifene is advantageously administered orally in a dosage of about 60 mg once a day, continuing the therapy for sufficient time to achieve and maintain a therapeutic effect. Anastrozole is advantageously administered orally in a dosage of about 1 mg once a day. Droloxifene is advantageously administered orally in a dosage of about 20-100 mg once a day. Raloxifene is advantageously administered orally in a dosage of about 60 mg once a day. Exemestane is advantageously administered orally in a dosage of about 25 mg once a day.

Antibodies are advantageously administered in a dosage of about 1 to 5 mg per square meter (mg/m²) of body surface area, or as known in the art, if different. Trastuzumab is advantageously administered in a dosage of 1 to 5 mg per square meter (mg/m²) of body surface area, particularly 2 to 4 mg/m² per course of treatment. These dosages may be administered for example once, twice or more per course of treatment, which may be repeated for example every 7, 14, 21 or 28 days.

The following examples illustrate the present invention. In case no specific stereochemistry is indicated for a stereocenter of a compound, this means that the compound was obtained as a mixture of the R and the S enantiomers. For a number of compounds, melting points (m.p.) were determined with a DSC 1 STAR$^e$ System from Mettler Toledo. Melting points were measured with a temperature gradient of 10° C./minute up to 350° C. Melting points are given by peak values.

EXAMPLES

Hereinafter, the term "NaH" means sodium hydride (60% in mineral oil); "DCM" means dichloromethane; "TBAF" means tetrabutylammonium fluoride; "Pd(tBu$_3$P)$_2$" means bis[tris(1,1-dimethylethyl)phosphine]-palladium; "quant." means quantitative; "Ac" means acetyl; "MeI" means iodomethane; "sat." means saturated; "DBU" means 1,8-diazabicyclo[5.4.0]undecene-7; "LAH" means lithium aluminium hydride; "NBS" means N-bromosuccinimide; "sol." means solution; "prep." means preparative; "MeMgCl" means Methylmagnesium chloride; "nBuLi" means n-butyllithium; "aq." means aqueous; "Int." Means Intermediate; "Co." means compound; "r.t." means room temperature; "r.m." means reaction mixture; "KOAc" means potassium acetate; "AcONH$_4$" means ammonium acetate; "BisPin" means bis(pinacolato)diboron; "DCE" means 1,2-dichloroethane; "DIPE" means diisopropyl ether; "Boc" or "BOC" means tert-butoxycarbonyl; "CDI" means 1,1'-carbonyldiimidazole; "N-Boc sarcosine" means N-[(1,1-dimethylethoxy)carbonyl]-N-methyl-Glycine; "Boc-glycinol" means N-(tert-Butoxycarbonyl)ethanolamine; "(BOC)$_2$O" means di-tert-butyl dicarbonate; "ACN" means acetonitrile; "EDCI" means N-(ethylcarbonimidoyl)-N,N-dimethyl-1,3-propanediamine monohydrochloride; "HOBT" means 1-hydroxy-1H-benzotriazole; "TBDPS" means tert-butyldiphenylsilyl; "OTBDPS" means tert-butyldiphenylsilyloxy; "TBDMS" means tert-butyldimethylsilyl: "TBDMSO" or "OTBDMS" means tert-butyldimethylsilyloxy; "S-Phos" means 2-dicyclohexylphosphino-2',6'-dimethoxybiphenyl; "LiHMDS" means lithium hexamethyldisilazane; "DMAP" means 4-(dimethylamino)pyridine; "MeOH" means methanol; "PCy$_3$" means tricyclohexylphosphine; "LC" means liquid chromatography; "LCMS" means Liquid Chromatography/Mass spectrometry; "HATU" means 1-[bis(dimethylamino)methylene]-1H-[1,2,3]triazolo[4,5-b]pyridin-1-ium 3-oxide hexafluorophosphate; "HPLC" means high-performance liquid chromatography; "TFA" means trifluoroacetic acid; "mp." means melting point; "N$_2$" means nitrogen; "DBAD" means di-tert-butyl azodicarboxylate; "RP" means reversed phase; "min" means minute(s); "EtOAc" means ethyl acetate; "Et$_3$N" means triethylamine; "EtOH" means ethanol; "THF" means tetrahydrofuran; "Celite®" means diatomaceous earth; "DMF" means N,N-dimethyl formamide; "DMSO" means dimethyl sulfoxide; "iPrOH" means 2-propanol; "iPrNH$_2$" means isopropylamine; "SFC" means Supercritical Fluid Chromatography; "DIPEA" means N,N-diisopropylethylamine: "Pd(PPh$_3$)$_4$" means tetrakis(triphenylphosphine)palladium; "w/v" means weight/volume; "PPh$_3$" means triphenylphosphine; "PPh$_3$ supp." means triphenylphosphine supported (polymer bound): "Et$_2$O" means diethyl ether; "Pd/C" means palladium on carbon; "Pt/C" means platina on carbon; "Pd(OAc)$_2$" means palladium(II) acetate; "Et" means ethyl; "Me" means methyl: "h" means hours; "precatalyst" means (SP-4-4)-[2'-(amino-κN)[1,1'-biphenyl]-2-yl-κC]chloro[dicyclohexyl [2',4',6'-tris(1-methylethyl)[1,1-biphenyl]-2-yl]phosphine]-palladium (CAS registry number [1310584-14-5]); and "PdCl$_2$(dppf)" means [1,1'-bis(diphenylphosphino-KP)ferrocene]dichloropalladium.

Hereinafter, "Int. 1 or 1" is '3-(4-pyridinyl)-1H-pyrazole-5-carboxylic acid, ethyl ester'; "Int. 6 or 6" is '4-(1-methylethyl)-benzenemethanol'; "Int. 7 or 7" is '4-hydroxybenzeneboronic acid pinacol ester'; "Int. 8 or 8" is '(1-(bromomethyl)-4-(1-methylethyl)-benzene)'; "Int. 9 or 9" is '4-[[4-(1-methylethyl)phenyl]methoxy]-benzoic acid, methyl ester'; "Int. 13 or 13" is '4-[[4-(1-methylethyl) phenyl]methoxy]-benzaldehyde'; "Int. 19 or 19" is '2-cyano-3-[4-[(4-methoxyphenyl)-methoxy]phenyl]-2-propenoic acid, ethyl ester'; "Int. 29 or 29 " is '6-cyclopropyl-3-pyridinemethanol'; "Int. 31 or 31 " is '4-cyclopropyl-benzenemethanol'; "Int. 33 or 33 " is '4-hydroxy-benzoic acid, methyl ester'; "Int. 39 or 39" is '4-hydroxy-2-fluorophenylboronic acid pinacol ester'.

Preparation of the Intermediates and the Final Compounds

Example A1

Preparation of Co. 1 (1st Approach)

a—Synthesis of Int. 2:

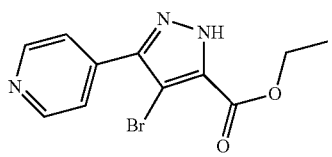 [SMILES: CCOC(=O)c1[nH]nc(-c2ccncc2)c1Br]

A sol. of 1 (3-(4-pyridinyl)-1H-pyrazole-5-carboxylic acid, ethyl ester) (34.7 g; 160 mmol) in DCM (464 mL) was treated with NBS (31.3 g; 176 mmol) and stirred at r.t. for 20 h. The crude mixture was concentrated in vacuo and then taken up in Et$_2$O (200 mL) and filtered on a glass frit. The solid was washed with Et$_2$O (100 mL) and twice with MeOH and Et$_2$O (10 mL/40 mL). The solid was collected and dried in vacuo to give 43.57 g of the Int. 2 (92%).

b—Synthesis of Int. 3:

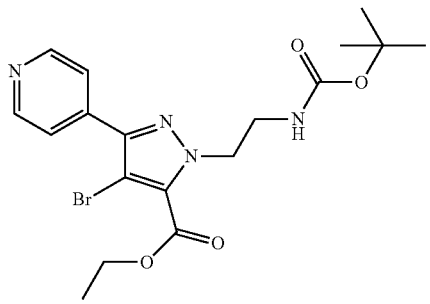 [SMILES: CCOC(=O)c1c(Br)c(-c2ccncc2)nn1CCNC(=O)OC(C)(C)C]

To a mixture of 2 (Int. 2) (25 g, 84.4 mmol), tert-butyl N-(2-hydroxyethyl)carbamate (20.4 g, 126 mmol) and PPh$_3$ supp. (39.6 g, 127 mmol) in dry THF (700 mL) was added DBAD (29.2 g, 126.6 mmol). The mixture was stirred for 4 h at r.t. then filtered through a glass frit. The filtrate was evaporated in vacuo to give 79.8 g of a residue which was purified by chromatography over silica gel (Irregular SiOH 35-40 μm; 330 g; mobile phase from 100% DCM to 97% DCM, 3% MeOH, 0.1% NH$_4$OH). The pure fractions were collected and evaporated to give 33.2 g of Int. 3 (90%).

c—Synthesis of Int. 4:

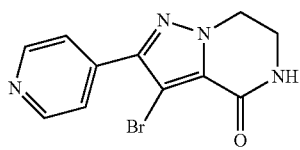 [SMILES: O=C1NCCn2nc(-c3ccncc3)c(Br)c21]

TFA (49.5 mL, 646 mmol) was added to a sol. of 3 (35.5 g, 80.8 mmol) in DCM (320 mL) and the r.m. was stirred at r.t. for 17 h. The r.m. was quenched with a sat. sol. of NaHCO$_3$ (2000 mL) and stirred for 10 min. The precipitate was filtered on a glass frit and washed with Et$_2$O and dried in vacuo to give 23 g of a residue as a white solid. The residue was put in suspension in MeOH (150 mL) and treated with Cs$_2$CO$_3$ (5.27 g, 16.2 mmol). The r.m. was stirred at r.t. for 17 h. The crude mixture was filtered through a glass frit. The white precipitate was washed with water (2×50 mL), with MeOH (2×10 mL) and with Et$_2$O (4×50 mL). The white precipitate was collected and dried in vacuo to afford 17.8 g of Int. 4 as a white solid (75%).

d—Synthesis of Int. 5:

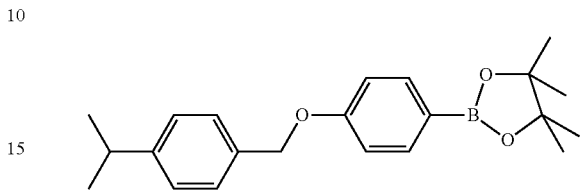

To a suspension of 7 (4-hydroxybenzeneboronic acid pinacol ester) (5.00 g, 22.7 mmol), 6 (4-(1-methylethyl)-benzenemethanol) (5.12 g, 34.1 mmol), PPh$_3$ supp. (8.94 g, 34.1 mmol) in dry DCM (150 mL) was added DBAD (7.85 g, 34.1 mmol) and the r.m. was stirred at r.t. for 18 h. The r.m. was then filtered through a glass frit and washed with EtOAc. The filtrate was evaporated in vacuo to give a residue (27 g) as a yellow oil. The residue was purified by chromatography over silica gel (irregular SiOH 15-40 μm, 150 g, mobile phase: 90% Heptane, 10% EtOAc). The pure fractions were collected and the solvent evaporated to give 8.00 g of 5 as a white gum (Quant.). Alternative method for the synthesis of Int. 5:

A sol. of 7 (7.00 g, 31.8 mmol) in ACN (75 mL) was treated with K$_2$CO$_3$ (5.28 g, 38.2 mmol) and 8 (1-(bromomethyl)-4-(1-methylethyl)-benzene) (6.03 mL, 35.0 mmol) at r.t. The r.m. was stirred at r.t. overnight. Then, the r.m. was filtered on a pad of Celite® and washed with DCM. The solvents were evaporated to a volume of 100 mL and Et$_2$O and heptane were added. The solvents were evaporated in vacuo to afford 12.36 g of a residue as a yellow solid. This residue was purified by prep. LC (Regular SiOH 50 μm, 220 g Grace, mobile phase gradient from Heptane 100% to Heptane 80%, EtOAc 20%). The fractions were collected and the solvent was evaporated to give 9.88 g of the Int. 5 as a white sticky solid (88%).

e—Synthesis of Co. 1:

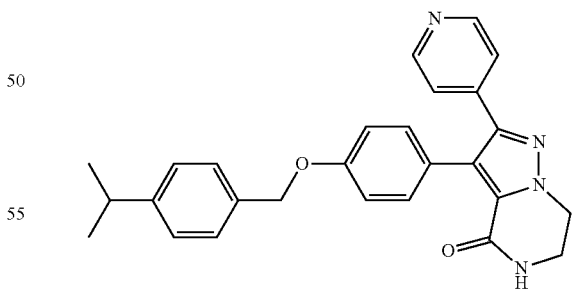

A mixture of 4 (9.5 g, 32.4 mmol), 5 (22.8 g, 64.7 mmol), K$_3$PO$_4$ (27.5 g, 0.13 mol) in 1,4-dioxane (165 mL) and H$_2$O (60 mL) was carefully purged with N$_2$. PCy$_3$ (1.8 g, 6.5 mmol) and Pd(OAc)$_2$ (0.73 g, 3.2 mmol) were added and the r.m. was purged again with N$_2$. The r.m. was stirred for 18 h at 80° C. The crude material was poured in water and EtOAc was added. This mixture was filtered through a pad of Celite®. The pad of Celite® was washed twice with a hot sol. of DCM+MeOH and the filtrate was evaporated until dryness, then diluted in DCM (500 mL) and purified by chromatography over silica gel (irregular SiOH 15-40 µm, 400 g, mobile phase gradient from 100% DCM to 95% DCM, 5% MeOH, 0.1% NH$_4$OH). The pure fractions were collected and evaporated until dryness to give 6.4 g of a first residue and 2.25 g of a second residue. The first residue was washed with MeOH, filtered and dried to yield 6.07 g of Co. 1 (43%). m.p.: 264° C. (DSC). The second residue was washed with MeOH, filtered and dried to yield 2.02 g of Co. 1 (95% pure) (14%).

Example A2

Preparation of Co. 1 (2$^{nd}$ Approach)

a—Synthesis of Int. 10:

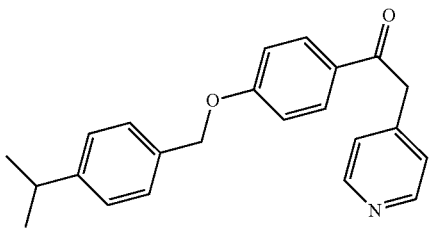 [SMILES: CC(C)c1ccc(COc2ccc(C(=O)Cc3ccncc3)cc2)cc1]

In a dry flask under N$_2$, a sol. of 9 (4-[[4-(1-methylethyl) phenyl]methoxy]-benzoic acid, methyl ester) (45 g, 0.158 mol) and 4-picoline (16.9 mL, 0.174 mol) in THF (350 mL) was cooled to 0° C. and treated with LiHMDS (316.5 mL, 0.317 mol) (slow addition). The r.m. was stirred at r.t. for 20 h and quenched with a sat. aq. sol. of NH$_4$Cl. EtOAc was added and the insoluble was filtered, washed with H$_2$O then Et$_2$O and dried to yield 33.7 g of a first batch of 10 (62%). The organic layer was extracted and evaporated. The residue was crystallized from Et$_2$O and H$_2$O, filtered and dried to give 17.22 g of a 2$^{nd}$ batch of Int. 10 (31%). The organic layer was extracted and evaporated to give 5.8 g of a residue. The residue was purified by chromatography over silica gel (SiOH 35-40 µm, 80 g, mobile phase gradient from 100% DCM to 98% DCM, 2% MeOH). The pure fractions were collected and evaporated to yield 1.14 g of the third batch of Int. 10 (2%) (Global ield 95%)

b—Synthesis of Int. 11:

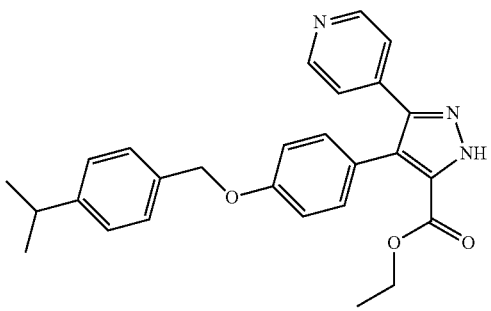 [SMILES: CCOC(=O)c1[nH]nc(-c2ccncc2)c1-c1ccc(OCc2ccc(C(C)C)cc2)cc1]

Quantities were divided into four parts of Q.

To a suspension of 10 (93 g, 0.269 mol) in ACN (837 mL) was added DBU (68.5 mL, 0.458 mol) and ethyldiazoacetate (45.3 mL, 0.431 mol). The mixture was stirred at r.t. for 1 h. The mixture was poured into a sat. aq. sol. of NaHCO$_3$ and extracted with EtOAc. The aq. mixture was filtered, the filter was washed with EtOAc and the filter residue was dried to yield 66.44 g of the first batch of Int. 11 (56%). The organic layer was dried (MgSO$_4$), filtered and evaporated to give 75 g of a residue. The residue was purified by chromatography over silica gel (irregular SiOH 35-40 µm, 2×330 g, mobile phase gradient from 100% DCM to 95% DCM, 5% MeOH, 0.1% NH$_4$OH). The pure fractions were collected and evaporated to give 28.95 g of the second batch of Int. U (24%). Global yield: 80%.

c—Synthesis of Int. 12:

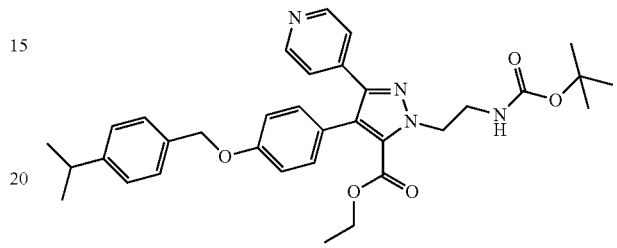

DBAD (31.9 g, 0.139 mol) was added portionwise to a sol. of 11 (51 g, 0.116 mol), Boc-glycinol (27.9 g, 0.173 mol), PPh$_3$ (36.4 g, 0.139 mol) in THF (960 mL) at r.t. under N$_2$ flow. The mixture was stirred for 2 h at r.t., poured into H$_2$O and K$_2$CO$_3$ and extracted with EtOAc. The organic layer was dried (MgSO$_4$), filtered and evaporated until dryness to give 154 g of a residue. The residue was purified by chromatography over silica gel (irregular SiOH 35-40 µm, 330 g, mobile phase gradient from 100% DCM to 97% DCM, 3% CH$_3$OH, 0.1% NH$_4$OH). The pure fractions were collected and evaporated until dryness to give 126.1 g of a residue. The residue was purified by achiral SFC on (2-ethylpyridine 6 µm 150×21.2 m, mobile phase 90% CO$_2$, 10% MeOH). The pure fractions were collected and evaporated until dryness to give 59.6 g of Int. 12 (88%).

d—Synthesis of Co. 1:

A solution of 12 (54.6 g, 0.093 mol) and HCl 3N (155 mL, 0.465 mol) in ACN (1600 mL) was stirred at 80° C. for 2 h. The solvent was evaporated, a sat. aq. sol. of NaHCO$_3$ was added and the mixture was stirred at r.t. The organic layer was extracted with DCM, dried (MgSO$_4$) and concentrated. The residue was stirred for 3 days with Cs$_2$CO$_3$ (61 g, 0.187 mol) in MeOH (2700 mL) at r.t. The mixture was filtered, the filter was washed with MeOH and the filter residue was dried to give 37.4 g of Co. 1 (88%).

Example A3

Preparation of Co. 1 (3$^{rd}$ Approach)

a—Synthesis of Int. 14:

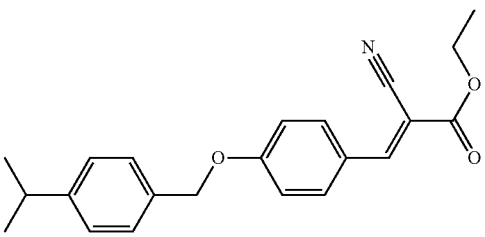 [SMILES: CCOC(=O)/C(C#N)=C/c1ccc(OCc2ccc(C(C)C)cc2)cc1]

To a sol. of ethylcyanoacetate (2.6 mL, 24 mmol) in EtOH (15 mL) was added 13 (4-[[4-(1-methylethyl)phenyl]methoxy]-benzaldehyde) (5.9 g, 23 mmol) and piperidine (46.0 µL; 0.46 mmol). The mixture was refluxed for 2 h then allowed to cool down to r.t. overnight. The precipitate formed was filtered on a glass frit and was dried in vacuo to give 6.8 g of Int. 14 as white needles (84%).

b—Synthesis of Int. 15:

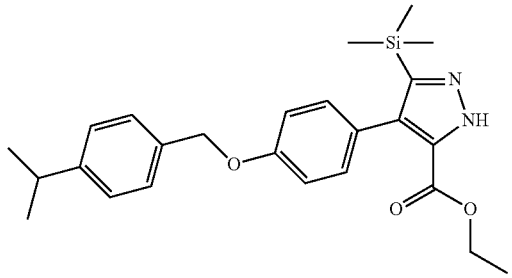 [SMILES: CCOC(=O)c1[nH]nc([Si](C)(C)C)c1-c1ccc(OCc2ccc(C(C)C)cc2)cc1]

To a sol. of trimethylsilyldiazomethane (40 mL, 80 mmol) in dry THF (100 mL) at −78° C. under N₂ was added nBuLi (50 mL, 80 mmol) dropwise. The sol. was stirred for 30 min at −78° C. and a sol. of 14 (18.6 g, 53.33 mmol) in dry THF (100 mL) was added dropwise at −78° C. The sol. was stirred for 1 h at −78° C. then at r.t. for 16 h. EtOAc was added and the organic layer was washed twice with a sat. aq. sol. of NaHCO₃, dried (MgSO₄), filtered off and evaporated in vacuo to give a brown residue. The residue was purified by filtration on silica with a mixture of 97% DCM 3% MeOH to give 16.6 g of Int. 15 as a brown residue (71%).

c—Synthesis of Int. 16:

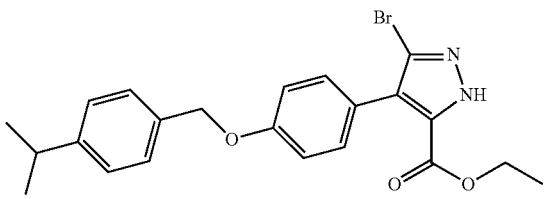 [SMILES: CCOC(=O)c1[nH]nc(Br)c1-c1ccc(OCc2ccc(C(C)C)cc2)cc1]

To a sol. of 15 (3.8 g, 8.7 mmol) in ACN (80 mL) was added NBS (1.63 g, 9.1 mmol) in ACN (40 mL) and the pale brown mixture was stirred at r.t. for 18 h. The solvent was removed in vacuo and EtOAc and a sat. aq. sol. of K₂CO₃ were added to the residue.

The organic layer was separated, dried over MgSO₄, filtered off and evaporated in vacuo to give 4.04 g of a brown oil. The residue was purified by prep. LC (Irregular SiOH 15-40 µm, 80 g GraceResolv™, mobile phase gradient from 80% heptane, 20% EtOAc to 70% heptanes, 30% EtOAc). The pure fractions were collected and evaporated until dryness to give 2.5 g of Int. 16 as a beige foam (65%).

d—Synthesis of Int. 17 and Int. 18

Int. 17

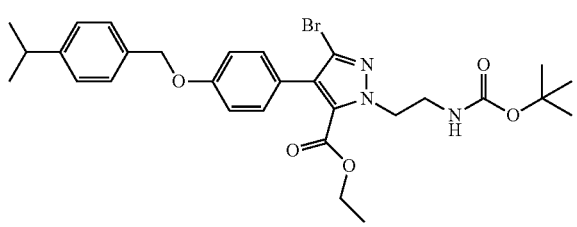

Int. 18

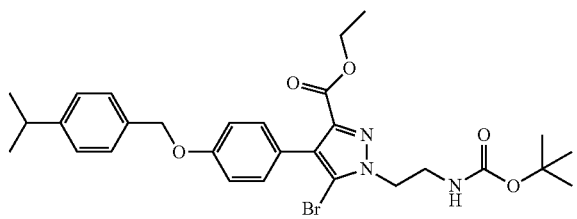

To a mixture of 16 (1.4 g, 3.2 mmol), Boc-Glycinol (0.76 g, 4.7 mmol) and PPh₃ supp. (1.5 g, 4.7 mmol) in dry THF (51 mL) was added DBAD (1.1 g, 4.7 mmol). The mixture was stirred at r.t. for 4 h. The mixture was filtered through a pad of Celite®, concentrated and purified by chromatography over silica gel (irregular SiOH 30 µm; 80 g; mobile phase 70% Heptane, 30% EtOAc). The fractions were collected and evaporated until dryness to give 2.35 g of Int. 17 (used like this in the next step) and 0.24 g of Int. 18.

e—Synthesis of Int. 12:

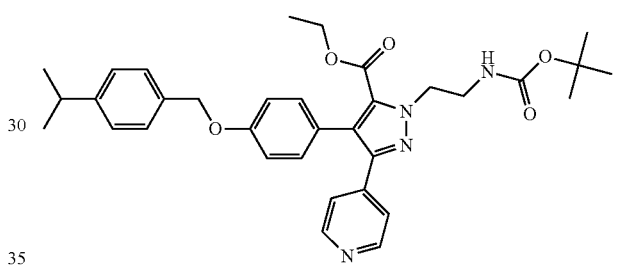

In a schlenk tube, a mixture of 17 (0.3 g, 0.51 mmol), 4-(4,4,5,5-tetramethylL-1,3,2-dioxaborolan-2-yl)pyridine (314 mg, 1.5 mmol), K₃PO₄ (0.43 g, 2.0 mmol) in 1,4-dioxane (1.4 mL) and H₂O (0.5 mL) was carefully degassed with N₂. PCy₃ (30 mg, 0.11 mmol) and Pd(OAc)₂ (12 mg, 0.054 mmol) were added and the r.m. was purged again with N₂. The r.m. was stirred overnight at 80° C. The crude material was dissolved in water (50 mL) and extracted with DCM. The organic phase was dried (MgSO₄), filtered and evaporated in vacuo. This residue was purified by chromatography over silica gel (irregular SiOH 15-40 µm, 24 g Interchim, mobile phase gradient from 98% DCM, 2% MeOH, 0.1% NH₄OH to 96% DCM, 4% MeOH, 0.1% NH₄OH). The pure fractions were collected and evaporated to give 0.166 g of Int. 12 as a colorless oil (56%).

f—Synthesis of Co. 1:

A mixture of 12 (166 mg, 0.28 mmol) and an aq. sol. of HCl 3N (0.47 mL, 1.4 mmol) in ACN (5 mL) was heated at 80° C. for 2 h. The solvent was evaporated and an aq. sol. of K₂CO₃ 10% (20 mL) was added. The mixture was extracted with DCM, dried and concentrated. The residue was taken up in MeOH and the white solid formed was filtered and dried to give 27 mg of the first batch of Co. 1 (22%). The filtrate was concentrated and the residue was washed with water. The white solid in suspension was filtrated and dried to yield 74 mg of a 2$^{nd}$ batch of Co. 1 as a beige powder (59%).

Example A4

Preparation of Co. 1 (4<sup>th</sup> Approach)

a—Synthesis of Int. 20:

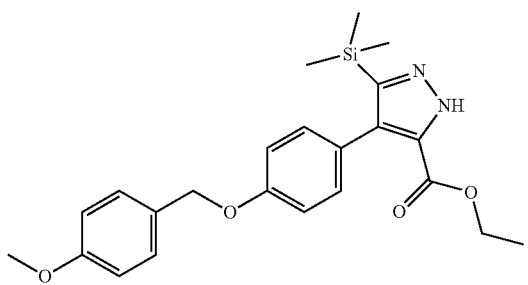 [SMILES: CCOC(=O)c1[nH]nc([Si](C)(C)C)c1-c1ccc(OCc2ccc(OC)cc2)cc1]

To a sol. of Trimethylsilyldiazomethane (17.1 mL, 34.2 mmol) in dry THF (40 mL) at −78° C. under N₂ was added dropwise nBuLi (21.4 mL, 34.2 mmol). The sol. was stirred for 30 min at −78° C. and a suspension of 19 (2-cyano-3-[4-[(4-methoxyphenyl)methoxy]phenyl]-2-propenoic acid, ethyl ester) (7.7 g, 22.8 mmol) in dry THF (60 mL) was added dropwise at −78° C. The sol. was stirred for 1 h at −78° C. then at r.t. for 16 h. EtOAc was added and the organic layer was washed twice with a sat. aq. sol. of NaHCO₃, dried (MgSO₄), filtered off and evaporated in vacuo to give a brown solid. The residue was triturated in Et₂O and filtered on a glass frit to give 4.59 g of Int. 20 as a pale brown solid (47%).

b—Synthesis of Int. 21:

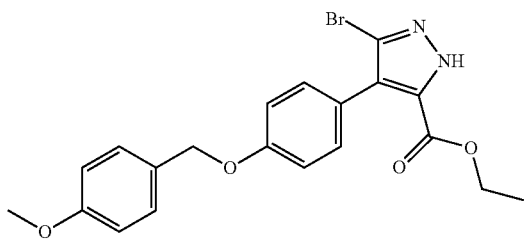 [SMILES: CCOC(=O)c1[nH]nc(Br)c1-c1ccc(OCc2ccc(OC)cc2)cc1]

To a suspension of 20 (9.2 g, 21.67 mmol) in ACN (190 mL) was added NBS (3.86 g, 21.67 mmol) in ACN (95 mL) and the pale brown mixture was stirred at r.t. for 18 h. The solvent was removed in vacuo. DCM and a sat. aq. sol. of NaHCO₃ were added to the residue. The organic layer was separated, washed 2× with a aq. sol. of K₂CO₃ 10%, dried (MgSO₄), filtered off and evaporated in vacuo to give 9.07 g of Int. 21 as a brown solid (97%).

c—Synthesis of Int. 22:

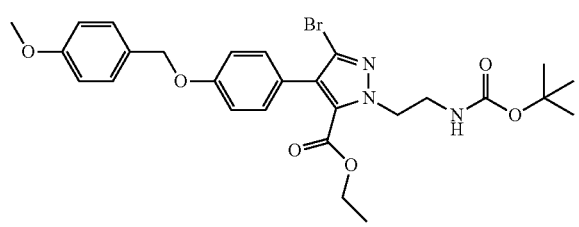 [SMILES: CCOC(=O)c1c(-c2ccc(OCc3ccc(OC)cc3)cc2)c(Br)nn1CCNC(=O)OC(C)(C)C]

To a suspension of 21 (2.0 g, 4.6 mmol), Boc-Glycinol (1.1 mL, 7.0 mmol) and diphenylphosphinopolystyrene (2.2 g, 7.0 mmol) in dry THF (60 mL) was added DBAD (1.6 g, 7.0 mmol). The mixture was stirred at r.t. for 4 h. The sol. was filtered through a pad of Celite®, the polymer was washed with EtOAc and the filtrate was evaporated in vacuo. The residue was purified by chromatography over silica gel (Regular SiOH, 30 µm, 80 g GraceResolv™, mobile phase gradient from 75% Heptane, 25% EtOAc to 70% Heptane, 30% EtOAc). The fractions were collected and evaporated until dryness to give 2.58 g of Int. 22 as a yellow solid used without further purification for the next step.

d—Synthesis of Int. 23:

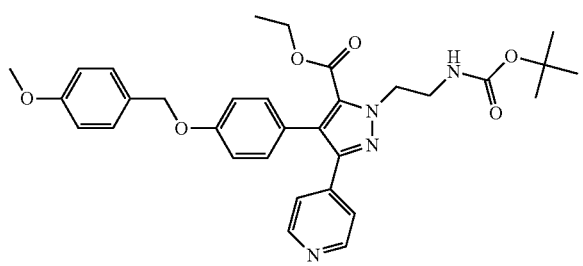 [SMILES: CCOC(=O)c1c(-c2ccc(OCc3ccc(OC)cc3)cc2)c(-c2ccncc2)nn1CCNC(=O)OC(C)(C)C]

A mixture of 22 (2.5 g, 4.4 mmol), 4-(4,4,5,5-tetramethyl-1,3,2-dioxaborolan-2-yl)pyridine (2.7 g, 13 mmol), K₃PO₄ (3.7 g, 17 mmol) in 1,4-dioxane (11 mL) and distilled water (4.) was carefully degassed with N₂. PCy₃ (256 mg, 0.91 mmol) and Pd(OAc)₂ (103 mg, 0.46 mmol) were added and the r.m. was purged again with N₂. The r.m. was stirred overnight at 80° C. The crude material was dissolved in water (100 mL) and extracted with DCM. The organic phase was dried over MgSO₄, filtered through a pad of Celite® and evaporated in vacuo. This residue was purified by chromatography over silica gel (irregular SiOH 30 µm, 80 g, mobile phase from 40% Heptane, 60% EtOAc to 20% Heptane, 80% EtOAc). The pure fractions were collected and evaporated until dryness to give 1.49 g of Int. 23 as a beige powder (60%).

e—Synthesis of Int. 24:

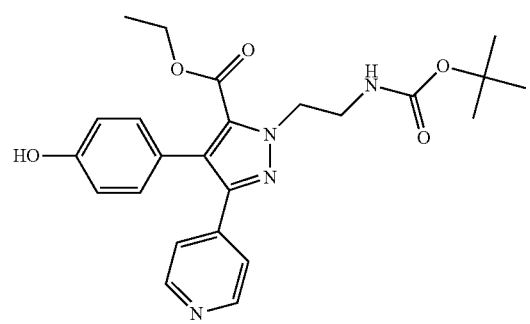 [SMILES: CCOC(=O)c1c(-c2ccc(O)cc2)c(-c2ccncc2)nn1CCNC(=O)OC(C)(C)C]

Pd/C (10%) (520 mg, 0.49 mmol) was added to a N₂ degassed sol. of 23 (1.4 g, 2.4 mmol) in EtOH (28 mL). The mixture was hydrogenated under 4 bars of H₂ pressure overnight at r.t. The mixture was filtered through a pad of Celite® which was washed with EtOAc, MeOH and DCM. The combined filtrates were concentrated. The residue (863 mg) was purified by chromatography over silica gel (Regular SiOH; 30 µm, 40 g, mobile phase gradient from 98% DCM, 2% MeOH, 0.1% NH₄OH to 96% DCM, 4% MeOH, 0.1% NH₄OH). The pure fractions were collected and evaporated until dryness to give 160 mg of Int. 24 as a colorless oil (14%).

f—Synthesis of Int. 12:

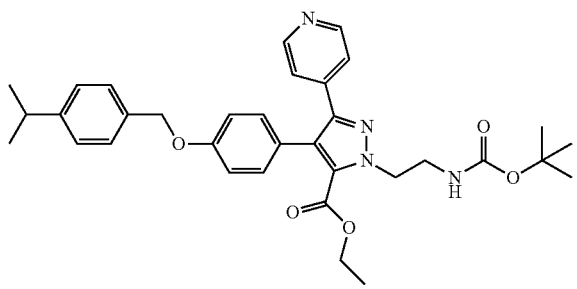 [SMILES: CCOC(=O)c1c(-c2ccc(OCc3ccc(C(C)C)cc3)cc2)c(-c2ccncc2)nn1CCNC(=O)OC(C)(C)C]

To a mixture of 24 (158 mg, 0.35 mmol), 6 (79 mg, 0.53 mmol) and PPh₃ (164 mg, 0.53 mmol) in dry THF (11 mL) was added DBAD (121 mg, 0.53 mmol). The mixture was stirred at r.t. overnight. The mixture was filtered through a pad of Celite®, washed with DCM and the solvent was concentrated. The residue was purified by chromatography over silica gel (irregular SiOH 15-40 μm, 12 g, mobile phase gradient from 98% DCM, 2% MeOH, 0.1% NH₄OH to 94% DCM, 6% MeOH, 0.1% NH₄OH) to give 140 mg of the Int. 12 (69%).

Finally, Int. 12 was reacted to Co. 1 by analogous methods as described in Example A2.d or A3.e.

Example A5

Preparation of Co. 70 and Co. 1 (5th Approach)

a—Synthesis of Int. 25:

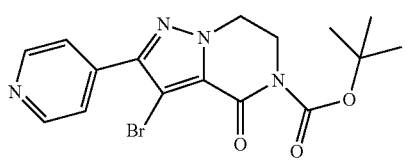 [SMILES: CC(C)(C)OC(=O)N1CCn2nc(-c3ccncc3)c(Br)c2C1=O]

To a suspension of 4 (7.5 g, 34.1 mmol), DMAP (0.83 g, 6.8 mmol), Et₃N (14.3 mL, 102 mmol) in THF (170 mL), (Boc)₂O was added portionwise at r.t. The r.m. was stirred at r.t for 3 h. H₂O and DCM were added. The organic layer was extracted, dried over MgSO₄, filtered and evaporated. The residue was purified by prep. LC (Irregular SiOH 35-40 μm, 120 g GraceResolv™, mobile phase gradient from 100% DCM to 95% DCM 5% MeOH 0.1% NH₄OH). The fractions were collected and evaporated until dryness to give 12.4 g of Int. 25 (92%).

b—Synthesis of Co. 70:

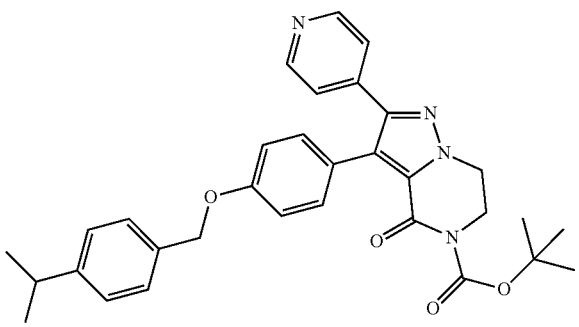 [SMILES: CC(C)c1ccc(COc2ccc(-c3c(-c4ccncc4)nn4c3C(=O)N(C(=O)OC(C)(C)C)CC4)cc2)cc1]

A mixture of 25 (29.4 g, 74.8 mmol), 5 (34.2 g, 97.2 mmol), K₃PO₄ (63.5 g, 300 mmol) in 1,4-dioxane (380 mL) and H₂O (120 mL) was purged with N₂ for 10 min. Then PdCl₂(dppf) (6.1 g, 7.5 mmol) was added and purged with N₂ for 10 min. The reaction was heated to 72° C. for 3 h. The mixture was poured into a aq. sol. of K₂CO₃ and extracted with EtOAc. The organic layer was dried over MgSO₄, filtered and evaporated until dryness. The residue was purified by prep. LC (irregular SiOH 220 g 35-40 μm GraceResolv™+300 g 30 μm Interchim, mobile phase gradient from 100% DCM to 95% DCM, 5% MeOH, 0.1% NH₄OH). The fractions were collected and evaporated until dryness to give two fractions: 28 g of impure Co.70 and 20.6 g of the Co. 70. The impure fraction (28 g) was purified by prep. LC (irregular SiOH 220 g+330 g 35-40 μm GraceResolv™, mobile phase gradient from 100% DCM to 95% DCM, 5% MeOH, 0.1% NH₄OH). The pure fractions were collected and evaporated until dryness to give 11.14 g of Co. 70. Global yield: 31.7 g of Co. 70 (79%).

c—Synthesis of Co. 1:

A sol. of Co. 70 (34.6 g, 64.2 mmol) and HCl 3N (215 mL) in ACN (1700 mL) was heated to 80° C. for 1 h. Ice was added and the mixture was basified with K₂CO₃ and stirred for 10 min. The mixture was filtered off, washed with H₂O then ACN and dried to give 24.55 g of Co. 1 (87%). m.p.: 262° C. (DSC).

Example A6

Preparation of Co. 2 (1st Approach)

a—Synthesis of Int. 27:

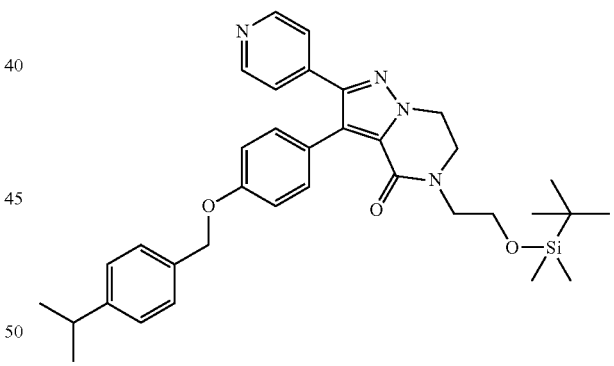

NaH (60%) (1.64 g, 41 mmol) was slowly added to a suspension of Co. 1 (12 g, 27.4 mmol) in DMF (180 mL) at r.t. under N₂. The mixture was stirred for 2 h. Then (2-bromomethoxy)-tert-butyldimethylsilane (7 mL, 32.8 mmol) was added and the r.m. was stirred for 15 h. The reaction was poured into water and K₂CO₃ and extracted with EtOAc. The organic layer was evaporated until dryness. The residue was taken up with DCM, dried over MgSO₄, filtered and evaporated until dryness. The residue was purified by prep. LC (Irregular silica gel 35-40 μm, 330 g GraceResolv™, mobile phase gradient from 100% DCM to 95% DCM, 5% MeOH, 0.1% NH₄OH). The fractions were collected and evaporated to give 15.52 g of Int. 27 (95%).

b—Synthesis of Co. 2:

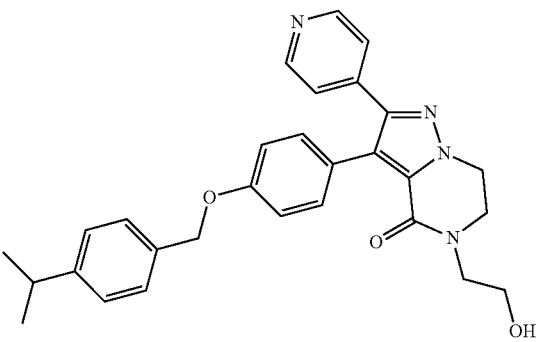 [SMILES: CC(C)c1ccc(COc2ccc(-c3c(-c4ccncc4)nn4c3C(=O)N(CCO)CC4)cc2)cc1]

TBAF (1M in THF) (30.6 mL, 30.6 mmol) was added dropwise to a sol. of 27 (15.2 g, 25.5 mmol) in THF (150 mL) at room temperature. The mixture was stirred for 2 days. The mixture was evaporated. The residue was purified by prep. LC (Irregular silica gel SiOH 35-40 μm, 330 g GraceResolv™, mobile phase gradient from 100% DCM to 95% DCM, 5% MeOH, 0.1% NH$_4$OH). The fractions were collected and evaporated until dryness to give 11.9 g of Co. 2 (97%).

Example A7

Preparation of Co. 2 (2$^{nd}$ Approach)

a—Synthesis of Int. 28:

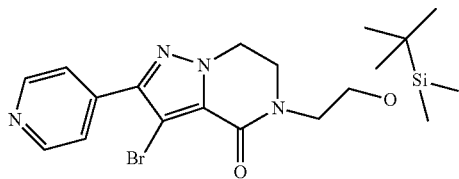

NaH (60%) (4.9 g, 123 mmol) was added to a suspension of 4 (30 g, 102 mmol) in DMSO (450 mL) at r.t. under N$_2$. The mixture was stirred for 2 h. (2-Bromomethoxy)-tert-butyldimethylsilane (26.35 mL, 123 mmol) was added and stirred for 24 h. The mixture was poured into a sat. aq. sol. of K$_2$CO$_3$ and extracted with EtOAc. The organic layer was evaporated until dryness. The residue was taken up with DCM, filtered and the filtrate was evaporated until dryness. The residue was purified by prep. LC (Irregular silica gel 35-40 μm, 330 g GraceResolv™, gradient from 100% DCM to 95% DCM, 5% MeOH, 0.1% NH$_4$OH). The fractions were collected and evaporated until dryness to give 37.3 g of the Int. 28 (81%).

b—Synthesis of Int. 27:

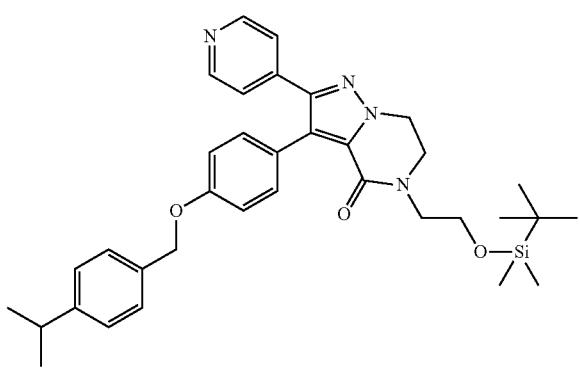 [SMILES: CC(C)c1ccc(COc2ccc(-c3c(-c4ccncc4)nn4c3C(=O)N(CCO[Si](C)(C)C(C)(C)C)CC4)cc2)cc1]

28 (26 g, 57.6 mmol), f (26.4 g, 74.9 mmol) and K$_3$PO$_4$ (47 g, 230 mmol) in 1,4-dioxane (270 mL) and H$_2$O (91 mL) in a sealed reactor were purged with N$_2$ for 10 min. PdCl$_2$(dppf) (4.7 g, 5.8 mmol) was added and purged with N$_2$ for 10 min. The mixture was heated to 82° C. for 20 h. The r.m. was poured into a sat. aq. sol. of K$_2$CO$_3$ and extracted with EtOAc. The organic layer was dried over MgSO$_4$, filtered and evaporated until dryness. The residue was purified by prep. LC (irregular SiOH 35-40 μm, 330 g GraceResolv™, gradient from 100% DCM to 97% DCM, 3% MeOH, 0.1% NH$_4$OH). The fractions were collected and evaporated until dryness to give 32 g of Int. 27 (97%).

c—Synthesis of Co. 2: same procedure as A6b

Example A8

Preparation of Co. 3 a—Synthesis of Int. 30:

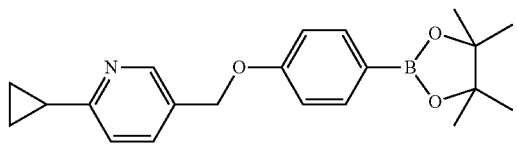

DBAD (2.01 g, 8.71 mmol) was added to a mixture of 7 (1.48 g, 6.70 mmol), 29 (6-cyclopropyl-3-pyridinemethanol) (1.3 g, 8.71 mmol) and PPh$_3$ supp. (2.91 g, 8.71 mmol) in DCM (30 mL). The r.m. was stirred under N$_2$ for 17 h at r.t. The sol. was filtered and the residual polymer was washed with DCM. Then, the filtrate was evaporated in vacuo to give 4.80 g of a residue. This residue was purified by prep. LC (irregular SiOH 15-40 nm, 50 g Merck, mobile phase gradient: from Heptane 100% to EtOAc 20%, Heptane 80%). The pure fractions were collected and solvent was evaporated until dryness to give 2.22 g of the Int. 30 as a white solid (94%).

b—Synthesis of Co. 3:

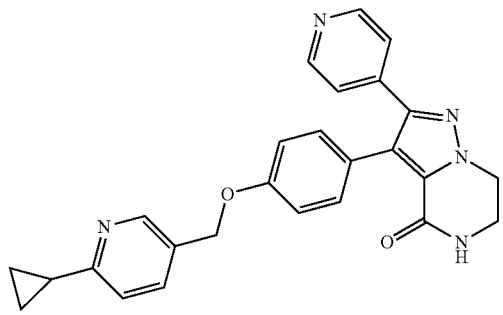 [SMILES: O=C1NCCn2nc(-c3ccncc3)c(-c3ccc(OCc4ccc(C5CC5)nc4)cc3)c21]

In a Schlenk tube, a mixture of 4 (0.3 g, 1.02 mmol), 30 (1.08 g, 3.07 mmol), K$_3$PO$_4$ (0.869 g, 4.09 mmol) in 1,4-dioxane (4.5 mL) and H$_2$O (1.5 mL) was carefully purged with N$_2$. PCy$_3$ (57 mg, 0.205 mmol) and Pd(OAc)$_2$ (23 mg, 102 mol) were added and the r.m. was purged again with N$_2$. The Schlenk tube was then sealed and the r.m. was stirred for 17 h at 80° C. The crude material was dissolved in water (7 mL) and filtered on glass frit. The grey precipitate was washed with water (2×20 mL) and with Et$_2$O (2×40 mL). The solid was collected to afford 360 mg of a residue as a grey solid. This residue was purified by prep. LC (irregular SiOH 15-40 μm, 30 g Merck, mobile phase gradient: from DCM 100% to DCM 90%, MeOH 10%) to give 260 mg of Co. 3 as a white solid (58%). m.p.: 276° C. (DSC).

Example A9

Preparation of Co. 4 a—Synthesis of Int. 32:

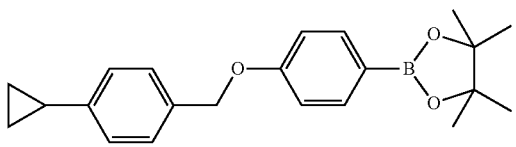 [SMILES: CC1(C)OB(c2ccc(OCc3ccc(C4CC4)cc3)cc2)OC1(C)C]

Under $N_2$, DBAD (15.5 g, 67 mmol) was added portionwise to a sol. of 31 (4-cyclopropyl-benzenemethanol) (10 g, 67 mmol), 7 (15 g, 67 mmol), $PPh_3$ (17.7 g, 67 mmol) in dry THF (500 mL). The r.m. was stirred at r.t. overnight THF was evaporated to give 64 g of a residue as a yellow oil. The crude residue was purified by prep. LC (irregular SiOH 30 μm 220+330 g GraceResolv™, mobile phase: 90% Heptane, 10% EtOAc). The pure fractions were collected and solvent evaporated to give 19.7 g of Int. 32 as white solid (83%).

b—Synthesis of Co. 4:

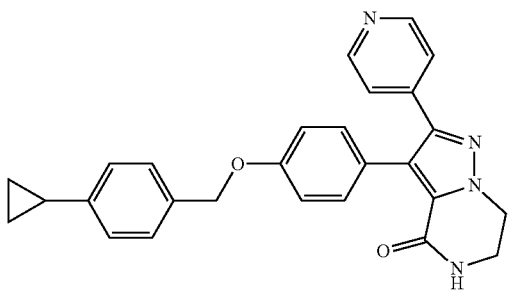 [SMILES: O=C1NCCn2nc(-c3ccncc3)c(-c3ccc(OCc4ccc(C5CC5)cc4)cc3)c21]

A mixture of 4 (1 g, 3.4 mmol), 32 (2.39 g, 6.8 mmol), $K_3PO_4$ (2.9 g, 13.6 mmol) in 1,4-dioxane (17 mL) and $H_2O$ (6.2 mL) was carefully purged with $N_2$. $Pd(OAc)_2$ (0.077 g, 0.34 mmol) and $PCy_3$ (0.19 g, 0.68 mmol) were added and the r.m. was purged again with $N_2$. The r.m. was stirred for 20 h at 80° C. The mixture was poured into water and EtOAc was added. The mixture was filtered off and washed with DCM and MeOH. The different organic layers were put together, dried over $MgSO_4$, filtered and evaporated until dryness to give 2.5 g of a residue. This residue was purified by prep. LC (regular of SiOH 30 μm, 40 g Interchim, mobile phase gradient from 100% DCM to 95% DCM, 5% MeOH, 0.1% $NH_4OH$). The fractions were collected and evaporated until dryness to give a residue which was crystallized from MeOH, filtered and dried to give 0.708 g. The product was purified by prep. LC on (irregular SiOH 15-40 μm 30 g MERCK, mobile phase 0.1% $NH_4OH$, 98% DCM, 2% MeOH). The pure fractions were collected and the solvent was evaporated until dryness to give 600 mg which was crystallized from $Et_2O$, filtered and dried to give 587 mg of Co. 4 (39%). m.p.: 262° C. (dsc).

Example A10

Preparation of Co. 5 a—Synthesis of Int. 34:

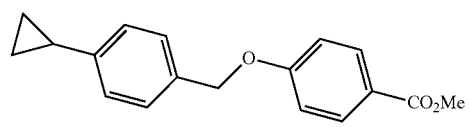 [SMILES: COC(=O)c1ccc(OCc2ccc(C3CC3)cc2)cc1]

To a mixture of 33 (3.94 g, 25.9 mmol), 31 (4.60 g, 31.0 mmol) and diphenylphosphinopolystyrene (10.3 g, 31.0 mmol) in dry THF (40 mL) was added DBAD (7.15 g, 31.0 mmol). The mixture was stirred at r.t. for 18 h, then filtered on a glass frit and the solid was washed with EtOAc. The filtrate was evaporated in vacuo to give a residue as a yellow solid. The residue was triturated with $Et_2O$ to give 4.50 g of Int. 34 as an off-white solid (62%).

b—Synthesis of Int. 35:

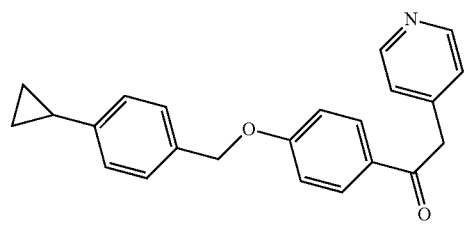 [SMILES: O=C(Cc1ccncc1)c1ccc(OCc2ccc(C3CC3)cc2)cc1]

In a dry flask under $N_2$, a sol. of 34 (4.50 g, 15.9 mmol) and 4-picoline (1.71 mL, 17.5 mmol) in THF (30 mL) was cooled to 0° C. and treated with LiHMDS (47.8 mL, 47.8 mmol) (slow addition over 10 min). The r.m. was stirred at r.t. for 17 h and quenched with a sat. aq. sol. of $NH_4Cl$. The insoluble was filtered off, washed with $Et_2O$ and dried in vacuo to give 4.52 g of Int. 35, as a yellow solid (83%).

c—Synthesis of Int. 36:

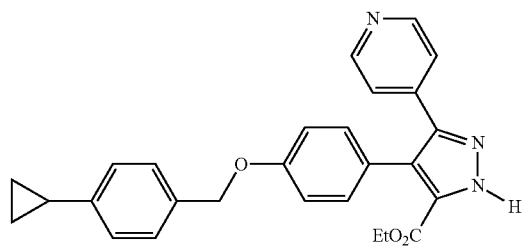 [SMILES: CCOC(=O)c1[nH]nc(-c2ccncc2)c1-c1ccc(OCc2ccc(C3CC3)cc2)cc1]

To a suspension of 35 (4.50 g, 13.1 mmol) in ACN (45 mL) in a sealed tube was added DBU (1.96 mL, 13.1 mmol) and ethyl diazoacetate (2.34 mL, 22.3 mmol). The mixture was heated at 100° C. for 2 h then cooled down to r.t. The solvent was removed in vacuo and the residue was diluted with DCM. The organic layer was successively washed with a sat. aq. sol. of $NaHCO_3$ and water, dried ($MgSO_4$), filtered and evaporated in vacuo to give a brown residue. The residue was dissolved in DCM and a precipitate was filtered to give 2.84 g of Int. 36 as a pale yellow solid (49%). The filtrate was purified by prep. LC (Irregular SiOH 15-40 μm, 50 g Merck, mobile phase gradient: from DCM 100% to DCM 90%, MeOH 10%). The pure fractions were collected and solvent was evaporated to give 754 mg of Int. 36 as yellow solid (13%). Global yield: 62%.

d—Synthesis of Int. 37:

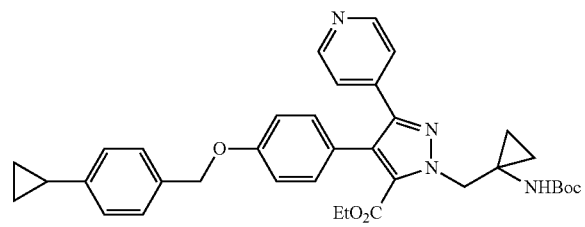 [SMILES: CCOC(=O)c1c(-c2ccc(OCc3ccc(C4CC4)cc3)cc2)c(-c2ccncc2)nn1CC1(NC(=O)OC(C)(C)C)CC1]

To a mixture of 36 (0.615 g, 1.40 mmol), 1-(boc-amino)cyclopropylmethanol (0.275 g, 1.47 mmol) and diphenylphosphinopolystyrene (0.933 g, 2.80 mmol) in dry THF (12 mL) was added DBAD (0.644 g, 2.80 mmol). The mixture was stirred for 72 h at r.t. then filtered through a glass frit and washed with EtOAc. The filtrate was evaporated in vacuo to give 1.54 g of yellow oil. The residue was purified by prep. LC (Irregular SiOH, 15-40 µm, 50 g Merck, mobile phase gradient: from DCM 100% to DCM 60%, EtOAc 40%) to give 636 mg of Int. 37 as a white foam (75%).

e—Synthesis of Int. 38:

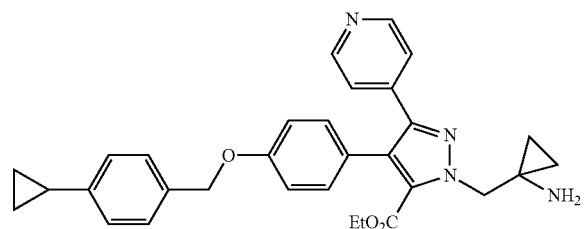

To a sol. of 37 (0.636 g, 1.05 mmol) in 1,4-dioxane (8 mL) was added HCl 4M in dioxane (2.10 mL, 8.36 mmol). The sol. was stirred at r.t. for 18 h and was then poured out into Et$_2$O. The precipitate was filtered through a glass frit to give 584 mg of Int. 8 as a white solid (100%).

f—Synthesis of Co. 5:

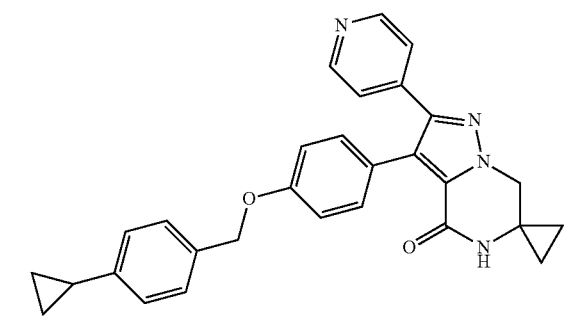 [SMILES: O=C1NC2(CC2)Cn2nc(-c3ccncc3)c(-c3ccc(OCc4ccc(C5CC5)cc4)cc3)c21]

To a sol. of 38 (0.584 g, 1.07 mmol) in MeOH (10 mL) was added Cs$_2$CO$_3$ (1.75 g, 5.36 mmol) and the mixture was stirred at r.t. for 4 h. The solvent was removed in vacuo and water (25 mL) and DCM (25 mL) were added to the residue. The layers were separated and the aq. layer was extracted with DCM (25 mL). The organic layers were combined, dried over MgSO4, filtered off and evaporated in vacuo to give 419 mg of Co. 5 as a white solid (85%). m.p.: 239° C. (DSC).

Example A11

Preparation of Co. 6 a—Synthesis of Int. 41:

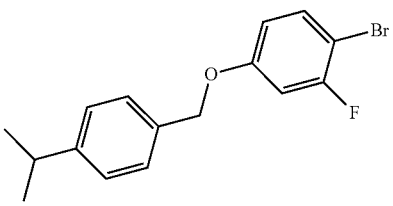 [SMILES: CC(C)c1ccc(COc2ccc(Br)c(F)c2)cc1]

Under N$_2$, a sol. of 40 (4-bromo-3-fluorophenol) (1 g, 58 mmol) in ACN (150 mL) was treated with K$_2$CO$_3$ (16 g, 117 mmol) and 8 (4-isopropylbenzyl bromide) (9.7 mL, 58 mmol) and the r.m. was stirred under reflux for 2 h. The sol. was filtrated and concentrated to give 18.9 g of Int. 41 colorless oil (100%) which was used like this in the next step.

b—Synthesis of Int. 42:

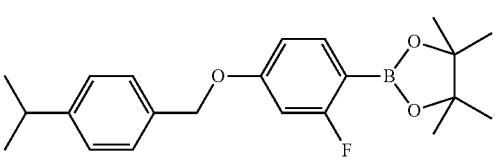 [SMILES: CC(C)c1ccc(COc2ccc(B3OC(C)(C)C(C)(C)O3)c(F)c2)cc1]

First method: In a sealed tube, a mixture of 41 (1.00 g, 3.09 mmol), KOAc (0.911 g, 9.28 mmol), BisPin (0.943 g, 3.71 mmol) in DME (9 mL) was carefully purged with N$_2$. PdCl$_2$(dppf) (0.253 g, 0.309 mmol) was added and the r.m. was purged again with N$_2$. The r.m. was stirred for 17 h at 100° C. The r.m. was diluted with EtOAc and washed with water (once) and with brine (3×). The organic phase was dried over MgSO$_4$, filtered and evaporated in vacuo to give 2.00 g of a brown oil. The residue was purified by prep. LC (irregular SiOH 15-40 µm, 50 g, MERCK, Mobile phase gradient from 100% Heptane to 80% Heptane, 20% EtOAc). The pure fractions were collected and solvent evaporated to give 903 mg of Int. 42, colorless oil (79%).

Second method: To a sol. of 39 (4-hydroxy-2-fluorophenylboronic acid pinacol ester) (1.10 g, 4.62 mmol) in ACN (45 mL) were added 8 (0.985 g, 4.62 mmol) and K$_2$CO$_3$ (1.28 g, 9.24 mmol). The reaction was heated at 80° C. for 2 h and cooled down to r.t. The mixture was filtered on a glass frit and evaporated in vacuo to give 1.78 g of Int. 42, colorless oil which crystallized as a white solid (100%). Int 42 was used without purification in the next step.

c—Synthesis of Co. 6

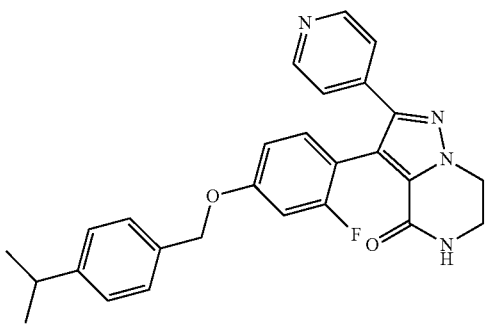 [SMILES: CC(C)c1ccc(COc2ccc(-c3c(-c4ccncc4)nn4c3C(=O)NCC4)c(F)c2)cc1]

In a microwave vial, a mixture of 4 (0.594 g, 2.0 mmol), 42 (1.5 g, 4.0 mmol), K₃PO₄ (1.72 g, 8.1 mmol) in 1,4-dioxane (9.0 mL) and H₂O (3.2 mL) was carefully purged with N₂. PdCl₂(dppf) (0.166 g, 202 μmol) was added and the r.m. was purged again with N₂. The r.m. was heated at 80° C. overnight. The crude material was diluted in DCM and washed with a sat. sol. of NaHCO₃. The organic layer was dried over MgSO₄, filtered and evaporated in vacuo to afford brown oil. The oil was purified by prep. LC (irregular SiOH 15-40 μm, 40 g GraceResolv™, mobile phase gradient: from DCM 100% to DCM 97%, MeOH 3%). The pure fractions were collected and solvent was evaporated until dryness to give 905 mg of a beige solide which was crystallized from MeOH, washed with Et₂O, filtrated and dried to give 560 mg of Co. 6 as a white powder (61%). m.p. 271° C. (dsc).

Example A12

Preparation of Co. 7 a—Synthesis of Int. 43:

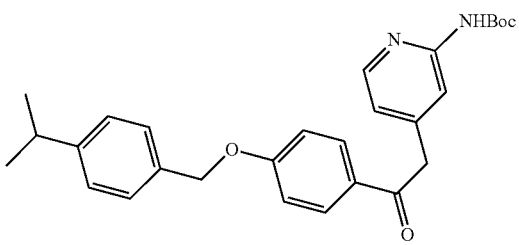 [SMILES: CC(C)c1ccc(COc2ccc(C(=O)Cc3ccnc(NC(=O)OC(C)(C)C)c3)cc2)cc1]

A sol. of 9 (2.0 g, 7.0 mmol) and 2-(4-methyl-2-pyridinyl)-imidodicarbonic acid, 1,3-bis(1,1-dimethylethyl) ester (2.17 g, 7.0 mmol) in dry THF (20 mL) was treated with LiHMDS (14 mL, 14 mmol) at 0° C. (addition over 10 min). After stirring for 1 h at 0° C., the reaction was allowed to warm to r.t. and was stirred for 17 h. The reaction was quenched with a 10% aq. sol. of NH₄Cl (50 mL). The mixture was extracted with DCM. The organic layers were collected and evaporated in vacuo and the residue was purified by prep. LC (Irregular SiOH 15-40 μm, 80 g GraceResolv™, mobile phase gradient: heptane/EtOAc from 80/20 to 60/40). The pure fractions were collected and evaporated to give 1.98 g of Int. 43 white solid (61%).

b—Synthesis of Int. 44:

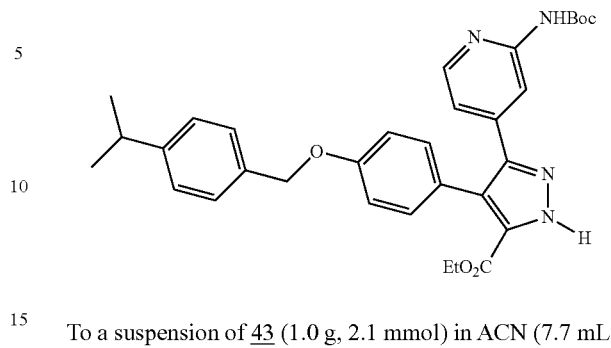

To a suspension of 43 (1.0 g, 2.1 mmol) in ACN (7.7 mL) in a sealed tube was added DBU (0.33 mL, 2.2 mmol) and ethyl diazoacetate (0.39 mL, 3.7 mmol). The mixture was heated at 100° C. for 2 h then cooled down to r.t. The solvent was removed in vacuo and the residue was diluted in EtOAc. The organic layer was washed with a sat. aq. sol. of NaHCO₃, water, dried over MgSO₄, filtered off and evaporated in vacuo. The residue was purified by prep. LC (irregular SiOH 15-40 μm, 40 g GraceResolv™, mobile phase gradient, from 70% Heptane, 30% EtOAc to 60% Heptane, 40% EtOAc). The pure fractions were collected and solvent was evaporated until dryness to give 504 mg of Int. 44, beige powder (42%).

c—Synthesis of Int. 45:

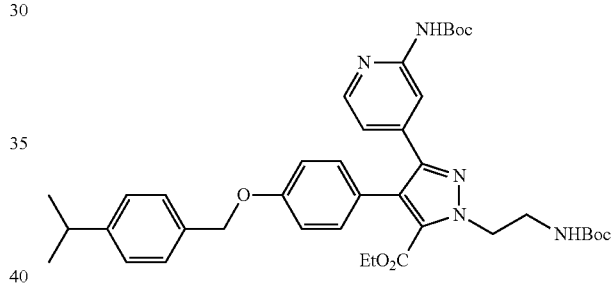

To a mixture of 44 (0.428 g, 0.77 mmol), Boc-Glycinol (0.149 g, 0.92 mmol) and PPh₃ (0.242 g, 0.92 mmol) in dry THF (20 mL) was added DBAD (0.212 g, 0.92 mmol). The mixture was stirred for 4 h at r.t. The mixture was concentrated and the residue was purified by prep. LC (irregular SiOH 15-40 μm, 40 g GraceResolv™, Mobile phase: 70% heptane, 30% EtOAc). The pure fractions were collected and solvent was evaporated until dryness to give 0.55 g of Int. 45, as a white solid (100%).

d—Synthesis of Int. 46:

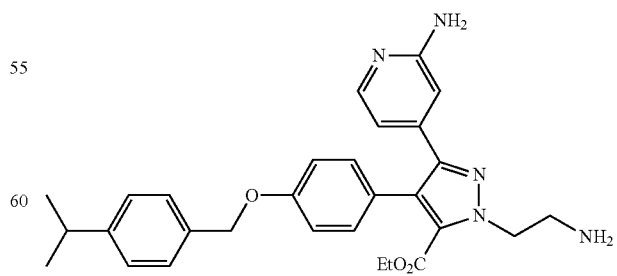

A solution of 45 (0.75 g, 1.1 mmol), HCl (3N) (1.8 mL, 5.4 mmol), in ACN (19 mL) was stirred at 80° C. for 3 h. ACN was concentrated, K₂CO₃ 10% aq was added and the mixture was extracted with DCM. The organic layer was dried over MgSO$_4$, filtered and evaporated in vacuo to give 0.49 g of Int. 46, white solid (92%).

e—Synthesis of Co. 7:

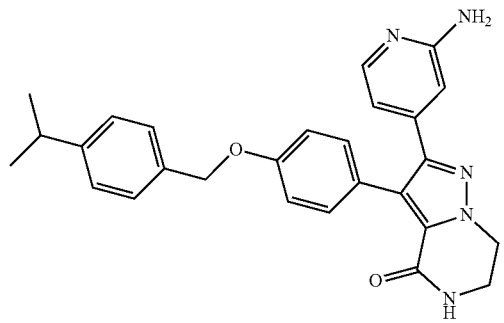 [SMILES: CC(C)c1ccc(COc2ccc(-c3c(-c4ccnc(N)c4)nn4c3C(=O)NCC4)cc2)cc1]

To a sol. of 46 (0.49 g, 0.98 mol) in MeOH (28 mL) was added Cs$_2$CO$_3$ (1.6 g, 4.9 mmol) and the mixture was stirred at r.t. overnight. The mixture was filtered, the white solid was collected and dried to give 0.28 g of Co. 7, white solid (63%). m.p.: 267° C. (dsc).

Example A13

Preparation of Co. 8 a—Synthesis of Int. 47

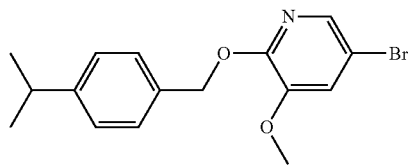 [SMILES: COc1cc(Br)cnc1OCc1ccc(C(C)C)cc1]

NaH 60% (0.275 g, 6.87 mmol) was added to a stirred suspension of 6 (0.967 g, 6.44 mmol) and 5-bromo-2-chloro-3-methoxypyridine (0.955 g, 4.29 mmol) in dry THF (16 mL) at 0° C. under N$_2$. The mixture was stirred 10 min at 0° C. under N$_2$, and the vial was sealed. Then the r.m. was stirred at 110° C. using one single mode microwave (Biotage Initiator EXP 60) with a power output ranging from 0 to 400 W for 140 min. [fixed hold time]. The crude mixture was quenched with water and extracted with EtOAc. The organic layer was separated, washed with brine, dried over MgSO$_4$, filtered and concentrated in vacuo. The solid residue was purified by trituration with MeOH, filtration and washing with MeOH, to give 0.785 g of Int. 47, white solid (54%).

b—Synthesis of Int. 48:

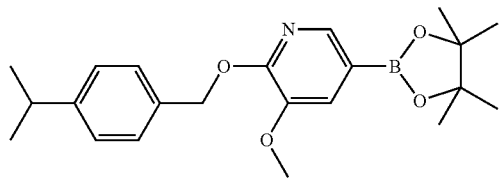

In a sealed tube, a mixture of 47 (751 mg, 2.23 mmol), BisPin (681 mg, 2.68 mmol) and KOAc (658 mg, 6.70 mmol) in DME (12.5 mL) was carefully purged with N$_2$. PdCl$_2$(dppf) (183 mg, 0.223 mmol) was added and the r.m. was purged again with N$_2$. The r.m. was stirred for 17 h at 100° C. The r.m. was diluted with EtOAc and water. The organic layer was washed with brine, dried over MgSO$_4$, filtered and evaporated in vacuo to give 572 mg of a solid. The residue was purified by prep. LC (irregular SiOH 15-40 µm, 50 g, Merck, Mobile phase gradient: from 100% Heptane to 60% Heptane, 40% EtOAc). The pure fractions were collected and solvent was evaporated until dryness to give 335 mg of Int. 48, solid (39%).

c—Synthesis of Co. 8:

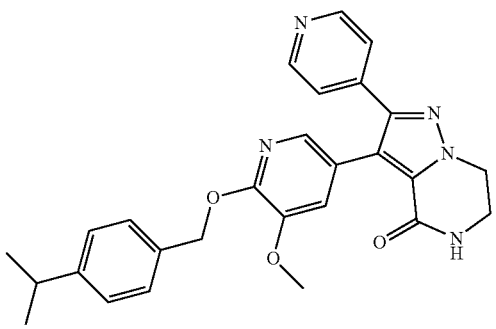 [SMILES: COc1cc(-c2c(-c3ccncc3)nn3c2C(=O)NCC3)cnc1OCc1ccc(C(C)C)cc1]

A mixture of 4 (128 mg, 0.437 mmol), 48 (335 mg, 0.874 mmol), K$_3$PO$_4$ (371 mg, 1.75 mmol) in 1,4-dioxane (3 mL) and H$_2$O (1 mL) was carefully purged with N$_2$. PCy$_3$ (25 mg, 87 µmol) and Pd(OAc)$_2$ (10 mg, 43.7 µmol) were added, and the r.m. was purged again with N$_2$, and stirred for 15 h at 80° C. The crude material was treated with water and extracted with DCM. The organic layer was washed with brine, dried over MgSO$_4$, filtered and evaporated in vacuo to give a black solid. The solid was purified by prep. LC on (irregular SiOH 15-40 µm 24 g Grace, Mobile phase gradient: from 100% DCM to 8% MeOH, 92% DCM). The fractions were combined and the solvent was removed in vacuo to give 146 mg of a white solid. The solid was purified by Reverse phase on (X-Bridge-C18 5 µm 30*150 mm, Mobile phase: Gradient from 40% formic acid 0.1%, 60% MeOH to 100% MeOH). The pure fractions were isolated and concentrated in vacuo to yield 110 mg of Co. 8, white solid (54%). m.p. 135° C. (dsc).

Example A14

Preparation of Co. 9a and 9 a—Synthesis of Int. 49:

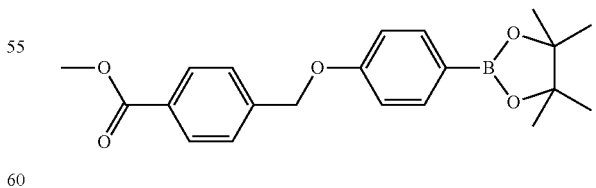

7 (1.1 g, 4.85 mmol), methyl 4-(bromomethyl)benzoate (1.1 g, 4.8 mmol), K$_2$CO$_3$ (1g, 7.2 mmol) in ACN (20 mL) were stirred at r.t. for 8 h. Then, the mixture treated with water and extracted with EtOAc. The organic phase was dried over MgSO4, filtered and evaporated in vacuo to give a solid. The solid was purified by prep. LC (irregular SiOH 15-40 µm, 40 g Grace, mobile phase: 70% heptanes, 30%

EtOAc). The pure fractions were collected and solvent was evaporated to give 1.5 g of Int. 49 (87%).

b—Synthesis of Co. 9a:

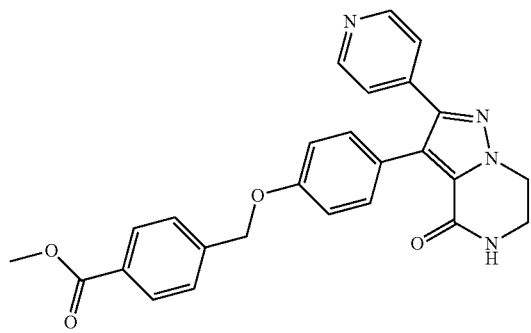 [SMILES: COC(=O)c1ccc(COc2ccc(-c3c(-c4ccncc4)nn4c3C(=O)NCC4)cc2)cc1]

In a sealed tube, a mixture of 4 (438 mg, 1.5 mmol), 49 (0.5 g, 1.3 mmol), $K_3PO_4$ (1.1 g, 5.4 mmol) in 1,4-dioxane (8 mL) and $H_2O$ (2 mL) was carefully purged with $N_2$. $PCy_3$ (80 mg, 0.28 mmol) and $Pd(OAc)_2$ (32 mg, 0.1 mmol) were added and the r.m. was purged again with $N_2$. The r.m. was stirred for 8 h at 80° C. Water and DCM were added, the mixture was extracted, the organic layer was separated, dried over $MgSO_4$, filtered and evaporated until dryness to give 0.8 g of a residue. The residue was purified by prep. LC on (irregular SiOH 15-40 µm 30 g Merck, Mobile phase: 0.1% $NH_4OH$, 96% DCM, 4% MeOH). The pure fractions were collected and the solvent evaporated until dryness to give 250 mg of Co. 9a. (41%, dsc m.p.: 254° C.).

c—Synthesis of Co. 9:

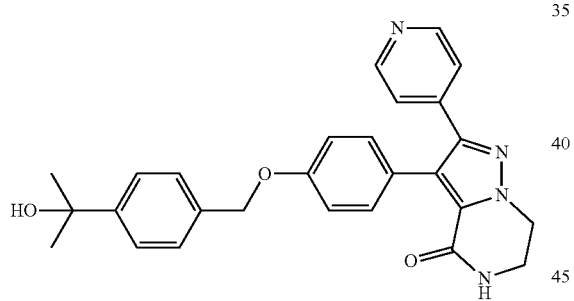

MeMgCl (0.567 mL, 1.68 mmol) was added to a stirred suspension of Co.9a (153 mg, 0.337 mmol) in THF (5 mL) under N2 at 0° C. The mixture was stirred at 0° C. for 5 min, and then it was warmed to r.t. and stirred for 2 h. The r.m. was quenched with 10% $NH_4Cl$ sol., and treated with EtOAc and a mixture of MeOH/DCM (90:10). The organic layer was separated, washed with brine, dried over $MgSO_4$, filtered and concentrated in vacuo to afford 143 mg of a white solid. The solid was purified by trituration with DCM, filtration and washing with DCM, to give a solid that was dried in vacuo. The residue (100 mg) was purified by achiral SFC (diethylaminopropyl 5 µm 150×21.2 mm; Mobile phase gradient: from 0.3% $iPrNH_2$, 80% $CO_2$, 20% MeOH to 0.3% $iPrNH_2$, 60% $CO_2$, 40% MeOH). The fractions were collected and concentrated in vacuo to yield 74 mg which was purified by Reverse phase (X-Bridge-C18 5 µm 30*150 mm; Mobile phase gradient: from 80% ($NH_4HCO_3$ 0.5% aq. sol.), 20% ACN to 100% ACN). The fractions were collected and concentrated in vacuo to give 28 mg of a solid residue. The resulting solid was suspended in ACN and water (20/80), freezed and dried in vacuo to afford 20 mg of Co. 9, white solid (13%). m.p.: 290° C. (dsc).

Example A15

Preparation of Co. 10 a—Synthesis of Int. 51:

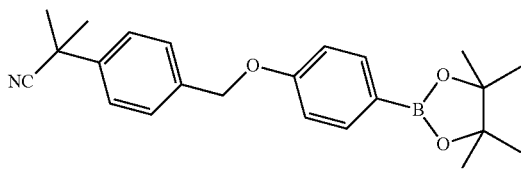 [SMILES: CC(C)(C#N)c1ccc(COc2ccc(B3OC(C)(C)C(C)(C)O3)cc2)cc1]

To a suspension of 7 (2.5 g, 11.3 mmol), 2-[4-(hydroxymethyl)phenyl]-2-methylpropanenitrile (1.8 g, 10.3 mmol), $PPh_3$ supp (3.8 g, 12.3 mmol) in dry DCM (50 mL) was added DBAD (2.8 g, 12.3 mmol) and the r.m. was stirred at r.t. for 18 h. The mixture was filtered through Celite®, washed with DCM and the filtrate was evaporated until dryness. The residue (7 g) was purified by prep. LC (irregular SiOH 35-40 µm, 90 g GraceResolv™, gradient from 95% heptanes, 5% EtOAc to 80% heptanes, 20% EtOAc). The fractions were collected and evaporated until dryness to give 2.1 g of Int. 51 (54%).

b—Synthesis of Co. 10:

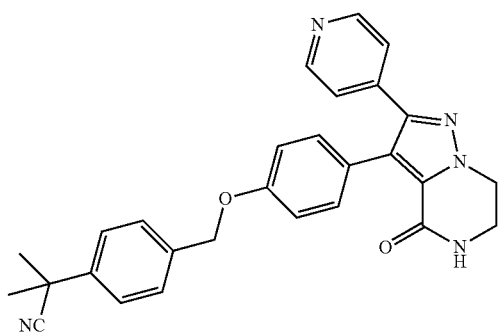 [SMILES: CC(C)(C#N)c1ccc(COc2ccc(-c3c(-c4ccncc4)nn4c3C(=O)NCC4)cc2)cc1]

A mixture of 4 (400 mg, 1.36 mmol), 51 (0.77 g, 2 mmol), $K_3PO_4$ (1.16 g, 5.46 mmol) in 1,4-dioxane (7 mL) and $H_2O$ (3 mL) was carefully purged with $N_2$. $PCy_3$ (80.4 mg, 0.29 mmol) and $Pd(OAc)_2$ (32 mg, 0.14 mmol) were added and the r.m. was purged again with $N_2$. The r.m. was stirred for 8 h at 80° C. The crude material was poured in water and EtOAc was added. The mixture was filtered through Celite®. The organic phase was dried over MgSO4, filtered and evaporated in vacuo to give 1.5 g of a pale yellow solid. The solid was taken up in $Et_2O$, the precipitate was filtered off and dried in vacuo to give 700 mg of a residue. The residue was purified by prep. LC on (Stability Silica 5 µm 150×30.0 mm, mobile phase Gradient: from $NH_4OH$/DCM/MeOH 0.2/98/2 to $NH_4OH$/DCM/MeOH 0.8/92/8). The pure fractions were collected and solvent was evaporated until dryness to give 250 mg which was crystallized from $Et_2O$, filtered and dried to give 210 mg of Co.10 (33%). m.p.: 280° C. (dsc).

Example A16

Preparation of Co. 11 a—Synthesis of Int. 52:

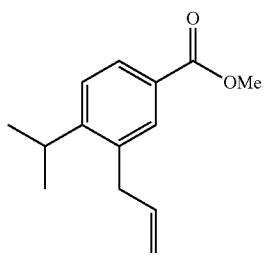 [SMILES: C=CCc1cc(C(=O)OC)ccc1C(C)C]

To a sol. of 3-bromo-4-(1-methylethyl)-benzoic acid, methyl ester (1.2 g, 4.7 mmol) in dry DMF (36 mL) degazed under N$_2$ were added Pd(PPh$_3$)$_4$ (270 mg, 0.23 mmol) and allyltri-N-butyltin (1.85 g, 5.6 mmol). The mixture was flushed again with N$_2$ for 5 min and heated at 80° C. overnight. After cooling, the mixture was partitioned between EtOAc and brine, and the organic layer was washed twice with brine, dried and concentrated to give 3.5 g of yellow oil. This oil was purified by prep. LC (irregular SiOH 15-40 µm, 80 g, GraceResolv™, Mobile phase gradient: from 95% heptane, 5% EtOAc to 90% heptane, 10% EtOAc). The pure fractions were collected and solvent was evaporated to give 900 mg of Int. 52, colorless oil (88%).

b—Synthesis of Int. 53:

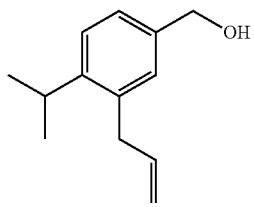

52 (900 mg, 4.1 mmol) in dry THF (6.5 mL) was added dropwise to a suspension of LAH (188 mg, 4.9 mmol) in dry THF (6.5 mL) at 0° C. under N2. The mixture was stirred for 30 min. H$_2$O (1 mL) then DCM were added very slowly and stirred for 20 min. The mixture was filtered on a pad of Celite® and the filtrate was dried over MgSO$_4$, filtered and evaporated until dryness to give 845 mg of Int. 53 colorless oil (100%).

c—Synthesis of Int. 54:

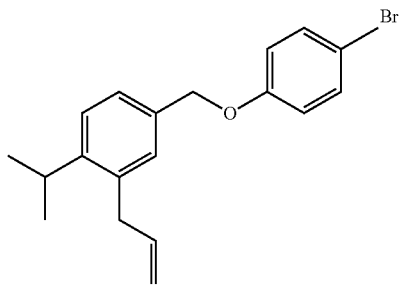 [SMILES: Br ; C=CCc1cc(COc2ccc(C)cc2)ccc1C(C)C]

To a suspension of 53 (6.52 g, 34 mmol), 4-bromophenol (5.9 g, 34 mmol) and PPh$_3$ (9.0 g, 34 mmol) in dry THF (210 mL) was added DBAD (7.9 g, 34 mmol). The mixture was stirred at r.t. overnight. The sol. was evaporated in vacuo to give 35 g of yellow oil. The residue was purified by prep. LC (Regular SiOH, 30 µm, 330 g GraceResolv™, mobile phase gradient: from 95% heptanes, 5% EtOAc to 90% heptane, 10% EtOAc). The pure fractions were collected and solvent was evaporated until dryness to give 9.6 g of Int. 54 pale yellow oil (81%).

d—Synthesis of Int. 55:

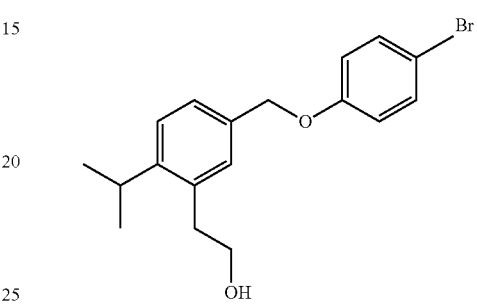

A sol. of 54 (2.0 g, 5.8 mmol) in MeOH (23 mL) was cooled to −78° C. Ozone was bubbled through the sol. until a red color developed (15 min). The excess of ozone was removed with a N$_2$ purge and the residue was partitioned between EtOAc and NH$_4$Cl 10% aq. The organic layer was washed with brine twice, dried over MgSO$_4$ and concentrated to give 2.2 g of colorless oil. The crude product was purified by prep. LC (irregular SiOH 30 µm, 40 g Interchim, mobile phase gradient from 80% heptane, 20% EtOAc to 70% heptanes, 30% EtOAc). The pure fractions were collected and solvent was evaporated until dryness to give 1.21 g of Int. 55 (60%, colorless oil).

e—Synthesis of Int. 56:

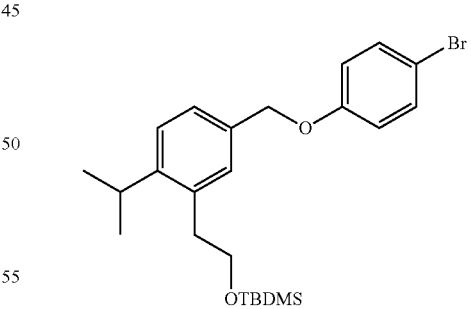

Under N$_2$, TBDMS-Cl (0.77 g, 5.1 mmol) was added to a sol. of 55 (1.2 g, 3.4 mmol) and imidazole (0.70 g, 10 mmol) in dry DCM (33 mL) at r.t. The mixture was stirred at r.t. for 75 min. The r.m. was quenched with water and extracted with DCM. The organic layer was decanted, washed with water then brine, dried over MgSO$_4$, filtered and evaporated to dryness to give 1.69 g of Int. 56 (100%, colorless oil). The product was used like this for the next step.

f—Synthesis of Int. 57:

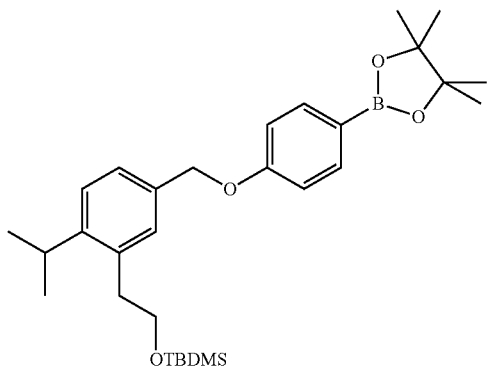 [SMILES: CC(C)c1ccc(COc2ccc(B3OC(C)(C)C(C)(C)O3)cc2)cc1CCO[Si](C)(C)C(C)(C)C]

In a microwave vial, a mixture of 56 (1.69 g, 3.6 mmol), KOAc (1.1 g, 11 mmol), BisPin (1.4 g, 5.5 mmol) in DME (11 mL) was carefully purged with N₂. PdCl₂(dppf) (0.30 g, 0.36 mmol) was added and the r.m. was purged again with N₂. The r.m. was stirred overnight at 100° C. The r.m. was diluted with EtOAc and washed with water (once) and with brine (3 times). The organic phase was dried over MgSO₄, filtered on a pad of Celite® and evaporated in vacuo to give 3.3 g of a brown oil. The residue was purified by prep. LC (irregular SiOH 15-40 μm, 80 g, Interchim, Mobile phase gradient: from 95% Heptane, 5% EtOAc, to 90% Heptane, 10% EtOAc). The pure fractions were collected and solvent was evaporated to give 1.2 g of Int. 57 (65%, colorless oil).

g—Synthesis of Int. 58:

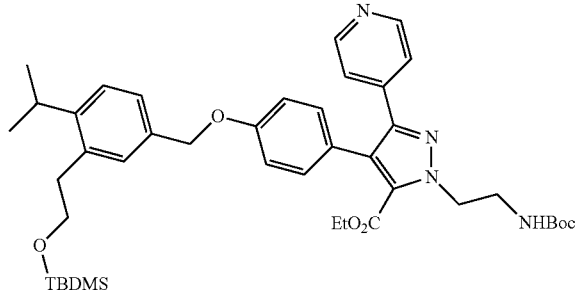

In a microwave vial, a mixture of 3 (0.86 g, 2.0 mmol), 57 (1.2 g, 2.35 mmol), K₃PO₄ (1.2 g, 5.9 mmol) in 1,4-dioxane (8.6 mL) and H₂O (3.1 mL) was carefully purged with N₂. PdCl₂(dppf) (0.16 g, 0.20 mmol) was added and the r.m. was purged again with N₂. The r.m. was heated at 80° C. overnight. The r.m. was diluted with EtOAc and washed with water (once) and with brine (3 times). The organic layer was dried over MgSO₄, filtered on a pad of Celite® and evaporated in vacuo to give a residue. The residue was purified by prep. LC (irregular SiOH 30 μm, 40 g, Interchim, Mobile phase: 60% heptane, 40% EtOAc). The pure fractions were collected and the solvent was evaporated until dryness to give 1.1 g of Int. 58 (76%).

h—Synthesis of Int. 59:

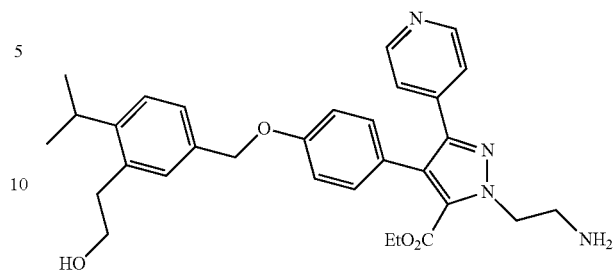

A solution of 58 (1.1 g, 1.5 mmol), HCl 3N (2.5 mL, 7.4 mmol), in ACN (26 mL) was stirred at 80° C. for 2 h. The mixture was concentrated, and NaHCO₃ sat aq (25 mL) was added and the mixture was stirred at r.t. 15 min and extracted with DCM. The organic layer was separated, dried and concentrated to give 780 mg of Int. 59 (100%). This residue was used like this for the next step.

i—Synthesis of Co. 11:

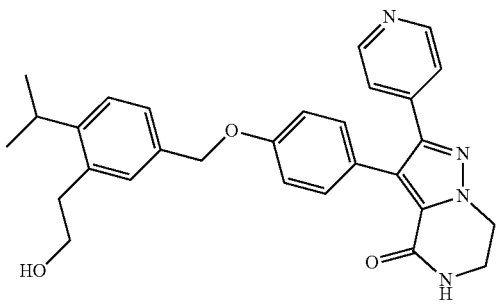 [SMILES: CC(C)c1ccc(COc2ccc(-c3c(-c4ccncc4)nn4c3C(=O)NCC4)cc2)cc1CCO]

To a sol. of 59 (780 mg, 1.5 mmol) in MeOH (42 mL) was added Cs₂CO₃ (2.4 g, 7.4 mmol) and the mixture was stirred at r.t. overnight. The mixture was filtered and the white solid was collected and dried to give 180 mg. The filtrate was concentrated and taken in DCM and washed once with brine, dried over MgSO4 and concentrated. The crude product was purified by prep. LC (irregular SiOH 30 μm, 25 g Interchim, mobile phase gradient from DCM/MeOH/NH₄OH 97/3/0.1 to 96/4/0.1). The pure fractions were collected and solvent was evaporated to give 460 mg of white solid. The solid was washed in Et₂O, dried and added to the first solid to give 500 mg. This solid was crystallized from isopropanol, filtrated and dried to give 470 mg of Co. 11, white solid (66%). m.p.: 195° C. (dsc).

Example A17

Preparation of Co. 12 a—Synthesis of Int. 60:

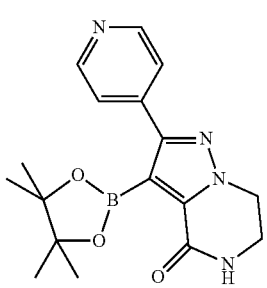 [SMILES: CC1(C)OB(c2c(-c3ccncc3)nn3c2C(=O)NCC3)OC1(C)C]

A mixture of 4 (800 mg, 2.73 mmol) in THF (16 mL) was carefully purged with N₂. Isopropylmagnesium chloride 2M in THF (5.5 mL, 10.9 mmol) was added at 0° C. and then the r.m. was stirred 4 h at r.t. Isopropoxyboronic acid pinacol ester (2.3 mL, 10.9 mmol) was added at 0° C. and the r.m. was stirred at r.t. for 90 min. The sol. was diluted in DCM and water and extracted with DCM. The organic layer was dried over MgSO₄, filtered and evaporated in vacuo to give 915 mg of Int. 60, white solid (99%).

b—Synthesis of Int. 61:

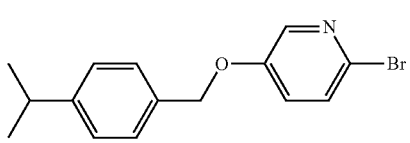 [SMILES: CC(C)c1ccc(COc2ccc(Br)nc2)cc1]

A sol. of 2-bromo-5-hydroxypyridine (800 mg, 4.60 mmol) in ACN (6 mL) and DMF (2 mL) was treated with K₂CO₃ (763 mg, 5.52 mmol) and 8 (0.833 mL, 4.83 mmol) at r.t. The r.m. was stirred for 16 h at r.t. Then water and EtOAc were added, and the organic layer was washed with brine, dried over MgSO₄, filtered and evaporated in vacuo to afford a solid. The solid was purified by prep. LC (Irregular SiOH 15-40 μm, 80 g Grace, mobile phase gradient: from Heptane 100% to Heptane 50%, EtOAc 50%). The pure fractions were collected and solvent was evaporated until dryness to give 840 mg of Int. 61 (60%).

c—Synthesis of Co. 12:

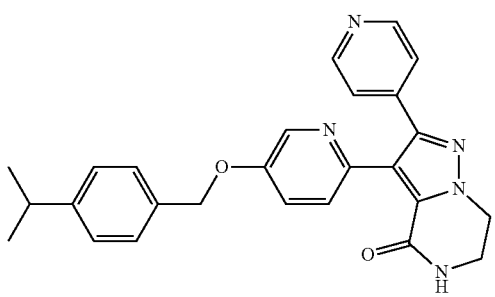 [SMILES: CC(C)c1ccc(COc2ccc(-c3c(-c4ccncc4)nn4c3C(=O)NCC4)nc2)cc1]

A mixture of 60 (417 mg, 1.23 mmol), 61 (751 mg, 2.45 mmol), K₃PO₄ (781 mg, 3.68 mmol) in THF (5 mL) and H₂O (5 mL) was carefully purged with N₂. Precatalyst (96 mg, 123 μmol) was added and the r.m. was purged again with N₂. The r.m. was stirred at r.t. for 18 h. The crude material was dissolved in water (20 mL) and extracted with EtOAc (2×40 mL). The organic layer was separated and evaporated in vacuo. The residue (500 mg yellow oil) was purified by prep. LC (irregular SiOH 15-40 μm, 30 g Merck, mobile phase gradient: from DCM 100% to DCM 90%, MeOH 10%) to give 290 mg of Co. 12, white solid (54%). m.p.: 84° C. (DSC).

Example A18

Preparation of Co. 13 a—Synthesis of Int. 62:

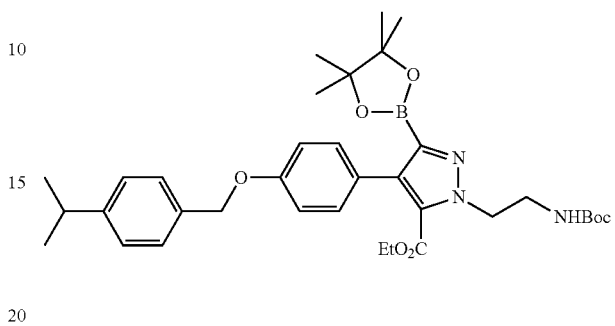

In a 20 mL microwave tube, a mixture of 17 (1.67 g, 2.85 mmol), KOAc (0.84 g, 8.5 mmol), BisPin (1.1 g, 4.3 mmol) in DME (8 mL) was carefully purged with N₂. PdCl₂(dppf) (233 mg, 0.29 mmol) was added and the r.m. was purged again with N₂. The r.m. was stirred overnight at 100° C. The r.m. was diluted with EtOAc and washed with water (once) and with brine (twice). The organic layer was dried over MgSO₄, filtered on a pad of Celite® and evaporated in vacuo to give a brown oil. This oil was purified by prep. LC (irregular SiOH 15-40 μm, 40 g, GraceResolv™, Mobile phase gradient: from 70% Heptane, 30% EtOAc to 50% Heptane, 50% EtOAc). The fractions were collected and solvent was evaporated to give 630 mg of a mixture of Int. 62 and another product (initial 17 without Br). This mixture was used as such for the next step.

b—Synthesis of Int. 63:

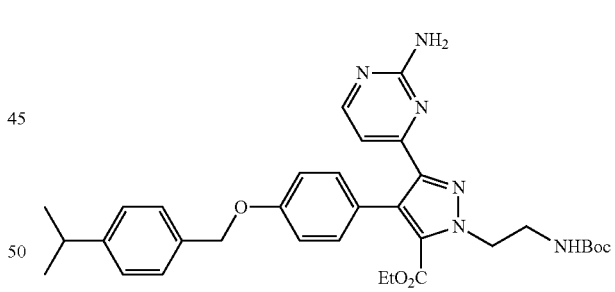

A mixture of 62 (impure) (630 mg, 0.99 mmol), 2-amino-4-bromopyrimidine (173 mg, 0.99 mmol), K₃PO₄ (633 mg, 2.98 mmol) in 1,4-dioxane (2.5 mL) and H₂O (1.1 mL) was carefully degassed with N₂. Pd(OAc)₂ (47 mg, 0.21 mmol) and PCy₃ (29 mg, 0.10 mmol) were added and the r.m. was purged again with N₂. The r.m. was stirred overnight at 80° C. The crude material was dissolved in water (30 mL) and extracted with DCM (2×). The organic layer was dried over MgSO₄, filtered through a pad of Celite® and evaporated in vacuo to give 800 mg of yellow oil. This residue was purified by prep. LC (irregular SiOH 30 µm, 40 g Interchim, mobile phase gradient from 98% DCM, 2% MeOH, 0.1% NH₄OH to 95% DCM, 5% MeOH, 0.1% NH₄OH). The pure fractions were collected and solvent was evaporated to give 170 mg of Int. 63, yellow oil (28%).

c—Synthesis of Int. 64:

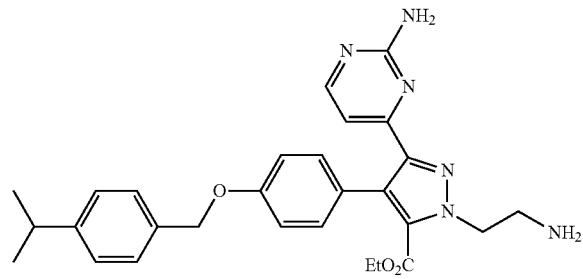 [SMILES: CCOC(=O)c1c(-c2ccc(OCc3ccc(C(C)C)cc3)cc2)c(-c2ccnc(N)n2)nn1CCN]

A solution of 63 (0.2 g, 0.33 mmol), HCl 3N (0.55 mL, 1.7 mmol), in ACN (6 mL) was heated at 80° C. for 2 h. ACN was concentrated, and NaHCO₃ sat aq (50 mL) was slowly added and the mixture was extracted with DCM, dried over MgSO₄ and concentrated until dryness to give 135 mg of Int. 64 (81%). This residue was used like this in the next step.

d—Synthesis of Co 13:

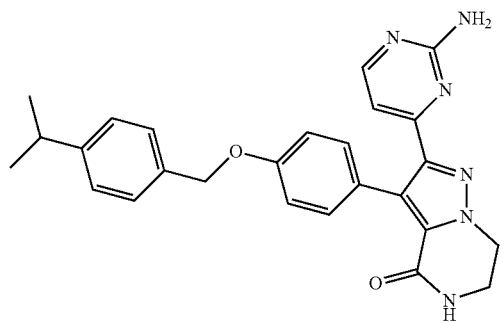

To a sol. of 64 (0.14 g, 0.28 mmol) in MeOH (8 mL) was added Cs₂CO₃ (0.46 g, 1.4 mmol) and the mixture was stirred at r.t. for 3 days. The mixture was concentrated and taken in DCM, the solid was filtered and the filtrate was concentrated to give 162 mg of a residue. The residue was purified by prep. LC on (Stability Silica 5 µm 150×30.0 mm), mobile phase (Gradient from NH₄OH/DCM/MeOH 0.2/98/2 to NH₄OH/DCM/MeOH 1/90/10). The pure fractions were collected and solvent was evaporated until dryness to give 9 mg of Co 13, white solid (7%).

Example A19

Preparation of Co. 14 a—Synthesis of Int. 65:

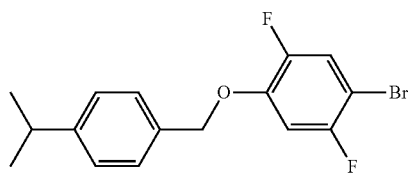 [SMILES: CC(C)c1ccc(COc2cc(F)c(Br)cc2F)cc1]

Under N₂, a sol. of 4-bromo-2,5-difluorophenol (12 g, 58 mmol) in ACN (150 mL) was treated with K₂CO₃ (16 g, 117 mmol) and 8 (9.7 mL, 58 mmol) and the r.m. was stirred under reflux for 2 h. The sol. was filtered and concentrated to give 20 g of Int. 65, colorless oil (100%). The product was used like this in the next step.

b—Synthesis of Int. 66:

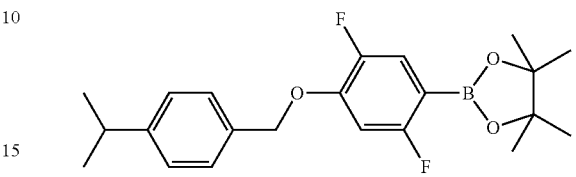

In a Schlenk tube, a mixture of 65 (10.0 g, 29 mmol), KOAc (8.6 g, 88 mmol), BisPin (11 g, 44 mmol) in dry DME (150 mL) was carefully purged with N₂. PdCl₂(dppf) (2.4 g, 2.9 mmol) was added and the r.m. was purged again with N₂. The r.m. was stirred overnight at 100° C. The r.m. was diluted with EtOAc and washed with water (1×) and with brine (2×). The organic layer was dried over MgSO₄ and evaporated in vacuo to give brown oil. The oil was purified by prep. LC (irregular SiOH 15-40 µm, 330 g, GraceResolv™, Mobile phase: Heptane 90%, EtOAc 10%). The pure fractions were collected and solvent was evaporated until dryness to give 10.9 g of Int. 66, yellow oil (96%).

c—Synthesis of Co. 14:

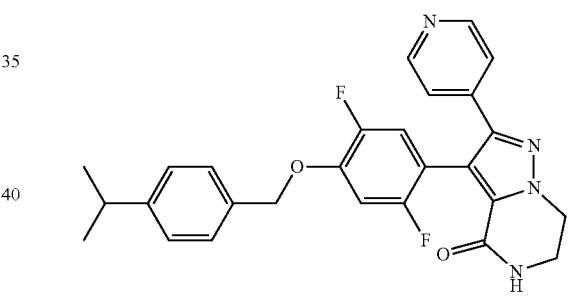

A sol. of 4 (660 mg, 2.25 mmol) and 66 (1.74 g, 4.50 mmol) in 1,4-dioxane (10 mL) and H₂O (8 mL) was treated with K₃PO₄ (1.43 g, 6.76 mmol) and purged with N₂. PdCl₂(dppf) (184 mg, 0.225 mmol) was then added and the r.m. was carefully purged with N₂. The mixture was heated at 120° C. using one single mode microwave (Biotage Initiator EXP 60) with a power output ranging from 0 to 400 W for 25 min [fixed hold time]. The crude mixture was diluted with DCM and washed with water. The organic layer was dried over MgSO₄ and evaporated to afford a brown residue. The residue was purified by prep. LC (Irregular SiOH 15-40 µm, 80 g Grace, mobile phase gradient: from DCM 100% to DCM 94%, MeOH 6%). The fractions containing pure Co. were combined and evaporated in vacuo to afford of Co. 14, white solid (13%). m.p.: 226° C. and 231° C. (DSC). The fractions containing impure Co. 14 were combined and evaporated in vacuo to afford 221 mg of Co. 14, brown solid (global yield: 33%).

Example A20

Preparation of Co. 15 a—Synthesis of Int. 67:

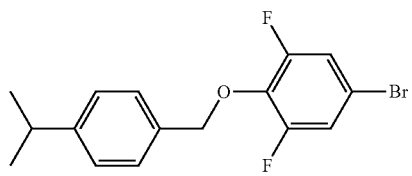 [SMILES: CC(C)c1ccc(COc2c(F)cc(Br)cc2F)cc1]

To a sol. of 4-bromo-2,6-difluorophenol (1 g, 4.79 mmol), 8 (0.84 mL, 5.02 mmol) in DMF (10 mL) was added K₂CO₃ (0.727 g, 5.26 mmol). The mixture was stirred at r.t. for 2 h. Water and DCM were added and the product was extracted with DCM. The organic layer was separated, dried, filtered and evaporated until dryness. The residue was purified by prep. LC on (Irregular SiOH 15-40 µm 50 g Merck, mobile phase: 80/20 Heptane/EtOAc). The pure fractions were collected and solvent was evaporated until dryness to give 1.62 g of Int. 67 (99%).

b—Synthesis of Int. 68:

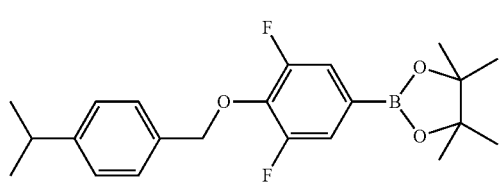 [SMILES: CC(C)c1ccc(COc2c(F)cc(B3OC(C)(C)C(C)(C)O3)cc2F)cc1]

In a sealed tube, a mixture of 67 (1.62 g, 4.75 mmol), BisPin (2.41 g, 9.5 mmol), KOAc (1.4 g, 14.2 mmol) in DME (15 mL) was carefully purged with N₂. PdCl₂(dppf) (0.117 g, 0.142 mmol) was added and the r.m. was purged again with N₂. The mixture was heated at 100° C. overnight. EtOAc and water were added and the mixture was extracted with EtOAc. The organic layer was separated, dried, filtered and evaporated until dryness to give 3.29 g of a residue. The residue was purified by prep. LC on (Irregular SiOH 15-40 µm 50 g Merck, mobile phase (90/10 Heptane/EtOAc). The pure fractions were collected and evaporated until dryness to give and 1.03 g of Int. 86 (56%).

c—Synthesis of Co. 15:

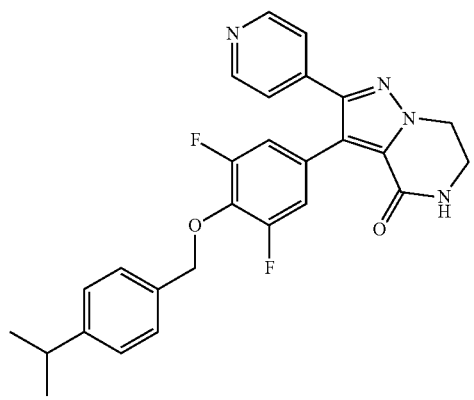 [SMILES: CC(C)c1ccc(COc2c(F)cc(-c3c(-c4ccncc4)nn4c3C(=O)NCC4)cc2F)cc1]

In a microwave vial, a mixture of 4 (0.3 g, 1.02 mmol), 68 (0.516 g, 1.33 mmol), K₃PO₄ (0.911 g, 4.29 mmol) in 1,4-dioxane (4.8 mL) and H₂O (1.6 mL) was carefully purged with N₂. PCy₃ (60 mg, 0.214 mmol) and Pd(OAc)₂ (24 mg, 0.11 mmol) were added and the r.m. was purged again with N₂. The r.m. was stirred for 16 h at 80° C. The crude material was put in water and extracted with EtOAc. The organic layer was dried over MgSO₄, filtered and evaporated in vacuo to give 756 mg of a residue. The residue was purified by prep. LC on (Stability Silica 5 µm 150×30.0 mm, mobile phase gradient from NH₄OH/DCM/MeOH 0.2/98/2 to NH₄OH/DCM/MeOH 0.8/92/8). The pure fractions were collected and evaporated to give 212 mg of a residue which was crystallized from DIPE, filtered and dried to give 189 mg of Co. 15 (39%).

Example A21

Preparation of Co. 16 a—Synthesis of Int. 69:

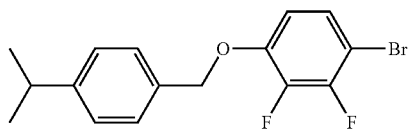 [SMILES: CC(C)c1ccc(COc2ccc(Br)c(F)c2F)cc1]

Under N₂, a sol. of 4-bromo-2,3-difluorophenol (5.00 g, 23.9 mmol) in DMF (25 mL) was treated with K₂CO₃ (3.97 g, 28.7 mmol) and 8 (4.80 mL, 28.7 mmol) and the r.m. was stirred for 18 h at rt, then extracted with water and EtOAc. The organic layer was washed with brine (twice), dried over MgSO₄, filtered off and evaporated in vacuo to give 9.49 g of Int. 69, colorless oil (100%).

b—Synthesis of Int. 70:

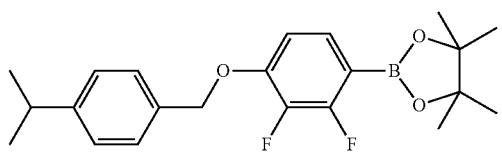 [SMILES: CC(C)c1ccc(COc2ccc(B3OC(C)(C)C(C)(C)O3)c(F)c2F)cc1]

A mixture of 69 (7.30 g, 19.3 mmol), BisPin (7.34 g, 28.9 mmol) and KOAc (5.67 g, 57.8 mmol) in DME (90 mL) was carefully purged with N₂. PdCl₂(dppf) (1.58 g, 1.93 mmol) was added and the r.m. was purged again with N₂. The r.m. was stirred at 18 h at 100° C. The r.m. was diluted with EtOAc and water. The organic layer was washed with brine, dried over MgSO₄, filtered and evaporated in vacuo to give 15.0 g of a brown solid. The solid was purified by prep. LC (irregular SiOH 15-40 µm, 150 g, Merck, mobile phase gradient: form Heptane 100% to Heptane 60%, EtOAc 40%). The pure fractions were collected and solvent was evaporated to give 6.60 g of Int. 70, colorless oil (88%).

c—Synthesis of Co. 16:

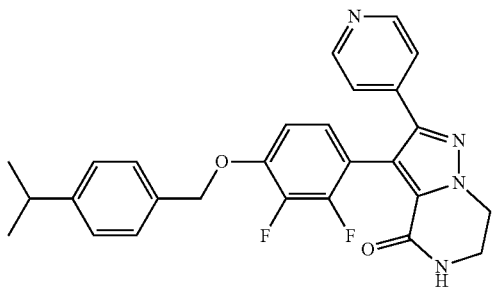 [SMILES: CC(C)c1ccc(COc2ccc(-c3c(-c4ccncc4)nn4c3C(=O)NCC4)c(F)c2F)cc1]

A stirred sol. of 4 (551 mg, 1.88 mmol), 70 (1.54 g, 3.97 mmol) and K₃PO₄ (1.2 g, 5.64 mmol) in 1,4-dioxane (8 mL) and H₂O (7.5 mL) was purged with N₂, and then PdCl₂(dppf) (84 mg, 0.102 mmol) was added at rt. The resulting mixture was purged again with N₂, and stirred at 120° C. using one single mode microwave (Biotage Initiator EXP 60) with a power output ranging from 0 to 400 W for 30 min. [fixed hold time]. DCM and water were added, the organic layer was separated, dried over MgSO4, filtered off and evaporated in vacuo to afford 2.07 g of a viscous black oil. This oil was purified by prep. LC (Irregular SiOH 50 μm, 120 g Grace, mobile phase gradient: from DCM 100% to DCM 92%, MeOH 8%). The fractions were collected and evaporated in vacuo. The solid (273 mg, pale grey solid) was crystallized from MeOH, filtered off and dried in vacuo to yield 111 mg of Co. 16, white solid (12%). m.p.: 214° C. (DSC).

Example A22

Preparation of Co. 17 a—Synthesis of Int. 71:

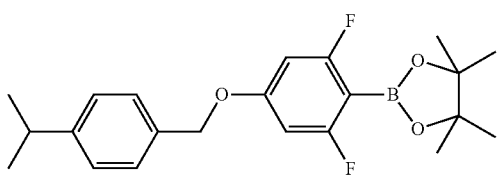

Under N₂, a sol. of 4-bromo-3,5-difluorophenol (3.0 g, 14.4 mmol) in ACN (37 mL) was treated with K₂CO₃ (4.0 g, 29 mmol) and 8 (2.4 mL, 14.4 mmol) and the r.m. was stirred under reflux for 2 h. The sol. was filtered and concentrated to give 4.9 g of Int. 71, colorless oil (100%). The product was used like this in the next step.

b—Synthesis of Int. 72:

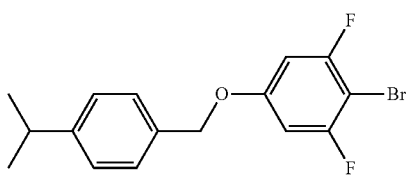 [SMILES: CC(C)c1ccc(COc2cc(F)c(Br)c(F)c2)cc1]

In a sealed tube, a mixture of 21 (1.34 g, 3.92 mmol), BisPin (1.15 g, 11.7 mmol), KOAc (1.19 g, 4.70 mmol) in DME (13 mL) was carefully purged with N₂. PdCl₂(dppf) (321 mg, 0.392 mmol) was added and the r.m. was purged again with N₂. The r.m. was stirred for 17 h at 100° C. The r.m. was diluted with EtOAc and washed with water (once) and with brine (thrice). The organic phase was dried over MgSO4, filtered and evaporated in vacuo to give 2.50 g of brown oil. The oil was purified by prep. LC (irregular SiOH 15-40 μm, 50 g, MERCK, Mobile phase gradient: from 100% Heptane to 90% Heptane, 10% EtOAc). The pure fractions were collected and solvent was evaporated until dryness to give 1.10 g of Int. 72 colorless oil (72%).

c—Synthesis of Int. 73:

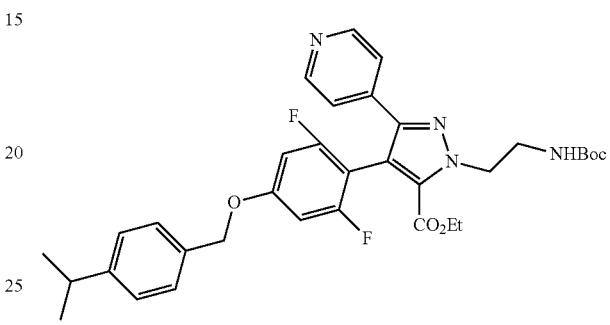

In a microwave vial, a mixture of 3 (570 mg, 1.3 mmol), 72 (1.0 g, 2.6 mmol), K₃PO₄ (1.1 g, 5.2 mmol) in 1,4-dioxane (5.7 mL) and H₂O (2.0 mL) was carefully purged with N₂. Precatalyst (100 mg, 130 μmol) was added and the r.m. was purged again with N₂. The resulting mixture was stirred at 120° C. using one single mode microwave (Biotage Initiator EXP 60) with a power output ranging from 0 to 400 W for 1 h. [fixed hold time]. The r.m. was diluted with EtOAc and washed with water (once) and with brine (3×). The organic phase was dried over MgSO₄, filtered on a pad of Celite® and evaporated in vacuo to give 1.4 g of a yellow oil. The oil was purified by prep. LC (irregular SiOH 15-40 μm, 40 g, Interchim, Mobile phase: DCM/MeOH/NH₄OH, gradient from 98/2/0.1 to 96/4/0.1). The pure fractions were collected and solvent was evaporated until dryness to give 65 mg of Int. 73 (8%).

d—Synthesis of Int. 74:

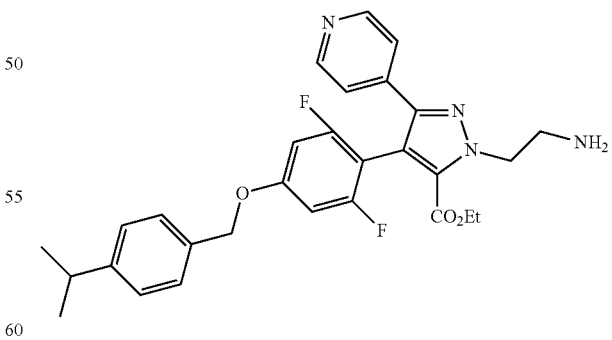

A solution of 73 (65 mg, 0.11 mmol), HCl 3N (0.18 mL, 0.53 mmol), in ACN (2 mL) was stirred at 80° C. for 2 h. ACN was concentrated, and NaHCO₃ sat aq (25 mL) was added and the mixture was stirred at r.t. 15 min, extracted with DCM, dried and concentrated to give 63 mg of Int. 74 (quant.). This residue was used like this in the next step.

e—Synthesis of Co. 17:

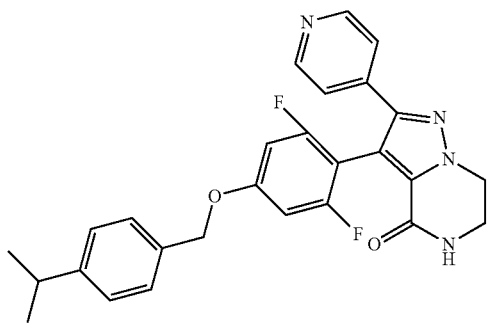 [SMILES: CC(C)c1ccc(COc2cc(F)c(-c3c(-c4ccncc4)nn4c3C(=O)NCC4)c(F)c2)cc1]

To a sol. of 74 (63 mg, 0.12 mmol) in MeOH (3.5 mL) was added Cs₂CO₃ (0.20 g, 0.61 mmol) and the mixture was stirred at r.t. overnight. The mixture was concentrated and taken in DCM and washed once with water, dried over MgSO₄ and concentrated. The crude product was purified by prep. LC (irregular SiOH 30 μm, 12 g GraceResolv™, mobile phase gradient from DCM/MeOH/NH₄OH 98:2:0.1 to 96/4/0.1). The fractions were collected and solvent was evaporated until dryness to give 37 mg, white solide. This solid was purified again by prep. LC on (irregular 15-40 μm 30 g Merck, mobile phase: 0.1% NH₄OH, 97% DCM, 3% MeOH. The pure fractions were collected and solvent was evaporated until dryness to give 22 mg of Co. 17, white solid (38%). m.p.: 235° C. (dsc)

Example A23

Preparation of Co. 18 a—Synthesis of Int. 75:

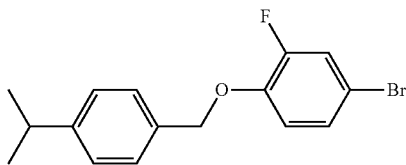

To a sol. of 4-bromo-2-fluorophenol (5 g, 26.1 mmol), 8 (4.6 mL; 27.5 mmol) in ACN (50 mL) was added K₂CO₃ (3.98 g, 28.8 mmol). The mixture was stirred at r.t. overnight. Water and DCM were added and the product was extracted with DCM. The organic layer was separated, dried, filtered and evaporated until dryness. The residue was purified by prep. LC on (Irregular SiOH 15-40 μm 50 g Merck, mobile phase: 80/20 Heptane/EtOAc). The pure fractions were collected and evaporated until dryness to give 8.2 g of Int. 75 (97%).

b—Synthesis of Int. 76:

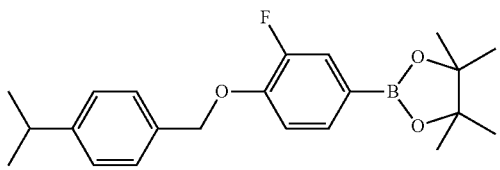

First method: In a sealed tube, a mixture of 75 (3 g, 9.3 mmol), BisPin (4.7 g, 18.6 mmol), KOAc (2.73 g, 27.8 mmol) in DME (30 mL) was purged with N₂. PdCl₂(dppf) (0.228 g, 0.278 mmol) was added and the r.m. was purged again with N₂. The mixture was heated at 100° C. overnight. EtOAc and water were added and the mixture was extracted with EtOAc. The organic layer was separated, dried, filtered and evaporated until dryness to give 6.7 g of a residue. The residue was purified by prep. LC on (Irregular SiOH 15-40 μm 90 g Merck, mobile phase: 90/10 Heptane/EtOAc). The pure fractions were collected and evaporated until dryness to 3.56 g of Int. 76, 100%.

Second method: A sol. of 3-fluoro-4-hydroxyphenylboronic acid pinacol ester (0.91 g, 3.82 mmol) in ACN (10 mL) was treated with K₂CO₃ (0.634 g, 4.56 mmol) and 8 (0.725 mL, 4.2 mmol) at r.t. The r.m. was stirred for 18 h at r.t. Then water and DCM were added, and the organic layer was washed with brine, separated, dried over MgSO₄, filtered and concentrated in vacuo to afford 1.46 g of a residue. The residue was purified by prep. LC on (Irregular SiOH 15-40 μm 50 g Merck, mobile phase: 90/10 Heptane/EtOAc). The pure fractions were collected and evaporated until dryness to give 677 mg of Int. 76, 48%.

c—Synthesis of Co. 18:

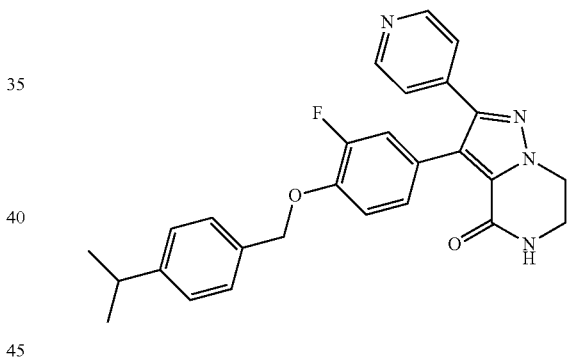

In a microwave vial, a mixture of 4 (0.3 g, 1.02 mmol), 76 (0.53 g, 1.43 mmol), K₃PO₄ (0.91 g, 4.29 mmol) in 1,4-dioxane (4.8 mL) and H₂O (1.6 mL) was carefully purged with N₂. PCy₃ (60 mg, 0.214 mmol) and Pd(OAc)₂ (24 mg, 0.107 mmol) were added and the r.m. was purged again with N₂. The r.m. was stirred for 16 h at 80° C. The crude material was dissolved in water and extracted with EtOAc. The organic layer was dried over MgSO₄, filtered and evaporated in vacuo to give 881 mg of a residue. The residue was purified by prep. LC on (irregular 15-40 μm 30 g Merck, mobile phase: NH₄OH/DCM/MeOH 0.3/97/3). The pure fractions were collected and the solvent was evaporated until dryness to give 330 mg which was crystallized from DIPE, filtered and dried to give 317 mg of Co. 18 (68%). m.p.: 241° C. (dsc).

Example A24

Preparation of Co. 19 a—Synthesis of Int. 77:

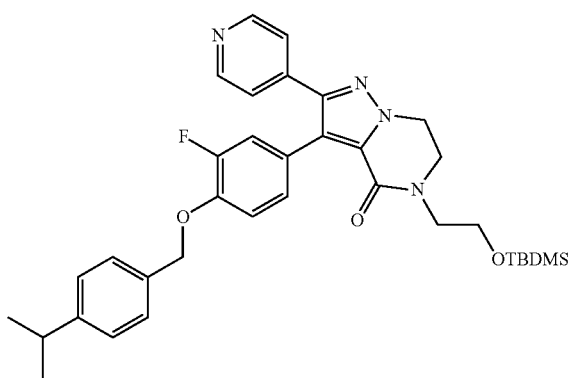 [SMILES: CC(C)c1ccc(COc2ccc(-c3c(-c4ccncc4)nn4c3C(=O)N(CCO[Si](C)(C)C(C)(C)C)CC4)cc2F)cc1]

In a microwave vial, a mixture of 28 (0.4 g, 0.886 mmol), 76 (0.427 g, 1.15 mmol), K$_3$PO$_4$ (0.788 g, 3.7 mmol) in 1,4-dioxane (4.2 mL) and H$_2$O (1.4 mL) was carefully purged with N$_2$. PdCl$_2$(dppf) (73 mg, 0.09 mmol) was added and the r.m. was purged again with N$_2$. The r.m. was stirred for 16 h at 80° C. The crude material was dissolved in water and extracted with EtOAc. The organic phase was dried over MgSO$_4$, filtered and evaporated in vacuo to give 838 mg of a residue. The residue was purified by prep. LC on (Irregular SiOH 15-40 µm 50 g Merck, mobile phase gradient: from DCM 100% to DCM 97%, MeOH 3%). The pure fractions were collected and evaporated until dryness to give 370 mg of Int. 77, 68%.

b—Synthesis of Co. 19:

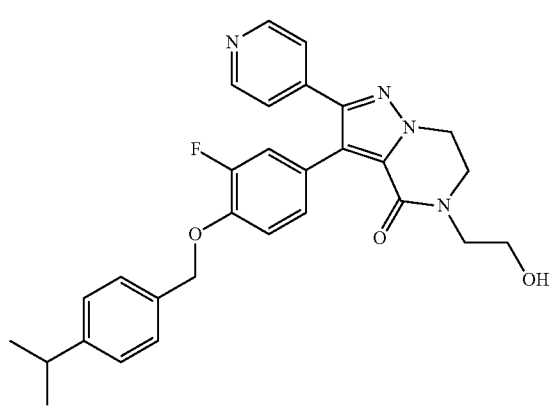 [SMILES: CC(C)c1ccc(COc2ccc(-c3c(-c4ccncc4)nn4c3C(=O)N(CCO)CC4)cc2F)cc1]

TBAF (0.86 mL, 0.86 mmol) was added dropwise to a sol. of 77 (0.442 g, 0.72 mmol) in THF (4 mL) at r.t. The mixture was stirred for 3 h at rt. The mixture was poured into water and basified with K$_2$CO$_3$, extracted with EtOAc. The organic layer was dried over MgSO$_4$, filtered and evaporated until dryness to give 422 mg of a residue. The residue was purified by prep. LC (Stationary phase: Stability Silica 5 µm 150×30.0 mm), Mobile phase: Gradient from NH$_4$OH/DCM/MeOH 0.2/98/2 to NH$_4$OH/DCM/MeOH 0.9/90/9). The pure fractions were collected and evaporated until dryness to give 230 mg which was crystallized from Et$_2$O, filtered and dried to give 196 mg of Co. 19 (54%) m.p.: 172° C. (dsc).

Example A25

Preparation of Co. 20 a—Synthesis of Int. 78:

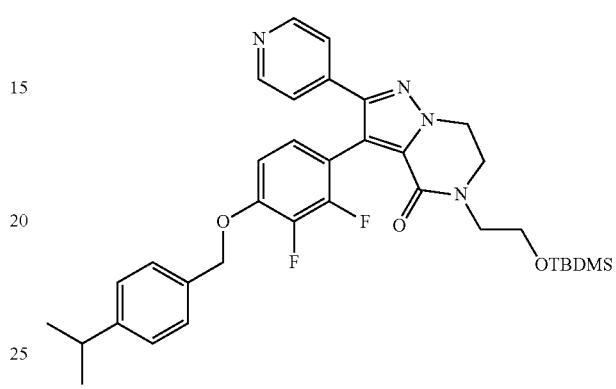

Under N$_2$, a sol. of Co. 16 (915 mg, 1.93 mmol) in dry DMSO (17 mL) was treated with NaH (60%) (116 mg, 2.89 mmol). The r.m. was stirred at r.t. for 2 h. Then, (2-bromomethoxy)-tert-butyldimethylsilane (496 µL, 2.31 mmol) was added and the reaction was stirred at r.t. for 17 h. The crude mixture was poured in EtOAc and washed with brine. The organic layer was dried over MgSO$_4$ and evaporated in vacuo to afford 1.00 g of a crude mixture containing 29% of Int. 78 (brown residue). The residue was used as such for the next reaction step.

b—Synthesis of Co. 20:

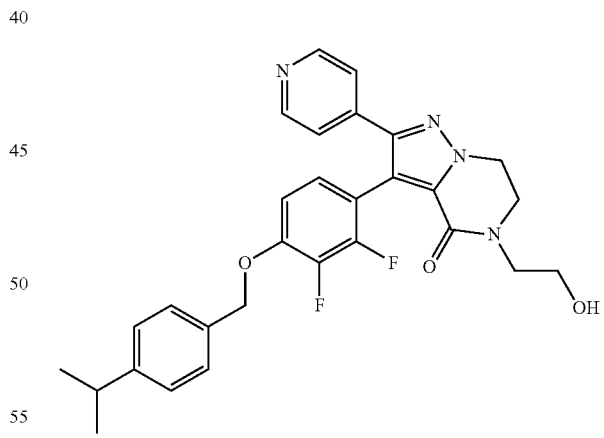

A sol. of mixture with 78 (1.00 g) in THF (35 mL) was treated with TBAF (790 µL, 790 µmol) and stirred at r.t. for 4 h. The crude mixture was then diluted in DCM, washed with water and brine. The organic layer was dried over MgSO$_4$ and evaporated in vacuo to afford a brown residue. The residue was purified by prep. LC (irregular SiOH 15-40 µm, 30 g, GraceResolv™, Mobile phase gradient: from DCM 100% to DCM 94%, MeOH 6%). The pure fractions were collected and solvent was evaporated to give 162 mg of Co. 20, white solid. m.p.: 138° C. (DSC).

Example A26

Preparation of Co. 21 a—Synthesis of Int. 79:

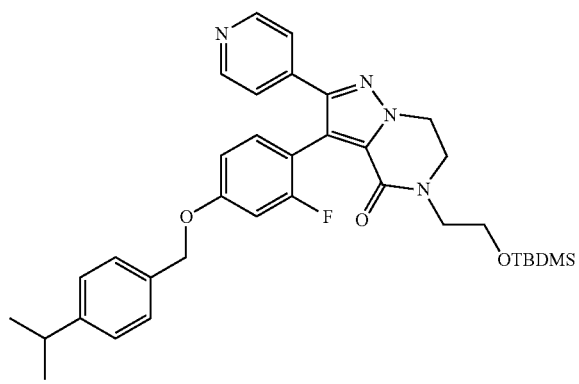 [SMILES: CC(C)c1ccc(COc2ccc(-c3c(-c4ccncc4)nn4c3C(=O)N(CCO[Si](C)(C)C(C)(C)C)CC4)c(F)c2)cc1]

NaH (60%) (0.50 g, 12 mmol) was added slowly to a suspension of Co. 6 (3.8 g, 8.3 mmol) in dry DMF (49 mL) at r.t. under $N_2$. The mixture was stirred for 2 h then (2-bromomethoxy)-tert-butyldimethylsilane (2.1 mL, 10 mmol) was added and the resulting mixture was stirred overnight. Water was added and the mixture was concentrated under reduced pressure. The residue was taken up in EtOAc and washed five times with brine. The organic layer was dried on $MgSO_4$, filtered and concentrated to give 4.7 g of a mixture of 79 (50%) and the deprotected product (35%) as a yellow oil. This crude mixture was used like this in the next step.

b—Synthesis of Co. 21:

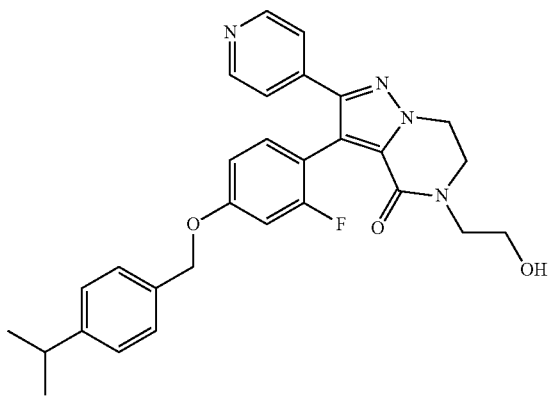 [SMILES: CC(C)c1ccc(COc2ccc(-c3c(-c4ccncc4)nn4c3C(=O)N(CCO)CC4)c(F)c2)cc1]

TBAF (9.2 mL, 9.2 mmol) was added dropwise to a sol. of the mixture with 79 (4.7 g, 7.6 mmol) in THF (75 mL) at r.t. The mixture was stirred overnight at r.t. The mixture was concentrated and the residue was purified by prep. LC (Regular SiOH, 30 µm, 120 g GraceResolv™, mobile phase: DCM/MeOH/$NH_4OH$ 98/2/0.1). The fractions were collected and solvent was evaporated until dryness to give 2.5 g of a residue. The residue was purified by achiral SFC (Stationary phase: diethylaminopropyl 5 µm 150×21.2 mm, Mobile phase: 90% $CO_2$, 10% MeOH). The pure fractions were collected and solvent was evaporated to give 2.1 g which was crystallized from $Et_2O$, filtrated and dried to give 1.9 g of Co. 21, white solid (50%). m.p.: 141° C. (dsc).

Example A27

Preparation of Co. 22a and Co. 22 a—Synthesis of Co. 22a:

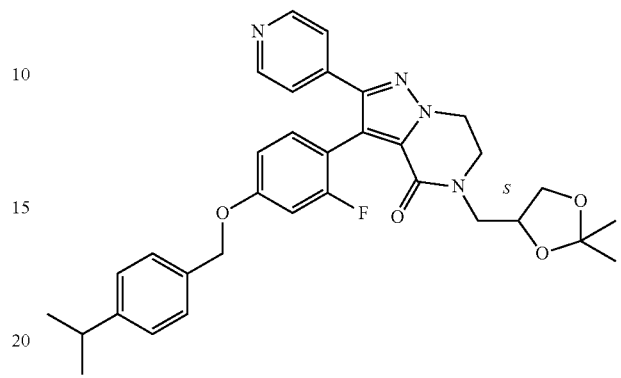

NaH (60%) (79 mg, 2.0 mmol) was added to Co. 6 (0.60 g, 1.3 mmol) in DMF (8 mL) at r.t. under $N_2$. The mixture was stirred for 2 h then (R)-(−)-2,2-dimethyl-1,3-dioxolane-4-ylmethyl P-toluenesulfonate (0.57 g, 2.0 mmol) was added and the mixture was stirred overnight. Water was added and the mixture was diluted with 150 mL of EtOAc and washed 4× with brine. The organic layer was dried on $MgSO_4$ and evaporated until dryness to give a white solid. The solid was purified by prep. LC (irregular SiOH 15-40 µm, 12 g, GraceResolv™, Mobile phase: DCM/MeOH/$NH_4OH$, 98/2/0.1). The pure fractions were collected and solvent was evaporated until dryness to give 200 mg of Co. 22a (S), colorless oil (27%).

b—Synthesis of Co. 22:

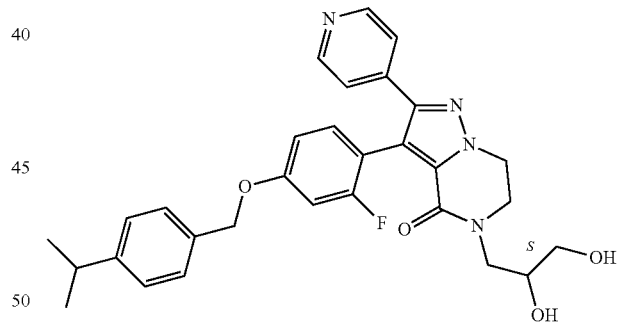

A sol. of Co. 22a (0.2 g, 0.35 mmol) and HCl 3N (0.58 mL, 1.7 mmol) in 1,4-dioxane (7.8 mL) was heated to reflux for 3 h. The mixture was cooled to r.t., poured into sat. $NaHCO_3$ and extracted with DCM. The organic layer was dried over $MgSO_4$, filtered and evaporated until dryness. The residue was purified by prep. LC (irregular SiOH 15-40 µm, 4 g, GraceResolv™, Mobile phase: DCM/MeOH/$NH_4OH$, from 97/3/0.1 to 95/5/0.1). The pure fractions were collected and the solvent was evaporated until dryness to give 150 mg of colorless oil. This oil was taken in $Et_2O$ and triturated and the white solid formed was progressively solubilized in $Et_2O$. The sol. was left standing at r.t. overnight. Then, the solid was filtrated and dried to give 110 mg of Co. 22 (S), white powder (59%). m.p.: 188° C. (dsc); $[\alpha]_d$: −18.42° (589 nm, c 0.2715 w/v %, DMF, 20° C.).

Example A28

Preparation of Co. 23a and Co. 23 a—Synthesis of Co. 23a:

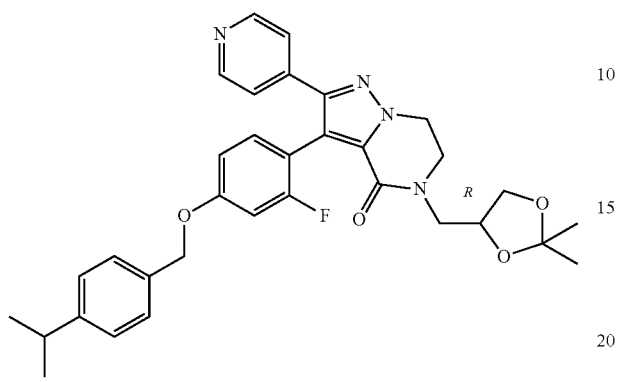

NaH (60%) (79 mg, 2.0 mmol) was added to Co. 6 (0.60 g, 1.3 mmol) in DMF (8 mL) at r.t. under $N_2$. The mixture was stirred for 2 h then (S)-(−)-2,2-dimethyl-1,3-dioxolane-4-ylmethyl P-toluenesulfonate (0.57 g, 2.0 mmol) was added and the mixture was stirred overnight. Water was added and the mixture was diluted with 200 mL of EtOAc and washed four times with brine. The organic layer was dried on $MgSO_4$ and evaporated until dryness to give 0.80 g, white solid. The residue was purified by prep. LC (irregular SiOH 15-40 μm, 12 g, GraceResolv™, Mobile phase: DCM/MeOH/$NH_4OH$, 98/2/0.1). The pure fractions were collected and solvent was evaporated until dryness to give 165 mg of Co. 23a (R), colorless oil (22%).

b—Synthesis of Co. 23:

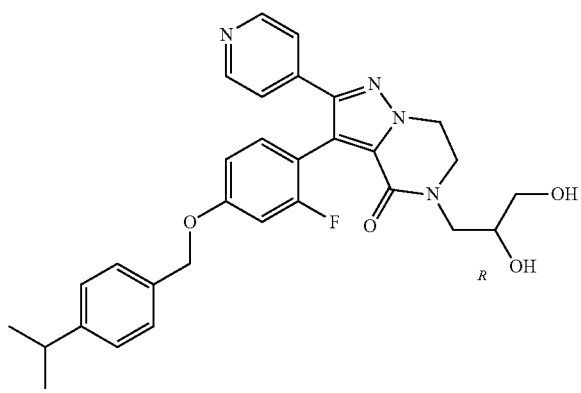

A sol. of Co. 23a (0.165 g, 0.29 mmol) and HCl 3N (0.48 mL, 1.5 mmol) in 1,4-dioxane (6.4 mL) was heated to reflux for 2 h. The mixture was cooled to r.t., poured into sat. $NaHCO_3$ and extracted with DCM. The organic layer was dried ($MgSO_4$), filtered and evaporated until dryness. The residue was purified by prep. LC (irregular SiOH 15-40 μm, 4 g, GraceResolv™, Mobile phase: DCM/MeOH/$NH_4OH$ from 97/3/0.1 to 95/5/0.1). The pure fractions were collected and solvent was evaporated until dryness to give 114 mg of colorless oil. This oil was crystallized from $Et_2O$ and the white solid formed was filtrated and dried to give 92 mg of Co. 23 (R), white powder (60%). m.p.: 192° C. (dsc); $[\alpha]_d$: +18.59° (589 nm, c 0.2475 w/v %, DMF, 20° C.).

Example A29

Preparation of Co. 24 a—Synthesis of Int. 82:

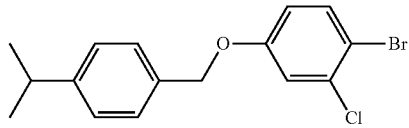

A sol. of 4-bromo-3-chlorophenol (2.00 g, 9.64 mmol) in ACN (25 mL) was treated with $K_2CO_3$ (1.6 g, 11.6 mmol) and 8 (1.83 mL, 10.6 mmol) at r.t. The r.m. was stirred for 17 h at r.t. Then, water and DCM were added, and the organic layer was washed with brine, separated, dried over $MgSO_4$, filtered and concentrated in vacuo to afford 3.43 g of a residue. The residue was purified by prep. LC (irregular SiOH 15-40 μm, 120 g Grace, mobile phase gradient: from Heptane 100% to Heptane 85%, EtOAc 15%). The pure fractions were collected and solvent was evaporated until dryness to give 3.07 g of Int. 82, white solid (88%).

b—Synthesis of Int. 83:

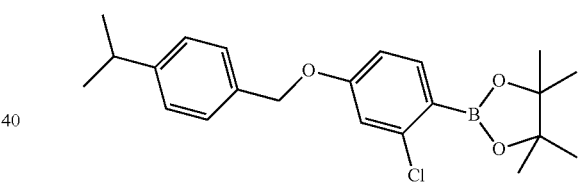

nBuLi 1.6N in hexane (4.25 mL, 6.8 mmol) was added to a stirred sol. of 82 (2.34 g, 6.48 mmol) in anhydrous THF (30 mL) at −78° C. under $N_2$. The mixture was stirred at −78° C. for 30 min, and then isopropoxyboronic acid pinacol ester (1.36 mL, 6.67 mmol) was added at −78° C. under $N_2$. The r.m. was stirred at −78° C. for 75 min. The crude material was dissolved in water and extracted with EtOAc. The organic phase was washed with brine, dried over $MgSO_4$, filtered and evaporated in vacuo to give 2.37 g of a residue. The residue was purified by prep. LC (irregular SiOH 15-40 μm, 120 g Grace, mobile phase gradient: from Heptane 100% to EtOAc 20%, Heptane 80%). The pure fractions were collected and solvent was evaporated to give 1.91 g of a solid. The solid was purified by prep. LC (irregular SiOH 15-40 μm, 50 g Grace, mobile phase gradient: from Heptane 100% to EtOAc 20%, Heptane 80%). The pure fractions were collected and solvent was evaporated until dryness to give 1.12 g of Int. 83 (45%).

c—Synthesis of Co. 24:

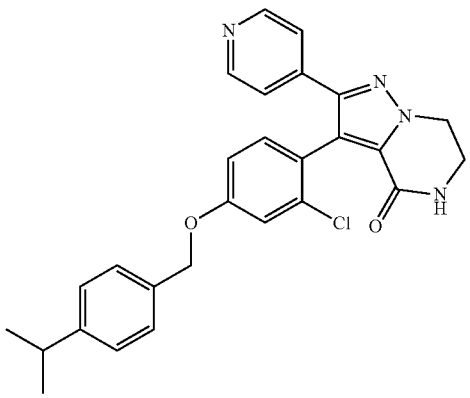 [SMILES: CC(C)c1ccc(COc2ccc(-c3c(-c4ccncc4)nn4c3C(=O)NCC4)c(Cl)c2)cc1]

A sol. of 4 (258 mg, 0.882 mmol), 83 (750 mg, 1.94 mmol) and K₃PO₄ (655 mg, 3.09 mmol) in 1,4-dioxane (3.8 mL) and H₂O (1.2 mL) in a sealed tube was purged with N₂. Precatalyst (69 mg, 88.2 µmol) was added, the mixture was purged again with N₂ and stirred at 130° C. using one single mode microwave (Biotage Initiator EXP 60) with a power output ranging from 0 to 400 W for 15 min [fixed hold time]. The r.m. was treated with DCM and water, and the organic layer was separated, washed with brine and evaporated in vacuo to yield 1.5 g of a yellow solid. The solid was purified by prep. LC (irregular SiOH 15-40 µm 300 g Merck, mobile phase: 0.1% NH₄OH, 97% DCM, 3% MeOH). The pure fractions were collected and the solvent was removed in vacuo to give 98 mg of a pale yellow solid which was triturated with pentane, and the solvent was removed in vacuo to yield 69 mg of Co. 24, white solid (17%). m.p.: 267° C. (DSC).

Example A30

Preparation of Co. 25 a—Synthesis of Int. 84:

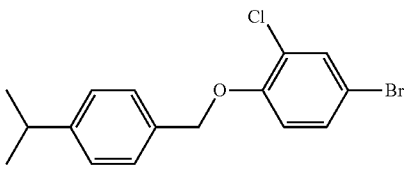

To a sol. of 4-bromo-2-chlorophenol (0.6 g, 2.89 mmol), 8 (0.508 mL, 3.04 mmol) in DMF (6 mL) was added K₂CO₃ (0.44 g, 3.18 mmol). The mixture was stirred at r.t. for 2 h. Water and DCM were added and the product was extracted with DCM. The organic layer was separated, dried, filtered and evaporated until dryness to give 933 mg of Int. 84 (95%).

b—Synthesis of Int. 85:

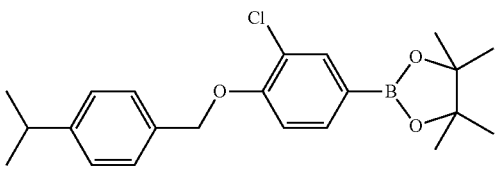

In a sealed tube, a mixture of 84 (0.5 g, 1.47 mmol), BisPin (0.486 g, 1.91 mmol), KOAc (0.433 g, 4.42 mmol) in DME (7 mL) was carefully purged with N₂. PdCl₂(dppf) (36 mg, 0.044 mmol) was added and the r.m. was purged again with N₂. The mixture was heated at 100° C. overnight. EtOAc and water were added and the mixture was extracted with EtOAc. The organic layer was separated, dried, filtered and evaporated to give 89 2 mg of a residue. The residue was purified by prep. LC on (Irregular SiOH 15-40 µm 50 g Merck, mobile phase: 80/20 Heptane/EtOAc. The pure fractions were collected and evaporated to give 437 mg of Int. 85 (77%).

c—Synthesis of Co. 25:

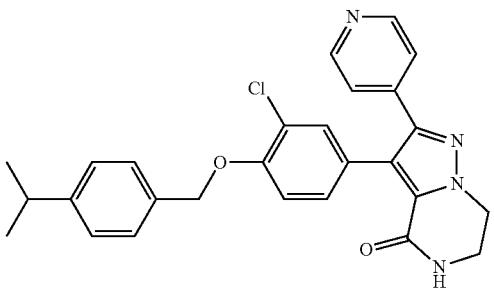

In a microwave vial, a mixture of 4 (251 mg, 0.86 mmol), 85 (430 mg, 1.11 mmol), K₃PO₄ (761 mg, 3.59 mmol) in 1,4-dioxane (1.6 mL) and H₂O (0.53 mL) was carefully purged with N₂. PCy₃ (50 mg, 0.18 mmol) and Pd(OAc)₂ (20 mg; 0.09 mmol) were added and the r.m. was purged again with N₂. The r.m. was stirred for 16 h at 80° C. The crude material was dissolved in water and extracted with EtOAc. The organic phase was dried over MgSO₄, filtered and evaporated in vacuo to give 765 mg of a residue. The residue was purified by prep. LC on (irregular 15-40 µm 30 g Merck, mobile phase: NH₄OH/DCM/MeOH 0.3/97/3). The pure fractions were collected and the solvent was evaporated until dryness to give 250 mg which was crystallized from DIPE, filtered and dried to give 188 mg of Co. 25 (46%). m.p.: 251° C. (dsc).

Example A31

Preparation of Co. 26 a—Synthesis of Int. 86:

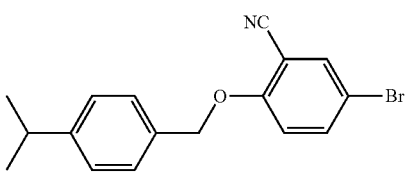

To a sol. of 5-bromo-2-hydroxybenzonitrile (0.6 g, 3.03 mmol), 8 (0.532 mL, 3.18 mmol) in DMF (6 mL) was added K₂CO₃ (0.46 g, 3.33 mmol). The mixture was stirred at r.t. for 2 h. Water and DCM were added and the product was extracted with DCM. The organic layer was separated, dried, filtered and evaporated until dryness to give 1 g of Int. 86 (100%).

b—Synthesis of Int. 87:

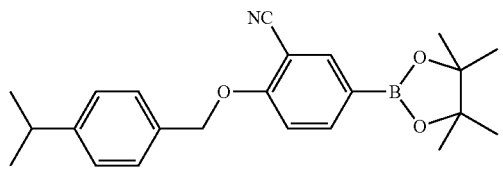 [SMILES: CC(C)c1ccc(COc2ccc(B3OC(C)(C)C(C)(C)O3)cc2Cl)cc1]

In a sealed tube, a mixture of 86 (0.296 g, 0.896 mmol), BisPin (0.455 g, 1.79 mmol), KOAc (0.264 g, 2.69 mmol) in DME (5 mL) was carefully purged with $N_2$. $PdCl_2$(dppf) (22 mg, 0.027 mmol) was added and the r.m. was purged again with $N_2$. The mixture was heated at 100° C. overnight. EtOAc and water were added and the mixture was extracted with EtOAc. The organic layer was separated, dried, filtered and evaporated. The residue (644 mg) was purified by prep. LC on (Irregular SiOH 15-40 μm 50 g Merck, mobile phase: 80/20 Heptane/EtOAc). The pure fractions were collected and evaporated to give 370 mg of Int. 87 (100%).

c—Synthesis of Co. 26:

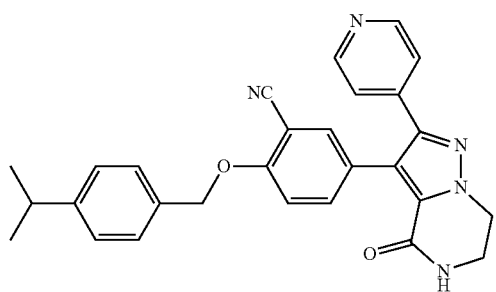 [SMILES: CC(C)c1ccc(COc2ccc(-c3c(-c4ccncc4)nn4c3C(=O)NCC4)cc2C#N)cc1]

In a microwave vial, a mixture of 4 (0.17 g, 0.58 mmol), 87 (0.371 g, 0.86 mmol), $K_3PO_4$ (0.516 g, 2.43 mmol) in 1,4-dioxane (2.72 mL) and $H_2O$ (0.91 mL) was carefully purged with $N_2$. $PCy_3$ (34 mg, 0.122 mmol) and Pd(OAc)$_2$ (14 mg, 0.061 mmol) were added and the r.m. was purged again with $N_2$. The r.m. was stirred for 16 h at 80° C. The crude material was dissolved in water and extracted with EtOAc. The organic phase was dried over $MgSO_4$, filtered and evaporated in vacuo to give 332 mg of a residue. The residue was purified by prep. LC on (irregular 15-40 μm 50 g Merck, mobile phase: $NH_4OH$/DCM/MeOH 0.2/96/4). The pure fractions were collected and the solvent was evaporated until dryness to give 85 mg which was crystallized from DIPE, filtered and dried to give 84 mg of Co. 26 (31%). m.p.: 235° C. (dsc).

Example A32

Preparation of Co. 27 a—Synthesis of Int. 88:

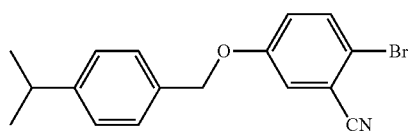 [SMILES: CC(C)c1ccc(COc2ccc(Br)c(C#N)c2)cc1]

A sol. of 2-bromo-5-hydroxybenzonitrile (6.29 g, 31.8 mmol) in ACN (90 mL) and DMF (10 mL) was treated with $K_2CO_3$ (4.83 g, 34.9 mmol) and 8 (7.11 g, 33.4 mmol) at rt.

The r.m. was stirred for 18 h at r.t. Then, water and EtOAc were added, and the organic layer was washed with brine, separated, dried over $MgSO_4$, filtered and concentrated in vacuo to afford 11.4 g of Int. 88, white solid (quant.).

b—Synthesis of Int. 89:

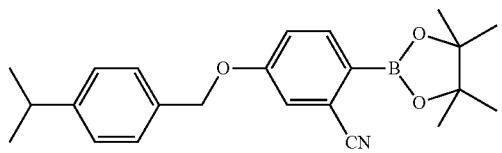 [SMILES: CC(C)c1ccc(COc2ccc(B3OC(C)(C)C(C)(C)O3)c(C#N)c2)cc1]

A mixture of 88 (4.72 g, 14.3 mmol), BisPin (5.45 g, 21.4 mmol) and KOAc (4.21 g, 42.9 mmol) in DME (90 mL) was carefully purged with $N_2$. $PdCl_2$(dppf) (1.17 g, 1.43 mmol) was added and the r.m. was purged again with $N_2$. The r.m. was stirred at 100° C. for 18 h. The r.m. was diluted with EtOAc and water. The organic layer was washed with brine and sat $NaHCO_3$ sol., dried over $MgSO_4$, filtered and evaporated in vacuo to give 9.09 g of a black solid. The solid was purified by prep. LC (irregular SiOH 15-40 μm, 220 g, Grace, mobile phase gradient: Heptane 100% to EtOAc 30%, Heptane 70%). The pure fractions were collected and solvent was evaporated until dryness to give 3.26 g of Int. 89 white solid (60%).

c—Synthesis of Co. 27:

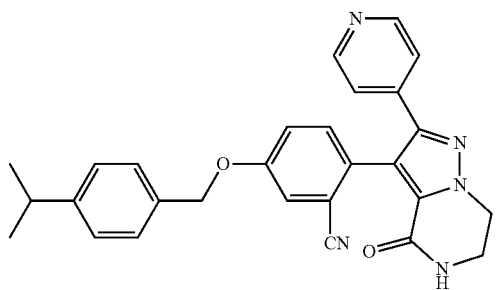 [SMILES: CC(C)c1ccc(COc2ccc(-c3c(-c4ccncc4)nn4c3C(=O)NCC4)c(C#N)c2)cc1]

A sol. of 4 (0.8 g, 2.73 mmol), 89 (1.85 g, 4.91 mmol) and $Cs_2CO_3$ (2.22 g, 6.82 mmol) in DMF (16 mL) in a sealed tube was purged with $N_2$. $Pd(PPh_3)_4$ (0.315 g, 0.273 mmol) was added, and the mixture was purged again with $N_2$ and stirred at 150° C. using one single mode microwave (Biotage Initiator EXP 60) with a power output ranging from 0 to 400 W for 30 min [fixed hold time]. The crude mixture was diluted with a DCM/MeOH sol. (95/5) and brine. The organic layer was separated, dried over $MgSO_4$, filtered off and evaporated in vacuo to yield 1.85 g of a sticky brown solid. The solid was purified by prep. LC (Irregular SiOH 50 μm, 80 g Grace, mobile phase gradient: from DCM 100% to DCM 85%, MeOH 15%). The fractions were collected and evaporated in vacuo to give 333 mg of a yellow solid. This solid was triturated with pentane. The solvent was removed in vacuo and the remaining solid was purified by prep. LC (Irregular SiOH 50 μm, 40 g Grace, mobile phase gradient: from DCM 100% to DCM 90%, MeOH 10%). The fractions were combined and evaporated in vacuo to give 180 mg of a pale yellow solid which was crystallized from a mixture of $Et_2O$/EtOH (3/1). The solvents were removed, and the remaining solid was triturated with $Et_2O$. The solid was filtered and dried to give 135 mg of Co. 27, pale yellow solid (11%). m.p.: 268° C. (DSC)

Example A33

Preparation of Co. 28 a—Synthesis of Int. 90:

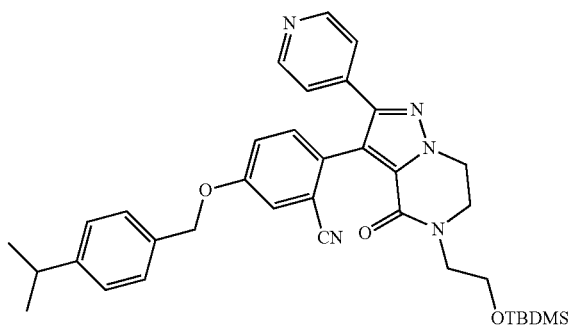 [SMILES: CC(C)c1ccc(COc2ccc(-c3c(-c4ccncc4)nn4c3C(=O)N(CCO[Si](C)(C)C(C)(C)C)CC4)c(C#N)c2)cc1]

A sol. of 28 (1.20 g, 2.66 mmol), 89 (1.81 g, 4.79 mmol) and Cs₂CO₃ (2.17 g, 6.65 mmol) in DMF (16 mL) in a sealed tube was purged with N₂. Pd(PPh₃)₄ (0.307 g, 0.266 mmol) was added, and the mixture was purged again with N₂ and stirred at 150° C. using one single mode microwave (Biotage Initiator EXP 60) with a power output ranging from 0 to 400 W for 30 min [fixed hold time]. Then, additional 89 (1.00 g, 2.66 mmol), Cs₂CO₃ (0.866 g, 2.66 mmol) and Pd(PPh₃)₄ (0.154 g, 0.133 mmol) were added, and the mixture was purged again with N₂ and stirred at 150° C. using one single mode microwave (Biotage Initiator EXP 60) with a power output ranging from 0 to 400 W for 15 min [fixed hold time]. The crude mixture was concentrated in vacuo, and then diluted with a DCM/MeOH sol. (95/5) and water. The organic layer was separated, washed with brine, dried over MgSO4, filtered off and evaporated in vacuo to yield 3.69 g of a sticky brown solid. The solid was purified by prep. LC (Irregular SiOH 50 μm, 120 g Grace, mobile phase gradient: from DCM 100% to DCM 97%, MeOH 3%). The fractions were collected and evaporated in vacuo to give 510 mg of Int. 90, yellow oil with a purity of 70%. The product was used as such as for the next step.

b—Synthesis of Co. 28:

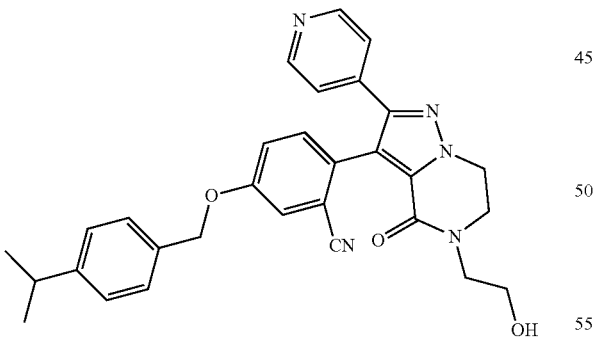

TBAF (0.580 mL, 0.580 mmol) was added to a stirred sol. of 90 (510 mg, 0.574 mmol) in THF (5 mL) at 0° C., and the r.m. was stirred at r.t. for 18 h. The crude mixture was diluted with water and a sol. of DCM/MeOH (96:4). The organic layer was separated, washed with brine, dried over MgSO₄, filtered and evaporated in vacuo. The residue (790 mg) was purified by prep. LC (Irregular SiOH 50 μm, 30 g Grace, mobile phase gradient: from DCM 100% to DCM 94%, MeOH 6%). The fractions were collected and evaporated in vacuo to give 231 mg of a white solid. This solid was solubilized in MeOH (1 mL). The solvent was allowed to evaporate slowly to give 230 mg of Co. 28, crystalline white solid (79%). m.p.: 185° C. (DSC).

Example A34

Preparation of Co. 29 a—Synthesis of Int. 91:

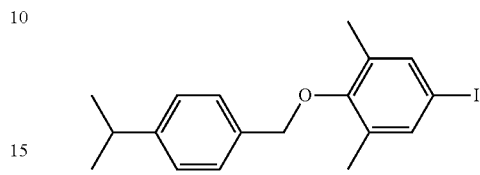

To a sol. of 2,6-dimethyl-4-iodophenol (2.48 g, 10 mmol), 8 (1.76 mL, 10.5 mmol) in ACN (25 mL) was added K₂CO₃ (1.52 g, 11 mmol). The mixture was stirred at r.t. overnight. Water and DCM were added and the product was extracted with DCM. The organic layer was separated, dried, filtered and evaporated until dryness to give 3.43 g of a residue. The residue was purified by prep. LC on (Irregular SiOH 15-40 μm 50 g Merck, mobile phase: 90/10 Heptane/EtOAc). The pure fractions were collected and evaporated until dryness to give 2.5 g of Int. 91 (66%).

b—Synthesis of Int. 92:

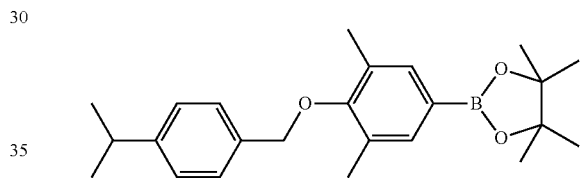

In a sealed tube, a mixture of 91 (2.45 g, 6.44 mmol), BisPin (2.45 g, 9.66 mmol), KOAc (1.89 g, 19.3 mmol) in DME (25 mL) was carefully purged with N₂. PdCl₂(dppf) (0.158 g, 0.193 mmol) was added and the r.m. was purged again with N₂. The mixture was heated at 100° C. overnight. EtOAc and water were added and the mixture was extracted with EtOAc. The organic layer was separated, dried, filtered and evaporated until dryness to give 4.09 g of a residue. The residue was purified by prep. LC on (Irregular SiOH 15-40 μm 90 g Merck, mobile phase: 90/10 Heptane/EtOAc). The pure fractions were collected and evaporated until dryness to 2.43 g of Int. 92 (yield 99%; purity 75%). The product was used as such for the next reaction step.

c—Synthesis of Co. 29:

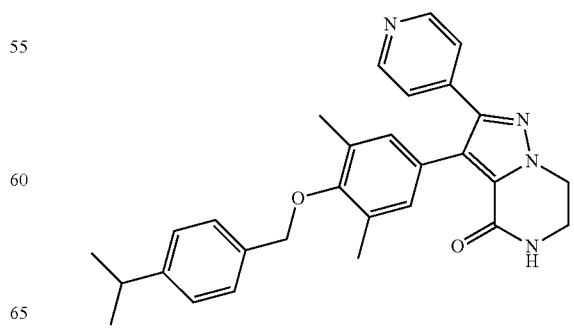

In a microwave vial, a mixture of 4 (0.4 g, 1.37 mmol), 92 (0.843 g, 1.77 mmol), K₃PO₄ (1.21 g, 5.72 mmol) in 1,4-dioxane (6.4 mL) and H₂O (2.13 mL) was carefully purged with N₂. PdCl₂(dppf) (112 mg, 0.14 mmol) was added and the r.m. was purged again with N₂. The r.m. was stirred for 16 h at 80° C. The crude material was dissolved in water and extracted with EtOAc. The organic phase was dried over MgSO₄, filtered and evaporated in vacuo to give 1.16 g of a residue. The residue was purified by prep. LC (Stationary phase: irregular SiOH 15-40 m 300 g Merck, Mobile phase: NH₄OH/DCM/MeOH 0.2/97/3). The pure fractions were collected and evaporated until dryness to give 475 mg which was crystallized from Et₂O, filtered and dried to give 443 mg of Co. 29 (70%). m.p.: 260° C. (dsc)

Example A35

Preparation of Co. 30 a—Synthesis of Int. 93:

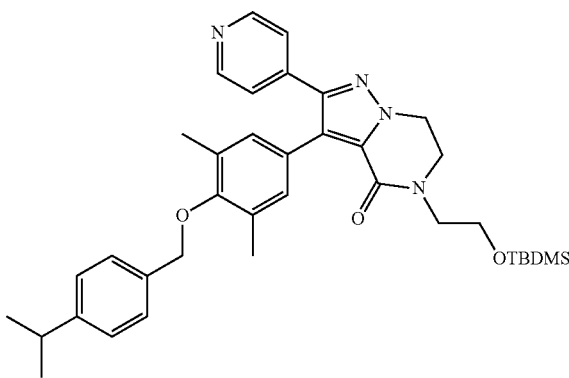 [SMILES: Cc1cc(-c2c(-c3ccncc3)nn3c2C(=O)N(CCO[Si](C)(C)C(C)(C)C)CC3)cc(C)c1OCc1ccc(C(C)C)cc1]

In a microwave vial, a mixture of 28 (0.6 g, 1.33 mmol), 92 (0.758 g, 1.6 mmol), K₃PO₄ (1.13 g, 5.3 mmol) in 1,4-dioxane (5.84 mL) and H₂O (2 mL) was carefully purged with N₂. PdCl₂(dppf) (109 mg, 0.13 mmol) was added and the r.m. was purged again with N₂. The r.m. was heated at 80° C. overnight. The r.m. was diluted with EtOAc and washed with water (once) and with brine (twice). The organic phase was dried over MgSO₄, filtered on a pad of Celite® and evaporated in vacuo to give 1.39 g of an oil. This oil was purified by prep. LC (irregular SiOH 30 μm, 40 g Interchim, mobile phase: DCM/MeOH/NH₄OH 98/2/0.1.) The pure fractions were collected and evaporated until dryness to give 111 mg of 93 and 648 mg of a 2$^{nd}$ residue. The 2$^{nd}$ residue was purified by prep. LC (irregular SiOH 30 μm, 40 g Interchim, mobile phase: DCM/MeOH/NH₄OH 98/2/0.1). The pure fractions were collected and evaporated until dryness to give 588 mg of 93. Both fractions were combined to yield 699 mg of Int. 93 (84%).

b—Synthesis of Co. 30:

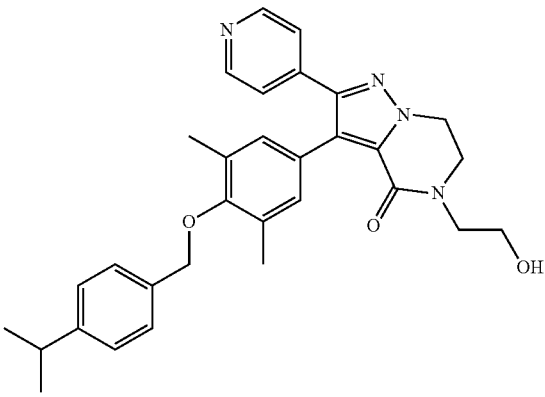 [SMILES: Cc1cc(-c2c(-c3ccncc3)nn3c2C(=O)N(CCO)CC3)cc(C)c1OCc1ccc(C(C)C)cc1]

TBAF (1.44 mL, 1.44 mmol) was added dropwise to a sol. of 93 (0.752 g, 1.2 mmol) in THF (12 mL) at r.t. The mixture was stirred for 3 h at r.t. EtOAc and water were added. The organic layer was separated, dried, filtered and evaporated until dryness to give 626 mg of a residue. The residue was purified by prep. LC (Regular SiOH, 30 μm, 12 g GraceResolv™, mobile phase gradient: DCM/MeOH/NH₄OH from 98/2/0.1 to 96/4/0.1). The pure fractions were collected and evaporated until dryness to give 317 mg which was crystallized from Et₂O, filtered and dried to give 218 mg of Co. 30 (35%). m.p.: 170° C. (dsc).

Example A36

Preparation of Co. 31 a—Synthesis of Int. 94:

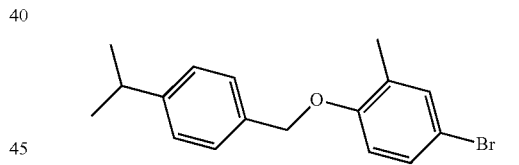

To a sol. of 4-bromo-2-methylphenol (2.5 g, 13.4 mmol), 8 (2.35 mL, 14 mmol) in ACN (25 mL) was added K₂CO₃ (2.03 g, 14.7 mmol). The mixture was stirred at r.t. overnight. Water and DCM were added and the product was extracted with DCM. The organic layer was separated, dried, filtered and evaporated until dryness to give 4.33 g of Int. 94 (100%).

b—Synthesis of Int. 95:

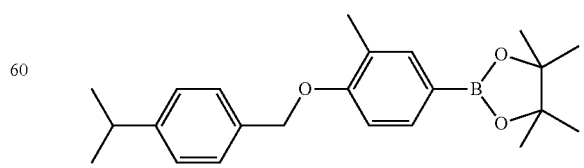

In a sealed tube, a mixture of 94 (3 g, 9.4 mmol), BisPin (3.58 g, 14 mmol), KOAc (2.77 g, 28.2 mmol) in DME (30 mL) was carefully purged with N₂. PdCl₂(dppf) (0.230 g, 0.282 mmol) was added and the r.m. was purged again with N₂. The mixture was heated at 100° C. overnight. EtOAc and water were added and the mixture was extracted with EtOAc. The organic layer was separated, dried, filtered and evaporated until dryness to give 6 g of a residue. The residue was purified by prep. LC on (Irregular SiOH 15-40 μm 90 g Merck, mobile phase: 90/10 Heptane/EtOAc). The fractions were collected and evaporated until dryness to give 1.34 g of a first fraction and 1.11 g of a second fraction. Both fractions were purified by prep. LC on (Irregular SiOH 15-40 μm 50 g Merck, mobile phase: from 98/2 Heptane/EtOAc to 95/5 Heptane/EtOAc). The pure fractions were collected and evaporated to give 1.46 g of Int. 95 (42%).

c—Synthesis of Int. 96:

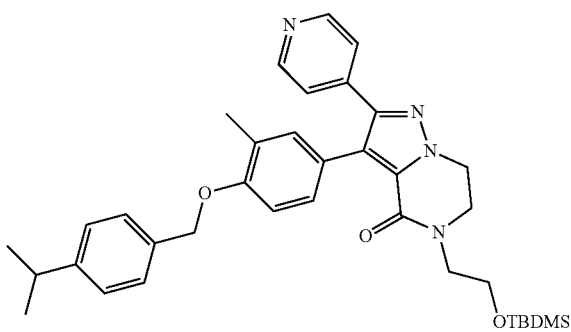 [SMILES: Cc1cc(-c2c(-c3ccncc3)nn3c2C(=O)N(CCO[Si](C)(C)C(C)(C)C)CC3)ccc1OCc1ccc(C(C)C)cc1]

In a microwave vial, a mixture of 28 (0.7 g, 1.55 mmol), 95 (0.738 g, 2.02 mmol), K₃PO₄ (1.32 g, 6.2 mmol) in 1,4-dioxane (6.8 mL) and H₂O (2.42 mL) was carefully purged with N₂. PdCl₂(dppf) (127 mg, 0.16 mmol) was added and the r.m. was purged again with N₂. The r.m. was heated at 80° C. overnight. The r.m. was diluted with EtOAc and washed with water (once) and with brine (3×). The organic phase was dried over MgSO₄, filtered and evaporated in vacuo to give 1.73 g of a residue. The residue was purified by prep. LC (irregular SiOH 30 μm, 40 g Interchim, mobile phase: from DCM 100% to DCM/MeOH/NH₄OH 97/3/0.1). The pure fractions were collected and evaporated until dryness to give 1.2 g of Int. 96 (100%).

d—Synthesis of Co. 31:

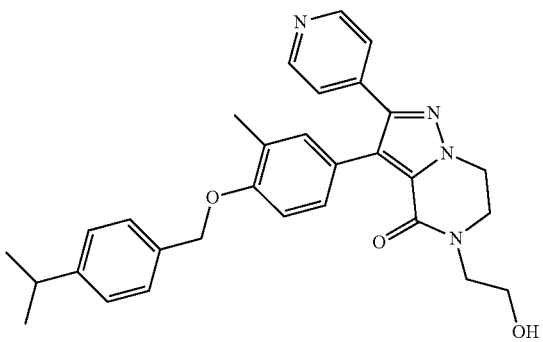 [SMILES: Cc1cc(-c2c(-c3ccncc3)nn3c2C(=O)N(CCO)CC3)ccc1OCc1ccc(C(C)C)cc1]

TBAF (2.36 mL, 2.36 mmol) was added dropwise to a sol. of 96 (1.2 g, 1.96 mmol) in THF (20 mL) at r.t. The mixture was stirred for 3 h at r.t. EtOAc and water were added. The organic layer was separated, dried, filtered and evaporated until dryness to give 980 mg of a residue. The residue was purified by prep. LC (Regular SiOH, 30 μm, 24 g GraceRe-solv™, mobile phase gradient: from DCM 100% to DCM/MeOH/NH₄OH, 95/5/0.1). The pure fractions were collected and evaporated until dryness to give 780 mg which was crystallized from DIPE, filtered and dried to give 491 mg of Co. 31 (50%).

Example A37

Preparation of Co. 32 a—Synthesis of Int. 97:

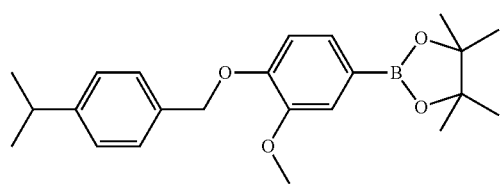

A flask was charged with 4-hydroxy-3-methoxyphenyl boronic acid pinacol ester (1.50 g, 6.00 mmol), 6 (1.35 g, 9.00 mmol), diphenylphosphinopolystyrene (3.00 g, 9.00 mmol) and DCM (40 mL). DBAD (2.07 g, 9.00 mmol) was then added and the r.m. was stirred at r.t. for 17 h. After filtration on a glass frit, the residual polymer was washed with DCM. The filtrate was evaporated in vacuo to afford yelow oil. This oil was purified by prep. LC (irregular SiOH 15-40 μm, 80 g Grace, dry loading, mobile phase gradient: from 100% heptane to heptane 90%, EtOAc 10%). The pure fractions were collected and solvent was evaporated until dryness to give 1.61 g of Int. 97, white solid (70%).

b—Synthesis of Co. 32:

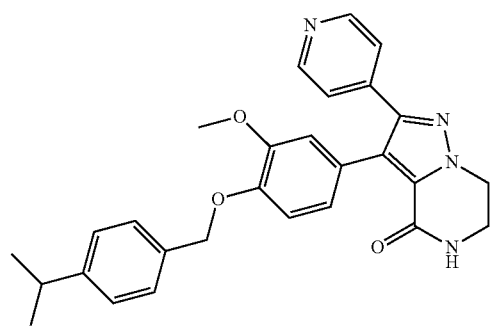 [SMILES: COc1cc(-c2c(-c3ccncc3)nn3c2C(=O)NCC3)ccc1OCc1ccc(C(C)C)cc1]

In a Schlenk tube, a mixture of 4 (250 mg, 0.853 mmol), 97 (815 mg, 2.13 mmol), K₃PO₄ (724 mg, 3.41 mmol) in 1,4-dioxane (6 mL) and H₂O (2 mL) was carefully purged with N₂. Pd(OAc)₂ (19 mg, 85.3 μmol) and PCy₃ (48 mg, 171 μmol) were added and the r.m. was purged again with N₂. The Schlenk tube was then sealed and the r.m. was stirred for 17 h at 80° C. The crude mixture was then diluted in DCM and washed with water (2×20 mL). The organic layer was collected, dried over MgSO₄ and evaporated in vacuo to afford brown oil. The oil was purified by prep. LC (irregular SiOH 15-40 μm, 40 g Merck, Mobile phase gradient: from 100% DCM to DCM 95%, MeOH 5%) to give 330 mg of Co. 32, white solid (83%). m.p.: 187° C. (DSC).

147

Example A38

Preparation of Co. 33 a—Synthesis of Int. 98:

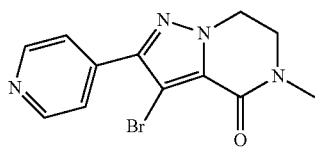 [SMILES: CN1CCn2nc(-c3ccncc3)c(Br)c2C1=O]

NaH (60%) (655 mg, 216.4 mmol) was added to a suspension of 4 (4.00 g, 13.6 mmol) in DMSO (50 mL) at r.t. under $N_2$. The mixture was stirred for 2 h. MeI (1020 μL, 16.4 mmol) was added and the mixture was stirred for 2 h. The mixture was poured into water and extracted with EtOAc. The organic layer was dried over $MgSO_4$, filtered and evaporated until dryness to give 5.00 g of Int. 98, yellow solid (quant.).

b—Synthesis of Co. 33:

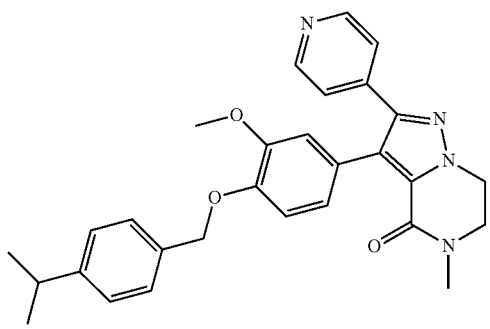 [SMILES: COc1cc(-c2c(-c3ccncc3)nn3c2C(=O)N(C)CC3)ccc1OCc1ccc(C(C)C)cc1]

In a sealed tube, a mixture of 98 (154 mg, 501 μmol), 97 (766 mg, 2.00 mmol), $K_3PO_4$ (425 mg, 2.00 mmol) in 1,4-dioxane (3 mL) and $H_2O$ (1 mL) was carefully purged with $N_2$. $PCy_3$ (28 mg, 100 μmol) and $Pd(OAc)_2$ (11 mg, 50.1 μmol) were added and the r.m. was purged again with $N_2$. The r.m. was stirred for 17 h at 100° C. The crude material was dissolved in water (20 mL) and extracted with EtOAc (2×40 mL). The organic phase was dried over $MgSO_4$, filtered and evaporated in vacuo to give 874 mg of black oil. The black oil was purified by prep. LC (irregular SiOH 15-40 μm, 30 g Merck, mobile phase gradient: from DCM 100% to DCM 95%, MeOH 5%). The pure fractions were collected and evaporated until dryness to give 200 mg of a white solid which was tritured with $Et_2O$, filtered off and dried to give 196 mg of Co. 33, white solid (83%). m.p.: 151° C. (DSC).

Example A39

Preparation of Co. 34 a—Synthesis of Int. 99:

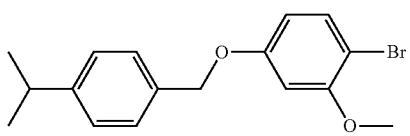 [SMILES: COc1cc(OCc2ccc(C(C)C)cc2)ccc1Br]

148

Under $N_2$, a sol. of 4-bromo-3-methoxyphenol (4.00 g, 19.7 mmol) in ACN (19 mL) was treated with $K_2CO_3$ (3.00 g, 21.7 mmol) and 8 (3.63 mL, 21.7 mmol) and the r.m. was stirred for 18 h at r.t., then extracted with water and EtOAc. The organic layer was washed with brine (twice), dried over $MgSO_4$, filtered off and evaporated in vacuo to give 7.99 g of yellow oil. This oil was diluted in $Et_2O$ and washed with brine (3×50 mL), the organic phase was dried over $MgSO_4$, filtered and evaporated in vacuo to give 6.8 g of Int. 99, yellow oil (quant.).

b—Synthesis of Int. 100:

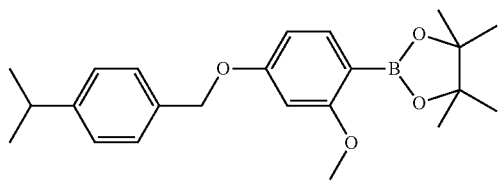 [SMILES: COc1cc(OCc2ccc(C(C)C)cc2)ccc1B1OC(C)(C)C(C)(C)O1]

A mixture of 99 (5.57 g, 16.6 mmol) in dry THF (70 mL) was carefully purged with $N_2$. nBuLi 1.6N in hexane (11.4 mL, 18.3 mmol) was added at −78° C. and the r.m. was stirred 2 h at −78° C. Isopropoxyboronic acid pinacol ester (3.8 mL, 18.3 mmol) was added at −78° C. and the r.m. was stirred for 3 h at −78° C. The sol. was diluted in DCM and water. The organic layer was washed with HCl 1N, dried over $MgSO_4$, filtered and evaporated in vacuo to give 7.7 g of colorless oil. This oil was purified by prep. LC (irregular SiOH 15-40 μm, 30 g Merck, mobile phase: Heptane 50%, EtOAc 50%). The pure fractions were collected and solvent was evaporated to give 6.6 g of Int. 100 (quant.).

c—Synthesis of Co. 34:

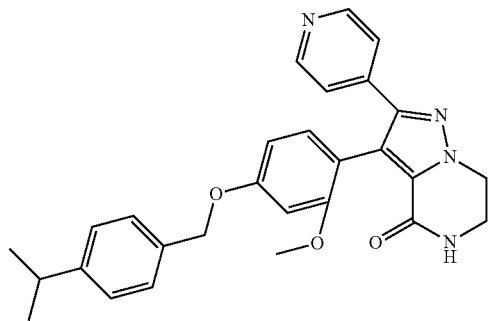 [SMILES: COc1cc(OCc2ccc(C(C)C)cc2)ccc1-c1c(-c2ccncc2)nn2c1C(=O)NCC2]

In a sealed tube, a mixture of 4 (500 mg, 1.71 mmol), 100 (1.63 g, 4.26 mmol), $K_3PO_4$ (1.45 g, 6.82 mmol) in 1,4-dioxane (8 mL) and $H_2O$ (2.6 mL) was carefully purged with $N_2$. $PCy_3$ (96 mg, 341 μmol) and $Pd(OAc)_2$ (38 mg, 171 μmol) were added and the r.m. was purged again with $N_2$. The r.m. was stirred for 18 h at 100° C. The crude material was dissolved in water and extracted with EtOAc. The organic phase was dried over $MgSO_4$, filtered and evaporated in vacuo to give 1.20 g of brown oil. This oil was purified by prep. LC (irregular SiOH 15-40 μm, 30 g Merck, mobile phase gradient: from DCM 100% to DCM 95%, MeOH 5%). The pure fractions were collected and solvent was evaporated to give 205 mg of a white solid. The solid was triturated in pentane and evaporated in vacuo to give 175 mg of Co. 34, white solid (16%). m.p.: 276° C. (DSC).

Example A40

Preparation of Co. 35 a—Synthesis of Int. 101:

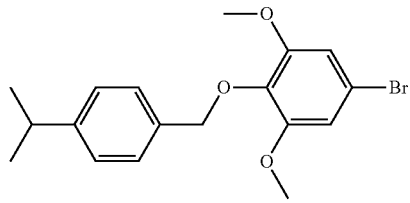 [SMILES: COc1cc(Br)cc(OC)c1OCc1ccc(C(C)C)cc1]

To a sol. of 4-bromo-2,6-dimethoxyphenol (2 g, 8.6 mmol), 8 (1.5 mL, 9 mmol) in ACN (25 mL) was added K$_2$CO$_3$ (1.31 g, 9.4 mmol). The mixture was stirred at r.t. overnight. Water and DCM were added and the product was extracted with DCM. The organic layer was separated, dried, filtered and evaporated until dryness to give 3.37 g of a residue. The residue was purified by prep. LC on (Irregular SiOH 15-40 μm 50 g Merck, mobile phase: 90/10 Heptane/EtOAc). The fraction was collected and evaporated until dryness to give 2.82 g which was purified again by prep. LC on (Irregular SiOH 15-40 μm 50 g Merck, mobile phase: 95/5 Heptane/EtOAc). The pure fractions were collected and evaporated until dryness to give 1.82 g of Int. 101 (58%).

b—Synthesis of Int. 102:

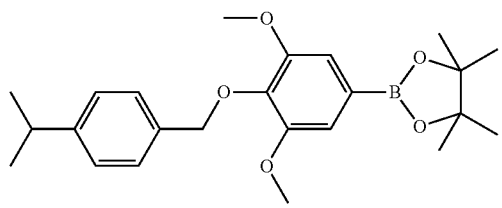 [SMILES: COc1cc(B2OC(C)(C)C(C)(C)O2)cc(OC)c1OCc1ccc(C(C)C)cc1]

In a sealed tube, a mixture of 101 (1.82 g, 4.98 mmol), BisPin (1.9 g, 7.47 mmol), KOAc (1.47 g, 14.9 mmol) in DME (20 mL) was carefully purged with N$_2$. PdCl$_2$(dppf) (0.122 g, 0.15 mmol) was added and the r.m. was purged again with N$_2$. The mixture was heated at 100° C. overnight. EtOAc and water were added and the mixture was extracted with EtOAc. The organic layer was separated, dried, filtered and evaporated until dryness to give 3.05 g of a residue. The residue was purified by prep. LC on (Irregular SiOH 15-40 μm 50 g Merck, mobile phase: 90/10 Heptane/EtOAc). The pure fraction was collected and evaporated until dryness to give 1.79 g of Int. 102 (87%; 80% purity). The product was used like that for the next step.

c—Synthesis of Co. 35:

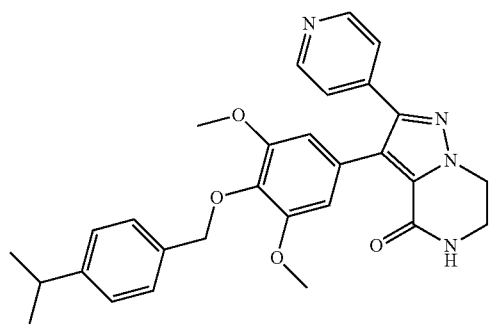 [SMILES: COc1cc(-c2c(-c3ccncc3)nn3c2C(=O)NCC3)cc(OC)c1OCc1ccc(C(C)C)cc1]

In a microwave vial, a mixture of 4 (0.3 g, 1.02 mmol), 102 (0.686 g, 1.33 mmol), K$_3$PO$_4$ (0.911 g, 4.29 mmol) in 1,4-dioxane (4.8 mL) and H$_2$O (1.6 mL) was carefully purged with N$_2$. PdCl$_2$(dppf) (84 mg, 0.1 mmol) was added and the r.m. was purged again with N$_2$. The r.m. was stirred for 16 h at 80° C. The crude material was dissolved in water and extracted with EtOAc. The organic phase was dried over MgSO$_4$, filtered and evaporated in vacuo to give 759 mg of a residue. The residue was purified by prep. LC (Stationary phase: irregular 15-40 μm 24 g Grace, mobile phase gradient: from DCM 100% to 0.1% NH$_4$OH, 95% DCM, 5% MeOH). The pure fractions were collected and evaporated until dryness to give 290 mg which was crystallized in Et$_2$O, filtered and dried to give 255 mg of Co. 35 (50%). m.p.: 192° C. (dsc).

Example A41

Preparation of Co. 36 a—Synthesis of Int. 103:

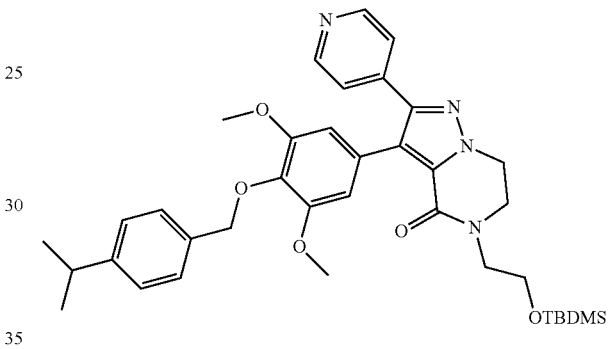

In a microwave vial, a mixture of 28 (0.7 g, 1.55 mmol), 102 (0.96 g, 1.86 mmol), K$_3$PO$_4$ (1.32 g, 6.2 mmol) in 1,4-dioxane (6.8 mL) and H$_2$O (2.42 mL) was carefully purged with N$_2$. PdCl$_2$(dppf) (127 mg, 0.16 mmol) was added and the r.m. was purged again with N$_2$. The r.m. was heated at 80° C. overnight. The r.m. was diluted with EtOAc and washed with water (once) and with brine (3x). The organic phase was dried over MgSO$_4$, filtered on a pad of Celite® and evaporated in vacuo to give 1.3 g of a residue. The residue was purified by prep. LC (irregular SiOH 30 μm, 40 g Interchim, mobile phase: from DCM 100% to DCM/MeOH/NH$_4$OH 97/3/0.1). The pure fractions were collected and evaporated until dryness to give 0.538 g of Int. 103 (53%).

b—Synthesis of Co. 36:

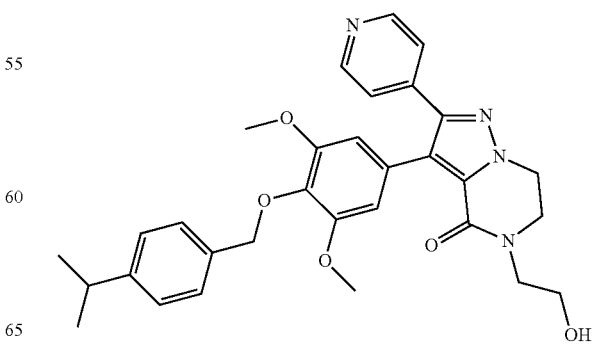

TBAF (0.93 mL, 0.93 mmol) was added dropwise to a sol. of 103 (509 mg, 0.775 mmol) in THF (8 mL) at r.t. The mixture was stirred for 3 h at r.t. EtOAc and water were added. The organic layer was separated, dried, filtered and evaporated until dryness to give 463 mg of a residue. The residue was purified by prep. LC (Regular SiOH, 30 µm, 12 g GraceResolv™, mobile phase gradient: from DCM 100% to DCM/MeOH/NH$_4$OH 95/5/0.1). The pure fractions were collected and evaporated until dryness. The residue (330 mg) was crystallized from DIPE, filtered and dried to give 303 mg of Co. 36 (72%). m.p.: 176° C. (dsc).

Example A42

Preparation of Co. 37 a—Synthesis of Int. 104:

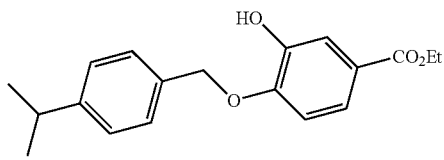 [SMILES: CCOC(=O)c1ccc(OCc2ccc(C(C)C)cc2)c(O)c1]

DBAD (7.6 g, 33 mmol) was added to a sol. of ethyl-3,4-dihydroxybenzoate (4 g, 22 mmol), PPh$_3$ supp. (10.3 g, 33 mmol), 6 (4 mL, 26.3 mmol) in THF (100 mL). The mixture was stirred at r.t. for 5 h. Water and EtOAc were added, the mixture was extracted, the organic layer was separated, dried over MgSO$_4$, filtered and evaporated until dryness to give 14.2 g of a residue. The residue was purified by prep. LC on (Irregular SiOH 20-45 µm 450 g MATREX, mobile phase: 85% Heptane, 15% EtOAc).

The pure fractions were collected and solvent was evaporated until dryness to give 2.2 g of Int. 104 (32%).

b—Synthesis of Int. 105:

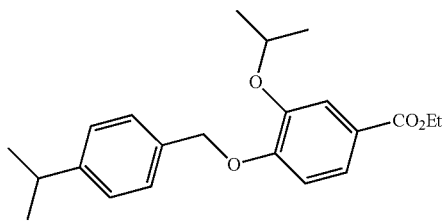 [SMILES: CCOC(=O)c1ccc(OCc2ccc(C(C)C)cc2)c(OC(C)C)c1]

A solution of 104 (1.5 g, 4.8 mmol), 2-bromopropane (0.5 ml, 5.2 mmol), K$_2$CO$_3$ (1 g, 7.1 mmol) in ACN (20 ml) was stirred at 80° C. for 18 h. Water and EtOAc were added, the mixture was extracted, the organic layer was separated, dried over MgSO$_4$, filtered and evaporated. The residue was purified by prep. LC on (Irregular SiOH 20-45 µm 450 g MATREX, mobile phase: 85% Heptane, 15% EtOAc). The pure fractions were collected and solvent was evaporated until dryness to give 1.1 g of Int. 105 (65%).

c—Synthesis of Int. 106:

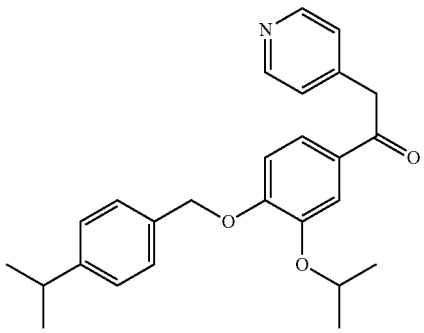 [SMILES: CC(C)Oc1cc(C(=O)Cc2ccncc2)ccc1OCc1ccc(C(C)C)cc1]

A sol. of 105 (1 g, 2.8 mmol) and 4-picoline (0.3 ml, 3.1 mmol) in dry THF (30 mL) was treated with LiHMDS (5.6 ml, 5.6 mmol) at 0° C. (addition over 10 min). After stirring for 1 h at 0° C., the reaction was allowed to warm to r.t. and was stirred for a weekend. The reaction was quenched with a 10% aq. sol. of NH$_4$Cl (50 mL). The mixture was extracted with DCM. The organic layer was separated, dried over MgSO$_4$, filtered and evaporated. The residue was purified by prep. LC (Irregular SiOH 20-45 µm 80 g MATREX, mobile phase: 95/5/0.1 DCM/MeOH/NH$_4$OH). The pure fractions were collected and the solvent was evaporated to give 900 mg of Int. 106 (80%).

d—Synthesis of Int. 107:

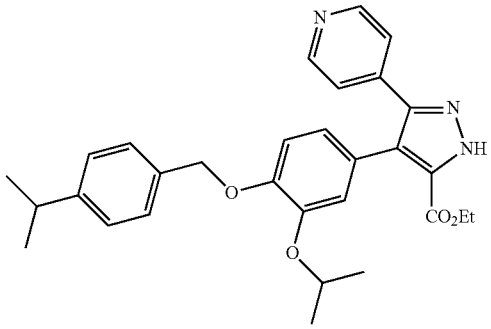 [SMILES: CCOC(=O)c1[nH]nc(-c2ccncc2)c1-c1ccc(OCc2ccc(C(C)C)cc2)c(OC(C)C)c1]

To a suspension of 106 (900 mg, 2.23 mmol) in ACN (5 mL) was added DBU (0.33 mL, 2.23 mmol) and ethyl diazoacetate (0.4 mL, 3.8 mmol). The mixture was stirred at r.t. for 2 h. The solvent was removed in vacuo and the residue was diluted in EtOAc.

The organic layer was washed with a sat. aq. sol. of NaHCO$_3$, dried over MgSO$_4$, filtered off and evaporated in vacuo. The residue was purified by prep. LC (irregular SiOH 15-40 µm, 40 g Grace, mobile phase: 97/3 DCM/MeOH). The pure fractions were collected and the solvent was evaporated until dryness to give 460 mg of Int. 107 (41%, beige powder).

e—Synthesis of Int. 108:

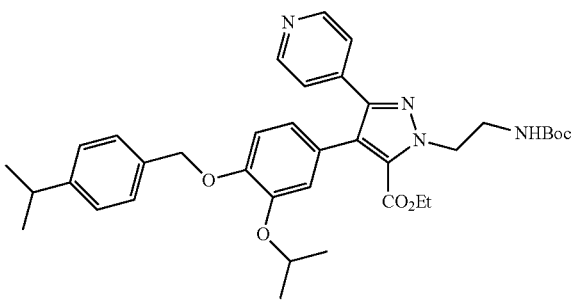 [SMILES: CCOC(=O)c1c(-c2ccc(OCc3ccc(C(C)C)cc3)c(OC(C)C)c2)c(-c2ccncc2)nn1CCNC(=O)OC(C)(C)C]

To a mixture of 107 (460 mg, 0.921 mmol), Boc-Glycinol (222 mg, 1.4 mmol) and PPh₃ supp. (362 mg, 1.4 mmol) in dry THF (10 mL) was added DBAD (318 mg, 1.4 mmol). The mixture was stirred for 4 h at r.t. The mixture was filtered and the filtrate was evaporated until dryness to give 1.4 g of a residue. The residue was purified by prep. LC on (irregular SiOH 15-40 μm 300 g Merck, mobile phase: 59% Heptane, 6% MeOH, 35% EtOAc). The pure fractions were collected and the solvent was evaporated until dryness to give 320 mg of Int. 108 (54%).

f—Synthesis of Int. 109:

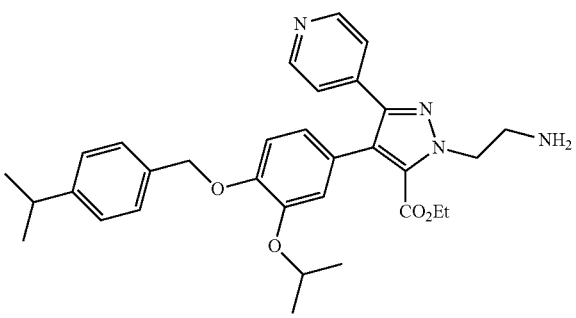 [SMILES: CCOC(=O)c1c(-c2ccc(OCc3ccc(C(C)C)cc3)c(OC(C)C)c2)c(-c2ccncc2)nn1CCN]

A solution of 108 (250 mg, 0.39 mmol) and HCl 3N (0.65 mL, 1.9 mmol) in ACN (5 mL) was stirred at 80° C. for 2 h. K₂CO₃ 10% and EtOAc were added and the mixture was extracted. The organic layer was separated, dried over MgSO₄, filtered and evaporated to give 250 mg of Int. 109 (100%).

g—Synthesis of Co. 37:

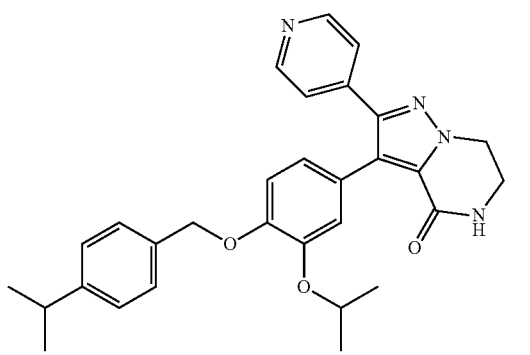 [SMILES: CC(C)Oc1cc(-c2c(-c3ccncc3)nn3c2C(=O)NCC3)ccc1OCc1ccc(C(C)C)cc1]

To a sol. of 109 (250 mg, 0.46 mmol) in MeOH (10 mL) was added Cs₂CO₃ (750 mg, 2.3 mmol) and the mixture was stirred at r.t. overnight. The mixture was filtered, the white solid was collected, washed with Et₂O and dried to give 138 mg. The solid was taken up in H₂O and DCM and extracted. The organic layer was separated, dried over MgSO₄, filtered and evaporated. The residue was taken up in Et₂O, the precipitate was filtered off and dried to give 97 mg of Co. 37 (42%). m.p.: 206° C. (dsc).

Example A43

Preparation of Co. 38 and Co. 39 a—Synthesis of Int. 120:

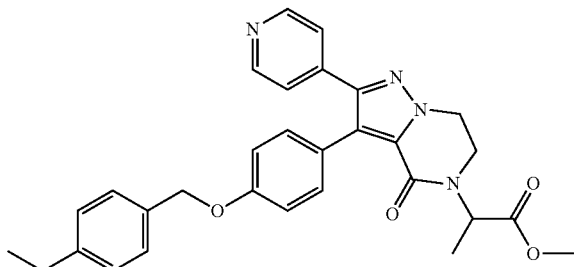

NaH 60% (274 mg, 6.8 mmol) was added slowly to a suspension of Co. 1 (2 g, 4.6 mmol) in dry DMSO (40 mL) at r.t. under N2. The mixture was stirred for 2 h. Then, methyl-2-bromopropionate (1.02 mL, 9.1 mmol) was added and the final mixture was stirred for 20 h. The mixture was poured into water and K₂CO₃, and extracted with EtOAc. The organic layer was evaporated until dryness. The residue was taken up with DCM, dried over MgSO₄, filtered and evaporated until dryness to give 2.6 g. The residue was purified by prep. LC (80 g of SiOH 30 μm Interchim, mobile phase gradient: from 100% DCM to 95% DCM 5% MeOH 0.1% NH₄OH). The pure fractions were collected and evaporated until dryness to give 2.47 g of Int. 120 (100%).

b—Synthesis of Co. 38 and Co. 39:

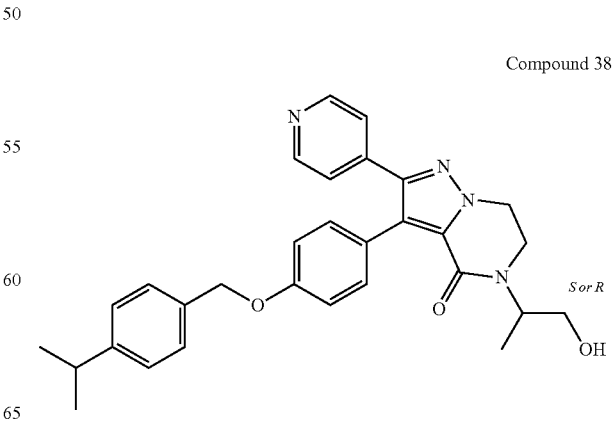

Compound 38

-continued

Compound 39

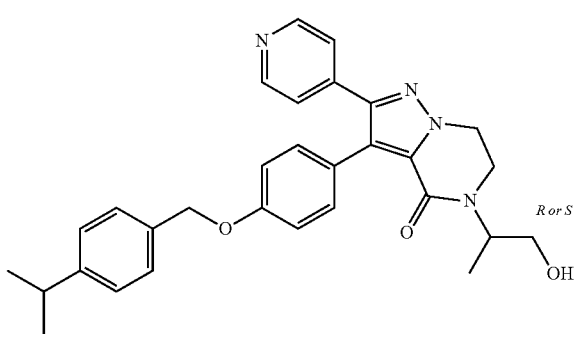
R or S 120 (2.47 g, 4.7 mmol) in THF (20 mL) was added dropwise to a suspension of LAH (268 mg, 7.06 mmol) in THF (30 mL) at 0° C. under N2. The mixture was stirred for 1.5 h. Ice water was added dropwise then DCM was added. The mixture was filtered and the filtrate was dried over MgSO₄, filtered and evaporated until dryness to give 2.6 g which was purified by prep. LC (80 g of irregular SiOH 30 μm Interchim, graduent from 100% DCM to 95% DCM 5% CH₃OH 0.1% NH₄OH). The fractions were collected and evaporated until dryness to give 0.467 g of a residue. This residue was purified by achiral SFC (Stationary phase: AMINO 6 μm 150×21.2 mm), Mobile phase: 80% CO₂, 20% MeOH). The fractions were collected and evaporated until dryness to give 290 mg which was purified by chiral SFC (Stationary phase: Chiralpak IC 5 μm 250×20 mm), Mobile phase: 60% CO₂, 40% iPrOH). The pure fractions were collected and evaporated until dryness to give 130 mg of a first residue and 130 mg of a second residue. The first residue was crystallized from Et₂O, filtered and dried to give 97 mg of Co. 39 (4%). m.p.: 144° C. (dsc). The second residue was crystallized from Et₂O, filtered and dried to give 100 mg of Co. 38 (4%). m.p.: 144° C. (dsc).

Co. 39: $[\alpha]_d$: +19.74° (589 nm, c 0.309 w/v %, DMF, 20° C.);

Co. 38: $[\alpha]_d$: −18.36° (589 nm, c 0.305 w/v %, DMF, 20° C.).

Example A44

Preparation of Co. 40

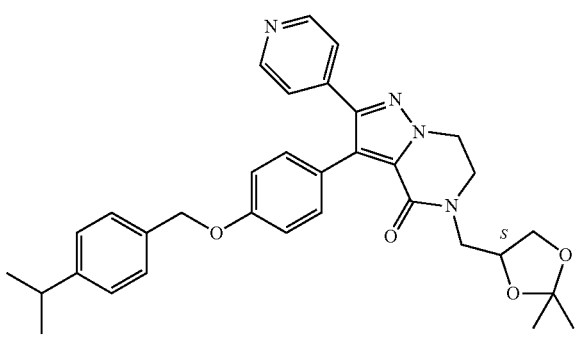

NaH 60% (0.82 g, 20.5 mmol) was added to Co. 1 (6 g, 13.7 mmol) in DMF (160 mL) at r.t. under N₂. The mixture was stirred for 2 h then (R)-(−)-2,2-dimethyl-1,3-dioxolane-4-ylmethyl P-toluenesulfonate (5.9 g, 20.5 mmol) was added portionwise and stirred for 15 h. The mixture was poured into water and K₂CO₃ and extracted with EtOAc. The organic layer was evaporated until dryness. The residue was taken up with DCM, dried over MgSO₄, filtered and evaporated until dryness to give 14 g which was purified by prep. LC (Stationary phase: Irregular SiOH 20-45 μm 450 g MATREX, Mobile phase: 0.1% NH₄OH, 98% DCM, 2% MeOH). The pure fractions were collected and evaporated until dryness to give 4.4 g of a residue (58%). A part of the residue was crystallized from Et₂O, filtered and dried to give 258 mg of Co. 40 (S).

m.p.: 113° C. (dsc); $[\alpha]_d$: −16.95° (589 nm, c 0.295 w/v %, meOH, 20° C.).

Example A45

Preparation of Co. 41

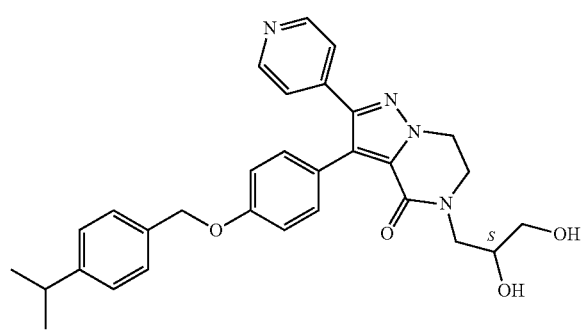

Co. 40 (3.7 g, 6.7 mmol), HCl 3N (11.1 mL, 33.5 mmol) in 1,4-dioxane (140 mL) were heated to 80° C. for 0.5 h. The mixture was cooled to r.t., poured into water and K₂CO₃ and extracted with EtOAc. The organic layer was dried over MgSO₄, filtered and evaporated until dryness. The residue was purified by prep. LC (80 g of SiOH 30 m Interchim, mobile phase gradient: from 100% DCM to 90% DCM 10% CH₃OH 0.1% NH₄OH). The fractions were collected and evaporated until dryness to give a residue which was crystallized from Et₂O, filtered and dried to give 2.97 g of Co. 41 (S) (87%). m.p.: 191° C. (dsc); $[\alpha]_d$: −18.85° (589 nm, c 0.2705 w/v %, DMF, 20° C.)

Example A46

Preparation of Co. 42

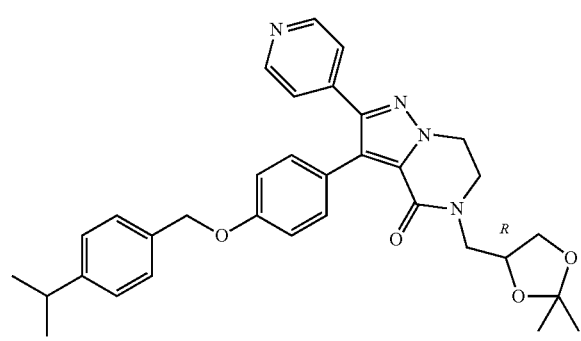

NaH 60% (0.684 g, 17.1 mmol) was added to Co. 1 (5 g, 11.4 mmol) in DMF (125 mL) at r.t. under $N_2$. The mixture was stirred for 2 h then (S)-(−)-2,2-dimethyl-1,3-dioxolane-4-ylmethyl P-toluenesulfonate (4.9 g, 17.1 mmol) in DMF (10 mL) was added dropwise and stirred for 15 h at rt. The mixture was poured into water and $K_2CO_3$ and extracted with EtOAc. The organic layer was evaporated until dryness. The residue was taken up with DCM, dried over $MgSO_4$, filtered and evaporated until dryness to give 9.7 g which was purified by prep. LC (120 g of silica gel 30 μm Interchim, mobile phase gradient: from 100% DCM to 95% DCM 5% $CH_3OH$ 0.1% $NH_4OH$). The desired fractions were collected and evaporated until dryness to give 2.12 g of a first residue and 2.1 g of a second residue. The second residue was purified by prep. LC (80 g of silica gel 30 μm Interchim, mobile phase gradient: from 100% DCM to 95% DCM 5% $CH_3OH$ 0.1% $NH_4OH$). The fractions were collected and evaporated until dryness to give 1.58 g a residue. The first residue and the last one were brought together to give 3.7 g of Co. 42 (59%). A part of Co. 42 was crystallized from $Et_2O$, filtered and dried to give 250 mg of Co. 42 (R). m.p.: 114° C. (dsc); $[\alpha]_d$: +9.98° (589 nm, c 0.2405 w/v %, meOH, 20° C.).

Example A47

Preparation of Co. 43

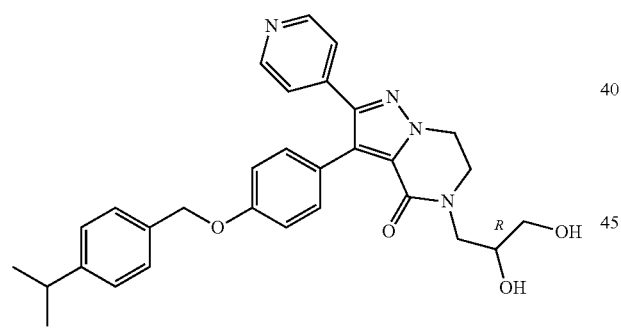

Co. 42 (3.17 g, 5.7 mmol), HCl 3N (9.6 mL, 28.7 mmol) in 1,4-dioxane (120 mL) were heated to 80° C. for 1 h. The mixture was cooled to r.t., poured into water and $K_2CO_3$ and extracted with EtOAc. The organic layer was dried over $MgSO_4$, filtered and evaporated until dryness to give 3.36 g. The residue was purified by prep. LC (80 g of SiOH 30 μm Interchim, mobile phase gradient: from 100% DCM to 90% DCM 10% $CH_3OH$ 0.1% $NH_4OH$). The fractions were collected and evaporated until dryness to give 2.76 g of a residue which was crystallized from $Et_2O$, filtered and dried to give 2.56 g of Co. 43 (R) (87%). m.p.: 190° C. (dsc); $[\alpha]_d$: +17.39° (589 nm, c 0.2875 w/v %, DMF, 20° C.).

Example A48

Preparation of Co. 44

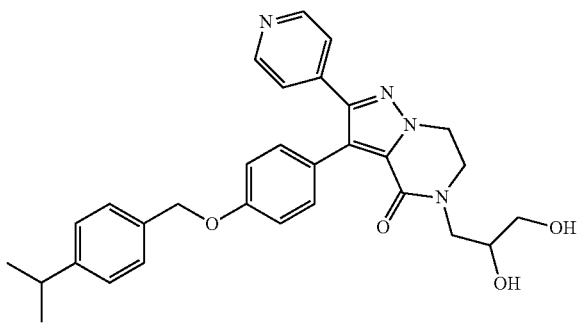 [SMILES: CC(C)c1ccc(COc2ccc(-c3c(-c4ccncc4)nn4c3C(=O)N(CC(O)CO)CC4)cc2)cc1]

NaH 60% (55 mg, 1.4 mmol) was added slowly to a suspension of Co. 1 (0.4 g, 0.91 mmol) in dry DMSO (5 mL) at r.t. under $N_2$. The mixture was stirred for 2 h then 3-bromo-1,2-propanediol (88 μL, 1.0 mmol) was added and stirred overnight. Water was added and the mixture was filtered, dissolved in DCM with $CH_3OH$. The organic layer was separated, dried on $MgSO_4$ and evaporated until dryness to give 530 mg of a residue. This residue was purified by prep. LC (irregular SiOH 30 μm, 25 g, Interchim, mobile phase gradient: DCM/MeOH/$NH_4OH$ from 96/4/0.1 to 92/8/0.1). The pure fractions were collected and solvent was evaporated until dryness to give colorless oil. This oil was taken up in $Et_2O$ and triturated. The vhite solid formed was filtrated and dried to give 294 mg of Co. 44, white solid (63%). m.p.: 192° C. (dsc).

Example A49

Preparation of Co. 45 a—Synthesis of Int. 121:

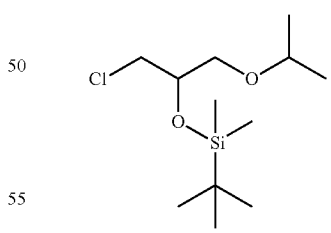

Tert-butyldimethylsilyl chloride (0.44 g, 2.9 mmol) was added to a sol. of 1-chloro-3-isopropoxy-2-propanol (0.3 g, 1.9 mmol) and imidazole (0.4 g, 5.8 mmol) in DCM (19 mL) at r.t. The r.m. was stirred at r.t. overnight. The mixture was quenched with water and extracted with DCM. The organic layer was decanted, washed with $H_2O$ then brine, dried ($MgSO_4$), filtered and evaporated to dryness to give 0.5 g of Int. 121, colorless oil (purity 70%), used as such for the next step.

b—Synthesis of Co. 45:

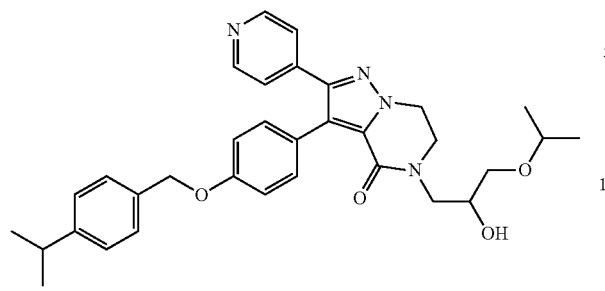

NaH 60% (71 mg, 1.8 mmol) was added slowly to a suspension of Co. 1 (0.52 g, 1.2 mmol) in dry DMF (7.1 mL) at r.t. under $N_2$. The mixture was stirred for 2 h then 121 (500 mg, 1.3 mmol) in dry DMF (4 mL) was added and the r.m. was stirred overnight. Water was added and the mixture was concentrated under reduced pressure. The residue was taken in EtOAc and washed (5×) with brine. The organic layer was dried on $MgSO_4$, filtered and concentrated to give 0.4 g of a residue. The residue was purified by prep. LC (Stationary phase: Sunfire Silica 5 µm 150×30.0 mm, mobile phase gradient: from 71% Heptane, 1% MeOH (+10% $NH_4OH$), 28% EtOAc to 20% MeOH (+10% $NH_4OH$), 80% EtOAc). The pure fractions were collected and solvent was evaporated until dryness to give 72 mg which was taken in $Et_2O$ and triturated. The white solid formed was filtrated and dried to give 45 mg of Co. 45, white solid (7%). m.p.: 148° C. (dsc).

Example A50

Preparation of Co. 46 and Co. 47 a—Synthesis of Int. 122:

NaH 60% (137 mg, 3.4 mmol) was added to a sol. of Co. 1 (1 g, 2.28 mmol) in DMSO (20 mL) at r.t. under $N_2$. The mixture was stirred for 2 h. (2-Bromo-1-methylethoxy)(1,1-dimethylethyl)dimethyl silane (0.87 g, 3.4 mmol) was added and the r.m. was stirred for 3 days. The mixture was poured into water, $K_2CO_3$ and extracted with EtOAc. The organic layer was evaporated until dryness to give 1.21 g. The residue was taken up in DCM, dried over $MgSO_4$, filtered and evaporated until dryness to give 1.1 g. The residue was purified by prep. LC on (25 g of SiOH 30 µm Interchim, mobile phase: DCM 100% to 0.1% $NH_4OH$, 95% DCM, 5% $CH_3OH$). The pure fractions were collected and solvent was evaporated until dryness to give 0.68 g of Int. 122 (49%).

b—Synthesis of Co. 46 and Co. 47:

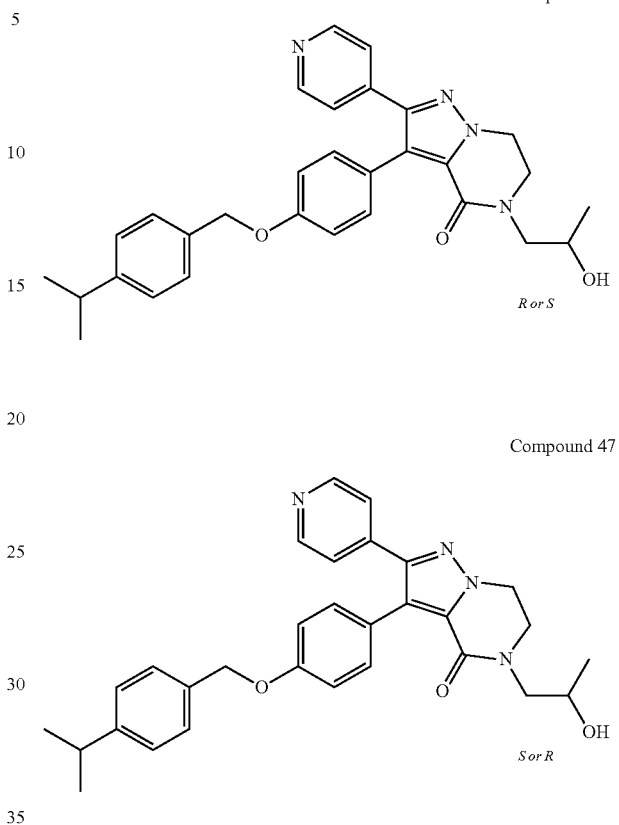

TBAF (1.49 mL, 1.49 mmol) was added dropwise to a sol. of 122 (0.76 g, 1.24 mmol) in THF (7 mL) at r.t. The mixture was stirred for 15 h. The mixture was evaporated until dryness. The residue was purified by prep. LC (25 g of SiOH 30 µm Interchim, mobile phase gradient from 100% DCM to 95% DCM 5% MeOH 0.1% $NH_4OH$). The fractions were collected and evaporated until dryness to give 0.47 g of racemic Co. This racemic Co. and 0.53 g of another batch were put together to give 1g of racemic Co. which was purified by chiral SFC on (Chiralpak IC 5 µm 250×20 mm), mobile phase (50% $CO_2$, 50% iPrOH). The fractions were collected and solvent was evaporated until dryness to give 485 mg of a first enantiomer and 467 mg of a second enantiomer. The first one was purified again by achiral SFC on (Amino 6 µm 150×21.2 mm), mobile phase (80% $CO_2$, 20% MeOH). The fractions were collected and solvent was evaporated until dryness to give 340 mg of the first enantiomer which was crystallized in $Et_2O$, filtered and dried to give 288 mg of Co. 46 (global yield: 13%). m.p.: 177° C. (dsc). The second enantiomer (467 mg) was crystallized in $Et_2O$, filtered and dried to give 395 mg of Co. 47 (global yield: 17%). m.p.: 177° C. (dsc).

Co. 46: $[\alpha]_d$: −27.34° (589 nm, c 0.256 w/v %, DMF, 20° C.);

Co. 47: $[\alpha]_d$: +27.06° (589 nm, c 0.3585 w/v %, DMF, 20° C.).

Example A51

Preparation of Co. 48

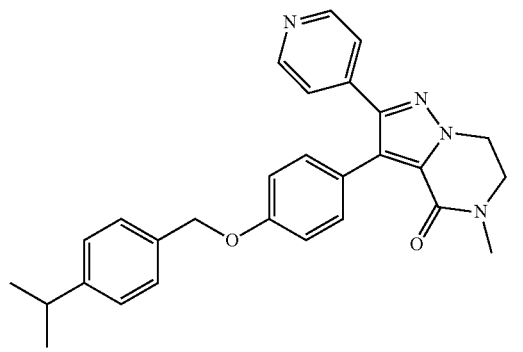 [SMILES: CC(C)c1ccc(COc2ccc(-c3c(-c4ccncc4)nn4c3C(=O)N(C)CC4)cc2)cc1]

In a sealed tube, a mixture of 98 (250 mg, 0.81 mmol), 9 (1.15 g, 3.26 mmol), $K_3PO_4$ (724 mg, 3.41 mmol) in 1,4-dioxane (3.8 mL) and $H_2O$ (1.3 mL) was carefully purged with $N_2$. $PCy_3$ (48 mg, 0.171 mmol) and $Pd(OAc)_2$ (19 mg, 0.085 mmol) were added and the r.m. was purged again with $N_2$. The r.m. was stirred for 17 h at 100° C. The crude material was dissolved in water (10 mL) and extracted with $Et_2O$ (2×40 mL). The organic phase was dried over $MgSO_4$, filtered and evaporated in vacuo to give 1.10 g of yellow oil. This oil was purified by prep. LC (irregular SiOH 15-40 µm, 30 g Merck, mobile phase gradient: from DCM 100% to DCM 90%, MeOH 10%). The pure fractions were collected and solvent was evaporated until dryness to give 270 mg of Co. 48, white solid (73%). m.p.: 155° C. (dsc).

Example A52

Preparation of Co. 49

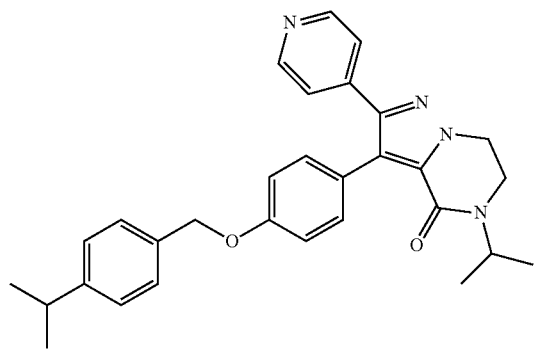 [SMILES: CC(C)c1ccc(COc2ccc(/C(C(=N)c3ccncc3)=C3/NCCN(C(C)C)C3=O)cc2)cc1]

NaH 60% (41 mg, 1 mmol) was added slowly to a suspension of Co. 1 (0.3 g, 0.68 mmol) in DMSO (4 mL) at r.t. under $N_2$. The mixture was stirred for 2 h then 2-iodopropane (0.137 mL, 1.4 mmol) was added and stirred for 17 h. Water was added, the mixture was filtered and washed with water. The residue was dissolved in DCM, dried over $MgSO_4$, filtered and evaporated until dryness to give 0.34 g which was purified by prep. LC (irregular SiOH 12 g 35-40 µm GraceResolv™, mobile phase gradient from 100% DCM to 95% DCM 5% MeOH 0.1% $NH_4OH$). The fractions were collected and evaporated until dryness to give 203 mg of Co. 49 (62%). This batch was put together with another one (125 mg) and crystallized from $Et_2O$, filtered and dried to give 289 mg of Co. 49 (global yield 44%). m.p.: 168° C. (dsc).

Example A53

Preparation of Co. 50

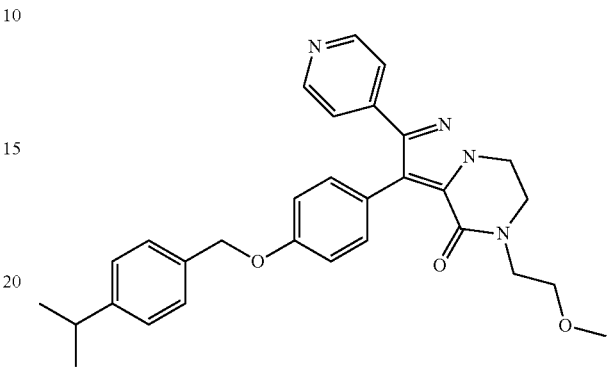

NaH 60% (55 mg, 1.4 mmol) was added slowly to a suspension of Co. 1 (0.4 g, 0.91 mmol) in dry DMSO (5 mL) at r.t. under $N_2$. The mixture was stirred for 2 h then 2-bromo ethyl methyl ether (94 µL, 1.0 mmol) was added and the r.m. was stirred overnight. Water was added and the insoluble was filtered, then dissolved in DCM, dried over $MgSO_4$ and evaporated to give 580 mg. The residue was purified by prep. LC (Regular SiOH, 30 µm, 25 g Interchim, mobile phase gradient: DCM/MeOH/$NH_4OH$ from 98/2/0.1 to 97/3/0.1). The pure fractions were collected and solvent was evaporated to give 390 mg of colorless oil. This oil was taken up in $Et_2O$ and the solid formed was filtrated and dried to give 360 mg of Co. 50, white solid (79%). m.p.: 167° C. (dsc).

Example A54

Preparation of Co. 51

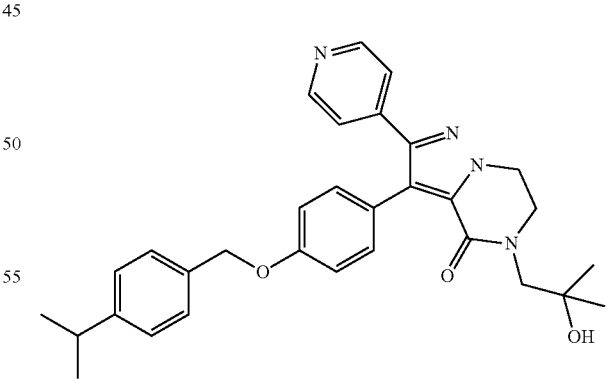

NaH 60% (0.34 g, 8.6 mmol) was added portionwise to a suspension of Co. 1 (2.5 g, 5.7 mmol) in dry DMSO (31 mL) at r.t. under $N_2$. The mixture was stirred for 2 h then 1-chloro-2-methyl-2-propanol (0.66 mL, 6.3 mmol) was added and the r.m. was stirred for overnight. Water was added and the insoluble was filtered, then dissolved in DCM, dried on $MgSO_4$ and evaporated until dryness to give 2.9 g, white solid. The solid was purified by prep. LC (Stationary phase: irregular SiOH 15-40 µm, 300 g MERCK, mobile phase): 0.1% NH₄OH, 98% DCM, 2% MeOH). The pure fractions were collected and the solvent was evaporated until dryness to give 290 mg of 2.1 g of Co. 1 and Co. 51, white solid (10%). m.p.: 21 PC (dsc).

Example A55

Preparation of Co. 52

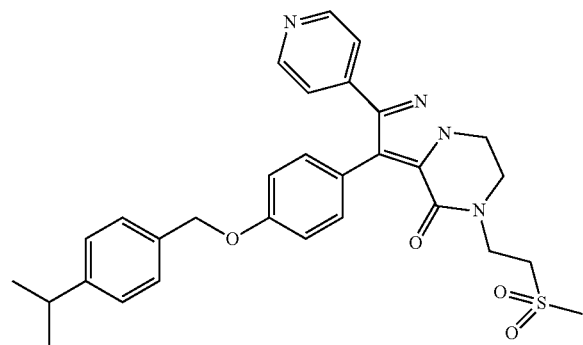 [SMILES: CC(C)c1ccc(COc2ccc(/C(C(=N)c3ccncc3)=C3/NCCN(CCS(C)(=O)=O)C3=O)cc2)cc1]

NaH 60% (53 mg, 1.3 mmol) was added slowly to a suspension of Co. 1 (0.39 g, 0.89 mmol) in dry DMSO (5 mL) at r.t. under N₂. The mixture was stirred for 2 h then 2-bromoethyl-methylsulfone (183 mg, 0.98 mmol) was added and the r.m. was stirred overnight. Water was added and the insoluble was filtered off, then dissolved in DCM and MeOH, dried on MgSO₄ and evaporated until dryness to give 780 mg, beige solid. The residue was purified by prep. LC (irregular SiOH 30 µm, 25 g, Interchim, Mobile phase: DCM 97%, MeOH 3%, NH₄OH 0.1%). The fractions were collected and the solvent was evaporated to give 450 mg of colorless oil. The residue was purified again by prep. LC on (Stability Silica 5 µm 150×30.0 mm, mobile phase gradient: from 100% DCM to NH₄OH/DCM/MeOH 0.8/92/8). The pure fractions were collected and solvent was evaporated. The white solid obtained was triturated in Et₂O, filtrated and dried to give 245 mg of Co. 52, white powder (51%). m.p.: 219° C. (dsc).

Example A56

Preparation of Co. 2 and Co. 53

Compound 2

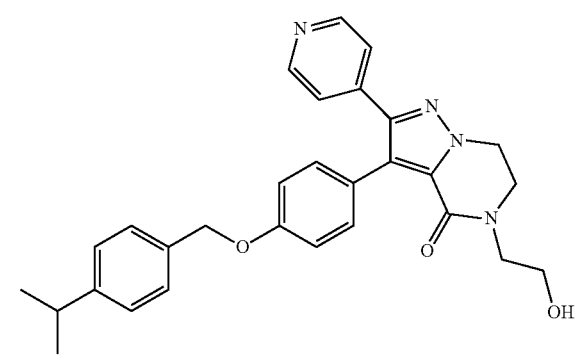

Compound 53

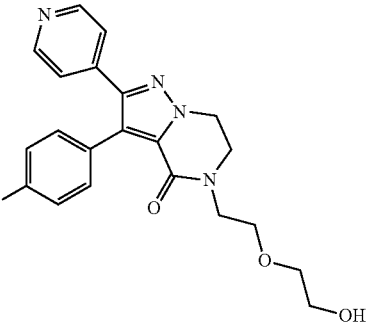

TBAF (23.3 mL, 23.3 mmol) was added dropwise to a sol. of 27 (11.58 g, 19.4 mmol) in THF (100 mL) at r.t. The mixture was stirred for 15 h. The mixture was evaporated until dryness to give 18 g. The residue was purified by prep. LC (330 g of SiOH 35-40 µm GraceResolv™, mobile phase gradient: from 100% DCM to 95% DCM 5% MeOH 0.1% NH₄OH). The fractions were collected and evaporated until dryness to give 8.76 g (94%). Another batch (4 g) was purified by prep. LC (120 g of SiOH 35-40 µm GraceResolv™, mobile phase gradient: from 100% DCM to 96% DCM 4% MeOH 0.1% NH₄OH). The fractions were collected and evaporated until dryness to give 3.11 g of a residue. Both residues (8.76 g and 3.11 g) were put together and gave 11.8 g which was crystallized from Et₂O, filtered and dried to give 10.64 g of a mixture (majority Co. 2 and 8% of Co. 53). This mixture was purified by achiral SFC (Stationary phase: Amino 6 µm 150×21.2 mm, mobile phase: 80% CO₂, 20% MeOH). The fractions were collected and evaporated until dryness to give 9.5 g of Co. 2 and 0.81 g of a residue. This residue was purified by achiral SFC (Stationary phase: Amino 6 µm 150×21.2 mm, mobile phase: 80% CO₂, 20% MeOH). The pure fractions were collected and solvent was evaporated to give 641 mg which was crystallized from Et₂O, filtered and dried to give 557 mg of Co. 53. m.p.: 121° C. (dsc).

Example A57

Preparation of Co. 54

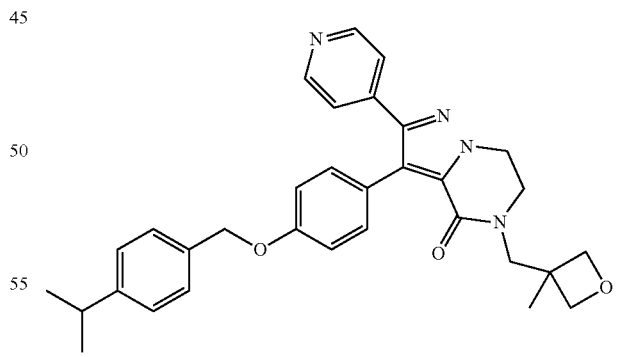

NaH 60% (54.7 mg, 1.4 mmol) was added slowly to a suspension of Co. 1 (0.4 g, 0.9 mmol) in DMSO (5 mL) at r.t. under N₂. The mixture was stirred for 2 h, then 2-(chloromethyl)-2-methyl-1,3-epoxypropane (0.12 mL, 1 mmol) was added and the r.m. was stirred for 24 h. Water was added and the insoluble was filtered off. The insoluble was dissolved in DCM and MeOH, dried over MgSO₄ and evaporated until dryness to give 0.49 g of a residue. The residue was purified by prep. LC on (Stability Silica 5 µm 150×30.0 mm, mobile phase gradient from: NH₄OH/DCM/MeOH 0.2/98/2 to NH₄OH/DCM/MeOH 1/90/10). The pure fractions were collected and solvent was evaporated until dryness to give a residue (272 mg) which was crystallized from Et₂O, filtered and dried to give 256 mg of product (traces impurities). The product (256 mg) was taken up with MeOH, filtered and dried to give 221 mg of Co. 54 (46%). m.p.: 204° C. (dsc).

Example A58

Preparation of Co. 55

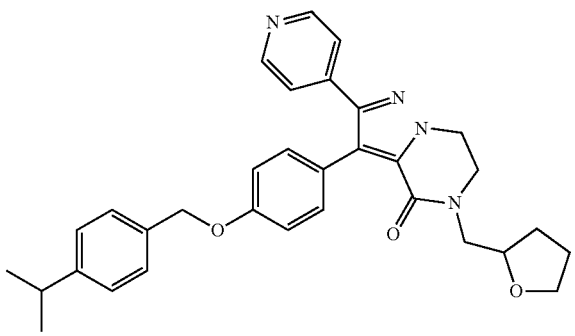 [SMILES: CC(C)c1ccc(COc2ccc(/C(C(=N)c3ccncc3)=C3/NCCN(CC4CCCO4)C3=O)cc2)cc1]

NaH 60% (55 mg, 1.4 mmol) was added portionwise to a suspension of Co. 1 (0.4 g, 0.91 mmol) in dry DMF (5.5 mL) at r.t. under N₂. The mixture was stirred for 2 h then tetrahydrofurfuryl bromide (0.18 g, 1.0 mmol) was added and the r.m. was stirred overnight. Water was added and the mixture was diluted with 150 mL of EtOAc and washed 4× with brine. The organic layer was dried on MgSO₄ and evaporated until dryness. The residue (0.55 g) was purified by prep. LC (irregular SiOH 15-40 µm, 12 g, GraceResolv™, Mobile phase: DCM/MeOH/NH₄OH, 97/3/0.1). The fractions were collected and solvent was evaporated until dryness to give 195 mg of white solid. This fraction was purified again by prep. LC (Stationary phase: Sunfire Silica 5 µm 150×30.0 mm, mobile phase gradient: from 71% Heptane, 1% MeOH, 28% EtOAc to 20% MeOH, 80% EtOAc). The pure fractions were collected and solvent was evaporated until dryness to give 150 mg which was crystallized from Et₂O, filtrated and dried to give 90 mg of Co. 55, white solid (19%). m.p.: 165° C. (dsc).

Example A59

Preparation of Co. 56

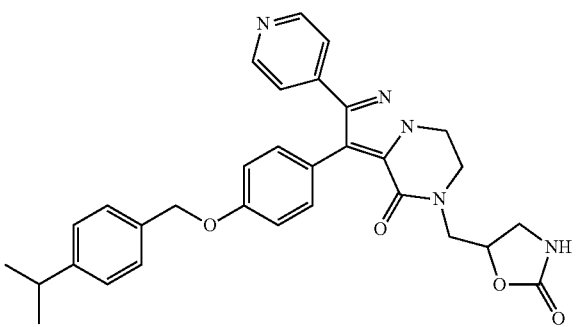 [SMILES: CC(C)c1ccc(COc2ccc(/C(C(=N)c3ccncc3)=C3/NCCN(CC4CNC(=O)O4)C3=O)cc2)cc1]

NaH 60% (82 mg, 0.21 mmol) was added slowly to a suspension of Co. 1 (0.60 g, 1.4 mmol) in dry DMF (8.0 mL) at r.t. under N₂. The mixture was stirred for 2 h then tert-butyl N-(2-oxiranyl-methyl) carbamate (355 mg, 2.1 mmol) was added and the r.m. was stirred overnight. Water was added and the mixture was concentrated under reduced pressure. The residue was taken up in EtOAc and washed with brine. The organic layer was dried over MgSO₄, filtered and concentrated to give 1.13 g. The residue was purified by prep. LC (Stationary phase: irregular SiOH 15-40 µm 300 g Merck, mobile phase gradient: from 42% Heptane, 8% MeOH (+10% NH₄OH), 50% EtOAc to 40% Heptane, 10% MeOH (+10% NH₄OH), 50% EtOAc). The pure fractions were collected and the solvent was evaporated until dryness to give 390 mg of Co. 1 and 27 mg of a white powder residue. The residue was taken in Et₂O, triturated and the white solid formed was filtrated and dried to give 17 mg of Co. 56 (2.3%).

Example A60

Preparation of Co. 57

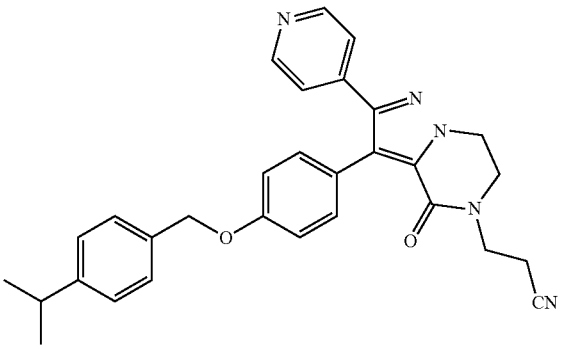 [SMILES: CC(C)c1ccc(COc2ccc(/C(C(=N)c3ccncc3)=C3/NCCN(CCC#N)C3=O)cc2)cc1]

NaH 60% (55 mg, 1.4 mmol) was added portionwise to a suspension of Co. 1 (0.40 g, 0.91 mmol) in dry DMF (5.5 mL) at r.t. under N₂. The mixture was stirred for 2 h then 3-bromopropionitrile (0.13 g, 1.0 mmol) was added and the r.m. was stirred overnight at r.t. Water was added and the mixture was diluted with 150 mL of EtOAc and washed 4× with brine. The organic layer was dried on MgSO₄ and evaporated until dryness to give 0.62 g. The residue was purified by prep. LC (irregular SiOH 15-40 µm, 12 g, GraceResolv™, Mobile phase: DCM/MeOH/NH₄OH, 98/2/0.1). The pure fractions were collected and the solvent was evaporated until dryness to give 211 mg of colorless oil. This oil was triturated in Et₂O. The solid formed was filtered and dried to give 132 mg of Co. 57, white solid (29%). m.p.: 158° C. (dsc).

Example A61

Preparation of Co. 58 and Co. 58 a—Synthesis of Co. 58a

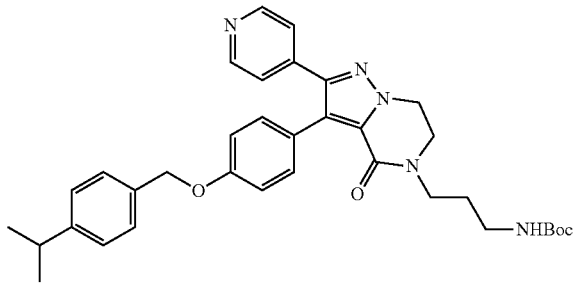 [SMILES: CC(C)c1ccc(COc2ccc(-c3c(-c4ccncc4)nn4c3C(=O)N(CCCNC(=O)OC(C)(C)C)CC4)cc2)cc1]

NaH 60% (68 mg, 1.7 mmol) was added slowly to a suspension of Co. 1 (0.5 g, 1.1 mmol) in dry DMF (7.0 mL) at r.t under $N_2$. The mixture was stirred for 2 h then tert-butyl N-(3-bromopropyl) carbamate (543 mg, 2.3 mmol) was added and the r.m. was stirred overnight. Water was added and the mixture was concentrated. The residue was taken in EtOAc and washed 3× with brine, dried and concentrated to give 680 mg of Co. 58a, white solid (100%). The product was used like this in the next step.

b—Synthesis of Co. 58:

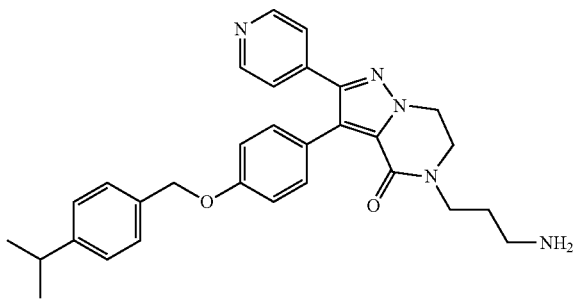 [SMILES: CC(C)c1ccc(COc2ccc(-c3c(-c4ccncc4)nn4c3C(=O)N(CCCN)CC4)cc2)cc1]

A solution of Co. 58a (680 mg, 1.1 mmol), HCl 3N (1.9 mL, 5.7 mmol), in ACN (20 mL) was stirred at 80° C. for 2 h. The mixture was concentrated, and $NaHCO_3$ sat aq (100 mL) was added and the mixture was stirred at r.t. for 15 min, extracted with DCM, dried and concentrated. The residue (550 mg) was purified by prep. LC (Regular SiOH, 30 µm, 12 g Interchim, mobile phase gradient: DCM/MeOH/$NH_4OH$ from 88/12/0.1). The pure fractions were collected and solvent was evaporated until dryness to give 340 mg as an oil. This oil was taken in $Et_2O$. The solid formed was filtered and dried to give 192 mg of Co. 58, white solid (34%).

Example A62

Preparation of Co. 238, Co. 59a and Co. 59 a—Synthesis of Co. 238

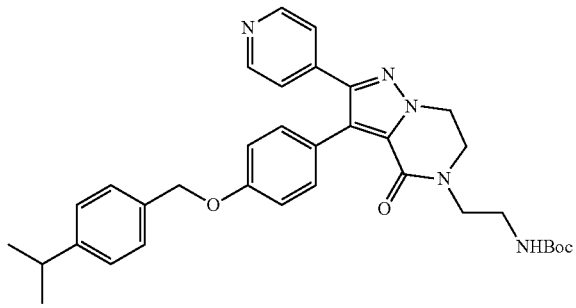 [SMILES: CC(C)c1ccc(COc2ccc(-c3c(-c4ccncc4)nn4c3C(=O)N(CCNC(=O)OC(C)(C)C)CC4)cc2)cc1]

NaH 60% (0.41 g, 10.3 mmol) was added slowly to a suspension of Co. 1 (3 g, 6.8 mmol) in dry DMSO (45 mL) at r.t. under $N_2$. The mixture was stirred for 2 h then tert-butyl N-(2-bromoethyl) carbamate (2.3 g, 10.26 mmol) was added and the r.m was stirred for 20 h. The mixture was poured into water and EtOAc was added. The insoluble was filtered and washed with EtOAc. $K_2CO_3$ was added to the filtrate and the organic layer was extracted, separated and evaporated until dryness. The residue was taken up with DCM, dried over $MgSO_4$, filtered and evaporated until dryness to give 2.08 g of a residue. The residue was purified by prep. LC (Stationary phase: Irregular SiOH 20-45 µm 450 g MATREX, mobile phase: 40% Heptane, 10% MeOH, 50% EtOAc). The pure fractions were collected and the solvent was evaporated to give 1.2 g of Co. 238 (30%).

b—Synthesis of Co. 59a and Co. 59:

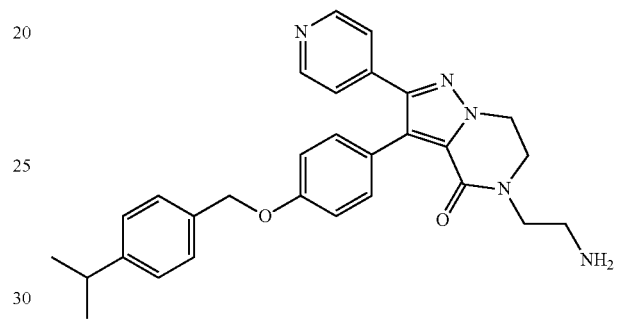

Co. 238 (650 mg, 1.12 mmol), HCl 3N (1.9 mL, 5.6 mmol) in ACN (20 mL) was heated at 70° C. for 1.5 h. The mixture was cooled to r.t. and the insoluble was filtered, washed with ACN and $Et_2O$ and dried to give 379 mg of Co. 59a (HCl salt; 0.2 HCl 0.1.78 $H_2O$) (58%). Part of Co. 59a was converted to the free base (Co. 59).

Example A63

Preparation of Co. 60a and Co. 60 a—Synthesis of Co. 60a

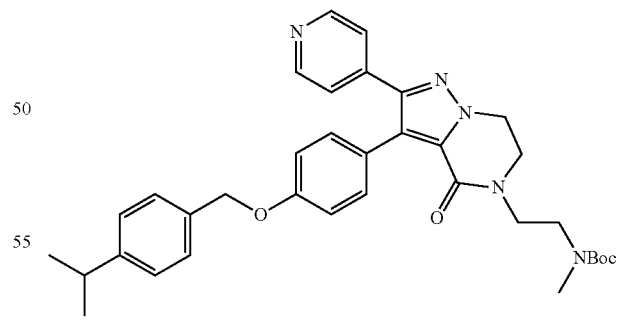

NaH 60% (50.2 mg, 1.3 mmol) was added to Co. 238 (487 mg, 0.84 mmol) in DMF (8 mL) at r.t. under $N_2$. The mixture was stirred for 2 h, then MeI (62.5 µL, 1 mmol) was added dropwise and stirred for 2.5 h. The mixture was poured into water and $K_2CO_3$ and extracted with EtOAc. The organic layer was dried over $MgSO_4$, filtered and evaporated until dryness. The residue (0.7 g) was purified by prep. LC (40 g of SiOH 15 µm Interchim, mobile phase gradient from 100%

DCM to 96% DCM 4% MeOH 0.1% NH₄OH). The fractions were collected and evaporated until dryness to give 308 mg of Co. 60a (62%).

b—Synthesis of Co. 60:

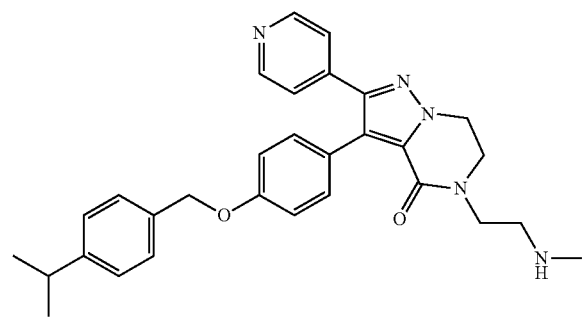 [SMILES: CNCCN1CCn2nc(-c3ccncc3)c(-c3ccc(OCc4ccc(C(C)C)cc4)cc3)c2C1=O]

Co. 60a (308 mg, 0.52 mmol) and HCl 3N (0.86 mL, 2.6 mmol) in ACN (10 mL) was heated at 70° C. for 1.5 h, cooled to r.t. and the mixture was poured into water and K₂CO₃ and extracted with DCM. The organic layer was dried over MgSO₄, filtered and evaporated until dryness. The residue (0.22 g) was purified by achiral SFC (Stationary phase: Amino 6 µm 150×21.2 mm, mobile phase: 70% CO₂, 30% MeOH (0.3% iPrNH₂)). The pure fractions were collected and the solvent was evaporated until dryness to give 180 mg which was crystallized from Et₂O, filtered and dried to give 131 mg of Co. 60 (51%).

Example A64

Preparation of Co. 61

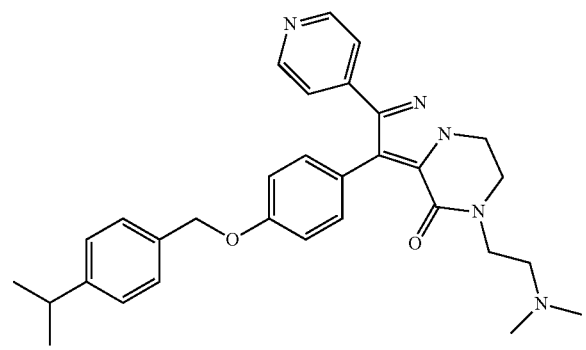 [SMILES: CC(C)c1ccc(COc2ccc(/C(C(=N)c3ccncc3)=C3/NCCN(CCN(C)C)C3=O)cc2)cc1]

Formaldehyde (46.7 µL, 0.623 mmol) was added to a sol. of Co. 59 (100 mg, 0.21 mmol) in DCM (2 mL) and THF (1 mL) at r.t. The mixture was stirred for 1 h then sodium triacetoxyborohydride (88 mg, 0.415 mmol) was added and the r.m. was stirred for 15 h. The mixture was poured into water and K₂CO₃ and extracted with DCM. The organic layer was dried over MgSO₄, filtered and evaporated until dryness. The residue (103 mg) was purified by prep. LC (Stationary phase: irregular 15-40 µm 30 g Merck, mobile phase: 1% NH₄OH, 69% toluene, 30% iPrOH). The pure fractions were collected and solvent was evaporated until dryness to give 30 mg of Co. 61 (28%).

Example A65

Preparation of Co. 62 a—Synthesis of Int. 126:

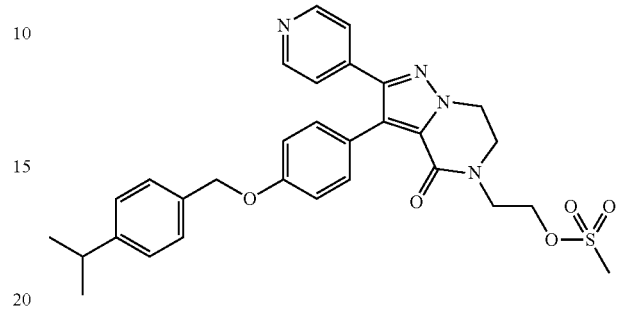

Methanesulfonyl chloride (49 µL, 0.64 mmol) was added dropwise to a sol. of Co. 2 (205 mg, 0.43 mmol) and Et₃N (178 µL, 1.3 mmol) in dry DCM (5 mL) at 0° C. under N₂ atmosphere. The r.m. was stirred at 0° C. for 2 h. Water was added and the mixture was extracted with DCM. The organic layer was separated, dried over MgSO₄, filtered and the solvent was evaporated until dryness to give 280 mg of Int. mixture 126, yellow solid. The solid was used in the next reaction step without further purification.

b—Synthesis of Co. 62:

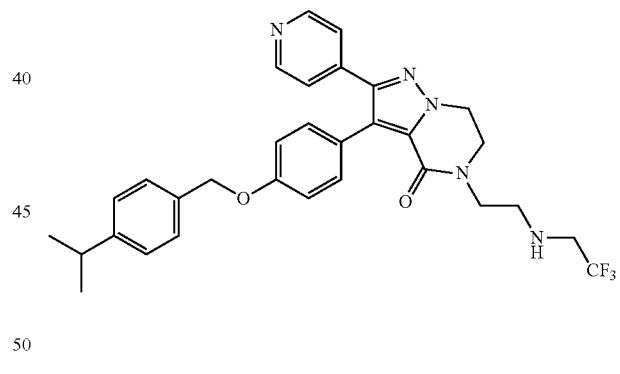

In a microwave vial, a sol. of 126 (225 mg, 0.43 mmol) in 2,2,2-trifluoroethylamine (6.3 mL, 80 mmol) was stirred at 80° C. overnight. Water was added and the mixture was extracted with DCM. The organic layer was separated, dried over MgSO₄, filtered and the solvent was concentrated to obtain a residue (120 mg). The aq. layer was basified with NaHCO₃ sat. and extracted 3× with DCM, dried and concentrated. This residue was combined with the earlier residue (120 mg) to give 220 mg of yellow oil. This oil was purified by prep. LC (Stationary phase: Stability Silica 5 µm 150×30.0 mm, mobile phase: Gradient from 100% DCM to NH₄OH/DCM/MeOH 0.9/91/9). The pure fractions were collected and evaporated until dryness to give 46 mg of Co. 62, beige solid (17%).

Example A66

Preparation of Co. 63

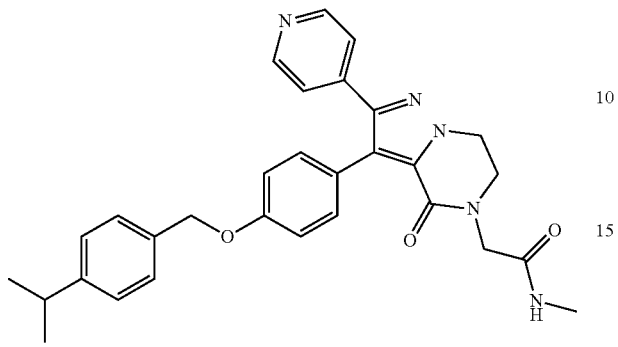

NaH 60% (27.4 mg, 0.68 mmol) was added to a sol. of Co. 1 (200 mg, 0.46 mmol) in DMSO (4 mL) at r.t. under $N_2$. The mixture was stirred for 2 h. 2-bromo-N-methylacetamide (104 mg, 0.68 mmol) was added and stirred for 15 h. The mixture was poured into water and extracted with EtOAc (another batch with 102 mg of initial reactant, Co. 1 was put together for work up). The organic layer was dried over $MgSO_4$, filtered and evaporated until dryness to give 0.35 g. The residue was purified by prep. LC on (Stability Silica 5 µm 150×30.0 mm, mobile phase gradient: from $NH_4OH$/DCM/MeOH 0.2/98/2 to $NH_4OH$/DCM/MeOH 0.8/92/8). The pure fractions were collected and solvent was evaporated to give 290 mg which was crystallized from $Et_2O$, filtered and dried to give 233 mg of Co. 63, (global yield: 66%). m.p.: 161° C. (dsc).

Example A67

Preparation of Co. 64

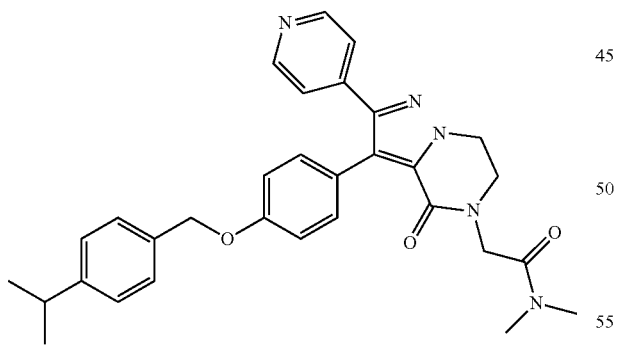

NaH 60% (72 mg, 1.8 mmol) was added portionwise to a suspension of Co. 1 (0.52 g, 1.2 mmol) in dry DMF (7.1 mL) at r.t. under $N_2$. The mixture was stirred for 2 h then N,N-dimethylchloroacetamide (0.18 mL, 1.8 mmol) was added and the r.m. was stirred overnight at r.t. Water was added and the mixture was concentrated under reduced pressure. The residue was taken in EtOAc and washed 5× with brine. The organic layer was dried over $MgSO_4$, filtrated and concentrated. The residue was purified by prep. LC (irregular SiOH 15-40 µm, 25 g, Interchim, mobile phase: DCM/MeOH/$NH_4OH$, 97/3/0.1). The pure fractions were collected and solvent was evaporated until dryness to give 0.46 g of colorless oil. This oil was triturated in $Et_2O$. The solid formed was filtered and dried to give 390 mg of Co. 64, white solid (63%).

Example A68

Preparation of Co. 65

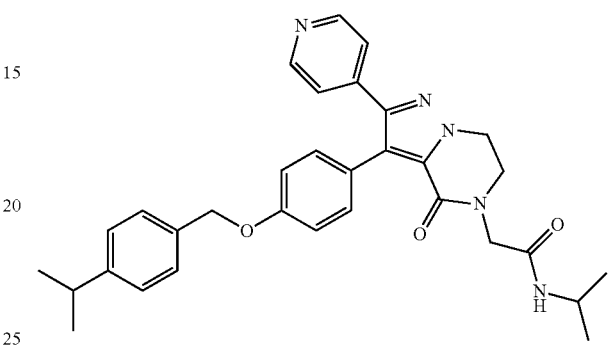

NaH 60% (72 mg, 1.8 mmol) was added portionwise to a suspension of Co. 1 (0.52 g, 1.2 mmol) in dry DMF (7.1 mL) at r.t. under $N_2$. The mixture was stirred for 2 h then N-isopropyl-2-chloroacetamide (0.24 g, 1.8 mmol) was added and stirred overnight at r.t. Water was added and the mixture was concentrated under reduced pressure. The residue was taken in EtOAc and washed 5× with brine. The organic layer was dried over $MgSO_4$, filtrated and concentrated to give 0.7 g. The residue was purified by prep. LC (irregular SiOH 15-40 µm, 25 g, GraceResolv™, mobile phase: DCM/MeOH/$NH_4OH$, 97/3/0.1). The pure fractions were collected and solvent was evaporated until dryness to give 500 mg of colorless oil. This oil was triturated in $Et_2O$. The solid formed was filtered and dried to give to give 312 mg of Co. 65, white solid (49%).

Example A69

Preparation of Co. 66

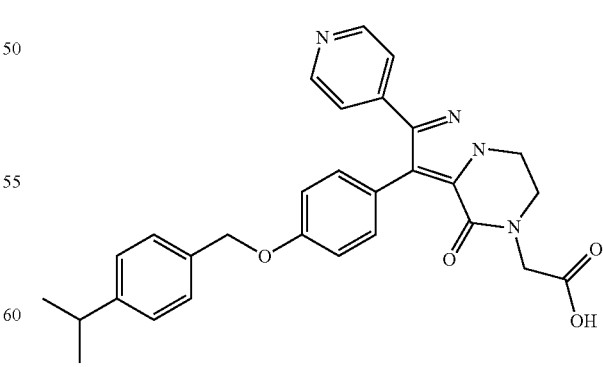

NaH 60% (68 mg, 1.7 mmol) was added slowly to a suspension of Co. 1 (0.50 g, 1.1 mmol) in dry DMSO (6.3 mL) at r.t. under $N_2$. The mixture was stirred for 2 h and then methylbromoacetate (0.12 mL, 1.25 mmol) was added and

Example A70

Preparation of Co. 67 a—Synthesis of Int. 127:

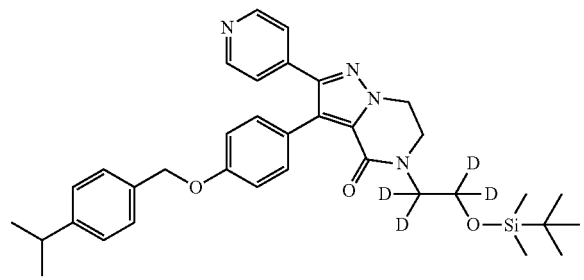 [SMILES: [2H]C([2H])(O[Si](C)(C)C(C)(C)C)C([2H])([2H])N1CCn2nc(-c3ccncc3)c(-c3ccc(OCc4ccc(C(C)C)cc4)cc3)c2C1=O]

NaH 60% (68 mg, 1.7 mmol) was added slowly to a suspension of Co. 1 (0.5 g, 1.1 mmol) in dry DMF (7.0 mL) at r.t. under $N_2$. The mixture was stirred for 2 h then (2-bromoethoxy-1,1,2,2-$d_4$)(1,1-dimethylethyl)dimethyl-silane (554 mg, 2.3 mmol) was added and the r.m. was stirred overnight. Water was added and the mixture was concentrated. The residue was taken in EtOAc and washed 3× with brine, dried over $MgSO_4$, filtered and concentrated to give 750 mg of Int. 127, yellow oil as a mixture which was used like this in the next step.

b—Synthesis of Co. 67:

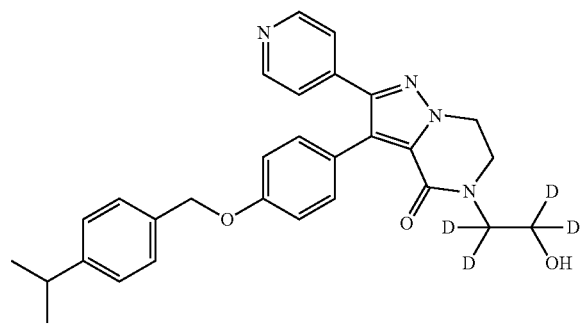 [SMILES: [2H]C([2H])(O)C([2H])([2H])N1CCn2nc(-c3ccncc3)c(-c3ccc(OCc4ccc(C(C)C)cc4)cc3)c2C1=O]

TBAF (1.0 mL, 1.0 mmol) was added dropwise to a sol. of 177 (0.75 g, 0.88 mmol) in THF (8.5 mL) at r.t. The mixture was stirred overnight at r.t. The mixture was concentrated and the residue was purified by prep. LC (Regular SiOH, 30 μm, 25 g GraceResolv™, mobile phase: DCM/MeOH/$NH_4OH$ 96/4/0.1). The pure fractions were collected and the solvent was evaporated until dryness to give 360 mg of colorless oil which was triturated in $Et_2O$. The white solid formed was filtered, washed and dried to give 0.286 g of Co. 67, white solid (67%). m.p.: 179° C. (dsc).

Example A71

Preparation of Co. 68

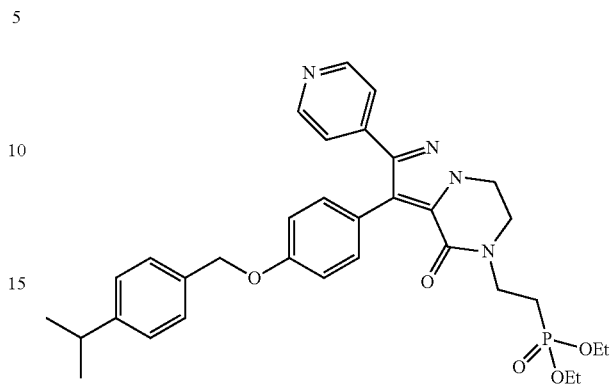

NaH 60% (27.4 mg, 0.68 mmol) was added to Co. 1 (0.2 g, 0.46 mmol) in DMSO (2.8 mL) at r.t. under $N_2$. The mixture was stirred for 2 h then diethyl-2-bromoethylphosphonate (0.13 mL, 0.68 mmol) was added and the r.m. was stirred for 20 h. The mixture was poured into water, $K_2CO_3$ was added and extracted with EtOAc. The organic layer was evaporated until dryness. The residue was taken up with EtOAc and water. The organic layer was extracted, dried over $MgSO_4$, filtered and evaporated. The residue (0.27 g) was purified by prep. LC (25 g of irregular SiOH 35-40 μm GraceResolv™, mobile phase gradient from 100% DCM to 95% DCM 5% MeOH 0.1% $NH_4OH$). The pure fractions were collected and evaporated to give 0.2 g which was crystallized from DIPE, filtered and dried to give 137 mg of Co. 68 (50%). m.p.: 90° C. (dsc).

Example A72

Preparation of Co. 69

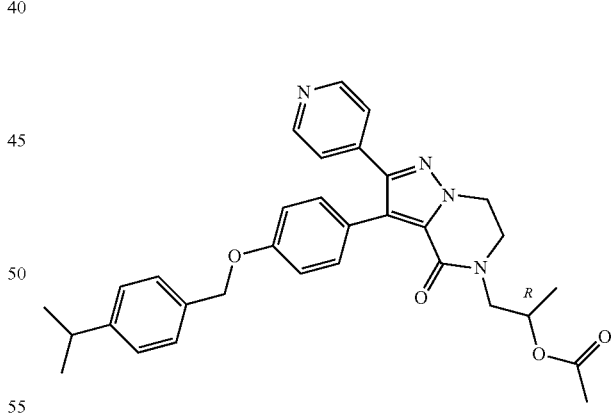

NaH 60% (480 mg, 12 mmol) was added slowly to a suspension of Co. 1 (3.5 g, 8.0 mmol) in dry DMF (47 mL) at r.t. under $N_2$. The mixture was stirred for 2 h then (R)-(+) propylene oxide (1.1 mL, 16 mmol) was added and stirred overnight. Water was added and the mixture was concentrated under reduced pressure. The residue was taken in EtOAc and washed 5× with brine. The organic layer was dried on $MgSO_4$, filtrated and concentrated to give 5.9 g. The residue was purified by prep. LC (irregular SiOH 15-40 μm, 120 g GraceResolv™, mobile phase gradient: from 100% DCM to DCM 95%, MeOH 5%). The fractions were collected and evaporated until dryness to give 1.2 g of initial reactant Co. 1 and a residue which was purified by prep. LC (Stationary phase: irregular SiOH 15-401 µm 300 g MERCK, mobile phase: 42% Heptane, 8% MeOH (+10% NH₄OH), 50% EtOAc). The pure fractions were collected and the solvent was evaporated to give 1.02 g which was triturated in Et₂O and the white solid formed was filtrated and dried to give 450 mg of Co. 69 (R) (10%).

Example A73

Preparation of Co. 71 a—Synthesis of Int. 128:

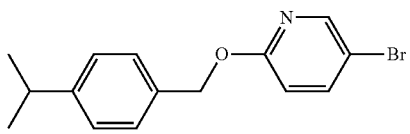

A sol. of 6 (3.1 g, 20 mmol) in dry DMF (50 mL) was treated at 0° C. with NaH 60% (818 mg, 20 mmol). After stirring for 1 h at r.t., 5-bromo-2-fluoropyridine (3.0 g, 17 mmol) was added and the r.m. was stirred at r.t. for 3 days. The r.m. was quenched with water 200 mL and the white solid formed was filtrated. This solid was solubilized in EtOAc and dried on MgSO₄, filtrated and concentrated to give 5.9 g of Int. 128, white solid (100%).

b—Synthesis of Int. 129:

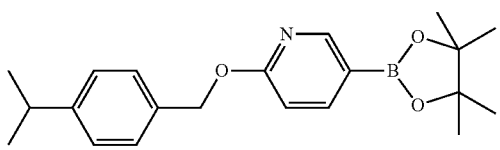 [SMILES: CC(C)c1ccc(COc2ccc(B3OC(C)(C)C(C)(C)O3)cn2)cc1]

BisPin (5.2 g, 20 mmol) and KOAc (3.3 g, 34 mmol) were added to a sol. of 128 (5.2 g, 17 mmol) in 1,4-dioxane (57 mL). The sol. was purged with N₂ and charged with PdCl₂(PPh₃)₂ (0.60 g, 0.85 mmol). The resulting sol. was purged again with N₂ and stirred at 80° C. for 17 h. After dilution in EtOAc, the crude material was washed with water and brine. The organic layer was dried over MgSO₄ and evaporated to afford 12 g of brown oil. This oil was purified by prep. LC (irregular SiOH 15-40 µm, 120 g GraceResolv™, mobile phase: heptane/EtOAc 80/20). The pure fractions were collected and solvent was evaporated to give 5.6 g of Int. 129 brown solid (93%).

c—Synthesis of Co. 71:

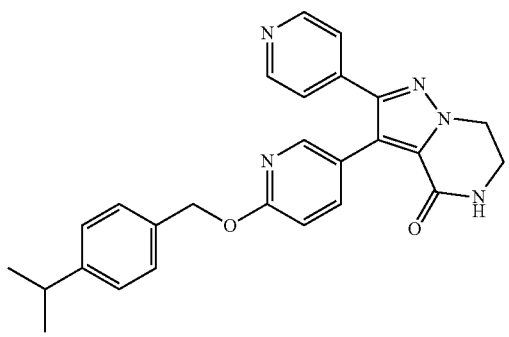 [SMILES: CC(C)c1ccc(COc2ccc(-c3c(-c4ccncc4)nn4c3C(=O)NCC4)cn2)cc1]

In a Schlenk tube, a mixture of 4 (150 mg, 0.512 mmol), 129 (452 mg, 1.28 mmol), K₃PO₄ (434 mg, 2.05 mmol) in 1,4-dioxane (3.75 mL) and H₂O (1.5 mL) was carefully purged with N₂. Pd(OAc)₂ (11 mg, 51.2 µmol) and PCy₃ (29 mg, 102 µmol) were added and the r.m. was purged again with N₂. The Schlenk tube was then sealed and the r.m. was stirred for 17 h at 80° C. The crude mixture was then diluted in DCM and washed with water (2×10 mL). The organic layer was collected, dried over MgSO₄ and evaporated in vacuo to afford brown oil. This oil was purified by prep. LC (irregular SiOH 15-40 µm, 50 g Merck, Mobile phase gradient: from 100% DCM to DCM 95%, MeOH 5%). The pure fractions were collected and solvent was evaporated until dryness to give 169 mg of Co. 71, white solid (75%). m.p.: 199° C. (dsc).

Example A74

Preparation of Co. 72 a—Synthesis of Int. 130:

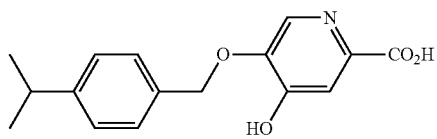 [SMILES: CC(C)c1ccc(COc2cnc(C(=O)O)cc2O)cc1]

A sol. of 5-[[4-(1-methylethyl)phenyl]methoxy]-4-oxo-4H-pyran-2-carboxylic acid (2.82 g, 9.78 mmol) in NH₃ (28% in water) (18 mL) was stirred at 90° C. for 4 h. Then the solvent was evaporated in vacuo to afford 2.13 g of Int. 130, brown solid (76%).

b—Synthesis of Int. 131:

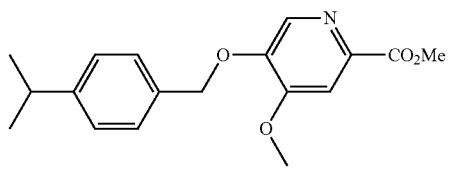

(Trimethylsilyl)diazomethane, 2M in hexane (10.4 mL, 20.8 mmol) was added to a stirred sol. of 130 (1.05 g, 3.66 mmol) in MeOH (5 mL) and toluene (20 mL) at 0° C. under N₂. The crude mixture was stirred warming to r.t. for 1 h, and then water and EtOAc were added. The organic layer was washed with brine, separated, dried over MgSO₄, filtered and evaporated in vacuo to afford 830 mg of a brown solid. Another batch, 400 mg was combined to 830 mg, and the mixture was purified by prep. LC (irregular SiOH 15-40 µm, 45 g Grace, mobile phase gradient: from EtOAc 10%, Heptane 90% to EtOAc 75%, Heptane 25%). The pure fractions were collected and solvent was evaporated until dryness to give 370 mg of Int. 131 (global yield: 22%).

c—Synthesis of Int. 132:

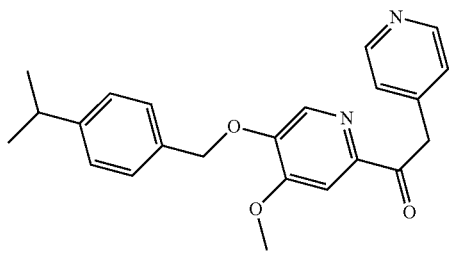 [SMILES: COc1cc(C(=O)Cc2ccncc2)ncc1OCc1ccc(C(C)C)cc1]

In a dry flask under N₂, a sol. of 131 (283 mg, 0.897 mmol) and 4-picoline (0.140 mL, 1.44 mmol) in THF (7 mL) was cooled to 0° C. and treated with LiHMDS (1.80 mL, 1.80 mmol). The r.m. was stirred at r.t. for 20 h. The crude mixture was quenched with an aq. sol. of NH₄Cl, and EtOAc was added. The organic layer was washed with brine, dried over MgSO₄, filtered and evaporated in vacuo to yield 295 mg of Int. 132, a brown solid (66%) which was used as such in the next reaction step.

d—Synthesis of Int. 133:

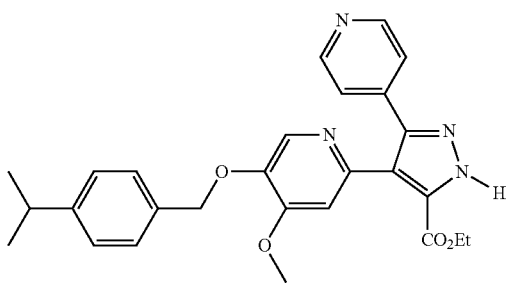 [SMILES: CCOC(=O)c1[nH]nc(-c2ccncc2)c1-c1cc(OC)c(OCc2ccc(C(C)C)cc2)cn1]

A suspension of 132 (287 mg, 0.572 mmol) in ACN (5 mL) was treated with DBU (103 μL, 0.686 mmol) then with ethyl diazoacetate (96 μL, 0.915 mmol). The r.m. was stirred at r.t. for 20 h. Then, EtOAc and water were added, and the organic layer was washed with brine, separated, dried over MgSO₄, filtered and evaporated in vacuo to yield 330 mg of a brown solid. The solid was purified by prep. LC (irregular SiOH 15-40 μm, 24 g, GraceResolv™, mobile phase gradient: from DCM 100% to DCM 93%, MeOH 7%). The pure fractions were collected and solvent was evaporated until dryness to give 169 mg of Int. 133, pale yellow solid (63%).

e—Synthesis of Int. 134:

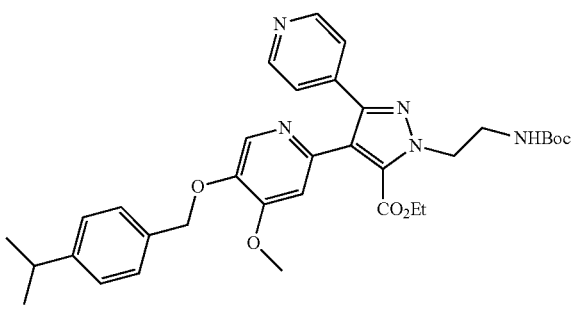 [SMILES: CCOC(=O)c1c(-c2cc(OC)c(OCc3ccc(C(C)C)cc3)cn2)c(-c2ccncc2)nn1CCNC(=O)OC(C)(C)C]

DBAD (123 mg, 0.533 mmol) was added to a stirred sol. of 133 (140 mg, 0.296 mmol), Boc-glycinol (86 mg, 0.533 mmol) and PPh₃ (140 mg, 0.533 mmol) in dry DCE (3 mL) at r.t. under N₂. The r.m. was stirred at r.t. for 20 h, and then water and EtOAc were added. The organic layer was washed with brine, dried over MgSO₄, filtered and evaporated in vacuo to give 490 mg of yellow oil. This oil was purified by prep. LC (irregular SiOH 15-40 μm, 24 g, GraceResolv™, mobile phase gradient: from DCM 100% to EtOAc 100%). The pure fractions were collected and solvent was evaporated until dryness to give 203 mg of Int. 134, viscous yellow solid (100%).

f—Synthesis of Co. 72:

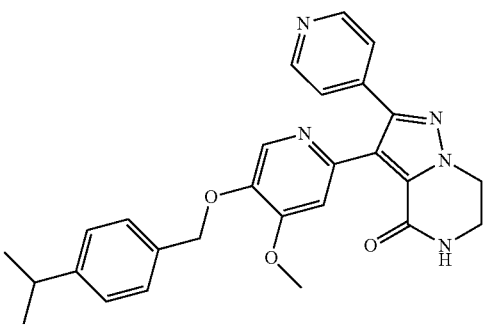 [SMILES: COc1cc(-c2c(-c3ccncc3)nn3c2C(=O)NCC3)ncc1OCc1ccc(C(C)C)cc1]

A sol. of 134 (190 mg, 0.309 mmol) and HCl 3N (0.514 mL, 1.54 mmol) in ACN (5 mL) was stirred at 80° C. for 90 min. Then, EtOAc and a sat. sol. of NaHCO₃ were added, and the r.m. was stirred at r.t. for 20 h. Water and more EtOAc were added, and the organic layer was separated, washed with brine, dried over MgSO₄, filtered and evaporated in vacuo. The residue (114 mg) was purified by prep. LC (Irregular SiOH 50 μm, 10 g Grace, mobile phase gradient: from DCM 100% to DCM 92%, MeOH 8%). The fractions were collected and evaporated in vacuo to give 79 mg of a white solid. This solid was dissolved in MeOH, and the solvent was allowed to evaporate slowly. After crystallization, the remaining solvent was removed. The solid was dried for 4 h, yielding 70 mg of Co. 72, white solid (48%). m.p.: 231° C. (DSC).

Example A75

Preparation of Co. 73 a—Synthesis of Int. 135:

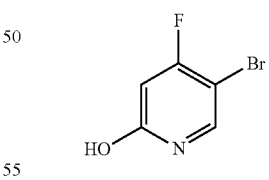

To a sol. of 2-hydroxy-4-fluoropyridine (1.0 g, 8.8 mmol) in ACN (23 mL) was added dropwise N-bromosuccinimide (1.6 g, 8.8 mmol) in ACN (23 mL) at r.t. in darkness. The sol. was stirred at r.t. for 3 days. The solvent was removed in vacuo. EtOAc and a sat. aq. sol. of brine were added to the residue, the organic layer was washed, separated, dried on MgSO₄, filtered and evaporated in vacuo to give 1.44 g of a white solid. This solid was taken in DCM and the solid was filtered. The filtrate was concentrated and the purification was carried out by prep. LC (Interchim, 40 g, mobile phase: DCM/MeOH/NH₄OH, 96/4/0.1). The pure fractions were collected and the solvent was evaporated until dryness to give 540 mg of Int. 135, white solid (32%).

b—Synthesis of Int. 136:

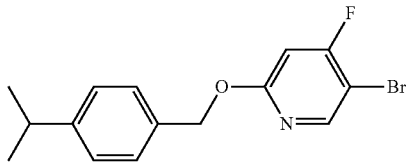 [SMILES: CC(C)c1ccc(COc2cc(F)c(Br)cn2)cc1]

8 (0.49 mL, 2.9 mmol) was added to a sol. of 135 (0.54 g, 2.0 mmol) and Ag$_2$CO$_3$ (2.3 g, 8.4 mmol) in ACN (15 mL). The mixture was stirred overnight at 80° C. The mixture was filtrated on Celite® and the filtrate was concentrated to give 0.76 g, white oil. This oil was taken in DCM and the white solid was filtrated off. The filtrate was concentrated and it was purified by prep. LC (irregular SiOH 15-40 μm, 25 g GraceResolv™, mobile phase gradient: heptane/EtOAc from 100/0 to 93/7). The pure fractions were collected and solvent was evaporated until dryness to give 350 mg of Int. 136, colorless oil (39%).

c—Synthesis of Int. 137,

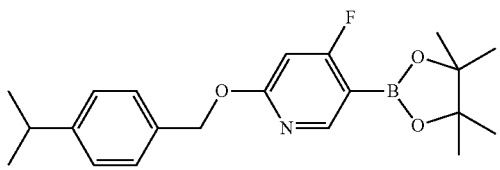 [SMILES: CC(C)c1ccc(COc2cc(F)c(B3OC(C)(C)C(C)(C)O3)cn2)cc1]

In a microwave vial, BisPin (0.33 g, 1.3 mmol) and KOAc (0.21 g, 2.2 mmol) were added to a sol. of 136 (0.35 g, 1.1 mmol) in 1,4-dioxane (3.6 mL). The sol. was purged with N$_2$ and charged with PdCl$_2$(dppf) (38 mg, 54 μmol). The resulting sol. was purged again with N$_2$ and stirred at 80° C. for 17 h. After dilution in EtOAc, the crude material was washed with water and brine. The organic layer was dried over MgSO$_4$ and evaporated to afford 680 mg of dark oil. This oil was purified by prep. LC (irregular SiOH 15-40 μm, 12 g GraceResolv™, mobile phase: heptane/EtOAc 90/10). The pure fractions were collected and evaporated until dryness to give 390 mg of Int. 137, colorless oil (97%).

d—Synthesis of Co. 73:

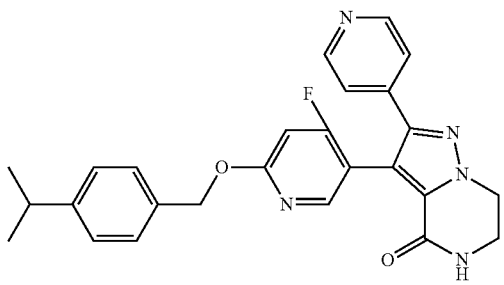 [SMILES: CC(C)c1ccc(COc2cc(F)c(-c3c(-c4ccncc4)nn4c3C(=O)NCC4)cn2)cc1]

In a microwave vial, a mixture of 4 (0.26 g, 0.88 mmol), 137 (0.39 g, 1.1 mmol), K$_3$PO$_4$ (0.74 g, 3.5 mmol) in 1,4-dioxane (3.8 mL) and H$_2$O (1.4 mL) was carefully purged with N$_2$. PdCl$_2$(dppf) (72 mg, 88 μmol) was added and the r.m. was purged again with N$_2$. The r.m. was heated at 80° C. overnight. The r.m. was diluted with EtOAc and washed with water (once) and with brine (3 times). The organic phase was dried over MgSO$_4$, filtered on a pad of Celite® and evaporated in vacuo to give 550 mg, brown solid. The solid was purified by prep. LC (Stationary phase: Spherical bare silica 5 μm 150×30.0 mm, mobile phase gradient: from NH$_4$OH/DCM/MeOH 0.1/99/1 to NH$_4$OH/DCM/MeOH 0.7/93/7). The pure fractions were collected and solvent was evaporated until dryness to give 61 mg of colorless product which was crystallized from Et$_2$O. The solid was filtrated and dried to give 33 mg of Co. 73, white solid (8%). m.p.: 207° C. (dsc).

Example A76

Preparation of Co. 74 a—Synthesis of Int. 138:

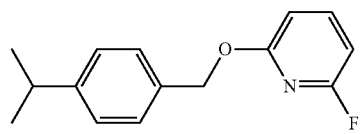

A sol. of 6 (3.1 g, 20 mmol) in dry DMF (60 mL) was treated at 0° C. with NaH 60% (0.99 g, 25 mmol). After stirring for 1 h at r.t., 2,6-difluoro-pyridine (2.4 g, 21 mmol) was added and the r.m. was stirred at r.t. overnight. The r.m. was quenched with water 200 mL and the mixture was extracted with DCM 3×. The organic layer was dried and concentrated to give 5.7 g of Int. 138, colorless oil (100%, purity 89%) which was used like this in the next step.

b—Synthesis of Int. 139:

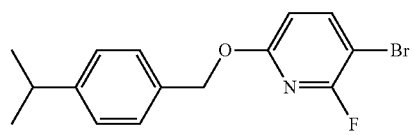

To a sol. of 138 (4.7 g, 17 mmol) in ACN (60 mL) was slowly added N-bromosuccinimide (3.0 g, 17 mmol) in ACN (60 mL) at r.t. The sol. was stirred at 80° C. overnight. The solvent was removed in vacuo and the residue was taken in EtOAc and washed with NaCl sat, NaHCO$_3$, filtrated and dried. The residue and the mixture was purified by prep. LC (irregular SiOH 15-40 μm, 120 g Interchim, mobile phase: heptane/EtOAc, 98/2). The fractions were collected and solvent was evaporated to give 3.0 g. This fraction was purified by prep. LC (irregular SiOH 15-40 μm, 40 g Interchim, mobile phase: heptane/EtOAc, 98/2). The pure fractions were collected and solvent was evaporated until dryness to give 2.6 g Int. 139, colorless oil (47%, purity: 80%) which was used such as for the next step.

c—Synthesis of In, 140:

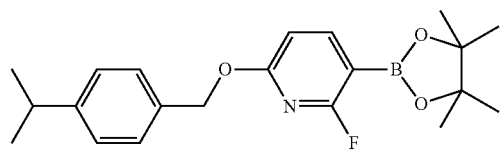 [SMILES: CC(C)c1ccc(COc2ccc(B3OC(C)(C)C(C)(C)O3)c(F)n2)cc1]

BisPin (0.94 g, 3.7 mmol) and KOAc (0.61 g, 6.2 mmol) were added to a sol. of 139 (1 g, 3.1 mmol) in 1,4-dioxane (10 mL). The sol. was purged with N₂ and charged with PdCl₂(dppf) (0.11 g, 0.15 mmol). The resulting sol. was purged again with N₂ and stirred at 80° C. for 17 h. After dilution in EtOAc, the crude material was washed with water and brine. The organic layer was dried over MgSO₄ and evaporated to afford dark oil. This oil was purified by prep. LC (irregular SiOH 15-40 µm, 25 g GraceResolv™, mobile phase: heptane/EtOAc 90/10). The fractions were collected and solvent was evaporated until dryness to give 1.1 g of Int. 140, yellow oil (48%, purity 50%) which was used like this in the next step.

d—Synthesis of Co. 74

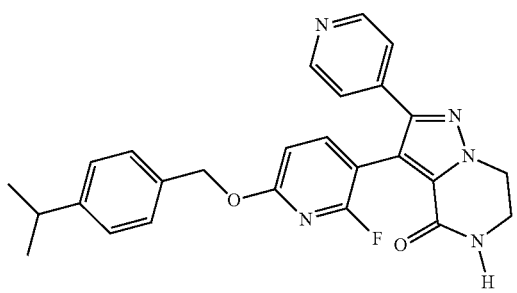 [SMILES: CC(C)c1ccc(COc2ccc(-c3c(-c4ccncc4)nn4c3C(=O)NCC4)c(F)n2)cc1]

In a microwave vial, a mixture of 4 (0.72 g, 2.5 mmol), 140 (1.1 g, 3.0 mmol), K₃PO₄ (2.1 g, 10 mmol) in 1,4-dioxane (11 mL) and H₂O (4 mL) was carefully purged with N₂. PdCl₂(dppf) (200 mg, 0.25 mmol) was added and the r.m. was purged again with N₂. The r.m. was heated at 80° C. overnight. The r.m. was diluted with EtOAc and washed with water (once) and with brine (3 times). The organic phase was dried over MgSO₄, filtered on a pad of Celite® and evaporated in vacuo to give a brown solid. It was purified by prep. LC (irregular SiOH 15-40 µm, 40 g GraceResolv™, mobile phase: DCM 96%, MeOH 4%). The fractions were collected and solvent was evaporated until dryness to give 610 mg of white solid. The solid was purified by prep. LC (Stationary phase: Spherical bare silica 5 µm 150×30.0 mm, mobile phase gradient: from NH₄OH/DCM/MeOH 0.2/98/2 to NH₄OH/DCM/MeOH 0.9/91/9). The pure fractions were collected and solvent was evaporated until dryness to give 152 mg of a white solid which was triturated with Et₂O. The solid was filtrated and dried to give 0.129 g of Co. 74, white solid (11%, mp: 275° C.).

Example A77

Preparation of Co. 75 a—Synthesis of Int. 141:

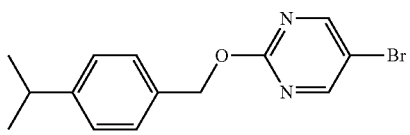

A sol. of 6 (4.66 g, 31.0 mmol) in dry THF (200 mL) was treated with NaH 60% (1.29 g, 32.3 mmol) and stirred at r.t. for 10 min. 5-bromo-2-chloropyrimidine (5.00 g, 25.8 mmol) was then added and the r.m. was stirred at r.t. for 17 h. The r.m. was then heated at 70° C. for 5 extra h and concentrated in vacuo. The concentrate was taken up with EtOAc, washed with water and brine, dried over MgSO₄ and evaporated in vacuo to give yellow oil. This oil was purified by prep. LC (irregular SiOH 15-40 µm, 80 g, Grace, dry loading, mobile phase: heptane 80% to EtOAc 20%). The pure fractions were collected and solvent was evaporated to give 5.92 g of Int. 141, white solid (75%).

b—Synthesis of Int. 142:

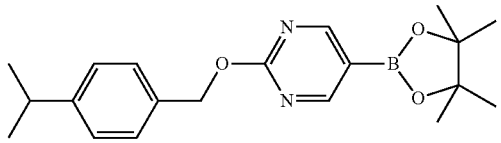 [SMILES: CC(C)c1ccc(COc2ncc(B3OC(C)(C)C(C)(C)O3)cn2)cc1]

In a Schlenk tube, a sol. of 141 (3.0 g, 9.77 mmol), BisPin (4.96 g, 19.5 mmol) and KOAc (2.88 g, 29.3 mmol) in DME (60 mL) was purged with N₂. PdCl₂(dppf) (800 mg, 0.977 mmol) was added to the mixture and the mixture was purged with N₂ again. The reaction was heated at 110° C. for 17 h then poured in EtOAc. The organic layer was washed with water and brine, dried over MgSO₄ and evaporated in vacuo to give a black residue. The residue was filtered through a short pad of silica gel (eluent: EtOAc 100%) and the filtrate was evaporated in vacuo to give a brown solid. This solid was purified by prep. LC (irregular SiOH 15-40 µm, 80 g, Grace, dry loading, mobile phase: heptane 80% to EtOAc 20%). The pure fractions were collected and solvent was evaporated to give 2.20 g of Int. 142 white solid (64%).

c—Synthesis of Co. 75:

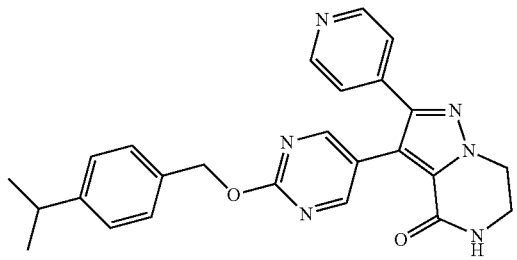 [SMILES: CC(C)c1ccc(COc2ncc(-c3c(-c4ccncc4)nn4c3C(=O)NCC4)cn2)cc1]

A sol. of 4 (400 mg, 1.37 mmol) and 142 (967 mg, 2.73 mmol) in 1,4-dioxane (8 mL) and H₂O (4 mL) was treated with K₃PO₄ (869 mg, 4.09 mmol) and purged with N₂. PdCl₂(dppf) (112 mg, 137 µmol) was then added and the r.m. was carefully purged with N₂. The mixture was heated at 120° C. using one single mode microwave (Biotage Initiator EXP 60) with a power output ranging from 0 to 400 W for 20 min [fixed hold time]. The r.m. was poured in DCM/MeOH (95/5) and washed with water and brine. The organic layer was dried over MgSO₄ and evaporated in vacuo to give a black residue which was purified by prep. LC (irregular SiOH 15-40 µm, 45 g, Merck, dry loading, mobile phase gradient: from DCM 100% to DCM 92%, MeOH 8%). The pure fractions were collected and solvent was evaporated until dryness to give 170 mg of an off-white solid. The solid was crystallized from EtOH, filtered on a glass frit and washed with Et₂O. The solid was collected and dried in vacuo to give 145 mg of a white solid which was solubilized in MeOH. The solvent was allowed to evaporate slowly overnight. The solid was triturated in Et₂O, filtered and dried in vacuo to give 132 mg of Co. 75 (white solid; 22%). m.p.: 126° C. (dsc).

Example A78

Preparation of Co. 76 a—Synthesis of Int. 143:

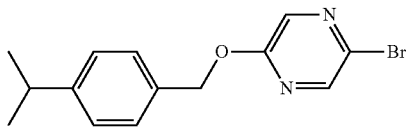

Under N₂, a sol. of 2,5-dibromopyrazine (1.97 g, 8.28 mmol) and 6 (1.57 mL, 9.94 mmol) in dry DMF (45 mL) was treated with NaH 60% (397 mg, 9.94 mmol) and stirred at r.t. for 18 h. The r.m. was poured in EtOAc and water, and the organic layer was washed with brine (twice), dried over MgSO₄, filtered and evaporated in vacuo to give 2.83 g, brown oil. This oil was purified by prep. LC (irregular SiOH 15-40 μm, 120 g, GraceResolv™, mobile phase gradient: from heptane 100% to heptane 50%, EtOAc 50%). The pure fractions were collected and solvent was evaporated until dryness to give 2.25 g of Int. 143 yellow oil (88%).

b—Synthesis of Co. 76:

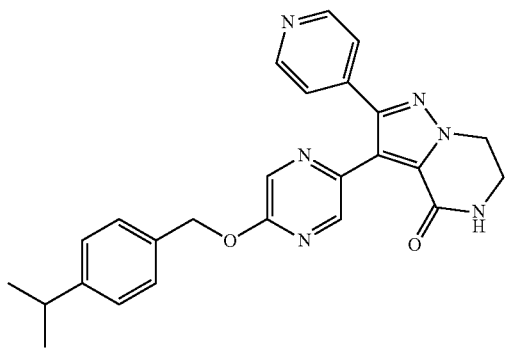 [SMILES: CC(C)c1ccc(COc2cnc(-c3c(-c4ccncc4)nn4c3C(=O)NCC4)cn2)cc1]

A mixture of 60 (304 mg, 0.894 mmol), 143 (549 mg, 1.79 mmol), K₃PO₄ (569 mg, 2.68 mmol) in THF (6 mL) and H₂O (3 mL) was carefully purged with N₂. Precatalyst (70 mg, 89.4 pimol) was added and the r.m. was purged again with N₂. The r.m. was stirred at r.t. for 66 h, and then a sol. of DCM/MeOH 95:5 and water were added. The organic layer was washed with brine, separated and evaporated in vacuo to afford 3.00 g of a solid. The solid was diluted in a sol. of DCM/MeOH 50:50, and filtered off. The filtrate was evaporated in vacuo to yield 930 mg of a pale yellow solid. This solid was purified by prep. LC (Irregular SiOH 50 μm, 40 g Grace, mobile phase gradient: from DCM 100% to DCM 91%, MeOH 9%). The desired fractions were collected and evaporated in vacuo to give 188 mg of a white solid. The residue was purified by achiral SFC (Stationary phase: 2-ethylpyridine 6 μm 150×30 mm, mobile phase: 85% CO₂, 15% MeOH (0.3% iPrNH₂). The pure fractions were collected and solvent was evaporated until dryness to yield 126 mg which was crystallized from EtOH. The solid was filtered, washed with Et₂O, and dried in vacuo to yield 81 mg of Co. 76, white solid (21%). m.p.: 225° C. (dsc).

Example A79

Preparation of Co. 77 a—Synthesis of Int. 153:

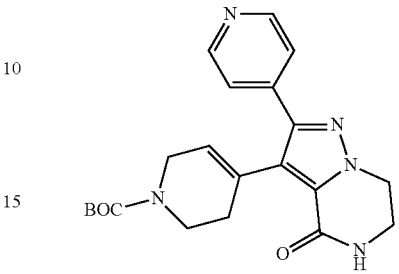

4 (1.9 g, 6.5 mmol), N-Boc-1,2,5,6-tetrahydropyridine-4-boronic acid pinacol ester (2 g, 6.5 mmol), Na₂CO₃ (13 mL, 13 mmol) in 1,4-dioxane (21 mL) were degassed with N₂. PdCl₂(dppf) (0.53 g, 0.65 mmol) was added and heated to 110° C. in sealed tube for 20 h. The mixture was poured into water and extracted with EtOAc. The organic layer was dried over MgSO₄, filtered and evaporated until dryness to give 3.5 g. The residue was purified by LC prep. (80 g of SiOH 30 μm Interchim, mobile phase gradient: from 100% DCM to 90/10/0.1 DCM/CH₃OH/NH₄OH). The pure fractions were collected and evaporated until dryness to give 2.3 g of Int. 153 (89%).

b—Synthesis of Int. 154:

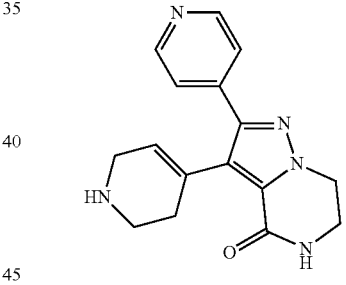

HCl 3N (9.7 mL, 29.08 mmol) was added to 153 (2.3 g, 5.8 mmol) in ACN (100 mL). The mixture was heated for 30 min at 80° C. and poured into water, basified with K₂CO₃ and extracted with EtOAc. The organic layer was dried over MgSO₄, filtered and evaporated until dryness to give 0.62 g of Int. 154 (36%).

c—Synthesis of Co. 77:

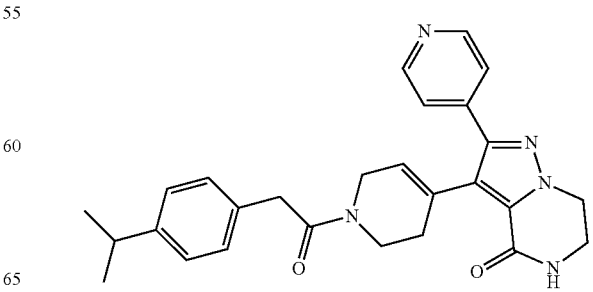

4-(1-methylethyl)-benzeneacetyl chloride (0.31 g, 1.56 mmol) in DCM (4 mL) was added dropwise to a sol. of 154 (384 mg, 1.3 mmol), Et₃N (0.27 mL, 1.95 mmol) in DCM (11 mL) at 5° C. The mixture was stirred for 15 h and poured into water. The organic layer was separated, dried over MgSO₄, filtered and evaporated to give a residue (0.63 g) which was purified by prep. LC (40 g of SiOH 15 μm Interchim, mobile phase gradient from 100% DCM to 90% DCM 10%, MeOH 0.1%, NH₄OH). The fractions were collected and evaporated until dryness to give 315 mg which was crystallized from Et₂O, filtered and dried to give 246 mg of Co. 77 (41%).

Example A80

Preparation of Co. 78a and Co. 78 a—Synthesis of Int. 155:

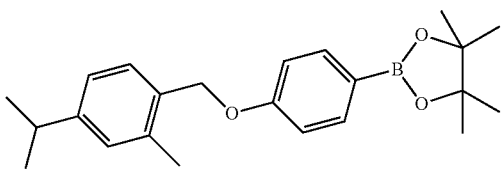 [SMILES: Cc1cc(C(C)C)ccc1COc1ccc(B2OC(C)(C)C(C)(C)O2)cc1]

To a sol. of 2-methyl-4-(1-methylethyl)-benzenemethanol (0.97 g, 5.9 mmol), 7 (1.3 g, 5.9 mmol), PPh₃ (1.7 g, 6.5 mmol) in dry DCM (40 mL) was added DBAD (1.5 g, 6.5 mmol) and the r.m. was stirred at r.t. for 2 days. The mixture was poured into water and the organic layer was extracted, dried over MgSO₄, filtered and evaporated until dryness to give 6 g. The residue was tritured in heptane and the solid formed was filtered off. The filtrate was concentrated and injected to be purified by prep. LC (80 g of irregular SiOH 35-40 μm GraceResolv™, mobile phase gradient: from 100% heptane to 80% heptane 20% EtOAc). The fractions were collected and evaporated until dryness to give 1.7 g of Int. 155 (78%)

b—Synthesis of Co. 78a:

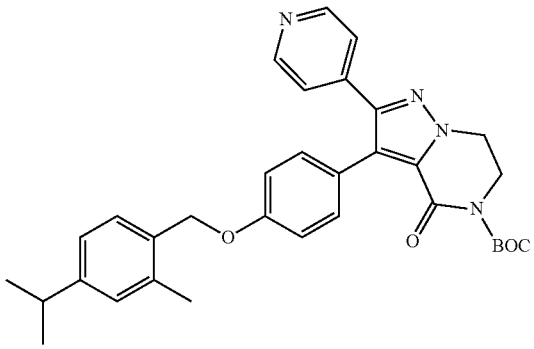 [SMILES: Cc1cc(C(C)C)ccc1COc1ccc(-c2c(-c3ccncc3)nn3c2C(=O)N(C(=O)OC(C)(C)C)CC3)cc1]

25 (0.97 g, 2.5 mmol), 155 (0.94 g, 2.5 mmol), K₃PO₄ (2.1 g, 9.8 mmol) in 1,4-dioxane (13 mL) and H₂O (3.5 mL) were purged with N₂ for 10 min. Then, PdCl₂(dppf) (0.2 g, 0.25 mmol) was added and purged with N₂ for 10 min. The mixture was heated to 75° C. for 15 h, cooled to r.t., poured into water and K₂CO₃ and extracted with EtOAc. The organic layer was dried over MgSO₄, filtered and dried to give 1.9 g. The residue was purified by prep. LC (40 g of irregular SiOH 35-40 μm GraceResolv™, mobile phase gradient: from 100% DCM to 90% DCM 10% MeOH 0.1% NH₄OH). The pure fractions were collected and solvent was evaporated until dryness to give 510 mg of Co. 78a (37%).

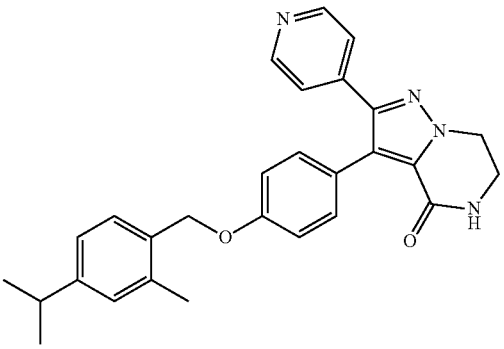 [SMILES: Cc1cc(C(C)C)ccc1COc1ccc(-c2c(-c3ccncc3)nn3c2C(=O)NCC3)cc1]

c—Synthesis of Co. 78:

Co. 78a (510 mg, 0.92 mmol), ACN (24 mL), HCl 3N (3 mL) were heated to 80° C. for 1 h. The mixture was cooled to r.t., poured into water and basified with K₂CO₃ and EtOAc was added. The insoluble was filtered and the organic layer was separated, dried over MgSO₄, filtered and evaporated until dryness. The residue was purified by prep. LC (40 g of SiOH 30 μm Interchim, mobile phase gradient: from 100% DCM to 90% DCM 10% MeOH 0.1% NH₄OH). The pure fractions were collected and evaporated until dryness to give 153 mg which was crystallized from Et₂O, filtered and dried to give 136 mg of Co. 78 (33%). m.p.: 247° C. (dsc).

Example A81

Preparation of Co. 79 a—Synthesis of Int. 157:

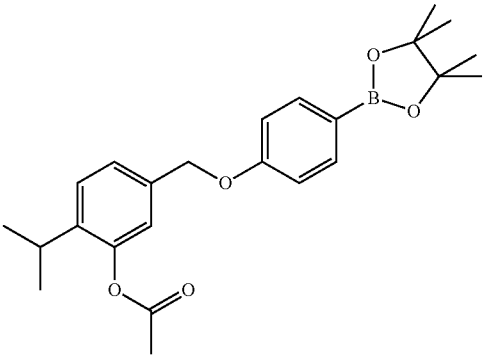 [SMILES: CC(=O)Oc1cc(COc2ccc(B3OC(C)(C)C(C)(C)O3)cc2)ccc1C(C)C]

To a suspension of 3-(acetoxy)-4-(1-methylethyl)-benzenemethanol (498 mg, 2.39 mmol), 7 (632 mg, 2.87 mmol), PPh₃ supp. (661 mg, 2.87 mmol) in dry DCM (10 mL) was added DBAD (897 mg, 2.87 mmol) and the r.m. was stirred at r.t. for 18 h. The insoluble was filtered through Celite®, washed with DCM. Water was added and the organic layer was separated, dried, filtered and concentrated to give 1.66 g. The residue was purified by prep. LC on (Irregular SiOH 30 μm 40 g Interchim, mobile phase gradient: from Heptane 95/EtOAc 5 to Heptane 90/EtOAc 10). The pure fractions were collected and evaporated until dryness to give 413 mg of Int. 157 (42%).

b—Synthesis of Int. 158 and Int. 160:

Int. 158

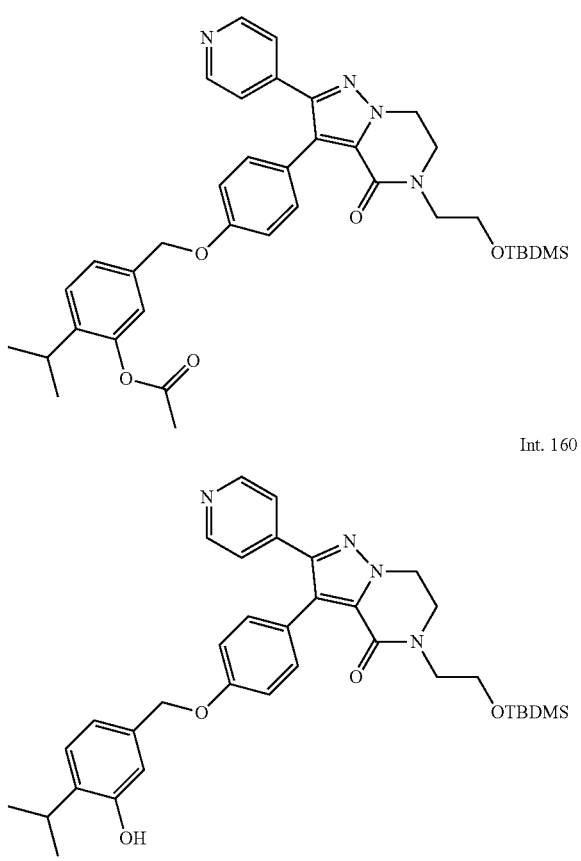

Int. 160

In a microwave vial, a mixture of 28 (0.413 g, 0.92 mmol), 157 (0.413 g, 1 mmol), K₃PO₄ (0.78 g, 3.7 mmol) in 1,4-dioxane (4 mL) and H₂O (1.43 mL) was carefully purged with N₂. PdCl₂(dppf) (75 mg, 0.09 mmol) was added and the r.m. was purged again with N₂. The r.m. was heated at 80° C. overnight. The r.m. was diluted with EtOAc and washed with water (once) and with brine (3 times). The organic phase was dried over MgSO₄, filtered and evaporated in vacuo to give 792 mg. The residue was purified by prep. LC (irregular SiOH 30 μm, 40 g Interchim, mobile phase gradient: from DCM 100% to DCM/MeOH/NH₄OH 95/5/0.1). The fractions were collected and solvent was evaporated until dryness to give 270 mg of Int. 158 (purity 50%) and 271 mg of Int. 160 (purity 79%). 158 and 160 were used as such for the next steps.

c—Synthesis of Int. 160:

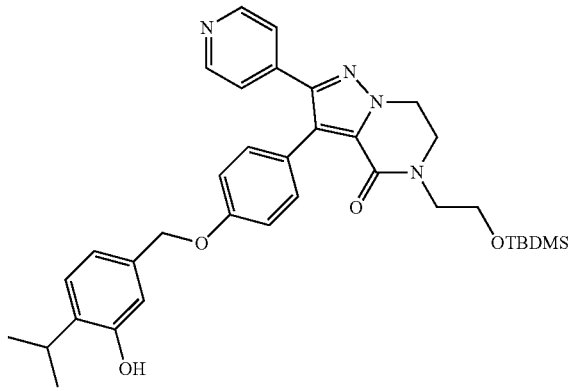 [SMILES: CC(C)c1ccc(COc2ccc(-c3c(-c4ccncc4)nn4c3C(=O)N(CCO[Si](C)(C)C(C)(C)C)CC4)cc2)cc1O]

To a sol. of 158 (270 mg, 0.41 mmol) in MeOH (4 mL) was added KOH (69 mg, 1.24 mmol) and the mixture was heated at 50° C. for 3 h. Water and DCM were added and the organic layer was separated, dried, filtered and concentrated until dryness to give 235 mg of Int. 160 as a (crude) mixture which was used as such for the next step.

d—Synthesis of Co. 79:

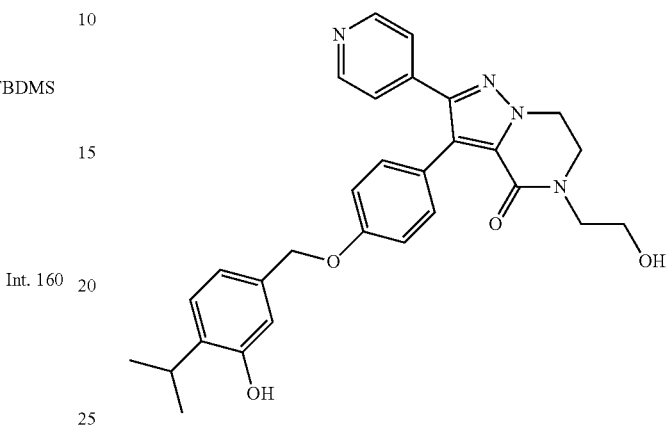

TBAF (1.03 mL, 1.03 mmol) was added dropwise to a sol. of 160 (506 mg) in THF (8.5 mL) at r.t. The mixture was stirred for 3 h at r.t. EtOAc and water were added. The organic layer was separated, dried, filtered and evaporated until dryness to give 395 mg. The residue was purified by prep. LC (Regular SiOH, 30 μm, 12 g GraceResolv™, mobile phase gradient: from DCM 100% to DCM/MeOH/NH₄OH 95/5/0.1). The pure fractions were collected and evaporated until dryness to give 291 mg which was crystallized from DIPE, filtered and dried to give 265 mg of Co. 79. m.p.: 236° C. (dsc).

Example A82

Preparation of Co. 80 a—Synthesis of Int. 161:

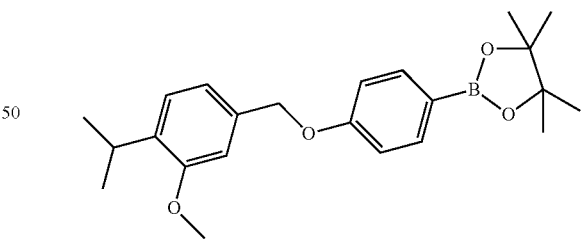

To a suspension of 3-methoxy-4-isopropylbenzenemethanol (0.29 g, 1.6 mmol), 7 (0.425 g, 1.93 mmol), DBAD (0.45 g, 1.93 mmol) in dry DCM (5 mL) was added PPh₃ supp. (0.6 g, 1.93 mmol) and the r.m. was stirred at r.t. for 18 h. The insoluble was filtered through Celite®, washed with DCM. Water was added and the organic layer was separated, dried, filtered and concentrated until dryness to give 1.07 g. The residue was purified by prep. LC on (Irregular SiOH 15-40 μm 30 g Merck, mobile phase: 90/10 Heptane/EtOAc). The pure fractions were collected and evaporated until dryness to give 411 mg of Int. 161 (67%).

b—Synthesis of Co. 80:

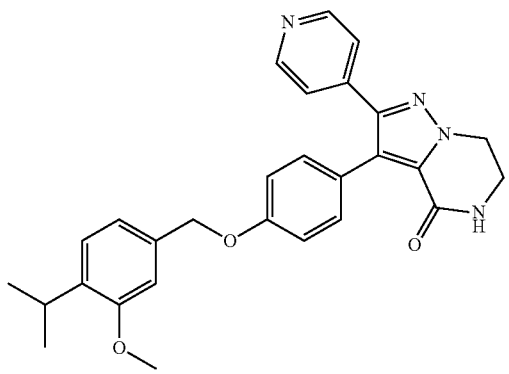 [SMILES: COc1cc(COc2ccc(-c3c(-c4ccncc4)nn4c3C(=O)NCC4)cc2)ccc1C(C)C]

In a microwave vial, a mixture of 4 (0.25 g, 0.853 mmol), 161 (0.391 g, 1.023 mmol), K$_3$PO$_4$ (0.76 g, 3.58 mmol) in 1,4-dioxane (4 mL) and H$_2$O (1.33 mL) was carefully purged with N$_2$. PCy$_3$ (50 mg, 0.179 mmol) and Pd(OAc)$_2$ (20 mg, 0.089 mmol) were added and the r.m. was purged again with N$_2$. The r.m. was stirred for 16 h at 80° C. The crude material was dissolved in water and extracted with EtOAc. The organic phase was dried over MgSO$_4$, filtered and evaporated in vacuo to give 506 mg. The residue was purified by prep. LC on (irregular SiOH 15-40 µm 300 g Merck, mobile phase: 40% Heptane, 10% MeOH (+10% NH$_4$OH), 50% EtOAc). The desired fractions were combined and the solvent was removed in vacuo to give 80 mg which was crystallized from DIPE, filtered and dried to give 70 mg of Co. 80 (18%). m.p.: 232° C. (dsc).

Example A83

Preparation of Co. 81 a—Synthesis of Int. 162:

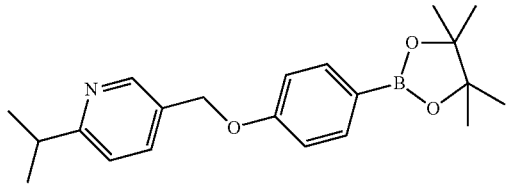 [SMILES: CC(C)c1ccc(COc2ccc(B3OC(C)(C)C(C)(C)O3)cc2)cn1]

A mixture of 7 (2.20 g, 10.0 mmol), 6-(1-methylethyl)-3-pyridinemethanol (1.97 g, 13.0 mmol) and PPh$_3$ (3.41 g, 13.0 mmol) in dry THF (30 mL) was treated with DBAD (2.99 g, 13.0 mmol) and stirred at r.t. for 2 h. The r.m. was poured in water and DCM. The organic layer was separated, washed with water, dried over MgSO$_4$ and evaporated in vacuo to afford yellow oil. The oil was purified by prep. LC (irregular SiOH 15-40 µm, 80 g Grace Resolv, solid loading, mobile phase gradient: from heptane 80%, EtOAc 20% to heptane 60%, EtOAc 40%). The pure fractions were collected and solvent evaporated until dryness to give 4.08 g of Int. 162, colorless oil (Quant.).

b—Synthesis of Int. 163:

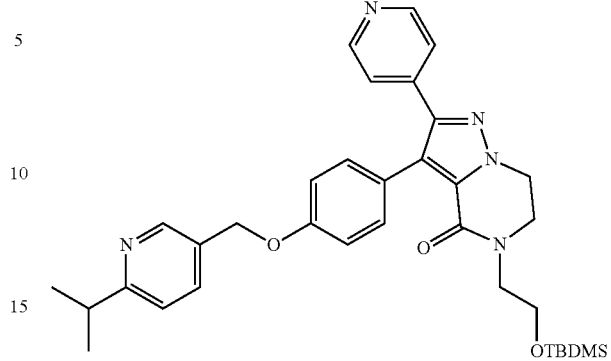

A sol. of 28 (800 mg, 1.77 mmol) and 162 (1.25 g, 3.54 mmol) in 1,4-dioxane (11 mL) and H$_2$O (5.5 mL) was treated with K$_3$PO$_4$ (1.13 g, 5.32 mmol) and purged with N$_2$. PdCl$_2$(dppf) (145 mg, 0.177 mmol) was then added and the r.m. was carefully purged with N$_2$. The mixture was heated at 120° C. using one single mode microwave (Biotage Initiator EXP 60) with a power output ranging from 0 to 400 W for 30 min [fixed hold time]. The crude mixture was diluted with DCM and washed with water. The organic layer was dried over MgSO$_4$ and evaporated to afford a brown residue. The brown residue was purified by prep. LC (irregular SiOH 15-40 µm, 80 g, GraceResolv™, solid loading, Mobile phase gradient: from DCM 100% to DCM 94%, MeOH 6%). The pure fractions were collected and solvent evaporated to give 1.30 g of Int. 163, yellow oil which was used such as for the next step.

c—Synthesis of Co. 81:

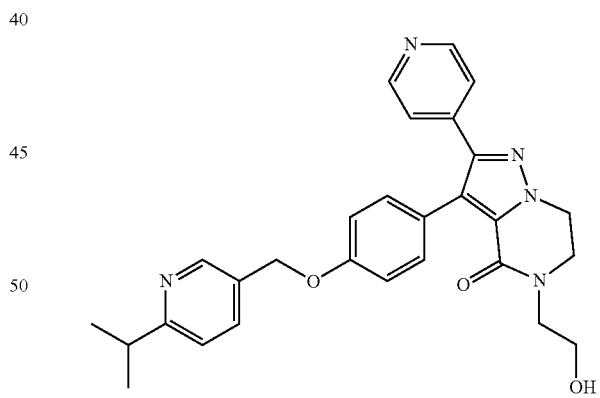

A sol. of 163 (1.30 g, 2.18 mmol) in THF (40 mL) was treated with TBAF (1.74 mL, 1.74 mmol) and stirred for 2 h at r.t. The r.m. was poured in H$_2$O and extracted 2× with DCM. The organic layers were combined, dried over MgSO$_4$ and evaporated in vacuo to afford yellow oil. The oil was purified by prep. LC (irregular SiOH 15-40 µm, 80 g, GraceResolv™, solid loading, Mobile phase gradient: from DCM 100% to DCM 94%, MeOH 6%). The pure fractions were collected and solvent evaporated to give 540 mg of Co. 81, white solid (51%). m.p.: 93° C. (DSC).

Example A84

Preparation of Co. 82 a—Synthesis of Int. 164:

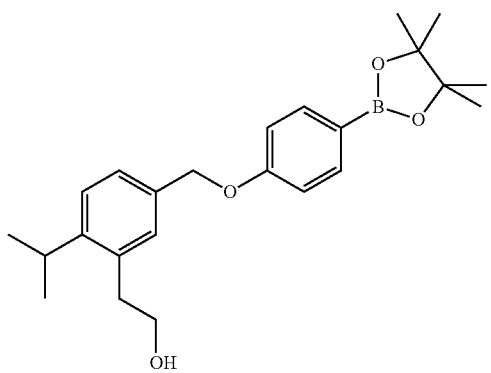 [SMILES: CC(C)c1ccc(COc2ccc(B3OC(C)(C)C(C)(C)O3)cc2)cc1CCO]

A stirred sol. of 55 (1.02 g, 2.92 mmol), BisPin (1.11 g, 4.38 mmol) and KOAc (860 mg, 8.76 mmol) in E (15 mL) was carefully purged with $N_2$, and $PdCl_2(dppf)$ (239 mg, 292 µmol) was added. The r.m. was purged again with $N_2$, and stirred for 18 h at 100° C. The r.m. was diluted with EtOAc and washed with water and brine. The organic layer was dried over $MgSO_4$ and evaporated in vacuo. The black residue was purified by prep. LC (irregular SiOH 15-40 µm, 40 g, Merck, mobile phase gradient: from heptane 80%, EtOAc 20% to heptane 60%, EtOAc 40%). The pure fractions were collected and solvent was evaporated to give 1.10 g of Int. 164 (95%).

b—Synthesis of Co. 82:

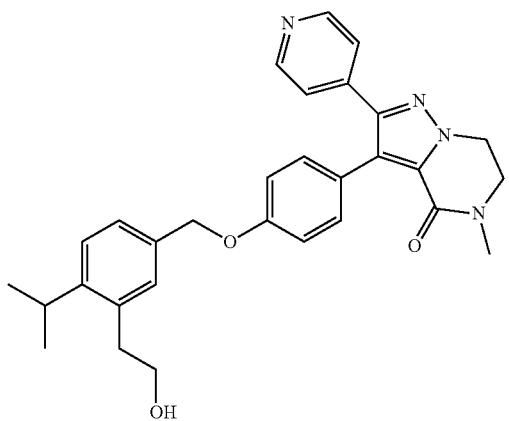 [SMILES: CC(C)c1ccc(COc2ccc(-c3c(-c4ccncc4)nn4c3C(=O)N(C)CC4)cc2)cc1CCO]

A mixture of 98 (600 mg, 1.95 mmol), 164 (1.16 g, 2.93 mmol) and KOAc (1.04 g, 4.88 mmol) in 1,4-dioxane (12 mL) and $H_2O$ (6 mL) was purged with $N_2$. $PdCl_2(dppf)$ (160 mg; 195 µmol) was then added. The mixture was purged again with $N_2$ and heated at 120° C. using one single mode microwave (Biotage Initiator EXP 60) with a power output ranging from 0 to 400 W for 25 min [fixed hold time]. The r.m. was then poured in DCM and water. The organic layer was separated. The aq. layer was extracted again with DCM. The organic layers were combined, dried over $MgSO_4$ and evaporated in vacuo. The brown residue was purified by prep. LC (irregular SiOH 15-40 µm, 80 g, GraceResolv™, dry loading, mobile phase gradient: from DCM 100% to DCM 96%, MeOH 4%). The pure fractions were collected and solvent was evaporated until dryness to give 744 mg of a residue, beige foam. This residue was purified by prep. LC (irregular SiOH 15-40 µm, 45 g, Merck, dry loading, mobile phase gradient: from DCM 100% to DCM 95%, MeOH 5%). The pure fractions were collected and solvent was evaporated to give 460 mg of a residue which was purified again by Reverse phase (Stationary phase: X-Bridge-C18 5 µm 30*150 mm; Mobile phase Gradient: from 80% ($NH_4HCO_3$ 0.5% aq. sol.), 20% ACN to 100% ACN). The fractions containing the pure product were combined and evaporated in vacuo to give 340 mg, a white foam. The residue was finally dissolved in a small amount of MeOH and triturated while $Et_2O$ was added. The white solid was filtered on a glass frit and washed with $Et_2O$. The solid was collected and dried in vacuo to afford 225 mg of Co. 82, white solid (23%).

Example A85

Preparation of Co. 83 a—Synthesis of Int. 165:

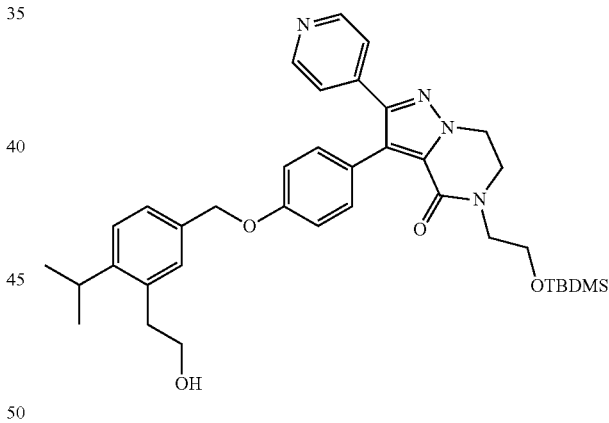

A mixture of 28 (0.680 g, 1.51 mmol), 164 (0.963 g, 2.26 mmol) and $K_3PO_4$ (0.959 g, 4.52 mmol) in 1,4-dioxane (9 mL) and $H_2O$ (4 mL) was purged with $N_2$. $PdCl_2(dppf)$ (0.100 g, 0.122 mmol) was then added. The mixture was purged again with $N_2$ and stirred at 120° C. using one single mode microwave (Biotage Initiator EXP 60) with a power output ranging from 0 to 400 W for 25 min [fixed hold time]. Then, a sol. of DCM/MeOH (94:6) and water were added. The organic layer was washed with brine, dried over $MgSO_4$, filtered and evaporated in vacuo to give a dark solid. The solid was purified by prep. LC (Irregular SiOH 50 µm, 80 g Grace, mobile phase gradient: from DCM 100% to DCM 94%, MeOH 6%). The desired fractions were evaporated in vacuo to yield 1.10 g of Int. 165, oil (97%, purity 85%) used as such for the next step.

b—Synthesis of Co. 83:

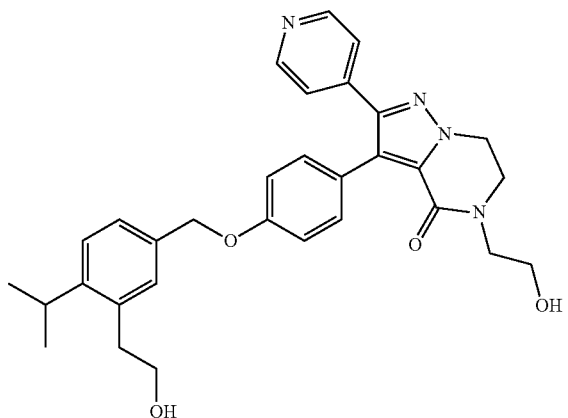 [SMILES: CC(C)c1ccc(COc2ccc(-c3c(-c4ccncc4)nn4c3C(=O)N(CCO)CC4)cc2)cc1CCO]

TBAF (1.47 mL, 1.47 mmol) was added to a stirred sol. of 165 (1.10 g, 1.46 mmol) in 1,4-dioxane (14 mL) at 0° C., and the r.m. was stirred at r.t. for 18 h. The crude mixture was diluted with water and a sol. of DCM/MeOH (96/4). The organic layer was washed with brine, dried over MgSO$_4$, filtered and evaporated in vacuo to afford 790 mg of a solid. This solid was purified by prep. LC (Irregular SiOH 50 µm, 50 g Grace, mobile phase gradient: from DCM 100% to DCM 94%, MeOH 6%). The desired fractions were collected and evaporated in vacuo to give 253 mg which was solubilized in MeOH (1 mL). The solvent was allowed to slowly evaporate, yielding 246 mg of Co. 83, crystalline white solid (32%). m.p.: 176° C. (DSC).

Example A86

Preparation of Co. 84 a—Synthesis of Int. 166:

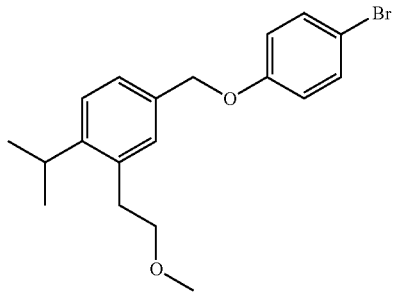 [SMILES: COCCc1cc(COc2ccc(Br)cc2)ccc1C(C)C]

NaH 60% (53 mg, 1.3 mmol) was added slowly to a suspension of 55 (0.30 g, 0.88 mmol) in THF (5.0 mL) at r.t. under N$_2$. The mixture was stirred for 2 h then MeI (0.08 mL, 1.3 mmol) was added and stirred overnight. Water was added and the mixture was extracted with DCM (3×), dried on MgSO$_4$ and evaporated until dryness and give 334 mg of yellow oil. This oil was purified by prep. LC (irregular SiOH 15-40 µm, 12 g, GraceResolv™, Mobile phase: Heptane/EtOAc, 95/5). The pure fractions were collected and solvent was evaporated to give 253 mg of Int. 166 (79%).

b—Synthesis of Int. 167:

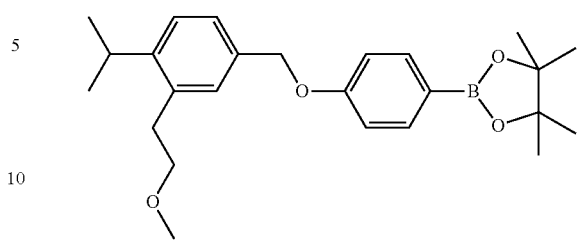

In a microwave vial, a mixture of 166 (0.25 g, 0.69 mmol), KOAc (0.20 g, 2.1 mmol), BisPin (0.26 g, 1.0 mmol) in DME (2 mL) was carefully purged with N$_2$. PdCl$_2$(dppf) (56 mg, 69 µmol) was added and the r.m. was purged again with N$_2$. The r.m. was stirred overnight at 100° C. The r.m. was diluted with EtOAc and washed with water (1×) and with brine (3×). The organic phase was dried over MgSO$_4$, filtered on a pad of Celite® and evaporated in vacuo to give 530 mg of brown oil. This oil was purified by prep. LC (irregular SiOH 15-40 µm, 12 g, GraceResolv™, Mobile phase: Heptane/EtOAc, gradient from 95/5 to 90/10). The pure fractions were collected and solvent was evaporated until dryness to give 307 mg of Int. 167, colorless oil (100%).

c—Synthesis of Co. 84:

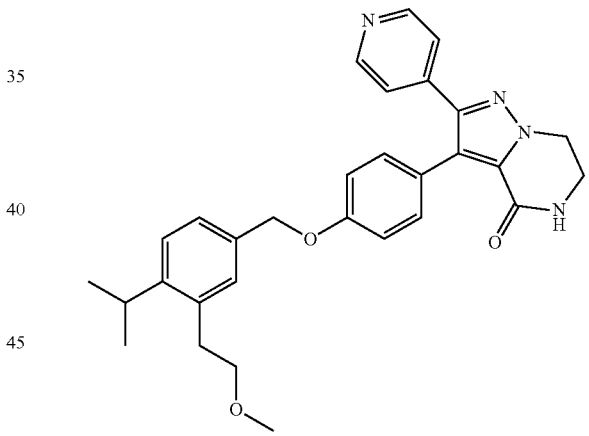

In a microwave vial, a mixture of 4 (167 mg, 0.57 mmol), 167 (0.28 g, 0.68 mmol), K$_3$PO$_4$ (0.36 g, 1.7 mmol) in 1,4-dioxane (2.5 mL) and H$_2$O (0.89 mL) was carefully purged with N$_2$. PdCl$_2$(dppf) (47 mg, 57 µmol) was added and the r.m. was purged again with N$_2$. The r.m. was heated at 80° C. overnight. The r.m. was diluted with EtOAc and washed with water (once) and with brine (3 times). The organic layer was dried over MgSO$_4$, filtered on a pad of Celite® and evaporated in vacuo to give 295 mg of brown oil. This oil was purified by prep. LC (irregular SiOH 30 µm, 25 g, Interchim, Mobile phase: DCM/MeOH/NH$_4$OH 97/3/ 0.1). The pure fractions were collected and solvent was evaporated until dryness to give 230 mg of white solid. This solid was washed with Et$_2$O, filtered and dried to give 210 mg of Co. 84, white solid (74%). m.p.: 208° C. (dsc).

Example A87

Preparation of Co. 85 and Co. 86 a—Synthesis of Int. 168:

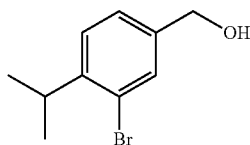

LAH (5.52 g, 145 mmol) was added to a stirred sol. of methyl-3-bromo-4-isopropylbenzoate (34.0 g, 132 mmol) in THF (600 mL) at −20° C. The r.m. was stirred at −20° C. for 2 h. The r.m. was quenched with $H_2O$ (5.26 mL), NaOH 3N (5.52 mL) and $H_2O$ (16 mL). The cake was filtered and washed (DCM). The filtrate was evaporated in vacuo to give 20.0 g of Int. 168, yellow oil (66%).

b—Synthesis of Int. 169:

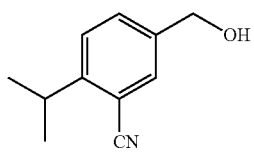

Pd(PPh$_3$)$_4$ (1.6 g, 1.4 mmol) was added to a mixture of 168 (3.2 g, 14 mmol) and Zn(CN)$_2$ (1.7 g, 14 mmol) in DMF (10 mL) in a sealed tube. The mixture was heated at 120° C. for 60 min using one single mode microwave (Biotage) with a power output ranging from 0 to 400 W. The r.m. was cooled to r.t., poured into ice water and extracted (DCM). The organic layer was separated, dried over MgSO$_4$, filtered and the solvent was evaporated until dryness to give 2.6 g. The residue was purified by prep. LC on (Irregular SiOH 15-40 µm 50 g Merck, mobile phase: 70/30 heptane/EtOAc). The pure fraction was collected and evaporated to give 1.4 g of Int. 169 (57%).

c—Synthesis of Int. 170:

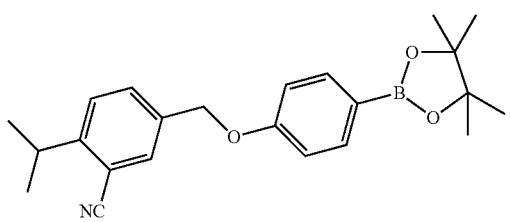 [SMILES: CC(C)c1ccc(COc2ccc(B3OC(C)(C)C(C)(C)O3)cc2)cc1C#N]

DBAD (1.3 g, 5.5 mmol) was added portionwise to a sol. of 69 (0.8 g, 4.6 mmol), 2 (1.2 g, 5.5 mmol), PPh$_3$ supp. (1.7 g, 5.5 mmol) in dry THF (30 mL). The mixture was stirred at r.t. overnight. The mixture was filtered. The filtrate was evaporated to give 3.7 g yellow oil. The crude residue was purified by prep. LC (irregular SiOH 30 µm 80 g Interchim, mobile phase: heptane/EtOAc 90/10). The pure fractions were collected and solvent was evaporated until dryness to give 1.0 g of Int. 170, colorless oil which crystallized in white solid (58%).

d—Synthesis of Co. 85:

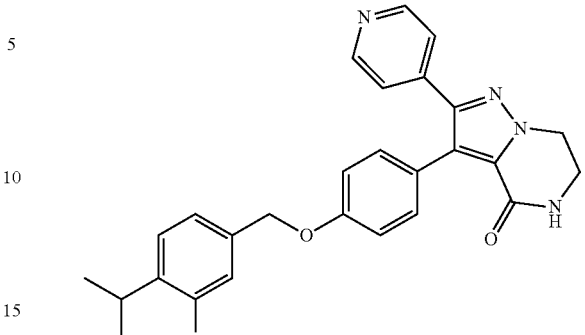

A mixture of 4 (867 mg, 2.96 mmol), 170 (0.93 g, 2.5 mmol), K$_3$PO$_4$ (1.57 g, 7.4 mmol) in 1,4-dioxane (11 mL) and $H_2O$ (4 mL) was carefully purged with N$_2$. PdCl$_2$(dppf) (201.7 mg, 0.25 mmol) were added and the r.m. was purged again with N$_2$. The r.m. was stirred for 8 h at 80° C. in a sealed tube. Water and DCM were added, the mixture was extracted, the organic layer was separated, dried over MgSO$_4$, filtered and evaporated. The residue was purified by prep. LC on (irregular 15-40 µm 30 g Merck, mobile phase: 98% DCM, 2% MeOH). The pure fractions were collected and the solvent evaporated until dryness to give 570 mg which was crystallized from Et$_2$O, the precipitate was filtered off and dried to give 453 mg of Co. 85 (40%). m.p.: 240° C. (dsc).

e—Synthesis of Co. 86:

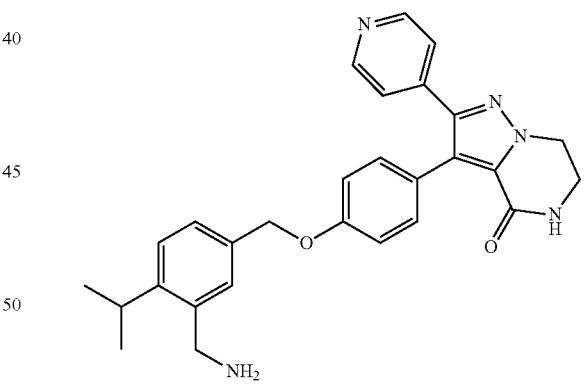

A solution of Co. 85 (280 mg, 0.604 mmol), MeOH/NH$_3$ (10 mL), Ni Raney (300 mg), THF (5 mL), DCM (5 mL) was hydrogenated under a 3 bars pressure at r.t. overnight. The catalyst was filtered over a Celite® pad, the filtrate was evaporated and the residue was purified by prep. LC (irregular SiOH 30 µm, 25 g, Interchim, Mobile phase gradient: DCM/MeOH/NH$_4$OH from 96/4/0.1 to 92/8/0.1). The pure fractions were put together and evaporated. The residue was taken up in Et$_2$O, filtrated and dried to give 15 mg of Co. 86 (5%).

Example A88

Preparation of Co. 87 a—Synthesis of Int. 171:

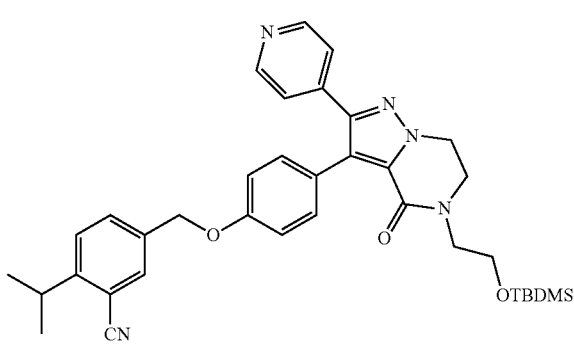 [SMILES: CC(C)c1ccc(COc2ccc(-c3c(-c4ccncc4)nn4c3C(=O)N(CCO[Si](C)(C)C(C)(C)C)CC4)cc2)cc1C#N]

In a microwave vial, a mixture of 28 (0.5 g, 1.1 mmol), 170 (0.5 g, 1.3 mmol), K₃PO₄ (0.94 g, 4.4 mmol) in 1,4-dioxane (4.9 mL) and H₂O (1.7 mL) was carefully purged with N₂. PdCl₂(dppf) (90 mg, 0.11 mmol) was added and the r.m. was purged again with N₂. The r.m. was heated at 80° C. overnight. The r.m. was diluted with EtOAc and washed with water (once) and with brine (3 times). The organic phase was dried over MgSO₄, filtered on a pad of Celite® and evaporated in vacuo to give a residue. The residue was purified by prep. LC (irregular SiOH 30 μm, 40 g Interchim, mobile phase: DCM/MeOH/NH₄OH 98/2/0.1). The pure fractions were collected and solvent was evaporated until dryness to give 0.72 g of Int. 171, beige solid (100%).

b—Synthesis of Co. 87:

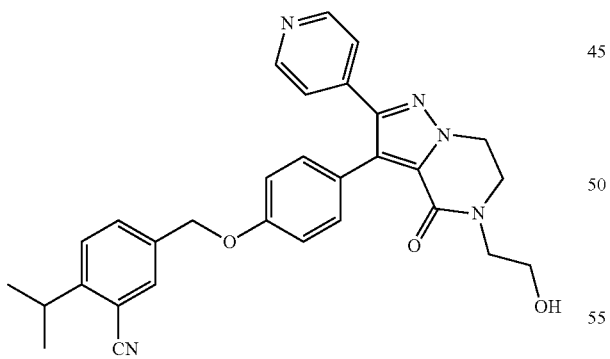

TBAF (1.4 mL, 1.4 mmol) was added dropwise to a sol. of 171 (0.72 g, 1.2 mmol) in THF (11 mL) at r.t. The mixture was stirred overnight at r.t. The mixture was concentrated and the residue was purified by prep. LC (Regular SiOH, 30 μm, 25 g GraceResolv™, mobile phase: DCM/MeOH/NH₄OH 98/2/0.1). The pure fractions were collected and the solvent was evaporated until dryness to give 0.38 g which was triturated in Et₂O. The white solid formed was filtered and dried to give 0.32 g of Co. 87 (55%). mp.: 160° C. (dsc).

Example A89

Preparation of Co. 88a and Co. 88 a—Synthesis of Int. 172:

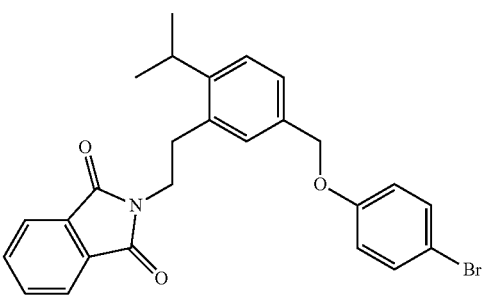 [SMILES: CC(C)c1ccc(COc2ccc(Br)cc2)cc1CCN1C(=O)c2ccccc2C1=O]

DBAD (99 mg, 0.43 mmol) was added portionwise to a sol. of 55 (100 mg, 0.29 mmol), phthalimide (63 mg, 0.43 mmol), diphenylphosphinopolystyrene (134 mg, 0.43 mmol) in THF (3.3 mL) at r.t. under N₂. The mixture was stirred for 3 days. The mixture was filtrated through a pad of Celite®, washed with EtOAc and concentrated. The crude residue was purified by prep. LC (irregular SiOH 35-40 μm 12 g GraceResolv™, mobile phase gradient: heptane/EtOAc from 90/10 to 85/15). The pure fractions were collected and solvent was evaporated until dryness to give 63 mg of Int. 172 (46%).

b—Synthesis of Int. 173:

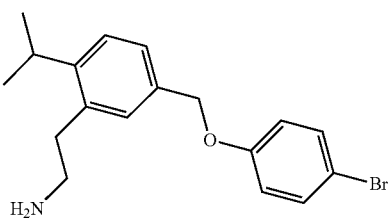 [SMILES: CC(C)c1ccc(COc2ccc(Br)cc2)cc1CCN]

In a microwave vial, hydrazine hydrate (230 μL, 2.4 mmol) was added to a suspension of 172 (380 mg, 0.79 mmol) in EtOH (5 mL) and the mixture was heated at 70° C. for 1 h. The white solid was filtered and washed with EtOH to give 295 mg of Int. 173 (used like this in the next step).

c—Synthesis of Int. 174: NHBoc

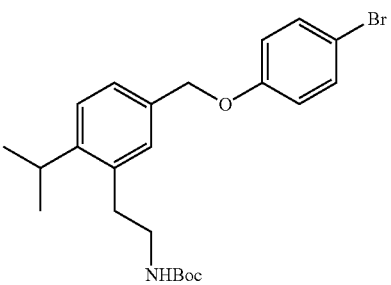 [SMILES: CC(C)c1ccc(COc2ccc(Br)cc2)cc1CCNC(=O)OC(C)(C)C]

Boc₂O (203 mg, 0.93 mmol) and Et₃N (0.35 mL, 2.5 mmol) were added to a suspension of 173 (295 mg, 0.85 mmol) in DCM (4.5 mL). The mixture was stirred at r.t.

overnight. The mixture was diluted with DCM and quenched with water. The organic layer was decanted, washed with water, with NaHCO₃, dried over MgSO₄, filtered and evaporated to give 300 mg of Int. 174, colorless oil (79%).

d—Synthesis of Int. 175:

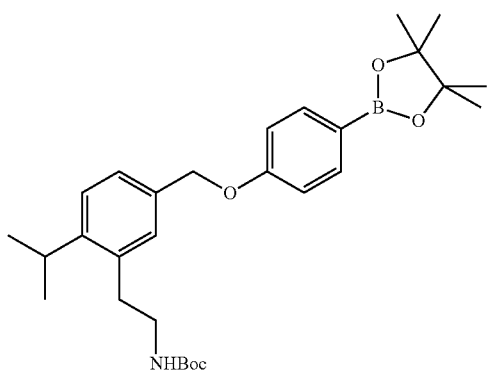 [SMILES: CC(C)c1ccc(COc2ccc(B3OC(C)(C)C(C)(C)O3)cc2)cc1CCNC(=O)OC(C)(C)C]

In a microwave vial, a mixture of 174 (0.30 g, 0.67 mmol), KOAc (0.20 g, 2.0 mmol), BisPin (0.26 g, 1.0 mmol) in DME (5.1 mL) was carefully purged with N₂. PdCl₂(dppf) (55 mg, 67 µmol) was added and the r.m. was purged again with N₂. The r.m. was stirred overnight at 100° C. The r.m. was diluted with EtOAc and washed with water (once) and with brine (3 times). The organic phase was dried over MgSO₄, filtered on a pad of Celite® and evaporated in vacuo to give 540 mg. The residue was purified by prep. LC (irregular SiOH 15-40 µm, 12 g, GraceResolv™, mobile phase gradient: Heptane/EtOAc, from 85/15 to 80/20). The pure fractions were collected and solvent was evaporated until dryness to give 333 mg of Int. 175, colorless oil (100%).

e—Synthesis of Co. 88a

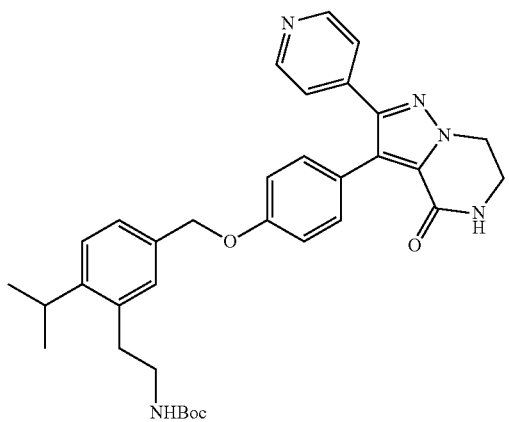 [SMILES: CC(C)c1ccc(COc2ccc(-c3c(-c4ccncc4)nn4c3C(=O)NCC4)cc2)cc1CCNC(=O)OC(C)(C)C]

In a microwave vial, a mixture of 4 (164 mg, 0.56 mmol), 175 (333 mg, 0.67 mmol), K₃PO₄ (357 mg, 1.68 mmol) in 1,4-dioxane (2.5 mL) and H₂O (0.8 mL) was carefully purged with N₂. PdCl₂(dppf) (46 mg, 56 µmol) was added and the r.m. was purged again with N₂. The r.m. was heated at 80° C. overnight. The r.m. was diluted with EtOAc and washed with water (once) and with brine (3 times). The organic phase was dried over MgSO₄, filtered on a pad of Celite® and evaporated in vacuo to give 390 mg. The residue was purified by prep. LC (irregular SiOH 30 µm, 12 g, GraceResolv™, Mobile phase gradient: DCM/MeOH/

NH₄OH from 98/2/0.1 to 97/3/0.1). The pure fractions were collected and solvent was evaporated until dryness to give 220 mg of Co. 88a, white solid (68%).

f—Synthesis of Co. 88:

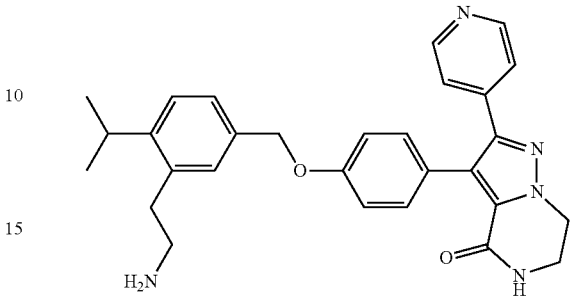

A solution of Co. 88a (220 mg, 0.38 mmol), HCl 3N (0.63 mL, 1.9 mmol), in ACN (6.7 mL) was stirred at 80° C. for 2 h. The mixture was concentrated, and NaHCO₃ sat aq was added and the mixture was stirred at r.t. 15 min. The mixture was extracted with DCM, dried, filtered and concentrated to give 213 mg of a solid. This solid was triturated in Et₂O, filtrated and dried to give 127 mg of Co. 88, beige powder (70%). m.p.: 181° C. (dsc).

Example A90

Preparation of Co. 89 a—Synthesis of Int. 177:

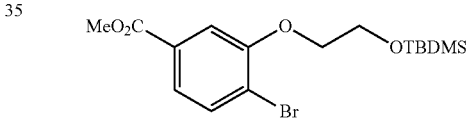

A solution of Methyl 4-bromo-3-hydroxybenzoate (2.5 g, 10.8 mmol), (2-bromoethoxy)-tert-butyldimethylsilane (2.5 mL, 11.9 mmol), K₂CO₃ (2.2 g, 16.2 mmol) in ACN (50 mL) was stirred at 80° C. overnight. Water and EtOAc were added, the mixture was extracted, the organic layer was separated, dried over MgSO₄, filtered and evaporated. The residue was purified by prep. LC (Regular SiOH, 30 µm, 120 g Grace, mobile phase: 80/20 heptane/EtOAc). The pure fractions were collected and the solvent was evaporated until dryness to give 3.2 g of Int. 177 (76%).

b—Synthesis of Int. 178:

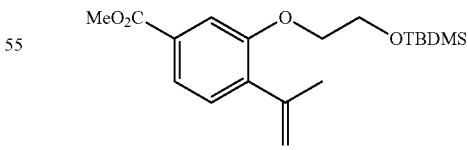

A solution of 177 (3.2 g, 8.2 mmol), Pd(tBu₃P)₂ (210 mg, 0.4 mmol), CsF (2.7 g, 18 mmol), 2-isopropenyl-4,4,5,5-tetramethyl-1,3,2-dioxaborolane (1.5 g, 9 mmol) in THF (30 mL) was refluxed overnight. Water and EtOAc were added, the mixture was filtered over a Celite® pad, washed with EtOAc. The mixture was extracted, the organic layer was separated, dried over MgSO₄, filtered and evaporated until dryness to give 3.4 g. The residue was purified by prep. LC on (irregular SiOH 30 μm, 90 g, GraceResolv™, Mobile phase: 80/20 heptane/EtOAc). The pure fractions were collected and evaporated till dryness yielding 2.5 g of Int. 178 (87%).

c—Synthesis of Int. 179:

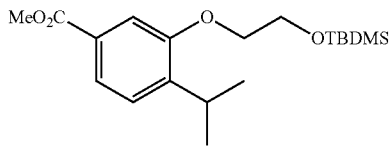 [SMILES: COC(=O)c1ccc(C(C)C)c(OCCO[Si](C)(C)C(C)(C)C)c1]

A solution of 178 (2.5 g, 7.1 mmol), ammonium formate (2.6 g, 43 mmol), Pd/C 10% (379 mg, 0.3 mmol) in THF (10 mL) and MeOH (30 mL) were refluxed for 90 min. The mixture was filtered through Celite®, washed with EtOAc, and the filtrate was concentrated to give 3.8 g. Water and EtOAc were added, the mixture was extracted, the organic layer was separated, dried over MgSO₄, filtered and dried to give 2.2 g of Int. 179 (87%) used as such for the next step.

d—Synthesis of Int. 180:

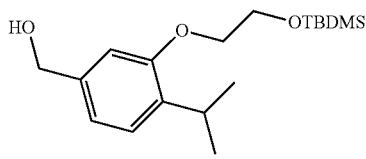 [SMILES: CC(C)c1ccc(CO)cc1OCCO[Si](C)(C)C(C)(C)C]

LAH (310 mg, 8.2 mmol) was added carefully at 5° C. to a sol. of 179 (2.4 g, 6.8 mmol) in THF (40 mL). The mixture was stirred at r.t. for 1 h. Water was carefully added at 5° C. and EtOAc were added, the mixture was extracted, the organic layer was separated, dried over MgSO₄, filtered and evaporated until dryness to give 2.4 g of Int. 180 (quant.).

e—Synthesis of Int. 181:

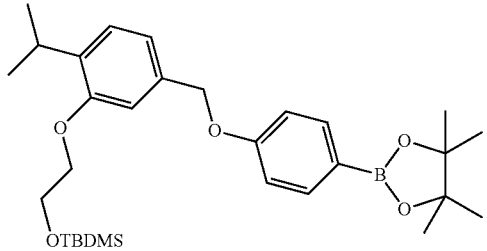 [SMILES: CC(C)c1ccc(COc2ccc(B3OC(C)(C)C(C)(C)O3)cc2)cc1OCCO[Si](C)(C)C(C)(C)C]

DBAD (0.7 g, 2.9 mmol) was added portionwise to 180 (640 mg, 2 mmol), 7 (520 mg, 2.4 mmol), PPh₃ supp. (0.9 g, 3 mmol) in THF (10 mL). The mixture was stirred at r.t. overnight. PPh₃ supp. was filtered and the filtrate was evaporated. The residue was purified by prep. LC on (Stability Silica 5 μm 150×30.0 mm, Mobile phase Gradient from 85% Heptane, 15% EtOAc to 100% EtOAc). The pure fractions were collected and the solvent was evaporated to give 260 mg of Int. 181 (25%).

f—Synthesis of Int. 182:

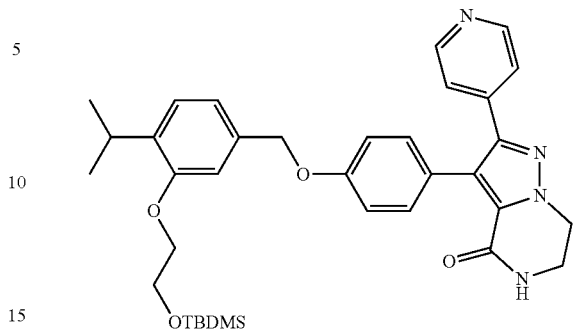

In a microwave vial, a mixture of 4 (768 mg, 2.6 mmol), 181 (1.15 g, 2.2 mmol), K₃PO₄ (1.4 g, 6.5 mmol) in 1,4-dioxane (10 mL) and H₂O (3 mL) was carefully purged with N₂. PdCl₂(dppf) (179 mg, 218 mmol) was added and the r.m. was purged again with N₂. The r.m. was heated at 80° C. overnight. The r.m. was diluted with EtOAc and washed with water (once) and with brine (3×). The organic phase was dried over MgSO₄, filtered on a pad of Celite® and evaporated in vacuo. The residue was purified by prep. LC (Stationary phase: irregular SiOH 15-40 μm 300 g Merck, mobile phase: 43% Heptane, 7% MeOH, 50% EtOAc). The pure fractions were collected and evaporated till dryness to give 640 mg of Int. 182 (48%).

g—Synthesis of Co. 89:

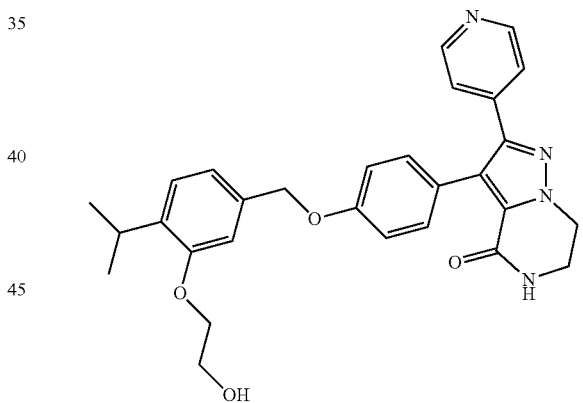

TBAF (0.45 mL, 0.45 mmol) was added dropwise to a sol. of 182 (230 mg, 0.375 mmol) in THF (5 mL) at r.t. The mixture was stirred 90 min at r.t. The mixture was poured into water, extracted with DCM. The organic layer was dried over MgSO₄, filtered and evaporated until dryness. The residue was purified by prep. LC (Regular SiOH, 30 μm, 25 g grace, mobile phase gradient: DCM/MeOH/NH₄OH from 97/3/0.1 to 94/6/0.1). The pure fractions were collected and solvent was evaporated until dryness to give 170 mg which was purified by achiral SFC on (Chiralpak IA 5 μm 250*20 mm, mobile phase: 50% CO₂, 50% MeOH). The pure fractions were collected and evaporated till dryness to give 105 mg. The product was crystallized from Et₂O. The solid was filtered off and dried to give 91 mg of Co. 89 (49%).

Example A91

Preparation of Co. 90 a—Synthesis of Int. 183:

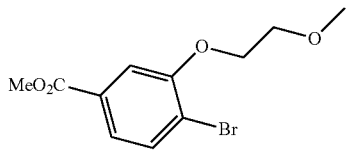 [SMILES: COCCOc1cc(C(=O)OC)ccc1Br]

Methyl 4-bromo-3-hydroxybenzoate (2 g, 8.6 mmol), 2-bromo ethyl methylether (0.9 mL, 9.5 mmol), K₂CO₃ (1.8 g, 13 mmol) in ACN (40 ml) at 80° C. overnight. Water and EtOAc were added, the mixture was extracted, the organic layer was separated, dried over MgSO₄, filtered and evaporated. The residue was purified by prep. LC on (Irregular SiOH 20-45 μm 450 g MATREX, Mobile phase: 85% heptane, 15% EtOAc). The pure fractions were collected and solvent was evaporated until dryness to give 2.1 g of Int. 183 (84%).

b—Synthesis of Int. 184:

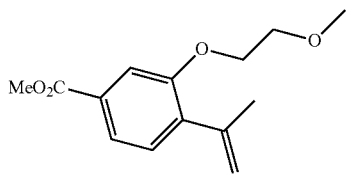

A solution of 183 (1.9 g, 6.6 mmol), CsF (2.2 g, 14.4 mmol), 2-isopropenyl-4,4,5,5-tetramethyl-1,3,2-dioxaborolane (1.2 g, 7.2 mmol), Pd(tBu₃P)₂ (168 mg, 0.3 mmol) in THF (30 mL) was refluxed overnight. Water and EtOAc were added, the mixture was filtered over Celite®, washed with EtOAc. The organic layer was separated, dried over MgSO₄, filtered and evaporated. The residue was purified by prep. LC on (Irregular SiOH 20-45 μm 40 g Grace, mobile phase: 85% heptane, 15% EtOAc). The pure fractions were collected and the solvent was evaporated until dryness to give 560 mg of Int. 184 (34%).

c—Synthesis of Int. 185:

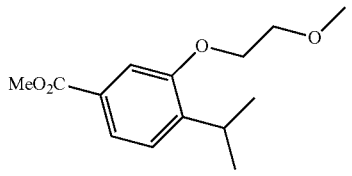 [SMILES: COCCOc1cc(C(=O)OC)ccc1C(C)C]

A solution of 184 (450 mg, 1.8 mmol), ammonium formate (658 mg, 10.8 mmol), 10% Pd/C (95 mg, 0.09 mmol) in THF (3 mL) and MeOH (10 mL) was refluxed for 30 min. The mixture (combined with another batch) was filtered through Celite®, washed with EtOAc, and the filtrate was concentrated until dryness to give 590 mg of Int. 185 (global yield 100%).

d—Synthesis of Int. 186:

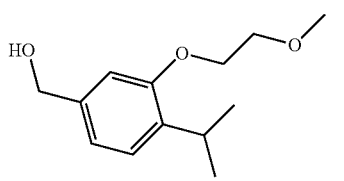 [SMILES: COCCOc1cc(CO)ccc1C(C)C]

LAH (106 mg, 2.8 mmol) was added carefully at 5° C. to a sol. of 185 (590 mg, 2.3 mmol) in THF (10 mL). The mixture was stirred at r.t. for 1 h. Water was carefully added at 5° C. and EtOAc was added, the mixture was extracted, the organic layer was separated, dried over MgSO₄, filtered and evaporated until dryness to give 450 mg of Int. 186 (86%).

e—Synthesis of Int. 187:

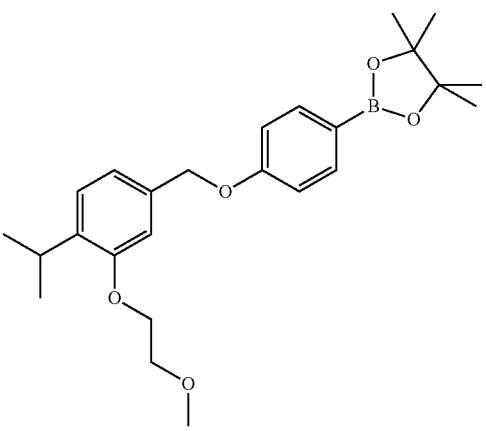 [SMILES: COCCOc1cc(COc2ccc(B3OC(C)(C)C(C)(C)O3)cc2)ccc1C(C)C]

DBAD (692 mg, 3 mmol) was added portionwise to 186 (450 mg, 2 mmol), 7 (529 mg, 2.4 mmol), PPh₃ supp. (0.94 g, 3 mmol) in THF (10 mL). The mixture was stirred at r.t. overnight. PPh₃ supp. was filtered and the filtrate was evaporated. The residue was purified by prep. LC on (Stability Silica 5 μm 150×30.0 mm, mobile phase gradient: from 85% heptane, 15% EtOAc to 100% EtOAc). The pure fractions were collected and solvent was evaporated until dryness to give 350 mg of a first residue and 300 mg of second residue. The last residue was purified by prep. LC on (Stability Silica 5 μm 150×30.0 mm, mobile phase Gradient: from 85% heptane, 15% EtOAc to 100% EtOAc). The pure fractions were collected and solvent was evaporated to give 160 mg of Int. 187. Both fractions (350 mg and 160 mg) were put together to give 510 mg of Int. 187 (60%).

f—Synthesis of Co. 90:

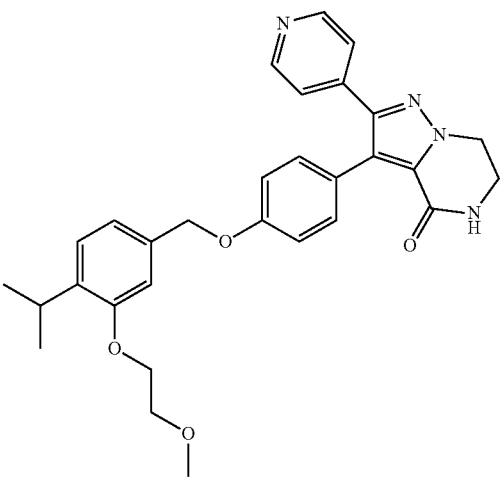 [SMILES: COCCOc1cc(COc2ccc(-c3c(-c4ccncc4)nn4c3C(=O)NCC4)cc2)ccc1C(C)C]

A mixture of 4 (265 mg, 0.9 mmol), 187 (0.35 g, 0.82 mmol), K₃PO₄ (0.7 g, 3.3 mmol) in 1,4-dioxane (5 mL) and H₂O (1.2 mL) was carefully purged with N₂. PCy₃ (48 mg, 0.17 mmol) and Pd(OAc)₂ (19 mg, 0.09 mmol) were added and the r.m. was purged again with N₂. The r.m. was stirred for 8 h at 80° C. in a sealed tube. Water and DCM were added, the mixture was extracted, the organic layer was separated, dried over MgSO₄, filtered and evaporated until dryness to give 530 mg. The residue was purified by prep. LC on (irregular 15-40 µm 30 g Merck, mobile phase: 0.1% NH₄OH, 98% DCM, 2% MeOH). The pure fractions were collected and the solvent evaporated until dryness to give 130 mg which was taken up in Et₂O. The solid was filtered off and dried to give 90 mg of Co. 90 (21%). m.p.: 209° C. (dsc).

Example A92

Preparation of Co. 91

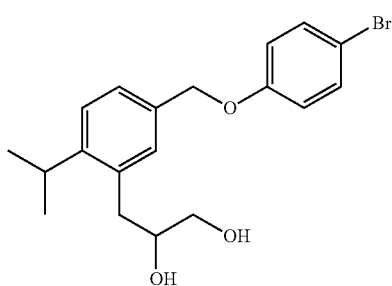 [SMILES: CC(C)c1ccc(COc2ccc(Br)cc2)cc1CC(O)CO]

a—Synthesis of Int. 188:

Under N₂ atmosphere, to a sol. of 54 (0.75 g, 2.2 mmol) in acetone (16 mL) and H₂O (2 mL), was successively added 4-methylmorpholine-4-oxide (305 mg, 2.6 mmol) and OsO₄ 2.5% in butanol (1.5 mL, 0.11 mmol). The mixture was stirred at r.t. overnight. An aq. sol. of Na₂SO₃ sol. (7.5 mL, 10%) was added to the r.m. and the mixture was stirred for 30 min at r.t. Then, the solvent was evaporated in vacuo and the residue was extracted with EtOAc (30 mL). The extract was washed with brine (3×10 mL) and the organic layer, after drying over MgSO₄ and filtration, was evaporated until dryness to give 1 g, brown oil. This oil and another batch were purified by prep. LC (irregular SiOH 30 µm, 25 g, Interchim, Mobile phase: heptane/EtOAc 60/40). The pure fractions were collected and solvent was evaporated until dryness to give 820 mg of Int. 188, white solid (global yield: 88%).

b—Synthesis of Int. 189: TMS

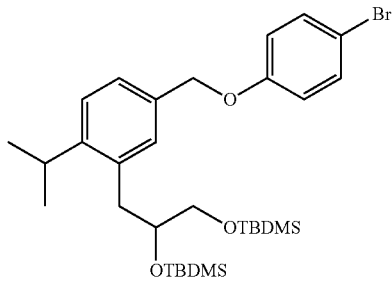 [SMILES: CC(C)c1ccc(COc2ccc(Br)cc2)cc1CC(CO[Si](C)(C)C(C)(C)C)O[Si](C)(C)C(C)(C)C]

Under N₂, tert-butyldimethylsilyl chloride (0.97 g, 6.4 mmol) was added to a sol. of 188 (0.82 g, 2.1 mmol) and imidazole (0.87 g, 13 mmol) in dry DCM (21 mL) at r.t. The mixture was stirred at r.t. for 1 h. The mixture was quenched with water and extracted with DCM. The organic layer was decanted, washed with water then brine, dried over MgSO₄, filtered and evaporated to dryness to give 1.29 g of Int. 189, colorless oil (99%).

c—Synthesis of Int. 190:

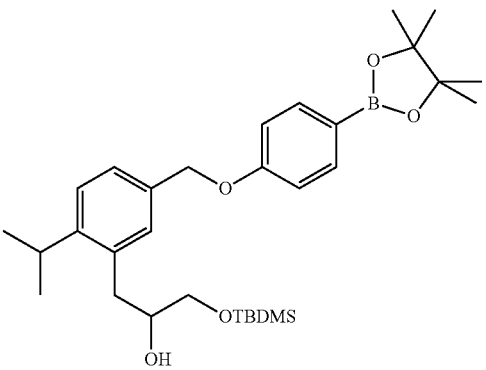 [SMILES: CC(C)c1ccc(COc2ccc(B3OC(C)(C)C(C)(C)O3)cc2)cc1CC(O)CO[Si](C)(C)C(C)(C)C]

In a microwave vial, a mixture of 189 (1.3 g, 2.1 mmol), KOAc (0.63 g, 6.4 mmol), BisPin (0.82 g, 3.2 mmol) in DME (6.2 mL) was carefully purged with N₂. PdCl₂(dppf) (0.18 g, 0.21 mmol) was added and the r.m. was purged again with N₂. The r.m. was stirred overnight at 100° C. The r.m. was diluted with EtOAc and washed with water (once) and with brine (3 times). The organic layer was dried over MgSO₄, filtered on a pad of Celite® and evaporated in vacuo to give a brown oil. This oil was purified by prep. LC (irregular SiOH 15-40 µm, 40 g, Interchim, Mobile phase gradient: Heptane/EtOAc, from 95/5 to 90/10). The pure fractions were collected and solvent was evaporated until dryness to give 0.6 g of Int. 1902 colorless oil (52%).

d—Synthesis of Int. 191:

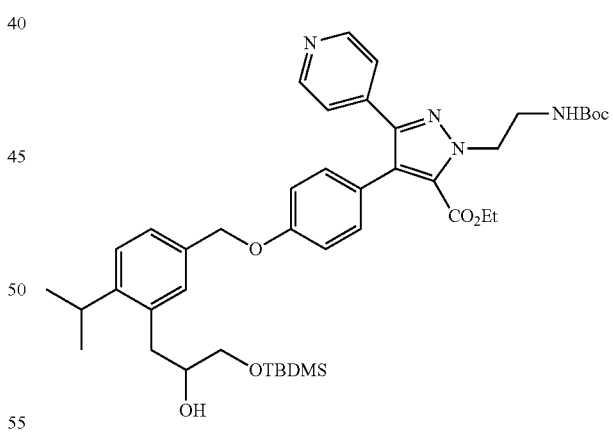

In a microwave vial, a mixture of 3 (0.41 g, 0.93 mmol), 190 (0.60 g, 1.1 mmol), K₃PO₄ (0.59 g, 2.8 mmol) in 1,4-dioxane (4.1 mL) and H₂O (1.5 mL) was carefully purged with N₂. PdCl₂(dppf) (75 mg, 92 µmol) was added and the r.m. was purged again with N₂. The r.m. was heated at 80° C. for 3 days. The r.m. was diluted with EtOAc and washed with water (once) and with brine (3 times). The organic phase was dried over MgSO₄, filtered on a pad of Celite® and evaporated in vacuo to give 1.2 g, brown oil. This oil was purified by prep. LC (irregular SiOH 30 µm, 25 g, Interchim, Mobile phase gradient: heptane/EtOAc from 60/40 to 45/55). The pure fractions were collected and solvent was evaporated until dryness to give 0.5 g of Int. 191, colorless oil (70%).

e—Synthesis of Int. 192:

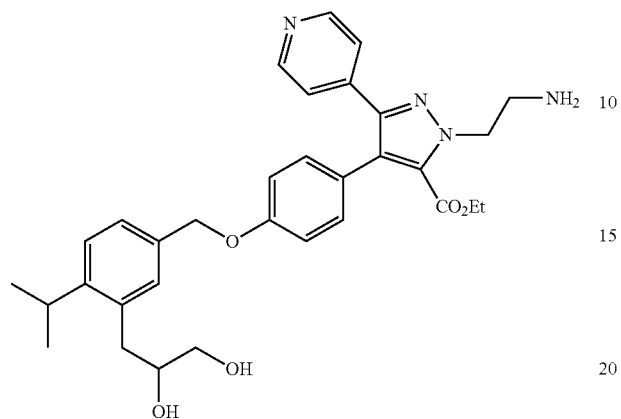

A solution of 191 (0.50 g, 0.65 mmol), HCl 3N (1.1 mL, 3.2 mmol), in ACN (11 mL) was stirred at 80° C. for 2 h. The mixture was concentrated, and NaHCO₃ sat. aq. (25 mL) was added and the mixture was extracted with DCM, dried and evaporated until dryness to give 0.36 g of Int. 191 (quant.). This residue was used like this in the next step.

f—Synthesis of Co. 91:

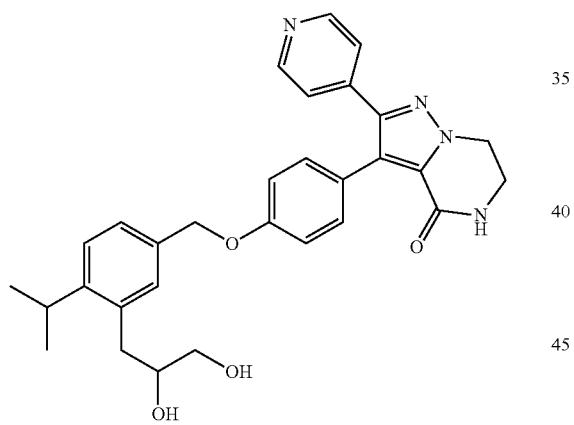

To a sol. of 192 (360 mg, 0.64 mmol) in MeOH (18 mL) was added Cs₂CO₃ (1.1 g, 3.2 mmol) and the mixture was stirred at r.t. overnight. The mixture was concentrated and taken in DCM and washed once with brine, dried of MgSO₄ and concentrated till dryness to give 520 mg, white solid. The crude product was purified by prep. LC (irregular SiOH 30 μm, 12 g graceResolv™, mobile phase gradient from DCM/MeOH/NH₄OH 97:3:0.1 to 95/5/0.1). The pure fractions were collected and solvent was evaporated until dryness to give 190 mg of white solid which was purified by prep. LC (Stationary phase: Stability Silica 5 μm 150×30.0 mm, mobile phase gradient: from 47% EtOAc, 3% MeOH (+0.2% NH₄OH), 50% Heptane to 75% EtOAc, 25% MeOH (+0.2% NH₄OH)). The pure fractions were collected and solvent was evaporated until dryness to give 130 mg. This residue was purified by achiral SFC (Stationary phase: Diethylaminopropyl 5 μm 150×21.2 mm, mobile phase: CO₂, MeOH (0.3% iPrNH₂)) followed by prep. LC (Stationary phase: irregular 15-401 μm 30 g Merck, mobile phase: 0.5% NH₄OH, 95% DCM, 5% MeOH). 108 mg of white solid was collected and it was washed with Et₂O. The white solid was filtered and dried to give 90 mg of Co. 91 (27%).

Example A93

Preparation of Co. 92 a—Synthesis of Int. 193:

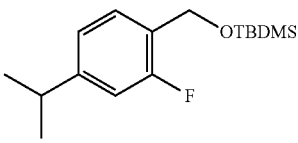 [SMILES: CC(C)c1ccc(CO[Si](C)(C)C(C)(C)C)c(F)c1]

Under N₂, a sol. of [(4-bromo-2-fluorobenzyl)oxy](tert-butyl)dimethylsilane (6.0 g, 18.8 mmol) in dry THF (50 mL) was treated with isopropylmagnesium chloride 2M in THF (47.0 mL, 94.0 mmol) at r.t. The r.m. was then purged with N₂ and PdCl₂(dppf) (1.54 g, 1.88 mmol) was added. The r.m. was purged again with N₂ and stirred at 50° C. for 5 h. After being quenched with water, the r.m. was diluted with Et₂O, washed with water (1×) and brine (2×). The organic layer was dried over MgSO₄ and evaporated in vacuo to afford a brown residue. The residue was supported on silica gel and purified through a short pad of silica (mobile phase: heptane 90%, Et₂O 10%). The filtrate was collected and evaporated in vacuo to give 5.0 g of Int. 193, yellow oil (94%).

b—Synthesis of Int. 194:

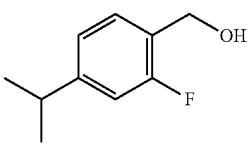

A sol. of 193 (5.0 g, 17.7 mmol) in THF (150 mL) was cooled to 0° C. and treated with TBAF (21.2 mL, 21.2 mmol). The r.m. was stirred for 90 min at 0° C., concentrated and poured in Et₂O. The organic layer was washed with water (3×50 mL), dried over MgSO₄ and evaporated in vacuo to afford a yellow oil (3.3 g) which was purified by prep. LC (irregular SiOH 15-40 μm, 80 g GraceResolv™, Mobile phase gradient: from heptane 100% to heptane 50%, EtOAc 50%). The pure fractions were collected and solvent evaporated to give 2.18 g Int. 194 (colorless oil; 73%).

c—Synthesis of Int. 195: PP-0

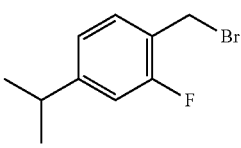

To a sol. of 194 (1.12 g, 6.66 mmol) in dry Et₂O (19 mL) at 0° C. was added dropwise Phosphorus tribromide (0.626 mL, 6.66 mmol). The ice bath was removed and the reaction stirred for 3 h. Then, water was carefully added to the mixture, and the layers were separated. The organic layer was washed with brine, dried over MgSO₄, filtered off and evaporated in vacuo to afford 1.49 g of Int. 195 colorless liquid (97%).

d—Synthesis of Int. 196:

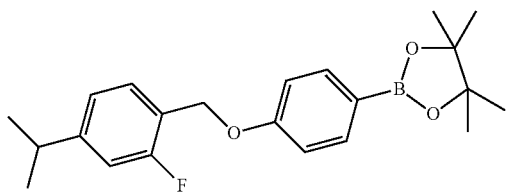 [SMILES: CC(C)c1ccc(COc2ccc(B3OC(C)(C)C(C)(C)O3)cc2)c(F)c1]

A sol. of 195 (1.49 g, 5.87 mmol) in ACN (15 mL) was treated with K₂CO₃ (1.10 g, 7.98 mmol) and 7 (1.17 g, 5.32 mmol) at r.t. The r.m. was stirred for 20 h at r.t. DMF (11 mL) was added and the r.m. was stirred at r.t. for 90 h. Water and EtOAc were added, and the organic layer was washed with brine, separated, dried over MgSO₄, filtered and concentrated in vacuo to afford 2.07 g, pale oil. This oil was purified by prep. LC (Irregular SiOH 50 μm, 80 g Grace, mobile phase gradient: from Heptane 100% to EtOAC 10%, Heptane 90%). The fractions were collected and evaporated in vacuo to give 360 mg of Int. 196 colorless oil which crystallized in a solid (68%).

e—Synthesis of Int. 197:

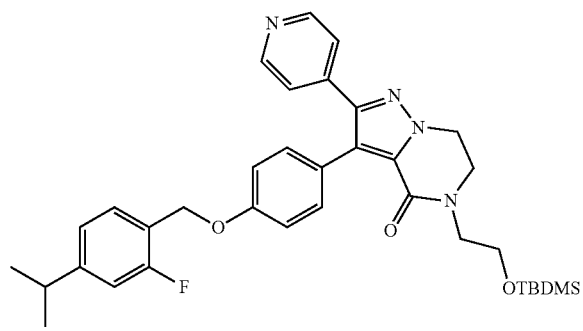 [SMILES: CC(C)c1ccc(COc2ccc(-c3c(-c4ccncc4)nn4c3C(=O)N(CCO[Si](C)(C)C(C)(C)C)CC4)cc2)c(F)c1]

PdCl₂(dppf) (0.141 g, 0.172 mmol) was added to a stirred sol. of 28 (0.778 g, 1.72 mmol), 196 (1.33 g, 3.45 mmol) and K₃PO₄ (1.10 g, 5.17 mmol) in 1,4-dioxane (10.6 mL) and H₂O (5.3 mL) at r.t., under N₂. The resulting mixture was stirred at 120° C. using one single mode microwave (Biotage Initiator EXP 60) with a power output ranging from 0 to 400 W for 30 min. [fixed hold time]. The crude material was diluted with DCM and water, and the organic layer was washed with brine, dried over MgSO₄, filtered and evaporated in vacuo to give 2.4 g, dark oil. This oil was purified by prep. LC (Irregular SiOH 50 μm, 80 g Grace, mobile phase gradient: from DCM 100% to EtOAc 60%, DCM 40%). The fractions were collected and evaporated in vacuo to give 1.03 g of Int. 197, pale yellow oil (89%).

f—Synthesis of Co. 92:

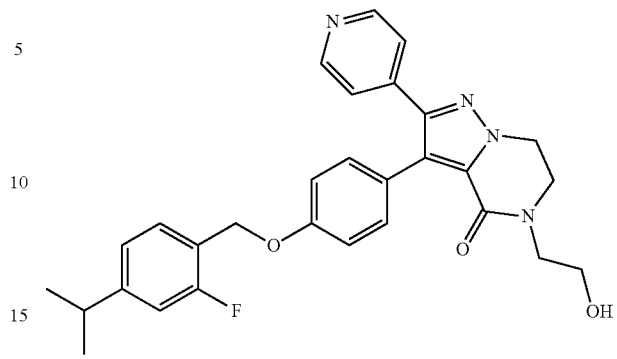

TBAF (1.85 mL, 1.85 mmol) was added to a stirred sol. of 197 (1.03 g, 1.54 mmol) in THF (12 mL) at 0° C., and the r.m. was stirred at 0° C. for 90 min. The crude mixture was diluted with brine and EtOAc. The organic layer was dried over MgSO₄, filtered and evaporated in vacuo to afford 790 mg of a sticky solid. This solid was purified by prep. LC (Irregular SiOH 50 μm, 80 g Grace, mobile phase gradient: from DCM 100% to DCM 92%, MeOH 8%). The fractions were collected and evaporated in vacuo to give 735 mg of colorless sticky oil. This oil was triturated with pentane, and the solvent was removed in vacuo to yield 640 mg of white amorphous solid. So it was crystallized from MeOH, and the solvent was evaporated in vacuo to yield 560 mg of white solid. This solid was purified by prep. LC (Irregular SiOH 50 μm, 80 g Grace, mobile phase gradient: from DCM 100% to DCM 95%, MeOH 5%). The fractions were collected and evaporated in vacuo to give 555 mg, white solid. The residue was purified by achiral SFC (Stationary phase: Chiralpak AD-H 5 μm 250×20 mm, mobile phase: 70% CO₂, 30% mixture of MeOH/iPrOH 50/50 v/v). The pure fractions were collected and solvent evaporated until dryness to give a colorless oil which was crystallized from ACN, filtered and dried to give 331 mg of Co. 92, white solid (43%). m.p.: 132° C. (dsc).

Example A94

Preparation of Co. 93 a—Synthesis of Int. 198:

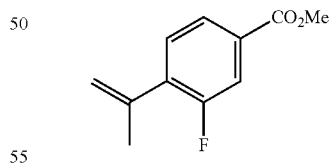

A sol. of methyl 4-bromo-3-fluorobenzoate (=4-Bromo-3-fluorobenzoic acid methyl ester) (1.22 g, 5.24 mmol) and potassium isopropenyltrifluoroborate (1.60 g, 10.5 mmol) in isopropanol (14 mL) was treated with Et₃N (2.92 mL, 21.0 mmol) and purged with N₂. PdCl₂(dppf) (215 mg, 262 μmol) was then added and the r.m. was carefully purged with N₂. The mixture was heated at 120° C. using one single mode microwave (Biotage Initiator EXP 60) with a power output ranging from 0 to 400 W for 30 min [fixed hold time]. The crude mixtures were combined and diluted with EtOAc and washed with water and brine. The organic layer was dried over MgSO₄ and evaporated to afford 4.53 g of Int. 198, brown oil (quant. but impurities), used as such for the next step.

b—Synthesis of Int. 199:

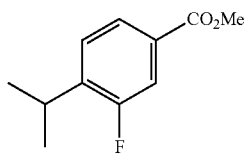

A catalytic amount of Pd/C 10% (600 mg, 564 µmol) was added into a sol. of 198 (4.53 g, 23.3 mmol) in EtOH (50 mL). The r.m. was hydrogenated (7 bars) for 3 h at r.t. The sol. was filtered through a short pad of Celite® and evaporated to afford a red residue. The residue was filtered through a pad of silica gel (mobile phase: Et₂O). The filtrate was evaporated until dryness to afford 2.79 g of Int. 199, yellow oil (61%).

c—Synthesis of Int. 200:

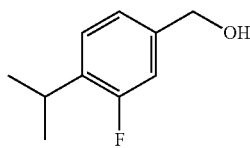

A sol. of 199 (2.69 g, 13.1 mmol) in Et₂O (50 mL) was cooled to 0° C. and treated with LAH (1.04 g, 27.4 mmol). The r.m. was stirred at 0° C. for 90 min. then quenched with water (1.0 mL), a 3N sol. of NaOH (1.0 mL) and water (3 mL). The sol. was filtered on a glass frit and the filtrate was evaporated. The yellow oil was purified by prep. LC (irregular SiOH 15-40 µm, 40 g Merck, Mobile phase gradient: from heptane 80%, EtOAc 20% to heptane 70%, EtOAc 30%). The pure fractions were collected and solvent evaporated to give 1.25 g of Int. 200, colorless oil (52%).

d—Synthesis of Int. 201:

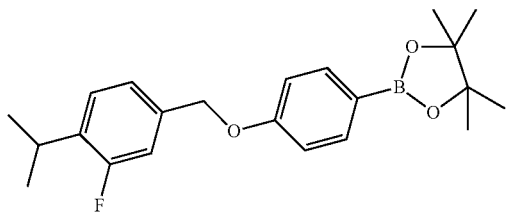 [SMILES: CC(C)c1ccc(COc2ccc(B3OC(C)(C)C(C)(C)O3)cc2)cc1F]

A sol. of 7 (1.36 g, 6.19 mmol) and 200 (1.25 g, 7.43 mmol) in dry THF (20 mL) was treated with PPh₃ (1.95 g, 7.43 mmol) and DBAD (1.71 g, 7.43 mmol). The r.m. was stirred at r.t. for 17 h then concentrated in vacuo. The concentrate was poured in EtOAc, washed with water, dried over MgSO₄ and evaporated in vacuo to give an oil. The oil was purified prep. LC (irregular SiOH 15-40 µm, 45 g, Merck, dry loading, mobile phase gradient: from heptane 90%, EtOAc 10% to heptane 70%, EtOAc 30%). The pure fractions were collected and solvent evaporated until dryness to give 2.25 g of Int. 201, white solid (98%).

e—Synthesis of Int. 202:

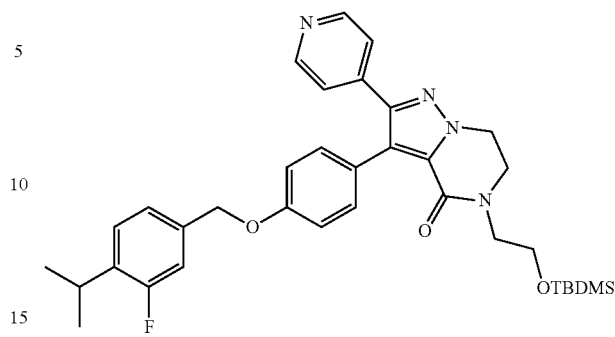

A sol. of 21 (1.20 g, 2.66 mmol) and 201 (1.97 g, 5.32 mmol) in 1,4-dioxane (12 mL) and H₂O (6 mL) was treated with K₃PO₄ (1.69 g, 7.98 mmol) and purged with N₂. PdCl₂(dppf) (218 mg, 266 µmol) was then added and the r.m. was carefully purged with N₂. The mixture was heated at 120° C. using one single mode microwave (Biotage Initiator EXP 60) with a power output ranging from 0 to 400 W for 30 min [fixed hold time]. The crude mixture was poured in DCM and water. The organic layer was separated, dried over MgSO₄ and evaporated in vacuo to give a black residue. The residue was purified by prep. LC (Irregular SiOH 50 µm, 80 g Grace, mobile phase gradient: from DCM 100% to DCM 94%, MeOH 6%). The pure fractions were collected and solvent evaporated until dryness to give 1.53 g of Int. 202, white solid (94%).

f—Synthesis of Co. 93:

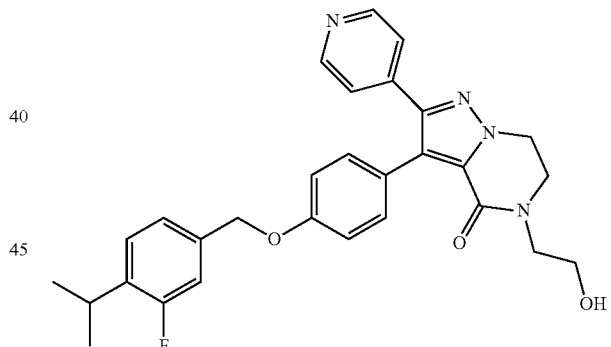

TBAF (2.51 mL, 2.51 mmol) was added to a stirred sol. of 202 (1.53 g, 2.49 mmol) in THF (25 mL) at 0° C., and the r.m. was stirred at 0° C. for 90 min. The crude mixture was diluted with water and a sol. of DCM/MeOH (95:5). The organic layer was washed with brine, dried over MgSO₄, filtered and evaporated in vacuo to afford 1.52 g. The residue was purified by prep. LC (Irregular SiOH 50 µm, 80 g Grace, mobile phase gradient: from DCM 100% to DCM 92%, MeOH 8%). The desired fractions were collected and evaporated in vacuo to give 572 mg, sticky oil which was crystallized from EtOH, filtered and dried to give 224 mg, white solid. The filtrate and the solid were combined and evaporated in vacuo to give 417 mg of a residue. This residue was purified by achiral SFC (Stationary phase: Chiralpak IA 5 µm 250*20 mm, mobile phase: 70% CO₂, 30% mixture of MeOH/iPrOH 50/50 v/v). The pure fractions were collected and solvent evaporated until dryness to give 267 mg which was crystallized from EtOH, filtered and dried to give 256 mg of Co. 93, white solid (45%). m.p.: 183° C. (dsc).

Example A95

Preparation of Co. 94 a—Synthesis of Int. 203:

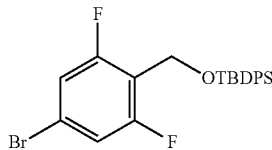

Tert-butyldiphenylchlorosilane (4.3 mL, 17 mmol) was added to a sol. of 4-bromo-2,6-difluorobenzyl alcohol (2.5 g, 11 mmol) and imidazole (2.3 g, 33 mmol) in DCM (106 mL) at r.t. The mixture was stirred at r.t. overnight. The mixture was quenched with water and extracted with DCM. The organic layer was decanted, washed with water then brine, dried over MgSO₄, filtered and evaporated to dryness to give 7.5 g, colorless oil. This oil was purified by prep. LC (irregular SiOH 30 μm 120 g GraceResolv™, mobile phase gradient: heptane/EtOAc from 95/15 to 85/15/0.1). The desired fractions were collected and solvent evaporated to give 6.2 g of Int. 203, colorless oil used as such as for the next step.

b—Synthesis of Int. 204:

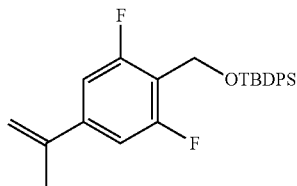

In a microwave vial, a mixture of 203 (2.0 g, 4.3 mmol), CsF (1.5 g, 9.5 mmol) and 2-isopropenyl-4,4,5,5-tetramethyl-1,3,2-dioxaborolane (0.9 mL, 4.8 mmol) in dry THF (40 mL) was purged with N₂. Pd(tBu₃P)₂ (111 mg, 0.22 mmol) was added and the mixture was purged again with N₂ and heated at 80° C. overnight. Water and EtOAc were added, the organic layer was separated, washed with brine, dried over MgSO₄, filtered on Celite® and evaporated. The residue was purified by prep. LC (Regular SiOH, 30 μm, 80 g GraceResolv™, mobile phase: Heptane/EtOAc 95/5). The pure fractions were collected and solvent evaporated to give 1.8 g of Int. 204, yellow oil (98%).

c—Synthesis of Int. 205:

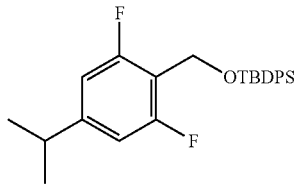

A solution of 204 (1.8 g, 4.3 mmol), ammonium formate (1.6 g, 26 mmol), Pd/C 10% (226 mg, 0.21 mmol) in THF (7 mL) and MeOH (22 mL) was refluxed for 30 min. The mixture was filtered through Celite®, washed with EtOAc, and the filtrate was concentrated. The residue was partitioned between water and EtOAc. The organic layer was separated, dried over MgSO₄, filtered and evaporated until dryness to give 1.7 g of Int. 205, colorless oil (94%).

d—Synthesis of Int. 206:

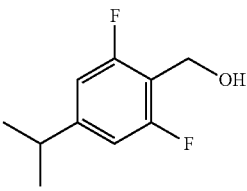

TBAF (4.8 mL, 4.8 mmol) was added dropwise to a sol. of 205 (1.7 g, 4.0 mmol) in THF (39 mL) at r.t. The mixture was stirred for 10 h at r.t. The mixture was concentrated and the residue was purified by prep. LC (Regular SiOH, 30 μm, 40 g GraceResolv™, mobile phase: Heptane/EtOAc 80/20). The pure fractions were collected and solvent evaporated until dryness to give 1.2 g of crude Int. 206, used like this in the next step.

e—Synthesis of Int. 207:

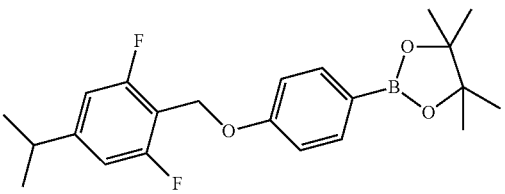 [SMILES: CC(C)c1cc(F)c(COc2ccc(B3OC(C)(C)C(C)(C)O3)cc2)c(F)c1]

Under N₂, DBAD (1.4 g, 6.2 mmol) was added portionwise to a sol. of 206 (1.2 g, 5.1 mmol), 7 (1.4 g, 6.2 mmol), PPh₃ supp. (1.9 g, 6.2 mmol) in dry THF (30 mL). The r.m. was stirred at r.t. for 3 days. PPh₃ supp. was filtered and the filtrate was evaporated to give 5.0 g, yellow oil. The crude residue was purified by prep. LC (irregular SiOH 30 μm 80 g GraceResolv™, mobile phase: heptane/EtOAc 90/10). The pure fractions were collected and the solvent evaporated until dryness to give 1.45 g of Int. 207, yellow solid (72%).

f—Synthesis of Int. 208:

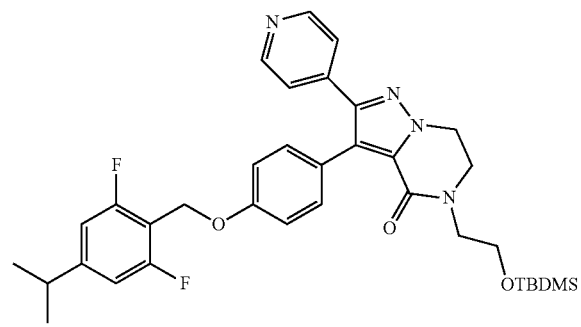 [SMILES: CC(C)c1cc(F)c(COc2ccc(-c3c(-c4ccncc4)nn4c3C(=O)N(CCO[Si](C)(C)C(C)(C)C)CC4)cc2)c(F)c1]

In a microwave vial, a mixture of 28 (0.48 g, 1.1 mmol), 207 (0.5 g, 1.3 mmol), K₃PO₄ (0.91 g, 4.3 mmol) in 1,4-dioxane (4.7 mL) and H₂O (1.7 mL) was carefully purged with N₂. PdCl₂(dppf) (88 mg, 0.11 mmol) was added and the r.m. was purged again with N₂. The r.m. was heated at 80° C. overnight. The r.m. was diluted with EtOAc and washed with water (once) and with brine (3×). The organic phase was dried over MgSO₄, filtered on a pad of Celite® and evaporated in vacuo to give 1 g, brown oil. This oil was purified by prep. LC (irregular SiOH 30 µm, 25 g Interchim, mobile phase gradient: DCM/MeOH/NH₄OH from 100/0/0 to 98/2/0.1). The pure fractions were collected and solvent evaporated until dryness to give 0.44 g of Int. 208, yellow oil used like this in the next step.

g—Synthesis of Co. 94:

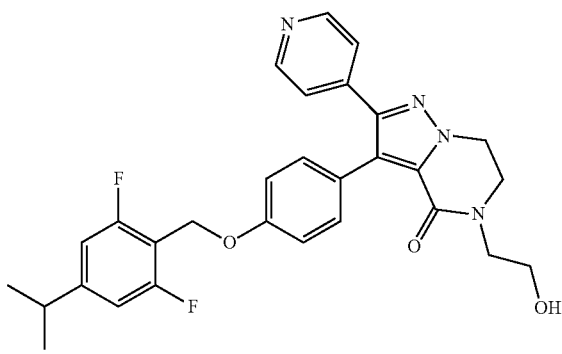 [SMILES: CC(C)c1cc(F)c(COc2ccc(-c3c(-c4ccncc4)nn4c3C(=O)N(CCO)CC4)cc2)c(F)c1]

TBAF (0.84 mL, 0.84 mmol) was added dropwise to a sol. of 208 (0.44 g, 0.69 mmol) in THF (7 mL) at r.t. The mixture was stirred overnight at r.t. The mixture was concentrated. The residue was purified by prep. LC (Regular SiOH, 30 µm, 12 g GraceResolv™, mobile phase: DCM/MeOH/NH₄OH 97/3/0.1). The pure fractions were collected and solvent evaporated until dryness to give 210 mg which was triturated in Et₂O. The white solid was filtrated, washed and dried to give 145 mg of Co. 94, white solid (40%). m.p.: 194° C. (dsc).

Example A96

Preparation of Co. 95a and Co. 95 a—Synthesis of Int. 209:

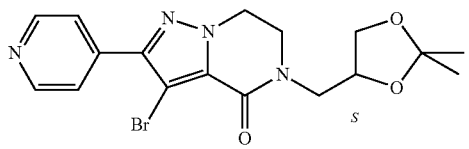

NaH 60% (2.5 g, 61.4 mmol) was added to 4 (12 g, 41 mmol) in DMSO (120 mL) at r.t. under N₂. The mixture stirred for 2 h then (R)-(−)-2,2-dimethyl-1,3-dioxolane-4-ylmethyl p-toluenesulfonate (14 g; 49.1 mmol) was added portionwise and the r.m. was stirred for 15 h. The mixture was poured into water and K₂CO₃ and extracted with EtOAc. The organic layer was evaporated until dryness. The residue was taken up with DCM and water. The organic layer was extracted, dried over MgSO₄, filtered and evaporated to give 15 g. The residue was purified by prep. LC (120 g of irregular SiOH 35-40 µm GraceResolv™, mobile phase gradient: from 100% DCM to 95% DCM 5% CH₃OH 0.1% NH₄OH). The fractions were collected and evaporated to give 8 g of Int. 209 (S) (48%).

b—Synthesis of Co. 95a:

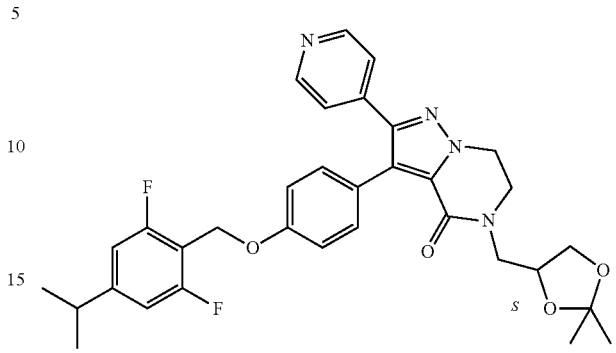

In a microwave vial, a mixture of 209 (0.44 g, 1.1 mmol), 207 (0.5 g, 1.3 mmol), K₃PO₄ (0.91 g, 4.3 mmol) in 1,4-dioxane (4.7 mL) and H₂O (1.7 mL) was carefully purged with N₂. PdCl₂(dppf) (88 mg, 0.11 mmol) was added and the r.m. was purged again with N₂. The r.m. was heated at 80° C. overnight. The r.m. was diluted with EtOAc and washed with water (once) and with brine (3 times). The organic phase was dried over MgSO₄, filtered on a pad of Celite® and evaporated in vacuo to give 0.85 g, brown oil. This oil was purified by prep. LC (irregular SiOH 30 µm, 25 g Interchim, mobile phase gradient: DCM/MeOH/NH₄OH from 100/0/0 to 98/2/0.1). The fractions were collected and evaporated until dryness to give 0.3 g of Co. 95a (S), yellow oil (47%).

c—Synthesis of Co. 95: OH

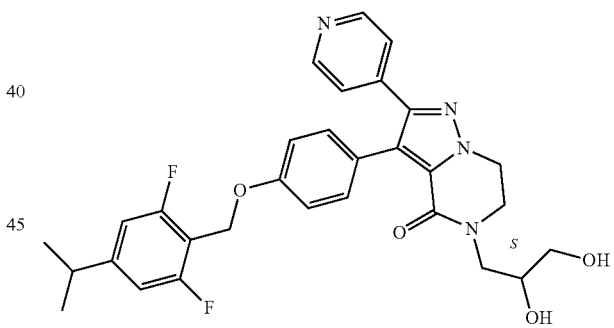

A sol. of Co. 95a (0.3 g, 0.51 mmol) and HCl 3N (0.85 mL, 2.5 mmol) in 1,4-dioxane (11 mL) were heated to reflux for 1 h. The mixture was cooled to r.t., poured into sat. NaHCO₃ and extracted with DCM. The organic layer was dried over MgSO₄, filtered and evaporated until dryness. The residue was purified by prep. LC (irregular SiOH 15-40 µm, 4 g, GraceResolv™, Mobile phase gradient: DCM/MeOH/NH₄OH, from 97/3/0.1 to 95/5/0.1). The desired fractions were collected and evaporated until dryness to give 141 mg. The residue was purified again, by prep. LC (Stationary phase: irregular SiOH 15-40 µm 300 g Merck, Mobile phase: 40% Heptane, 10% MeOH, 50% EtOAc). The pure fractions were collected and the solvent evaporated to give 103 mg of white solid. The solid was triturated in Et₂O, filtrated and dried to give 99 mg of Co. 95 (S), white powder (35%). m.p.: 227° C. (dsc); [α]$_d$: −18.24° (589 nm, c 0.34 w/v %, DMF, 20° C.)

Example A97

Preparation of Co. 96a and Co. 96 a—Synthesis of Int. 211:

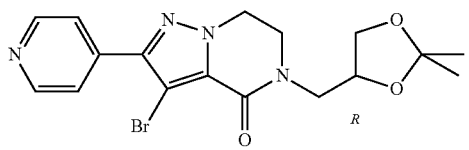

NaH 60% (1.64 g, 41 mmol) was added to 4 (8 g, 27.3 mmol) in DMSO (80 mL) at r.t. under $N_2$. The mixture was stirred for 2 h then (S)-(−)-2,2-dimethyl-1,3-dioxolane-4-ylmethyl P-toluenesulfonate (9.4 g, 32.7 mmol) was added portionwise and the r.m. was stirred for 15 h. The mixture was poured into water and $K_2CO_3$ and extracted with EtOAc. The organic layer was evaporated until dryness. The residue was taken up with DCM and water. The organic layer was separated, dried over $MgSO_4$, filtered and evaporated until dryness to give 10.75 g. The residue was purified by prep. LC (120 g of irregular SiOH 35-40 μm GraceResolv™, mobile phase gradient: from 100% DCM to 95% DCM 5% $CH_3OH$ 0.1% $NH_4OH$). The fractions were collected and evaporated until dryness to give 5.55 g of Int. 211 (R) (50%).

b—Synthesis of Co. 96a:

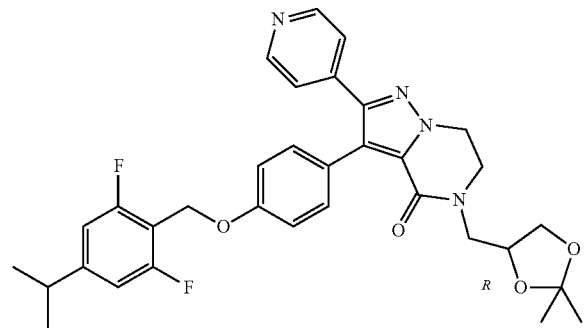

In a microwave vial, a mixture of 211 (0.41 g, 1.0 mmol), 207 (0.47 g, 1.2 mmol), $K_3PO_4$ (0.86 g, 4.0 mmol) in 1,4-dioxane (4.4 mL) and $H_2O$ (1.6 mL) was carefully purged with $N_2$. $PdCl_2(dppf)$ (83 mg, 0.10 mmol) was added and the r.m. was purged again with $N_2$. The r.m. was heated at 80° C. overnight. The r.m. was diluted with EtOAc and washed with water (once) and with brine (3 times). The organic layer was dried over $MgSO_4$, filtered on a pad of Celite® and evaporated in vacuo to give 1.1 g, brown oil. The mixture was purified by prep. LC (irregular SiOH 30 μm, 25 g Interchim, mobile phase: DCM/MeOH/$NH_4OH$ 98/2/0.1). The fractions were collected and evaporated until dryness to give 0.2 g of Co. 96a (R), colorless oil.

c—Synthesis of Co. 96:

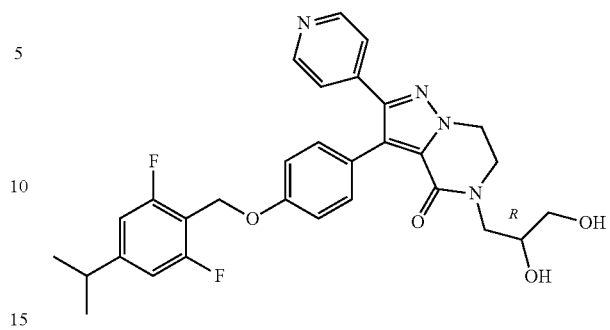

A sol. of Co. 96a (0.2 g, 0.34 mmol) and HCl 3N (0.57 mL, 1.7 mmol) in 1,4-dioxane (7.5 mL) were heated to reflux for 1 h. The mixture was cooled to r.t., poured into sat. $NaHCO_3$ and extracted with DCM. The organic layer was dried over $MgSO_4$, filtrated and evaporated until dryness to give 190 mg, colorless oil. This oil was purified by prep. LC (Stationary phase: Sunfire Silica 5 μm 150×30.0 mm, Mobile phase Gradient: from 0.2% $NH_4OH$, 98% DCM, 2% MeOH to 1% $NH_4OH$, 90% DCM, 10% MeOH). The pure fractions were collected and solvent evaporated until dryness to give 63 mg of white solid. This solid was triturated in $Et_2O$, filtrated and dried to give 50 mg of Co. 96 (R), white solid (27%). m.p.: 228° C. (dsc); $[\alpha]_d$: +17.22° (589 nm, c 0.302 w/v %, DMF, 20° C.)

Example A98

Preparation of Co. 97 a—Synthesis of Int. 213:

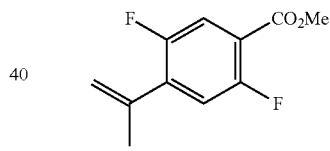

In a microwave vial, a mixture of methyl 4-bromo-2,5-difluorobenzoate (1.5 g, 6.0 mmol), CsF (2.0 g, 13 mmol) and 2-isopropenyl-4,4,5,5-tetramethyl-1,3,2-dioxaborolane (1.2 mL, 6.6 mmol) in dry THF (60 mL) was purged with $N_2$. $Pd(tBu_3P)_2$ (153 mg, 0.30 mmol) was added and the mixture was purged again with $N_2$ and heated at 80° C. overnight. Water and EtOAc were added, the organic layer was separated, washed with brine, dried on $MgSO_4$, filtered over Celite® and evaporated to give 2 g. The residue was purified by prep. LC (Regular SiOH, 30 μmm, 40 g Interchim, mobile phase: Heptane/EtOAc 95/5). The pure fractions were collected and solvent evaporated until dryness to give 1 g of Int. 213, yellow oil (79%).

b—Synthesis of Int. 214:

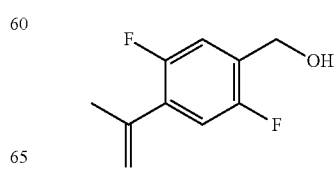

213 (1.0 g, 4.7 mmol) in dry THF (7.5 mL) was added dropwise to a suspension of LAH (0.39 g, 10 mmol) in dry THF (7.5 mL) at 0° C. under $N_2$. The mixture was stirred overnight at r.t. Water (1.4 mL) then DCM (75 mL) were added very slowly and the mixture was stirred for 20 min. $MgSO_4$ was added and the insoluble was filtered on a pad of Celite® and evaporated until dryness to give 0.89 g of Int. 214, pale brown oil (100%).

c—Synthesis of Int. 215:

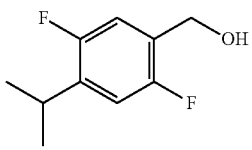

A solution of 214 (0.89 g, 4.8 mmol), ammonium formate (1.8 g, 29 mmol), Pd/C 10% (258 mg, 0.24 mmol) in THF (7 mL) and MeOH (22 mL) was refluxed for 30 min. The mixture was filtered through Celite®, washed with EtOAc, and the filtrate was concentrated. The residue was partitioned between water and EtOAc. The organic layer was separated, dried on $MgSO_4$, filtered and evaporated until dryness to give 0.83 g of Int. 215, colorless oil (92%).

d—Synthesis of Int. 216:

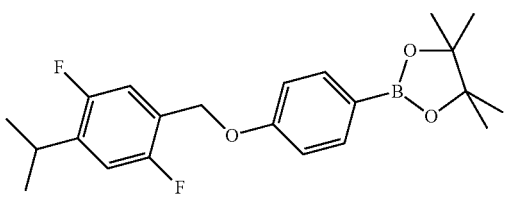 [SMILES: CC(C)c1cc(F)c(COc2ccc(B3OC(C)(C)C(C)(C)O3)cc2)cc1F]

Under $N_2$, DBAD (1.2 g, 5.3 mmol) was added portionwise to a sol. of 215 (0.83 g, 4.5 mmol), 7 (1.2 g, 5.3 mmol), $PPh_3$ supp. (1.7 g, 5.3 mmol) in dry THF (30 mL). The mixture was stirred at r.t. overnight. $PPh_3$ supp. was filtered and the filtrate was evaporated to give 4.0 g, yellow oil. The crude residue was purified by prep. LC (irregular SiOH 30 μm 120 g GraceResolve™, mobile phase: heptane/EtOAc 90/10). The pure fractions were collected and solvent evaporated until dryness to give 1.26 g of Int. 216, pale yellow oil (73%).

e—Synthesis of Int. 217:

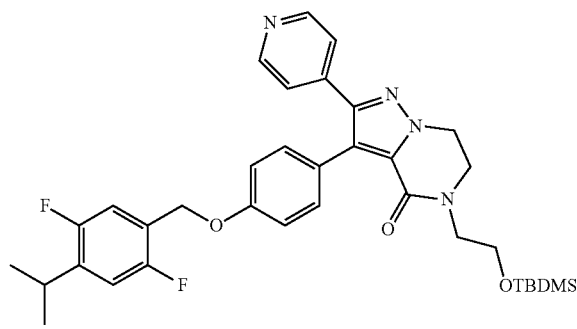 [SMILES: CC(C)c1cc(F)c(COc2ccc(-c3c(-c4ccncc4)nn4c3C(=O)N(CCO[Si](C)(C)C(C)(C)C)CC4)cc2)cc1F]

In a microwave vial, a mixture of 28 (0.42 g, 0.94 mmol), 216 (0.4 g, 1.0 mmol), $K_3PO_4$ (0.80 g, 3.7 mmol) in 1,4-dioxane (4.1 mL) and $H_2O$ (1.5 mL) was carefully purged with $N_2$. $PdCl_2(dppf)$ (77 mg, 0.10 mmol) was added and the r.m. was purged again with $N_2$. The r.m. was heated at 80° C. overnight. The r.m. was diluted with EtOAc and washed with water (once) and with brine (3 times). The organic phase was dried over $MgSO_4$, filtered on a pad of Celite® and evaporated in vacuo to give 0.9 g, brown oil. The crude was purified by prep. LC (irregular SiOH 30 μm, 25 g GraceResolve™, mobile phase: DCM/MeOH/$NH_4OH$ 98/2/0.1). The pure fractions were collected and solvent evaporated until dryness to give 0.55 g of Int. 217, pale yellow oil (93%).

f—Synthesis of Co. 97:

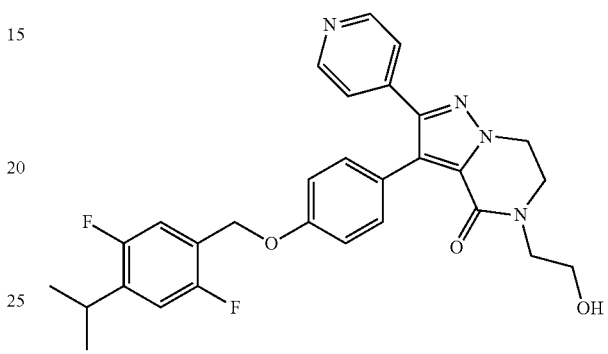

TBAF (1.0 mL, 1.0 mmol) was added dropwise to a sol. of 217 (0.55 g, 0.87 mmol) in THF (8.5 mL) at r.t. The mixture was stirred overnight at r.t. The mixture was concentrated and the residue was purified by prep. LC (Regular SiOH, 30 μm, 25 g GraceResolv™, mobile phase gradient: DCM/MeOH/$NH_4OH$ from 97/3/0.1 to 95/5/0.1). The pure fractions were collected and solvent evaporated until dryness to give 370 mg which was triturated in $Et_2O$. The white solid formed was filtrated, washed and dried to give 0.23 g, white solid. The white solid and filtrate were put together and evaporated to give a residue. The residue was purified by achiral SFC (Stationary phase: Amino 6 μm 150×21.2 mm, Mobile phase: 85% $CO_2$, 15% MeOH (0.3% $iPrNH_2$)). The pure fractions were collected and solvent evaporated until dryness to give 287 mg which was triturated in $Et_2O$. The white solid formed was filtrated and dried to give 199 mg of Co. 97, white solid (44%). m.p.: 147° C. (dsc).

Example A99

Preparation of Co. 98a and Co. 98 a—Synthesis of Co. 98a:

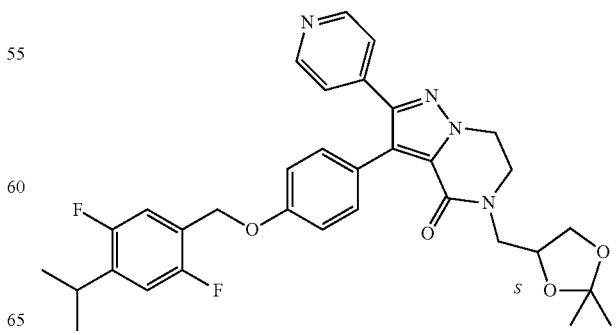

In a microwave vial, a mixture of 209 (0.38 g, 0.94 mmol), 216 (0.4 g, 1.0 mmol), K₃PO₄ (0.80 g, 3.7 mmol) in 1,4-dioxane (4.1 mL) and H₂O (1.5 mL) was carefully purged with N₂. PdCl₂(dppf) (77 mg, 0.10 mmol) was added and the r.m. was purged again with N₂. The r.m. was heated at 80° C. overnight. The r.m. was diluted with EtOAc and washed with water (1×) and with brine (3×). The organic layer was dried over MgSO₄, filtered on a pad of Celite® and evaporated in vacuo to give a brown oil (Ig). The crude was purified by prep. LC (irregular SiOH 30 μm, 25 g Interchim, mobile phase: DCM/MeOH/NH₄OH 98/2/0.1). The pure fractions were collected and solvent evaporated until dryness to give 0.43 g of Co. 98a (S), beige powder (78%).

b—Synthesis of Co. 98:

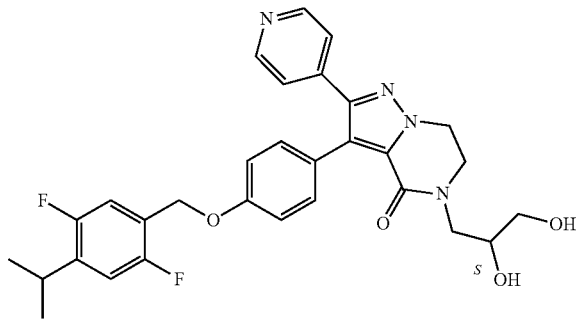

A sol. of Co. 98a (0.43 g, 0.73 mmol) and HCl 3N (1.2 mL, 3.6 mmol) in 1,4-dioxane (16 mL) were heated to reflux for 1 h. The mixture was cooled to r.t., poured into sat. NaHCO₃ and extracted with DCM. The organic layer was dried over MgSO₄, filtered and evaporated until dryness. The residue was purified by prep. LC (irregular SiOH 15-40 μm, 12 g, GraceResolv™, Mobile phase gradient: DCM/MeOH/NH₄OH, from 96/4/0.1 to 95/5/0.1). The pure fractions were collected and solvent evaporated until dryness to give 350 mg, colorless oil. This oil was crystallized from Et₂O and the white solid formed was filtrated and dried to give 318 mg. The solid was purified by achiral SFC (Stationary phase: Amino 6 μm 150×21.2 mm, Mobile phase: 80% CO₂, 20% MeOH (0.3% iPrNH₂)). The pure fractions were collected and solvent evaporated to give 241 mg, white solid, which was triturated in Et₂O, filtrated and dried to give 215 mg of Co. 98 (S), white solid (54%). m.p.: 184° C. (dsc); $[\alpha]_d$: −17.99° (589 nm, c 0.339 w/v %, DMF, 20° C.).

Example A100

Preparation of Co. 99a and Co. 99 a—Synthesis of Co. 99a:

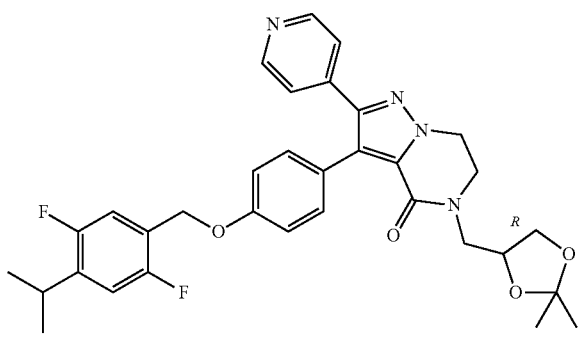

In a microwave vial, a mixture of 211 (0.38 g, 0.94 mmol), 216 (0.4 g, 1.0 mmol), K₃PO₄ (0.80 g, 3.7 mmol) in 1,4-dioxane (4.1 mL) and H₂O (1.5 mL) was carefully purged with N₂. PdCl₂(dppf) (77 mg, 0.10 mmol) was added and the r.m. was purged again with N₂. The r.m. was heated at 80° C. overnight. The r.m. was diluted with EtOAc and washed with water (once) and with brine (3 times). The organic phase was dried over MgSO₄, filtered on a pad of Celite® and evaporated in vacuo to give a brown oil. This oil was purified by prep. LC (irregular SiOH 30 μm, 25 g Interchim, mobile phase: DCM/MeOH/NH₄OH 98/2/0.1). The pure fractions were collected and solvent evaporated until dryness to give 0.32 g of Co. 99a (R), colorless oil (58%).

b—Synthesis of Co. 99:

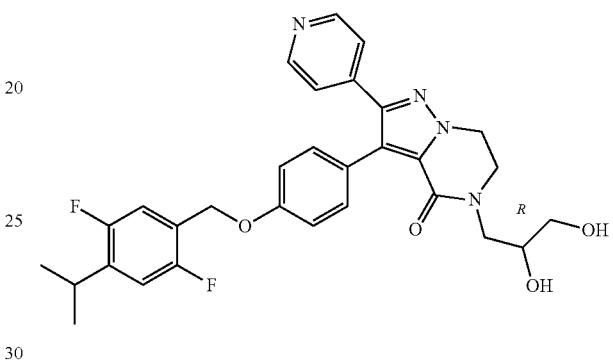

A sol. of Co. 99a (0.32 g, 0.54 mmol) and HCl 3N (0.91 mL, 2.7 mmol) in 1,4-dioxane (12 mL) were heated to reflux for 1 h. The mixture was cooled to r.t., poured into sat. NaHCO₃ and extracted with DCM. The organic layer was dried over MgSO₄, filtered and evaporated until dryness to give 300 mg. The residue was purified by achiral SFC (Stationary phase: Amino 6 μm 150×21.2 mm, Mobile phase: 80% CO₂, 20% MeOH (0.3% iPrNH₂)). The pure fractions were collected and solvent evaporated until dryness to give 191 mg of white solid. This solid was triturated in Et₂O, filtrated and dried to give 160 mg of Co. 99 (R), white solid (54%). m.p.: 183° C. (dsc); $[\alpha]_d$: +17.82° (589 nm, c 0.331 w/v %, DMF, 20° C.).

Example A101

Preparation of Co. 100 a—Synthesis of Int. 220:

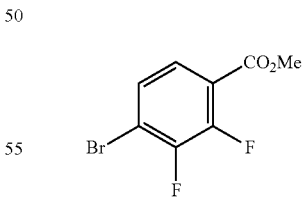

H₂SO₄ (1.1 mL, 21 mmol) was slowly added to a sol. of 4-bromo-2,3-difluorobenzoic acid (2.5 g, 10.5 mmol) in MeOH (40 mL). The mixture was heated at 50° C. for 3 days. The mixture was concentrated in vacuo and the residue was partitioned between EtOAc and water and basified with K₂CO₃. The combined organic layers were washed with brine, dried (MgSO₄), filtered and concentrated in vacuo to give 2.6 g of Int. 220, colorless oil which crystallized in white solid (98%).

b—Synthesis of Int. 221:

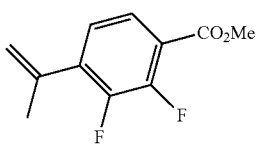

In a schlenk, a mixture of 220 (2.5 g), CsF (3.3 g, 22 mmol) and 2-isopropenyl-4,4,5,5-tetramethyl-1,3,2-dioxaborolane (2.0 mL, 11 mmol) in dry THF (60 mL) was purged with $N_2$. $Pd(tBu_3P)_2$ (254 mg, 0.50 mmol) was added and the mixture was purged again with $N_2$ and heated at 80° C. overnight. Water and EtOAc were added, the organic layer was separated, washed with brine, dried on $MgSO_4$, filtered over Celite® and evaporated. The residue was purified by prep. LC (Regular SiOH, 30 μm, 80 g GraceResolv™, mobile phase: Heptane/EtOAc 95/5). The pure fractions were collected and solvent evaporated to give 1.8 g of Int. 221, yellow oil (85%).

c—Synthesis of Int. 222:

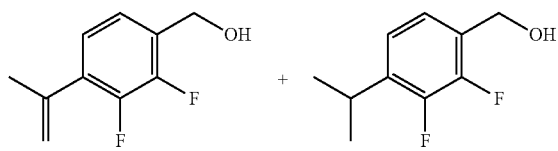

221 (1.8 g, 8.5 mmol) in dry THF (14 mL) was added dropwise to a suspension of LAH (0.39 g, 10 mmol) in dry THF (14 mL) at 0° C. under $N_2$. The mixture was stirred for 30 min. Water (1.4 mL) then DCM (75 mL) were added very slowly and stirred overnight. $MgSO_4$ was added and the insoluble was filtered on a pad of Celite® and the filtrate evaporated until dryness to give 1.5 g of Int. mixture 222, brown oil. The mixture was used like this in the next step.

d—Synthesis of Int. 223:

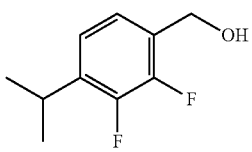

222 (1.5 g, 8.1 mmol), ammonium formate (3.0 g, 49 mmol), Pd/C 10% (433 mg, 0.41 mmol), THF (14 mL) and MeOH (44 mL) were refluxed for 30 min. The mixture was filtered through Celite®, washed with EtOAc, and the filtrate was concentrated. The residue was partitioned between brine and EtOAc. The organic layer was separated, dried on $MgSO_4$, filtered and evaporated until dryness to give 1.47 g of Int. 223, colorless oil (97%).

e—Synthesis of Int. 224:

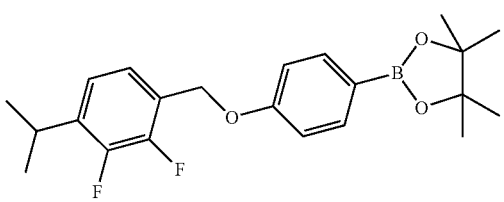 [SMILES: CC(C)c1ccc(COc2ccc(B3OC(C)(C)C(C)(C)O3)cc2)c(F)c1F]

Under $N_2$, DBAD (2.2 g, 9.5 mmol) was added portionwise to a sol. of 223 (1.47 g, 7.9 mmol), 7 (2.1 g, 9.5 mmol), $PPh_3$ supp. (3.0 g, 9.5 mmol) in dry THF (60 mL). The mixture was stirred at r.t. for 3 days. $PPh_3$ supp. was filtered and the filtrate was evaporated to give 8 g, yellow oil. The crude residue was purified by prep. LC (irregular SiOH 30 μm 120 g GraceResolv™, mobile phase: heptane/EtOAc 90/10). The pure fractions were collected and solvent evaporated until dryness to give 2.36 g of Int. 224, pale yellow oil which crystallized in beige solid (77%).

f—Synthesis of Int. 225:

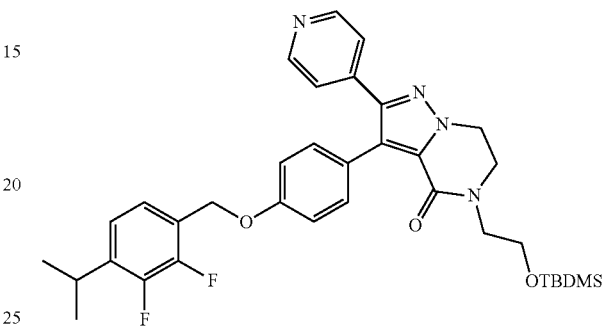

In a microwave vial, a mixture of 28 (0.42 g, 0.94 mmol), 224 (0.4 g, 1.0 mmol), $K_3PO_4$ (0.80 g, 3.7 mmol) in 1,4-dioxane (4.1 mL) and $H_2O$ (1.5 mL) was carefully purged with $N_2$. $PdCl_2(dppf)$ (77 mg, 0.10 mmol) was added and the r.m. was purged again with $N_2$. The r.m. was heated at 80° C. overnight. The r.m. was diluted with EtOAc and washed with water (once) and with brine (3 times). The organic phase was dried over $MgSO_4$, filtered on a pad of Celite® and evaporated in vacuo to give Ig of a residue which was purified by prep. LC (irregular SiOH 30 μm, 25 g GraceResolv™, mobile phase: DCM/MeOH/$NH_4OH$ 98/2/0.1). The pure fractions were collected and solvent evaporated until dryness to give 0.6 g of Int. 225, yellow oil (100%).

g—Synthesis of Co. 100:

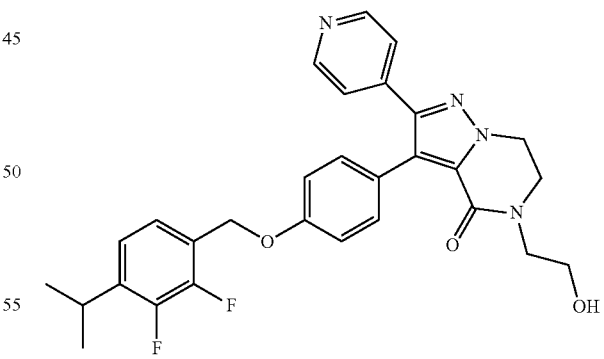

TBAF (1.1 mL, 1.1 mmol) was added dropwise to a sol. of 225 (0.60 g, 0.95 mmol) in THF (9.3 mL) at r.t. The mixture was stirred overnight at r.t. The mixture was concentrated and the residue was purified by prep. LC (Regular SiOH, 30 μm, 25 g GraceResolv™, mobile phase gradient: DCM/MeOH/$NH_4OH$ from 96/4/0.1 to 95/5/0.1). The pure fractions were collected and solvent evaporated until dryness to give 450 mg. This residue was purified by prep. LC (Stationary phase: Sunfire C18 Xbridge 5 μm 150×30.0 mm, Mobile phase Gradient: from 70% (NH₄HCO₃ 0.5% aq. sol.), 30% ACN to 100% ACN). 295 mg was collected and triturated in Et₂O. The white solid formed was filtrated, washed and dried to give 257 mg of Co. 100, white solid (52%). m.p.: 172° C. (dsc).

Example A102

Preparation of Co. 101a and Co. 101 a—Synthesis of Co. 101a

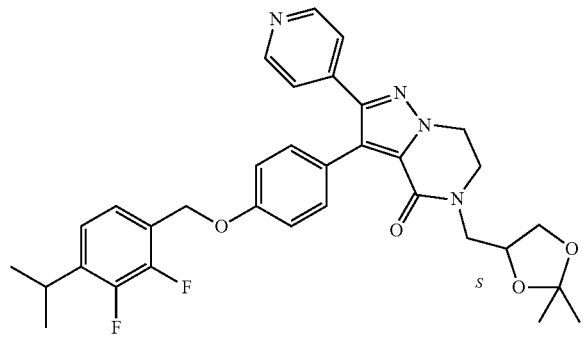

In a microwave vial, a mixture of 209 (0.38 g, 0.94 mmol), 224 (0.4 g, 1.), K₃PO₄ (0.80 g, 3.7 mmol) in 1,4-dioxane (4.1 mL) and H₂O (1.5 mL) was carefully purged with N₂. PdCl₂(dppf) (77 mg, 0.10 mmol) was added and the r.m. was purged again with N₂. The r.m. was heated at 80° C. overnight. The r.m. was diluted with EtOAc and washed with water (once) and with brine (3 times). The organic phase was dried over MgSO₄, filtered on a pad of Celite® and evaporated in vacuo to give brown oil. This oil was purified by prep. LC (irregular SiOH 30 μm, 25 g Interchim, mobile phase: DCM/MeOH/NH₄OH 98/2/0.1). The desired fractions were collected and solvent evaporated until dryness to give 0.33 g of Co. 101a (S), beige powder (60%).

b—Synthesis of Co. 101:

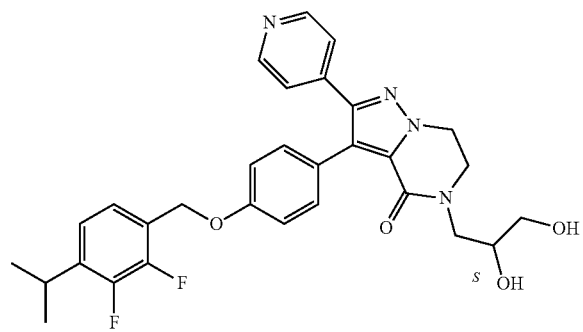

A sol. of Co. 101a (0.32 g, 0.54 mmol) and HCl 3N (0.91 mL, 2.7 mmol) in 1,4-dioxane (12 mL) were heated to reflux for 1 h. The mixture was cooled to r.t., poured into sat. NaHCO₃ and extracted with DCM. The organic layer was dried over MgSO₄, filtered and evaporated until dryness to give 0.4 g, colorless oil. This oil was purified by prep. LC (Stationary phase: Sunfire C18 Xbridge 5 μm 150×30.0 mm, Mobile phase Gradient: from 70% (NH₄HCO₃ 0.5% aq. sol.), 30% ACN to 100% ACN). The pure fractions were collected and solvent evaporated until dryness to give 210 mg which was triturated in Et₂O. The white solid formed was filtrated, washed and dried to give 0.18 g of Co. 101 (S), white solid (61%). m.p.: 192° C. (dsc); [α]_d: −19.88° (589 nm, c 0.2515 w/v %, DMF, 20° C.)

Example A103

Preparation of Co. 102a and Co. 102 a—Synthesis of Co. 102a:

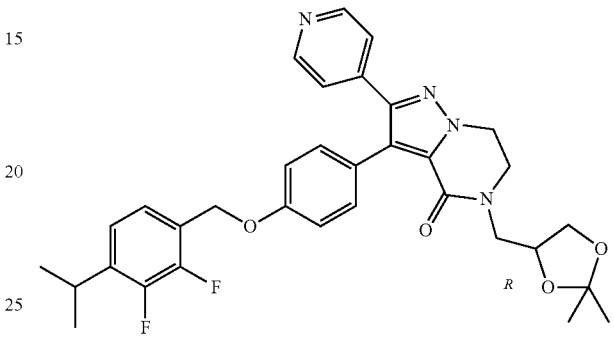

In a microwave vial, a mixture of 211 (0.38 g, 0.), 224 (0.4 g, 1.0 mmol), K₃PO₄ (0.80 g, 3.7 mmol) in 1,4-dioxane (4.1 mL) and H₂O (1.5 mL) was carefully purged with N₂. PdCl₂(dppf) (77 mg, 0.10 mmol) was added and the r.m. was purged again with N₂. The r.m. was heated at 80° C. overnight. The r.m. was diluted with EtOAc and washed with water (once) and with brine (3 times). The organic phase was dried over MgSO₄, filtered on a pad of Celite® and evaporated in vacuo to give brown oil. The crude mixture was purified by prep. LC (irregular SiOH 30 μm, 25 g Interchim, mobile phase: DCM/MeOH/NH₄OH 98/2/0.1). The pure fractions were collected and solvent evaporated until dryness to give 0.48 g of Co. 102a (R), colorless oil (87%).

b—Synthesis of Co. 102:

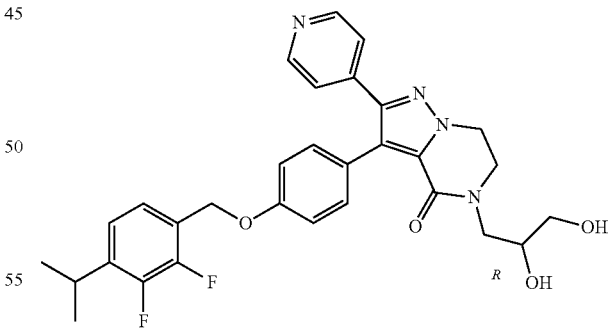

A sol. of Co. 102a (0.48 g, 0.82 mmol) and HCl 3N (1.4 mL, 4.1 mmol) in 1,4-dioxane (18 mL) were heated to reflux for 1 h. The mixture was cooled to r.t., poured into sat. NaHCO₃ and extracted with DCM. The organic layer was dried over MgSO₄, filtered and evaporated until dryness to give 520 mg, colorless oil. The crude was purified by prep. LC (Stationary phase: Sunfire C18 Xbridge 5 μm 150×30.0 mm, Mobile phase Gradient: from 70% (NH₄HCO₃ 0.5% aq. sol.), 30% ACN to 100% ACN). The pure fractions were collected and solvent evaporated until dryness to give 241 mg which was triturated in Et₂O. The white solid formed was filtrated, washed and dried to give 215 mg of Co. 102 (R), white solid (48%). m.p.=191° C. (dsc); [α]$_d$: +19.28° (589 nm, c 0.249 w/v %, DMF, 20° C.).

Example A104

Preparation of Co. 103 a—Synthesis of Int. 228:

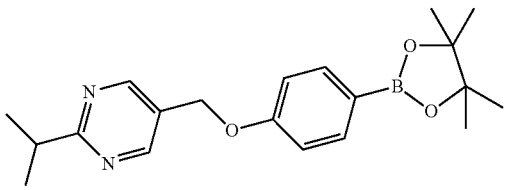 [SMILES: CC(C)c1ncc(COc2ccc(B3OC(C)(C)C(C)(C)O3)cc2)cn1]

DBAD (446 mg, 1.94 mmol) was added to a stirred sol. of 7 (305 mg, 1.38 mmol), (2-isopropylpyrimidin-5-yl) methanol (295 mg, 1.94 mmol) and PPh₃ supp. (606 mg, 1.94 mmol) in THF (7 mL) under N₂ at r.t. The mixture was stirred at r.t. for 16 h. Then, additional PPh₃ supp. (130 mg; 0.416 mmol) and DBAD (96 mg, 0.416 mmol) were added under N₂, and the mixture was stirred at r.t. for 16 h. The crude mixture was filtered off and the filtrate was evaporated in vacuo to give an oil. The oil was purified by prep. LC (Irregular SiOH 15-40 µm, 80 g Grace, mobile phase gradient: from Heptane 100% to EtOAc 50%, Heptane 50%). The desired fractions were collected and solvent evaporated until dryness to give 800 mg of a solid which was purified by prep. LC (Irregular SiOH 15-40 µm, 30 g Grace, mobile phase gradient: from Heptane 100% to EtOAc 40%, Heptane 60%). The pure fractions were collected and solvent evaporated until dryness to give 590 mg of Int. 228, solid (90%, purity 75%), used as such as for the next step.

b—Synthesis of Co. 103:

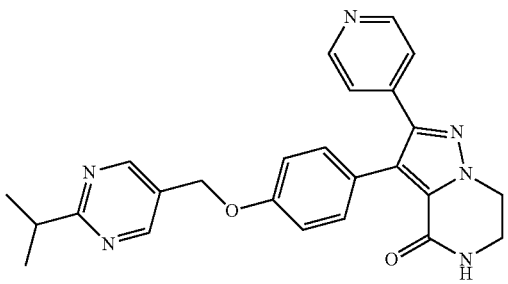 [SMILES: CC(C)c1ncc(COc2ccc(-c3c(-c4ccncc4)nn4c3C(=O)NCC4)cc2)cn1]

A mixture of 4 (150 mg, 0.512 mmol), 228 (590 mg, 1.25 mmol), K₃PO₄ (434 mg, 2.05 mmol) in 1,4-dioxane (3 mL) and H₂O (1 mL) was carefully purged with N₂. PCy₃ (29 mg, 0.102 mmol) and Pd(OAc)₂ (11 mg, 51.2 µmol) were added and the r.m. was purged again with N₂, and stirred for 68 h at 80° C. The crude material was treated with water and extracted with DCM. The organic phase was washed with brine, dried over MgSO₄, filtered and evaporated in vacuo to give a black solid. The solid was purified by prep. LC on (irregular SiOH 15-40 µm 24 g Grace, Mobile phase gradient: from DCM 100% to MeOH 10%, DCM 90%). The desired fractions were combined and the solvent was removed in vacuo to give 175 mg, white solid. The solid was purified by achiral SFC on (2-ethylpyridine 6 µm 150×21.2 mm; Mobile phase: 0.3% iPrNH₂, 80% CO₂, 20% MeOH). The pure fractions were collected and concentrated in vacuo to yield 161 mg of Co. 103, white solid (71%). m.p.: 235° C. (dsc).

Example A105

Preparation of Co. 104 a—Synthesis of Int. 229:

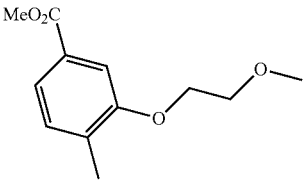 [SMILES: COCCOc1cc(C(=O)OC)ccc1C]

Methyl 3-hydroxy-4-methylbenzoate (2.5 g, 15 mmol), 2-bromoethyl methyl ether (1.5 mL, 16.5 mmol), K₂CO₃ (3.1 g, 22.5 mmol) in ACN (40 mL) at 80° C. overnight. Water and EtOAc were added, the mixture was extracted, the organic layer was separated, dried over MgSO₄, filtered and evaporated. The residue was purified by prep. LC on (Irregular SiOH 20-45 µm 40 g GRACE, Mobile phase gradient: 100% DCM to 99/1 DCM/MeOH). The pure fractions were collected and solvent evaporated until dryness to give 2.8 g of Int. 229 (78%).

b—Synthesis of Int. 230:

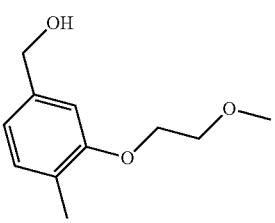

LAH (287 mg, 7.5 mmol) was added carefully at 5° C. to a sol. of 229 (1.5 g, 6.3 mmol) in THF (20 mL). The mixture was stirred at r.t. for 1 h. Water was carefully added at 5° C. and EtOAc were added. The mixture was extracted, the organic layer was separated, dried over MgSO₄, filtered and evaporated to give 1.2 g of Int. 230 (97%).

c—Synthesis of Int. 231:

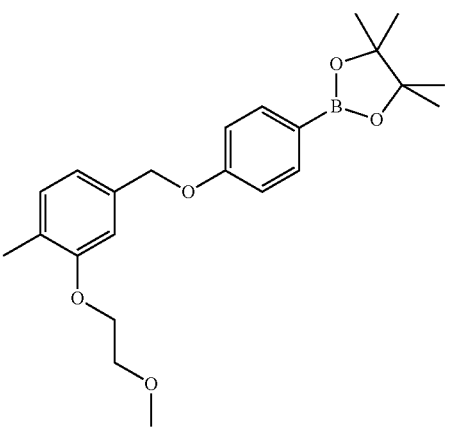

230 (1.2 g, 6.1 mmol), 7 (1.6 g, 7.3 mmol), PPh₃ supp. (2.4 g, 9.2 mmol) in THF (40 mL). DBAD (2.1 g, 9.2 mmol) was added portionwise at r.t. and the mixture was stirred at r.t. overnight. Water and EtOAc were added, the mixture was extracted, the organic layer was separated, dried over MgSO₄, filtered and evaporated. The residue was purified by prep. LC on (irregular 15-40 μm 30 g Merck, Mobile phase: 60/40 heptane/EtOAc). The pure fractions were collected and the solvent evaporated until dryness to give 1.2 g of Int. 231 (49%).

d—Synthesis of Co. 104:

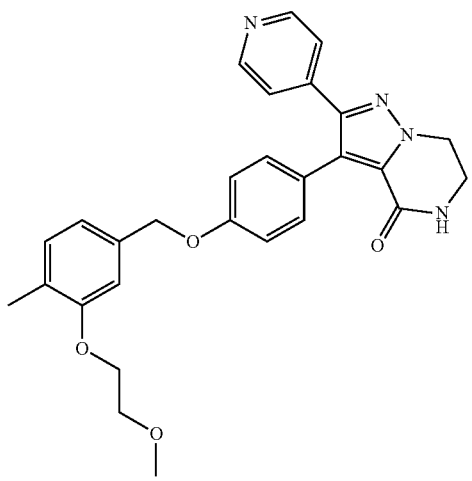 [SMILES: COCCOc1cc(COc2ccc(-c3c(-c4ccncc4)nn4c3C(=O)NCC4)cc2)ccc1C]

A mixture of 4 (400 mg, 1.36 mmol), 231 (0.71 g, 1.8 mmol), K₃PO₄ (1.16 g, 5.46 mmol) in 1,4-dioxane (7 mL) and H₂O (3 mL) was carefully purged with N₂. PCy₃ (80.4 mg, 0.29 mmol) and Pd(OAc)₂ (32 mg, 0.14 mmol) were added and the r.m. was purged again with N₂. The r.m. was stirred for 8 h at 80° C. The crude material was poured in water and DCM, the residue was taken up in DCM and the precipitate was filtered off. The mother layer was evaporated and the residue was purified by prep. LC on (Irregular SiOH 20-45 μm 40 g MATREX, Mobile phase: 97/3 DCM/MeOH). The pure fractions were collected and solvent evaporated until dryness to give 150 mg of a residue which was taken up in Et₂O, the precipitate was filtered off and dried to give 79 mg of Co. 104 (12%). m.p.: 190° C. (dsc).

Example A106

Preparation of Co. 105 a—Synthesis of Int. 232:

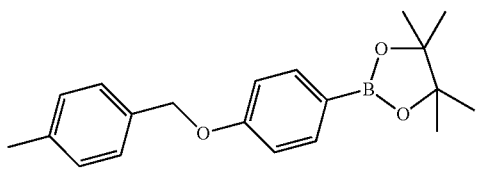

A sol. of 4-methylbenzylbromide (1.06 g, 4.81 mmol) in ACN (10 mL) was treated with K₂CO₃ (0.798 g, 5.78 mmol) and 7 (0.98 g, 5.3 mmol) at r.t. The r.m. was stirred for 18 h at r.t. Then, water and DCM were added, and the organic layer was washed with brine, separated, dried over MgSO₄, filtered and concentrated in vacuo to give 1.6 g of Int. 232 (100%).

b—Synthesis of Co. 105:

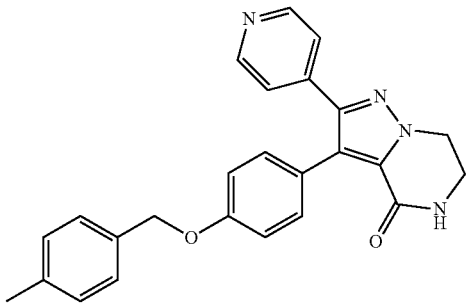 [SMILES: Cc1ccc(COc2ccc(-c3c(-c4ccncc4)nn4c3C(=O)NCC4)cc2)cc1]

In a microwave vial, a mixture of 4 (300 mg, 1.02 mmol), 232 (431 mg, 1.33 mmol), K₃PO₄ (911 mg, 4.29 mmol) in 1,4-dioxane (4.8 mL) and H₂O (1.6 mL) was carefully purged with N₂. PCy₃ (60 mg, 0.214 mmol) and Pd(OAc)₂ (24 mg, 0.107 mmol) were added and the r.m. was purged again with N₂. The r.m. was stirred for 16 h at 80° C.

The crude material was dissolved in water and extracted with EtOAc. The organic phase was dried over MgSO₄, filtered and evaporated in vacuo to give 530 mg of crude residue. The residue was purified by prep. LC on (Stability Silica 5 m 150×30.0 mm, Mobile phase Gradient: from 0.2% NH₄OH, 98% DCM, 2% MeOH to 1% NH₄OH, 89% DCM, 10% MeOH). The pure fractions were collected and the solvent was evaporated. 255 mg was obtained as a white solid. The solid was taken up in Et₂O, filtrated and dried to give 225 mg of Co. 105, white powder (54%). m.p.: 259° C. (dsc).

Example A107

Preparation of Co. 106 a—Synthesis of Int. 233:

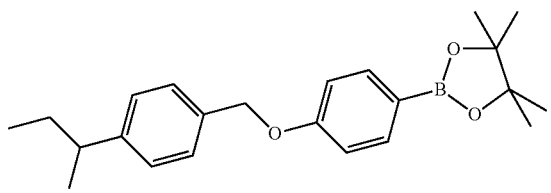 [SMILES: CCC(C)c1ccc(COc2ccc(B3OC(C)(C)C(C)(C)O3)cc2)cc1]

DBAD (3.8 g, 16.4 mmol) was added portionwise to a mixture of 4-(1-methylpropyl)-benzenemethanol (1.8 g, 11 mmol), 7 (2.4 g, 11 mmol), PPh₃ supp. (5.1 g, 16.4 mmol) in THF (30 mL) at r.t. The mixture was stirred for 15 h, filtered and washed with EtOAc. The filtrate was poured into water and K₂CO₃. The organic layer was dried over MgSO₄, filtered and evaporated until dryness to give 7 g. The residue was purified by prep. LC (120 g of SiOH 35-40 μm GraceResolv™, mobile phase gradient: from 95% heptane 5% EtOAc to 80% heptane 20% EtOAc). The fractions were collected and evaporated until dryness to give 3.3 g which was crystallized from heptane, filtered and dried to give 0.726 g of Int. 233 (18%). The filtrate was evaporated until dryness to give 2.6 g. This residue was purified by prep. LC (Stationary phase: irregular SiOH 15-40 μm 300 g MERCK, Mobile phase: 95% Heptane, 0.3% MeOH, 5% EtOAc). The desired fractions were collected and evaporated until dryness to give 1.75 g of Int. 233. The both fractions were put together to give 2.47 g of Int. 233 (Global yield: 62%).

b—Synthesis of Co. 106:

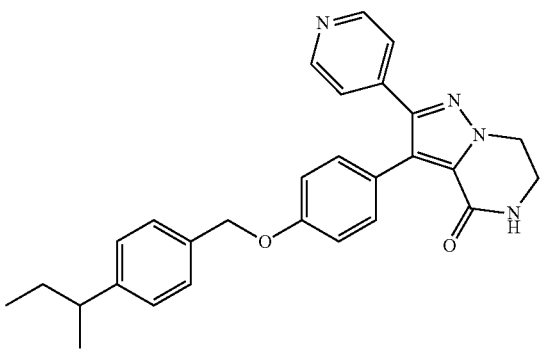 [SMILES: CCC(C)c1ccc(COc2ccc(-c3c(-c4ccncc4)nn4c3C(=O)NCC4)cc2)cc1]

A mixture of 4 (380 mg, 1.3 mmol), 233 (726 mg, 2 mmol), K₃PO₄ (1.1 g, 5.2 mmol) in 1,4-dioxane (7 mL) and H₂O (2.5 mL) was carefully purged with N₂. PCy₃ (72.7 mg, 0.26 mmol) and Pd(OAc)₂ (29.1 g, 0.13 mmol) were added and the r.m. was purged again with N₂. The r.m. was stirred for 18 h at 80° C. Water and K₂CO₃ were added then EtOAc. The mixture was filtered and the organic layer was extracted, dried over MgSO₄, filtered and evaporated until dryness. The residue was purified by prep. LC (40 g of irregular SiOH 35-40 μm GraceResolv™, mobile phase gradient: from 100% DCM to 95% DCM 5% CH₃OH 0.1% NH₄OH). The fractions were collected and evaporated until dryness. The product was crystallized from Et₂O, filtered and dried to give 188 mg of Co. 106 (32%). m.p.: 229° C. (dsc).

Example A108

Preparation of Co. 107 a—Synthesis of Int. 234:

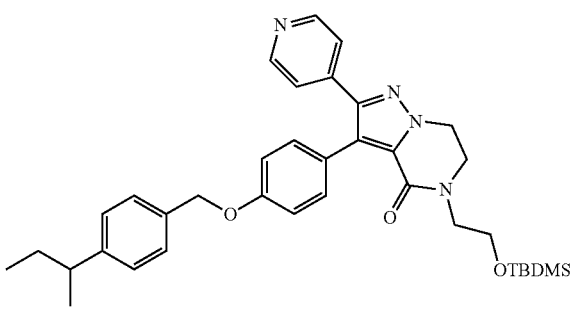 [SMILES: CCC(C)c1ccc(COc2ccc(-c3c(-c4ccncc4)nn4c3C(=O)N(CCO[Si](C)(C)C(C)(C)C)CC4)cc2)cc1]

NaH 60% (0.115 g, 2.9 mmol) was added to a suspension of Co. 106 (1 g, 2.21 mmol) in DMF (15 mL) at r.t. under N₂. The mixture was stirred for 2 h. (2-bromoethoxy)-tert-butyldimethylsilane (0.57 mL, 2.65 mmol) was added and stirred for 20 h. The mixture was poured into water and K₂CO₃ and extracted with EtOAc. The organic layer was dried (MgSO₄), filtered and evaporated until dryness. The residue was purified by prep. LC (120 g of irregular SiOH 35-40 μm GraceResolv™, mobile phase gradient: from 100% DCM to 97% DCM 3% CH₃OH 0.1% NH₄OH). The fractions were collected and evaporated to give 1.07 g of Int. 234 (79%).

b—Synthesis of Co. 107:

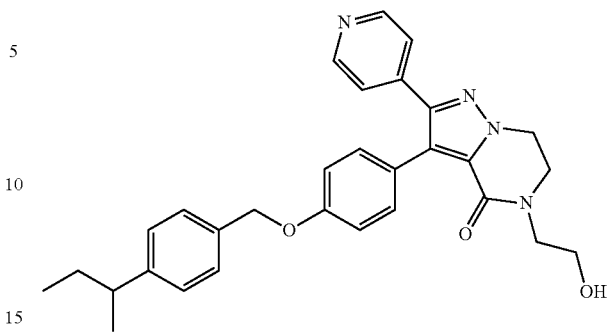

TBAF (2.1 mL, 2.1 mmol) was added dropwise to a sol. of 234 (1.1 g, 1.8 mmol) in THF (17 mL) at r.t. The mixture was stirred overnight at r.t. The mixture was concentrated and the residue was purified by prep. LC (Regular SiOH, 30 μm, 40 g Interchim, mobile phase gradient: DCM/MeOH/NH₄OH from 98/2/0.1 to 96/4/0.1).

The pure fractions were collected and solvent evaporated until dryness to give colorless oil which was crystallized from Et₂O. The white solid formed was filtrated, washed and dried to give 0.64 g of Co. 107 (74%). m.p.: 163° C. (dsc).

Example A109

Preparation of Co. 108 a—Synthesis of Int. 235:

DBAD (3.8 g, 16.4 mmol) was added portionwise to a mixture of 4-iso-butylbenzyl alcohol (1.8 g, 11 mmol), 7 (2.4 g, 11 mmol), PPh₃ supp. (5.1 g, 16.4 mmol) in THF (30 mL) at r.t. The mixture was stirred for 15 h. The insoluble was filtered and washed with EtOAc. The filtrate was poured in water and K₂CO₃. The organic layer was extracted, dried over MgSO₄, filtered and evaporated until dryness to give 7.9 g. Heptane was added and the insoluble was filtered. The filtrate was purified by prep. LC (120 g of SiOH 35-40 μm GraceResolv™, mobile phase gradient: from 100% heptane to 90% heptane 10% EtOAc). The fractions were collected and evaporated until dryness to give 2.8 g. The residue was purified by prep. LC (Stationary phase: irregular SiOH 15-40 μm 300 g MERCK, Mobile phase: 95% Heptane, 0.3% MeOH, 5% EtOAc). The pure fractions were collected and solvent evaporated until dryness to give 1.8 g of Int. 235 (37%).

b—Synthesis of Co. 108:

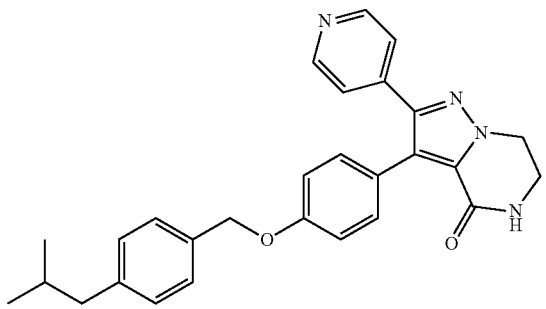 [SMILES: CC(C)Cc1ccc(COc2ccc(-c3c(-c4ccncc4)nn4c3C(=O)NCC4)cc2)cc1]

A mixture of 4 (0.96 g, 3.3 mmol), 235 (1.8 g, 4.9 mmol), K₃PO₄ (2.8 g, 13.1 mmol) in 1,4-dioxane (20 mL) and H₂O (2.5 mL) was carefully purged with N₂ in sealed tube. PCy₃ (184 mg, 0.655 mmol) and Pd(OAc)₂ (73.6 mg, 0.33 mmol) were added and the r.m. was purged again with N₂. The r.m. was stirred for 18 h at 80° C. Water and K₂CO₃ were added then EtOAc. The mixture was filtered and the organic layer was extracted, dried over MgSO₄, filtered and evaporated until dryness to give 2 g. The residue was crystallized from MeOH, filtered and dried to give 1.33 g which was purified by prep. LC (40 g of SiOH 30 μm Interchim, mobile phase gradient: from 100% DCM to 95% DCM, 5% CH₃OH, 0.1% NH₄OH). The pure fractions were collected and evaporated until dryness to give 0.88 g which was crystallized from MeOH, filtered and dried to give 249 mg of Co. 108 (17%). m.p.: 233° C. (dsc).

Example A110

Preparation of Co. 109 a—Synthesis of Int. 236:

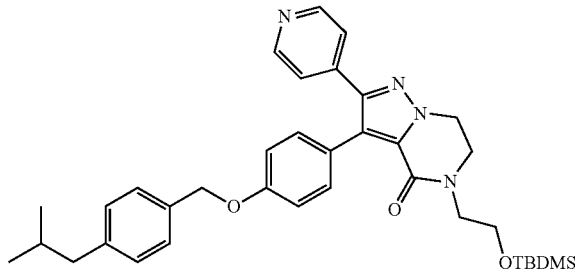 [SMILES: CC(C)Cc1ccc(COc2ccc(-c3c(-c4ccncc4)nn4c3C(=O)N(CCO[Si](C)(C)C(C)(C)C)CC4)cc2)cc1]

NaH 60% (78.1 mg, 1.9 mmol) was added to a suspension of Co. 108 (0.68 g, 1.5 mmol) in DMF (10 mL) at r.t. under N₂. The mixture was stirred for 2 h. (2-bromoethoxy)-tert-butyldimethylsilane (0.39 mL, 1.8 mmol) was added and stirred for 20 h. The mixture was poured into water and K₂CO₃, and extracted with EtOAc. The organic layer was dried over MgSO₄, filtered and evaporated until dryness. The residue was purified by prep. LC (120 g of irregular SiOH 35-40 μm GraceResolv™, mobile phase gradient: from 100% DCM to 97% DCM, 3% CH₃OH, 0.1% NH₄OH). The fractions were collected and evaporated until dryness to give 0.75 g of Int. 236 (86%).

b—Synthesis of Co. 109:

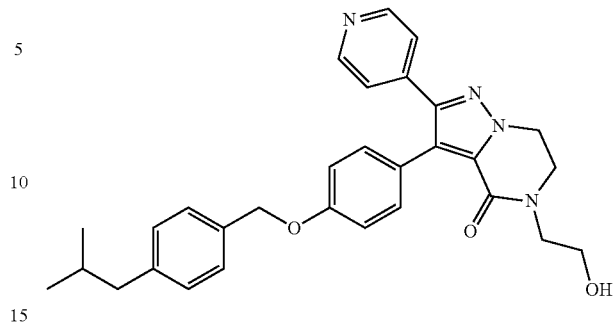

TBAF (1.5 mL, 1.5 mmol) was added dropwise to a sol. of 236 (0.75 g, 1.3 mnol) in THF (12 mL) at r.t. The mixture was stirred overnight at r.t. The mixture was concentrated and the residue was purified by prep. LC (Regular SiOH, 30 μm, 25 g Interchim, mobile phase: DCM/MeOH/NH₄OH, 98/2/0.1). The pure fractions were collected and solvent evaporated until dryness to give 0.60 g, colorless oil which was crystallized from Et₂O. The white solid formed was filtrated, washed and dried to give 0.38 g of Co. 109 (62%).

Example A111

Preparation of Co. 110 a—Synthesis of Int. 237:

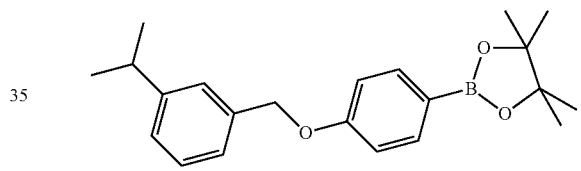

To a suspension of (3-isopropylphenyl)methanol (586 mg, 2.66 mmol), 7 (520 mg, 2.77 mmol), PPh₃ supp. (2.86 g, 3.46 mmol) in dry THF (30 mL) was added DBAD (797 mg, 3.46 mmol) and the r.m. was stirred at r.t. for 18 h. The r.m. was then filtered through a glass frit and washed with EtOAc. The filtrate was evaporated in vacuo to give 1.88 g. The residue was purified by prep. LC (irregular SiOH 15-40 μm, solid loading, 30 g Merck, mobile phase: heptane 90%, EtOAc 10%). The pure fractions were collected and solvent evaporated until dryness to give 710 mg of Int. 237, colorless oil (76%).

b—Synthesis of Co. 110:

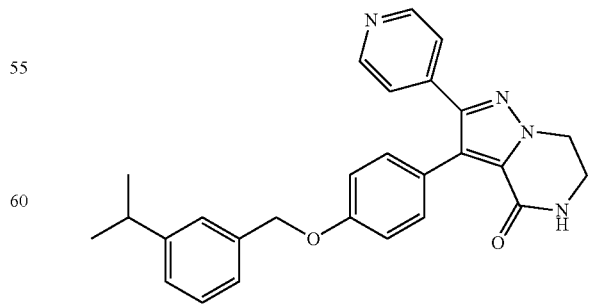

In a sealed tube, a mixture of 4 (197 mg, 0.672 mmol), 237 (710 mg, 2.015 mmol), K₃PO₄ (570 mg, 2.69 mmol) in 1,4-dioxane (3 mL) and H₂O (1 mL) was purged with N₂. PCy₃ (38 mg, 0.134 mmol) and Pd(OAc)₂ (15 mg, 67.2 μmol) were added and the r.m. was purged again with N₂. The tube was then sealed and the r.m. was stirred for 18 h at 80° C. The crude material was dissolved in water (30 mL) and extracted with EtOAc (2×40 mL). The organic phase was dried over MgSO₄, filtered and evaporated in vacuo to give 600 mg, brown oil. This oil was purified by prep. LC (irregular SiOH 15-40 μm, 30 g Merck, mobile phase gradient: from DCM 100% to DCM 95%, MeOH 5%). The pure fractions were collected and solvent evaporated until dryness to give 269 mg, white solid. The solid was washed by Et₂O, filtered and dried to give 202 mg of Co. 110, white solid (69%). m.p.: 268° C. (dsc).

Example A112

Preparation of Co. 111 a—Synthesis of Int. 238:

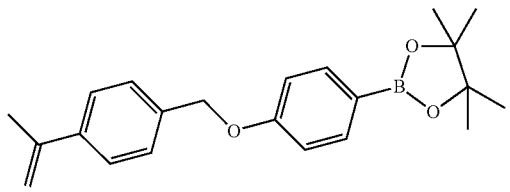 [SMILES: C=C(C)c1ccc(COc2ccc(B3OC(C)(C)C(C)(C)O3)cc2)cc1]

To a suspension of 4-(1-methylethenyl)-benzenemethanol (0.675 g, 4.56 mmol), 7 (1.2 g, 5.47 mmol), DBAD (1.26 g, 5.47 mmol) in dry DCM (10 mL) was added PPh₃ supp. (1.7 g, 5.47 mmol) and the r.m. was stirred at r.t. for 18 h. The insoluble was filtered through Celite®, washed with DCM. Water was added and the organic layer was separated, dried, filtered and concentrated until dryness to give 2.76 g. The residue was purified by prep. LC on (Irregular SiOH 15-40 μm 50 g Merck, Mobile phase: Heptane 90/EtOAc 10). The fractions were collected and evaporated until dryness to give 648 mg of Int. 238 (40%, purity 70%). The Co. was used as such for the next step.

b—Synthesis of Int. 239:

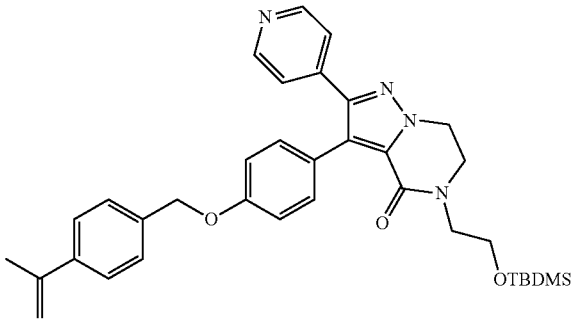 [SMILES: C=C(C)c1ccc(COc2ccc(-c3c(-c4ccncc4)nn4c3C(=O)N(CCO[Si](C)(C)C(C)(C)C)CC4)cc2)cc1]

In a microwave vial, a mixture of 2 (0.663 g, 1.47 mmol), 238 (0.617 g, 1.76 mmol), K₃PO₄ (1.25 g, 5.87 mmol) in 1,4-dioxane (6.5 mL) and H₂O (2.3 mL) was carefully purged with N₂. PdCl₂(dppf) (120 mg, 0.15 mmol) was added and the r.m. was purged again with N₂. The r.m. was heated at 80° C. overnight. The r.m. was diluted with EtOAc and washed with water (1×) and with brine (3×). The organic phase was dried over MgSO₄, filtered on a pad of Celite® and evaporated in vacuo to give 1.39 g. The residue was purified by prep. LC (Stationary phase: irregular SiOH 15-40 μm 300 g Merck, Mobile phase: 0.1% NH₄OH, 99% DCM, 1% MeOH). The desired fractions were collected and solvent evaporated until dryness to give 736 mg. This residue was purified again by achiral SFC (Stationary phase: Amino 6 μm 150×21.2 mm, Mobile phase: 90% CO₂, 10% MeOH). The pure fractions were collected and the solvent evaporated until dryness to give 385 mg of Int. 239 (44%).

c—Synthesis of Co. 111:

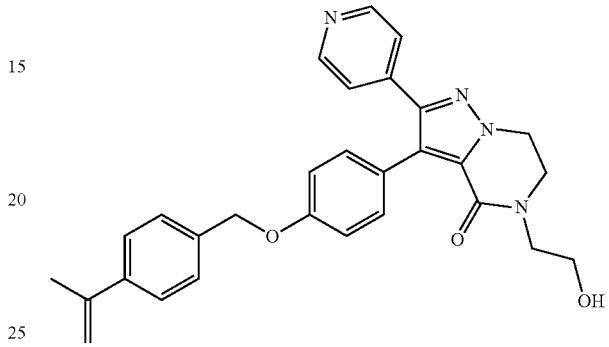

TBAF (0.78 mL, 0.78 mmol) was added dropwise to a sol. of 239 (0.385 g, 0.65 mmol) in THF (6 mL) at r.t. The mixture was stirred for 3 h at r.t. EtOAc and water were added. The organic layer was separated, dried, filtered and evaporated until dryness to give 356 mg. The residue was purified by prep. LC (Regular SiOH, 30 μm, 12 g GraceResolv™, mobile phase gradient: from DCM 100% to DCM/MeOH/NH₄OH 95/5/0.1). The pure fractions were collected and evaporated until dryness to give 282 mg which was crystallized from DIPE, filtered and dried to give 235 mg of Co. 111 (76%). m.p.: 165° C. (dsc).

Example A113

Preparation of Co. 112

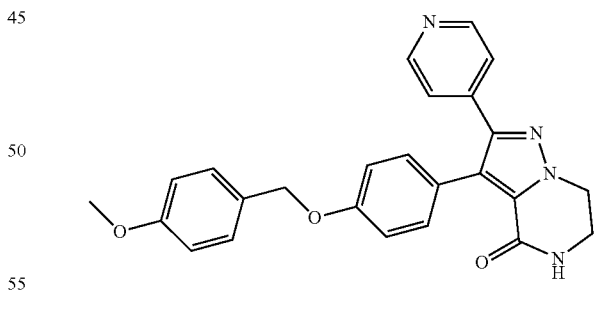

In a Schlenk tube, a mixture of 4 (700 mg, 2.39 mmol), 4-(4'-methoxybenzyloxy)phenylboronic acid (1.85 g, 7.16 mmol), K₃PO₄ (2.03 g, 9.55 mmol) in 1,4-dioxane (10.5 mL) and H₂O (3.5 mL) was carefully purged with N₂. PCy₃ (134 mg, 0.478 mmol) and Pd(OAc)₂ (54 mg, 239 μmol) were added and the r.m. was purged again with N₂. The Schlenk tube was then sealed and the r.m. was stirred for 17 h at 80° C. The crude material was dissolved in water (17 mL) and filtered on glass frit. The grey precipitate was washed with water (2×20 mL) and with Et₂O (2×40 mL). The solid was collected to afford 1.40 g which was purified by prep. LC (irregular SiOH 15-40 µm, 50 g Merck, mobile phase gradient: from DCM 100% to DCM 85%, MeOH 15%). The pure fractions were collected and solvent evaporated to give 700 mg of Co. 112, white solid (69%).

Example A114

Peroration of Co. 113 a—Synthesis of Int. 240:

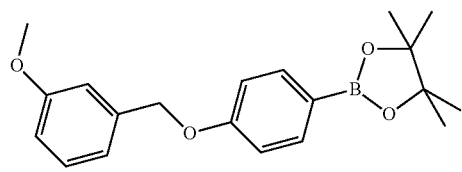 [SMILES: COc1cccc(COc2ccc(B3OC(C)(C)C(C)(C)O3)cc2)c1]

A sol. of 7 (500 mg, 2.27 mmol) in ACN (5 mL) and DMF (1 mL) was treated with $K_2CO_3$ (377 mg, 2.73 mmol) and 3-methoxybenzyl bromide (360 µL, 2.50 mmol) at r.t. The r.m. was stirred for 54 h at rt. Then water and EtOAc were added, and the organic layer was washed with brine, separated, dried over $MgSO_4$, filtered and concentrated in vacuo to afford 800 mg of Int. 240, colorless oil (quant. yield).

b—Synthesis of Co. 113:

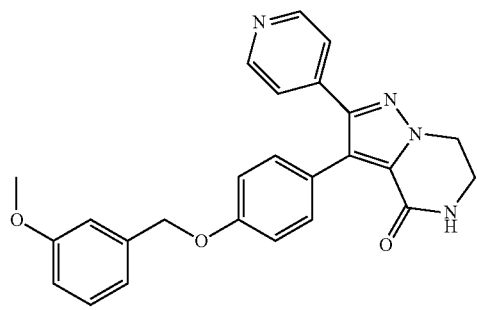 [SMILES: COc1cccc(COc2ccc(-c3c(-c4ccncc4)nn4c3C(=O)NCC4)cc2)c1]

In a sealed tube, a mixture of 4 (230 mg, 0.784 mmol), 240 (800 mg, 2.35 mmol), $K_3PO_4$ (665 mg, 3.14 mmol) in 1,4-dioxane (3.5 mL) and $H_2O$ (1.2 mL) was carefully purged with $N_2$. $PCy_3$ (44 mg, 0.157 mmol) and $Pd(OAc)_2$ (18 mg, 78.4 µmol) were added and the r.m. was purged again with $N_2$. The sealed tube was then sealed and the r.m. was stirred for 17 h at 80° C. The crude material was dissolved in water (10 mL) and extracted with EtOAc (2×40 mL). The organic phase was dried over $MgSO_4$, filtered and evaporated in vacuo to give 640 mg. The residue was purified by prep. LC (irregular SiOH 15-40 µm, 30 g Merck, mobile phase gradient: from DCM 100% to DCM 90%, MeOH 10%). The pure fractions were collected and solvent evaporated until dryness to give 50 mg, white solid, which was washed by $Et_2O$, filtered and dired to give 36 mg of Co. 113, a white solid (11%). m.p.: 242° C. (dsc).

Example A115

Preparation of Co. 114 a—Synthesis of Int. 241:

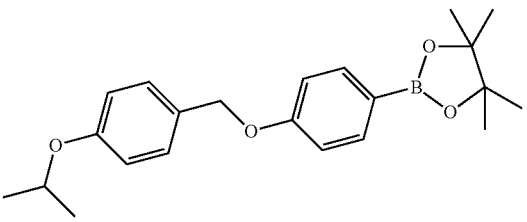 [SMILES: CC(C)Oc1ccc(COc2ccc(B3OC(C)(C)C(C)(C)O3)cc2)cc1]

A sol. of 7 (700 mg, 3.18 mmol), 4-isopropoxybenzylalcohol (793 mg, 4.77 mmol) and $PPh_3$ (1.25 g, 4.77 mmol) in dry DCM (20 mL) was treated with DBAD (1.10 g; 4.77 mmol) and stirred at r.t. for 18 h. The crude mixture was diluted with water and EtOAc. The organic layer was separated, dried over $MgSO_4$, filtered and evaporated in vacuo to give 590 mg of residue was purified by prep. LC (Irregular SiOH 15-40 µm, 30 g Merck, mobile phase gradient: from DCM 100% to MeOH 3%, DCM 97%). The desired fractions were collected and solvent evaporated until dryness to give 590 mg of a solid which was purified by prep. LC (Irregular SiOH 15-40 µm, 24 g Grace, mobile phase gradient from Heptane 100% to EtOAc 40%, Heptane 60%). The pure fractions were collected and solvent evaporated to give 472 mg of Int. 241 (solid; 40%).

b—Synthesis of Co. 114:

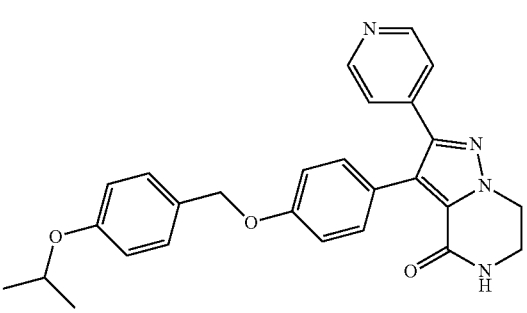 [SMILES: CC(C)Oc1ccc(COc2ccc(-c3c(-c4ccncc4)nn4c3C(=O)NCC4)cc2)cc1]

A mixture of 4 (120 mg, 0.409 mmol), 241 (471 mg, 1.02 mmol), $K_3PO_4$ (348 mg, 1.64 mmol) in 1,4-dioxane (2.1 mL) and $H_2O$ (0.7 mL) was carefully purged with $N_2$. $PCy_3$ (23 mg, 81.9 µmol) and $Pd(OAc)_2$ (9 mg, 40.9 µmol) were added and the r.m. was purged again with $N_2$, and stirred for 17 h at 80° C. The crude material was dissolved in water and extracted with DCM. The organic phase was dried over $MgSO_4$, filtered and evaporated in vacuo to give 447 mg, brown solid. The crude residue was purified by prep. LC on (irregular SiOH 15-40 µm 300 g MERCK, Mobile phase: 95% DCM, 5% MeOH). The desired fractions were combined and the solvent was removed in vacuo to give 100 mg of Co. 114, white solid (54%). m.p.: 252° C. (dsc).

Example A116

Preparation of Co. 115 a—Synthesis of Int. 242:

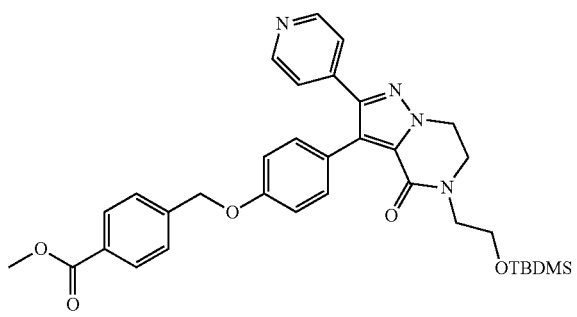 [SMILES: COC(=O)c1ccc(COc2ccc(-c3c(-c4ccncc4)nn4c3C(=O)N(CCO[Si](C)(C)C(C)(C)C)CC4)cc2)cc1]

In a microwave vial, a mixture of 28 (0.8 g, 1.77 mmol), 49 (0.848 g, 2.3 mmol), K₃PO₄ (1.51 g, 7.1 mmol) in 1,4-dioxane (7.8 mL) and H₂O (2.8 mL) was carefully purged with N₂. PdCl₂(dppf) (0.145 g, 0.18 mmol) was added and the r.m. was purged again with N₂. The r.m. was heated at 80° C. overnight. The r.m. was diluted with EtOAc and washed with water and with brine. The organic phase was dried over MgSO₄, filtered and evaporated in vacuo to give 1.66 g. The residue was purified by prep. LC (irregular SiOH 30 µm, 40 g Interchim, mobile phase gradient: from DCM 100% to DCM/MeOH/NH₄OH 97/3/0.1). The pure fractions were collected and evaporated until dryness to give 1.11 g of Int. 242 (100%).

b—Synthesis of Int. 243:

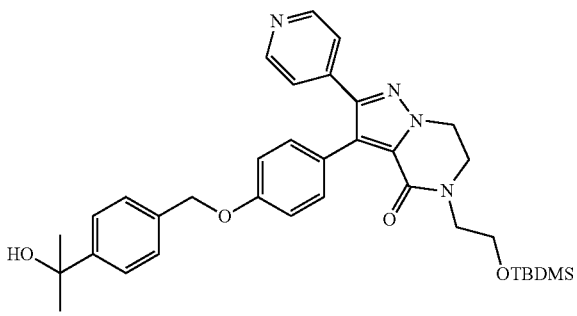 [SMILES: CC(C)(O)c1ccc(COc2ccc(-c3c(-c4ccncc4)nn4c3C(=O)N(CCO[Si](C)(C)C(C)(C)C)CC4)cc2)cc1]

MeMgCl (3.05 mL, 9.06 mmol) was added to a stirred suspension of 242 (1.11 g, 1.81 mmol) in THF (17 mL) under N₂ at 0° C. The mixture was stirred at 0° C. for 5 min, and then it was warmed to r.t. and stirred for 2 h. The r.m. was quenched with 10% NH₄Cl sol., and treated with EtOAc. The organic layer was separated, washed with brine, dried over MgSO₄, filtered and concentrated in vacuo to afford 1.09 g of Int. 243 (quant.), used as such for next step.

c—Synthesis of Co. 115:

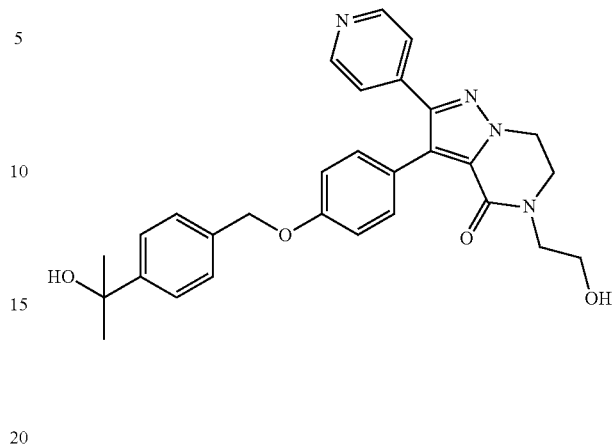

TBAF (2.02 mL, 2.02 mmol) was added dropwise to a sol. of 243 (1.03 g, 1.68 mmol) in THF (17 mL) at r.t. The mixture was stirred for 3 h at r.t. EtOAc and water were added. The organic layer was separated, dried, filtered and evaporated until dryness to give 712 mg. The residue was purified by prep. LC (Regular SiOH, 30 µm, 24 g GraceResolv™, mobile phase gradient: from DCM 100% to DCM/MeOH/NH₄OH 95/5/0.1). The pure fractions were collected and evaporated until dryness to give 490 mg which was crystallized from Et₂O, filtered and dried to give 413 mg of Co. 115, white solid (49%). m.p.: 193° C. (dsc).

Example A117

Preparation of Co. 116 a—Synthesis of Int. 244:

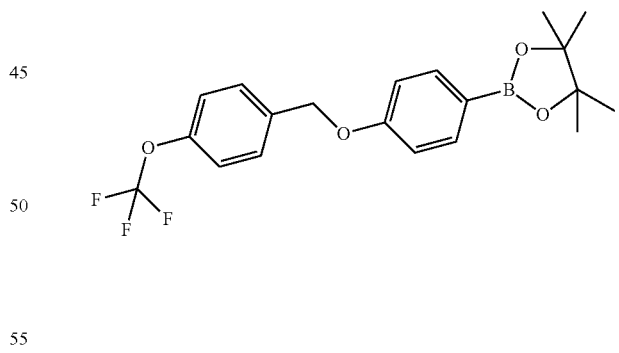

DBAD (2.04 g, 8.86 mmol) was added to a mixture of 7 (1.50 g, 6.82 mmol), 4-(trifluoromethoxy)benzyl alcohol (1.28 mL; 8.86 mmol) and PPh₃ supp. (2.95 g; 8.86 mmol) in DCM (30 mL) and the r.m. was stirred under N₂ for 17 h at rt. The r.m. was then filtered through a glass frit and washed with EtOAc. After concentration of the filtrate, the residue was purified by prep. LC (irregular SiOH 15-40 µm, solid loading, 30 g Merck, mobile phase: heptane 80%, EtOAc 20%). The pure fractions were collected and solvent evaporated until dryness to give 2.00 g of Int. 244, yellow oil (74%).

b—Synthesis of Co. 116:

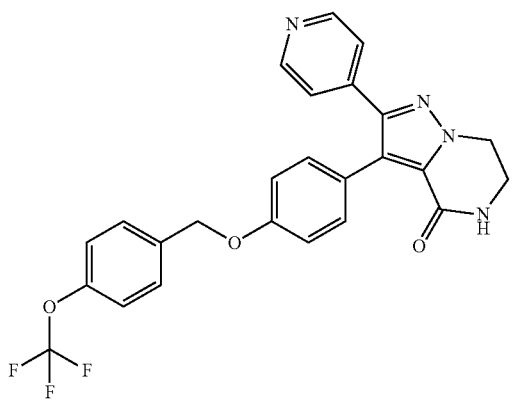 [SMILES: O=C1NCCn2nc(-c3ccncc3)c(-c3ccc(OCc4ccc(OC(F)(F)F)cc4)cc3)c21]

In a microwave vial, a mixture of 4 (150 mg, 512 μmol), 244 (504 mg, 1.28 mmol), K$_3$PO$_4$ (455 mg, 2.15 mmol) in 1,4-dioxane (2.4 mL) and H$_2$O (0.8 mL) was carefully purged with N$_2$. PCy$_3$ (30 mg, 107 μmol) and Pd(OAc)$_2$ (12 mg, 53.6 μmol) were added and the r.m. was purged again with N$_2$. The r.m. was stirred for 17 h at 80° C. The crude material was dissolved in water (10 mL) and extracted with EtOAc (2×40 mL). The organic phase was dried over MgSO$_4$, filtered and evaporated in vacuo to give 400 mg, brown solid. The solid was purified by prep. LC (irregular SiOH 15-40 μm, 30 g Merck, mobile phase gradient: from DCM 100% to DCM 90%, MeOH 10%). The pure fractions were collected and solvent evaporated until dryness to give 180 mg of Co. 116, white solid (73%). m.p.: 260° C. (dsc).

Example A118

Preparation of Co. 117 a—Synthesis of Int. 245:

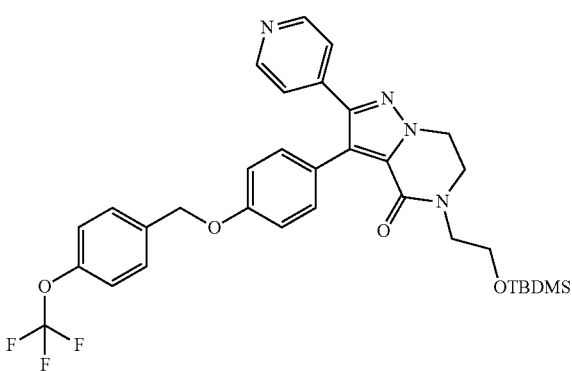 [SMILES: CC(C)(C)[Si](C)(C)OCCN1CCn2nc(-c3ccncc3)c(-c3ccc(OCc4ccc(OC(F)(F)F)cc4)cc3)c2C1=O]

In a microwave vial, a mixture of 28 (0.7 g, 1.55 mmol), 244 (0.935 g, 2 mmol), K$_3$PO$_4$ (1.32 g, 6.2 mmol) in 1,4-dioxane (6.8 mL) and H$_2$O (2.42 mL) was carefully purged with N$_2$. PdCl$_2$(dppf) (127 mg, 0.155 mmol) was added and the r.m. was purged again with N$_2$. The r.m. was heated at 80° C. overnight. The r.m. was diluted with EtOAc and washed with water (1×) and with brine (3×). The organic phase was dried over MgSO$_4$, filtered and evaporated in vacuo to give 2.17 g. The residue was purified by prep. LC (irregular SiOH 30 μm, 40 g Interchim, mobile phase: from DCM 100% to DCM/MeOH/NH$_4$OH 97/3/0.1). The pure fractions were collected and evaporated until dryness to give 923 mg of Int. 245 (93%, purity 85%), used as such for the next step.

b—Synthesis of Co. 117:

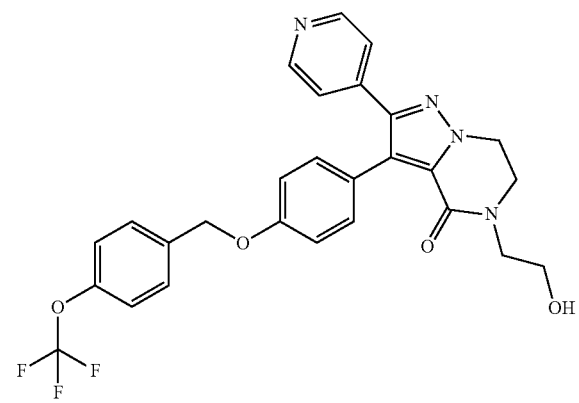 [SMILES: O=C1c2c(-c3ccc(OCc4ccc(OC(F)(F)F)cc4)cc3)c(-c3ccncc3)nn2CCN1CCO]

TBAF (1.73 mL, 1.73 mmol) was added dropwise to a sol. of 245 (920 mg, 1.44 mmol) in THF (14 mL) at r.t. The mixture was stirred for 3 h at r.t. EtOAc and water were added. The organic layer was separated, dried, filtered and evaporated until dryness to give 865 mg. The residue was purified by prep. LC (Regular SiOH, 30 μm, 12 g GraceResolv™, mobile phase gradient: from DCM 100% to DCM/MeOH/NH$_4$OH 95/5/0.1). The pure fractions were collected and evaporated until dryness to give 345 mg which was crystallized from DIPE, filtered and dried to give 319 mg of Co. 117 (42%). m.p.: 134° C. (dsc).

Example A119

Preparation of Co. 118 a—Synthesis of Int. 246:

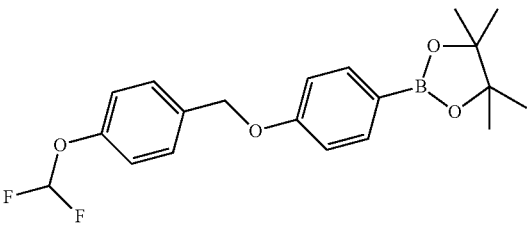 [SMILES: CC1(C)OB(c2ccc(OCc3ccc(OC(F)F)cc3)cc2)OC1(C)C]

A sol. of 7 (0.76 g, 3.45 mmol) in ACN (10 mL) was treated with K$_2$CO$_3$ (0.572 g, 4.14 mmol) and 4-(difluoromethoxy)benzyl bromide (0.9 g, 3.8 mmol) at r.t. The r.m. was stirred for 18 h at r.t. Then, water and DCM were added, and the organic layer was washed with brine, separated, dried over MgSO$_4$, filtered and concentrated in vacuo to give 1.29 g. The residue was purified by prep. LC on (Irregular SiOH 15-40 μm 30 g Merck, Mobile phase: DCM 100%). The pure fractions were collected and evaporated until dryness to give 0.73 g of Int. 246 (56%).

b—Synthesis of Co. 118:

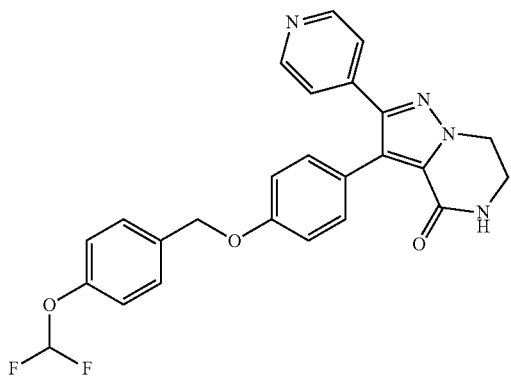 [SMILES: O=C1NCCn2nc(-c3ccncc3)c(-c3ccc(OCc4ccc(OC(F)F)cc4)cc3)c21]

In a microwave vial, a mixture of 4 (0.3 g, 1.023 mmol), 246 (0.5 g, 1.33 mmol), K$_3$PO$_4$ (0.91 g, 4.29 mmol) in 1,4-dioxane (4.8 mL) and H$_2$O (1.6 mL) was carefully purged with N$_2$. PCy$_3$ (60 mg, 0.214 mmol) and Pd(OAc)$_2$ (24 mg, 0.11 mmol) were added and the r.m. was purged again with N$_2$. The r.m. was stirred for 16 h at 80° C. The crude material was dissolved in water and extracted with EtOAc. The organic phase was dried over MgSO$_4$, filtered and evaporated in vacuo to give 745 mg. The residue was purified by prep. LC on (irregular SiOH 15-40 μm 300 g MERCK, Mobile phase: 40% Heptane, 10% MeOH (+10% NH$_4$OH), 50% EtOAc). The desired fractions were combined and the solvent was removed in vacuo to give 295 mg which was crystallized from DIPE, filtered and dried to give 287 mg of Co. 118 (61%). m.p.: 250° C. (dsc).

Example A120

Preparation of Co. 119 a—Synthesis of Int. 247:

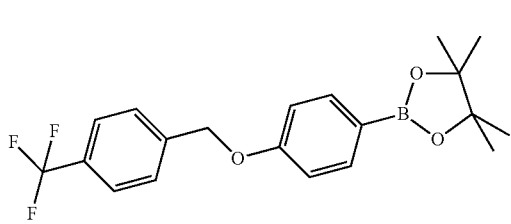 [SMILES: CC1(C)OB(c2ccc(OCc3ccc(C(F)(F)F)cc3)cc2)OC1(C)C]

DBAD (2.04 g, 8.86 mmol) was added to a mixture of 7 (1.50 g; 6.82 mmol), 4-(trifluoromethyl)benzyl alcohol (1.21 mL, 8.86 mmol) and PPh$_3$ supp. (2.95 g, 8.86 mmol) in DCM (30 mL) and the r.m. was stirred under N$_2$ for 17 h at rt. The r.m. was then filtered through a glass frit and washed with EtOAc. The sol. was concentrated to give 5.50 g, yellow oil. The residue was purified by prep. LC (irregular SiOH 15-40 μm, solid loading, 50 g Merck, mobile phase: heptane 80%, EtOAc 20%). The pure fractions were collected and solvent evaporated until dryness to give 2.23 g of Int. 247, yellow oil (87%).

b—Synthesis of Co. 119:

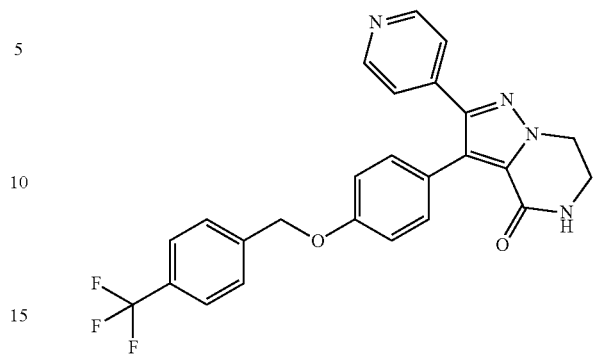

In a sealed tube, a mixture of 4 (150 mg, 512 μmol), 247 (484 mg, 1.28 mmol), K$_3$PO$_4$ (455 mg, 2.15 mmol) in 1,4-dioxane (2.4 mL) and H$_2$O (0.8 mL) was carefully purged with N$_2$. PCy$_3$ (30 mg, 107 μmol) and Pd(OAc)$_2$ (12 mg, 53.6 μmol) were added and the r.m. was purged again with N$_2$. The r.m. was stirred for 17 h at 80° C. The crude material was dissolved in water (10 mL) and extracted with EtOAc (2×40 mL). The organic phase was dried over MgSO$_4$, filtered and evaporated in vacuo to give 400 mg, brown solid. The residue was purified by prep. LC (irregular SiOH 15-40 μm, 30 g Merck, mobile phase gradient: from DCM 100% to DCM 90%, MeOH 10%). The pure fractions were collected and solvent evaporated until dryness to give 109 mg of Co. 119, white solid (46%). m.p.: 280° C. (dsc).

Example A121

Preparation of Co. 120 a—Synthesis of Int. 248:

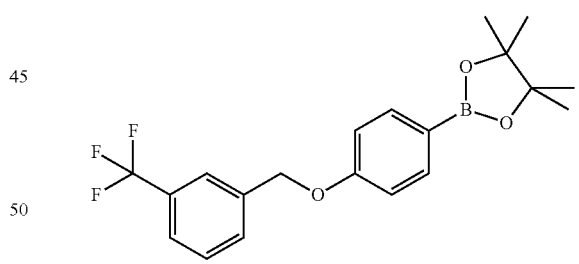

K$_2$CO$_3$ (0.455 g, 3.29 mmol) and 3-(trifluoromethyl) benzyl alcohol (0.479 mL, 3.14 mmol) were successively added to a sol. of 7 (0.345 g, 1.57 mmol) in ACN (7.84 mL). The r.m. was stirred at r.t. for 18 h. K$_2$CO$_3$ (0.130 g, 0.941 mmol) and 3-(trifluoromethyl)benzyl alcohol (0.120 mL, 0.784 mmol) were then successively added again. After 3 h at r.t., the r.m. was filtrated, washed with EtOAc and concentrated to dryness. The residue was purified by column chromatography over silica gel (15-40 μm, 50 g, mobile phase gradient: cyclohexane/DCM 50/50 to 0/100). The product fractions were collected and the solvent was evaporated until dryness to give 0.560 g of Int. 248, white solid (94%).

b—Synthesis of Co. 120:

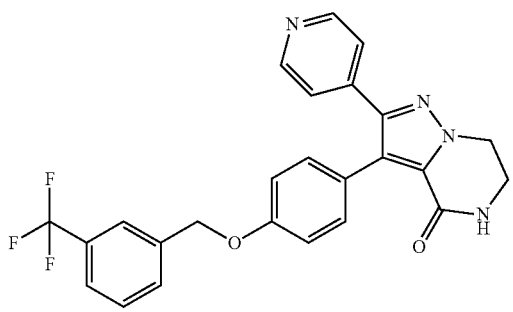 [SMILES: O=C1NCCn2nc(-c3ccncc3)c(-c3ccc(OCc4cccc(C(F)(F)F)c4)cc3)c21]

A sol. of 4 (0.14 3 g, 0.488 mmol), 248 (0.554 g, 1.46 mmol) and K₃PO₄ (0.414 g, 1.95 mmol) in 1,4-dioxane/H₂O, 3/1 (2.9 mL) was degassed with an Ar-stream for 20 min and Pd(OAc)₂ (0.011 g, 0.049 mmol) and PCy₃ (0.027 g, 0.098 mmol) were then successively added. The r.m. was heated at 80° C. for 16 h and at 120° C. for 20 h. The r.m. was diluted with water (10 mL) and extracted with EtOAc (3×20 mL). The combined organic layers were washed with a sat. aq. NaCl sol. (20 mL), filtered and concentrated to dryness. The combined aq. layers were extracted with a mixture DCM/MeOH (9/1, 3×50 mL), dried over sodium sulfate, filtered and concentrated to dryness. The residues were combined to afford 0.517 g, white powder. The powder was purified by column chromatography over silica gel (15-40 μm, 40 g, mobile phase gradient: DCM/MeOH 97/3 to 95/5). The pure fractions were collected and the solvent was evaporated to afford 0.115 g, white powder which was triturated in pentane (2 mL), filtered, washed with pentane (2 mL) and Et₂O (2×1 mL) and dried to give 0.104 g of Co. 120, white solid (46%). m.p.: 293° C. (dsc).

Example A122

Preparation of Co. 121

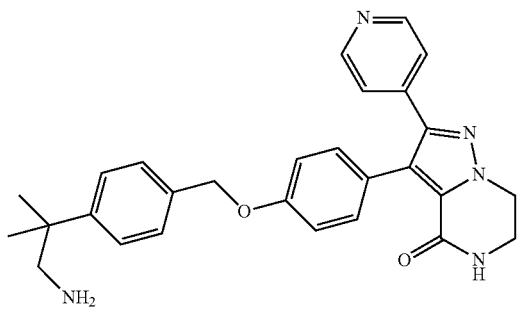 [SMILES: CC(C)(CN)c1ccc(COc2ccc(-c3c(-c4ccncc4)nn4c3C(=O)NCC4)cc2)cc1]

Co. 10 (210 mg, 0.45 mmol), Ni (210 mg) in MeOH (5 mL) was hydrogenated under 3 bars at r.t. for 4 h. The catalyst was filtered over a Celite® pad, the filtrate was evaporated. The residue was purified by prep. LC (Irregular SiOH 35-40 μm 40 g GraceResolv™, mobile phase: 90/10/0.1 DCM/MeOH/NH₄OH). The fractions were collected and evaporated to give 106 mg of initial Co., Co. 10 and 49 mg of a residue. This residue was taken up in Et₂O, the precipitate was filtered off and dried to give 39 mg which was purified again by prep. LC (Irregular SiOH 35-40 μm 40 g GraceResolv™, mobile phase: 95/5/0.1 DCM/MeOH/NH₄OH). The fractions were collected and evaporated to give 15 mg of Co. 121 (7%). m.p.: 233° C. (dsc).

Example A123

Preparation of Co. 122 a—Synthesis of Int. 249:

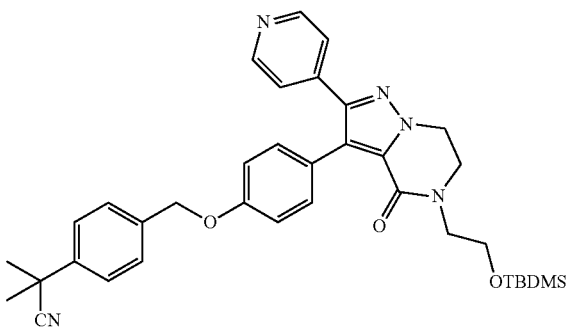 [SMILES: CC(C)(C#N)c1ccc(COc2ccc(-c3c(-c4ccncc4)nn4c3C(=O)N(CCO[Si](C)(C)C(C)(C)C)CC4)cc2)cc1]

NaH 60% (33.6 mg, 0.8 mmol) was added slowly to a suspension of Co. 10 (260 mg, 0.56 mmol) in DMSO (5.0 mL) at r.t. under N₂. The mixture was stirred for 2 h, then (2-bromoethoxy)-tert-butyldimethylsilane (128 μl, 0.62 mmol) was added and stirred overnight. Water and DCM were added, the mixture was extracted, the organic layer was separated, dried over MgSO₄, filtered and evaporated until dryness to give 440 mg of Int. 249 (mixture with Co. 122). The mixture was used as such for the final step.

b—Synthesis of Co. 122:

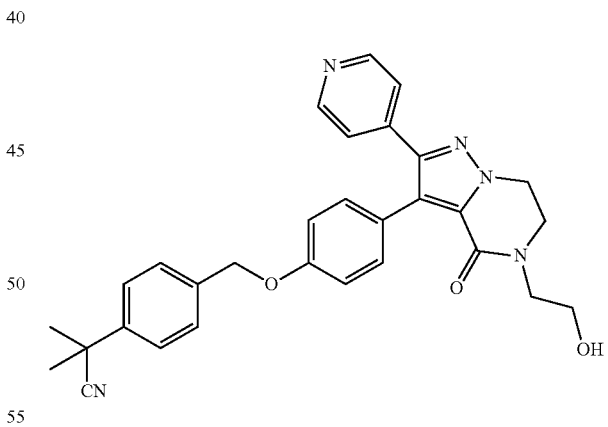

TBAF (0.90 mL, 0.90 mmol) was added dropwise to a sol. of 249 (440 mg, 0.71 mmol) in THF (10 mL) at r.t. The mixture was stirred 90 min at r.t. and poured into water, extracted with DCM. The organic layer was dried over MgSO₄, filtered and evaporated until dryness. The residue was purified by prep. LC (Regular SiOH, 30 μm, 25 g grace, mobile phase gradient: DCM/MeOH/NH₄OH from 97/3/0.1 to 94/6/0.1). The pure fractions were collected and solvent evaporated until dryness to give 150 mg. The residue was crystallized from Et₂O, the solid was filtered off and dried to give 120 mg of Co. 122 (33%). m.p.: 199° C. (dsc).

Example A124

Preparation of Co. 123 a—Synthesis of Int. 250:

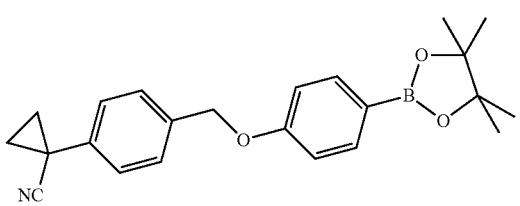 [SMILES: CC1(C)OB(c2ccc(OCc3ccc(C4(C#N)CC4)cc3)cc2)OC1(C)C]

PPh₃ supp. (1.55 g, 4.97 mmol) and DBAD (1.15 g, 4.97 mmol) were added to a stirred sol. of 7 (912 mg, 4.14 mmol) and 1-[4-(hydroxymethyl)phenyl]cyclopropane-1-carbonitrile (970 mg, 4.14 mmol) in anhydrous DCM (20 mL) under N₂ at r.t. The r.m. was stirred at r.t. for 2 h, and then the crude mixture was filtered off and the filtrate was diluted with DCM and sat NaHCO₃. The organic layer was separated, dried over MgSO₄, filtered and evaporated in vacuo to give 2.81 g, brown solid. The solid was purified by prep. LC (Irregular SiOH 50 µm, 120 g Grace, mobile phase gradient: from DCM 40%, Heptane 60% to DCM 100%). The desired fractions were collected and evaporated in vacuo to give 910 mg of Int. 250 (a solid) which was used as such for the next reaction step.

b—Synthesis of Co. 123:

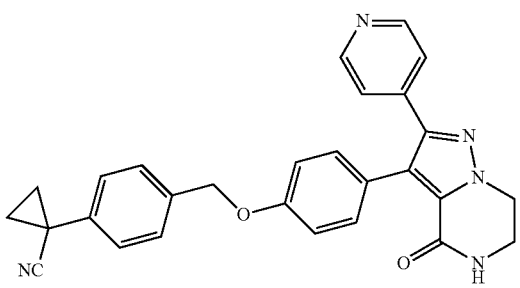 [SMILES: N#CC1(c2ccc(COc3ccc(-c4c(-c5ccncc5)nn5c4C(=O)NCC5)cc3)cc2)CC1]

A mixture of 4 (0.464 g, 1.58 mmol), 250 (0.900 g, 2.40 mmol) and K₃PO₄ (1.01 g, 4.75 mmol) in 1,4-dioxane (9 mL) and H₂O (3 mL) was carefully purged with N₂. PCy₃ (89 mg, 0.317 mmol) and Pd(OAc)₂ (36 mg, 0.158 mmol) were added and the r.m. was purged again with N₂. The r.m. was stirred for 18 h at 80° C. The crude material was dissolved in water and extracted with DCM. The organic phase was washed with brine, dried over MgSO₄, filtered and evaporated in vacuo to give 2.29 g, yellow solid. The solid was purified by prep. LC (irregular SiOH 15-40 µm, 80 g Grace, mobile phase gradient: from DCM 100% to DCM 95%, MeOH 5%). The desired fractions were collected and solvent evaporated to give 253 mg, white solid. The residue was purified by prep. LC (Stationary phase: X-Bridge-C18 5 µm 30*150 mm, Mobile phase gradient: from 70% (NH₄HCO₃ 0.5% aq. sol.), 30% ACN to 100% ACN). The desired fractions were isolated and evaporated in vacuo to yield 70 mg of Co. 123, white solid (10%). m.p.: 260° C. (dsc).

Example A125

Preparation of Co. 124 a—Synthesis of Int. 251:

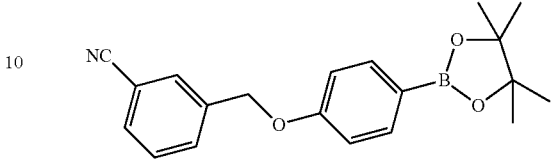

A sol. of 7 (1.5 g, 6.82 mmol) in ACN (15 mL) and DMF (3 mL) was treated with C (1.13 g; 8.18 mmol) and 3-(bromomethyl)benzonitrile (1.55 g, 7.50 mmol) at rt. The r.m. was stirred for 36 h at r.t. Water and EtOAc were added, and the organic layer was washed with brine, separated, dried over MgSO₄, filtered and evaporated in vacuo to afford 2.63 g of Int. 251, (quant. yield).

b—Synthesis of Co. 124:

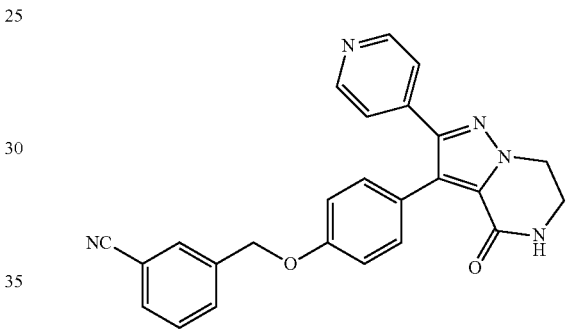

A mixture of 4 (0.87 g, 2.98 mmol), 251 (2.63 g, 7.45 mmol), K₃PO₄ (2.53 g, 11.9 mmol) in 1,4-dioxane (12 mL) and H₂O (4 mL) was carefully purged with N₂. PCy₃ (167 mg, 0.596 mmol) and Pd(OAc)₂ (67 mg, 0.298 mmol) were added, and the r.m. was purged again with N₂. The r.m. was stirred for 17 h at 80° C. The crude material was dissolved in water and extracted with EtOAc. The organic phase was washed with brine, dried over MgSO₄, filtered and evaporated in vacuo to give a solid. This solid was purified by prep. LC (irregular SiOH 15-40 rm, 120 g Grace, mobile phase gradient: from DCM 100% to DCM 89%, MeOH 11%). The pure fractions were collected and solvent evaporated until dryness to give 1.09 g, white solid. The solid was triturated with DCM, filtered and dried to yield 576 mg of Co. 124, white solid (46%). m.p.: 238° C. (dsc).

Example A126

Preparation of Co. 125 a—Synthesis of Int. 252:

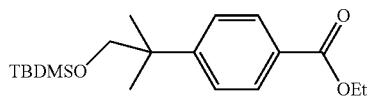

4-(2-hydroxy-1,1-dimethylethyl)-benzoic acid, ethyl ester (0.513 g, 2.3 mmol), tert-butyldimethylsilyl chloride (0.522 g, 3.46 mmol), and imidazole (0.47 g, 6.92 mmol) in DMF (6 mL) was stirred at r.t. for 3 h. Water and DCM were added and the mixture was extracted with DCM. The organic layer was dried, filtered and evaporated to give 667 mg of Int. 252 (86%).

b—Synthesis of Int. 253:

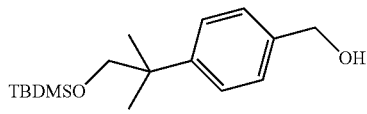 [SMILES: CC(C)(CO[Si](C)(C)C(C)(C)C)c1ccc(CO)cc1]

LAH (36 mg, 0.94 mmol) was added carefully at 5° C. to a sol. of 252 (210 mg, 0.62 mmol) in THF (3 mL). The mixture was stirred at r.t. for 1 h. Water was carefully added at 5° C. and EtOAc was added. The mixture was extracted, the organic layer was separated, dried over MgSO₄, filtered and evaporated to give 180 mg of Int. 253 (98%).

c—Synthesis of Int. 254:

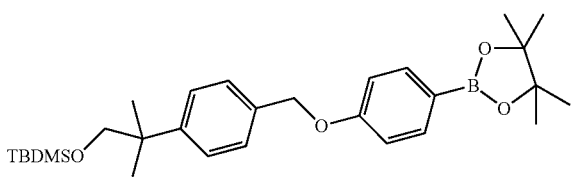 [SMILES: CC(C)(CO[Si](C)(C)C(C)(C)C)c1ccc(COc2ccc(B3OC(C)(C)C(C)(C)O3)cc2)cc1]

To a suspension of 253 (0.515 g, 1.75 mmol), 7 (0.462 g, 2.1 mmol), DBAD (0.483 g, 2.1 mmol) in dry DCM (6 mL) was added PPh₃ supp. (0.656 g, 2.1 mmol) and the r.m. was stirred at r.t. for 18 h. The insoluble was filtered through Celite®, washed with DCM. Water was added and the organic layer was separated, dried, filtered and concentrated until dryness to give 1.29 g. The residue was purified by prep. LC on (Irregular SiOH 15-40 μm 50 g Merck, Mobile phase gradient: from 100% Heptane to 95/5 Heptane/EtOAc). The pure fractions were collected and evaporated until dryness to give 625 mg of Int. 254 (72%).

d—Synthesis of Int. 255:

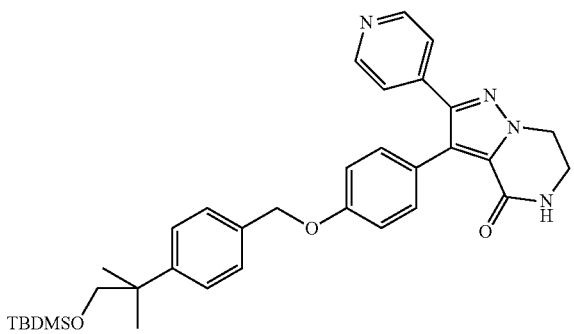 [SMILES: CC(C)(CO[Si](C)(C)C(C)(C)C)c1ccc(COc2ccc(-c3c(-c4ccncc4)nn4c3C(=O)NCC4)cc2)cc1]

In a microwave vial, a mixture of 4 (0.218 g, 0.744 mmol), 254 (0.6 g, 0.967 mmol), K₃PO₄ (0.662 g, 3.12 mmol) in 1,4-dioxane (3.5 mL) and H₂O (1.2 mL) was carefully purged with N₂. PdCl₂(dppf) (61 mg, 0.074 mmol) was added and the r.m. was purged again with N₂. The r.m. was stirred for 16 h at 80° C. The crude material was dissolved in water and extracted with EtOAc. The organic phase was dried over MgSO₄, filtered and evaporated in vacuo to give 828 mg. The residue was purified by prep. LC (Stationary phase: irregular 15-40 μm 30 g Merck, Mobile phase: NH₄OH/DCM/MeOH 0.4/96/4) to give 180 mg of Int. 255 (42%).

e—Synthesis of Co. 125:

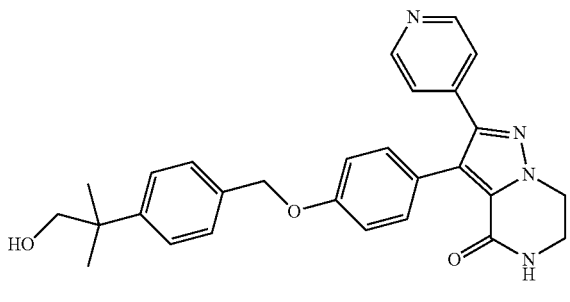 [SMILES: CC(C)(CO)c1ccc(COc2ccc(-c3c(-c4ccncc4)nn4c3C(=O)NCC4)cc2)cc1]

TBAF (0.37 mL, 0.37 mmol) was added dropwise to a sol. of 255 (0.18 g, 0.31 mmol) in THF (3.0 mL) at r.t. The mixture was stirred 2 h at r.t. 1 equivalent of TBAF was added and the reaction was let at r.t. overnight to complete the reaction. The mixture was evaporated to dryness and purified by prep. LC (irregular SiOH 15-40 μm, 12 g, GraceResolv™, Mobile phase: DCM/MeOH/NH₄OH, 96/4/0.1). The pure fractions were collected and solvent was evaporated until dryness to give 110 mg, white solid. The solid was triturated in Et₂O, filtrated and dried to give 97 mg of Co. 125, white solid (67%). m.p.: 280° C. (dsc).

Example A127

Preparation of Co. 126 a—Synthesis of Int. 256:

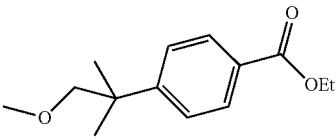 [SMILES: CCOC(=O)c1ccc(C(C)(C)COC)cc1]

To a sol. of 4-(2-hydroxy-1,1-dimethylethyl)-benzoic acid, ethyl ester (0.54 g, 2.43 mmol) in DMF (8 mL) was added MeI (0.76 mL, 12.1 mmol) and NaH 60% (0.146 g, 3.65 mmol). The mixture was stirred at r.t. for 3 h. The reaction was quenched with water, and extracted with EtOAc. The organic layer was separated, washed with K₂CO₃ 10%, dried over MgSO₄, filtered and concentrated to give 566 mg of Int. 256 (99%, mixture of ethyl and methyl ester 88/12 was observed).

b—Synthesis of Int. 257:

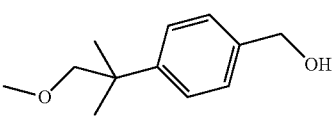

LAH (0.111 g, 2.92 mmol) was added carefully at 10° C. to a sol. of 256 (0.46 g, 1.95 mmol) in THF (6 mL). Cooled bath was removed immediately and the mixture was stirred at r.t. for 1 h. Water was carefully added at 5° C. and EtOAc was added, the mixture was extracted, the organic layer was separated, dried over MgSO₄, filtered and evaporated to give 370 mg of Int. 257 (98%).

c—Synthesis of Int. 258:

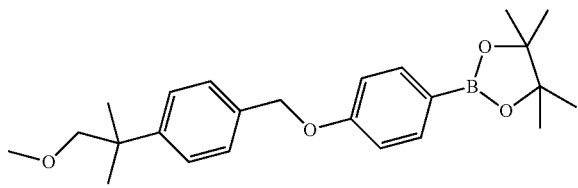

To a suspension of 257 (0.37 g, 1.91 mmol), 7 (0.504 g, 2.2 9 mmol), PPh₃ supp. (0.716 g, 2.29 mmol) in dry DCM (6 mL) was added DBAD (0.528 g, 2.29 mmol) and the r.m. was stirred at r.t. for 18 h. The insoluble was filtered through Celite® pad, washed with DCM. Water was added and the organic layer was separated, dried, filtered and concentrated until dryness to give 1.45 g. The residue was purified by prep. LC on (Irregular SiOH 15-40 µm 50 g Merck, Mobile phase gradient: from 95/5 Heptane/EtOAc to 90/10 Heptane/EtOAc). The pure fractions were collected and evaporated until dryness to give 421 mg of Int. 258 (56%).

d—Synthesis of Co. 126:

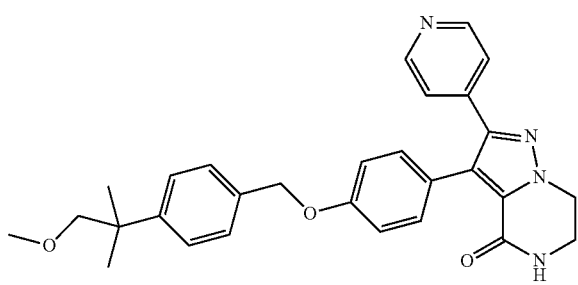 [SMILES: COCC(C)(C)c1ccc(COc2ccc(-c3c(-c4ccncc4)nn4c3C(=O)NCC4)cc2)cc1]

In a microwave vial, a mixture of 4 (0.2 g, 0.682 mmol), 258 (0.439 g, 0.887 mmol), K₃PO₄ (0.607 g, 2.86 mmol) in 1,4-dioxane (3.2 mL) and H₂O (1 mL) was carefully purged with N₂. PdCl₂(dppf) (56 mg, 0.068 mmol) was added and the r.m. was purged again with N₂. The r.m. was stirred for 16 h at 80° C. The crude material was dissolved in water and extracted with EtOAc. The organic phase was dried over MgSO₄, filtered and evaporated in vacuo to give 680 mg. The residue was purified by prep. LC (Stationary phase: Stability Silica 5 µm 150×30.0 mm, Mobile phase gradient: from 0.2% NH₄OH, 98% DCM, 2% MeOH to 1% NH₄OH, 89% DCM, 10% MeOH). The pure fractions were collected and solvent was evaporated until dryness to give 85 mg which was crystallized from Et₂O, filtered and dried to give 46 mg of Co. 126 (14%). m.p.: 212° C. (dsc).

Example A128

Preparation of Co. 127 a—Synthesis of Int. 259:

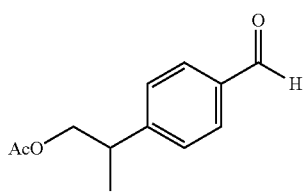

A mixture of 2-phenyl-1-propanol acetate (3.0 g, 16.8 mmol) and Alpha,alpha dichloromethyl methyl ether (3.87 g, 33.7 mmol) in dry DCM (15 mL) was cooled to 0° C. and treated with Titanium(IV) chloride 1M in DCM (84 mL, 84.2 mmol) over 15 min. The r.m. was then warmed to r.t. and stirred for 17 h at r.t. The crude mixture was poured into ice. DCM was added and the organic layer was separated, washed with brine, dried over MgSO₄ and evaporated in vacuo to afford 3.8 g of Int. 259, black oil (quant.), used as such for the next step.

b—Synthesis of Int. 260:

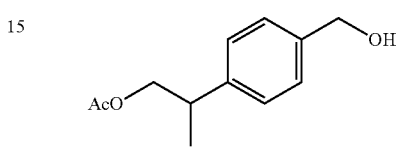

A sol. of 259 (3.70 g, 17.9 mmol) in THF (40 mL) was treated with NaBH₄ (1.36 g, 35.9 mmol) and stirred at r.t. for 1 h. After addition of water and DCM, the organic layer was separated, washed with brine, dried over MgSO₄ and evaporated in vacuo to give 3.6 g. The crude mixture was purified by prep. LC (irregular SiOH 15-40 µm, 120 g, GraceResolv™, solid loading, mobile phase gradient: from heptane 60%, EtOAc 40% to heptane 20%, EtOAc 80%). The pure fractions were collected and solvent evaporated until dryness to give 2.19 g of Int. 260, yellow oil (59%).

c—Synthesis of Int. 261:

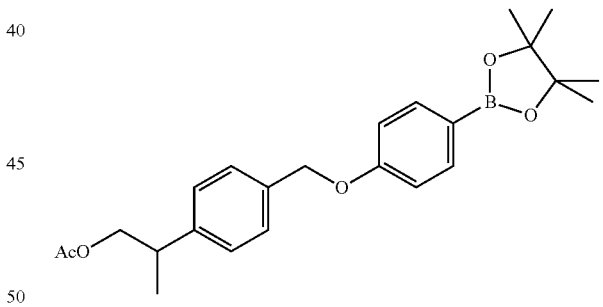

A mixture of 260 (2.19 g, 10.5 mmol), 7 (1.78 g; 8.09 mmol), PPh₃ (2.76 g, 10.5 mmol) in dry THF (50 mL) was treated with DBAD (2.42 g, 10.5 mmol) and stirred at r.t. for 2h 30. The r.m. was then poured in DCM, washed with water, dried over MgSO₄ and evaporated in vacuo to afford a residue. The residue was purified by prep. LC (irregular SiOH 15-40 µm, 120 g, GraceResolv™, solid loading, mobile phase gradient: from heptane 90%, EtOAc 10% to heptane 60%, EtOAc 40%). The pure fractions were collected and solvent evaporated until dryness to give 3.18 g of Int. 261, colorless oil (96%).

d—Synthesis of Co. 127:

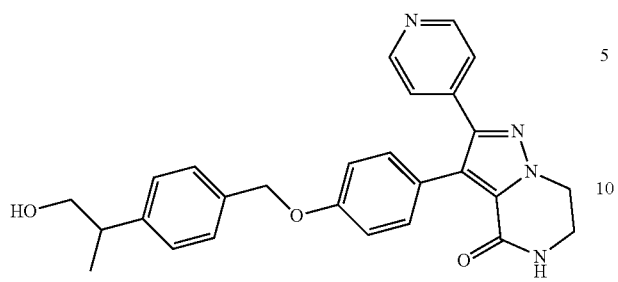

A mixture of 4 (500 mg, 1.71 mmol), 261 (1.40 g, 3.41 mmol) and K₃PO₄ (1.27 g, 5.97 mmol) in 1,4-dioxane (5 mL) and H₂O (10 mL) was purged with N₂. Then, PdCl₂(dppf) (140 mg, 171 µmol) was added. The mixture was purged again with N₂ and heated at 120° C. using one single mode microwave (Biotage Initiator EXP 60) with a power output ranging from 0 to 400 W for 30 min [fixed hold time]. The r.m. was poured in MeOH (20 mL) and stirred at 100° C. for 2 h and poured in DCM and water. The organic layer was separated, washed with brine, dried over MgSO₄ and evaporated in vacuo. The brown residue was purified by prep. LC (irregular SiOH 15-40 µm, 80 g, GraceResolv™, Mobile phase gradient: from DCM 100% to DCM 92%, MeOH 8%). The pure fractions were collected and solvent evaporated to give 720 mg of off-white solid. The solid was triturated in MeOH. After filtration, the white solid was washed with Et₂O, collected and dried in vacuo to afford 558 mg of Co. 127, white solid (72%). m.p.: 259° C. (dsc).

Example A129

Preparation of Co. 128 a—Synthesis of Int. 262:

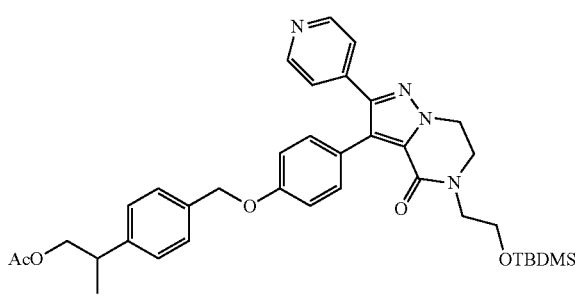 [SMILES: CC(=O)OCC(C)c1ccc(COc2ccc(-c3c(-c4ccncc4)nn4c3C(=O)N(CCO[Si](C)(C)C(C)(C)C)CC4)cc2)cc1]

In a microwave vial, a mixture of 28 (0.8 g, 1.77 mmol), 261 (0.945 g, 2.3 mmol), K₃PO₄ (1.51 g, 7.09 mmol) in 1,4-dioxane (7.8 mL) and H₂O (2.8 mL) was carefully purged with N₂. PdCl₂(dppf) (0.145 g, 0.18 mmol) was added and the r.m. was purged again with N₂. The r.m. was heated at 80° C. overnight. The r.m. was diluted with EtOAc and washed with water and with brine. The organic phase was dried over MgSO₄, filtered and evaporated in vacuo to give 2.5 g. The residue was purified by prep. LC (irregular SiOH 15-40 µm, 80 g grace, mobile phase gradient: from DCM 100% to DCM/MeOH/NH₄OH 97/3/0.1). The desired fractions were collected and evaporated until dryness to give 1.3 g. The residue was purified by prep. LC (Regular SiOH 30 µm, 40 g Interchim, liquid loading, mobile phase gradient: DCM 100% to DCM 97%, MeOH 3%). The pure fractions were collected and the solvent was evaporated until dryness to give 996 mg of Int. 262 (yield 86%; purity 100%) and 229 mg of impure Int. 262 (yield 20%; purity 78%). Both fractions were combined and used as such, together, for the next step. Global yield: 1.2 g of Int. 262.

b—Synthesis of Int. 263:

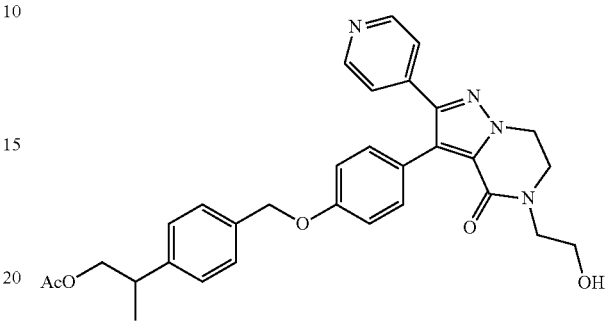

TBAF (2.25 mL, 2.25 mmol) was added dropwise to a sol. of 262 (1.23 g, 1.89 mmol) in THF (18 mL) at r.t. The mixture was stirred for 2 h at r.t. EtOAc and water were added. The organic layer was separated, dried, filtered and evaporated until dryness to give 1.04 g of Int. 263 (100%).

c—Synthesis of Co. 128:

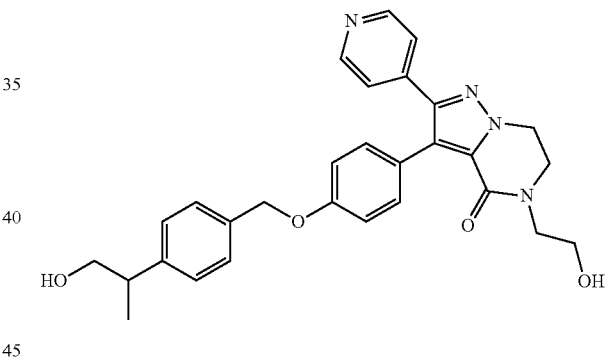

To a sol. of 263 (1 g, 1.85 mmol) in MeOH (12 mL) was added Potassium hydroxide (399 mg, 5.55 mmol) and the mixture was heated at 50° C. for 3 h. The solid formed was filtered and washed from Et₂O then poured into water and extracted with DCM and few MeOH several times. The organic layer was separated, dried, filtered and evaporated until dryness to give 764 mg. The residue was purified by prep. LC (irregular SiOH 15-40 µm, 24 g grace, mobile phase gradient: from DCM 100% to DCM/MeOH/NH₄OH 94/6/0.1). The pure fractions were collected and evaporated until dryness to give 648 mg which was crystallized from Et₂O, filtered and dried to give 538 mg. This residue was purified by achiral SFC (Stationary phase: Chiralpak IA 5 µm 250*20 mm, Mobile phase: 55% CO₂, 45% MeOH (0.3% iPrNH₂)). The pure fractions were collected and evaporated until dryness to give 400 mg which was crystallized from Et₂O, filtered off and dried to give 384 mg of Co. 128 (42%).

Example A130

Preparation of Co. 129 a—Synthesis of Int. 264:

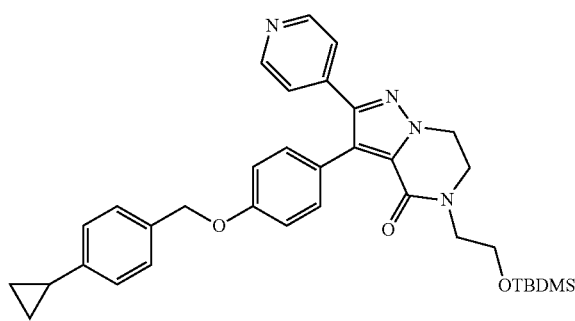

In a schlenk tube, a mixture of 28 (4.0 g, 8.9 mmol), 32 (3.4 g, 9.8 mmol), $K_3PO_4$ (7.5 g, 35 mmol) in 1,4-dioxane (39 mL) and $H_2O$ (14 mL) was carefully purged with $N_2$. $PdCl_2$(dppf) (726 mg, 0.89 mmol) was added and the r.m. was purged again with $N_2$. The r.m. was heated at 80° C. overnight. The r.m. was diluted with EtOAc and washed with water (once) and with brine (3 times). The organic phase was dried over $MgSO_4$, filtered on a pad of Celite®) and evaporated in vacuo to give 7.5 g of Int. 264, brown oil (quant., purity 70%). The Co. was used like this in the next step.

b—Synthesis of Co. 129:

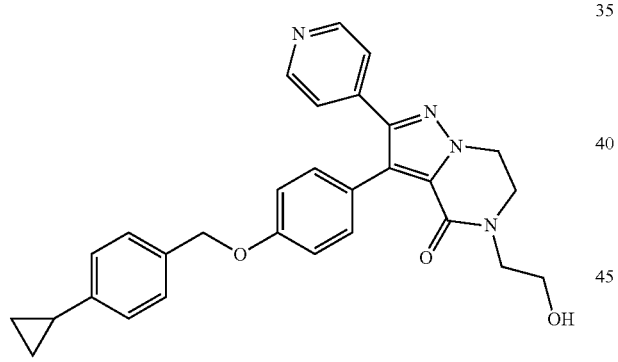

TBAF (10.6 mL, 10.6 mmol) was added dropwise to a sol. of 264 (7.5 g, 8.8 mmol, 70%) in THF (86 mL) at r.t. The mixture was stirred overnight at r.t. The mixture was concentrated and the residue was purified by prep. LC (Regular SiOH, 30 µm, 120 g GraceResolv™, mobile phase: DCM/MeOH/$NH_4OH$ 96/4/0.1). The desired fractions were collected and solvent evaporated until dryness to give 4.0 g of colorless oil which was triturated in $Et_2O$. The white solide formed was filtrated, washed and dried to give 3.22 g, white solide (3% of TBAF). The residue was added to the previous filtrate and evaporated to give 4.0 g, grey solid and it was purified by achiral SFC (Stationary phase: 2-ethylpyridine 6 µm 150×21.2 mm, Mobile phase: 80% $CO_2$, 20% MeOH (0.3% iPrNH$_2$)). The pure fractions were collected and solvent evaporated until dryness to give 2.96 g which was triturated in $Et_2O$. The white solid formed was filtrated and dried to give 2.85 g of Co. 129, white solid (67%). m.p.: 194° C. (dsc).

Example A131

Preparation of Co. 130 a—Synthesis of Int. 265:

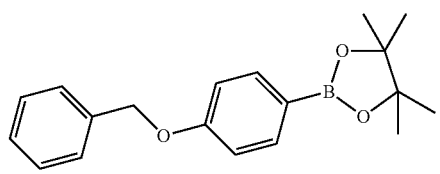 [SMILES: CC1(C)OB(c2ccc(OCc3ccccc3)cc2)OC1(C)C]

To a suspension of 7 (0.3 g, 1.36 mmol), benzyl alcohol (0.169 mL, 1.63 mmol), PPh$_3$ supp. (0.43 g, 1.63 mmol) in dry DCM (10 mL) was added DBAD (0.377 g, 1.63 mmol) and the r.m. was stirred at r.t. for 18 h. The insoluble was filtered through Celite®, washed with DCM. Water was added and the organic layer was separated, dried, filtered and concentrated until dryness to give 756 mg. The residue was purified by prep. LC (irregular SiOH 15-40 µm 30 g Merck, mobile phase gradient: from DCM 100% to DCM 98%, MeOH 2%). The fractions were collected and evaporated until dryness to give 217 mg of Int. 265 (51%).

b—Synthesis of Co. 130:

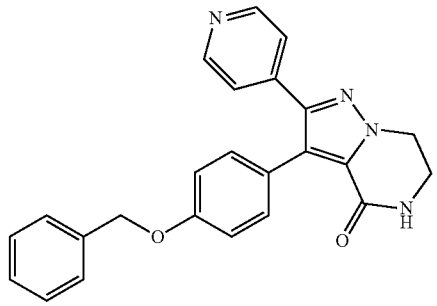 [SMILES: O=C1NCCn2nc(-c3ccncc3)c(-c3ccc(OCc4ccccc4)cc3)c21]

In a microwave vial, a mixture of 4 (0.137 g, 0.466 mmol), 265 (0.217 g, 0.7 mmol), $K_3PO_4$ (0.415 g, 1.96 mmol) in 1,4-dioxane (2.19 mL) and $H_2O$ (0.73 mL) was carefully purged with $N_2$. PCy$_3$ (27 mg, 0.098 mmol) and Pd(OAc)$_2$ (11 mg, 0.049 mmol) were added and the r.m. was purged again with $N_2$. The r.m. was stirred for 16 h at 80° C. The crude material was dissolved in water and extracted with EtOAc. The organic phase was dried over MgSO$_4$, filtered and evaporated in vacuo to give 272 mg. The residue was purified by prep. LC on (Sunfire Silica 5 µm 150×30.0 nm, Mobile phase Gradient: from 70% Heptane, 2% MeOH, 28% EtOAc to 20% MeOH, 80% EtOAc). The pure fractions were collected and evaporated until dryness to give 42 mg which was crystallized from DIPE, filtered and dried to give 40 mg of Co. 130 (22%). m.p.: 260° C. (dsc).

Example A132

Preparation of Co. 131 a—Synthesis of Int. 266:

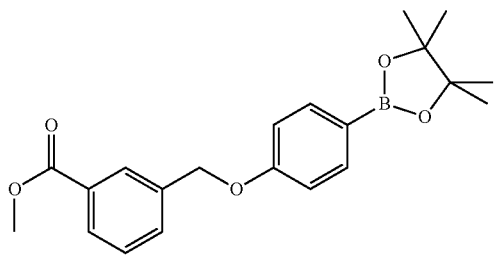 [SMILES: COC(=O)c1cccc(COc2ccc(B3OC(C)(C)C(C)(C)O3)cc2)c1]

7 (2.00 g, 9.09 mmol) was dissolved in ACN (20 mL). K₂CO₃ (1.51 g, 10.9 mmol) and methyl 3-(bromomethyl)benzoate (2.19 g, 9.54 mmol) were added. The r.m. was stirred for 2 h at r.t. An extra amount of methyl 3-(bromomethyl)benzoate (0.208 g, 0.909 mmol) was then added, as well as DMF (1 mL). The r.m. was stirred at r.t. for 17 h. The crude mixture was diluted in EtOAc, washed with water and brine (3 times). The organic layer was separated, dried over MgSO₄ and evaporated in vacuo to afford 3.82 g of Int. 266, pale pink oil (Quant.).

b—Synthesis of Co. 131:

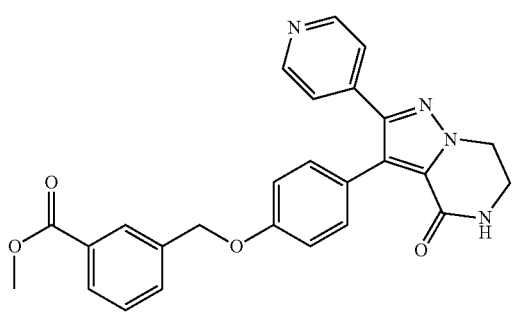 [SMILES: COC(=O)c1cccc(COc2ccc(-c3c(-c4ccncc4)nn4c3C(=O)NCC4)cc2)c1]

A mixture of 4 (800 mg, 2.73 mmol), 266 (2.01 g, 5.46 mmol), K₃PO₄ (1.74 g, 8.19 mmol) in 1,4-dioxane (45 mL) and H₂O (15 mL) was carefully purged with N₂. PCy₃ (153 mg, 0.546 mmol) and Pd(OAc)₂ (61 mg, 273 μmol) were added, and the r.m. was purged again with N₂. The r.m. was stirred for 17 h at 80° C. The crude material was dissolved in water and extracted 2× with DCM. The organic phase was separated, dried over MgSO₄, filtered and evaporated in vacuo to give a solid. The solid was purified by prep. LC (irregular SiOH 15-40 μm, 30 g Merck, dry loading, mobile phase gradient: from DCM 100% to DCM 95%, MeOH 5%). The pure fractions were collected and solvent evaporated until dryness to give 782 mg, white solid. The solid was triturated in pentane and the supernatant was removed. This operation was repeated twice and the solid was dried in vacuo to give 700 mg of Co. 131, white solid (56%). m.p.: 222° C. (dsc).

Example A133

Preparation of Co. 132 and Co. 133 a—Synthesis of Int. 267:

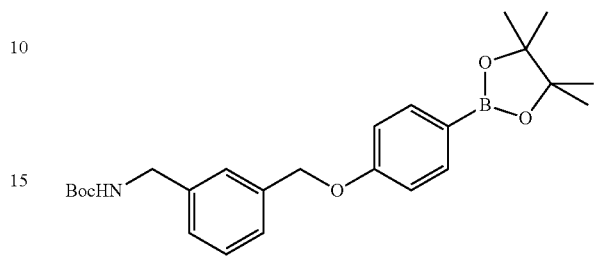

A mixture of 7 (337 mg, 1.53 mmol), (3-hydroxymethylbenzyl)-carbamic acid tert-butyl ester (450 mg, 1.84 mmol) and PPh₃ supp. (523 mg, 1.99 mmol) in DCM (15 mL) was treated with DBAD (459 mg, 1.99 mmol) and stirred at r.t. for 17 h. Silica gel was added and the crude mixture was directly evaporated in vacuo to afford a silica supported material. The material was purified by prep. LC (irregular SiOH 15-40 μm, 40 g Merck, mobile phase: DCM 100%). The pure fractions were collected and solvent evaporated to give 470 mg of Int. 267, colorless oil (70%).

b—Synthesis of Co. 132:

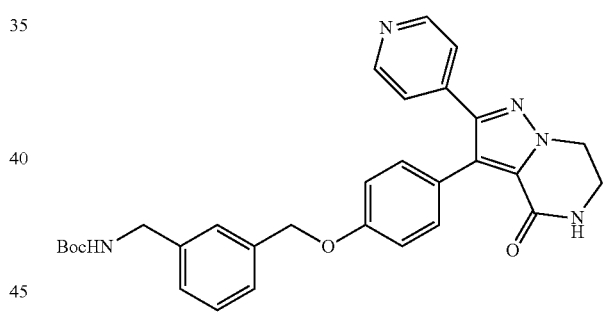

A mixture of 4 (180 mg, 0.614 mmol), 267 (470 mg, 1.07 mmol), K₃PO₄ (391 mg, 1.84 mmol) in 1,4-dioxane (10 mL) and H₂O (4 mL) was carefully purged with N₂. PCy₃ (34 mg, 0.123 mmol) and Pd(OAc)₂ (14 mg, 61.4 μmol) were added, and the r.m. was purged again with N₂. The r.m. was stirred for 17 h at 80° C. The crude material was dissolved in water and extracted 2× with DCM. The organic phase was separated, dried over MgSO₄, filtered and evaporated in vacuo to give a solid. The solid was purified by prep. LC (irregular SiOH 15-40 μm, 30 g Merck, mobile phase gradient: from DCM 100% to DCM 95%, MeOH 5%). The pure fractions were collected and solvent evaporated until dryness to give 300 mg, white solid. This solid was triturated in pentane and the supernatant was removed. This operation was repeated 2× and the solid was dried in vacuo to afford 280 mg of Co. 132, white solid (87%). m.p.: 186° C. and 194° C. (dsc).

259
c—Synthesis of Co. 133:

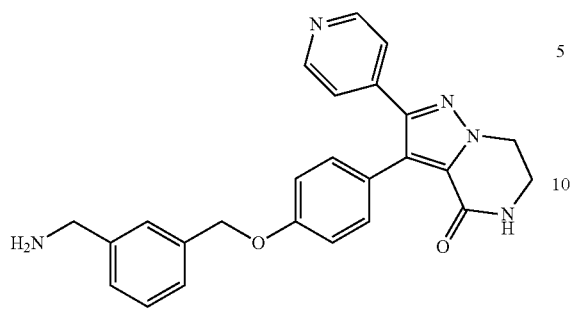

A sol. of Co. 132 (230 mg, 0.438 mmol) in HCl 3N (5 mL) and EtOH (5 mL) was stirred for 17 h at r.t. The r.m. was diluted in DCM and basified with a sat. aq. sol. of NaHCO₃. The organic layer was separated, dried over MgSO₄ and evaporated in vacuo to afford 180 mg. The solid was triturated in Et₂O and the supernatant was removed. This operation was repeated twice and the white powder was dried in vacuo to afford 150 mg. This solid was purified by prep. LC (irregular SiOH 15-40 µm, 12 g Merck, mobile phase gradient: from DCM 98%, MeOH 2% to DCM 95%, MeOH 4.8%, NH₄OH 0.2%). The pure fractions were collected and solvent evaporated until dryness to give 132 mg of Co. 133, white solid (71%). m.p.: 154° C. and 238° C. (dsc).

Example A134

Preparation of Co. 134

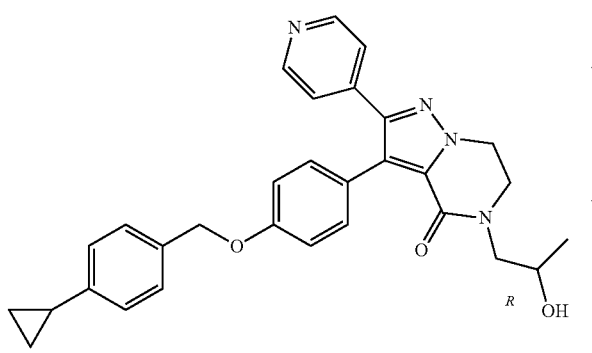

NaH (825 mg, 20.6 mmol) was added slowly to a suspension of Co. 4 (6 g, 13.75 mmol) in dry DMF (80 mL) at r.t. under N₂. The mixture was stirred for 2 h then (R)-(+)-propylene oxide (1.92 mL, 27.5 mmol) was added and stirred overnight. The mixture was poured into water and K₂CO₃ and extracted with EtOAc. The organic layer was evaporated until dryness to give 6.7 g. The residue was purified by prep. LC (120 g of SiOH 35-40 µm GraceResolv™, mobile phase gradient: from 100% DCM to 90% DCM, 10% CH₃OH, 0.1% NH₄OH). The desired fractions were collected and the solvent was evaporated to give a residue (2.96 g) which was crystallized from Et₂O, filtered and dried to give 2.71 g of Co. 134 (R) (40%). m.p.: 196° C. (dsc); [α]$_d$: −25.87° (589 nm, c 0.2435 w/v %, DMF, 20° C.)

260
Example A135

Preparation of Co. 135

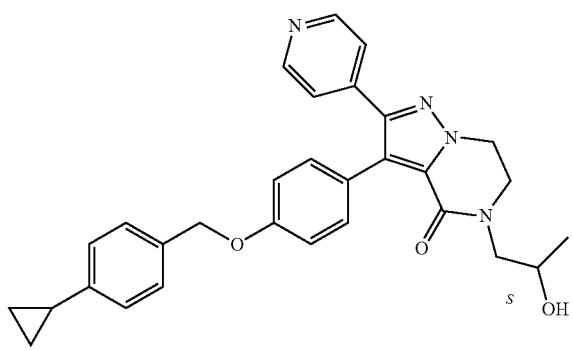

NaH (0.825 g, 20.6 mmol) was added portionwise to a suspension of Co. 4 (6 g, 13.75 mmol) in DMF (80 mL) at r.t. under N₂. The mixture was stirred for 2 h. (S)-(−)-propylene oxide (1.92 mL, 27.5 mmol) was added dropwise and stirred for 20 h. The mixture was poured into water and K₂CO₃ and extracted with EtOAc. The organic layer was evaporated until dryness to give 6.6 g. The residue was purified by prep. LC (120 g of SiOH 35-40 µm GraceResolv™, mobile phase gradient: from 100% DCM to 90% DCM, 10% MeOH, 0.1% NH₄OH). The desired fractions were collected and evaporated to give a residue (2.96 g) which was crystallized from Et₂O, filtered and dried to give 2.74 g of Co. 135 (S) (40%). m.p.: 197° C.; (dsc); [α]$_d$: +23.76° (589 nm, c 0.2525 w/v %, DMF, 20° C.)

Example A136

Preparation of Co. 136 a—Synthesis of Int. 268:

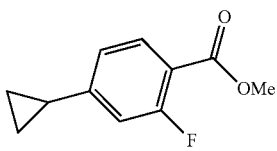 [SMILES: COC(=O)c1ccc(C2CC2)cc1F]

in a microwave vial, a mixture of methyl 4-bromo-2-fluorobenzoate (1.00 g, 4.3 mmol), cyclopropylboronic acid (1.1 g, 13 mmol) and KF (0.75 g, 13 mmol) in dry Toluene (10 mL) was purged with N₂. Pd(PPh₃)₄ (0.25 g, 0.22 mmol) was added and the mixture was purged again with N₂ and heated at 150° C. for 2 h. The crude mixture was partitioned between DCM and water. The organic layer was separated, dried over MgSO₄, filtered through a pad of silica gel and evaporated in vacuo to give 1.0 g of Int. 268 (quant.) used like this in the next step.

b—Synthesis of Int. 269:

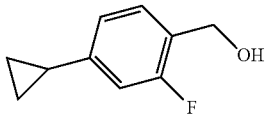 [SMILES: OCc1ccc(C2CC2)cc1F]

268 (1.0 g, 5.1 mmol) in dry THF (9 mL) was added dropwise to a suspension of LAH (0.24 g, 6.2 mmol) in dry THF (9 mL) at 0° C. under N₂. The mixture was stirred for 30 min. Water (0.9 mL) then DCM (75 mL) were added very slowly and stirred for 20 min. MgSO₄ was added and the insoluble was filtered on a pad of Celite® and evaporated until dryness to give 0.82 g of Int. 269, colorless oil used like this in the next step.

c—Synthesis of Int. 270:

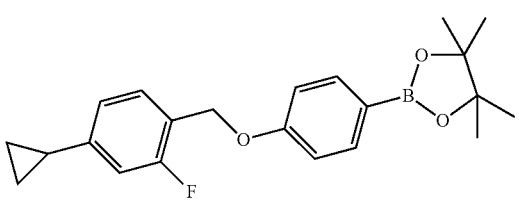 [SMILES: CC1(C)OB(c2ccc(OCc3ccc(C4CC4)cc3F)cc2)OC1(C)C]

DBAD (1.4 g, 5.9 mmol) was added portionwise to a sol. of 269 (0.82 g, 4.9 mmol), 7 (1.3 g, 5.9 mmol), PPh₃ supp. (1.9 g, 5.9 mmol) in dry THF (30 mL). The mixture was stirred at r.t. overnight. PPh₃ supp. was filtered and the filtrate was evaporated to give a yellow oil. The crude residue was purified by prep. LC (irregular SiOH 30 µm 80 g Interchim, mobile phase: heptane/EtOAc 90/10). The desired fractions were collected and solvent evaporated until dryness to give 0.75 g of Int. 270, pale yellow solid (41%).

d—Synthesis of Int. 271:

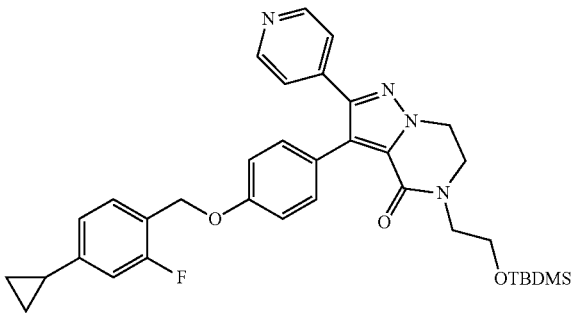 [SMILES: CC(C)(C)[Si](C)(C)OCCN1CCn2nc(-c3ccncc3)c(-c3ccc(OCc4ccc(C5CC5)cc4F)cc3)c2C1=O]

In a microwave vial, a mixture of 28 (0.77 g, 1.7 mmol), 270 (0.75 g, 2.0 mmol), K₃PO₄ (1.4 g, 6.8 mmol) in 1,4-dioxane (7.5 mL) and H₂O (2.7 mL) was carefully purged with N₂. PdCl₂(dppf) (140 mg, 0.17 mmol) was added and the r.m. was purged again with N₂. The r.m. was heated at 80° C. overnight. The r.m. was diluted with EtOAc and washed with water (once) and with brine (3 times). The organic phase was dried over MgSO₄, filtered on a pad of Celite® and evaporated in vacuo to give brown solid. The solid was purified by prep. LC (irregular SiOH 30 µm, 40 g Interchim, mobile phase: DCM/MeOH/NH₄OH 98/2/0.1). The desired fractions were collected and solvent evaporated until dryness to give 0.8 g of Int. 271, colorless oil (77%).

e—Synthesis of Co. 136:

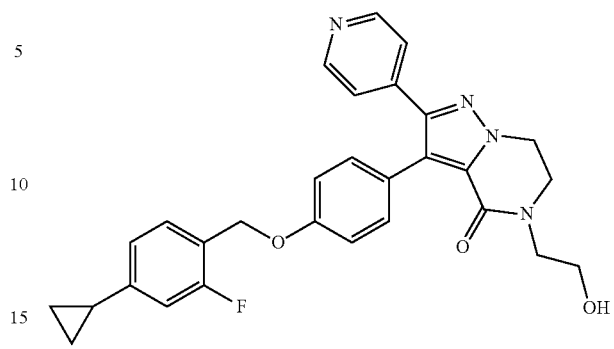

TBAF (1.6 mL, 1.6 mmol) was added dropwise to a sol. of 271 (0.8 g, 1.3 mmol) in THF (13 mL) at r.t. The mixture was stirred overnight at r.t. The mixture was concentrated and the residue was purified by prep. LC (Regular SiOH, 30 µm, 25 g Interchim, mobile phase: DCM/MeOH/NH₄OH 98/2/0.1). The pure fractions were collected and solvent evaporated to give 0.29 g of a colorless oil which was crystallized from Et₂O. The white solid formed was filtrated, washed and dried to give 276 mg of Co. 136, white solid (42%). m.p.: 183° C. (dsc).

Example A137

Preparation of Co. 137 a—Synthesis of Int. 272:

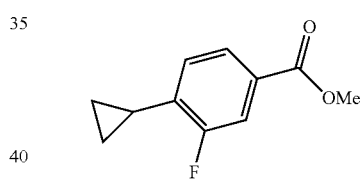

In a microwave vial, a mixture of methyl 4-bromo-3-fluorobenzoate (1.00 g 4.3 mmol), cyclopropylboronic acid (1.1 g, 13 mmol) and KF (0.75 g, 13 mmol) in dry toluene (10 mL) was purged with N₂. Pd(PPh₃)₄ (0.25 g, 0.22 mmol) was added and the mixture was purged again with N₂ and heated at 150° C. for 2 h. The crude was partitioned between DCM and water. The organic layer was separated, dried over MgSO₄, filtered through a pad of silica gel and evaporated in vacuo to give 0.85 g of Int. 272 (quant.) which was used as such in the next reaction step.

b—Synthesis of Int. 273:

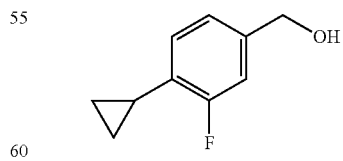

272 (1.0 g, 5.1 mmol) in dry THF (9 mL) was added dropwise to a suspension of LAH (0, 6.2 mmol) in dry THF (9 mL) at 0° C. under N₂. The mixture was stirred for 30 min. Water (0.9 mL) then DCM (75 mL) were added very slowly and stirred for 20 min. MgSO₄ was added and the insoluble was filtered on a pad of Celite® and evaporated

263 until dryness to give 0.88 g of Int. 273, brown oil (quant.) used like this in the next step.

c—Synthesis of Int. 274:

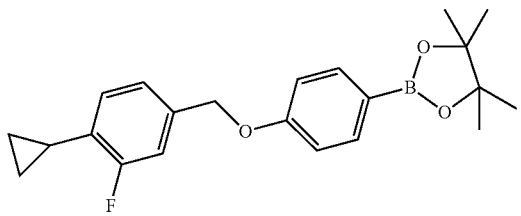 [SMILES: CC1(C)OB(c2ccc(OCc3ccc(C4CC4)c(F)c3)cc2)OC1(C)C]

DBAD (1.4 g, 5.9 mmol) was added portionwise to a sol. of 273 (0.82 g, 4.9 mmol), 7 (1.3 g, 5.9 mmol), PPh₃ supp. (1.9 g, 5.9 mmol) in dry THF (30 mL). The mixture was stirred at r.t. overnight. The resin was filtered and the filtrate was evaporated to give 4.3 g, yellow oil. The crude residue was purified by prep. LC (irregular SiOH 30 μm 80 g GraceResolv™, mobile phase: heptane/EtOAc 90/10). The desired fractions were collected and solvent evaporated until dryness to give 1.5 g of Int. 274 as a pale yellow oil used as such for the next reaction step.

d—Synthesis of Int. 275:

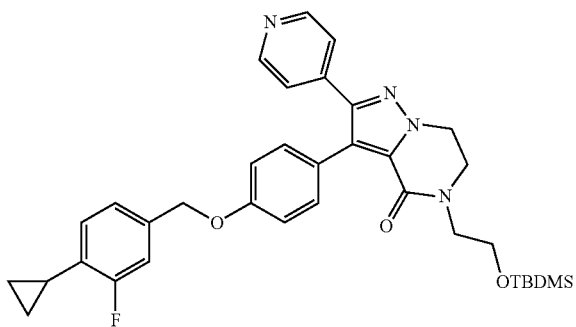 [SMILES: CC(C)(C)[Si](C)(C)OCCN1CCn2nc(-c3ccncc3)c(-c3ccc(OCc4ccc(C5CC5)c(F)c4)cc3)c2C1=O]

In a microwave vial, a mixture of 28 (1.1 g, 2.4 mmol), 274 (1.5 g, 2.9 mmol), K₃PO₄ (2.0 g, 9.5 mmol) in 1,4-dioxane (10 mL) and H₂O (3.7 mL) was carefully purged with N₂. PdCl₂(dppf) (194 mg, 0.24 mmol) was added and the r.m. was purged again with N₂. The r.m. was heated at 80° C. overnight. The r.m. was diluted with EtOAc and washed with water (once) and with brine (3 times). The organic phase was dried over MgSO₄, filtered on a pad of Celite® and evaporated in vacuo to give brown oil. The oil was purified by prep. LC (irregular SiOH 30 μm, 80 g Interchim, mobile phase: DCM/MeOH/NH₄OH 99/1/0.1). The desired fractions were collected and solvent evaporated until dryness to give 1.52 g of Int. 275, colorless oil (100%).

e—Synthesis of Co. 137:

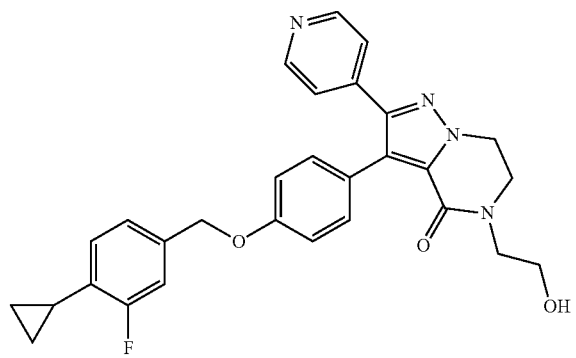 [SMILES: O=C1c2c(-c3ccc(OCc4ccc(C5CC5)c(F)c4)cc3)c(-c3ccncc3)nn2CCN1CCO]

264

TBAF (2.9 mL, 2.9 mmol) was added dropwise to a sol. of 275 (1.5 g, 2.5 mmol) in THF (24 mL) at r.t. The mixture was stirred overnight at r.t. The mixture was concentrated and the residue was purified by prep. LC (Regular SiOH, 30 μm, 40 g GraceResolv™, mobile phase gradient: DCM/MeOH/NH₄OH from 98/2/0.1 to 96/4/0.1). The pure fractions were collected and solvent evaporated to give white foam which was triturated in Et₂O. The white solid formed was filtrated, washed and dried to give 0.84 g of Co. 137, white solid (69%). m.p.: 185° C. (dsc).

Example A138

Preparation of Co. 138

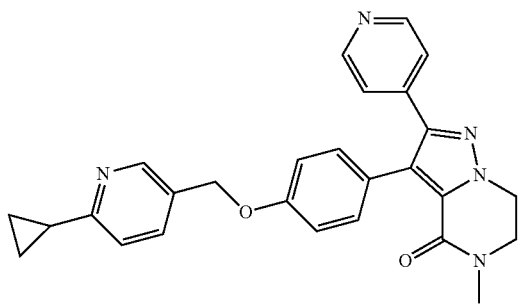 [SMILES: CN1CCn2nc(-c3ccncc3)c(-c3ccc(OCc4ccc(C5CC5)nc4)cc3)c2C1=O]

In a sealed tube, a mixture of 30 (200 mg, 651 μmol), 98 (915 mg, 2.61 mmol), K₃PO₄ (579 mg, 2.73 mmol) in 1,4-dioxane (3 mL) and H₂O (1 mL) was carefully purged with N₂. PCy₃ (38 mg, 136 μmol) and Pd(OAc)₂ (15 mg, 68.2 μmol) were added and the r.m. was purged again with N₂. The r.m. was stirred for 17 h at 100° C. The crude material was dissolved in water (10 mL) and extracted with EtOAc (2×40 mL). The organic phase was dried over MgSO₄, filtered and evaporated in vacuo to give 1.18 g, yellow oil. The crude mixture was purified by prep. LC (irregular SiOH 15-40 μm, 30 g Merck, mobile phase gradient: from DCM 100% to DCM 90%, MeOH 10%). The pure fractions were collected and solvent evaporated until dryness to give 230 mg. The residue was purified by achiral SFC on (2-ethylpyridine 6 μm 150×21.2 mm, mobile phase: 80% CO₂, 20% MeOH). The pure fractions were collected and solvent evaporated until dryness to give 216 mg of Co. 138, white solid (73%). m.p.: 175° C. (dsc).

Example A139

Preparation of Co. 139 a—Synthesis of Int. 276:

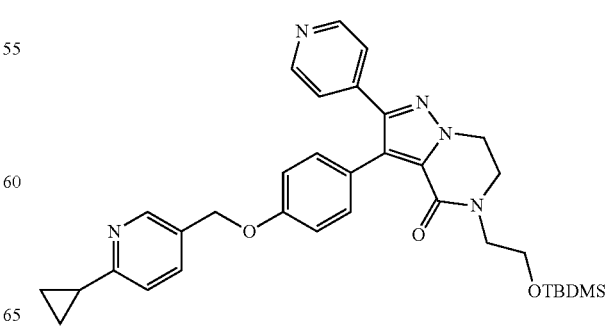

PdCl₂(dppf) (0.109 g, 0.133 mmol) was added to a stirred sol. purged with N₂ of 28 (0.600 g, 1.33 mmol), 30 (0.983 g, 2.66 mmol) and K₃PO₄ (0.846 g, 3.99 mmol) in 1,4-dioxane (7.5 mL) and H₂O (2.5 mL) at r.t. The resulting mixture was purged again with N₂, and stirred at 120° C. using one single mode microwave (Biotage Initiator EXP 60) with a power output ranging from 0 to 400 W for 30 min. [fixed hold time]. The crude material was diluted with a sol. of DCM/MeOH (95:5) and water, and the organic layer was washed with brine, dried over MgSO₄, filtered and evaporated in vacuo to give brown oil. This oil was purified by prep. LC (Irregular SiOH 50 μm, 80 g Grace, mobile phase gradient: from DCM 100% to MeOH 6%, DCM 94%). The desired fractions were collected and evaporated in vacuo to give 667 mg of Int. 276 (76%).

b—Synthesis of Co. 139:

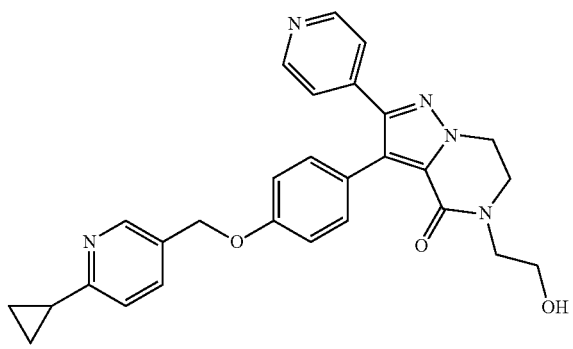

To a stirred sol. of 276 (667 mg, 1.01 mmol) in THF (10 mL) at 0° C. was added TBAF (1.02 mL, 1.02 mmol), and the r.m. was stirred warming to r.t. for 17 h. The mixture was diluted with water and a sol. of DCM/MeOH (95:5). The organic layer was washed (brine), dried (MgSO₄), filtered and evaporated in vacuo to afford an oil (590 mg) which was purified by prep. LC (Irregular SiOH 50 μm, 80 g Grace, mobile phase gradient: from DCM 100% to DCM 93%, MeOH 7%). The desired fractions were collected and evaporated in vacuo to give a sticky oil. The oil was triturated with a mixture of Et₂O/EtOH (3/1) and a solid was formed. The solvents were removed in vacuo to yield 266 mg of Co. 139, white solid (55%). m.p.: 97° C. (dsc).

Example A140

Preparation of Co. 140a and Co. 140 a—Synthesis of Int. 277:

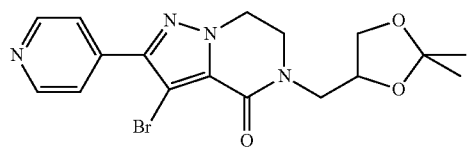 [SMILES: CC1(C)OCC(CN2CCn3nc(-c4ccncc4)c(Br)c3C2=O)O1]

NaH 60% (41 mg, 1 mmol) was added to 4 (0.2 g, 0.68 mmol) in DMSO (2 mL) at r.t. under N₂. The mixture was stirred for 2 h then 2,2-dimethyl-1,3-dioxolan-4-ylmethyl p-toluenesulfonate (0.29 g, 1 mmol) was added portionwise and the r.m. stirred for 2 days. The mixture was poured into water and K₂CO₃ and extracted with EtOAc. The organic layer was evaporated until dryness. The residue was taken up with DCM, stirred for 20 min then filtered. The filtrate was dried (MgSO₄), filtered and evaporated until dryness to give 0.26 g. The residue was purified by prep. LC (24 g of SiOH 35-40 μm GraceResolv™, mobil phase gradient: from 100% DCM to 95% DCM, 5% CH₃OH, 0.1% NH₄OH). The fractions were collected and evaporated to give 194 mg of Int. 277 (70%).

b—Synthesis of Co. 140a

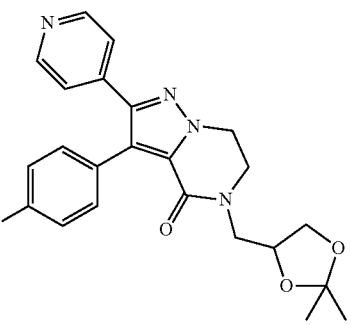

277 (800 mg, 1.96 mmol), 30 (1.04 g, 2.95 mmol), K₃PO₄ (1.25 g, 5.89 mmol) in 1,4-dioxane (8 mL) and H₂O (4 mL), in a sealed tube, were purged with N₂ for 10 min. Then, PdCl₂(dppf) (161 mg, 0.196 mmol) was added. The resulting mixture was purged again with N₂, and stirred at 120° C. using one single mode microwave (Biotage Initiator EXP 60) with a power output ranging from 0 to 400 W for 30 min. [fixed hold time]. The mixture was diluted in water and extracted with EtOAc. The organic layer was dried over MgSO₄, filtered and evaporated to give 1.08 g of Co. 140a, brown oil (quant.). The crude Co. 140a was used as such as for the next step.

c—Synthesis of Co. 140:

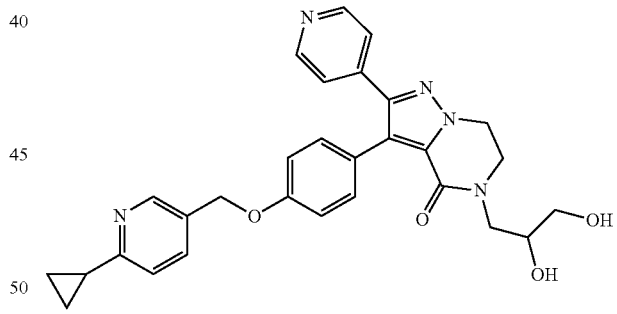

A sol. of Co. 140a (1.08 g, 1.95 mmol), HCl 3N (3.3 mL, 9.77 mmol) in 1,4-dioxane (40 mL) were heated to 80° C. for 30 min. The mixture was quenched with a 10% sol. of K₂CO₃ and extracted with EtOAc. The organic layer was separated, dried over MgSO₄, filtered and evaporated in vacuo to give 800 mg, brown oil. This oil was purified by prep. LC (irregular SiOH 15-40 μm, 80 g, Interchim, mobile phase gradient: from DCM 100% to DCM 94%, MeOH 6%). The desired fractions were collected and solvent evaporated until dryness to give 350 mg, grey solid. The solid was purified by prep. LC (irregular SiOH 15-40 μm, 45 g, Merck, mobile phase gradient: from DCM 100% to DCM 95%, MeOH 5%). The desired fractions were collected and solvent evaporated until dryness to give 310 mg, white solid (31%). The white solid was dissolved in MeOH and concentrated in vacuo to afford a thick oil. The oil was triturated with gradual addition of Et₂O to give a white precipitate. The precipitate was filtered off and washed with Et₂O. The solid was collected and dried in vacuo to give 292 mg. This 292 mg was recrystallized in EtOH (two times) overnight to give 158 mg of Co. 140, white solid (15%).

Example A141

Preparation of Co. 141 a—Synthesis of Int. 279:

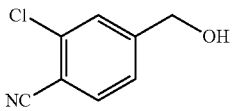

Pd(PPh₃)₄ (0.78 g, 0.68 mmol) was added to a mixture of 4-bromo-3-chlorobenzyl alcohol (1.5 g, 6.78 mmol) and Zn(CN)₂ (0.404 g, 3.39 mmol) in DMF (15 mL) in a sealed tube. The mixture was heated at 120° C. for 30 min using one single mode microwave (Biotage) with a power output ranging from 0 to 400 W. The r.m. was cooled to r.t., poured into ice water and extracted with DCM. The organic layer was separated, dried over MgSO₄, filtered and the solvent was evaporated until dryness. The residue was purified (with another batch, initial reactant 0.2 g) by prep. LC on (Irregular SiOH 15-40 µm 50 g Merck, Mobile phase gradient: from DCM 100% to DCM 97%, MeOH 3%). The pure fractions were collected and solvent evaporated until dryness to give 1.15 g of Int. 279 (89%).

b—Synthesis of Int. 280:

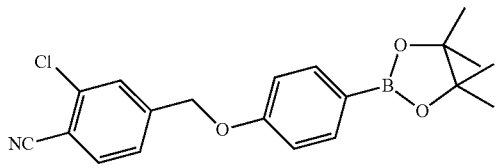 [SMILES: CC1(C)OB(c2ccc(OCc3ccc(C#N)c(Cl)c3)cc2)OC1(C)C]

To a suspension of 279 (0.6 g, 3.58 mmol), 7 (0.945 g, 4.3 mmol), DBAD (0.989 g, 4.3 mmol) in dry DCM (8 mL) was added PPh₃ supp. (1.34 g, 4.3 mmol) and the r.m. was stirred at r.t. for 18 h. The insoluble was filtered through Celite®, washed with DCM. Water was added and the organic layer was separated, dried, filtered and concentrated until dryness to give 2.4 g. The residue was purified by prep. LC on (Irregular SiOH 15-40 µm 50 g Merck, Mobile phase: DCM 100%). The pure fractions were collected and evaporated until dryness to give 679 mg of Int. 280 (51%).

c—Synthesis of Co. 141:

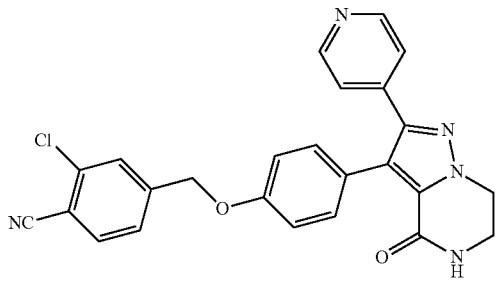 [SMILES: N#Cc1ccc(COc2ccc(-c3c(-c4ccncc4)nn4c3C(=O)NCC4)cc2)cc1Cl]

In a microwave vial, a mixture of 4 (0.3 g, 1.02 mmol), 280 (0.492 g, 1.33 mmol), K₃PO₄ (0.911 g, 4.29 mmol) in 1,4-dioxane (4.8 mL) and H₂O (1.6 mL) was carefully purged with N₂. PdCl₂(dppf) (84 mg, 0.1 mmol) was added and the r.m. was purged with N₂. The r.m. was stirred for 16 h at 80° C. The crude material was dissolved in water and extracted with EtOAc. The organic phase was dried over MgSO₄, filtered and evaporated in vacuo to give 680 mg. The residue was purified by prep. LC (Stationary phase: irregular 15-40 µm 30 g Merck, Mobile phase: 0.5% NH₄OH, 94.5% DCM, 5% MeOH). The pure fractions were collected and evaporated to give 330 mg which was crystallized in Et₂O, filtered and dired to give 275 mg of Co. 141 (59%). m.p.: 257° C. (dsc).

Example A142

Preparation of Co. 142 a—Synthesis of Int. 281:

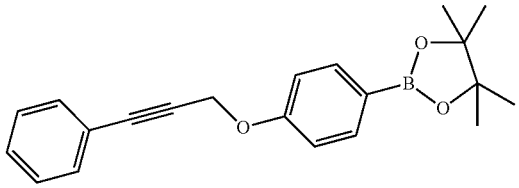 [SMILES: CC1(C)OB(c2ccc(OCC#Cc3ccccc3)cc2)OC1(C)C]

The reaction was performed in anhydrous conditions under Ar-atmosphere. K₂CO₃ (0.240 g, 1.73 mmol) and (3-bromo-1-propynyl)benzene (75% in toluene) (0.293 mL, 1.59 mmol) were successively added to a sol. of 7 (0.345 g, 1.57 mmol) in ACN (7.22 mL). The r.m. was stirred at r.t. for 18 h. K₂CO₃ (0.372 g, 2.69 mmol) and (3-bromo-1-propynyl)benzene (0.300 mL, 2.17 mmol) were then successively added again. After 22 h at r.t., the r.m. was filtrated, washed with EtOAc and concentrated to dryness. The residue was purified by prep. LC (15-40 µm, 50 g, mobile phase gradient: cyclohexane/DCM: 80/20 to 0/100). The pure fractions were collected and the solvent was evaporated to give 0.435 g of Int. 281, yellow solid (90%).

b—Synthesis of Co. 142:

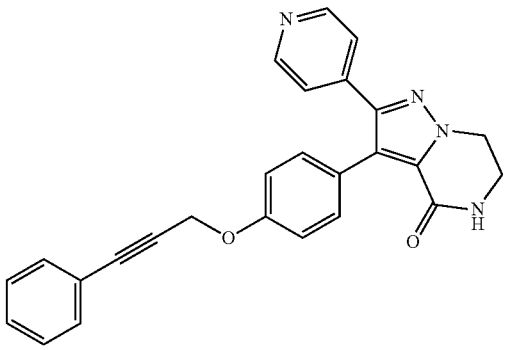 [SMILES: O=C1NCCn2nc(-c3ccncc3)c(-c3ccc(OCC#Cc4ccccc4)cc3)c21]

In a Schlenk tube, a mixture of 4 (125 mg, 0.426 mmol), 281 (427 mg, 1.), K₃PO₄ (362 mg, 1.) in 1,4-dioxane (1.8 mL) and H₂O (0.6 mL) was carefully purged with N₂. PCy₃ (24 mg, 85.2 µmol) and Pd(OAc)₂ (10 mg, 42.6 µmol) were added and the r.m. was purged again with N₂. The Schlenk tube was then sealed and the r.m. was stirred for 17 h at 80°

C. The crude material was dissolved in water (20 mL) and extracted with EtOAc (2×40 mL). The organic phase was dried over MgSO$_4$, filtered and evaporated in vacuo to give 300 mg, yellow oil. The crude mixture was purified by prep. LC (irregular SiOH 15-40 µm, 30 g Merck, mobile phase gradient: from DCM 100% to DCM 60%, Acetone 40%). The pure fractions were collected and solvent evaporated to give 90 mg of Co. 142, white solid (50%). m.p.: 245° C. (DSC).

Example A143

Preparation of Co. 143 a—Synthesis of Int. 282:

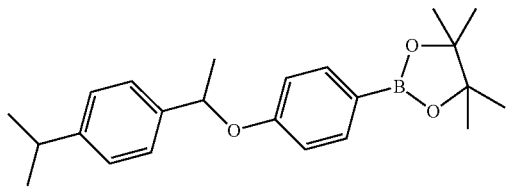 [SMILES: CC(C)c1ccc(C(C)Oc2ccc(B3OC(C)(C)C(C)(C)O3)cc2)cc1]

DBAD (1.05 g, 4.57 mmol) was added to a stirred sol. of 1-(4-iso-propylphenyl)ethanol (500 mg, 3.04 mmol), 7 (1.01 g, 4.57 mmol) and PPh$_3$ supp. (1.52 g, 4.57 mmol) in THF (18 mL) under N$_2$ at r.t., and the mixture was stirred at r.t. for 16 h. The crude mixture was filtered off and the filtrate was evaporated in vacuo to give an oil which was purified by prep. LC (Irregular SiOH 15-40 µm, 120 g Grace, mobile phase gradient: from Heptane 100% to EtOAc 30%, Heptane 70%). The pure fractions were collected and solvent evaporated to give 554 mg of Int. 282, solid (50%).

b—Synthesis of Co. 143:

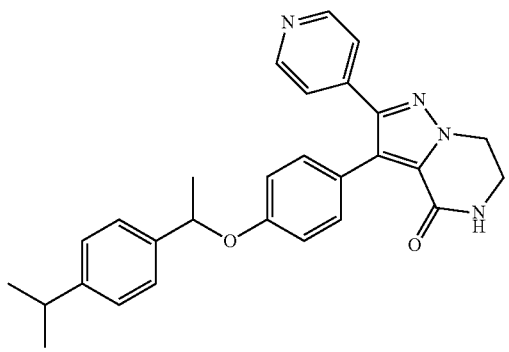 [SMILES: CC(C)c1ccc(C(C)Oc2ccc(-c3c(-c4ccncc4)nn4c3C(=O)NCC4)cc2)cc1]

A mixture of 4 (150 mg, 0.512 mmol), 282 (469 mg, 1.28 mmol), K$_3$PO$_4$ (434 mg, 2.05 mmol) in 1,4-dioxane (2.4 mL) and H$_2$O (0.8 mL) was carefully purged with N$_2$. PCy$_3$ (29 mg, 0.102 mmol) and Pd(OAc)$_2$ (11 mg, 51.2 µmol) were added and the r.m. was purged with N$_2$. The r.m. was stirred at 80° C. for 17 h. Then, additional 282 (100 mg, 0.273 mmol), PCy$_3$ (14 mg, 49.8 µmol) and Pd(OAc)$_2$ (6 mg, 25.6 µmol) were added under N$_2$ at r.t. The mixture was stirred at 80° C. for 16 h. The crude material was dissolved in water and extracted with DCM. The organic phase was dried over MgSO$_4$, filtered and evaporated in vacuo to give a solid which was purified by prep. LC (irregular SiOH 15-40 µm, 30 g Merck, mobile phase gradient: from DCM/MeOH 100/0 to 95/5). The pure fractions were collected and solvent evaporated to give 153 mg, white solid. The solid was triturated with Et$_2$O, and the solvent was separated. The solid was washed 2× with Et$_2$O and dried in vacuo to yield 105 mg of Co. 143, white solid (45%) m.p.: 217° C. (dsc).

Example A144

Preparation of Co. 144 and Co. 145 a—Synthesis of Int. 283:

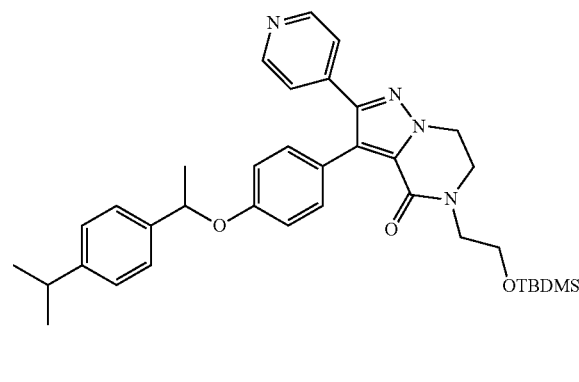 [SMILES: CC(C)c1ccc(C(C)Oc2ccc(-c3c(-c4ccncc4)nn4c3C(=O)N(CCO[Si](C)(C)C(C)(C)C)CC4)cc2)cc1]

In a microwave vial, a mixture of 28 (1.078 g, 2.39 mmol), 282 (2.1 g, 2.87 mmol), K$_3$PO$_4$ (2.03 g, 9.56 mmol) in 1,4-dioxane (10.5 mL) and H$_2$O (3.7 mL) was carefully purged with N$_2$. PdCl$_2$(dppf) (196 mg, 0.24 mmol) was added and the r.m. was purged again with N$_2$. The r.m. was heated at 80° C. overnight. The r.m. was diluted with EtOAc and washed with water (once) and with brine (3 times). The organic phase was dried over MgSO$_4$, filtered on a pad of Celite® and evaporated in vacuo to give 3.41 g. The residue was purified by prep. LC (Stationary phase: irregular SiOH 15-40 µm 300 g MERCK, Mobile phase: 0.1% NH$_4$OH, 99% DCM, 1% MeOH). The pure fractions were collected and evaporated until dryness to give 850 mg of Int. 283 (58%).

b—Synthesis of Co. 144 & Co. 145:

Compound 144

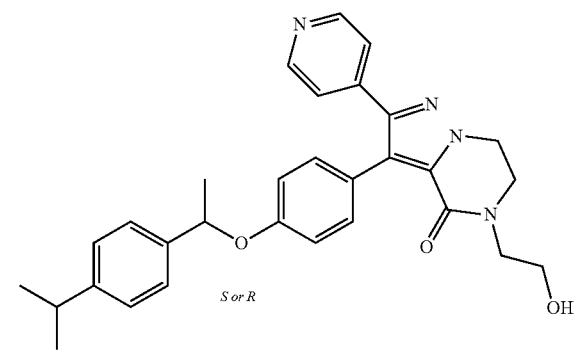

Compound 145

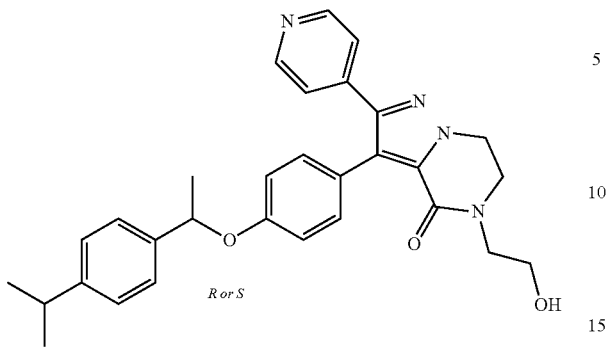

TBAF (1.67 mL, 1.67 mmol) was added dropwise to a sol. of 283 (0.85 g, 1.39 mmol) in THF (14 mL) at r.t. The mixture was stirred for 3 h at r.t. EtOAc and water were added. The organic layer was separated, dried, filtered and evaporated until dryness to give 845 mg. The crude mixture was purified by prep. LC (Stationary phase: Sunfire Silica 5 μm 150×30.0 mm, Mobile phase Gradient: from 0.2% NH$_4$OH, 98% DCM, 2% MeOH to 1.1% NH$_4$OH, 89% DCM, 10% MeOH). The pure fractions were collected and evaporated until dryness to give 512 mg. The residue was purified by chiral SFC (Stationary phase: Chiralcel OD-H 5 μm 250×20 mm, Mobile phase: 75% CO$_2$, 25% MeOH (0.3% iPrNH$_2$)). The pure fractions were collected and evaporated until dryness to give 238 mg of a first compound and 247 mg of a second compound. The first compound was crystallized from DIPE, filtered and dried to give 182 mg of Co. 144 (26%) m.p.: 148° C. (dsc). The second compound was crystallized from DIPE, filtered and dried to give 188 mg of Co. 145 (27%). m.p.: polymorph: 148° C. and 162° C. (dsc); Co. 144: [α]$_d$: −48.19° (589 nm, c 0.249 w/v %, DMF, 20° C.); Co. 145: [α]$_d$: +47.79° (589 nm, c 0.249 w/v %, DMF, 20° C.)

Example A145

Preparation of Co. 146a and Co. 146

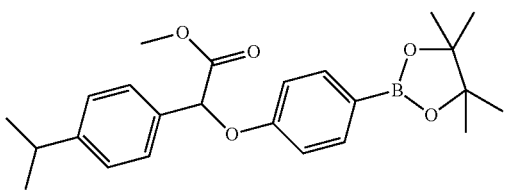 [SMILES: COC(=O)C(Oc1ccc(B2OC(C)(C)C(C)(C)O2)cc1)c1ccc(C(C)C)cc1]

a—Synthesis of Int. 284:

A sol. of methyl 2-hydroxy-2-[(4-(propan-2-yl)]acetate (500 mg, 2.40 mmol), 7 (687 mg, 3.12 mmol) and PPh$_3$ (756 mg, 2.88 mmol) in dry DCM (12 mL) was treated with DBAD (663 mg, 2.88 mmol) and stirred at r.t. for 19 h. Then, EtOAc and brine were added, and the organic layer was separated, dried over MgSO$_4$, filtered and evaporated in vacuo to afford 3.03 g, pale yellow oil. This oil was purified by prep. LC (irregular SiOH 15-40 μm, 120 g, GraceResolv™, mobile phase gradient: from heptane 100% to heptane/EtOAc 70/30). The pure fractions were collected and solvent evaporated until dryness to give 760 mg of Int. 284, sticky colorless solid (77%).

b—Synthesis of Co. 1H

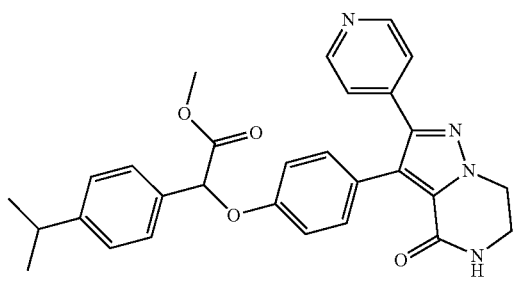 [SMILES: COC(=O)C(Oc1ccc(-c2c(-c3ccncc3)nn3c2C(=O)NCC3)cc1)c1ccc(C(C)C)cc1]

A mixture of 4 (0.298 g, 1.02 mmol), 284 (0.750 g, 1.83 mmol) and K$_3$PO$_4$ (0.539 g, 2.54 mmol) in 1,4-dioxane (3 mL) and H$_2$O (1.5 mL) was purged with N$_2$. PdCl$_2$(dppf) (71 mg, 86.3 μmol) was then added. The mixture was purged again with N$_2$ and stirred at 120° C. using one single mode microwave (Biotage Initiator EXP 60) with a power output ranging from 0 to 400 W for 20 min [fixed hold time]. Then a sol. of DCM/MeOH (95:5) and water were added. The organic layer was separated, washed with brine, separated, dried over MgSO$_4$, filtered and evaporated in vacuo to yield 570 mg, solid. The residue was purified by prep. LC (Irregular SiOH 50 μm, 40 g Grace, mobile phase gradient: from DCM 100% to DCM 93%, MeOH 7%). The desired fractions were evaporated in vacuo to give 226 mg of Co. 146a, white solid (45%).

c—Synthesis of Co. 146:

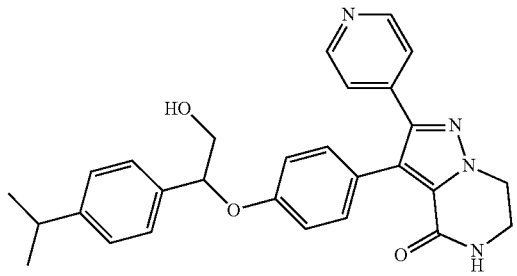

NaBH$_4$ (76 mg, 2.01 mmol) was added to a stirred suspension of Co. 146a (166 mg, 0.334 mmol) in dry THF (4 mL) and MeOH (0.75 mL) at r.t. under N$_2$. The r.m. was stirred at 50° C. for 3 h, and then a sat. sol. of NaHCO$_3$ and EtOAc were added. The organic layer was washed with brine, separated, dried over MgSO$_4$, filtered and evaporated in vacuo to yield 198 mg, white solid. The residue was purified by prep. LC (Irregular SiOH 50 μm, 40 g Grace, mobile phase gradient: from DCM 100% to DCM 91%, MeOH 9%). The desired fractions were evaporated in vacuo to give 66 mg, white solid. The solid was triturated in MeOH, and the solvent was allowed to evaporate slowly. The afforded solid was collected and dried in vacuo at 50° C. for 1 h to yield 65 mg of Co. 146, white solid (41%). m.p.: 228° C. and 238° C. (dsc—polymorphous compound).

Example A146

Preparation of Co. 147 a—Synthesis of Int. 286:

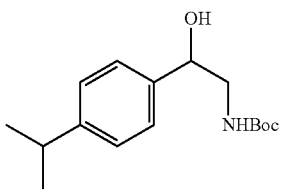 [SMILES: CC(C)c1ccc(C(O)CNC(=O)OC(C)(C)C)cc1]

BOC-anhydride (122 mg, 0.558 mmol) and DMAP (68 mg, 0.558 mmol) were added to a stirred sol. of 2-amino-1-(4-isopropylphenyl)ethanol (100 mg, 0.558 mmol) in ACN (3 mL) at rt. The r.m. was stirred at r.t. for 2 h. Another batch (717 mg of initial reactant) was combined with this reaction and the sol. was diluted in DCM and washed successively with HCl 1N and sat. NaHCO$_3$. The organic phase was dried over MgSO$_4$, filtered and evaporated in vacuo. The residue was purified by prep. LC (irregular SiOH 15-40 μm, 50 g, Merck, Mobile phase gradient: DCM/MeOH, from 100/0 to 80/20 The pure fractions were collected and solvent evaporated until dryness to give 500 mg of Int. 286, white solid (global yield: 39%).

b—Synthesis of Int. 287:

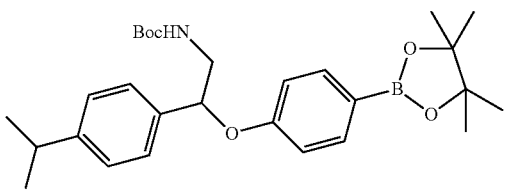 [SMILES: CC(C)c1ccc(C(CNC(=O)OC(C)(C)C)Oc2ccc(B3OC(C)(C)C(C)(C)O3)cc2)cc1]

DBAD (495 mg, 2.15 mmol) was added to a mixture of 7 (473 mg, 2.15 mmol), 286 (400 mg, 1.43 mmol) and PPh$_3$ supp. (563 mg, 2.15 mmol) in DCM (4 mL) and the r.m. was stirred under N$_2$ for 17 h at r.t. The sol. was filtered and the residual polymer was washed with DCM. The filtrate was evaporated in vacuo. The residue was purified by prep. LC (irregular SiOH 15-40 μm, 50 g Merck, mobile phase gradient: from Heptane 100% to EtOAc 10%, Heptane 90%). The pure fractions were collected and solvent evaporated to give 200 mg of Int. 287, white gum (29%).

c—Synthesis of Co. 147:

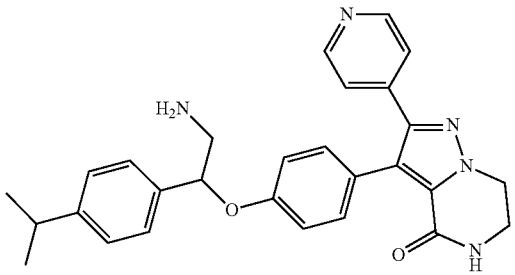 [SMILES: CC(C)c1ccc(C(CN)Oc2ccc(-c3c(-c4ccncc4)nn4c3C(=O)NCC4)cc2)cc1]

A sol. of 4 (82 mg, 0.277 mmol) and 287 (200 mg, 0.415 mmol) in 1,4-dioxane (2 mL) and H$_2$O (1 mL) was treated with K$_3$PO$_4$ (176 mg, 0.831 mmol) and purged with N$_2$. PdCl$_2$(dppf) (23 mg, 27.7 μmol) was then added and the r.m. was carefully purged with N$_2$. The mixture was heated at 120° C. using one single mode microwave (Biotage Initiator EXP 60) with a power output ranging from 0 to 400 W for 30 min [fixed hold time]. HCl 3N (2.5 mL) was then slowly added and the sol. was stirred at r.t. for 18 h. The r.m. was diluted with EtOAc and washed with aq. NaHCO$_3$ (twice). The organic phase was dried over MgSO$_4$, filtered and evaporated in vacuo to give 260 mg, brown oil. The residue was purified by prep. LC (irregular SiOH 15-40 μm, 50 g, MERCK, Mobile phase gradient: from DCM 100% to DCM 95%, MeOH 95%). The pure fractions were collected and solvent evaporated until dryness to give 75 mg of Co. 147, white solid. m.p.: 178° C. (dsc).

Example A147

Preparation of Co. 148 a—Synthesis of Int. 288:

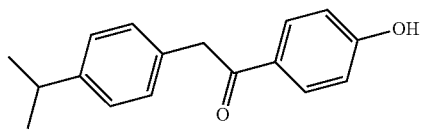 [SMILES: CC(C)c1ccc(CC(=O)c2ccc(O)cc2)cc1]

To a sol. of 1-(4-methoxyphenyl)-2-[4-(propan-2-yl)phenyl]ethan-1-one (6.26 g, 23.3 mmol) in acetic acid (43 mL) was added hydriodic acid 57% in water (14 mL, 167 mmol). The sol. was refluxed for 72 h and cooled down to 0° C. Water was carefully added and the precipitate was filtered on a glass frit. The brown solid obtained was washed with Et$_2$O and dried in vacuo to give 798 mg, beige solid (13%). The Et$_2$O filtrate was evaporated in vacuo and coevaporated with toluene (3 times). The residue was taken up in DCM and the precipitate was filtered on a glass frit, washed with DCM and dried in vacuo to give 2.07 g of pale brown solid (35%). The DCM filtrate was evaporated again, the residue was taken up in a minimum of DCM, the precipitate was filtered on a glass frit and dried in vacuo to give 687 mg of pale brown solid (12%). The three solids were put together to give 3.55 g of Int. 288 (60%).

b—Synthesis of Int. 289:

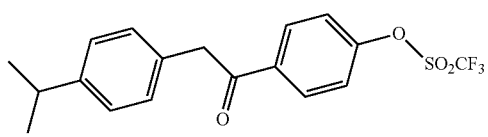

To a sol. of 288 (798 mg, 3.14 mmol) in DCM (7 mL) were added DMAP (38.3 mg, 0.314 mmol), Et$_3$N (1.31 mL, 9.41 mmol) and N-phenyltrifluoromethanesulfonimide (1.68 g, 4.71 mmol). The sol. was stirred at r.t. for 90 min then concentrated in vacuo. The residue was purified by prep. LC (Irregular SiOH 15-40 μm, 50 g Merck, solid deposit, mobile phase gradient: from heptane 100% to heptane 80, EtOAc 20%). The pure fractions were collected and solvent evaporated until dryness to give 1.17 g of Int. 289, yellow oil which crystallized (97%).

c—Synthesis of Int. 290:

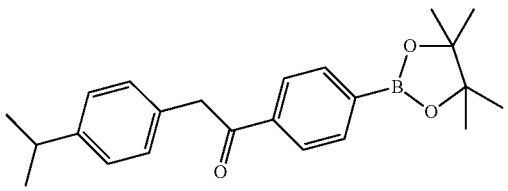 [SMILES: CC(C)c1ccc(CC(=O)c2ccc(B3OC(C)(C)C(C)(C)O3)cc2)cc1]

To a sol. of 289 (1.10 g, 2.85 mmol) in DME (12 mL) in a schlenk tube were added BisPin (1.08 g, 4.27 mmol) and KOAc (838 mg, 8.54 mmol). The mixture was carefully purged with $N_2$ and $PdCl_2$(dppf) (233 mg, 0.285 mmol) was added. The mixture was purged again with $N_2$ and heated at 80° C. for 18 h. EtOAc and water were added, the organic layer was separated, dried over $MgSO_4$, filtered off and evaporated in vacuo to give a brown oil. This oil was triturated in $Et_2O$ and the precipitate was filtered off on a glass frit. The filtrate was evaporated in vacuo to give a black residue. This residue was dissolved in MeOH, water was added and the mixture was evaporated in vacuo (process repeated 3×). The residue was diluted in DCM, dried over $MgSO_4$, filtered off and evaporated in vacuo to give 942 mg of Int. 290, black solid (91%).

d—Synthesis of Co. 148:

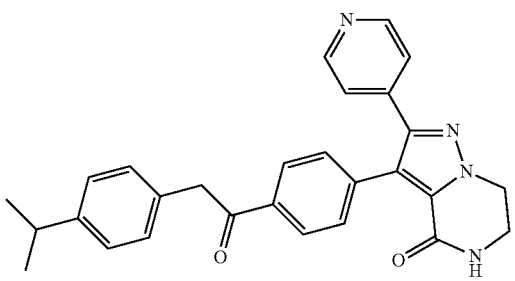 [SMILES: CC(C)c1ccc(CC(=O)c2ccc(-c3c(-c4ccncc4)nn4c3C(=O)NCC4)cc2)cc1]

A mixture of 4 (2.94 g, 10.0 mmol), 290 (3.65 g, 10.0 mmol) and $K_3PO_4$ (8.51 g, 40.1 mmol) in 1,4-dioxane (50 mL) and $H_2O$ (10 mL) in a Schlenk tube was purged with $N_2$. $PdCl_2$(dppf) (820 mg, 1.00 mmol) was added, the mixture was purged again with $N_2$ and heated at 80° C. for 18 h. Another batch (reactant 0.3 g of 4, in the same conditions) was combined with this reaction. The mixture was diluted with DCM and water and the organic layer was separated, dried over $MgSO_4$, filtered off and evaporated in vacuo to give 15 g of brown oil. This oil was purified by prep. LC (Irregular SiOH 15-40 µm, 330 g Grace, solid deposit, mobile phase gradient: from DCM 100% to DCM 95%, iPrOH 5%). The pure fractions were collected and solvent evaporated until dryness to give a beige solid which was triturated in $Et_2O$. The precipitate was filtered on a glass frit to give 3.20 g of Co. 148, off-white solid (global yield 64%, purity 97%). 405 mg of 3.2 g was purified by achiral SFC (Stationary phase: diethylaminopropyl 5 µm 150×21.2 mm, Mobile phase: 85% $CO_2$, 15% MeOH (0.3% $iPrNH_2$)). The pure fractions were collected and solvent evaporated until dryness to give 289 mg which was crystallized from iPrOH. The precipitate was filtered on a glass frit and the solid was washed with $Et_2O$ twice then dried under high vacuum at 50° C. for 18 h to give 178 mg of Co. 148, white solid. m.p.: 259° C. (dsc).

Example A148

Preparation of Co. 149 a—Synthesis of Int. 291:

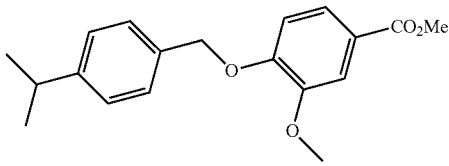 [SMILES: COC(=O)c1ccc(OCc2ccc(C(C)C)cc2)c(OC)c1]

Under $N_2$, to a suspension of methyl vanillate (2.0 g, 11 mmol), 4-isopropylbenzyl alcohol (1.7 mL, 11 mmol), $PPh_3$ supp. (3.4 g, 11 mmol) in dry DCM (48 mL) was added DBAD (2.5 g, 11 mmol) and the r.m. was stirred at r.t. for 3 h. The mixture was filtrated through a Celite® pad, evaporated in vacuo to give a colorless oil. This oil was purified by prep. LC (irregular SiOH 30 µm, 120 g Interchim, mobile phase gradient: heptane/EtOAc, from 90/10 to 80/20). The pure fractions were collected and solvent evaporated to give 2.22 g of Int. 291, white solid (64%).

b—Synthesis of Int. 292:

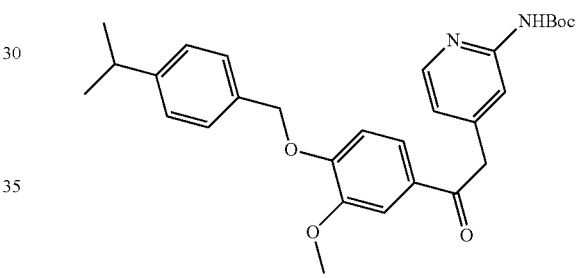

A sol. of 291 (2.2 g, 7.0 mmol) and 2-(4-methyl-2-pyridinyl)-imidodicarbonic acid, 1,3-bis(1,1-dimethylethyl) ester (2.17 g, 7.0 mmol) in dry THF (20 mL) was treated with LiHMDS (14 mL, 14 mmol) at 0° C. (addition over 10 min). After stirring for 1 h at 0° C., the reaction was allowed to warm to r.t. and was stirred for 17 h. The reaction was quenched with a 10% aq. sol. of $NH_4Cl$ (50 mL). The mixture was extracted with DCM. The organic layer was collected and evaporated in vacuo and the residue was taken in $Et_2O$, the solid formed was filtrated and dried to afford 1.59 g of Int. 292, beige powder (46%).

c—Synthesis of Int. 293:

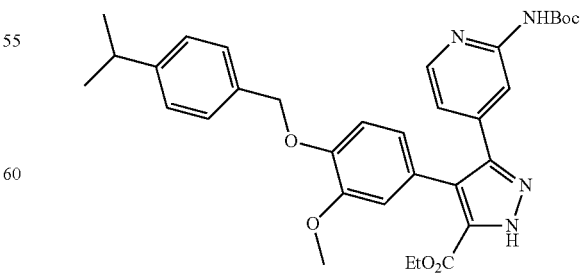

To a suspension of 292 (1.6 g, 3.2 mmol) in ACN (12 mL) was added 1,8-diazabicyclo(5.4.0)undec-7-ene (0.49 mL, 3.2 mmol) and ethyl diazoacetate (0.58 mL, 5.5 mmol). The mixture was heated at 100° C. for 2 h then cooled down to r.t. The solvent was removed in vacuo and the residue was diluted in EtOAc. The organic layer was washed with a sat. aq. sol. of NaHCO$_3$, dried over MgSO$_4$, filtered off and evaporated in vacuo. The residue was purified by prep. LC (irregular SiOH 15-40 µm, 80 g GraceResolv™, mobile phase gradient: from Heptane/EtOAc 70/30 to 60/40). The pure fractions were collected and solvent evaporated until dryness to give 670 mg of Int. 293, beige powder (35%).

d—Synthesis of Int. 294:

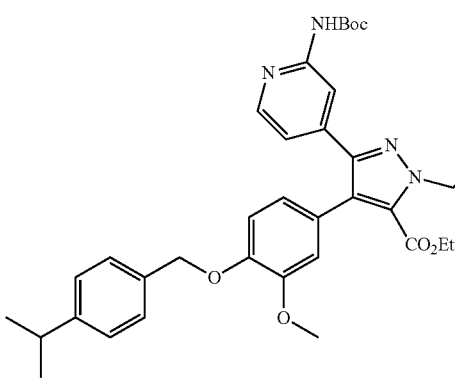

To a mixture of 293 (330 mg, 0.56 mmol), Boc-glycinol (136 mg, 0.84 mmol) and PPh$_3$ supp. (703 mg, 0.84 mmol) in dry THF (9 mL) was added DBAD (194 mg, 0.84 mmol). The mixture was stirred at r.t. for 12 h. The mixture was filtrated through a Celite® pad, concentrated and purified by prep. LC (irregular SiOH 30 µm, 40 g Interchim, Mobile phase gradient: from heptane/EtOAc 75/25 to 70/30). The pure fractions were collected and solvent evaporated until dryness to give 251 mg of Int. 294, white solid (61%).

e—Synthesis of Co. 149:

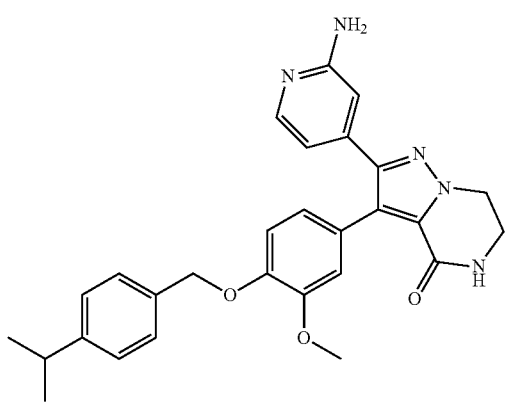 [SMILES: COc1cc(-c2c(-c3ccnc(N)c3)nn3c2C(=O)NCC3)ccc1OCc1ccc(C(C)C)cc1]

294 (250 mg, 0.34 mmol), HCl 3N (0.57 mL, 1.7 mmol), in ACN (6.1 mL) at 80° C. for 3 h. The mixture was concentrated, and K$_2$CO$_3$ 10% aq (20 mL) was added and the mixture was extracted with DCM, dried and concentrated. The mixture was put in DCM, filtrated and the filtrate was purified by prep. LC (Irregular SiOH 15-40 µm, 12 g GraceResolv™, mobile phase gradient: DCM/MeOH/ NH$_4$OH from 98/2/0.1 to 95/5/0.1) to give 58 mg of Co. 149, white solid (35%). m.p.: 179° C. (dsc).

Example A149

Preparation of Co. 150 a—Synthesis of Int. 295:

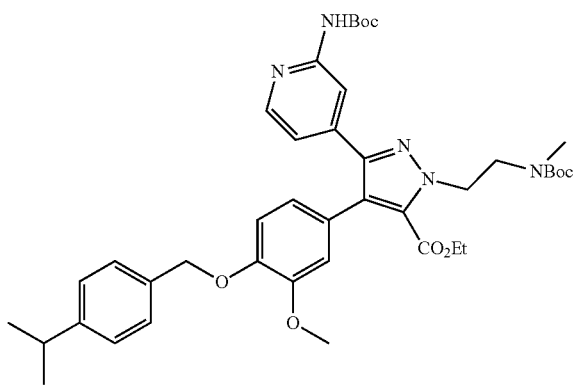 [SMILES: CCOC(=O)c1c(-c2ccc(OCc3ccc(C(C)C)cc3)c(OC)c2)c(-c2ccnc(NC(=O)OC(C)(C)C)c2)nn1CCN(C)C(=O)OC(C)(C)C]

To a mixture of 293 (260 mg, 0.44 mmol), 2-(N-Boc-methylamino)ethanol (116 mg, 0.66 mmol) and PPh$_3$ supp. (554 mg, 0.66 mmol) in dry THF (7 mL) was added DBAD (153 mg, 0.66 mmol). The mixture was stirred at r.t. for 3 h. The mixture was filtrated through a Celite® pad, concentrated and purified by prep. LC (irregular SiOH 30 µm, 40 g Interchim, Mobile phase gradient: from heptane/EtOAc 75/25 to 70/30). The pure fractions were collected and solvent evaporated until dryness to give 270 mg of Int. 295, white solid (82%).

b—Synthesis of Co. 150:

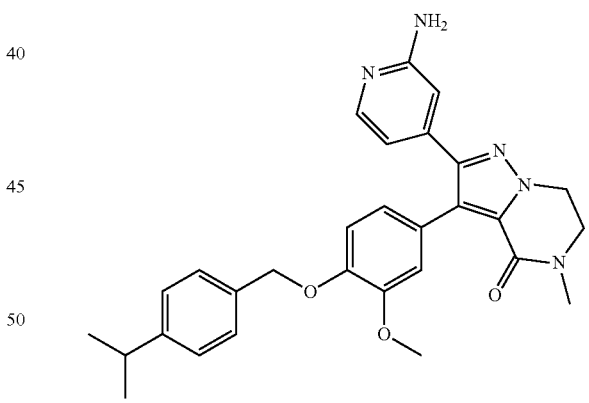

295 (270 mg, 0.36 mmol), HCl 3N (0.61 mL, 1.8 mmol), in ACN (6.4 mL) at 80° C. for 2 h. The mixture was concentrated, K$_2$CO$_3$ 10% aq (20 mL) was added and the mixture was stirred at r.t. for 30 min. The mixture was extracted with DCM (twice) and the organic layer was dried over MgSO$_4$, filtrated and evaporated. The residue was purified by prep. LC (Irregular SiOH 15-40 µm, 12 g GraceResolv™, mobile phase gradient: DCM/MeOH/ NH$_4$OH from 98/2/0.1 to 95/5/0.1). The pure fractions were collected and solvent evaporated until dryness to give 105 mg of Co. 150, white powder (58%).

Example A150

Preparation of Co. 151

First Method:
a—Synthesis of Int. 296:

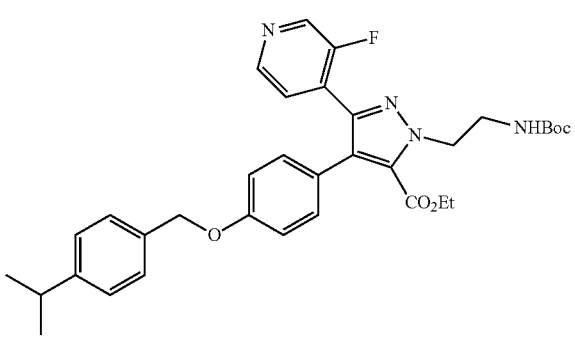 [SMILES: CCOC(=O)c1c(-c2ccc(OCc3ccc(C(C)C)cc3)cc2)c(-c2ccncc2F)nn1CCNC(=O)OC(C)(C)C]

A sol. of 17 (800 mg, 1.36 mmol), 3-fluoro-4-pyridine-boronic acide pinacol ester (608 mg, 2.73 mmol) and Na₂CO₃ (434 mg, 4.09 mmol) in toluene (10 mL), EtOH (5 mL) and H₂O (2 mL) in a sealed tube was purged with N₂. PdCl₂(dppf) (112 mg, 0.136 mmol) was added, the mixture was purged again with N₂ and heated at 130° C. using one single mode microwave (Biotage Initiator EXP 60) with a power output ranging from 0 to 400 W for 5 min [fixed hold time]. The mixture was diluted with DCM and washed with water. The organic layer was separated, dried over MgSO₄, filtered off and evaporated in vacuo to give 1.54 g, brown oil. This oil was purified by prep. LC (Irregular SiOH 15-40 µm, 80 g Grace, mobile phase gradient: from DCM 100% to DCM 90%, acetone 10%). The pure fractions were collected and solvent evaporated until dryness to give 720 mg of Int. 296, yellow oil (78%).

b—Synthesis of Co. 151:

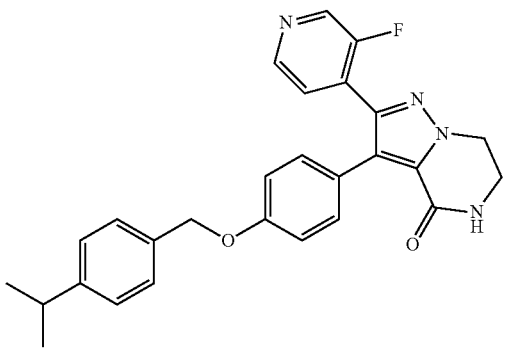 [SMILES: CC(C)c1ccc(COc2ccc(-c3c(-c4ccncc4F)nn4c3C(=O)NCC4)cc2)cc1]

To a sol. of 296 (720 mg, 1.20 mmol) in ACN (15 mL) was added HCl 3N (2.00 mL, 5.97 mmol). The sol. was heated at 80° C. for 2 h, cooled down to r.t. and the solvent was removed in vacuo. DCM and a sat. aq. sol. of NaHCO₃ were added to the residue, the mixture was stirred at r.t. for 10 min and the organic layer was separated, dried over MgSO₄, filtered off and evaporated in vacuo to give a brown oil which crystallized. The crude mixture was purified by prep. LC (Irregular SiOH 15-40 µm. 25 g Merck, solid deposit, mobile phase gradient: from DCM 100% to DCM 80%, acetone 20%). The pure fractions were collected and solvent evaporated until dryness to give 363 mg of Co. 151, white solid (67%). m.p.: 228° C., 235° C. (dsc—polymorphous compound).

Second Method:
a—Synthesis of Int. 297:

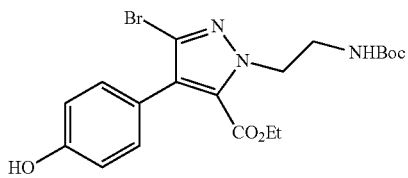 [SMILES: CCOC(=O)c1c(-c2ccc(O)cc2)c(Br)nn1CCNC(=O)OC(C)(C)C]

HCl 3N (8.37 mL, 33.5 mmol) was added to a sol. of 22 (3.91 g, 5.58 mmol) in 1,4-dioxane (30 mL) and the sol. was stirred for 60 h at 50° C. The precipitate formed was filtered on a glass frit and washed with Et₂O to give 2.75 g of Int. 297, white solid (quant. yield).

b—Synthesis of Int. 298:

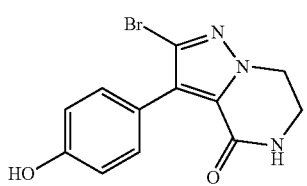 [SMILES: O=C1NCCn2nc(Br)c(-c3ccc(O)cc3)c21]

To a sol. of 297 (2.75 g, 5.93 mmol) in MeOH (40 mL) was added Cs₂CO₃ (9.66 g, 29.7 mmol) and the mixture was stirred at r.t. for 1 h. The solvent was removed in vacuo and the yellow solid obtained was dissolved in a minimum of water and acidified until pH3 with a 1N aq. sol. of HCl. The white precipitate formed was filtered on a glass frit, washed with Et₂O (3 times) and dried to give 1.86 g of Int. 298 white solid (quant. yield).

c—Synthesis of Int. 299:

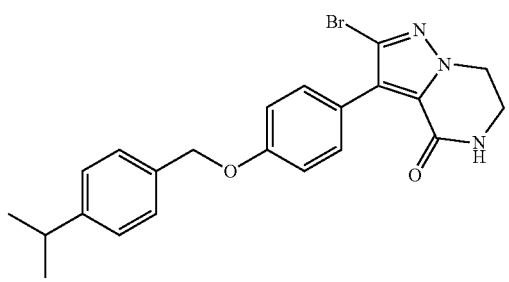 [SMILES: CC(C)c1ccc(COc2ccc(-c3c(Br)nn4c3C(=O)NCC4)cc2)cc1]

To a sol. of 298 (1.00 g, 3.25 mmol) in DMF (10 mL) were added K₂CO₃ (673 mg, 4.87 mmol), NaI (24.3 mg, 162 µmol) and 4-isopropylbenzyl bromide (543 µL, 3.25 mmol). The mixture was heated at 150° C. for 18 h and 4-isopropylbenzyl bromide (543 µL, 3.25 mmol) was added. The mixture was heated at 150° C. for 20 h and cooled down to r.t. Water and DCM were added to the crude mixture. The precipitate was filtered off on a glass frit to give a white solid. The organic layer was separated, dried over MgSO₄, filtered off and evaporated in vacuo to give a white solid. Both solids were combined, dissolved in a mixture of DCM/MeOH and purified by prep. LC (Irregular SiOH 15-40 µm, 25 g Merck, solid deposit, mobile phase gradient:

from DCM 100% to DCM 90%, acetone 10%). The pure fractions were collected and solvent evaporated to give 1.00 g of Int. 299, white solid (70%).

d—Synthesis of Co. 151:

In a sealed tube, a mixture of 299 (130 mg, 295 µmol), 3-fluoro-4-pyridineboronic acide pinacol ester (132 mg, 590 µmol), K₃PO₄ (251 mg, 1.18 mmol) in 1,4-dioxane (1.40 mL) and H₂O (0.50 mL) was carefully purged with N₂. PCy₃ (16.6 mg, 59.1 µmol) and Pd(OAc)₂ (6.63 mg, 29.5 µmol) were added, the r.m. was purged again with N₂ and heated at 100° C. for 18 h. After cooling down to rt, EtOAc and water were added to the crude mixture. The organic layer was separated, dried over MgSO₄, filtered off and evaporated in vacuo to give 137 mg of brown oil. This 137 mg was combined with 103 mg from another batch and purified by prep. LC (Irregular SiOH 15-40 µm, 10 g Merck, mobile phase gradient: from DCM 100% to DCM 80%, acetone 20%). The pure fractions were collected and solvent evaporated until dryness to give 65 mg of Co. 151, white solid (27%). m.p.: 222° C. (dsc).

Example A151

Preparation of Co. 152 a—Synthesis of Int. 300:

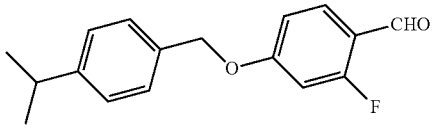 [SMILES: CC(C)c1ccc(COc2ccc(C=O)c(F)c2)cc1]

To a sol. of 2-fluoro-4-hydroxybenzaldehyde (1.3 g, 9.4 mmol) in ACN (34 mL) was added K₂CO₃ (3.2 g, 23 mmol) and 8 (2.1 g, 9.8 mmol), the r.m. was heated at 70° C. for 2 h. Then, the mixture was allowed to cool down to rt, filtered and concentrated to give 2.67 g of Int. 300, colorless oil which quickly crystallized in white solid (100%).

b—Synthesis of Int. 301:

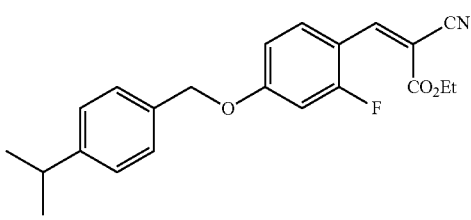 [SMILES: CCOC(=O)/C(C#N)=C\c1ccc(OCc2ccc(C(C)C)cc2)cc1F]

To a sol. of ethyl cyanoacetate (1.1 mL, 10.3 mmol) in EtOH (6.5 mL) was added 300 (2.67 g, 9.8 mmol) and piperidine (19 µL, 0.20 mmol). The mixture was refluxed for 2 h and then, allowed to cool down to r.t. overnight. The precipitate formed was filtered on a glass frit to give 2.68 g of Int. 301, pale yellow powder (74%).

c—Synthesis of Int. 302:

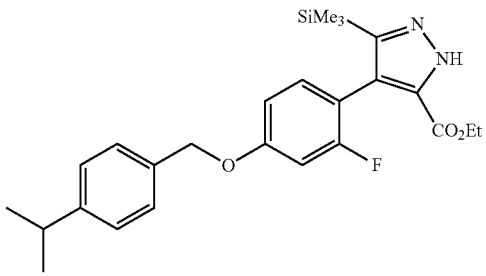 [SMILES: CCOC(=O)c1[nH]nc([Si](C)(C)C)c1-c1ccc(OCc2ccc(C(C)C)cc2)cc1F]

To a sol. of trimethylsilyldiazomethane (5.47 mL, 11 mmol) in dry THF (15 mL) at −78° C. under N₂ was added n-BuLi 1.6M in hexane (6.8 mL, 11 mmol) dropwise. The sol. was stirred for 30 min at −78° C. and a sol. of 301 (2.68 g, 7.3 mmol) in dry THF (15 mL) was added dropwise at −78° C. The sol. was stirred for 1 h at −78° C. then at r.t. for 16 h. EtOAc was added and the organic layer was washed twice with a sat. aq. sol. of NaHCO₃, dried over MgSO₄, filtered off and evaporated in vacuo to give brown oil. The residue was purified by prep. LC (Irregular SiOH 30 µm, 40 g Interchim, mobile phase gradient: from heptane/EtOAc, 75/25 to 65/35). The pure fractions were collected and solvent evaporated until dryness to give 2.0 g of Int. 302, orange solid (60%).

d—Synthesis of Int. 303:

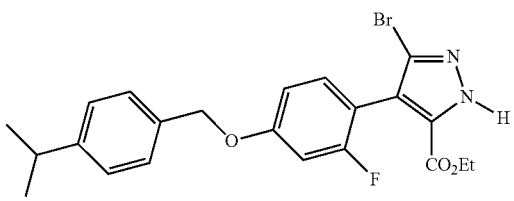 [SMILES: CCOC(=O)c1[nH]nc(Br)c1-c1ccc(OCc2ccc(C(C)C)cc2)cc1F]

To a sol. of 302 (2.0 g, 4.4 mmol) in ACN (40 mL) was added dropwise a sol. of N-Bromosuccinimide (0.82 g, 4.6 mmol) in ACN (20 mL) and the pale brown mixture was stirred at r.t. for 18 h. The solvent was removed in vacuo and EtOAc and a sat. aq. sol. of K₂CO₃ was added to the residue. The organic layer was separated, dried over MgSO₄, filtered off and evaporated in vacuo to give brown oil. The residue was purified by prep. LC (Irregular SiOH 30 µm, 40 g Interchim, mobile phase gradient: from heptane/EtOAc, 80/20 to 70/30). The desired fractions were collected and solvent evaporated to give 510 mg of Int. 303, yellow solid (25%).

e—Synthesis of Int. 304:

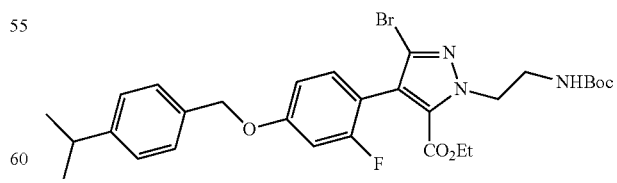

To a mixture of 303 (0.51 g, 1.1 mmol), Boc-Glycinol (267 mg, 1.7 mmol) and PPh₃ supp. (0.52 g, 1.7 mmol) in dry THF (18 mL) was added DBAD (0.38 g, 1.7 mmol). The mixture was stirred at r.t. for 3 days. The mixture was filtrated through a Celite® pad, concentrated and purified by prep. LC (irregular SiOH 30 µm, 25 g Interchim, Mobile phase gradient: heptane/EtOAc, from 80/20 to 60/40). The desired fractions were collected and solvent evaporated until dryness to give 735 mg of Int. 304, white solid. This was a mixture 60/40 of 60% Int. 304 and 40% of a dibrominated Co. This mixture was used as such in the next reaction step.

f—Synthesis of Int. 305:

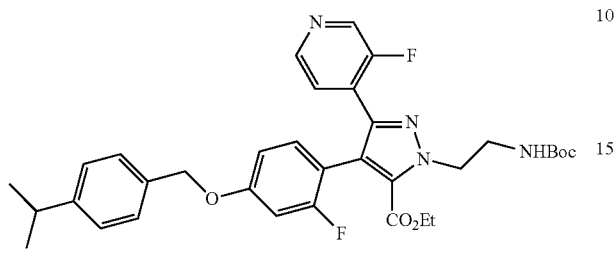

A mixture of 304 (0.35 g, 0.58 mmol), 3-fluoro-4-pyridineboronic acid pinacol ester (0.26 g, 1.2 mmol), $K_3PO_4$ (0.49 g, 2.3 mmol) in 1,4-dioxane (1.5 mL) and $H_2O$ (0.5 mL) was carefully degazed with $N_2$. $PCy_3$ (34 mg, 0.12 mmol) and $Pd(OAc)_2$ (14 mg, 61 µmol) were added and the r.m. was purged again with $N_2$. The r.m. was stirred overnight at 80° C. for a day. The crude material was dissolved in water (50 mL) and extracted with DCM. The organic phase was dried over $MgSO_4$, filtered through a pad of Celite® and evaporated in vacuo. This residue was purified by prep. LC (irregular SiOH 30 µm, 25 g Interchim, mobile phase gradient: from DCM/MeOH/$NH_4$OH 98/2/0.1 to 97/3/0.1). The pure fractions were collected and solvent evaporated until dryness to give 100 mg of Int. 305, pale yellow oil (28%).

g—Synthesis of Int. 306:

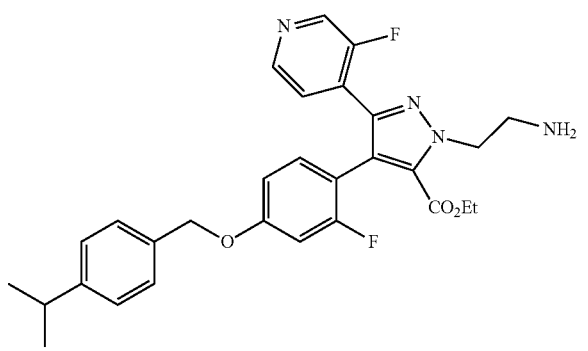 [SMILES: CCOC(=O)c1c(-c2ccc(OCc3ccc(C(C)C)cc3)cc2F)c(-c2ccncc2F)nn1CCN]

305 (100 mg, 0.16 mmol), HCl 3N (0.27 mL, 0.81 mmol), in ACN (2.9 mL) was stirred at 80° C. for 2 h. The mixture was concentrated, and $NaHCO_3$ sat aq (25 mL) was added and the mixture was stirred at r.t. 15 min, extracted with DCM, dried, filtered and concentrated to give 33 mg of Int. 306. This residue was used as such without further purification in the cyclisation step.

h—Synthesis of Co. 152:

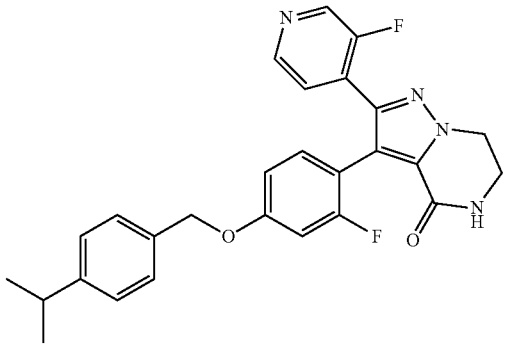 [SMILES: CC(C)c1ccc(COc2ccc(-c3c(-c4ccncc4F)nn4c3C(=O)NCC4)c(F)c2)cc1]

To a sol. of 306 (33 mg, 0.064 mmol) in MeOH (1.8 mL) was added $Cs_2SO_4$ (0.10 g, 0.32 mmol) and the mixture was stirred at r.t. overnight. The mixture was concentrated and taken in water and extracted with DCM. The organic layer was dried on $MgSO_4$ and concentrated to give 17 mg. The residue was purified by prep. LC on (Stability Silica 5 µm 150×30.0 mm, Mobile phase Gradient: from $NH_4$OH/DCM/MeOH 0.2/98/2 to $NH_4$OH/DCM/MeOH 0.8/92/8). The pure fractions were collected and solvent evaporated until dryness to give 12 mg of Co. 152, white solid (40%). m.p.: 262° C. (dsc).

Example A152

Preparation of Co. 153 a—Synthesis of Int. 307:

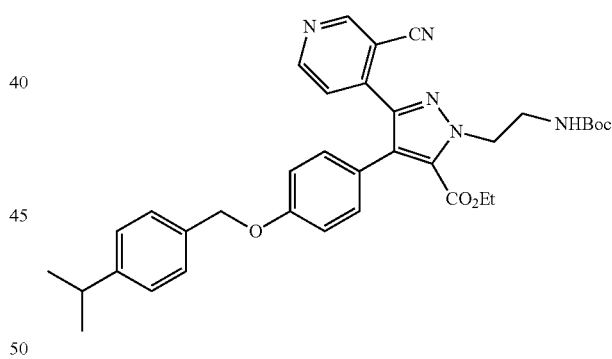

A sol. of 17 (553 mg, 0.943 mmol), 3-cyanopyridine-4-boronic acid pinacol ester (434 mg, 1.89 mmol) and $Na_2CO_3$ (300 mg, 2.83 mmol) in toluene (6.3 mL), EtOH (3.2 mL) and $H_2O$ (1.3 mL) in a sealed tube was purged with $N_2$. $PdCl_2$(dppf) (77.2 mg, 94.3 µmol) was added, the mixture was purged again with $N_2$ and heated at 130° C. using one single mode microwave (Biotage Initiator EXP 60) with a power output ranging from 0 to 400 W for 5 min [fixed hold time]. The crude was diluted with DCM and washed with water. The organic layer was separated, dried over $MgSO_4$, filtered off and evaporated in vacuo to give 1.16 g. The crude was purified by prep. LC (Irregular SiOH 15-40 µm, 80 g Grace, mobile phase gradient: from DCM 100% to DCM 80%, EtOAc 20%). The pure fractions were collected and solvent evaporated until dryness to give 84 mg of Int. 307, colorless oil (18%).

b—Synthesis of Int. 308:

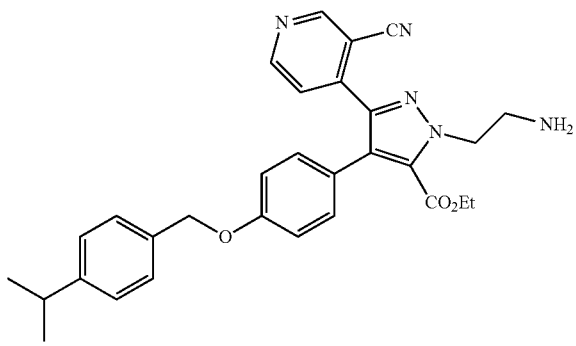 [SMILES: CCOC(=O)c1c(-c2ccc(OCc3ccc(C(C)C)cc3)cc2)c(-c2ccncc2C#N)nn1CCN]

To a sol. of 307 (108 mg, 0.177 mmol) in ACN (2 mL) was added HCl 3N (295 μL, 0). The sol. was heated at 80° C. for 10 min then stirred at r.t. for 10 min. DCM and a sat. aq. sol. of NaHCO₃ were added to the residue, the mixture was stirred at r.t. for 10 min and the organic layer was separated, dried over MgSO₄, filtered off and evaporated in vacuo to give 95 mg of Int. 308, pale yellow oil (quant. yield).

c—Synthesis of Co. 153:

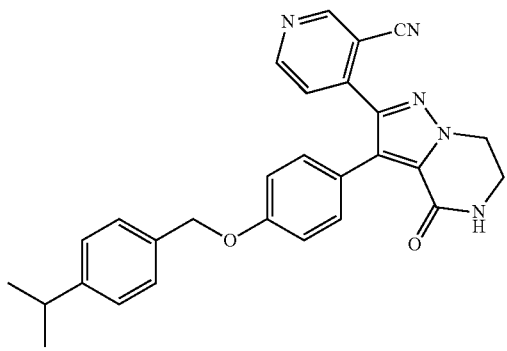 [SMILES: CC(C)c1ccc(COc2ccc(-c3c(-c4ccncc4C#N)nn4c3C(=O)NCC4)cc2)cc1]

To a sol. of 308 (120 mg, 0.235 mmol) in MeOH (2.5 mL) was added Cs₂CO₃ (384 mg, 1.18 mmol) and the mixture was stirred at r.t. for 15 min. The solvent was removed in vacuo and the residue was dissolved in DCM and water. The organic layer was separated, dried over MgSO₄, filtered off and evaporated in vacuo to give 96 mg, pale beige solid. The residue was purified by prep. LC (Irregular SiOH 15-40 μm, 10 g Merck, mobile phase gradient: from DCM 100% to DCM 98%, MeOH 2%). The pure fractions were collected and solvent evaporated until dryness to give 79 mg of Co. 153, white solid (72%). m.p.: 225° C. (dsc).

Example A153

Preparation of Co. 154 a—Synthesis of Int. 309:

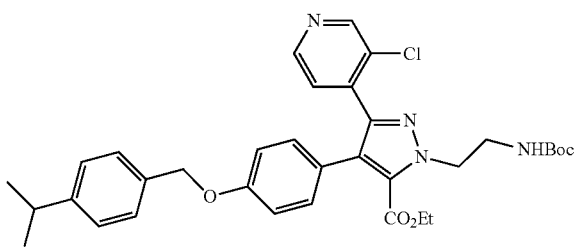 [SMILES: CCOC(=O)c1c(-c2ccc(OCc3ccc(C(C)C)cc3)cc2)c(-c2ccncc2Cl)nn1CCNC(=O)OC(C)(C)C]

A sol. of 17 (800 mg, 1.36 mmol), 3-chloro-4-pyridine-boronic acid pinacol ester (653 mg, 2.73 mmol) and Na₂CO₃ (434 mg, 4.09 mmol) in toluene (10 mL), EtOH (5 mL) and H₂O (2 mL) in a sealed tube was purged with N₂. PdCl₂(dppf) (112 mg, 0.136 mmol) was added, the mixture was purged again with N₂ and heated at 130° C. using one single mode microwave (Biotage Initiator EXP 60) with a power output ranging from 0 to 400 W for 5 min [fixed hold time]. The mixture was diluted with DCM and washed with water. The organic layer was separated, dried over MgSO₄, filtered off and evaporated in vacuo to give 2.07 g, brown oil. The crude was purified by prep. LC (Irregular SiOH 15-40 μm, 80 g Grace, mobile phase gradient: from DCM 100% to DCM 90%, acetone 10%). The pure fractions were collected and solvent evaporated until dryness to give 900 mg of Int. 309, yellow oil (95%).

b—Synthesis of Co. 154:

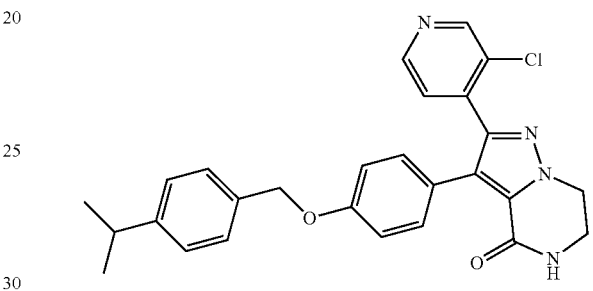

To a sol. of 309 (900 mg, 1.45 mmol) in ACN (20 mL) was added HCl 3N (2.42 mL, 7.27 mmol). The sol. was heated at 80° C. for 2 h, cooled down to r.t. and the solvent was removed in vacuo. DCM and a sat. aq. sol. of NaHCO₃ were added to the residue, the mixture was stirred at r.t. for 10 min and the organic layer was separated, dried over MgSO₄, filtered off and evaporated in vacuo. The brown oil was purified by prep. LC (Irregular SiOH 15-40 μm, 30 g Merck, mobile phase gradient: from DCM 100% to DCM 80%, acetone 20%). The pure fractions were collected and the solvent evaporated to give 458 mg of Co. 154, white solid (67%). m.p.: 207° C. (dsc).

Example A154

Preparation of Co. 155 a—Synthesis of Int. 310:

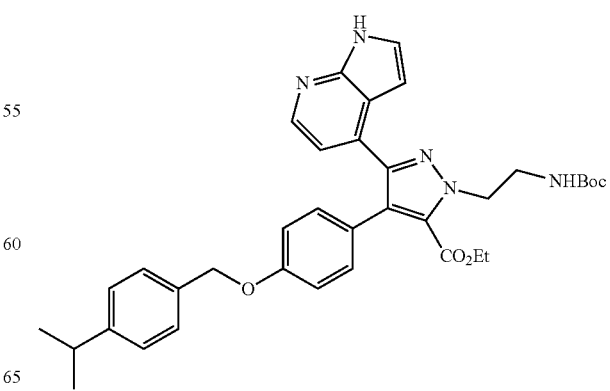

A mixture of 17 (650 mg, 1.11 mmol), 7-azaindole-4-boronic acid pinacol ester (325 mg, 1.33 mmol) and K₃PO₄ (941 mg, 4.43 mmol) in 1,4-dioxane (5 mL) and H₂O (1.2 mL) in a sealed tube was purged with N₂. PdCl₂(dppf) (91.0 mg, 0.111 mmol) was added, the mixture was purged again with N₂ and heated at 80° C. for 18 h. This mixture and another batch (with 142 mg of 17 in the same conditions) were combined, diluted with DCM and washed with water. The organic layer was separated, dried over MgSO₄, filtered off and evaporated in vacuo to give brown oil. The crude was purified by prep. LC (Irregular SiOH 15-40 µm, 80 g Grace, mobile phase gradient: from DCM 100% to DCM 80%, acetone 20%). The pure fractions were collected and solvent evaporated until dryness to give 478 mg of Int. 310, orange foam (57%).

b—Synthesis of Int. 311:

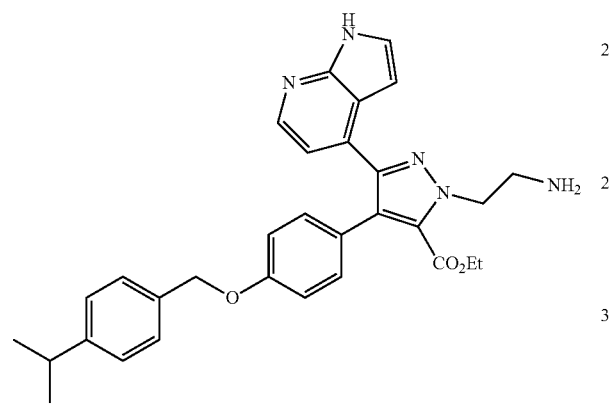 [SMILES: CCOC(=O)c1c(-c2ccc(OCc3ccc(C(C)C)cc3)cc2)c(-c2ccnc3[nH]ccc23)nn1CCNC(=O)OC(C)(C)C]

To a sol. of 310 (478 mg, 0.766 mmol) in ACN (6 mL) was added HCl 3N (1.28 mL, 3.83 mmol). The sol. was heated at 50° C. for 3 h then stirred at r.t. for 18 h. DCM and a sat. aq. sol. of NaHCO₃ were added. The organic layer was separated, dried over MgSO₄, filtered off and evaporated in vacuo to give 398 mg of Int. 311, brown oil (99%).

c—Synthesis of Co. 155:

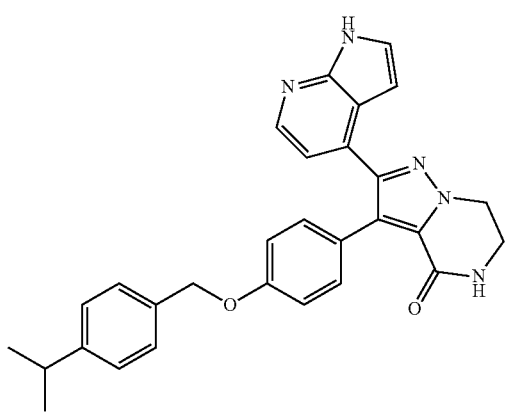 [SMILES: CC(C)c1ccc(COc2ccc(-c3c(-c4ccnc5[nH]ccc45)nn4c3C(=O)NCC4)cc2)cc1]

To a sol. of 311 (398 mg, 0.76 mmol) in MeOH (8 mL) was added Cs₂CO₃ (1.24 g, 3.80 mmol) and the mixture was stirred at r.t. for 15 min. The solvent was removed in vacuo and the residue was dissolved in DCM and water. The organic layer was separated, dried over MgSO₄, filtered off and evaporated in vacuo to give beige solid. This solid was purified by prep. LC (Irregular SiOH 15-40 µm, 12 g Grace, DCM 100% to DCM 95%, iPrOH 5%). The pure fractions were collected and solvent evaporated until dryness to give 289 mg, white solid (80%). 249 mg of this white solid was crystallized from MeCN. The precipitate was filtered on a glass frit and the filtrate was evaporated in vacuo. The residue was recrystallized again from ACN and the precipitate was filtered on a glass frit (process repeated 2×). The solids were combined and dried in high vacuum at 55° C. for 3 h to give 185 mg of Co. 155, white solid (51%). m.p.: 266° C. (dsc).

Example A155

Preparation of Co. 56 a—Synthesis of Int. 312:

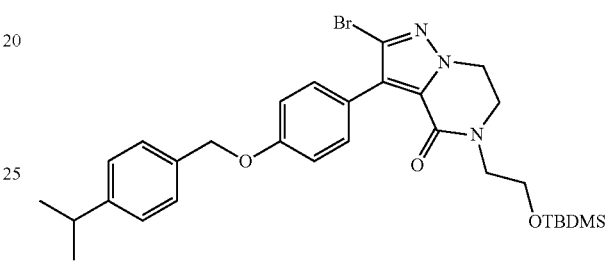

To a suspension of 299 (264 mg, 600 µmol) in DMSO ( ) at r.t. under N₂ was added NaH 60% (28.8 mg, 719 µmol). The mixture was stirred at r.t. for 2 h and (2-bromoethoxy)-tert-butyldimethylsilane (154 µL, 719 µmol) was added. The r.m. was stirred at r.t. for 2 h. Water and EtOAc were added. The organic layer was separated, washed with a sat. aq. sol. of NaCl (3 times), dried over MgSO₄, filtered and evaporated in vacuo to give 368 mg of Int. 312, yellow oil (quant.). The crude Int. 312 was used as such in the next reaction step without purification.

b—Synthesis of Int. 313:

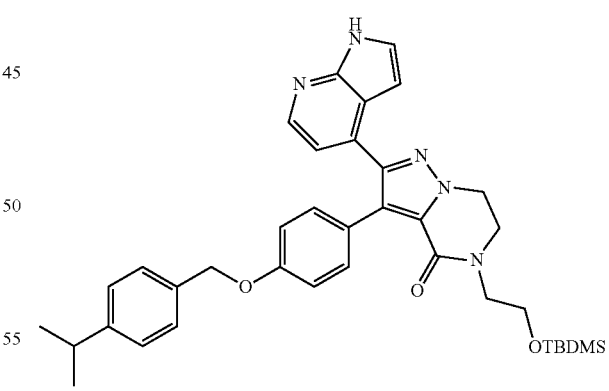

A mixture of 312 (150 mg, 251 µmol), 7-azaindole-4-boronic acid pinacol ester (73.4 mg, 301 mmol) and K₃PO₄ (213 mg, 1.00 mmol) in 1,4-dioxane (2.25 mL) and H₂O (450 µL) in a sealed tube was purged with N₂. PdCl₂(dppf) (20.5 mg, 25.1 µmol) was added, the mixture was purged again with N₂ and heated at 80° C. for 18 h. DCM and water were added to the crude mixture. The organic layer was separated, dried over MgSO₄, filtered off and evaporated in vacuo to give 300 mg, brown oil. The residue was purified by prep. LC (Irregular SiOH 15-40 µm, 12 g Grace, mobile phase gradient: from DCM 100% to DCM 95%, MeOH 5%). The pure fractions were collected and solvent evaporated until dryness to give 107 mg of Int. 313, yellow oil (67%).

c—Synthesis of Co. 156:

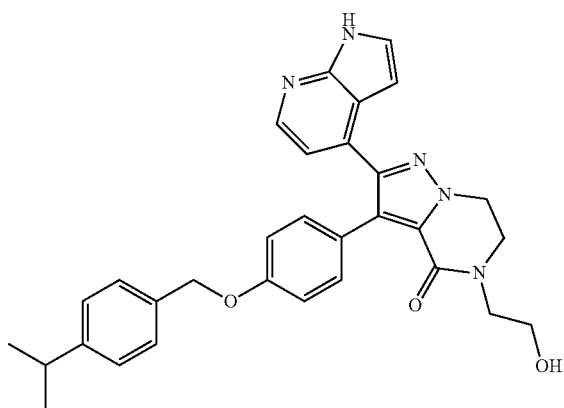 [SMILES: CC(C)c1ccc(COc2ccc(-c3c(-c4ccnc5[nH]ccc45)nn4c3C(=O)N(CCO)CC4)cc2)cc1]

To a sol. of 313 (107 mg, 0.168 mmol) in THF (4 mL) at 0° C. was added TBAF (252 µL, 0.252 mmol). The r.m. was allowed to warm to r.t. and stirred for 1 h. The crude mixture was diluted with water and DCM. The organic layer was separated, dried over MgSO₄, filtered off and evaporated in vacuo to give 90 mg, pale yellow oil. The residue was purified by prep. LC (Irregular SiOH 15-40 µm, 4 g Grace, mobile phase gradient: from DCM 100% to DCM 95%, MeOH 5%). The pure fractions were collected and solvent evaporated until dryness to give 72 mg of colorless oil (82%) which was crystallized from Et₂O and dried in vacuo to give 56 mg of Co. 156, white solid (64%). m.p.: 219° C. (dsc).

Example A156

Preparation of Co. 157 a—Synthesis of Int. 314:

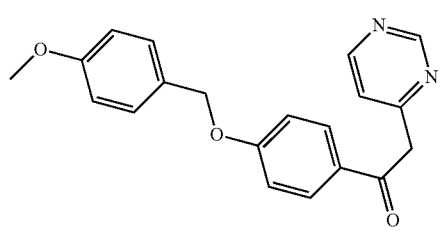 [SMILES: COc1ccc(COc2ccc(C(=O)Cc3ccncn3)cc2)cc1]

In a dry flask and under N₂ atmosphere, a sol. of Ethyl 4-(4-methoxybenzyloxy)benzoate (2.00 g, 6.99 mmol) and 4-methylpyrimidine (723 mg, 7.68 mmol) in dry THF (10 mL) was cooled to 0° C. and treated with LiHMDS (14.0 mL, 14.0 mmol) (slow addition over 10 min). After the end of the addition, the r.m. was allowed to warm to r.t. and stirred for 17 h. The r.m. was then poured in a 10% aq. sol. of NH₄Cl (100 mL). The mixture was filtered on a glass frit. The precipitate was washed with water (2×50 mL) and with Et₂O (2×50 mL). The solid was dissolved in a mixture of DCM and MeOH. The organic sol. was dried over MgSO₄ and evaporated in vacuo to give 2.14 g of Int. 314, white solid (92%).

b—Synthesis of Int. 315:

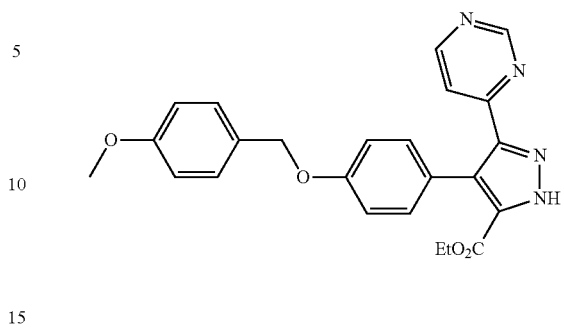

To a suspension of 314 (5.00 g, 15.0 mmol) in ACN (50 mL) in a sealed tube was added DBU (2.24 mL, 15.0 mmol) and ethyldiazoacetate (2.67 mL, 25.4 mmol). The mixture was heated at 60° C. for 2 h then cooled down to r.t. The solvent was removed in vacuo and the residue was diluted in DCM. The organic layer was washed with a sat. aq. sol. of NaHCO₃, water, dried over MgSO₄, filtered off and evaporated in vacuo to give 5.32 g, brown oil. This experiment and another batch (with 500 mg of 314 in the same conditions) were combined and purified by prep. LC (Irregular SiOH 15-40 µm, 220 g Grace, mobile phase gradient: from DCM 100% to DCM 95%, MeOH 5%). The pure fractions were collected and solvent evaporated until dryness to give 3.54 g. The residue was dissolved in DCM and a precipitate was filtered to give 2.30 g of Int. 315, yellow solid. The filtrate was purified by prep. LC (Irregular SiOH 15-40 µm, 80 g Grace, mobile phase gradient: from DCM 100% to DCM 50%, EtOAc 50%). The pure fractions were collected and solvent evaporated to give 784 mg of Int. 315, yellow solid (global yield: 4.32 g, 44%).

c—Synthesis of Int. 316:

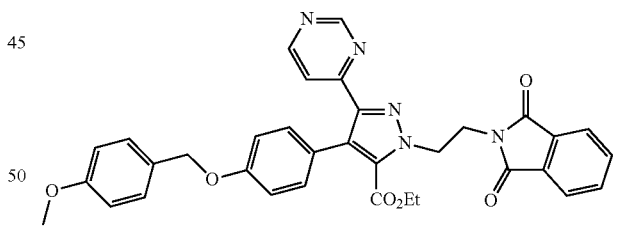

To a suspension of 315 (3.00 g, 6.97 mmol), N-(2-hydroxyethyl)phtalimide (1.60 g, 8.36 mmol) and diphenylphosphinopolystyrene (2.79 g, 8.36 mmol) in dry THF (60 mL) was added DBAD (1.93 g, 8.36 mmol). The mixture was stirred for 20 h at r.t. then filtered through a glass frit and washed with EtOAc. The filtrate was evaporated in vacuo to give 8.20 g, yellow oil. The residue was purified by prep. LC (Irregular SiOH, 15-40 µm, 150 g Merck, mobile phase gradient: from DCM 100% to DCM 70%, acetone 30%). The pure fractions were collected and solvent evaporated until dryness to give 2.82 g of Int. 316, off-white solid (67%).

d—Synthesis of Co. 157:

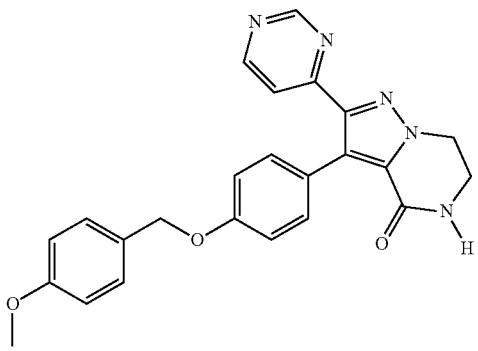 [SMILES: COc1ccc(COc2ccc(-c3c(-c4ccncn4)nn4c3C(=O)NCC4)cc2)cc1]

To a mixture of 316 (2.82 g, 4.67 mmol) in EtOH (50 mL) was added hydrazine hydrate (668 µL, 7.01 mmol) and the mixture was heated at 70° C. for 4 h. The precipitate formed was filtered on a glass frit to give 1.84 g of a white solid which was dissolved in a mixture of DCM/MeOH/EtOAc and the precipitate filtered on a glass frit. The solid was washed with MeOH and dried to give 986 mg of Co. 157, white solid (49%). m.p.: 264° C. (DSC).

Example A157

Preparation of Co. 158

First Method:
a—Synthesis of Int. 317:

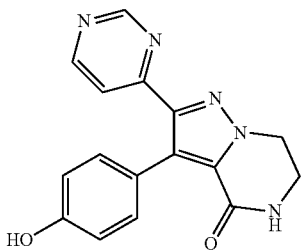 [SMILES: O=C1NCCn2nc(-c3ccncn3)c(-c3ccc(O)cc3)c21]

fluoroacetate salt

To a sol. of Co. 157 (200 mg, 0.468 mmol) in toluene (8 mL) in a sealed tube was added TFA (1.00 mL, 13.1 mmol) and the mixture was heated at 75° C. for 5 h. The yellow sol. was evaporated in vacuo and coevaporated 3× with toluene. The yellow residue was triturated in Et₂O and filtered on a glass frit to give 222 mg of Int. 317, yellow solid (quant. yield, trifluoroacetate salt).

b—Synthesis of Co. 158:

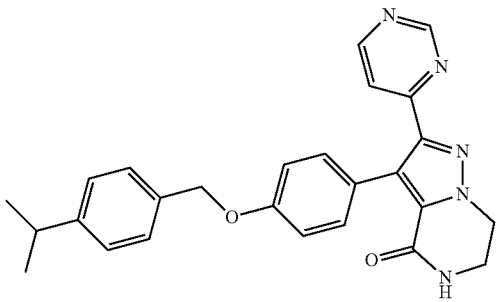 [SMILES: CC(C)c1ccc(COc2ccc(-c3c(-c4ccncn4)nn4c3C(=O)NCC4)cc2)cc1]

To a sol. of 317 (100 mg, 0.237 mmol) in DMF (2 mL) was added K₂CO₃ (98.4 mg, 0.712 mmol) and 8 (41.7 µL, 0.249 mmol). The mixture was heated at 50° C. for 18 h and refluxed for 18 h. 8 (20.0 µL, 0.119 mmol) and K₂CO₃ (16.4 mg, 0.119 mmol) were added and the mixture was refluxed for 60 h. 8 (20.0 µL, 0.119 mmol) and K₂CO₃ (16.4 mg, 0.119 mmol) were then added and the mixture was refluxed for 18 h. DCM was added to the residue and the organic layer was washed with water, dried over MgSO₄, filtered off and evaporated in vacuo to give 125 mg, yellow residue. The residue was purified by prep. LC (Irregular SiOH 15-40 µm, 10 g Merck, mobile phase gradient: from DCM 100% to DCM 50%, acetone 50%). The desired fractions were collected and solvent evaporated until dryness to give 46 mg, off-white residue. This residue was purified again by prep. LC on (Irregular SiOH 15-40 µm, 30 g Merck, mobile phase: 96% DCM, 4% MeOH, 0.1% NH₃ aq). The pure fractions were collected and solvent evaporated until dryness to give 24 mg of Co. 158, white solid (23%). m.p.: 252° C. (DSC).

Second Method:
a—Synthesis of Int. 318:

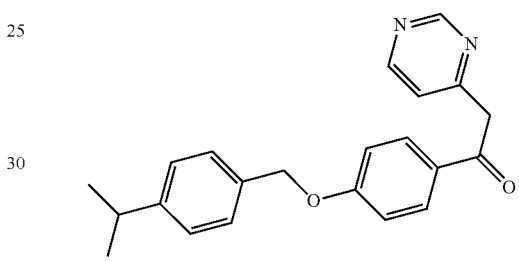

In a dry flask and under N₂ atmosphere, a sol. of 9 (16.8 g, 59 mmol) and 4-methylpyrimidine (6.1 g, 65 mmol) in dry THF (118 mL) was cooled to 0° C. and treated with LiHMDS (118 mL, 118 mmol) dropwise. The r.m. was allowed to warm to r.t. (over 1 h) and stirred for 17 h at this temperature. The r.m. was then poured in a 10% aq. sol. of NH₄Cl (300 mL). The mixture was extracted with DCM, dried on MgSO₄ and concentrated. The residue was taken up in Et₂O and the solid was filtrated, washed with Et₂O and dried to give 19.2 g of Int. 318, gold solid (94%).

b—Synthesis of Int. 319:

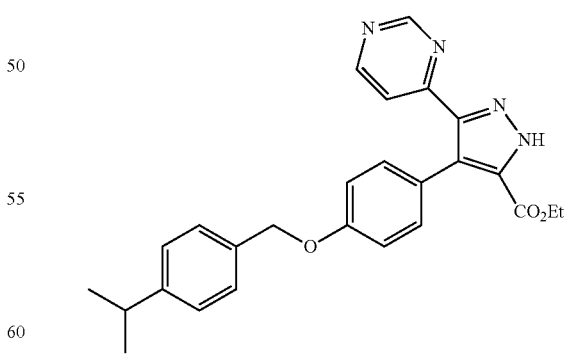

A suspension of 318 (23.7 g, 68.4 mmol) in ACN (400 mL) was treated with DBU (17.4 mL, 116 mmol) then with ethyl diazoacetate (11.5 mL, 109 mmol). The r.m. was stirred at r.t. for 3 h. The r.m. was poured in a sat. sol. of NaHCO₃ and extracted with EtOAc. The organic layer was

293 washed with brine, dried over MgSO₄ and evaporated in vacuo to give black oil. The oil was purified by prep. LC (irregular SiOH 15-40 μm, 220 g, Grace, mobile phase gradient: from DCM 100% to DCM 98%, MeOH 2%). The pure fractions were collected and solvent evaporated until dryness to give 21.1 g of Int. 319 (yield: 70%).

c—Synthesis of Int. 320:

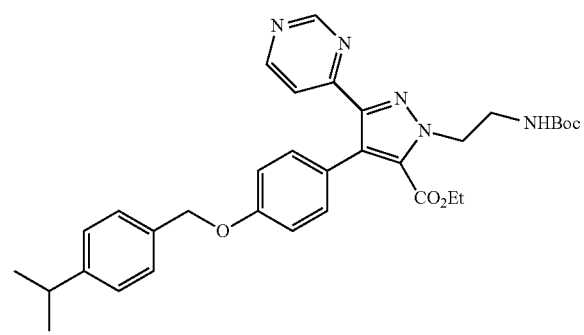 [SMILES: CCOC(=O)c1c(-c2ccc(OCc3ccc(C(C)C)cc3)cc2)c(-c2ccncn2)nn1CCNC(=O)OC(C)(C)C]

A sol. of 319 (13.8 g, 31.2 mmol) and Boc-Glycinol (7.24 mL, 46.8 mmol) in dry THF (250 mL) was treated with diphenylphosphinopolystyrene (14.6 g, 46.8 mmol) then with DBAD (10.8 g, 46.8 mmol). The r.m. was stirred at r.t. for 17 h, under N₂. The crude mixture was filtered through Celite® and evaporated in vacuo to give black oil. The oil was purified by prep. LC (irregular SiOH 15-40 μm, 220 g, Grace, dry loading, mobile phase gradient: from DCM 100% to DCM 96%, MeOH 4%). The fractions were collected and solvent evaporated until dryness to give 16.6 g of brown oil (which contained 2 isomers). This oil was purified by prep. LC (Stationary phase: Irregular SiOH 20-45 μm 450 g MATREX, Mobile phase: Gradient from NH₄OH/DCM/iPrOH 0.2/98/2 to NH₄OH/DCM/iPrOH 0.3/97/3). The pure fractions were collected and solvent evaporated until dryness to give 8.40 g of Int. 320, orange solid (46%).

d—Synthesis of Int. 321:

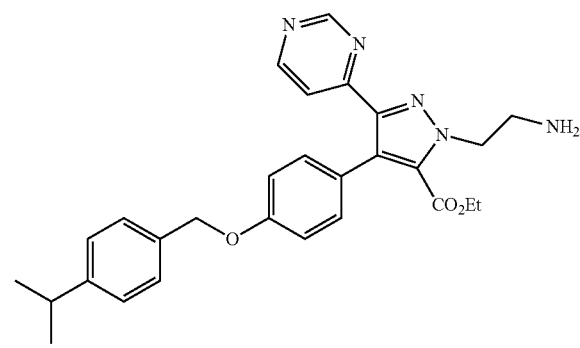 [SMILES: CCOC(=O)c1c(-c2ccc(OCc3ccc(C(C)C)cc3)cc2)c(-c2ccncn2)nn1CCN]

A mixture of 320 (3.7 g, 6.3 mmol), HCl 3N (10.5 mL, 32 mmol), in ACN (110 mL) was stirred at 80° C. for 2 h. The mixture was concentrated, and NaHCO₃ sat aq (200 mL) was added and the mixture was stirred at r.t. 15 min, extracted with DCM, dried and evaporated until dryness to give 3.05 g of Int. 321 (99%). The yellow solid obtained was used like in the next step.

e—Synthesis of Co. 158:

To a solution of 321 (1.62 g, 3.3 mmol) in MeOH (100 mL) was added Cs₂CO₃ (5.4 g, 17 mmol) and the mixture was stirred at r.t. for 3 days. The mixture was filtrated, the

294 white solid was collected, washed with Et₂O and dried to give 1.07 g of Co. 158 (73%). m.p.: 259° C. (dsc).

Example A158

Preparation of Co. 159 a—Synthesis of Int. 322:

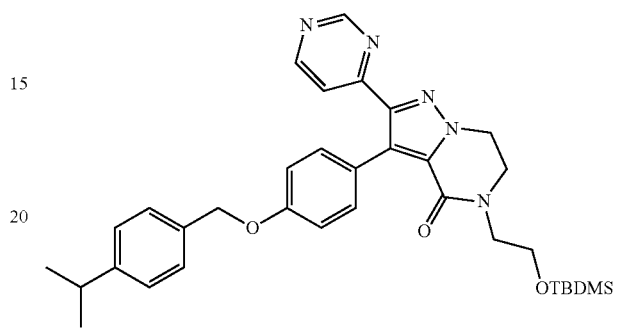

NaH 60% (68 mg, 1.7 mmol) was added slowly to a suspension of Co. 158 (0.50 g, 1.1 mmol) in DMF (6.8 mL) at r.t. under N₂. The mixture was stirred for 2 h then (2-bromoethoxy)-tert-butyldimethylsilane (0.28 mL, 1.4 mmol) was added and the r.m. stirred overnight. Water was added and the mixture was concentrated under reduced pressure. The residue was taken up in EtOAc and washed 5× with brine. The organic layer was dried, filtered and concentrated to give 0.68 g of Int. 322 (yellow oil; quant.), used as such in the next step.

b—Synthesis of Co. 159:

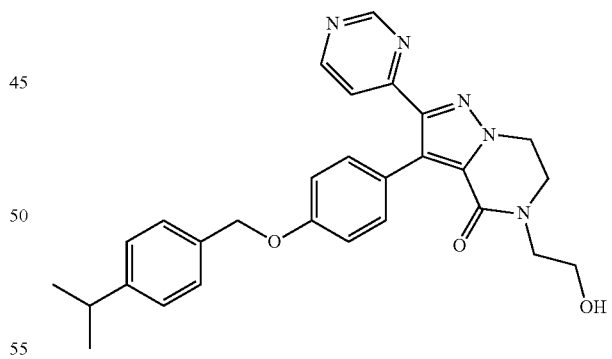

TBAF (1.4 mL, 1.4 mmol) was added dropwise to a sol. of 322 (0.68 g, 1.1 mmol) in THF (11 mL) at r.t. The mixture was stirred overnight at r.t. The mixture was concentrated and the residue was purified by prep. LC (Regular SiOH, 30 μm, 25 g GraceResolv™, mobile phase: DCM/MeOH/NH₄OH, 95/5/0.1). The pure fractions were collected and solvent evaporated until dryness to give 450 mg of colorless oil which was crystallized from Et₂O. The white solid formed was filtrated, washed and dried to give 0.42 g of Co. 159, white solid (77%). m.p.: 160° C. (dsc).

Example A159

Preparation of Co. 160

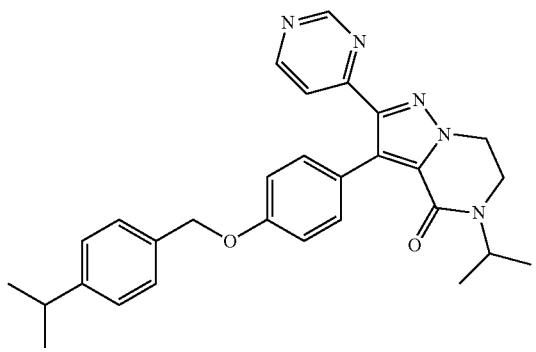 [SMILES: CC(C)c1ccc(COc2ccc(-c3c(-c4ccncn4)nn4c3C(=O)N(C(C)C)CC4)cc2)cc1]

NaH 60% (41 mg, 1.0 mmol) was added slowly to a suspension of Co. 158 (0.30 g, 0.68 mmol) in DMSO (3.8 mL) at r.t. under $N_2$. The mixture was stirred for 2 h (until a sol. was observed in the flask), then 2-iodopropane (75 μL; 0.75 mmol) was added and stirred overnight. Water was added and the insoluble was filtered, dissolved in DCM and MeOH, dried on $MgSO_4$ and evaporated until dryness to give 300 mg of white solid. The residue was purified by prep. LC (Regular SiOH, 30 μm, 25 g Interchim, mobile phase gradient: DCM/MeOH/$NH_4OH$, from 98/2/0.1 to 96/4/0.1). The pure fractions were collected and solvent evaporated until dryness to give 125 mg, colorless oil. This oil was taken in $Et_2O$, concentrated and dried to give 121 mg of Co. 160, white solid (37%). m.p.: 166° C. (dsc).

Example A160

Preparation of Co. 161a and Co. 161 a—Synthesis of Co. 161a

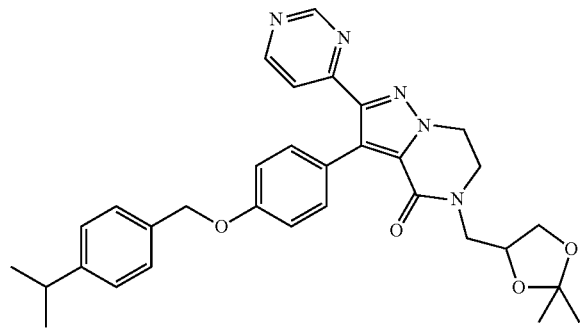 [SMILES: CC(C)c1ccc(COc2ccc(-c3c(-c4ccncn4)nn4c3C(=O)N(CC3COC(C)(C)O3)CC4)cc2)cc1]

To a suspension of Co. 158 (300 mg, 0.683 mmol) in DMSO (5.4 mL) was added NaH 60% (41.0 mg, 1.02 mmol). The mixture was stirred at r.t. for 4 h to obtain a clear yellow sol. and 2,2-dimethyl-1,3-dioxolan-4-ylmethyl p-toluenesulfonate (215 mg, 0.751 mmol) was added. The sol. was heated at 50° C. for 20 h. DCM and water were added, the organic layer was separated, dried, filtered off and evaporated in vacuo. The residue (670 mg) was purified by prep. LC (Irregular SiOH 15-40 μm, 30 g Merck, mobile phase gradient: from DCM 100% to DCM 95%, MeOH 5%). The pure fractions were collected and solvent evaporated to give 260 mg of Co. 161a (60%).

b—Synthesis of Co. 161:

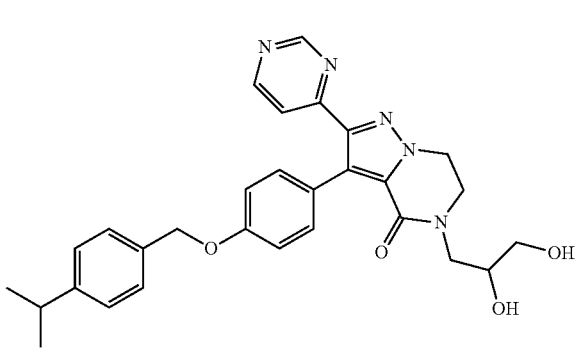

A sol. of Co. 161a (210 mg, 379 μmol) and HCl 3N (632 μL, 1.90 mmol) in 1,4-dioxane (8 mL) was stirred at r.t. for 1 h. The mixture was poured into a sat. aq. sol. of $NaHCO_3$ and extracted with DCM. The organic layer was separated, dried over $MgSO_4$, filtered and evaporated in vacuo to give 190 mg of Co. 161, white solid (98%). m.p.: 209° C. (DSC).

Example A161

Preparation of Co. 162 a—Synthesis of Int. 324:

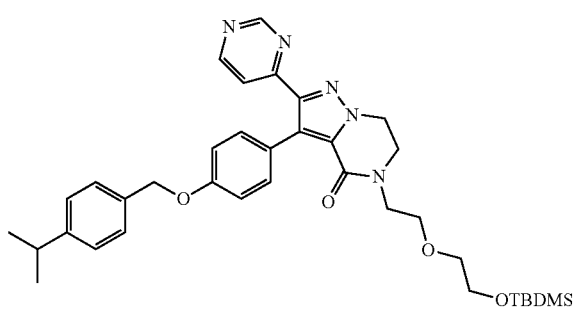 [SMILES: CC(C)c1ccc(COc2ccc(-c3c(-c4ccncn4)nn4c3C(=O)N(CCOCCO[Si](C)(C)C(C)(C)C)CC4)cc2)cc1]

To a suspension of Co. 158 (150 mg, 341 μmol) in DMSO (2 mL) at r.t. under $N_2$ was slowly added NaH 60% (20.5 mg, 512 μmol). The mixture was stirred at r.t. for 2 h until complete solubilization then tert-Butyl(2-(2-chloroethoxy)ethoxy)dimethylsilane (245 mg, 1.02 mmol) in DMSO (500 μL) was added. The sol. was heated at 80° C. for 18 h then cooled down to r.t. and water and DCM were added. The organic layer was separated, dried over $MgSO_4$, filtered off and evaporated in vacuo to give 640 mg of Int. 324, used as such in the next step without purification.

b—Synthesis of Co. 162:

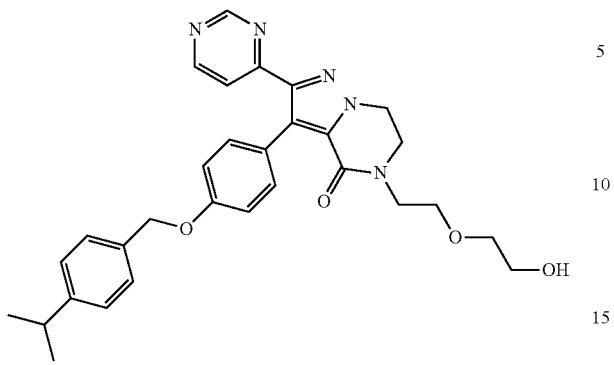

To a sol. of 324 (220 mg, 0.343 mmol) in THF (10 mL) at 0° C. was added TBAF (514 μL, 0.514 mmol), and the sol. was stirred at 0° C. for 2 h then at r.t. for 18 h. The sol. was diluted with water and DCM, the organic layer was separated, washed with a sat. aq. sol. of NaCl, dried over MgSO$_4$, filtered off and evaporated in vacuo to give 266 mg. The residue was purified by prep. LC (Stationary phase: Stability Silica 5 μm 150×30.0 mm, Mobile phase Gradient: from 50% Heptane, 3% MeOH (+10% NH$_4$OH), 47% EtOAc to 25% MeOH (+10% NH$_4$OH), 75% EtOAc). The pure fractions were collected and solvent evaporated to give 119 mg, colorless oil (66%). The Co. was diluted in a minimum of DCM and pentane was added until precipitation. The mixture was evaporated in vacuo to give 114 mg of Co. 162, off-white solid (63%).

Example A162

Preparation of Co. 163

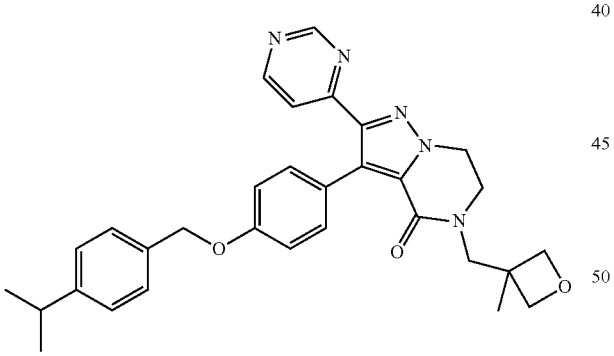

NaH 60% (55 mg, 1.4 mmol) was added slowly to a suspension of Co. 158 (0.40 g, 0.91 mmol) in DMSO (5.0 mL) at r.t. under N$_2$. The mixture was stirred for 2 h (until complete solubilization), then 2-(chloromethyl)-2-methyl-1,3-epoxypropane (110 μL, 1.0 mmol) was added and the r.m. stirred overnight. Water was added and the insoluble was filtrated, dissolved in DCM, dried on MgSO$_4$ and evaporated until dryness to give 620 mg, white solid. The residue was purified by prep. LC (Regular SiOH, 30 μm, 25 g Interchim, mobile phase gradient: DCM/MeOH/NH$_4$OH, from 98/2/0.1 to 96/4/0.1). The desired fractions were collected and solvent evaporated until dryness to give 450 mg, colorless oil. This residue was purified by prep. LC on (irregular 15-40 μm 50 g Merck, Mobile phase: 0.1% NH$_4$OH, 97% DCM, 3% MeOH). The desired fractions were collected and solvent evaporated until dryness 300 mg which was purified by achiral SFC on (2-ethylpyridine 6 μm 150×21.2 mm, Mobile phase: 85% CO$_2$, 15% MeOH). The pure fractions were collected and solvent evaporated until dryness to give 260 mg of Co. 163, white solid (55%).

Example A163

Preparation of Co. 164

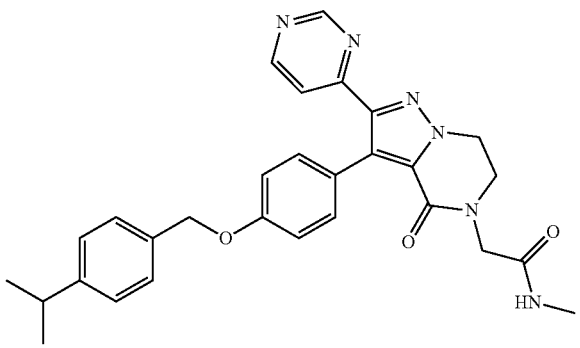 [SMILES: CNC(=O)CN1CCn2nc(-c3ccncn3)c(-c3ccc(OCc4ccc(C(C)C)cc4)cc3)c2C1=O]

To a suspension of Co. 158 (300 mg, 0.683 mmol) in DMF (6 mL) at r.t. under N$_2$ atmosphere was added NaH 60% (41.0 mg, 1.02 mmol). The mixture was stirred at r.t. until complete solubilization of the mixture (2 h). Then 2-bromo-N-methylacetamide (124 mg, 0.819 mmol) was added and the sol. was stirred at r.t. for 3 h. EtOAc and water were added and the organic layer was separated, washed with a sat. aq. sol. of NaCl (twice), dried over MgSO$_4$, filtered off and evaporated in vacuo. The residue (382 mg) was purified by prep. LC (Irregular SiOH 15-40 μm, 12 g Grace, mobile phase gradient: from DCM 100% to DCM 80%, iPrOH 20%). The pure fractions were collected and solvent evaporated until dryness to give 222 mg of colorless film which crystallized on standing. The precipitate was filtered on a glass frit to give a white solid (159 mg) of Co. 164 (46%). m.p.: 97° C. and 157° C. (DSC).

Example A164

Preparation of Co. 165a and Co. 165 a—Synthesis of Co. 165a

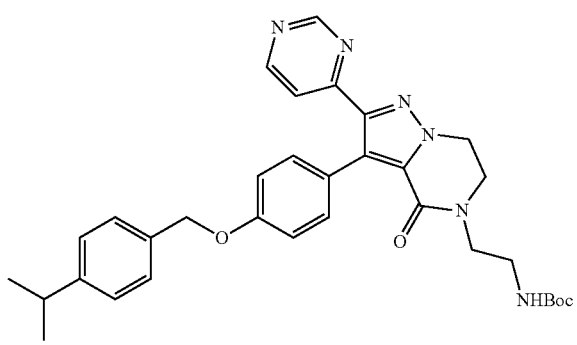 [SMILES: CC(C)c1ccc(COc2ccc(-c3c(-c4ccncn4)nn4c3C(=O)N(CCNC(=O)OC(C)(C)C)CC4)cc2)cc1]

NaH 60% (55 mg, 1.4 mmol) was added slowly to a suspension of Co. 158 (0.4 g, 0.91 mmol) in dry DMSO (5 mL) at r.t. under N$_2$. The mixture was stirred for 2 h then Boc-1-amino-2-bromoethane (224 mg, 1.0 mmol) was added and the r.m. stirred for 3 days. Water was added and the insoluble was filtered, dissolved in DCM and MeOH, dried over MgSO₄ and evaporated until dryness to give 550 mg of Co. 165a as a crude (mixture with starting material) which was used as such in the next reaction step.

b—Synthesis of Co. 165:

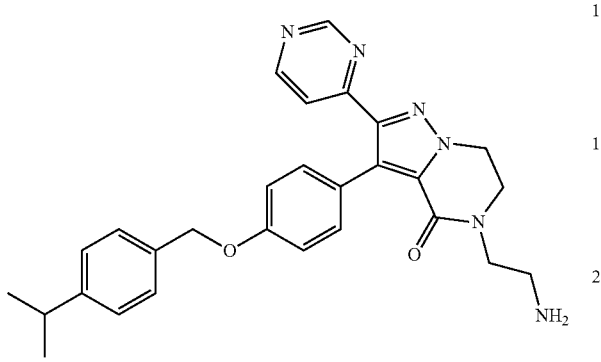

A mixture of Co. 165a (550 mg, 0.94 mmol), HCl 3N (1.6 mL, 4.7 mmol), in ACN (17 mL) was stirred at 80° C. for 2 h. The mixture was concentrated, and NaHCO₃ sat aq (200 mL) was added and the mixture was stirred at r.t. 15 min, extracted with DCM, dried, filtered and concentrated. The residue was purified by prep. LC (Regular SiOH, 30 μm, 25 g Interchim, mobile phase gradient: DCM/MeOH/NH₄OH, from 95/5/0.1 to 80/20/0.1). The pure fractions were collected and solvent evaporated until dryness to give 258 mg, colorless oil. This oil was taken in Et₂O, concentrated and dried to give 210 mg of Co. 165, white solid (46%).

Example A165

Preparation of Co. 166 a—Synthesis of Int. 326:

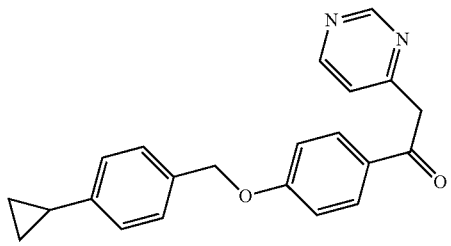 [SMILES: O=C(Cc1ccncn1)c1ccc(OCc2ccc(C3CC3)cc2)cc1]

In a dry flask and under N₂ atmosphere, a sol. of 34 (12.6 g, 45 mmol) and 4-methylpyrimidine (4.6 g, 49 mmol) in dry THF (90 mL) was cooled to 0° C. and treated with LiHMDS (90 mL, 90 mmol) dropwise. The r.m. was allowed to warm to r.t. (over 1 h) and stirred for 17 h at this temperature. The r.m. was then poured in a 10% aq. sol. of NH₄Cl (400 mL). The mixture was extracted with DCM, dried on MgSO₄ and concentrated. The residue was taken up in Et₂O and the solid was filtrated, washed with Et₂O and dried to give 13 g of Int. 326, yellow solid (85%).

b—Synthesis of Int. 327:

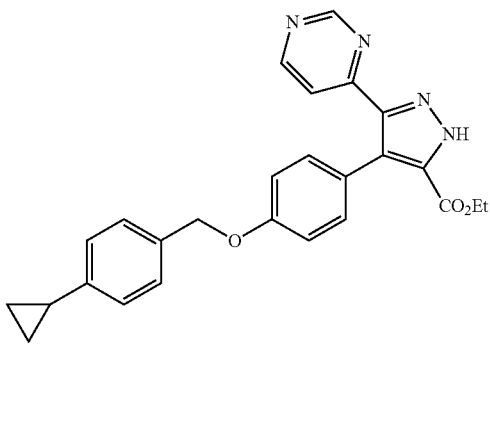 [SMILES: CCOC(=O)c1[nH]nc(-c2ccncn2)c1-c1ccc(OCc2ccc(C3CC3)cc2)cc1]

To a suspension of 326 (13 g, 38 mmol) in ACN (135 mL) was added DBU (5.6 mL, 38 mmol) and Ethyl diazoacetate (6.7 mL, 64 mmol). The mixture was heated for 3 h at 60° C. then cooled down to r.t. The solvent was removed in vacuo and the residue was diluted in EtOAc. The organic layer was washed with a sat. aq. sol. of NaHCO₃ (2*500 mL), dried over MgSO₄, filtered off and evaporated in vacuo to give 19 g of brown residue. The residue was purified by prep. LC (irregular SiOH 15-40 μm, 330 g GraceResolv™, mobile phase gradient, from DCM/MeOH/NH₄OH, 100/0/0 to 97/3/0.1). The desired fractions were collected and solvent evaporated to give 7.16 g of Int. 327, brown solid (43%) used as such for the next step.

c—Synthesis of Int. 328:

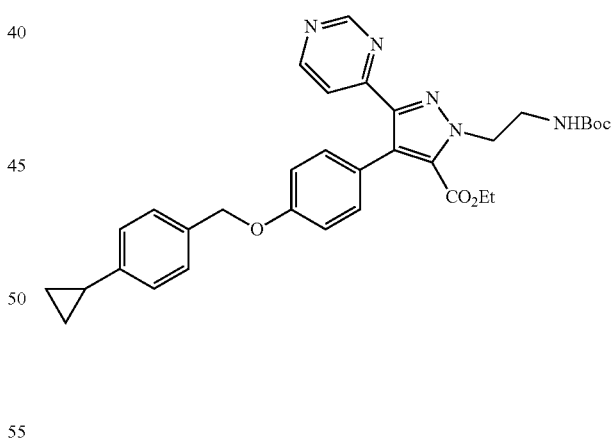

To a suspension of 327 (7.16 g, 16 mmol), Boc-Glycinol (3.9 g, 24 mmol) and Diphenylphosphinopolystryrene (7.6 g, 24 mmol) in dry THF (210 mL) was added DBAD (5.6 g, 24 mmol). The mixture was stirred at r.t. overnight. The sol. was filtrated through a pad of Celite®, and the polymer was washed with EtOAc and the filtrate was evaporated in vacuo. The residue was purified by prep. LC (Regular SiOH, 30 μm, 330 g GraceResolv™, mobile phase gradient: DCM/MeOH/NH₄OH, from 100/0/0 to 97/3/0.1). The desired fractions were collected and solvent evaporated until dryness to give 4.13 g of Int. 328, brown solid (crude).

d—Synthesis of Int. 329:

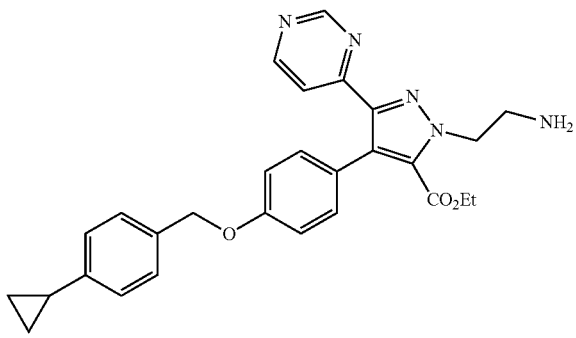 [SMILES: CCOC(=O)c1c(-c2ccc(OCc3ccc(C4CC4)cc3)cc2)c(-c2ccncn2)nn1CCN]

A solution of 328 (4.13 g, 7.1 mmol), HCl 3N (11.8 mL, 35 mmol), in ACN (125 mL) was stirred at 80° C. for 2 h. The mixture was concentrated, and NaHCO$_3$ sat aq (200 mL) was added and the mixture was stirred at r.t. 15 min, extracted with DCM, dried, filtered and concentrated to give 3.44 g of Int. 329, orange oil (quant.). This residue was used like this in the next step.

e—Synthesis of Co. 166:

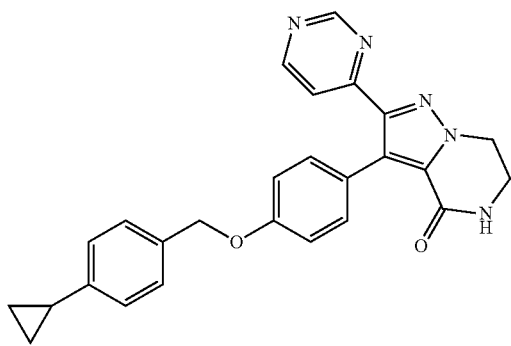

To a sol. of 329 (3.44 g, 7.1 mmol) in MeOH (203 mL) was added Cs$_2$CO$_3$ (4.6 g, 14 mmol) and the mixture was stirred at r.t. for overnight. The mixture was filtered. The white solid was collected, washed with Et$_2$O and dried to give 1.66 g of Co. 166, white solid (53%). M.p.: 268° C. (dsc).

Example A166

Preparation of Co. 167 a—Synthesis of Int. 330:

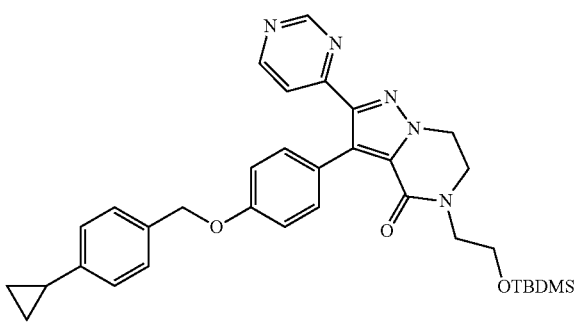 [SMILES: CC(C)(C)[Si](C)(C)OCCN1CCn2nc(-c3ccncn3)c(-c3ccc(OCc4ccc(C5CC5)cc4)cc3)c2C1=O]

NaH 60% (77 mg, 1.9 mmol) was added slowly to a suspension of Co. 166 (0.56 g, 1.3 mmol) in DMF (7.6 mL) at r.t. under N$_2$. The mixture was stirred for 2 h then (2-bromoethoxy)-tert-butyldimethylsilane (0.32 mL, 1.5 mmol) was added and stirred overnight. Water was added and the mixture was concentrated under reduced pressure. The residue was taken in EtOAc and washed 5× with brine. The organic layer was dried on MgSO$_4$, filtered and concentrated to give 0.76 g of Int. 330, yellow oil (quant: 80% of Int. 330 and 20% of Co. 167). This mixture was used like this in the deprotection step.

b—Synthesis of Co. 167:

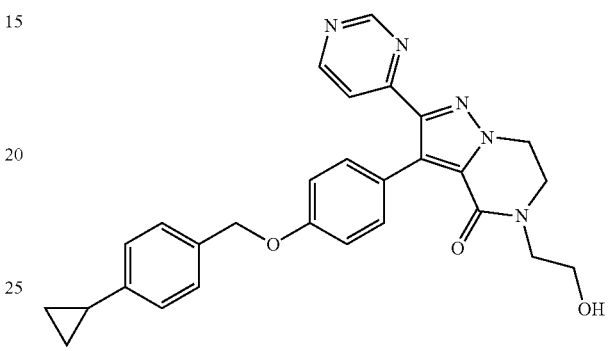

TBAF (1.5 mL, 1.5 mmol) was added dropwise to a sol. of 330 (0.76 g, 1.3 mmol) in THF (12.5 mL) at r.t. The mixture was stirred overnight at r.t. The mixture was concentrated and the residue was purified by prep. LC (Regular SiOH, 30 µm, 25 g GraceResolv™, mobile phase: DCM/MeOH/NH$_4$OH 95/5/0.1). The pure fractions were collected and solvent evaporated until dryness to give colorless oil which was crystallized from Et$_2$O. The white solid formed was filtrated, washed and dried to give 0.49 g of Co. 167 (80%).

Example A167

Preparation of Co. 168 a—Synthesis of Int. 331:

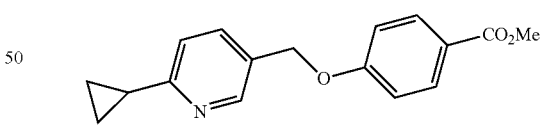

Under N$_2$ atmosphere, to a sol. of 4-hydroxybenzoic acid methyl ester (6.9 g, 45 mmol), 29 (6.7 g, 45 mmol), PPh$_3$ (11.8 g, 45 mmol) in THF (275 mL) was added DBAD (10.3 g, 45 mmol) and the r.m. was stirred at r.t. overnight. The mixture was evaporated in vacuo to give colorless oil (40 g) which was purified by prep. LC (irregular SiOH 15-40 µm, 330 g GraceResolv™, mobile phase: heptane/EtOAc 85/15). The desired fractions were collected and solvent evaporated to give 20.2 g, white solid. This solid was purified by prep. LC (Stationary phase: Irregular SiOH 20-45 µm 450 g MATREX, Mobile phase: 65% Heptane, 2% MeOH, 33% EtOAc). The pure fractions were collected and solvent evaporated to give 7.5 g of Int. 331 white solid (59%).

b—Synthesis of Int. 332:

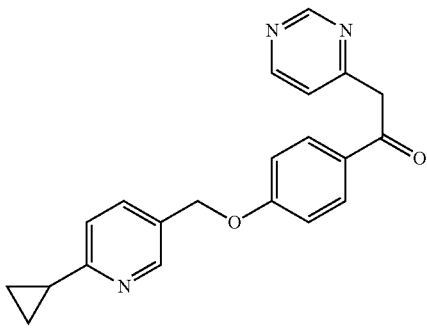 [SMILES: O=C(Cc1ccncn1)c1ccc(OCc2ccc(C3CC3)nc2)cc1]

In a dry flask and under N$_2$ atmosphere, a sol. of 331 (7.5 g, 26 mmol) and 4-methylpyrimidine (2.7 g, 29 mmol) in dry THF (53 mL) was cooled to 0° C. and treated with LiHMDS (53 mL, 53 mmol) dropwise. The r.m. was allowed to warm to r.t. (over 1 h) and stirred for 17 h at this temperature. The r.m. was then poured in a 10% aq. sol. of NH$_4$Cl (300 mL). The mixture was extracted with DCM, dried over MgSO$_4$ and concentrated. The residue was taken up in Et$_2$O and the solid was filtrated, washed with Et$_2$O and dried to give 8.0 g of Int. 332, gold solid (87%).

c—Synthesis of Int. 333:

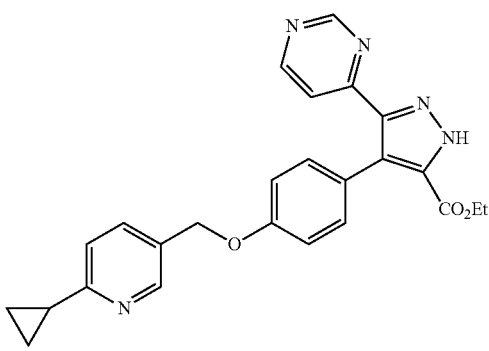

To a suspension of 332 (8.0 g, 23 mmol) in ACN (73 mL) was added DBU (5.9 mL, 39 mmol) and Ethyl diazoacetate (3.9 mL, 37 mmol). The mixture was stirred at r.t. for 1 h then cooled down to rt. The solvent was removed in vacuo and the residue was diluted in DCM. The organic layer was washed with a sat. aq. sol. of NaHCO$_3$, dried over MgSO$_4$, filtered off and evaporated in vacuo. The residue was purified by prep. LC (irregular SiOH 15-40 μm, 220 g GraceResolv™, mobile phase gradient, from DCM/MeOH/NH$_4$OH, 100/0/0 to 95/5/0.1). The desired fractions were collected and solvent evaporated to give 7.7 g of Int. 333, brown oil (with impurities).

d—Synthesis of Int. 334:

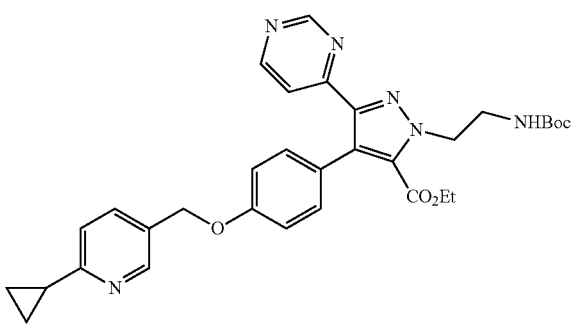

To a suspension of 333 (7.7 g, 17 mmol), Boc-Glycinol (3.1 g, 19 mmol) and Diphenylphosphinostyrene (6.0 g, 19 mmol) in THF (226 mL) was added DBAD (4.4 g, 19 mmol). The mixture was stirred at r.t. overnight. The sol. was filtered through a pad of Celite®, and the polymer was washed with EtOAc and the filtrate was evaporated in vacuo. The residue was purified by prep. LC (Regular SiOH, 30 μm, 220 g GraceResolv™, mobile phase gradient: DCM/MeOH/NH$_4$OH, from 100/0/0 to 97/3/0.1). The desired fractions were collected and solvent evaporated until dryness to give 6.0 g of Int. 334, yellow oil (59%).

e—Synthesis of Int. 335:

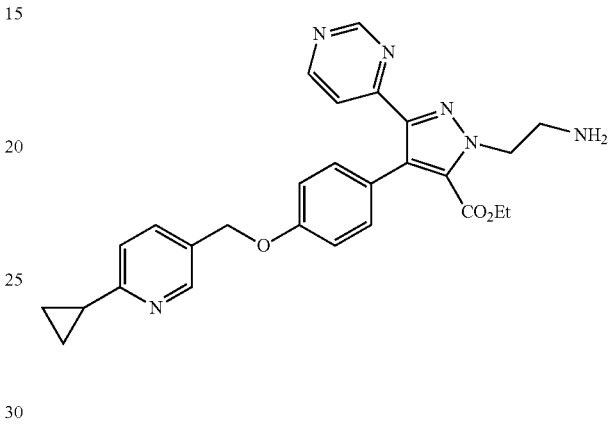

A solution of 334 (6.0 g, 10 mmol), HCl 3N (17 mL, 51 mmol), in ACN (182 mL) was stirred at 80° C. for 2 h. The mixture was concentrated, and NaHCO$_3$ sat aq (200 mL) was added and the mixture was stirred at r.t. 15 min, extracted with DCM, dried, filtered and concentrated to give 4.2 g of Int. 335 (mixture Int. 335 and Co. 168). The red solid obtained was used like this in the next step.

f—Synthesis of Co. 168:

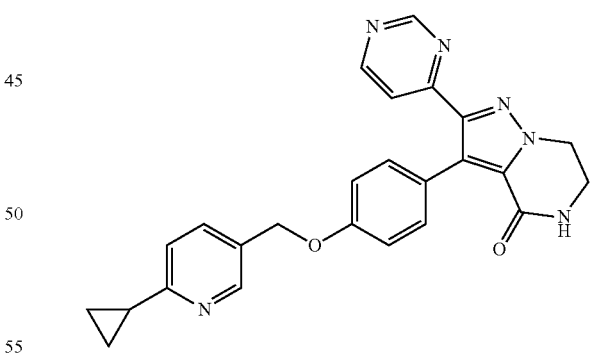

To a sol. of 335 (4.2 g, 8.7 mmol) in MeOH (250 mL) was added Cs$_2$CO$_3$ (14 g, 43 mmol) and the mixture was stirred at r.t. for overnight. The mixture was filtered. The white solid was collected, washed with Et$_2$O and dried to give 2.6 g of white solid (68%). 300 mg of 2.6 g was taken in DCM and washed with brine twice. The organic layer was then dried over MgSO$_4$, filtrated and concentrated to give a white solid which was triturated in Et$_2$O. The white solid was filtrated and dried to give 250 mg of Co. 168, white solid. m.p.: 254° C. (dsc).

Example A168

Preparation of Co. 169 a—Synthesis of Int. 336:

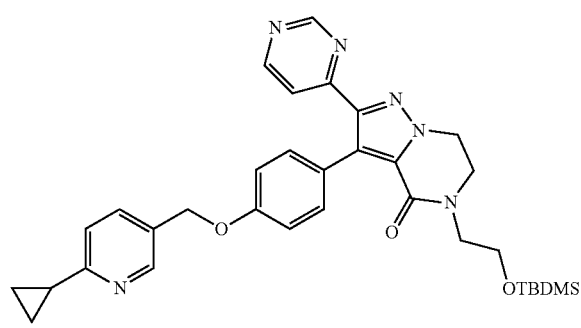 [SMILES: CC(C)(C)[Si](C)(C)OCCN1CCn2nc(-c3ccncn3)c(-c3ccc(OCc4ccc(C5CC5)nc4)cc3)c2C1=O]

NaH 60% (55 mg, 1.4 mmol) was added slowly to a suspension of Co. 168 (0.40 g, 0.91 mmol) in dry DMF (5.4 mL) at r.t. under $N_2$. The mixture was stirred for 2 h then (2-bromoethoxy)-tert-butyldimethylsilane (0.23 mL, 0.1 mmol) was added and the r.m. stirred overnight. Water was added and the mixture was concentrated under reduced pressure. The residue was taken in EtOAc and washed 5× with brine. The organic layer was dried on $MgSO_4$, filtered and concentrated to give 0.47 g of Int. 336 (mixture of Int. 336 (30%) and Co. 169 (70%)). This crude mixture was used like this in the deprotection step.

b—Synthesis of Co. 169:

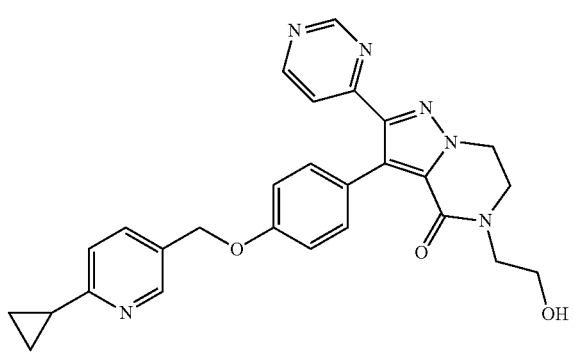 [SMILES: O=C1c2c(-c3ccc(OCc4ccc(C5CC5)nc4)cc3)c(-c3ccncn3)nn2CCN1CCO]

TBAF (0.95 mL, 0.95 mmol) was added dropwise to a sol. of mixture 336 (0.47 g) in THF (7.7 mL) at r.t. The mixture was stirred overnight at r.t. The mixture was concentrated and the residue was purified by prep. LC (Regular SiOH, 30 µm, 25 g GraceResolv™, mobile phase: DCM/MeOH/NH$_4$OH 96/4/0.1). The desired fractions were collected and solvent evaporated to give 340 mg of colorless oil. This oil was purified by achiral SFC (Stationary phase: Amino 6 µm 150×21.2 mm, Mobile phase: 80% CO$_2$, 20% MeOH). The pure fractions were collected and the solvent evaporated to give 206 mg of white solid. The solid was triturated in Et$_2$O, filtered, washed and dried to give 0.19 g of Co. 169, white solid (50%). m.p.: 143° C. (dsc).

Example A169

Preparation of Co. 170

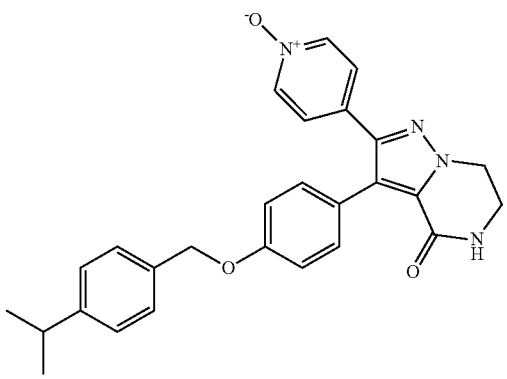

To a sol. of Co. 1 (133 mg, 0.303 mmol) in DCM (10 mL) at 0° C. was added portionwise 3-chloroperoxybenzoic acid (157 mg, 0.91 mmol). The r.m. was allowed to warm to r.t. and stirred overnight. The mixture was diluted with DCM and washed with a 10% sol. of Na$_2$CO$_3$. The organic layer was dried over MgSO$_4$, filtered and evaporated in vacuo. The residue (225 mg) was purified by prep. LC (Regular SiOH 50 µm, 24 g Grace, dry loading, mobile phase gradient: from DCM 100% to DCM 90%, MeOH 10%). The pure fractions were collected and solvent evaporated until dryness to give 88 mg of Co. 170, white solid (64%).

Example A170

Preparation of Co. 171

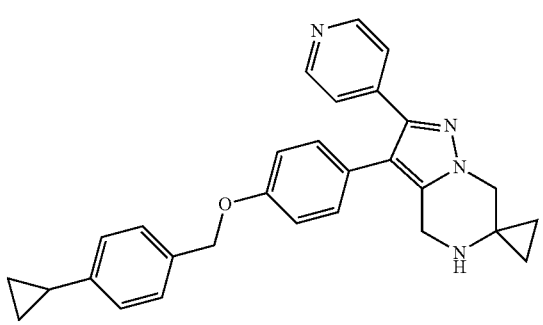 [SMILES: c1cc(-c2nn3c(c2-c2ccc(OCc4ccc(C5CC5)cc4)cc2)CNC2(CC2)C3)ccn1]

LAH (98.5 mg, 2.59 mmol) was added to a sol. of Co. 5 (200 mg, 0.432 mmol) in dry ethylene glycol dimethyl ether (8 mL). The r.m. was heated at 60° C. for 8 h and quenched with water (100 µL, very slow addition) and a 3N sol. of NaOH (100 µL). Et$_2$O was added and the crude mixture was filtered on a glass frit. The precipitate was washed with Et$_2$O and the filtrate was evaporated in vacuo to give 330 mg, yellow residue. The residue was purified by prep. LC (Irregular SiOH, 15-40 µm, 24 g Grace, mobile phase gradient: from DCM 100% to DCM 50%, acetone 50%). The pure fractions were collected and solvent evaporated until dryness to give 118 mg of Co. 171, white solid (49%). m.p.: 152° C. (DSC).

Example A171

Preparation of Co. 172

First Method

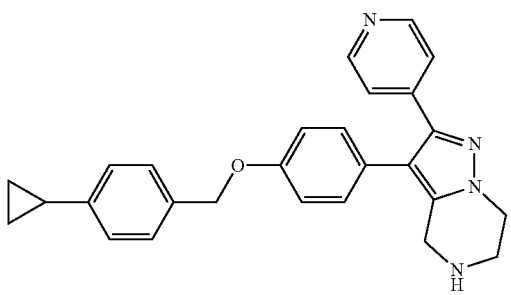 [SMILES: c1cc(-c2nn3c(c2-c2ccc(OCc4ccc(C5CC5)cc4)cc2)CNCC3)ccn1]

A sol. of Co. 4 (150 mg, 0.344 mmol) in dry THF (15 mL) was treated with LAH (52 mg, 1.37 mmol). The r.m. was stirred at room temperature for 18 h, then quenched with addition of water (75 μL, very slow addition), a 3N sol. of NaOH (75 μL) and water (250 μL). The crude mixture was filtered on glass frit and the filtrate was taken up in EtOAc, dried, filtered and evaporated in vacuo to afford 130 mg, white solid. The residue was purified by prep. LC (irregular SiOH 15-40 μm, 50 g Merck, mobile phase gradient: from DCM 100% to DCM 90%, MeOH 10%). The pure fractions were collected and solvent evaporated until dryness to give 82 mg of Co. 172, white solid (56%). m.p.: 215° C. (DSC).

Second Method
a—Synthesis of Int. 337:

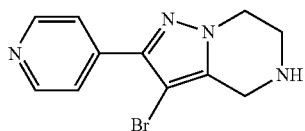 [SMILES: Brc1c(-c2ccncc2)nn2c1CNCC2]

A sol. of 2-pyridin-4-yl-4,5,6,7-tetrahydropyrazolo[1,5-a]pyrazine (3.98 g, 19.9 mmol) in HOAc (80 mL) was treated with N-bromosuccinimide (3.89 g, 21.9 mmol) and stirred at r.t. for 2 h. The crude mixture was taken up in a sol. of K₂CO₃ 10% and diluted in DCM. The organic phase was dried over MgSO₄, filtered and evaporated in vacuo. The crude mixture was coevaporated with toluene (2 times) to give 8.11 g, yellow oil. This oil was dissolved in DCM and the precipitate which formed was filtered to give 760 mg of Int. 337, yellow solid (14%). The filtrate was concentrated in vacuo and purified by prep. LC (irregular SiOH 15-40 μm, 30 g Merck, mobile phase gradient: from DCM 100% to DCM 90%, MeOH 10%). The pure fractions were collected and solvent evaporated to give 3.30 g of Int. 337, yellow solid (59%). (Global yield: 73%).

b—Synthesis of Co. 172:
In a sealed tube, a mixture of 337 (379 mg, 1.36 mmol), 32 (951 mg, 2.72 mmol), K₃PO₄ (1.15 g, 5.43 mmol) in 1,4-dioxane (7 mL) and H₂O (2.4 mL) was carefully purged with N₂. PdCl₂(dppf) (111 mg, 0.136 mmol) was added and the r.m. was purged again with N₂. The sealed tube was then sealed and the r.m. was stirred for 17 h at 80° C. The r.m. was diluted with EtOAc and washed with water (once) and with brine (twice). The organic phase was dried over MgSO₄, filtered and evaporated in vacuo to give 1.30 g, brown oil. The residue was purified by prep. LC (irregular SiOH 15-40 μm, 50 g Merck, mobile phase gradient: from DCM 100% to DCM 95%, MeOH 5%). The desired fractions were collected and solvent evaporated until dryness to give 350 mg, white solid which was triturated in Et₂O. The supernatent was removed and the solid was dried in vacuo to give 320 mg. The product was purified by prep. LC (on Spherical SiOH 10 μm 60 g PharmPrep Merck, mobile phase gradient: from DCM 98%, MeOH 2% to DCM 95%, MeOH 5%). The pure fractions were collected and solvent evaporated until dryness to give 210 mg of Co. 172, white solid (37%). m.p.: 209° C. (DSC).

Example A172

Preparation of Co. 173

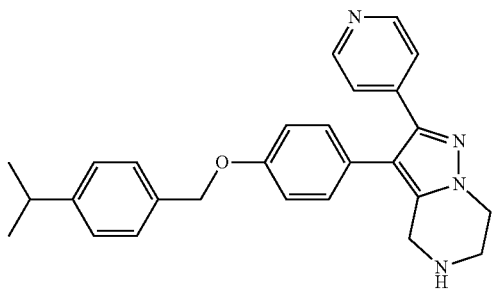 [SMILES: CC(C)c1ccc(COc2ccc(-c3c(-c4ccncc4)nn4c3CNCC4)cc2)cc1]

To a sol. of Co. 1 (330 mg, 0.753 mmol) in dry THF (17 mL) was added LAH (114 mg, 3.01 mmol) and the r.m. was stirred for 20 h at r.t., then quenched with addition of water (214 μL, very slow addition), a 3N sol. of NaOH (214 μL) and water (642 μL). The crude mixture was filtered on glass frit, the cake was washed with EtOAc and the filtrate was evaporated in vacuo to afford 300 mg of a white solid which was purified by prep. LC (irregular SiOH 15-40 μm, 30 g Merck, mobile phase gradient: DCM/MeOH from 100/0 to 90/10). The pure fractions were collected and solvent evaporated to give 185 mg of Co. 173, white solid (58%). m.p.: 194° C. (DSC).

Example A173

Preparation of Co. 174

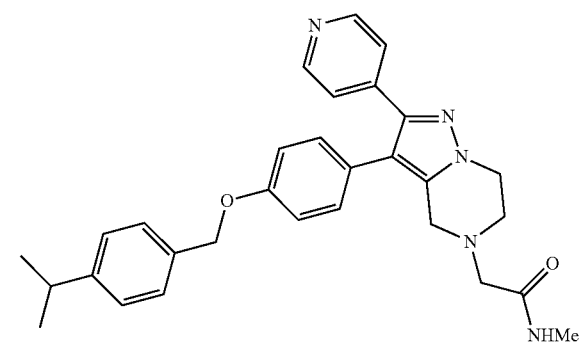 [SMILES: CNC(=O)CN1CCn2nc(-c3ccncc3)c(-c3ccc(OCc4ccc(C(C)C)cc4)cc3)c2C1]

2-Bromo-N-methylacetamide (0.252 g, 1.66 mmol) was added to a sol. of Co. 173 (0.4 g, 0.923 mmol) and K₂CO₃ (0.255 g, 1.85 mmol) in DMF (6 mL) at rt. The r.m. was stirred at r.t. for 16 h, and then water and EtOAc were added. The organic layer was washed with brine, separated, dried over MgSO₄, filtered and concentrated in vacuo to give 574 mg. The residue was combined with another batch (0.2 g of Co. 173 in the same conditions) and purified by prep. LC on (irregular 15-40 μm 30 g Merck, Mobile phase: 0.5% NH₄OH, 96% DCM, 4% MeOH). The pure fractions were collected and solvent was removed in vacuo to give 340 mg which was crystallized from DIPE, filtered and dried to give 279 mg of Co. 174 (40%). m.p.: 185° C. (dsc).

Example A174

Preparation of Co. 175 a—Synthesis of Int. 338:

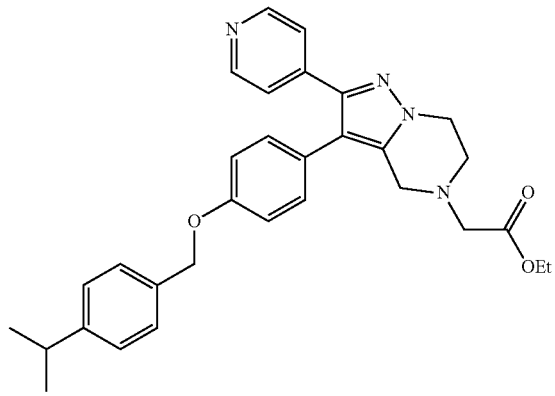 [SMILES: CCOC(=O)CN1CCn2nc(-c3ccncc3)c(-c3ccc(OCc4ccc(C(C)C)cc4)cc3)c2C1]

Ethylbromoacetate (276 μL, 2.49 mmol) was added to a sol. of Co. 173 (600 mg, 1.39 mmol) and K₂CO₃ (383 mg, 2.77 mmol) in DMF (9 mL) at r.t. The r.m. was then stirred at 55° C. for 2 h, then water and EtOAc were added. The organic layer was washed with brine, separated, dried over MgSO₄, filtered and concentrated in vacuo to afford 850 mg of Int. 338, red oil (crude), which was used as such in the next reaction step.

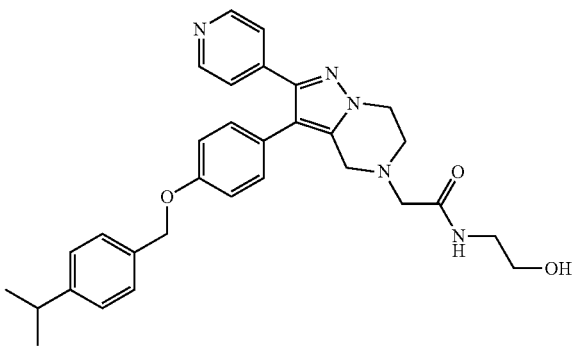 [SMILES: CC(C)c1ccc(COc2ccc(-c3c(-c4ccncc4)nn4c3CN(CC(=O)NCCO)CC4)cc2)cc1]

b—Synthesis of Co. 175:

In a sealed tube, a mixture of 338 (850 mg, 1.67 mmol), ethanolamine (5.0 mL, 83.2 mmol), Magnesium chloride hydrate (475 mg, 4.99 mmol) in 1,4-dioxane (10 mL) was heated at 180° C. using one single mode microwave (Biotage Initiator EXP 60) with a power output ranging from 0 to 400 W for 1 h [fixed hold time]. Water and EtOAc were added to the mixture. The organic layer was washed with brine, separated, dried over MgSO₄, filtered and evaporated in vacuo. The residue (500 mg, brown oil) was purified by prep. LC (irregular SiOH 15-40 μm, 80 g Grace, mobile phase gradient: from DCM 100% to DCM 92%, MeOH 8%). The pure fractions were collected and solvent evaporated to give 280 mg, yellow oil, which was diluted in a minimum amount of MeOH and triturated in Et₂O. The supernatant was removed and the solid formed was dried in vacuo to give 250 mg of Co. 175, white solid. m.p.: 189° C. (DSC).

Example A175

Preparation of Co. 176

First Method

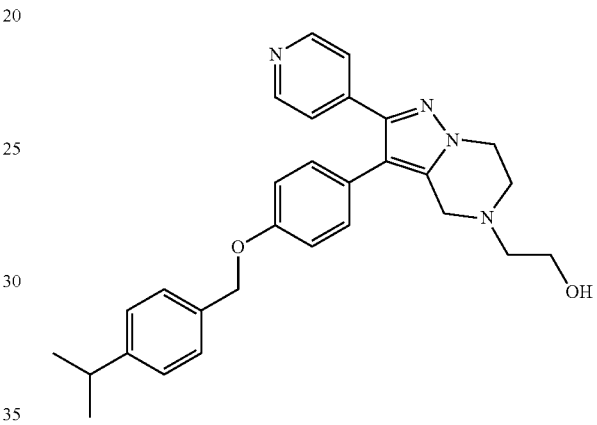

(2-Bromoethoxy)-tert-butyldimethysilane (0.133 mL, 0.612 mmol) was added to a stirred sol. of Co. 173 (200 mg, 0.471 mmol) and Et₃N (0.131 mL, 0.942 mmol) in DMF (2.5 mL) at r.t. The r.m. was stirred at 60° C. for 43 h. Then, further (2-bromoethoxy)-tert-butyldimethysilane (31 μL, 0.141 mmol) was added at r.t., and the r.m. was stirred at 60° C. for 16 h. The crude material was dissolved in water and extracted with EtOAc. The organic phase was washed with brine, dried over MgSO₄, filtered and evaporated in vacuo to give 250 mg, oil. Then, the oil was dissolved in THF (3 mL), and TBAF (0.942 mL, 0.942 mmol) was added at r.t. The r.m. was stirred at r.t. for 4 h. The crude material was diluted in a mixture of MeOH/DCM 8/92, and water was added. The organic phase was separated, washed with brine (twice), dried over MgSO₄, filtered and evaporated in vacuo. The residue (348 mg) was purified by prep. LC (irregular SiOH 15-40 μm, 12 g Grace, Mobile phase gradient: from DCM 100% to DCM 88%, MeOH 12%). The desired fractions were combined and the solvent was removed in vacuo. The residue (307 mg) was dissolved in a mixture of MeOH/DCM 2/98, and water was added. The organic phase was separated, washed with brine (twice), dried over MgSO₄, filtered and evaporated in vacuo to give 108 mg, pale brown solid. The solid was dissolved in EtOAc, and water was added. The organic phase was separated, washed with brine, dried over MgSO₄, filtered and evaporated in vacuo to give oil. The oil was triturated with a sol. of pentane/MeOH 70/30, and the solvents were removed in vacuo to afford 105 mg of Co. 176, pale brown solid (48%).

Second Method a—Synthesis of Int. 339:

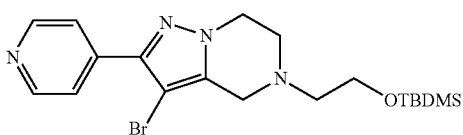 [SMILES: CC(C)(C)[Si](C)(C)OCCN1CCn2nc(-c3ccncc3)c(Br)c2C1]

(2-Bromoethoxy)-tert-butyldimethysilane (1.2 mL, 5.73 mmol) was added to a stirred sol. of 337 (1.00 g, 3.58 mmol) and Et₃N (1 mL, 7.17 mmol) in DMF (20 mL) at r.t. The r.m. was stirred at 60° C. for 18 h. The crude material was dissolved in water and extracted with EtOAc. The organic phase was washed with brine, dried over MgSO₄, filtered and evaporated in vacuo to give 2.00 g, brown oil. The residue was purified by prep. LC (irregular SiOH 15-40 µm, 50 g Grace, Mobile phase gradient: from DCM 100% to DCM 95%, MeOH 5%). The pure fractions were collected and solvent evaporated until dryness to give 1.00 g, colorless oil. This oil was dissolved in water and extracted with EtOAc. The organic phase was washed with brine (twice), dried over MgSO₄, filtered and evaporated in vacuo to give 690 mg of Int. 339, colorless oil (44%).

b—Synthesis of Int. 340:

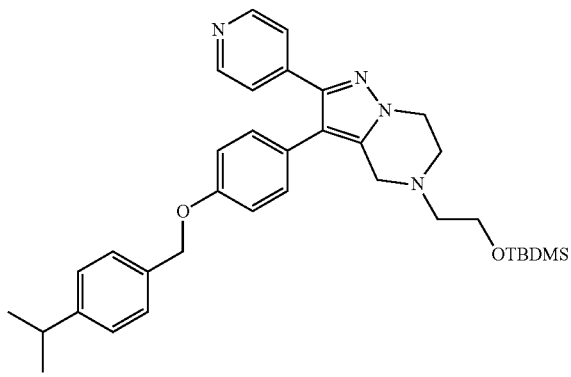 [SMILES: CC(C)c1ccc(COc2ccc(-c3c(-c4ccncc4)nn4c3CN(CCO[Si](C)(C)C(C)(C)C)CC4)cc2)cc1]

In a sealed tube, a mixture of 339 (400 mg, 0.914 mmol), 5 (644 mg, 1.83 mmol), K₃PO₄ (777 mg, 3.66 mmol) in 1,4-dioxane (4 mL) and H₂O (1.4 mL) was carefully purged with N₂. PdCl₂(dppf) (75 mg, 91.4 µmol) was added and the r.m. was purged again with N₂. The sealed tube was then sealed and the r.m. was stirred for 17 h at 80° C. The r.m. was diluted with EtOAc and washed with water (once) and with brine (2 times). The organic phase was dried over MgSO₄, filtered and evaporated in vacuo to give 1.50 g, brown oil. The residue was purified by prep. LC (irregular SiOH 15-40 µm, 50 g Merck, mobile phase gradient: from DCM 100% to DCM 95%, MeOH 5%). The desired fractions were collected and solvent evaporated until dryness to give 570 mg of Int. 340, orange oil (quant.). The product was used as such for the next step.

c—Synthesis of Co. 176:

A sol. of 340 (570 mg, 0.978 mmol) in THF (10 mL) was treated with TBAF (1.20 mL, 1.17 mmol) and stirred at 0° C. for 4 h. The crude material was dissolved in water and extracted with EtOAc. The organic phase was washed with brine, dried over MgSO₄, filtered and evaporated in vacuo to give 600 mg, brown oil. This oil was purified by prep. LC (irregular SiOH 15-40 µm, 50 g Merck, mobile phase gradient: from DCM 100% to DCM 95%, MeOH 5%). The pure fractions were collected and solvent evaporated until dryness to give 275 mg, yellow oil. This oil was triturated in Et₂O and the precipitate was dried in vacuo to give 275 mg, white solid. The white solid was diluted in DCM and Et₂O and the sol. was allowed to evaporate for 4 h, the white solid was dried in vacuo to give 275 mg of Co. 176, orange solid. m.p.: 150° C. (DSC).

Example A176

Preparation of Co. 177

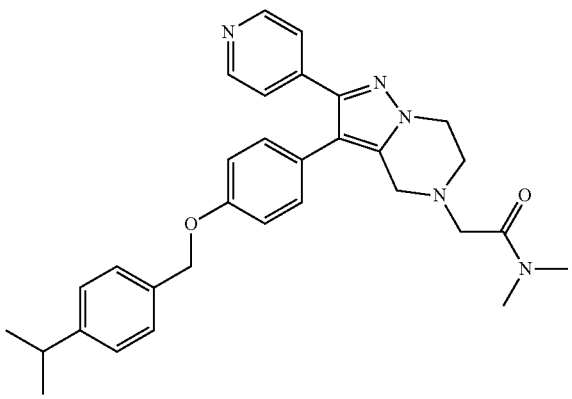 [SMILES: CC(C)c1ccc(COc2ccc(-c3c(-c4ccncc4)nn4c3CN(CC(=O)N(C)C)CC4)cc2)cc1]

2-Bromo-N,N-dimethylacetanide (268 mg, 1.62 mmol) was added to a sol. of Co. 173 (500 mg, 1.15 mmol) and K₂CO₃ (319 mg, 2.31 mmol) in DMF (7.5 mL) at r.t. The r.m. was stirred at 55° C. for 2 h. Then, water and EtOAc were added. The organic layer was separated, washed with brine, dried over MgSO₄ and evaporated in vacuo to afford brown oil. The oil was purified by prep. LC (irregular SiOH 15-40 µm, 80 g, GraceResolv™, mobile phase gradient: from DCM 100% to DCM 94%, MeOH 6%). The pure fractions were collected and solvent evaporated until dryness to give 170 mg, yellow solid. This solid was combined with another batch (0.4 g of Co. 173 as initial reactant in the same conditions), dissolved in EtOH and evaporated in vacuo to give a yellow foam which was dissolved in iPrOH (200 µL) to get a thick oil. The thick oil was triturated while Et₂O was slowly added. The solid formed was filtered on a glass frit, washed with Et₂O and dried in vacuo to give 190 mg of Co. 177, pale yellow solid (global yield: 15%). m.p.: 95° C. (DSC).

Example A177

Preparation of Co. 178

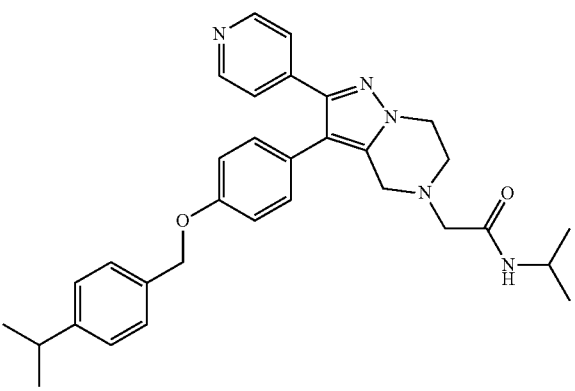 [SMILES: CC(C)NC(=O)CN1CCn2nc(-c3ccncc3)c(-c3ccc(OCc4ccc(C(C)C)cc4)cc3)c2C1]

2-Bromo-N-isopropylacetamide (150 mg, 0.831 mmol) was added to a sol. of Co. 173 (300 mg, 0.693 mmol) and K$_2$CO$_3$ (191 mg, 1.39 mmol) in DMF (5 mL) at r.t. The r.m. was stirred at 55° C. for 2 h and poured in a mixture of water and EtOAc. The organic layer was separated, washed with brine (3×), dried over MgSO$_4$ and evaporated in vacuo to give orange oil. The oil was purified by prep. LC (irregular SiOH 15-40 µm, 40 g Grace Resolv, mobile phase gradient: from DCM 100% to DCM 94%, MeOH 6%). The pure fractions were collected and solvent evaporated until dryness to give 180 mg of white solid. The solid was dissolved in MeOH (1 mL) and the MeOH was allowed to slowly evaporate overnight. The solid was crushed and dried in vacuo to give 180 mg of Co. 178, white solid (50%). m.p.: 188° C. (DSC).

Example A178

Preparation of Co. 179

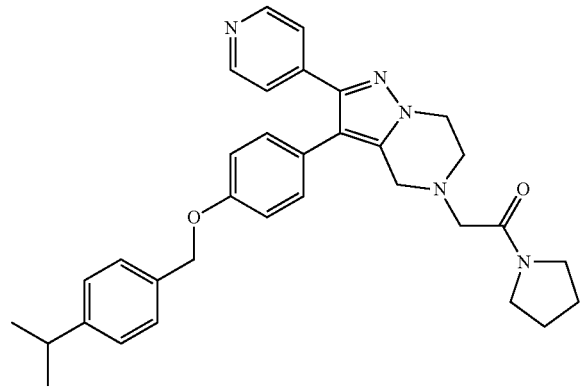 [SMILES: CC(C)c1ccc(COc2ccc(-c3c(-c4ccncc4)nn4c3CN(CC(=O)N3CCCC3)CC4)cc2)cc1]

A sol. of 2-bromo-1-(1-pyrrolidinyl)-ethanone (137 mg, 0.715 mmol) in DMF (0.5 mL) was added to a sol. of Co. 173 (172 mg, 0.397 mmol) and K$_2$CO$_3$ (110 mg, 0.794 mmol) in DMF (2.5 mL) at r.t. The r.m. was stirred at r.t. for 17 h, and water and EtOAc were added. The organic layer was washed with brine, separated, dried (MgSO$_4$), filtered and evaporated in vacuo. The residue (204 mg) was purified by prep. LC (irregular SiOH 15-40 µm, 12 g Grace, mobile phase gradient: from DCM 100% to DCM 90%, MeOH 10%). The pure fractions were collected and solvent evaporated to give a sticky solid. The solid was triturated with pentane, filtered off and dried to yield 71 mg of Co. 179, pale yellow solid (33%).

Example A179

Preparation of Co. 180

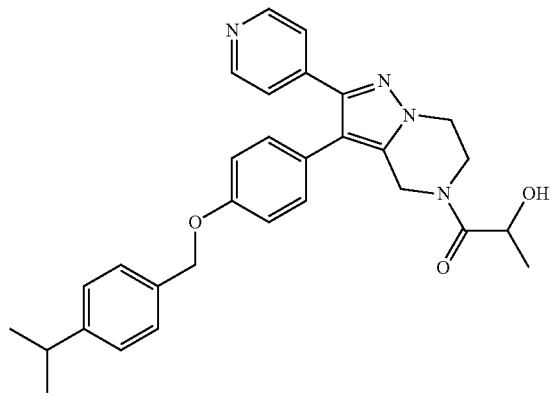 [SMILES: CC(O)C(=O)N1CCn2nc(-c3ccncc3)c(-c3ccc(OCc4ccc(C(C)C)cc4)cc3)c2C1]

Lactic Acid 85% (61 µL, 0.693 mmol) was added to a stirred sol. of HATU (298 mg, 0.785 mmol) and DIPEA (143 µL, 0.831 mmol) in DCM (3.5 mL) at r.t. under N$_2$. The mixture was stirred at r.t. for 65 min. Then, Co. 173 (200 mg, 0.462 mmol) was added, and the crude mixture was stirred for 17 h. Further additions of Lactic Acid 85% (40 µL, 0.462 mmol), HATU (211 mg, 0.555 mmol) and DIPEA (119 µL, 0.693 mmol) were done at r.t. under N$_2$, and the mixture was stirred at r.t. for 16 h. Then, water and a mixture of MeOH/DCM (4/96) were added. The organic layer was separated, washed with brine, separated, dried over MgSO$_4$, filtered and evaporated in vacuo to afford 256 mg. The residue was purified by prep. LC (irregular SiOH 15-40 µm, 30 g Grace, mobile phase gradient: from DCM 100% to DCM 91%, MeOH 9%). The desired fractions were collected and solvent evaporated to give 171 mg, white solid. This white solid was purified by prep. LC (irregular SiOH 15-40 µm, 12 g Grace, mobile phase gradient: from DCM 100% to DCM 91%, MeOH 9%). The desired fractions were collected and solvent evaporated to give 128 mg, white solid. This residue was purified by achiral SFC (diethylaminopropyl 5 µm 150×21.2 mm, Mobile phase: 80% CO$_2$, 20% MeOH). The desired fractions were combined and the solvent was removed in vacuo to give colorless oil. The oil was triturated with pentane, and the solvent was evaporated in vacuo to yield 90 mg, white solid. The residue was purified by Reverse phase (X-Bridge-C18 5 µm 30*150 mm, Mobile phase: Gradient from 70% (NH$_4$HCO$_3$ 0.5% aq. sol.), 30% ACN to 100% ACN). The pure fractions were collected and the solvent was removed in vacuo to give colorless oil. The oil was dissolved in DCM and the solvent was evaporated in vacuo. The remaining sticky solid was triturated with pentane, and the solvent was evaporated in vacuo to yield 50 mg of Co. 180, white solid (22%).

Example A180

Preparation of Co. 181

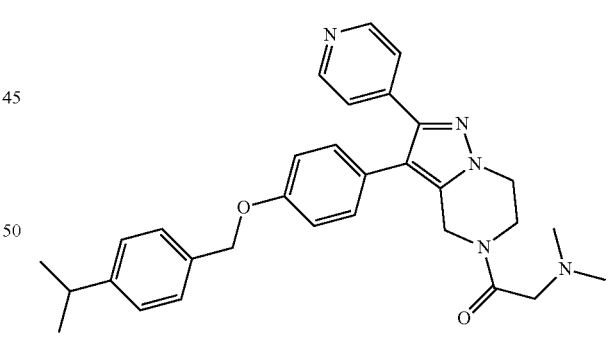

DIPEA (0.203 mL, 1.18 mmol) was added to a stirred sol. of Co. 173 (100 mg, 0.236 mmol) in DCM (2 mL) at 0° C. under N$_2$. Then, 2-(dimethylamino)-acetyl chloride, hydrochloride (88 mg, 0.471 mmol) was added at 0° C. under N$_2$, and the mixture was stirred at r.t. for 16 h. The crude material was quenched with water and extracted with DCM. The organic phase was washed with brine, dried over MgSO$_4$, filtered and evaporated in vacuo to give a solid which was purified by prep. LC (irregular SiOH 15-40 µm 12 g Grace, Mobile phase gradient: from DCM 100% to DCM 88%, MeOH 12%). The desired fractions were combined and the solvent was removed in vacuo to give 83 mg, white solid. The residue was purified by Reverse phase (X-Bridge-C18 5 μm 30*150 mm; Mobile phase gradient: from 50% (NH₄HCO₃ 0.5% aq. sol.), 50% MeOH to 100% MeOH). The pure fractions were collected and solvent evaporated to afford 55 mg, pale oil. The oil was diluted with Et₂O and then concentrated in vacuo to give 53 mg of Co. 181, waxy solid (44%).

Example A181

Preparation of Co. 182

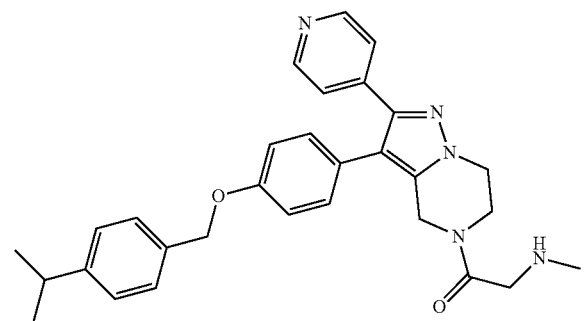 [SMILES: CNCC(=O)N1CCn2nc(-c3ccncc3)c(-c3ccc(OCc4ccc(C(C)C)cc4)cc3)c2C1]

N-Boc-sarcosine (152 mg, 0.801 mmol) was added to a sol. of CDI (130 mg, 0.801 mmol) in dry THF (1 mL) at r.t. under N₂. The mixture was stirred for 90 min at r.t., and then added over 25 min to a sol. of Co. 173 (200 mg, 0.400 mmol) in THF (1.5 mL) at r.t. under N₂. The r.m. was stirred for 16 h at r.t., and then a sol. of additional N-Boc-sarcosine (152 mg, 0.801 mmol) and CDI (130 mg, 0.801 mmol) in dry THF (1 mL) was added slowly at r.t. The r.m. was stirred for 2 h at r.t. TFA (1 mL, 26.1 mmol) was added at r.t., and the r.m. was stirred for 22 h. Then, additional TFA (1 mL, 26.1 mmol) was added, and the r.m. was stirred for 18 h. Then, the r.m. was heated at 80° C., and stirred for 160 min at 80° C. The crude material was dissolved in water and extracted with EtOAc. The organic phase was washed with brine, dried over MgSO₄, filtered and evaporated in vacuo to give oil. The oil was purified by prep. LC (irregular SiOH 15-40 μm, 12 g Grace, mobile phase gradient: from DCM 100% to DCM 90%, MeOH 9%, aq. NH₃ 1%). The pure fractions were collected and solvent evaporated to give 158 mg of Co. 182, white solid (80%).

Example A182

Preparation of Co. 183 a—Synthesis of Int. 341:

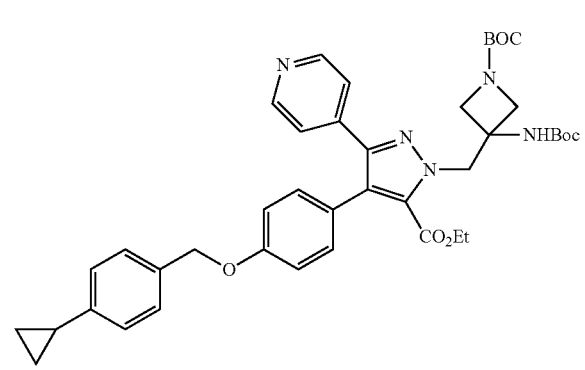 [SMILES: CCOC(=O)c1c(-c2ccc(OCc3ccc(C4CC4)cc3)cc2)c(-c2ccncc2)nn1CC1(NC(=O)OC(C)(C)C)CN(C(=O)OC(C)(C)C)C1]

To a suspension of 36 (396 mg, 0.902 mmol), 1-Boc-3-(Boc-amino)azetidine-3-methanol (300 mg, 0.992 mmol) and diphenylphosphinostyrene (601 mg, 1.80 mmol) in dry THF (8 mL) was added DBAD (415 mg, 1.80 mmol). The mixture was stirred at r.t. for 18 h. THF (4 mL) was added and the mixture was stirred at r.t. for 18 h, then, heated at 50° C. for 20 h and refluxed for 68 h. The crude mixture was then filtered through a glass frit and washed with EtOAc. The filtrate was evaporated in vacuo to give 1.26 g, yellow oil. The residue was purified by prep. LC (Irregular SiOH, 15-40 μm, 50 g Merck, mobile phase gradient: from DCM 100% to DCM 50%, EtOAc 50%). The pure fractions were collected and solvent evaporated until dryness to give 596 mg of Int. 341, off-white foam (91%).

b—Synthesis of Int. 342:

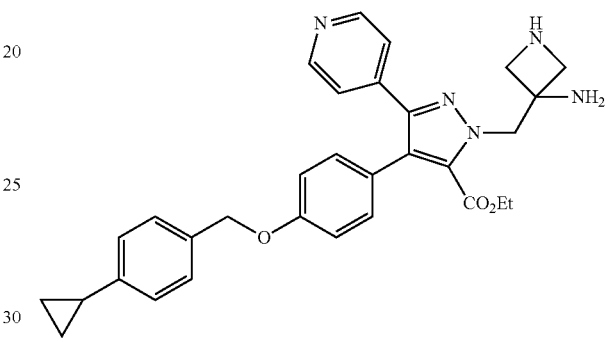

HCl salt

To a sol. of 341 (596 mg, 0.823 mmol) in 1,4-dioxane (6 mL) was added HCl 4N in dioxane (1.65 mL, 6.59 mmol). The mixture was stirred at r.t. for 18 h and HCl 4N in dioxane (0.823 mL, 3.29 mmol) was added. The mixture was stirred for 4 h then poured in Et₂O. The precipitate was filtered through a glass frit to give 470 mg of Int. 342, off-white solid (salt HCl, quant. yield).

c—Synthesis of Co. 183:

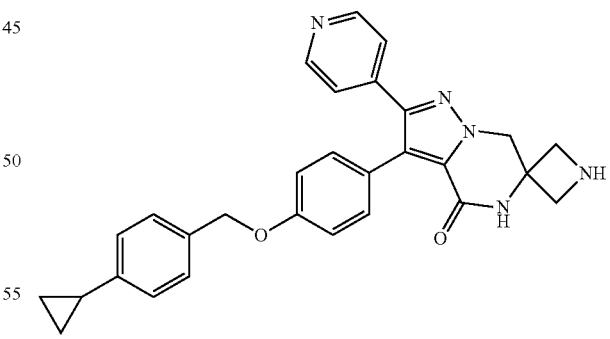

To a sol. of 342 (470 mg, 0.839 mmol) in MeOH (5 mL) was added Cs₂CO₃ (1.37 g, 4.20 mmol) and the mixture was stirred at r.t. for 18 h. The solvent was removed in vacuo and water and DCM were added. The layers were separated and the aq. layer was extracted with DCM. The organic layers were combined, dried over MgSO₄, filtered off and evaporated in vacuo to give 334 mg of white solid. 120 mg of this solid was purified by prep. LC (Irregular SiOH, 15-40 μm, 24 g Grace, mobile phase: DCM/MeOH/NH₃(aq.) 90/10/

0.5). The pure fractions were collected and solvent evaporated to give 108 mg of Co. 183, white solid. m.p.: 173° C. (DSC).

Example A183

Preparation of Co. 184a and Co. 184 a—Synthesis of Int. 343:

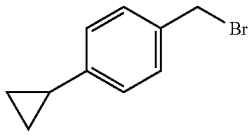 [SMILES: BrCc1ccc(C2CC2)cc1]

To a sol. of 31 (1 mL, 6.63 mmol) in dry Et$_2$O (20 mL) at 0° C. was added dropwise PBr$_3$ (620 µL, 6.63 mmol). The ice bath was removed and the r.m. was stirred for 2 h. Then, water was carefully added to the mixture and the layers separated. The organic one was washed with a sat. sol. of NaCl, dried (MgSO$_4$) and evaporated in vacuo to afford 1.38 g of Int. 343, colorless liquid (99%).

b—Synthesis of Int. 344:

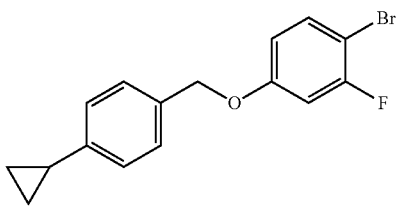 [SMILES: Fc1cc(OCc2ccc(C3CC3)cc2)ccc1Br]

Under N$_2$, a sol. of 4-bromo-3-fluorophenol (1.14 g, 5.94 mmol) in DMF (6 mL) was treated with K$_2$CO$_3$ (903 mg, 6.54 mmol) and 343 (1.38 g, 6.54 mmol) and the r.m. was stirred for 18 h at r.t. An extra amount of 1-(bromomethyl)-4-cyclopropyl-benzene (0.125 g, 0.594 mmol) was added and the r.m. was stirred for 4 h, and was then extracted with water and EtOAc. The organic layer was washed with brine (2×), dried (MgSO$_4$), filtered off and evaporated in vacuo to give 2.40 g of a colorless oil. The residue was purified by prep. LC (irregular SiOH 15-40 µm, 30 g Merck, mobile phase: DCM 100%). The pure fractions were collected and solvent evaporated to give 1.20 g of Int. 344, white solid (63%, purity 90%).

c—Synthesis of Int. 345:

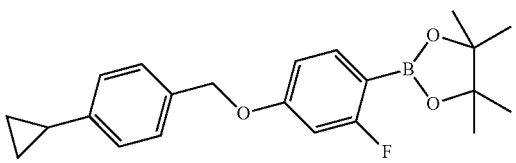 [SMILES: CC1(C)OB(c2ccc(OCc3ccc(C4CC4)cc3)cc2F)OC1(C)C]

In a sealed tube, a mixture of 344 (1.20 g, 3.74 mmol), BisPin (1.10 g, 11.2 mmol), KOAc (1.14 g, 4.48 mmol) in DME (11 mL) was carefully purged with N$_2$. PdCl$_2$(dppf) (306 mg, 0.374 mmol) was added and the r.m. was purged again with N$_2$. The r.m. was stirred for 17 h at 100° C. The r.m. was diluted with EtOAc and washed with water (once) and with brine (3 times). The organic phase was dried over MgSO$_4$, filtered and evaporated in vacuo to give 2.00 g, brown oil. The residue was purified by prep. LC (irregular SiOH 15-40 µm, 50 g, MERCK, Mobile phase: Heptane/EtOAc, gradient from 100/0 to 90/10). The pure fractions were collected and solvent evaporated until dryness to give 1.03 g of Int. 345, colorless oil (75%).

d—Synthesis of Int. 346:

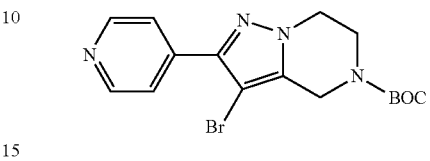

Et$_3$N (180 µL, 1.29 mmol) was added to a mixture of 337 (300 mg, 1.08 mmol) and Boc$_2$O (281 mg, 1.29 mmol) in DCM (5 mL). The r.m. was then stirred for 3 h at rt. The sol. was diluted with EtOAc and washed with water (once) and with K$_2$CO$_3$ 10% (2 times). The organic phase was dried over MgSO$_4$, filtered and evaporated in vacuo to give 400 mg of Int. 346, orange oil (98%).

e—Synthesis of Co. 184a

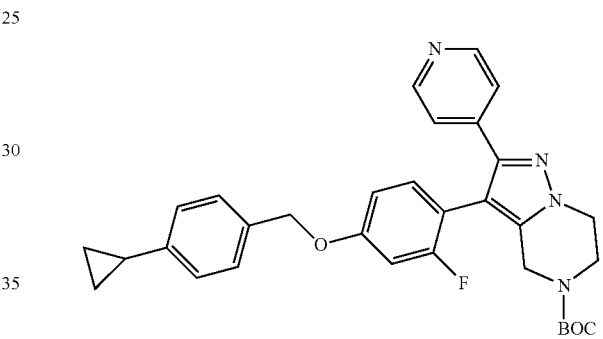

In a sealed tube, a mixture of 346 (330 mg, 870 µmol), 345 (641 mg, 1.74 mmol), K$_3$PO$_4$ (739 mg, 3.48 mmol) in 1,4-dioxane (7 mL) and H$_2$O (1.7 mL) was carefully purged with N$_2$. PdCl$_2$(dppf) (71 mg, 87.0 µmol) was added and the r.m. was purged with N$_2$. The sealed tube was then sealed and the r.m. was stirred for 17 h at 80° C. The r.m. was diluted with EtOAc and washed with water (once) and with brine (2 times). The organic phase was dried (MgSO$_4$), filtered and evaporated in vacuo to give 900 mg, brown oil. The residue was purified by prep. LC (irregular SiOH 15-40 µm, 50 g Merck, mobile phase gradient: from DCM 100% to DCM 95%, MeOH 5%). The pure fractions were collected and solvent evaporated to give 370 mg of Co. 184a, yellow oil (79%).

f—Synthesis of Co. 184:

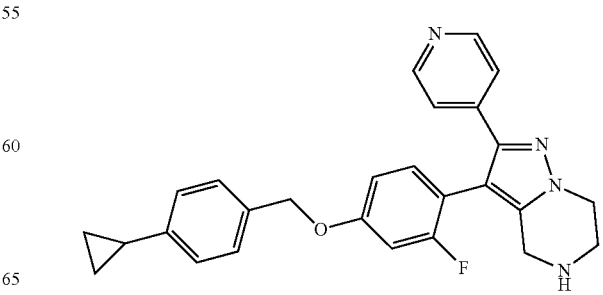

A sol. of Co. 184a (370 mg, 684 μmol) in MeOH (10 mL) and HCl 3N (5 mL) was stirred at 45° C. for 1 h 30. The sol. was then quenched with sat. NaHCO₃ and extracted with DCM. The organic phase was dried over MgSO₄, filtered and evaporated in vacuo to give 250 mg. The residue was purified by prep. LC (irregular SiOH 15-40 μm, 30 g Merck, mobile phase gradient: from DCM 100% to DCM 95%, MeOH 5%). The pure fractions were collected and solvent evaporated to give 127 mg of Co. 184, pink solid (42%). m.p.: 195° C. and 339° C., polymorph (DSC).

Example A184

Preparation of Co. 185

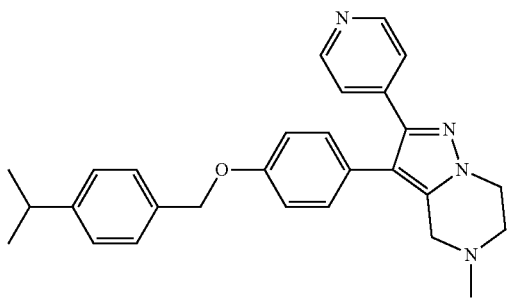 [SMILES: CC(C)c1ccc(COc2ccc(-c3c(-c4ccncc4)nn4c3CN(C)CC4)cc2)cc1]

A sol. of Co. 48 (120 mg, 0.265 mmol) in dry THF (6 mL) was treated with LAH (40 mg, 1.06 mmol). The r.m. was stirred at r.t. for 18 h, then, quenched with addition of water (75 μL, very slow addition), a 3N sol. of NaOH (75 μL) and water (190 μL). The crude mixture was filtered on glass frit, the cake was washed with EtOAc and the filtrate was, dried, filtered and evaporated in vacuo to afford 160 mg. The residue was purified by prep. LC (irregular SiOH 15-40 μm, 50 g Merck, mobile phase gradient: from DCM 100% to DCM 95%, MeOH 5%). The pure fractions were collected and solvent evaporated until dryness to give 71 mg, colorless oil which was crystallized from Et₂O, filtered and dried to give 71 mg of Co. 185, white solid (61%). m.p.: 120° C. (DSC).

Example A185

Preparation of Co. 186

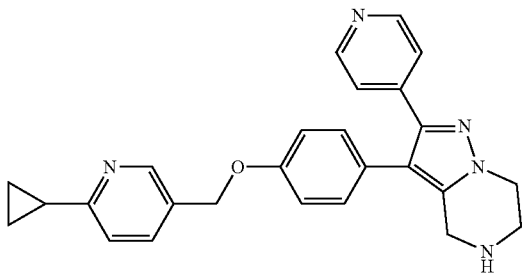 [SMILES: c1cc(-c2nn3c(c2-c2ccc(OCc4ccc(C5CC5)nc4)cc2)CNCC3)ccn1]

A sol. of Co. 3 (112 mg, 256 μmol) in dry THF (2 mL) was treated with LAH (58 mg, 1.54 mmol). The r.m. was stirred at r.t. for 18 h, then, quenched successively with addition of water (60 μL, very slow addition), a 3N sol. of NaOH (60 μL) and water (180 μL). The crude mixture was filtered on glass frit. The cake was washed with EtOAc, and the filtrate was evaporated in vacuo to afford 80 mg. The residue was purified by prep. LC (irregular SiOH 15-40 μm, 30 g Merck, mobile phase gradient: from DCM 100% to DCM 90%, MeOH 10%). The pure fractions were collected and solvent evaporated until dryness to give 75 mg of Co. 186, white solid (69%). m.p.: 195° C. (DSC).

Example A186

Preparation of Co. 187 a—Synthesis of Int. 348:

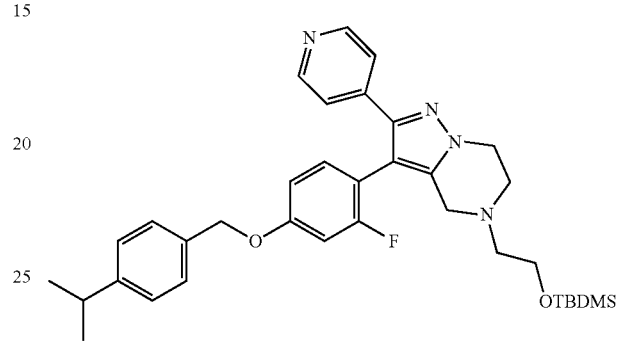

In a sealed tube, a mixture of 339 (240 mg, 549 μmol), 42 (406 mg, 1.10 mmol), K₃PO₄ (466 mg, 2.20 mmol) in 1,4-dioxane (5 mL) and H₂O (1.2 mL) was carefully purged with N₂. PdCl₂(dppf) (45 mg, 54.9 μmol) was added and the r.m. was purged again with N₂. The sealed tube was then sealed and the r.m. was stirred for 17 h at 80° C. The r.m. was diluted with EtOAc and washed with water (once) and with brine (2 times). The organic phase was dried over MgSO₄, filtered and evaporated in vacuo to give 500 mg, brown oil. The residue was purified by prep. LC (irregular SiOH 15-40 μm, 50 g Merck, mobile phase gradient: from DCM 100% to DCM 95%, MeOH 5%). The desired fractions were collected and solvent evaporated until dryness to give 320 mg of Int. 348, orange oil. The mixture was used as such for the next step without further purification.

b—Synthesis of Co. 187:

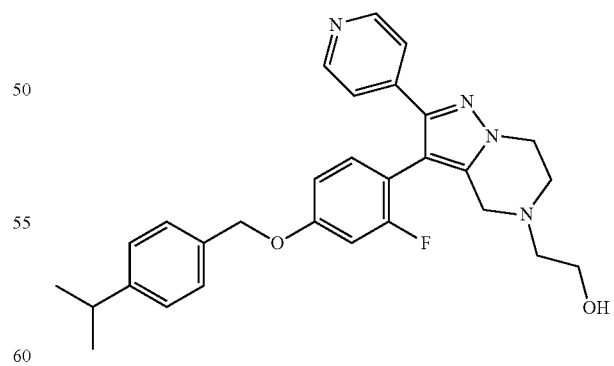

A sol. of 348 (320 mg, 0.533 mmol) in THF (5 mL) was treated with TBAF (640 μL, 0.639 mmol) and stirred at 0° C. for 2 h. The crude material was dissolved in water and extracted with EtOAc. The organic phase was washed with brine, dried over MgSO₄, filtered and evaporated in vacuo to give 350 mg, brown oil. The residue was purified by prep.

LC (irregular SiOH 15-40 µm, 30 g Merck, mobile phase gradient: from DCM 100% to DCM 98%, MeOH 2%). The pure fractions were collected and solvent evaporated to give 123 mg, yellow oil. This oil was diluted in pentane and evaporated in vacuo to give 123 mg of Co. 187, white solid (46%).

Example A187

Preparation of Co. 188

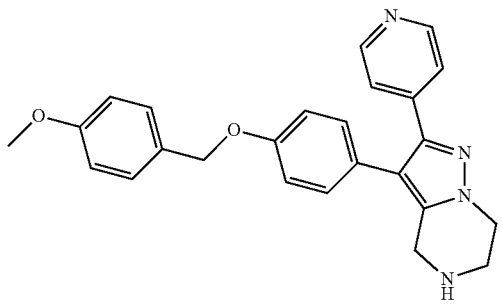 [SMILES: COc1ccc(COc2ccc(-c3c(-c4ccncc4)nn4c3CNCC4)cc2)cc1]

A sol. of Co. 112 (195 mg, 0.457 mmol) in dry THF (12 mL) was treated with LAH (69 mg, 1.83 mmol). The r.m. was stirred at r.t. for 18 h, then, quenched with addition of water (100 µL, very slow addition), a 3N sol. of NaOH (100 µL) and water (300 µL). The crude mixture was filtered on glass frit and the filtrate was taken up in EtOAc and evaporated in vacuo to afford 200 mg, white solid. The residue was purified by prep. LC (irregular SiOH 15-40 µm, 50 g Merck, mobile phase gradient: from DCM 100% to DCM 90%, MeOH 10%). The pure fractions were collected and solvent evaporated until dryness to give 130 mg, white solid. The solid was triturated in Et$_2$O and evaporated in vacuo to give 115 mg of Co. 188, white solid (61%). m.p.: 192° C. and 342° C. (DSC—polymorphous compound).

Example A188

Preparation of Co. 189 a—Synthesis of Int. 349:

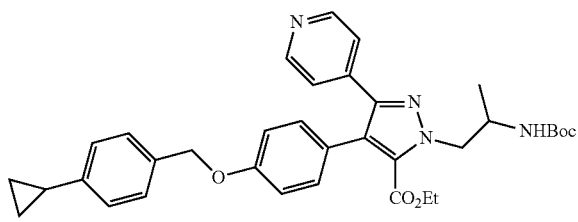 [SMILES: CCOC(=O)c1c(-c2ccc(OCc3ccc(C4CC4)cc3)cc2)c(-c2ccncc2)nn1CC(C)NC(=O)OC(C)(C)C]

To a mixture of 36 (700 mg, 1.59 mmol), N-Boc-2-amino-1-propanol (558 mg, 3.19 mmol) and diphenylphosphinopolystyrene (1.06 g, 3.19 mmol) in dry THF (13 mL) was added DBAD (734 mg, 3.19 mmol). The mixture was stirred for 2 h at r.t. then filtered through a glass frit and washed with EtOAc. The filtrate was evaporated in vacuo to give 2.00 g, yellow oil. This oil was purified by prep. LC (Irregular SiOH, 15-40 µm, 80 g Grace, mobile phase gradient: from DCM 100% to DCM 98%, MeOH 2%). The desired fractions were collected and solvent evaporated to give 1.20 g, pale yellow oil. The residue was purified again by prep. LC (Irregular SiOH, 15-40 µm, 30 g Merck, mobile phase gradient: from DCM 100% to DCM 60%, EtOAc 40%). The pure fractions were collected and solvent evaporated to give 753 mg of Int. 349, white foam (79%).

b—Synthesis of Int. 350:

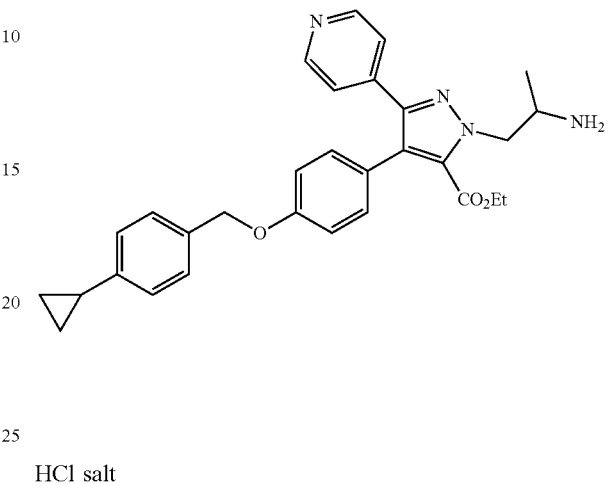

HCl salt

To a sol. of 349 (753 mg, 1.26 mmol) in 1,4-dioxane (10 mL) was added HCl 4N in dioxane (2.50 mL, 10.1 mmol). The sol. was stirred at r.t. for 18 h, then, poured with Et$_2$O. The supernatant was removed and the remaining solid was dried in vacuo. The residue was triturated 3× in Et$_2$O to give 686 mg of Int. 350, pale yellow solid (HCl salt, quant. yield).

c—Synthesis of Co. 189:

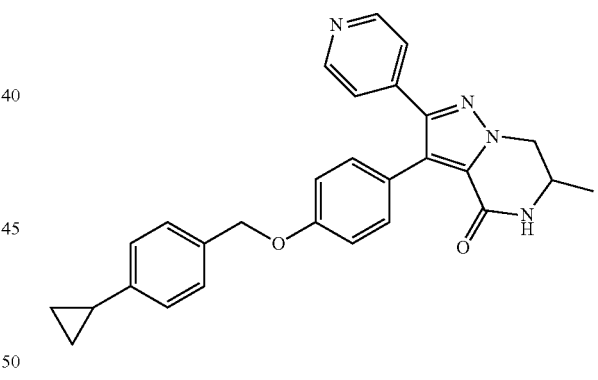

To a sol. of 350 (686 mg, 1.29 mmol) in MeOH (8 mL) was added Cs$_2$CO$_3$ (2.10 g, 6.43 mmol) and the mixture was stirred at r.t. for 6 h. The solvent was removed in vacuo and water (25 mL) and DCM (25 mL) were added to the residue. The layers were separated and the aq. layer was extracted with DCM (25 mL). The organic layers were combined, dried over MgSO$_4$, filtered off and evaporated in vacuo to give 507 mg, white solid. The residue was triturated in Et$_2$O and and the solid was filtered off on a glass frit to give 503 mg, white solid. The solid was triturated in a mixture of DCM/EtOAc 90/10 and was filtered off on a glass frit and dried to give 315 mg of Co. 189, white solid (54%). m.p.: 249° C. (DSC).

Example A189

Preparation of Co. 190

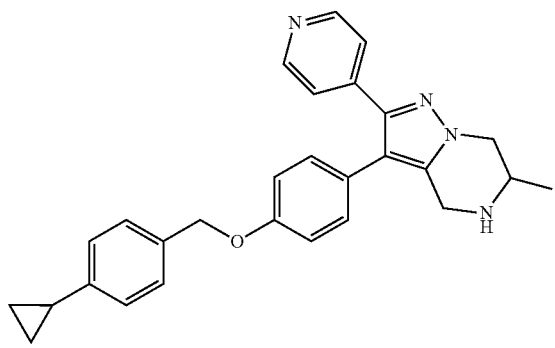 [SMILES: CC1Cn2nc(-c3ccncc3)c(-c3ccc(OCc4ccc(C5CC5)cc4)cc3)c2CN1]

LAH (88.5 mg, 2.33 mmol) was added to a sol. of Co. 189 (175 mg, 0.388 mmol) in dry THF (30 mL). The r.m. was stirred at r.t. for 18 h and LAH (44.2 mg, 1.17 mmol) was then added. The r.m. was stirred for an additional 18 h and quenched with addition of water (145 µL, very slow addition) and a 3N sol. of NaOH (145 µL). Et$_2$O was added and the crude mixture was filtered on a glass frit. The precipitate was washed with Et$_2$O and the filtrate was evaporated in vacuo to give 280 mg, yellow residue. The residue purified by prep. LC (Irregular SiOH, 15-40 µm, 24 g Grace, mobile phase gradient: from DCM 100% to DCM 50%, acetone 50%). The pure fractions were collected and solvent evaporated until dryness to give 137 mg of Co. 190, white solid (69%). m.p.: 166° C. and 177° C. (polymorph, DSC).

Example A190

Preparation of Co. 191 and Co. 192 a—Synthesis of Int. 351:

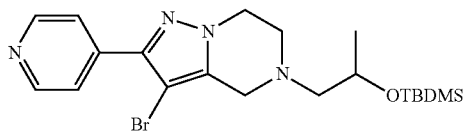 [SMILES: CC(CN1CCn2nc(-c3ccncc3)c(Br)c2C1)O[Si](C)(C)C(C)(C)C]

(2-bromo-1-methylethoxy)(1,1-dimethylethyl)dimethylsilane (2.59 g, 7.17 mmol) was added to a stirred sol. of 337 (1.00 g, 3.58 mmol) and Et$_3$N (1 mL, 7.17 mmol) in DMF (20 mL) at r.t. The r.m. was stirred at 60° C. for 7 days. The crude material was dissolved in water and extracted with EtOAc. The organic phase was washed with brine, dried over MgSO$_4$, filtered and evaporated in vacuo to give 350 mg of a brown oil. An extra amount of (2-bromo-1-methylethoxy)(1,1-dimethylethyl)dimethylsilane (2.59 g, 7.17 mmol) and Et$_3$N (1 mL, 7.17 mmol) in DMF (20 ml) was added to the mixture. The r.m. was then stirred at 60° C. for 1 week. The crude material was dissolved in water and extracted with EtOAc. The organic phase was washed with brine, dried over MgSO$_4$, filtered and evaporated in vacuo to give 4.47 g, brown oil. The residue was purified by prep. LC (irregular SiOH 15-40 µm, 50 g Grace, Mobile phase gradient: from DCM 100%, to DCM 95%, MeOH 5%). The desired fractions were collected and solvent evaporated until dryness to give 640 mg, colorless oil. This oil was dissolved in water and extracted with EtOAc. The organic phase was washed with brine (2×), dried over MgSO$_4$, filtered and evaporated in vacuo to give 530 mg of Int. 351, colorless oil (33%).

b—Synthesis of Int. 352:

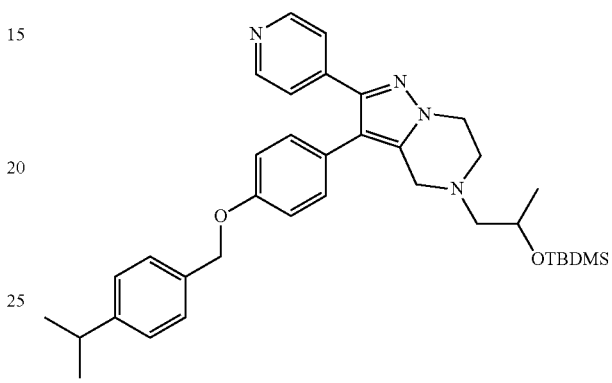

In a sealed tube, a mixture of 351 (530 mg, 1.17 mmol), 5 (827 mg, 2.35 mmol), K$_3$PO$_4$ (997 mg, 4.70 mmol) in 1,4-dioxane (5 mL) and H$_2$O (1.8 mL) was carefully purged with N$_2$. PdCl$_2$(dppf) (96 mg, 117 µmol) was added and the r.m. was purged again with N$_2$. The sealed tube was then sealed and the r.m. was stirred for 17 h at 80° C. The r.m. was diluted with EtOAc and washed with H$_2$O (1×) and brine (2×). The organic phase was dried (MgSO$_4$), filtered and evaporated in vacuo to give 1.20 g, brown oil. The residue was purified by prep. LC (irregular SiOH 15-40 µm, 50 g Merck, mobile phase gradient: from DCM 100% to DCM 95%, MeOH 5%). The pure fractions were collected and solvent evaporated to give 570 mg of Int. 352, orange oil (82%).

c—Synthesis of Co. 191 & Co. 192

Compound 191

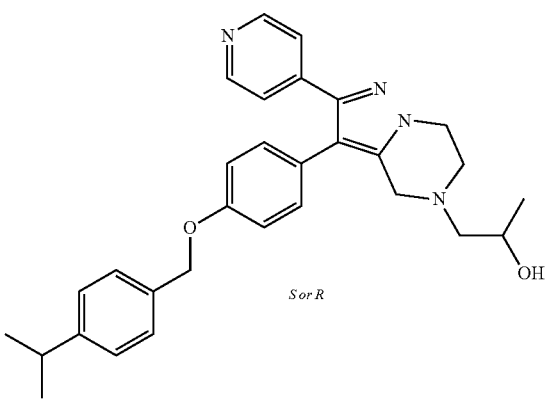

S or R

Compound 192

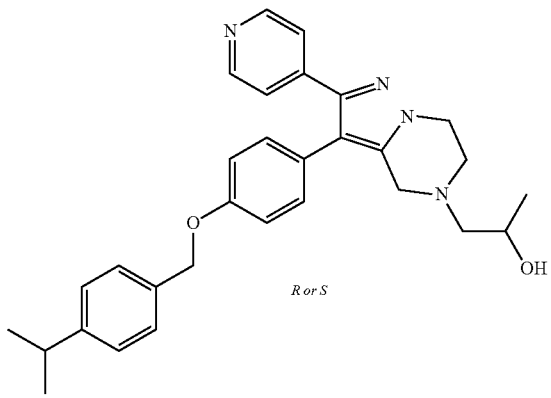

R or S

A sol. of 352 (576 mg, 0.965 mmol) in THF (9 mL) was treated with TBAF (1.2 mL, 1.16 mmol) and stirred at 0° C. for 1 h, then stirred at r.t. for 18 h. The crude material was dissolved in water and extracted with EtOAc. The organic phase was washed with brine, dried over MgSO₄, filtered and evaporated in vacuo to give 400 mg. The residue was purified by prep. LC (irregular SiOH 15-40 µm, 30 g Merck, mobile phase gradient: from DCM 100% to DCM 95%, MeOH 5%). The pure fractions were collected and solvent evaporated to give 305 mg, white solid. The solid was purified by chiral SFC (Stationary phase: Chiralpak AD-H 5 µm 250×20 mm, Mobile phase: 70% CO₂, 30% mixture of EtOH/iPrOH 50/50 v/v). The pure fractions were collected and solvent evaporated to give 117 mg of Co. 191 as a white solid (25%, m.p.: 148° C. (DSC)) and 116 mg of Co. 192 as a white solid (25%, m.p.: 151° C. (DSC)). Co. 191: [α]$_d$: −6.44° (589 nm, c 0.3105 w/v %, DMF, 20° C.). Co. 192: [α]$_d$: +6.85° (589 nm, c 0.292 w/v %, DMF, 20° C.).

Example A191

Preparation of Co. 193 a—Synthesis of Int. 353:

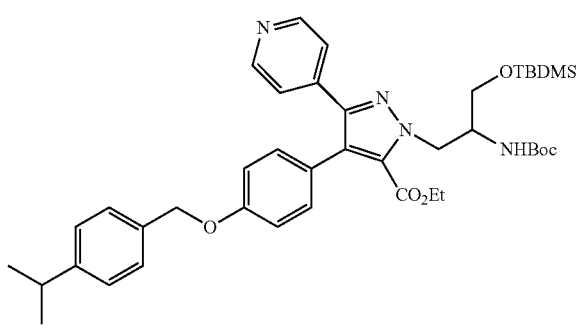 [SMILES: CCOC(=O)c1c(-c2ccc(OCc3ccc(C(C)C)cc3)cc2)c(-c2ccncc2)nn1CC(CO[Si](C)(C)C(C)(C)C)NC(=O)OC(C)(C)C]

DBAD (1.1 g, 5.0 mmol) was added portionwise to a sol. of 11 (2.0 g, 4.5 mmol), N-(tert-butoxycarbonyl)-O-(tert-butyldimethylsilyl)serinol (1.5 g, 5.0 mmol), diphenylphosphino-polystyrene (1.6 g, 5.0 mmol) in THF (53 mL) at r.t. under N₂. The mixture was stirred overnight at r.t. The mixture was filtrated through a pad of Celite®, washed with EtOAc and concentrated to give 4.7 g. The crude residue was purified by prep. LC (irregular SiOH 35-40 µm 120 g GraceResolv™, mobile phase: heptane/EtOAc from 80/20 to 70/30). The pure fractions were collected and solvent evaporated until dryness to give 2.41 g of Int. 353 as a colorless oil (73%).

b—Synthesis of Int. 354:

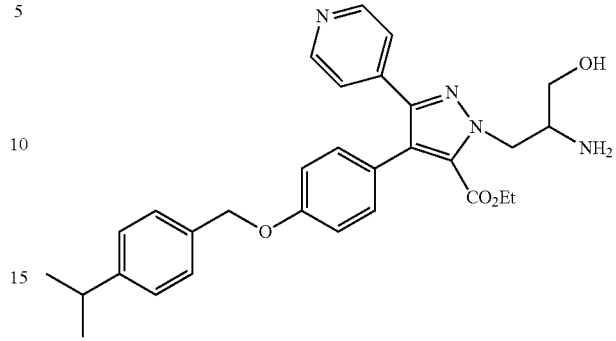

353 (277 mg, 0.38 mmol) and HCl 3N (0.63 mL, 1.9 mmol) in ACN (6.7 mL) was stirred at 80° C. for 2 h. The mixture was concentrated, NaHCO₃ sat aq (50 mL) was added and the mixture was stirred at r.t. for 15 min. Subsequently, the mixture was extracted with DCM, dried, filtered and evaporated to give 197 mg of Int. 354 (100%).

c—Synthesis of Co. 193:

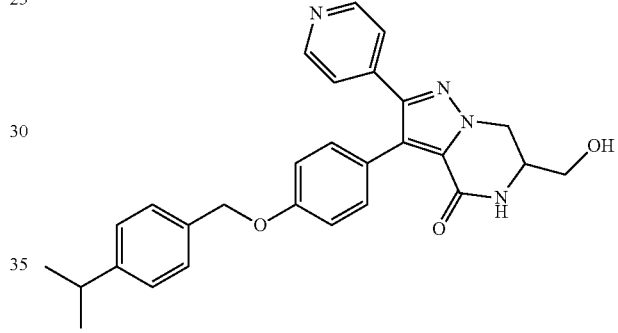

To a sol. of 354 (197 mg, 0.38 mmol) in MeOH (11 mL) was added Cs₂CO₃ (0.62 g, 1.9 mmol) and the mixture was stirred at r.t. overnight. The mixture was concentrated and taken in DCM and washed once with brine, dried over MgSO₄, filtered and concentrated. The crude product was purified by prep. LC (irregular SiOH 30 µm, 12 g GraceResolv™, mobile phase gradient: from DCM/MeOH/NH₄OH 97/3/0.1 to 95/5/0.1). The pure fractions were collected and solvent evaporated until dryness to give 146 mg, white solid. The solide was washed in Et₂O, filtrated and dried to give 136 mg of Co. 193, white solid (76%). m.p.: 254° C. (dsc).

Example A192

Preparation of Co. 194 a—Synthesis of Int. 355:

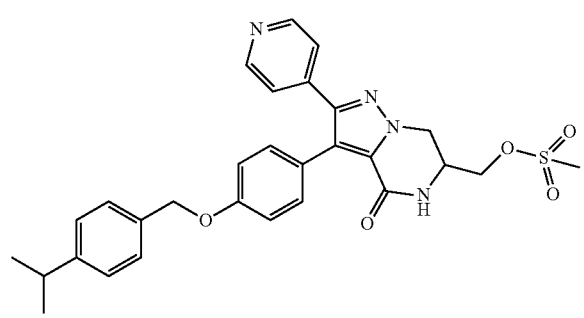 [SMILES: CC(C)c1ccc(COc2ccc(-c3c(-c4ccncc4)nn4c3C(=O)NC(COS(C)(=O)=O)C4)cc2)cc1]

Methanesulfonyl chloride (64 µL, 0.83 mmol) was added dropwise to a sol. of Co. 193 (260 mg, 0.56 mmol) and Et₃N (232 µL, 1.7 mmol) in dry DCM (5 mL) at r.t. under N₂ atmosphere. The r.m. was stirred at r.t. for 1 h. Water was added and the mixture was extracted with DCM. The organic layer was separated, dried over MgSO₄, filtered and the solvent was concentrated to give 300 mg of Int. 355, colorless oil (99%).

b—Synthesis of Co. 194:

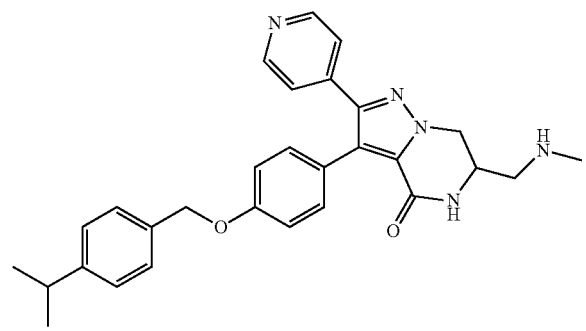 [SMILES: CNCC1Cn2nc(-c3ccncc3)c(-c3ccc(OCc4ccc(C(C)C)cc4)cc3)c2C(=O)N1]

In a microwave vial, a sol. of 355 (240 mg, 0.44 mmol) in methylamine in 2M THF (4.4 mL, 8.8 mmol) was stirred at 80° C. for 3 days. The mixture was concentrated to give 440 mg, yellow oil. The residue was purified by prep. LC (Stationary phase: irregular 15-40 µm 30 g Merck, Mobile phase: 0.5% NH₄OH, 96% DCM, 4% MeOH). The pure fractions were collected and solvent evaporated until dryness to give 46 mg which was triturated in Et₂O and the white solide formed was filtrated and dried to give 23 mg of Co. 194, white powder (11%). m.p.: 230° C. (dsc).

Example A193

Preparation of Co. 195

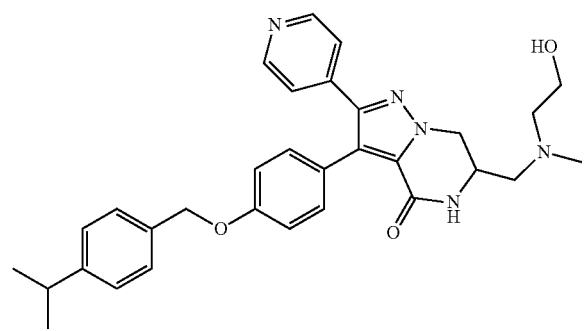 [SMILES: CC(C)c1ccc(COc2ccc(-c3c(-c4ccncc4)nn4c3C(=O)NC(CN(C)CCO)C4)cc2)cc1]

In a microwave vial, a sol. of 355 (300 mg, 0.55 mmol) and 2-(methylamino)ethanol (0.88 mL, 11 mmol) in THF (4.5 mL) was stirred at 80° C. overnight. The mixture was concentrated to give 1.3 g of yellow oil. The residue was purified by prep. LC (Stationary phase: irregular SiOH 15-40 µm 300 g Merck, Mobile phase: 0.5% NH₄OH, 96% DCM, 4% MeOH). The pure fractions were collected and solvent evaporated until dryness to give 105 mg which was crystallized from DIPE, filtered and dried to give 82 mg of Co. 195 (28%). m.p.: 193° C. (dsc).

Example A194

Preparation of Co. 196 a—Synthesis of Int. 356:

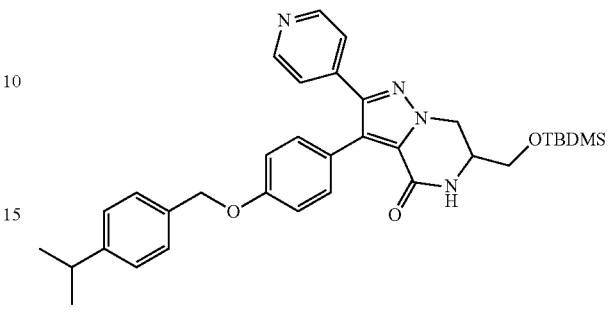

Under N₂, Tert-butyldimethylsilyl chloride (0.12 g, 0.79 mmol) was added to a sol. of Co. 193 (0.25 g, 0.53 mmol) and imidazole (0.11 g, 1.6 mmol) in dry DCM (5.1 mL) at r.t. The mixture was stirred at r.t. for 4 h. The mixture was quenched with water and extracted with DCM. The organic layer was decanted, washed with water then brine, dried over MgSO₄, filtered and evaporated to dryness to give 320 mg of crude Int. 356, white foam (quant.). The crude Int. 356 was used like this in the next step.

b—Synthesis of Int. 357:

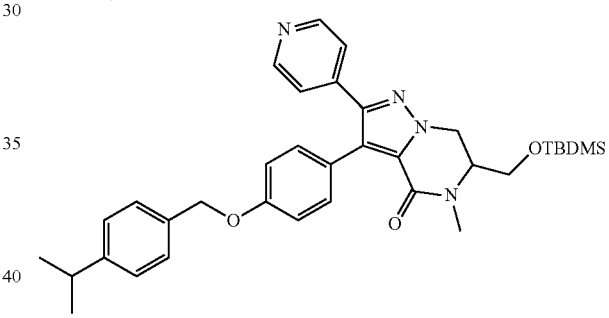

NaH 60% (33 mg, 0.82 mmol) was added slowly to a suspension of 356 (0.32 g, 0.55 mmol, 80%) in dry THF (3.1 mL) at r.t. under N₂. The mixture was stirred for 2 h, then, MeI (51 µL, 0.82 mmol) was added and stirred for 3 days at r.t. Water was added and the mixture was extracted with DCM (3×), dried over MgSO₄ and evaporated until dryness and give 0.33 g of Int. 357, pale yellow oil (quant.). The residue was used like this in the next step.

c—Synthesis of Co. 196:

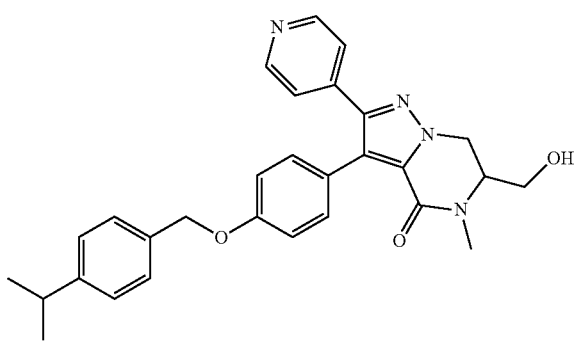 [SMILES: CC(C)c1ccc(COc2ccc(-c3c(-c4ccncc4)nn4c3C(=O)N(C)C(CO)C4)cc2)cc1]

TBAF (2.2 mL, 2.2 mmol) was added dropwise to a sol. of 357 (1.1 g, 1.8 mmol) in THF (18 mL) at r.t. The mixture was stirred overnight at r.t. The mixture was concentrated and the residue was purified by prep. LC (Regular SiOH, 30 µm, 40 g Interchim, mobile phase gradient: DCM/MeOH/NH₄OH, from 98/2/0.1 to 97/3/0.1). The pure fractions were collected and solvent evaporated until dryness to give 380 mg of colorless oil. This oil was purified again by prep. LC (Stationary phase: Sunfire Silica 5 µm 150×30.0 mm, Mobile phase Gradient: from NH₄OH/DCM/MeOH 0.2/98/2 to NH₄OH/DCM/MeOH 1/90/10). The pure fractions were collected and solvent evaporated until dryness to give 230 mg of white solide which was triturated in DIPE. The white solid was filtrated and dried to give 175 mg of Co. 196 (20%).

Example A195

Preparation of Co. 197a and Co. 197 a—Synthesis of Int. 358:

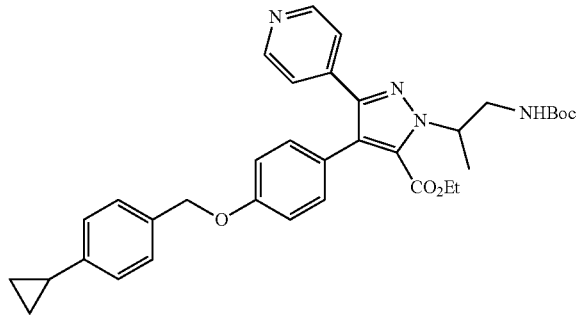 [SMILES: CCOC(=O)c1c(-c2ccc(OCc3ccc(C4CC4)cc3)cc2)c(-c2ccncc2)nn1C(C)CNC(=O)OC(C)(C)C]

To a mixture of 36 (350 mg, 0.796 mmol), 1-(Boc-amino)-2-propanol (279 mg, 1.59 mmol) and diphenylphosphinostyrene (531 mg, 1.59 mmol) in dry THF (6.50 mL) was added DBAD (367 mg, 1.59 mmol). The mixture was stirred for 2 h at r.t., then, filtered through a glass frit and washed with EtOAc. The filtrate was evaporated in vacuo to give 1.00 g, yellow oil. The residue was purified by prep. LC (Irregular SiOH, 15-40 µm, 50 g Merck, mobile phase gradient: from DCM 100% to DCM 99%, MeOH 1%). The pure fractions were collected and solvent evaporated until dryness to give 290 mg of Int. 358, colorless oil (61%).

b—Synthesis of Int. 359:

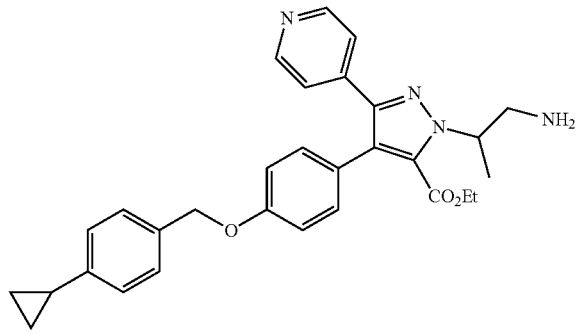 [SMILES: CCOC(=O)c1c(-c2ccc(OCc3ccc(C4CC4)cc3)cc2)c(-c2ccncc2)nn1C(C)CN]

To a sol. of 358 (290 mg, 0.486 mmol) in 1,4-dioxane (4 mL) was added HCl 4N in dioxane (0.970 mL, 3.89 mmol). The sol. was stirred at r.t. for 18 h. Then, Et₂O was added. The supernatant was removed and the remaining solid was dried in vacuo. The residue was triturated 3× in Et₂O, filtered and dried to give 248 mg of Int. 359, pale yellow solid (96%).

c—Synthesis of Co. 197a:

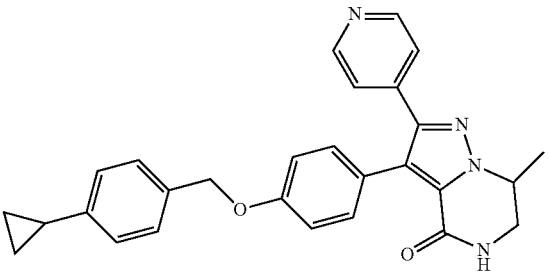 [SMILES: CC1CNC(=O)c2c(-c3ccc(OCc4ccc(C5CC5)cc4)cc3)c(-c3ccncc3)nn21]

To a sol. of 359 (248 mg, 0.465 mmol) in MeOH (2 mL) was added Cs₂CO₃ (758 mg, 2.33 mmol) and the mixture was stirred at r.t. for 6 h. The solvent was removed in vacuo and water and DCM were added to the residue. The layers were separated and the aq. layer was extracted with DCM. The organic layers were combined, dried over MgSO₄, filtered off and evaporated in vacuo to give 190 mg, white solid. The solid was triturated in Et₂O and the solid was filtered on a glass frit to give 140 mg of Co. 197a, white solid (67%).

d—Synthesis of Co. 197:

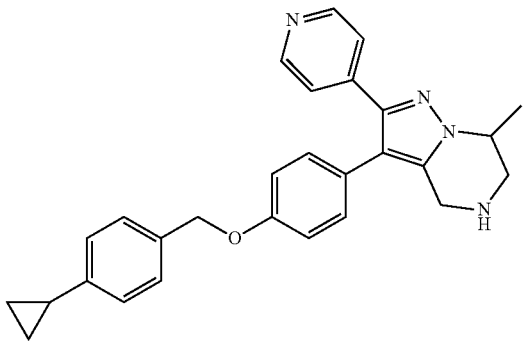 [SMILES: CC1CNCc2c(-c3ccc(OCc4ccc(C5CC5)cc4)cc3)c(-c3ccncc3)nn21]

LAH (55.6 mg, 1.47 mmol) was added to a sol. of Co. 197a (110 mg, 0.244 mmol) in dry THF (11 mL). The r.m. was stirred at r.t. for 18 h and quenched with water (60 µL, very slow addition) and a 3N sol. of NaOH (60 µL). Et₂O was added and the crude mixture was filtered on a glass frit. The precipitate was washed with Et₂O and the filtrate was evaporated in vacuo to give 127 mg, white residue. The residue was purified by prep. LC (Irregular SiOH, 15-40 jm, 10 g Merck, mobile phase gradient: from DCM 100% to DCM 95%, MeOH 5%). The desired fractions were collected and solvent was evaporated until dryness to give 117 mg. The residue was purified again by prep. LC (Irregular SiOH, 15-40 µm, 10 g Merck, mobile phase gradient: from DCM 100% to DCM 50%, acetone 50%). The pure fractions were collected and solvent was evaporated until dryness to give 115 mg, white solid. The white solid was purified by achiral SFC on (diethylaminopropyl 5 µm 150×21.2 mm, Mobile phase: iPrNH₂/CO₂/MeOH 0.3/70/30). The pure fractions were collected and solvent was evaporated to give 65 mg, colorless oil, which crystallized to give Co. 197 as a yellow solid (48%). m.p.: 153° C. (DSC).

Example A196

Preparation of Co. 198 a—Synthesis of Int. 361:

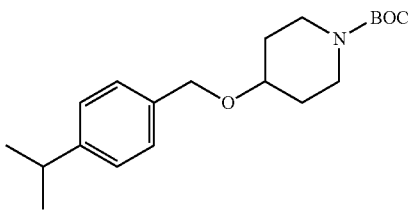 [SMILES: CC(C)c1ccc(COC2CCN(C(=O)OC(C)(C)C)CC2)cc1]

1-Boc-4-hydroxypiperidine (8 g, 39.7 mmol) was added to a suspension of NaH 60% (2.8 g, 119 mmol) in THF (100 mL). The mixture was stirred at r.t. for 10 min, 8 (8.6 mL, 51.7 mmol) was added. The mixture was stirred at r.t. for 16 h. Water and EtOAc were added, the mixture was extracted with EtOAc. The organic layer was separated, dried over MgSO$_4$, filtered and evaporated. The residue was purified by prep. LC on (Irregular SiOH 20-45 µm 40 g MATREX, Mobile phase: 70% Heptane, 30% EtOAc). The pure fractions were collected and solvent evaporated until dryness to give 12.4 g of Int. 361 (94%).

b—Synthesis of Int. 362:

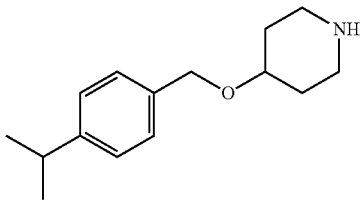 [SMILES: CC(C)c1ccc(COC2CCNCC2)cc1]

A mixture of 361 (0.223 g, 0.67 mmol), HCl 3N (0.89 mL, 2.68 mmol) in ACN (4 mL) was heated at 60° C. for 1 h. K$_2$CO$_3$ 10% and EtOAc were added and the mixture was extracted. The organic layer was separated, dried over MgSO$_4$, filtered and evaporated to give 150 mg of Int. 362 (96%).

c—Synthesis of Int. 363:

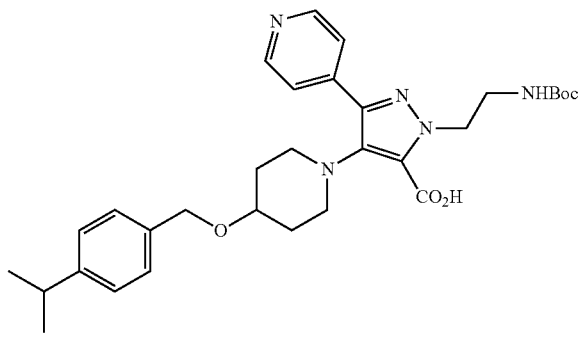 [SMILES: CC(C)c1ccc(COC2CCN(c3c(-c4ccncc4)nn(CCNC(=O)OC(C)(C)C)c3C(=O)O)CC2)cc1]

In a sealed tube, 3 (1 g, 2.3 mmol), CuI (44 mg, 228 µmol), Cs$_2$CO$_3$ (2.2 g, 6.8 mmol), 362 (610 mg, 2.6 mmol) in DMF (20 mL) was purged with N$_2$ (3×). Then, 2-acetyl-cyclohexanone (59.2 µl, 455 µmol) was added and the r.m. was stirred at 100° C. overnight. Water and EtOAc were added and the mixture was extracted. The organic layer was separated, dried over MgSO$_4$, filtered and evaporated to give 540 mg of a 1$^{st}$ residue. The aqueous layer was acidified by HCl 3N and extracted with EtOAc. The organic layer was separated, dried over MgSO$_4$, filtered and evaporated to give 220 mg of a 2$^{nd}$ residue. The 1$^{st}$ residue was purified by prep. LC (Irregular SiOH 20-45 µm 40 g MATREX, mobile phase: 85/15/1, DCM/MeOH/NH$_4$OH). The pure fractions were collected and the solvent evaporated to give 22 mg of Int. 363 (1.7%). The 2$^{nd}$ residue was purified by prep. LC (Irregular SiOH 20-45 µm 40 g MATREX, mobile phase: 85/15/1, DCM/MeOH/NH$_4$OH). The pure fractions were collected and the solvent evaporated until dryness to give 22 mg of Int. 363 (1.7%). The both fractions were put together for the next step (44 mg of Int. 363; 3.4%).

d—Synthesis of Int. 364:

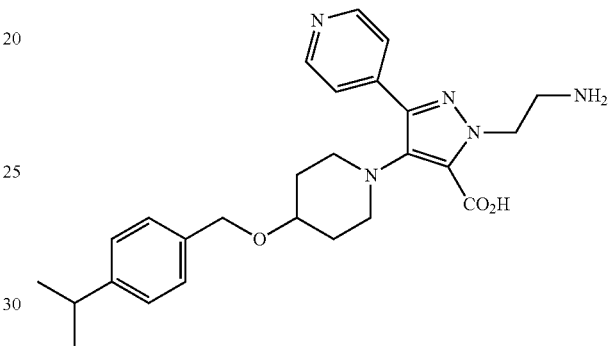

A mixture of 363 (27 mg, 47.9 µmol), HCl 3N (0.16 mL, 0.48 mmol) in ACN (2 mL) was heated at 80° C. for 4 h. K$_2$CO$_3$ 10% was added and the mixture was stirred at r.t. for 2 h. The mixture was extracted with EtOAc, the organic layer was separated, dried over MgSO$_4$, filtered and evaporated until dryness to give 16 mg of crude Int. 364 which was used as such for the next step.

e—Synthesis of Co. 198:

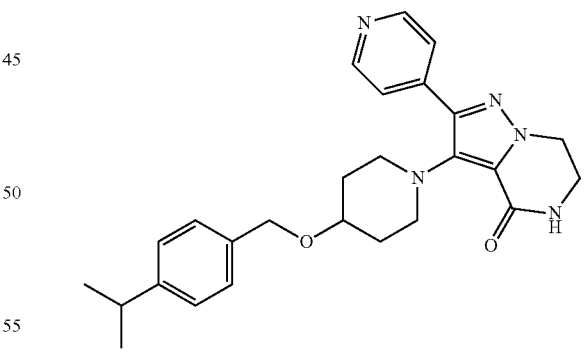

364 (16 mg, 0.03 mmol), EDCI (8 mg, 0.05 mmol), HOBT (7 mg, 0.05 mmol), Et$_3$N (14 µl, 0.1 mmol) in DCM (3 mL) was stirred at r.t. overnight. Water and DCM were added and the mixture was extracted. The organic layer was separated, dried over MgSO$_4$, filtered and evaporated. The residue was purified by prep. LC on (Irregular SiOH 20-45 µm 4 g GRACE, Mobile phase: 97/3, DCM/MeOH). The desired fractions were collected and solvent evaporated until dryness to give 8 mg which was purified by prep. LC on (Irregular SiOH 20-45 µm 4 g GRACE, Mobile phase: 97/3, DCM/MeOH). The pure fractions were collected and solvent evaporated until dryness to give 2 mg of Co. 198 (13%).

Example A197

Preparation of Co. 199 a—Synthesis of Int. 365:

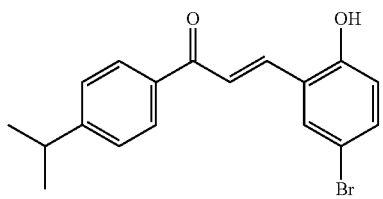 [SMILES: CC(C)c1ccc(C(=O)/C=C/c2cc(Br)ccc2O)cc1]

KOH 60% in H₂O (30 mL, 321 mmol) was added to a stirred sol. of 4'-isopropylacetophenone (10.00 g, 61.6 mmol) and 5-bromosalicylaldehyde (13.6 g; 67.8 mmol) in EtOH (30 mL) at 0° C. The r.m. was then stirred at r.t. for 4 h. The r.m. was diluted in DCM and quenched with HCl 1N. The precipitate was filtered and washed with water and DCM. The cake was dried in vacuo to give 19.8 g of Int. 365, a red solid (93%).

b—Synthesis of Int. 366:

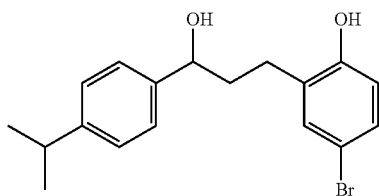 [SMILES: CC(C)c1ccc(C(O)CCc2cc(Br)ccc2O)cc1]

365 (10 g, 29.0 mmol) was added to a stirred sol. of NaBH₄ (1.64 g, 43.4 mmol) and indium chloride (3.20 g, 14.5 mmol) in ACN (120 mL) at r.t. The r.m. was then stirred at r.t. for 4 h. MeOH (30 mL) and NaBH₄ (2.2 g, 57.9 mmol) were added to the mixture. The sol. was then stirred 1 h at r.t. The sol. was then evaporated in vacuo. The residue was dissolved in Et₂O and washed with water (2×). The organic phase was dried (MgSO₄), filtered and evaporated in vacuo to give 9.00 g of Int. 366 (89%).

c—Synthesis of Int. 367:

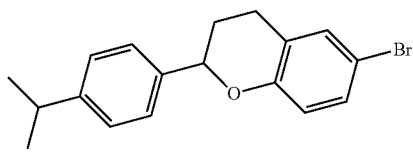 [SMILES: CC(C)c1ccc(C2CCc3cc(Br)ccc3O2)cc1]

DBAD (5.93 g, 25.8 mmol) was added to a stirred sol. of 366 (6.00 g, 17.2 mmol) and PPh₃ supp. (8.05 g, 25.8 mmol) in DCM (70 mL) at rt. The r.m. was stirred at r.t. for 18 h. Water was added to the mixture and the sol. was extracted with DCM. The organic phase was dried over MgSO₄, filtered and evaporated in vacuo. The residue was purified by prep. LC (irregular SiOH 15-40 μm, 80 g, Merck, Mobile phase: Heptane/EtOAc, 95/5). The pure fractions were collected and solvent evaporated until dryness to give 3.14 g of Int. 367, white solid (55%).

d—Synthesis of Int. 368:

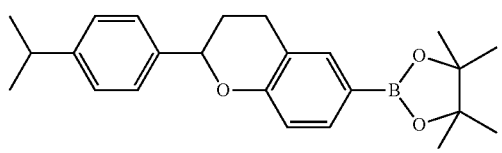 [SMILES: CC(C)c1ccc(C2CCc3cc(B4OC(C)(C)C(C)(C)O4)ccc3O2)cc1]

A mixture of 367 (3.14 g, 9.48 mmol), BisPin (3.61 g, 14.2 mmol) and KOAc (2.79 g, 28.4 mmol) in DME (45 mL) was carefully purged with N₂. PdCl₂(dppf) (776 mg, 0.948 mmol) was added and the r.m. was purged again with N₂. The r.m. was stirred at 18 h at 100° C. The r.m. was diluted with EtOAc and water. The organic layer was washed with brine, dried over MgSO₄, filtered and evaporated in vacuo to give brown solid. The residue was purified by prep. LC (irregular SiOH 15-40 μm, 80 g, Merck, Mobile phase: DCM 100%). The pure fractions were collected and solvent evaporated until dryness to give 4.15 g of Int. 368, yellow solid (quant.).

e—Synthesis of Co. 199:

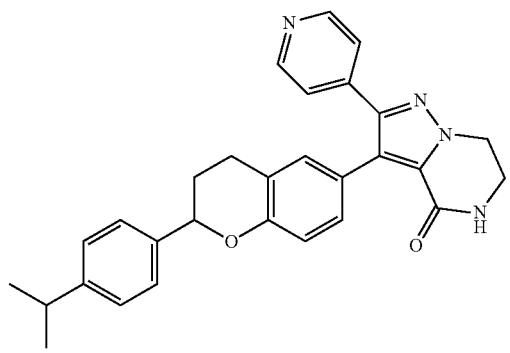 [SMILES: CC(C)c1ccc(C2CCc3cc(-c4c(-c5ccncc5)nn5c4C(=O)NCC5)ccc3O2)cc1]

A sol. of 4 (500 mg, 1.71 mmol) and 368 (1.29 g, 3.41 mmol) in 1,4-dioxane (10 mL) and H₂O (5 mL) was treated with K₃PO₄ (1.09 g, 5.12 mmol) and purged with N₂. PdCl₂(dppf) (140 mg, 171 μmol) was added and the r.m. was carefully purged with N₂. The mixture was heated at 120° C. using one single mode microwave (Biotage Initiator EXP 60) with a power output ranging from 0 to 400 W for 30 min [fixed hold time]. The r.m. was diluted with EtOAc and washed with water (1×) and with brine (2×). The organic phase was dried (MgSO₄), filtered and evaporated in vacuo. The residue was purified by prep. LC (irregular SiOH 15-40 μm, 50 g, Merck, Mobile phase gradient: from DCM 100% to DCM 95%, MeOH 5%. The pure fractions were collected and solvent evaporated until dryness to give 900 mg of a yellow solid which was recrystallized in EtOH. The precipitate which was formed after cooling was filtered, collected and dried in vacuo to give 500 mg of Co. 199 as a white solid (63%).

Example A198

Preparation of Co. 200 a—Synthesis of Int. 369:

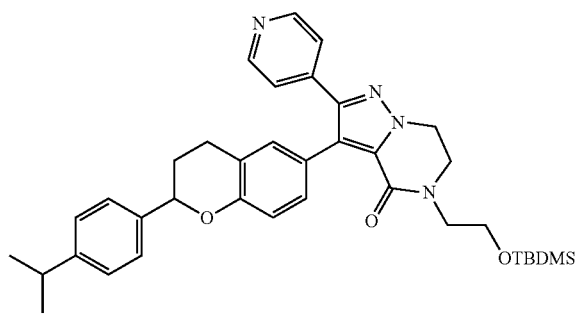 [SMILES: CC(C)c1ccc(C2CCc3cc(-c4c(-c5ccncc5)nn5c4C(=O)N(CCO[Si](C)(C)C(C)(C)C)CC5)ccc3O2)cc1]

NaH 60% (28 mg, 0.710 mmol) was added slowly to a suspension of Co. 199 (220 mg, 0.474 mmol) in DMF (3.5 mL) at r.t. under N₂. The mixture was stirred for 2 h, then (2-bromoethoxy)-tert-butyldimethylsilane (121 µL, 0.568 mmol) was added and stirred for 18 h. Water and K₂CO₃ were added and the mixture was extracted with EtOAc. The organic layer was dried (MgSO₄), filtered and evaporated in vacuo to give 300 mg of Int. 339 used as such for the next step.

b—Synthesis of Co. 200:

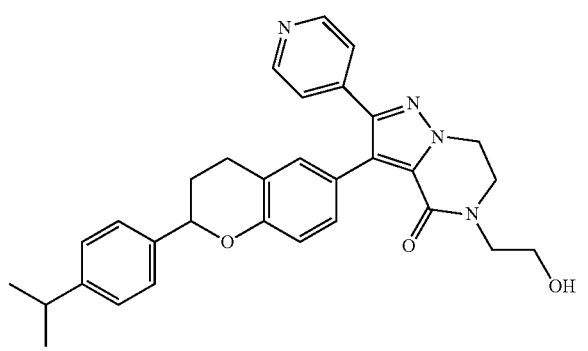 [SMILES: CC(C)c1ccc(C2CCc3cc(-c4c(-c5ccncc5)nn5c4C(=O)N(CCO)CC5)ccc3O2)cc1]

TBAF (722 µL, 722 µmol) was added dropwise to a sol. of 369 (300 mg, 482 µmol, 80%) in THF (3 mL) at r.t. and the sol. was stirred for 18 h. The mixture was evaporated in vacuo to give 250 mg of a brown oil. The residue was purified by prep. LC (irregular SiOH 15-40 µm, 50 g, MERCK, Mobile phase gradient: from DCM 100% to DCM 95%, MeOH 5%. The pure fractions were collected and solvent evaporated to give 156 mg of Co. 200 as a white solid (64%).

Example A199

Preparation of Co. 201 a—Synthesis of Int. 370:

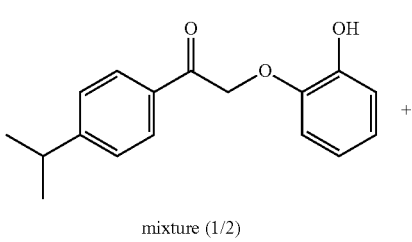

mixture (1/2)

-continued

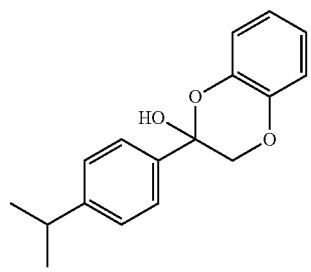

A mixture of 2-bromo-1-(4-isopropylphenyl)ethanone (4.0 g, 16.6 mmol), 1,2-benzenediol (1.83 g, 16.6 mmol) and Et₃N (2.8 mL, 19.9 mmol) in iPrOH (40 mL) was stirred at 70° C. for 4 h. The crude mixture was diluted in EtOAc washed with 1M HCl and water, dried over MgSO₄ and evaporated in vacuo to give brown oil. The residue was purified by prep. LC (irregular SiOH 15-40 µm, 80 g, GraceResolv™, dry loading, mobile phase: DCM 100%). The desired fractions were collected and solvent evaporated until dryness to give 1.58 g of Int. mixture 370, yellow oil (35%; mixture 1/2). The mixture was used as such for the next reaction step.

b—Synthesis of Int. 371:

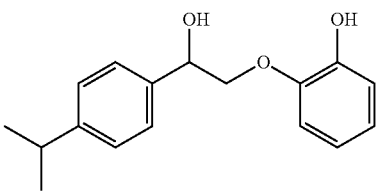 [SMILES: CC(C)c1ccc(C(O)COc2ccccc2O)cc1]

A sol. of 370 (1.58 g, 5.85 mmol) in dry THF (10 mL) and MeOH (2 mL) was treated with NaBH₄ (884 mg, 23.4 mmol) and stirred at r.t. for 4 h. The r.m. was diluted in EtOAc and a 1M aq. sol. of HCl. The organic layer was separated, washed with water, dried over MgSO₄ and evaporated in vacuo to give 1.66 g of Int. 371, yellow oil (Quant.).

c—Synthesis of Int. 372:

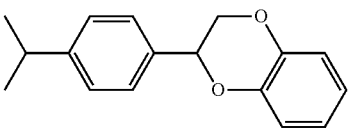 [SMILES: CC(C)c1ccc(C2COc3ccccc3O2)cc1]

A sol. of 371 (1.66 g, 6.10 mmol) and PPh₃ (2.24 g, 8.53 mmol) in DCM (30 mL) was treated with DBAD (1.97 g, 8.53 mmol) and stirred at r.t. for 17 h. The r.m. was poured in a 1M aq. sol. of HCl. The organic layer was separated, dried over MgSO₄ and evaporated in vacuo to give 5.2 g of a yellow oil. The residue was purified by prep. LC (irregular SiOH 15-40 µm, 120 g, Grace, mobile phase: heptane 80%, EtOAc 20%). The pure fractions were collected and solvent evaporated until dryness to give 1.59 g of Int. 372 as a yellow oil (Quant.).

d—Synthesis of Int. 373:

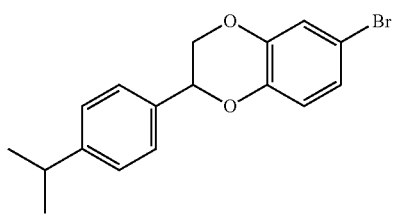 [SMILES: CC(C)c1ccc(C2COc3cc(Br)ccc3O2)cc1]

A sol. of 372 (1.42 g, 5.58 mmol) in HOAc (30 mL) was treated with NBS (0.994 g, 5.58 mmol) and stirred at 60° C. for 17 h. The r.m. was diluted in DCM, washed with a 10% sol. of $K_2CO_3$, dried over $MgSO_4$ and evaporated in vacuo to give 1.77 g of Int. 373 (95%; impure), used as such in the next step without any purification.

e—Synthesis of Int. 374:

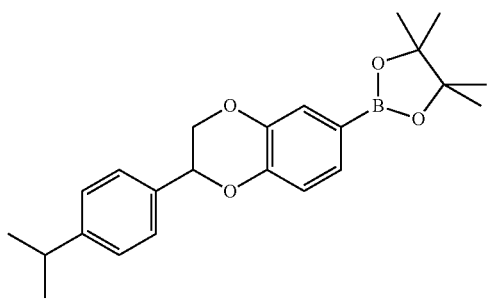 [SMILES: CC(C)c1ccc(C2COc3cc(B4OC(C)(C)C(C)(C)O4)ccc3O2)cc1]

A stirred sol. of 373 (1.77 g, 5.31 mmol), BisPin (2.02 g, 7.97 mmol) and KOAc (1.56 g, 15.) in DME (30 mL) was carefully purged with $N_2$, and $PdCl_2$(dppf) (348 mg, 425 µmol) was added. The r.m. was purged again with $N_2$ and stirred for 18 h at 105° C. The r.m. was poured in EtOAc and water. The organic layer was separated, washed with brine and evaporated in vacuo to give a black residue. The residue was purified by prep. LC (irregular SiOH 15-40 µm, 80 g, Grace, dry loading, mobile phase gradient: from heptane 90%, EtOAc 10% to heptane 80%, EtOAc 20%). The pure fractions were collected and solvent evaporated until dryness to give 1.89 g of Int. 374 (94%; impure), used as such in the next step without any purification.

f—Synthesis of Co. 201

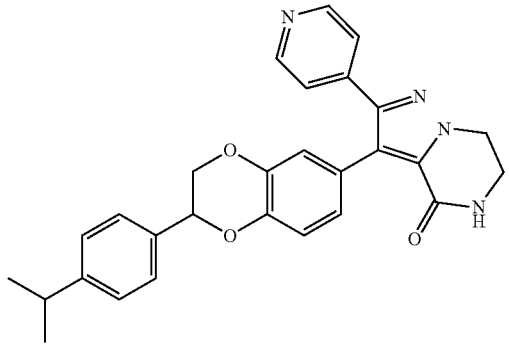 [SMILES: CC(C)c1ccc(C2COc3cc(/C(C(=N)c4ccncc4)=C4/NCCNC4=O)ccc3O2)cc1]

A sol. of 4 (899 mg, 3.07 mmol) and 374 (1.75 g, 4.60 mmol) in 1,4-dioxane (12 mL) and $H_2O$ (6 mL) was treated with $K_3PO_4$ (1.30 g, 6.14 mmol) and purged with $N_2$. $PdCl_2$(dppf) (201 mg, 245 µmol) was added and the r.m. was carefully purged with $N_2$. The mixture was heated at 120° C. using one single mode microwave (Biotage Initiator EXP 60) with a power output ranging from 0 to 400 W for 25 min [fixed hold time]. The r.m. was poured in water and in DCM/MeOH (98/2). The organic layer was separated, dried over $MgSO_4$ and evaporated in vacuo to give black oil. The oil was purified by prep. LC (irregular SiOH 15-40 µm, 220 g, Grace, mobile phase gradient: from DCM 100% to DCM 96%, MeOH 4%). The desired fractions were collected and solvent evaporated to give 1.47 g of yellow foam (mixture 2 isomers). The residue was purified by achiral SFC (Stationary phase: Chiralpak IA 5 µm 250*20 mm, Mobile phase: 55% $CO_2$, 45% iPrOH). The pure fractions were combined and evaporated in vacuo to give 410 mg of product which was recrystallized from EtOH. The white solid was collected by filtration, washed with $Et_2O$ and dried in wacuo to afford 300 mg of Co. 201, white solid (21%). m.p.: 290° C. (DSC).

Example A200

Preparation of Co. 203

First Method:
a—Synthesis of Int. 375:

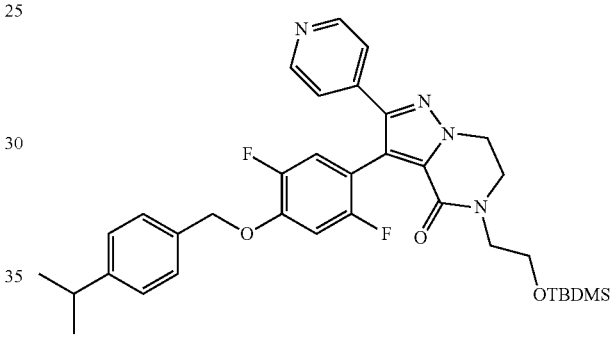

Under $N_2$, a sol. of Co. 14 (211 mg, 0.445 mmol) in dry DMSO (4 mL) was treated with NaH 60% (27 mg, 0.667 mmol). The r.m. was stirred at r.t. for 2 h. Then, (2-bromoethoxy)-tert-butyldimethylsilane (0.114 mL, 0.534 mmol) was added and the reaction was stirred at r.t. for 17 h. TBAF (0.222 mL, 0.222 mmol) was then added and the r.m. was stirred for 2 h at r.t. The mixture was poured in EtOAc (150 mL) and washed with brine (5×40 mL). The organic layer was dried over $MgSO_4$ and evaporated in vacuo to afford 220 mg of Int. 375 as a brown residue which was used as such for the next step.

b—Synthesis of Co. 203:

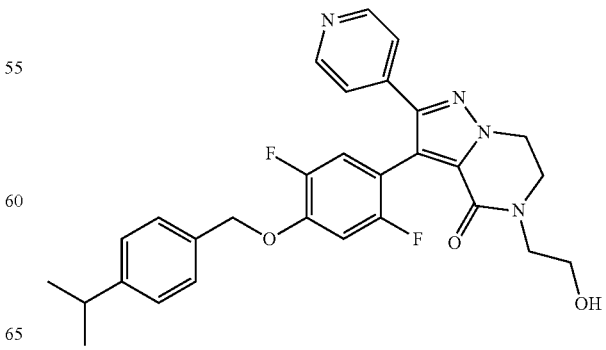

A sol. of mixture 375 (220 mg, 0.348 mmol) in THF (8 mL) was treated with TBAF (0.174 mL, 0.174 mmol) and stirred at r.t. for 72 h. The crude mixture was then diluted in DCM, washed with water and brine. The organic layer was dried over MgSO$_4$ and evaporated in vacuo to afford a brown residue. The residue was purified by prep. LC (irregular SiOH 15-40 µm, 30 g, GraceResolv™, Mobile phase gradient: from DCM 100% to DCM 94%, MeOH 6%). The pure fractions were collected and solvent evaporated until dryness to give 115 mg of Co. 203 as an off-white solid (64%). m.p.: 193° C. (DSC).

Second Method:

a—Synthesis of Int. 375:

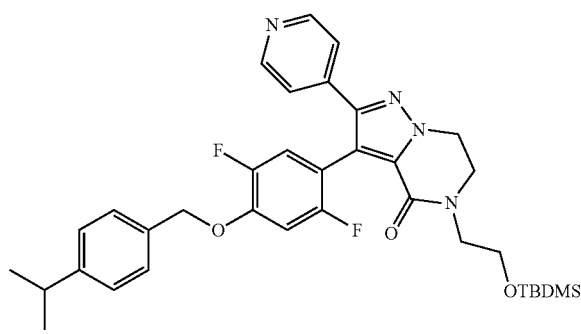 [SMILES: CC(C)c1ccc(COc2cc(F)c(-c3c(-c4ccncc4)nn4c3C(=O)N(CCO[Si](C)(C)C(C)(C)C)CC4)cc2F)cc1]

In a microwave vial, a mixture of 28 (3.4 g, 7.5 mmol), 66 (3.5 g, 9.0 mmol), K$_3$PO$_4$ (6.4 g, 30 mmol) in 1,4-dioxane (33 mL) and H$_2$O (11 mL) was carefully purged with N$_2$. PdCl$_2$(dppf) (620 mg, 0.75 mmol) was added and the r.m. was purged again with N$_2$. The r.m. was heated at 80° C. overnight. The r.m. was diluted with EtOAc and washed with water (1×) and with brine (3×). The organic phase was dried over MgSO$_4$, filtered on a pad of Celite® and evaporated in vacuo to give brown oil. The oil was purified by prep. LC (irregular SiOH 30 µm, 120 g GraceResolv™, mobile phase: DCM/MeOH/NH$_4$OH 99/1/0.1). The pure fractions were collected and solvent evaporated until dryness to give 3.0 g of Int. 375, pale yellow oil (63%).

b—Synthesis of Co. 203:

TBAF (5.7 mL, 5.7 mmol) was added dropwise to a sol. of 375 (3.0 g, 4.7 mmol) in THF (46 mL) at r.t. The mixture was stirred overnight at r.t. The mixture was concentrated (5.1 g) and the residue was purified by prep. LC (Regular SiOH, 30 µm, 80 g GraceResolv™, mobile phase: DCM/MeOH/NH$_4$OH 98/2/0.1). The pure fractions were collected and solvent evaporated to give colorless oil which was triturated in Et$_2$O. The white solide formed was filtrated, washed and dried to give 1.26 g of Co. 203 as a white solid (51% first batch). m.p.: 195° C. (dsc). The filtrate was concentrated and the residue was triturated in Et$_2$O, filtrated and dried to give 0.27 g of Co. 203 as a white solid (11%, second batch). m.p.: 197° C. (dsc).

Example A201

Preparation of Co. 204 a—Synthesis of Int. 376:

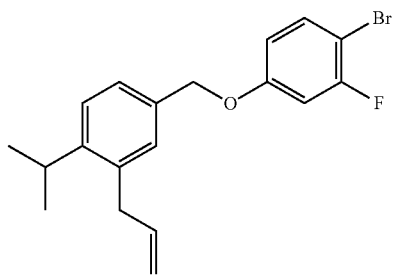 [SMILES: C=CCc1cc(COc2ccc(Br)c(F)c2)ccc1C(C)C]

To a sol. of 53 (10.0 g, 52.6 mmol) and 4-bromo-3-fluorophenol (10.0 g, 52.6 mmol) in dry DCM (265 mL) were added PPh$_3$ (15.2 g, 57.8 mmol) and DBAD (13.3 g, 57.8 g) at r.t. The r.m. was stirred at r.t. for 17 h. Then, EtOAc and brine were added, and the organic layer was dried over MgSO$_4$, filtered and evaporated in vacuo to afford 50.9 g of a residue which was filtered over silica washing with a sol. EtOAc/Heptane (30:70) to give 36.9 g, sticky brown solid. This solid was purified by prep. LC (Irregular SiOH 50 µm, 750 g Grace, mobile phase gradient: from Heptane 90%, DCM 10% to Heptane 60%, DCM 40%). The desired fractions were collected and solvent evaporated in vacuo to give 13.8 g of Int. 376, pale oil as a mixture which was used as such for the next step.

b—Synthesis of Int. 377:

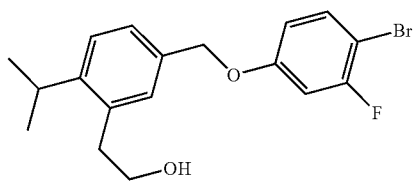 [SMILES: CC(C)c1ccc(COc2ccc(Br)c(F)c2)cc1CCO]

A sol. of mixture 376 (3.00 g, 8.26 mmol) in DCM (60 mL) was cooled to −78° C. O$_3$ was bubbled through the sol. (10 min). The excess of O$_3$ was removed (N$_2$ purge) and NaBH$_4$ (1.25 g, 33.0 mmol) and EtOH (20 mL) were added. The sol. was warmed to r.t. and stirred for 4 h. Then water and DCM were added, and the organic layer was washed (brine), dried (MgSO$_4$), filtered and evaporated in vacuo. The residue (3.2 g) was purified by prep. LC (Irregular SiOH 50 µm, 120 g Grace, mobile phase gradient: from Heptane 100% to Heptane 60%, EtOAc 40%). The desired fractions were collected and evaporated in vacuo to give 1.07 g of Int. 377, colorless oil (35%).

c—Synthesis of Int. 378:

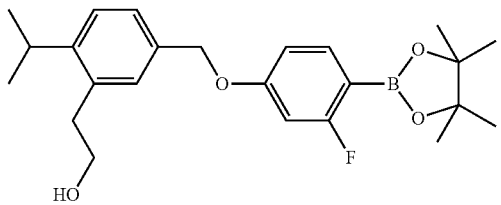 [SMILES: CC(C)c1ccc(COc2ccc(B3OC(C)(C)C(C)(C)O3)c(F)c2)cc1CCO]

A mixture of 377 (2.85 g, 7.76 mmol), BisPin (3.94 g, 15.5 mmol) and KOAc (2.29 g, 23.3 mmol) in DME (80 mL) was carefully purged with N₂. PdCl₂(dppf) (0.635 g, 0.776 mmol) was added and the r.m. was purged with N₂. The r.m. was stirred at 100° C. for 18 h. The r.m. was diluted with EtOAc and water. The organic layer was washed with brine, dried over MgSO₄, filtered and evaporated in vacuo to give 7.2 g of a black solid. The residue was purified by prep. LC (irregular SiOH 15-40 µm, 220 g, Grace, Mobile phase gradient: EtOAc 10%, Heptane 90% to EtOAc 40%, Heptane 60%). The pure fractions were collected and solvent evaporated to give 1.93 g of Int. 378 as a sticky oil (60%).

d—Synthesis of Co. 204:

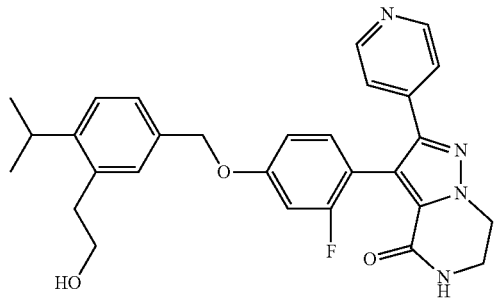 [SMILES: CC(C)c1ccc(COc2ccc(-c3c(-c4ccncc4)nn4c3C(=O)NCC4)c(F)c2)cc1CCO]

A mixture of 4 (280 mg, 0.955 mmol), 378(0.652 g, 1.43 mmol) and K₃PO₄ (0.507 g, 2.39 mmol) in 1,4-dioxane (3 mL) and H₂O (1.5 mL) was purged with N₂. PdCl₂(dppf) (78 mg, 95.5 µmol) was then added. The mixture was purged again with N₂ and stirred at 120° C. using one single mode microwave (Biotage Initiator EXP 60) with a power output ranging from 0 to 400 W for 25 min [fixed hold time]. Then, a sol. of DCM/MeOH (95/5) and water were added. The organic layer was separated, washed with brine, dried over MgSO₄, filtered and evaporated in vacuo to yield 620 mg of a brown solid. The residue was purified by prep. LC (Irregular SiOH 50 µm, 40 g Grace, mobile phase gradient: from DCM 100% to DCM 94%, MeOH 6%). The desired fractions were collected and evaporated in vacuo to give 289 mg of a pale beige solid. The residue was purified by achiral SFC (Stationary phase: 2-ethylpyridine 6 µm 150×30 mm, Mobile phase: 75% CO₂, 25% MeOH). The pure fractions were collected and solvent evaporated until dryness to yield 220 mg of Co. 204 as a white solid (46%). m.p.: 223° C. (DSC).

Example A202

Preparation of Co. 205 a—Synthesis of Int. 379:

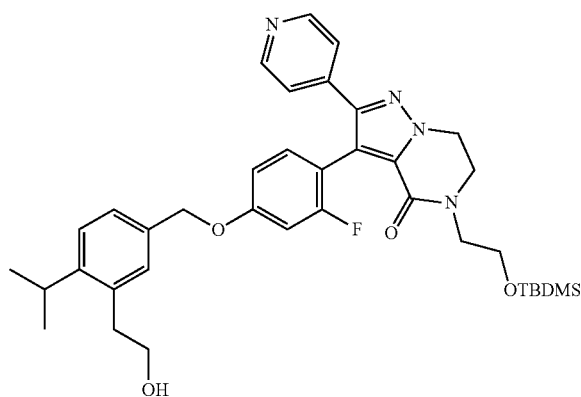 [SMILES: CC(C)c1ccc(COc2ccc(-c3c(-c4ccncc4)nn4c3C(=O)N(CCO[Si](C)(C)C(C)(C)C)CC4)c(F)c2)cc1CCO]

A mixture of 28 (0.680 g, 1.506 mmol), 378(1.03 g, 2.26 mmol) and K₃PO₄ (0.959 g, 4.52 mmol) in 1,4-dioxane (9 mL) and H₂O (3.5 mL) was purged with N₂. PdCl₂(dppf) (0.123 g, 0.151 mmol) was then added. The mixture was purged again with N₂ and stirred at 120° C. using one single mode microwave (Biotage Initiator EXP 60) with a power output ranging from 0 to 400 W for 25 min [fixed hold time]. Then, a sol. of DCM/MeOH (95/5) and water were added. The organic layer was washed with brine, dried over MgSO₄, filtered and evaporated in vacuo to yield 2.20 g, brown solid which was purified by prep. LC (Irregular SiOH50 µm, 80 g Grace, mobile phase gradient: from DCM 100% to DCM 94%, MeOH 6%). The desired fractions were collected and evaporated in vacuo to give 800 mg of Int. 379 used as such for the next step.

b—Synthesis of Co. 205:

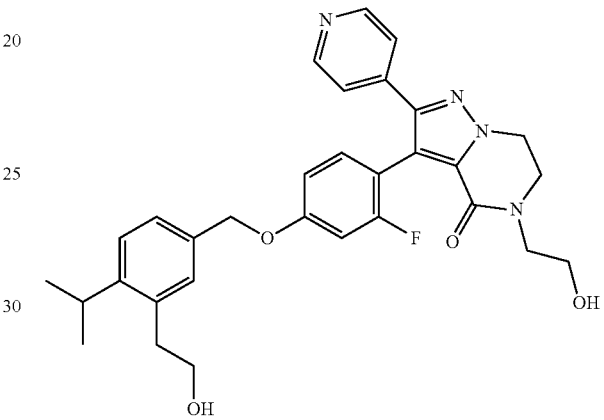

TBAF (0.858 mL, 0.858 mmol) was added to a stirred sol. of 379 (800 mg, 0.850 mmol) in THF (11 mL) at 0° C., and the r.m. was stirred at r.t. for 2 h. The crude mixture was diluted with water and a sol. of DCM/MeOH (96/4). The organic layer was washed with brine, dried over MgSO₄, filtered and evaporated in vacuo to afford 690 mg, solid.

The solid was purified by prep. LC (Irregular SiOH 50 µm, 30 g Grace, mobile phase gradient: from DCM 100% to DCM 91%, MeOH 9%). The desired fractions were collected and evaporated in vacuo to give 412 mg, white solid. The solid was triturated with DIPE, filtered off, washed with Et₂O and dried in vacuo to yield 385 mg, white solid which was solubilized in MeOH (1 mL). The solvent was allowed to evaporate slowly to give 374 mg of Co. 205, crystalline white solid (81%). m.p.: 151° C. (DSC).

Example A203

Preparation of Co. 206 a—Synthesis of Int. 380:

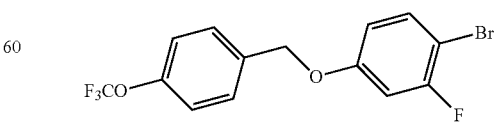

To a suspension of 4-(trifluoromethoxy)-benzyl alcohol (1 mL, 10.4 mmol), 4-bromo-3-fluorophenol (1.58 g, 8.28 mmol), DBAD (1.9 g, 8.28 mmol) in dry DCM (20 mL) was added PPh₃ supp. (2.59 g, 8.28 mmol) and the r.m. was stirred at r.t. for 18 h. The insoluble was filtered through Celite®, washed with DCM. Water was added and the organic layer was separated, dried, filtered and concentrated. The residue (4.24 g) was purified by prep. LC on (Irregular SiOH 15-40 µm 80 g Grace, Mobile phase: Heptane/EtOAc 98/2). The pure fractions were collected and evaporated until dryness to give 1.76 g of Int. 380 (70%).

b—Synthesis of Int. 381:

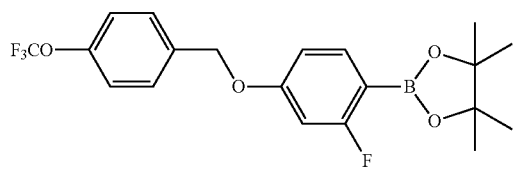 [SMILES: CC1(C)OB(c2ccc(OCc3ccc(OC(F)(F)F)cc3)cc2F)OC1(C)C]

In a sealed tube, a mixture of 380 (1.82 g, 4.98 mmol), BisPin (1.9 g, 7.47 mmol), KOAc (1.47 g, 14.9 mmol) in DME (20 mL) was carefully purged with N₂. PdCl₂(dppf) (0.122 g, 0.15 mmol) was added and the r.m. was purged again with N₂. The mixture was heated at 100° C. overnight. EtOAc and water were added and the mixture was extracted with EtOAc. The organic layer was separated, dried, filtered and evaporated until dryness to give 3.3 g. The residue was purified by prep. LC on (Irregular SiOH 15-40 µm 50 g Merck, Mobile phase: 90/10 Heptane/EtOAc). The pure fractions were collected and evaporated until dryness to give 495 mg of Int. 381 (24%).

c—Synthesis of Int. 382:

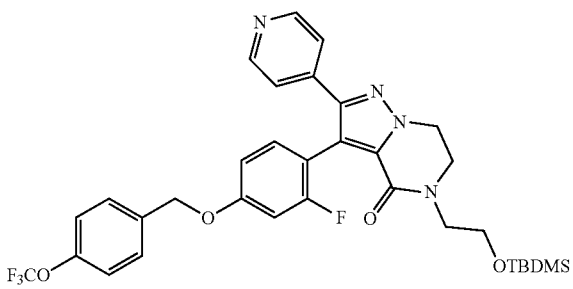 [SMILES: CC(C)(C)[Si](C)(C)OCCN1CCn2nc(-c3ccncc3)c(-c3ccc(OCc4ccc(OC(F)(F)F)cc4)cc3F)c2C1=O]

In a microwave vial, a mixture of 28 (0.7 g, 1.55 mmol), 381 (0.799 g, 1.94 mmol), K₃PO₄ (1.32 g, 6.2 mmol) in 1,4-dioxane (6.8 mL) and H₂O (2.4 mL) was carefully purged with N₂. PdCl₂(dppf) (127 mg, 0.16 mmol) was added and the r.m. was purged again with N₂. The r.m. was heated at 80° C. overnight. The r.m. was diluted with EtOAc and washed with water (once) and with brine (3×). The organic phase was dried over MgSO₄, filtered and evaporated in vacuo to give 1.65 g. The residue was purified by prep. LC (irregular SiOH 30 µm, 40 g Interchim, mobile phase: from DCM 100% to DCM/MeOH/NH₄OH 97/3/0.1). The pure fractions were collected and evaporated until dryness to give 717 mg of Int. 382 (70%).

d—Synthesis of Co. 206:

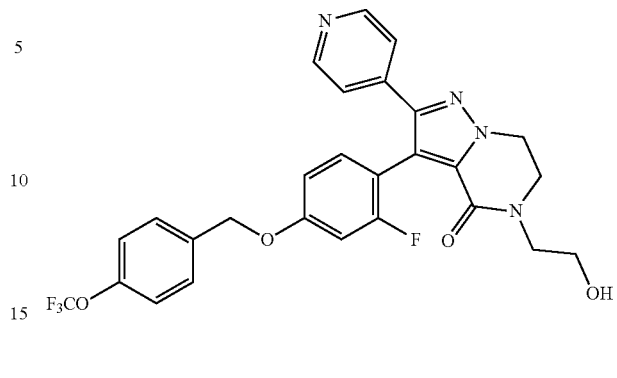

TABF (1.3 mL, 1.3 mmol) was added dropwise to a sol. of 382 (715 mg, 1.09 mmol) in THF (11 mL) at r.t. The mixture was stirred for 3 h at r.t. EtOAc and water were added.

The organic layer was separated, dried, filtered and evaporated until dryness to give 646 mg. The residue was purified by prep. LC (Regular SiOH, 30 µm, 24 g GraceResolv™, mobile phase gradient: from DCM 100% to DCM/MeOH/NH₄OH 95/5/0.1). The pure fractions were collected and evaporated until dryness to give 421 mg which was crystallized from DIPE, filtered and dried to give 390 mg of Co. 206 (66%). m.p.: 140° C. (dsc).

Example A204

Preparation of Co. 207 a—Synthesis of Int. 383:

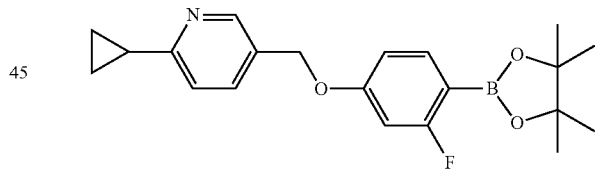

DBAD (3.14 g, 13.7 mmol) was added to a mixture of 3-fluoro-4-hydroxybenzeneboronic acid pinacol ester (2.50 g, 10.5 mmol), 6-cyclopropyl-3-pyridinemethanol (2.04 g, 13.6 mmol) and PPh₃ (3.58 g, 13.7 mmol) in dry THF (75 mL) and the r.m. was stirred under N₂ for 20 h at r.t. The crude mixture was diluted with EtOAc and water, and the organic layer was washed with brine, dried over MgSO₄, filtered and evaporated in vacuo to give 12.8 g. The residue was purified by prep. LC (irregular SiOH 15-40 µm, 330 g Grace, mobile phase gradient: from Heptane 100% to EtOAc 40%, Heptane 60%). The pure fractions were collected and solvent was evaporated until dryness to give 3.1 g of Int. 383, colorless oil (76%).

b—Synthesis of Int. 384:

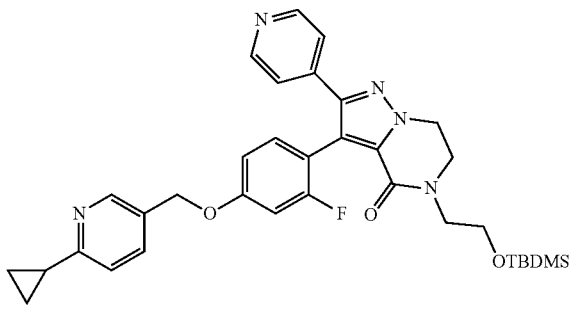 [SMILES: CC(C)(C)[Si](C)(C)OCCN1CCn2nc(-c3ccncc3)c(-c3ccc(OCc4ccc(C5CC5)nc4)cc3F)c2C1=O]

PdCl$_2$(dppf) (0.109 g, 0.133 mmol) was added to a stirred sol. of 28 (0.600 g, 1.33 mmol), 383 (1.03 g, 2.66 mmol) and K$_3$PO$_4$ (0.846 g, 3.99 mmol) in 1,4-dioxane (7.5 mL) and H$_2$O (2.5 mL) at r.t. under N$_2$. The resulting mixture was stirred at 120° C. using one single mode microwave (Biotage Initiator EXP 60) with a power output ranging from 0 to 400 W for 30 min. [fixed hold time]. The crude material was diluted with DCM and water, and the organic layer was washed with brine, dried (MgSO$_4$), filtered and evaporated in vacuo to yield 1.9 g of a dark oil. The residue was purified by prep. LC (Irregular SiOH 50 μm, 80 g Grace, mobile phase gradient: from DCM 100% to MeOH/DCM 8/92). The desired fractions were collected and evaporated in vacuo to give 796 mg of Int. 384, oil used as such for the next step.

c—Synthesis of Co. 207:

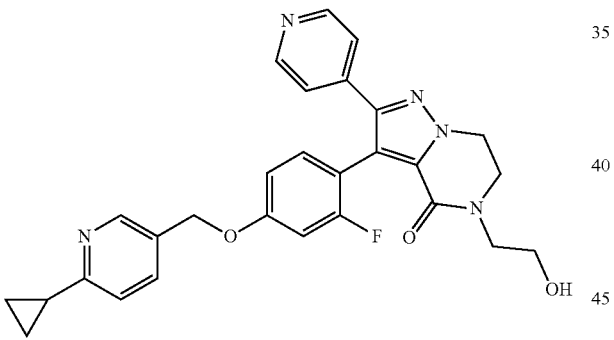

To a stirred sol. of 384 (796 mg, 0.973 mmol) in C (10 mL) at 0° C. was added TBAF (0.982 mL, 0.982 mmol), and the r.m. was stirred at 0° C. for 3 h. The crude mixture was diluted with water and a sol. of DCM/MeOH (95/5). The organic layer was washed with brine, separated, dried over MgSO$_4$, filtered and evaporated in vacuo to afford 490 mg, oil. This oil was purified by prep. LC (Irregular SiOH 50 μm, 40 g Grace, mobile phase gradient: from DCM 100% to DCM 92%, MeOH 8%). The desired fractions were collected and evaporated in vacuo to give 410 mg of sticky pale rose solid which was crystallized from MeOH and triturated in a mixture of Et$_2$O/MeOH (3/1). The solvents were evaporated in vacuo and the affording solid was dried under high vacuum at 55° C. to yield 360 mg of white solid which was recrystallized in EtOH, filtered on a glass frit and dried in vacuo to give 234 mg of white solid which was triturated with Et$_2$O, and the solvent was evaporated in vacuo to yield 156 mg of a white solid which was dried in vacuo at 50° C. for 20 h to yield 145 mg of Co. 207 as a white solid (30%).

Example A205

Preparation of Co. 208a and Co. 208 a—Synthesis of Co. 208a

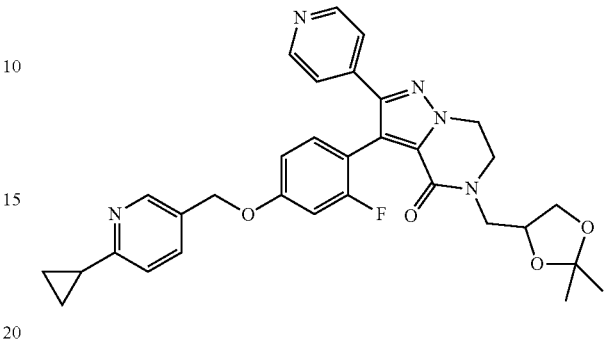

277 (800 mg, 1.96 mmol), 383 (1.04 g, 2.95 mmol), K$_3$PO$_4$ (1.25 g, 5.89 mmol) in 1,4-dioxane (8 mL) and H$_2$O (4 mL), were purged with N$_2$ for 10 min. Then, PdCl$_2$(dppf) (161 mg, 0.196 mmol) was added and purged with N$_2$ for 10 min. The resulting mixture was stirred at 120° C. using one single mode microwave (Biotage Initiator EXP 60) with a power output ranging from 0 to 400 W for 30 min. [fixed hold time]. The mixture was diluted in water and extracted with EtOAc. The organic layer was dried over MgSO$_4$, filtered and evaporated to give 1.20 g of Co. 208a, brown oil (quant.). The product was used for the next step without further purification.

b—Synthesis of Co. 208:

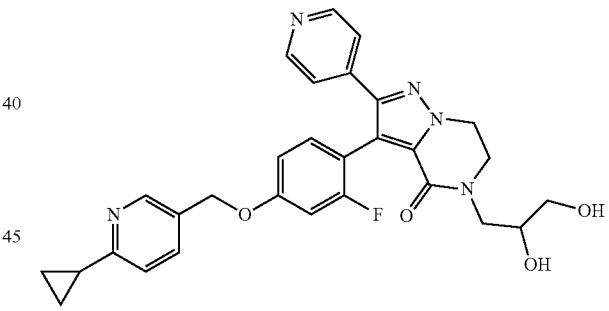

Co. 208a (1.08 g, 1.90 mmol), HCl 3N (3.16 mL, 9.48 mmol) in 1,4-dioxane (40 mL) were heated to 80° C. for 30 min. The mixture was quenched with a 10% sol. of K$_2$CO$_3$ and extracted with EtOAc. The organic layer was separated, dried over MgSO$_4$, filtered and evaporated in vacuo to give 880 mg of brown oil. The residue was purified by prep. LC (irregular SiOH 15-40 μm, 80 g, GraceResolv™, dry loading, mobile phase gradient: from DCM 100% to DCM 92%, MeOH 8%). The desired fractions were collected and solvent evaporated to give 570 mg, brown solid (57%). The solid was recrystallized in EtOH to give 450 mg, grey solid which was purified by prep. LC (irregular SiOH 15-40 μm, 80 g, GraceResolv™, dry loading, mobile phase gradient: from DCM 100% to DCM 92%, MeOH 8%). The pure fractions were collected and solvent evaporated to give 410 mg, white solid. The solid was recrystallized in EtOH three times to give 228 mg of Co. 208 as a white solid (23%). m.p.: 116° C. and 126° C. (DSC).

Example A206

Preparation of Co. 209 a—Synthesis of Int. 386:

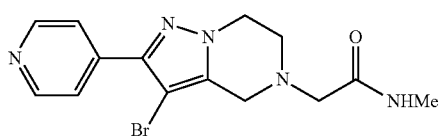 [SMILES: CNC(=O)CN1CCn2nc(-c3ccncc3)c(Br)c2C1]

A mixture of 337 (600 mg, 2.15 mmol), 2-bromo-N-methyl-acetamide (392 mg, 2.58 mmol) and K₂CO₃ (743 mg, 5.37 mmol) in DMF (8 mL) was stirred for 2 h at 55° C. The r.m. was then poured in DCM and water. The organic layer was separated, dried over MgSO₄ and evaporated in vacuo to afford brown oil. The residue was purified by prep. LC (irregular SiOH 15-40 µm, 40 g Gotech, mobile phase gradient: from DCM 100% to DCM 94%, MeOH 6%). The pure fractions were collected and solvent evaporated until dryness to give 314 mg of Int. 386, yellow solid (42%).

b—Synthesis of Co. 209:

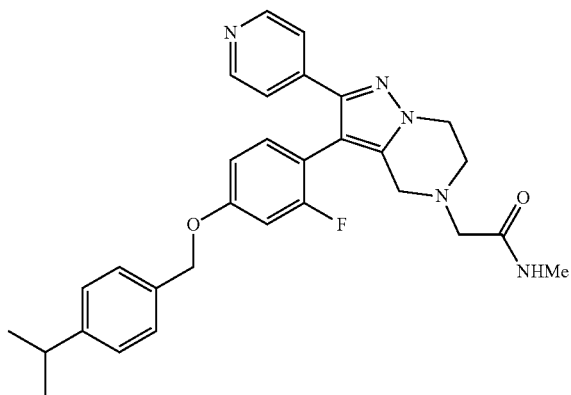 [SMILES: CNC(=O)CN1CCn2nc(-c3ccncc3)c(-c3ccc(OCc4ccc(C(C)C)cc4)cc3F)c2C1]

A mixture of 386 (314 mg, 0.897 mmol), 42 (664 mg, 1.79 mmol) and K₃PO₄ (571 mg, 2.69 mmol) in 1,4-dioxane (8 mL) and H₂O (4 mL) was purged with N₂. PdCl₂(dppf) (73 mg, 93.8 µmol) was then added. The mixture was purged again with N₂ and heated at 120° C. using one single mode microwave (Biotage Initiator EXP 60) with a power output ranging from 0 to 400 W for 35 min [fixed hold time]. The r.m. was then poured in DCM and water. The organic layer was separated. The aq. layer was extracted again with DCM. The organic layers were combined, dried over MgSO₄ and evaporated in vacuo to afford a brown residue. The residue was purified by prep. LC (irregular SiOH 15-40 µm, 80 g, GraceResolv™, dry loading, mobile phase gradient: from DCM 100% to DCM 92%, MeOH 8%). The desired fractions were collected and solvent evaporated to give 240 mg of a grey solid. The solid was combined with another batch (initial reactant 386, 280 mg, in the same conditions of reaction) and purified by prep. LC (irregular SiOH 15-40 µm, 40 g, Merck, mobile phase gradient: from DCM 100% to DCM 94%, MeOH 6%). The pure fractions were collected and solvent evaporated to give 280 mg of an off-white solid. The solid was dissolved in a small amount of MeOH and allowed to evaporate slowly overnight. The residue was scratched in Et₂O to obtain a white solid in suspension. The suspension was filtered off and the white precipitate was washed with Et₂O and dried in vacuo to give 238 mg of Co. 209 as a white solid (global yield: 27%). m.p.: 175° C., 159° C. (polymorph, DSC).

Example A207

Preparation of Co. 210a and Co. 210 a—Synthesis of Co. 210:

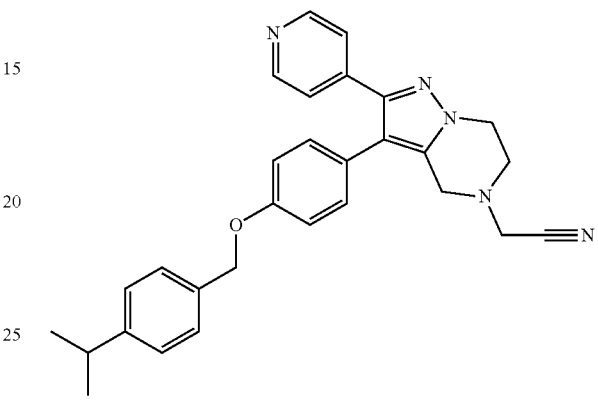

Bromoacetonitrile (43 µL, 0.601 mmol) was added to a stirred suspension of Co. 173 (250 mg, 0.501 mmol) and K₂CO₃ (104 mg, 0.751 mmol) in DMF (3 mL) at r.t. The r.m. was stirred at r.t. for 16 h, and then it was diluted with EtOAc and water. The organic layer was washed with brine, separated, dried over MgSO₄, filtered and evaporated in vacuo to afford 289 mg of Co. 210a, pale yellow solid (quant., purity 85%). The product was used as such for the next step.

b—Synthesis of Co. 210:

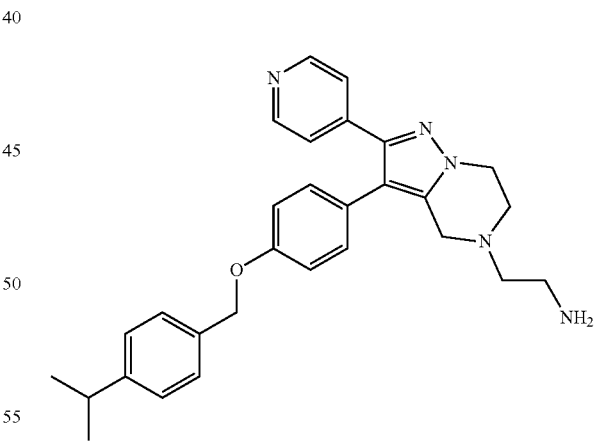

0.79 eq fumarate LAH (59 mg, 1.55 mmol) was added to a stirred sol. of Co. 210a (240 mg, 0.518 mmol) in THF (4.5 mL) under N₂ at 0° C. The r.m. was stirred at r.t. for 2 h. Then, the crude mixture was quenched with addition of water (60 µL, very slow addition), a 3N sol. of NaOH (60 µL) and water (190 µL). The crude mixture was filtered on a glass frit, the cake was washed with EtOAc and the filtrate was evaporated in vacuo to afford 194 mg of oil. The residue was purified by prep. LC (irregular SiOH 15-40 µm, 12 g Grace, Mobile phase gradient: from DCM 100% to DCM 90%, MeOH 9%, NH₄OH 1%). The fractions were combined and the solvent was removed in vacuo to give 108 mg, pale yellow oil. Then, MeOH (2 mL) and fumaric acid (25 mg, 0.215 mmol) were added, and the solvent was removed in vacuo to afford a sticky solid. The solid was triturated with Et₂O, and the solvent removed in vacuo to yield 130 mg of Co. 210, pale brown solid (45%; fumarate salt (0.79 eq fumarate)). m.p.: 197° C. (DSC).

Example A208

Preparation of Co. 211

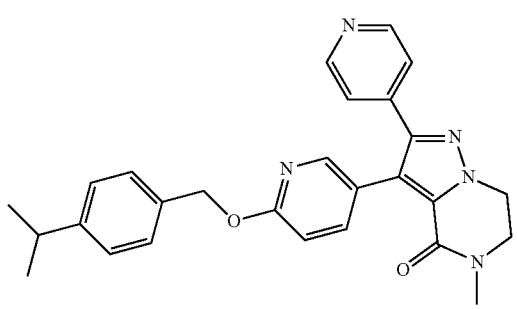 [SMILES: CC(C)c1ccc(COc2ccc(-c3c(-c4ccncc4)nn4c3C(=O)N(C)CC4)cn2)cc1]

A mixture of 98 (152 mg, 0.495 mmol), 129 (350 mg, 0.990 mmol) and K₃PO₄ (420 mg, 1.98 mmol) in 1,4-dioxane (3 mL) and H₂O (1 mL) was carefully purged with N₂. PCy₃ (28 mg, 99.0 μmol) and Pd(OAc)₂ (11 mg, 49.5 μmol) were added and the r.m. was purged again with N₂. The r.m. was stirred for 67 h at 80° C. The crude material was dissolved in water and extracted with EtOAc. The organic phase was washed with brine, dried (MgSO₄), filtered and evaporated in vacuo to give a solid which was purified by prep. LC (irregular SiOH 15-40 μm, 24 g Grace, mobile phase gradient: from DCM/MeOH from 100/0 to 91/9). The pure fractions were collected and evaporated to give 261 mg of a solid. The solid was purified by trituration with pentane to afford 206 mg of a solid. This solid was purified by achiral SFC (2-ethylpyridine 6 μm 150×21.2 mm. Mobile phase: 80% CO₂, 20% MeOH). The desired fractions were isolated and evaporated in vacuo to yield 161 mg of Co. 211 as a white solid (72%). m.p.: 57° C. (DSC).

Example A209

Preparation of Co. 212 a—Synthesis of Int. 388:

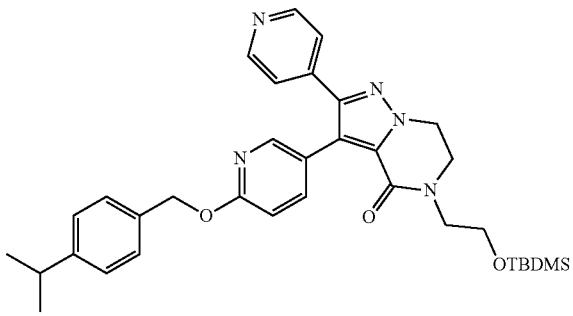 [SMILES: CC(C)c1ccc(COc2ccc(-c3c(-c4ccncc4)nn4c3C(=O)N(CCO[Si](C)(C)C(C)(C)C)CC4)cn2)cc1]

NaH 60% (48 mg, 1.2 mmol) was added slowly to a suspension of Co. 71 (0.35 g, 0.80 mmol) in dry DMF (4.7 mL) at r.t. under N₂. The mixture was stirred for 2 h then (2-bromoethoxy)-tert-butyldimethylsilane (0.20 mL, 0.96 mmol) was added and stirred overnight. Water was added and the mixture was concentrated under reduced pressure. The residue was taken in EtOAc and washed 5× with brine. The organic layer was dried on MgSO₄, filtrated and concentrated to give 0.45 g of Int. 388, yellow oil. This crude mixture was used like this in the next step.

b—Synthesis of Co. 212:

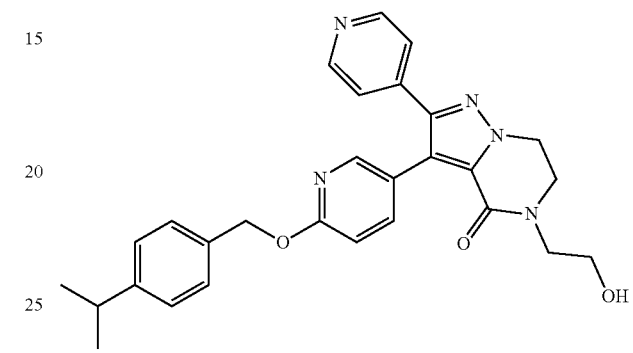

TBAF (0.9 mL, 0.9 mmol) was added dropwise to a sol. of 388 (0.45 g, 0.75 mmol) in THF (7.4 mL) at r.t. The mixture was stirred overnight at r.t. The mixture was concentrated and the residue was purified by prep. LC (Regular SiOH, 30 μm, 25 g GraceResolv™, mobile phase: DCM/MeOH/NH₄OH 96/4/0.1). The pure fractions were collected and solvent evaporated until dryness to give 350 mg of colorless oil which was triturated in Et₂O. The white solid formed was filtered, washed and dried to give 175 mg of Co. 212 as a white solid (48%). m.p.: polymorph 138° C., 161° C. (polymorph, dsc).

Example A210

Preparation of Co. 213

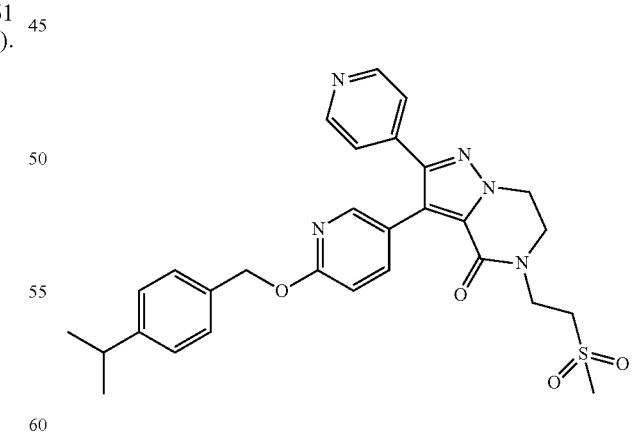

NaH 60% (48 mg, 1.2 mmol) was added slowly to a suspension of Co. 71 (0.35 g, 0.80 mmol) in dry DMF (4.7 mL) at r.t. under N₂. The mixture was stirred for 2 h then 2-bromoethyl-methylsulfone (164 mg, 0.88 mmol) was added and stirred overnight. Water was added and the mixture was concentrated under reduced pressure. The residue was taken in EtOAc and washed 5× with brine. The organic layer was dried on MgSO₄, filtrated and concentrated to give 0.30 g. The white solid obtained was triturated in Et₂O, filtrated and dried to give 296 mg of Co. 213 as a white powder (68%). m.p.: 200° C. (dsc).

Example A211

Preparation of Co. 214

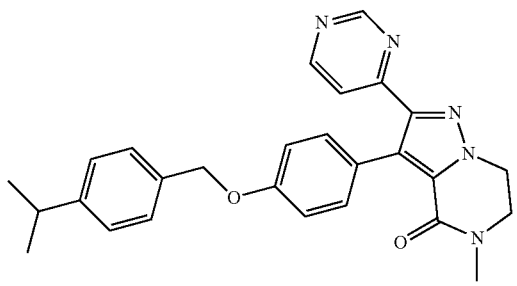 [SMILES: CC(C)c1ccc(COc2ccc(-c3c(-c4ccncn4)nn4c3C(=O)N(C)CC4)cc2)cc1]

NaH 60% (57 mg, 1.4 mmol) was added slowly to a suspension of Co. 158 (0.42 g, 0.96 mmol) in DMSO (5.2 mL) at r.t. under N₂. The mixture was stirred for 2 h, then, MeI (65 µL, 1 mmol) was added and stirred overnight. Water was added and the insoluble was filtered, dissolved in DCM and MeOH, dried on MgSO₄ and evaporated until dryness. The residue was purified by prep. LC (Regular SiOH, 30 µm, 25 g Interchim, mobile phase gradient: DCM/MeOH/NH₄OH from 98/2/0.1 to 96/4/0.1). The pure fractions were collected and solvent evaporated to give 372 mg of colorless oil which was crystallized from Et₂O, filtered and dried to give 283 mg of Co. 214 as a white solid (65%). m.p.: 160° C. (dsc).

Example A212

Preparation of Co. 215

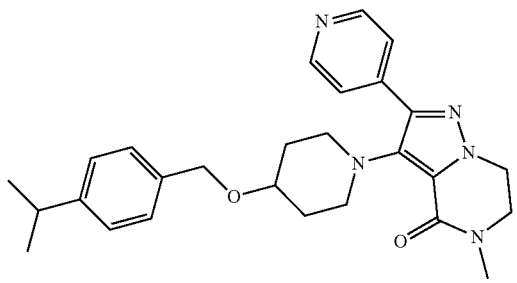 [SMILES: CC(C)c1ccc(COC2CCN(c3c(-c4ccncc4)nn4c3C(=O)N(C)CC4)CC2)cc1]

(SP-4-4)-[2-[2-(amino-κN)ethyl]phenyl-κC]chloro[dicyclohexyl[3,6-dimethoxy-2',4',6'-tris(1-methylethyl)[1,1'-biphenyl]-2-yl]phosphine-κP]-palladium (BrettPhos Palladacycle) (260 mg, 0.33 mmol) was added to a degassed suspension of 98 (500 mg, 1.6 mmol), 4-[(4-isopropylphenyl)methoxy]piperidine 362 (417 mg, 1.8 mmol), NaOtBu (469 mg, 4.9 mmol) in toluene (10 mL). The r.m. was heated at 90° C. for a weekend. Water and EtOAc were added, the mixture was filtered over a Celite® pad. The filtrate was extracted, the organic layer was separated, dried over MgSO₄, filtered and evaporated. The residue was purified by prep. LC (Irregular SiOH 20-45 µm 40 g MATREX, mobile phase: 70/29/1 toluene/iPrOH/NH₄OH). The fractions were collected and the solvent evaporated until dryness. The residue was again purified by prep. LC (irregular 15-40 µm 30 g Merck, Mobile phase: 99% DCM, 1% MeOH). The pure fractions were collected and evaporated. The residue was crystallized from Et₂O, the solid was filtered off and dried to give 40 mg of Co. 215 (5.3%). m.p.: 140° C. (dsc).

Example A213

Preparation of Co. 216 a—Synthesis of Int. 391:

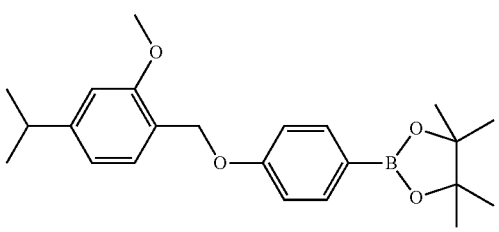 [SMILES: COc1cc(C(C)C)ccc1COc1ccc(B2OC(C)(C)C(C)(C)O2)cc1]

To a sol. of 2-methoxy-4-isopropyl-benzenemethanol (3.14 g, 17.4 mmol), 7 (3.8 g, 17.4 mmol), PPh₃ (5 g, 19.2 mmol) in dry DCM (120 mL) was added DBAD (4.4 g, 19.2 mmol) and the r.m. was stirred at r.t. for 15 h. The mixture was poured into water. The organic layer was extracted, dried over MgSO₄, filtered and evaporated until dryness. The residue was taken up in heptane, stirred for 1.5 h and filtered. The filtrate was purified by prep. LC (120 g of irregular SiOH 35-40 µm GraceResolv™, mobile phase gradient: from 100% heptane to 80% heptane 20% EtOAc). The pure fractions were collected and evaporated until dryness to give 2.26 g of Int. 391 (34%).

b—Synthesis of Co. 216:

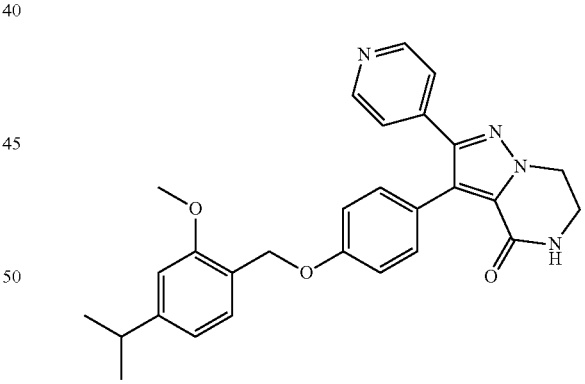

A mixture of 4 (0.5 g, 1.7 mmol), 391 (0.72 g, 1.9 mmol), K₃PO₄ (1.45 g, 6.8 mmol) in 1,4-dioxane (10 mL) and H₂O (2.7 mL) was purged with N₂ for 15 min. Then, PdCl₂(dppf) (0.14 g, 0.17 mmol) was added and purged again for 10 min. The mixture was heated to 80° C. for 15 h and cooled to r.t. The mixture was poured into water, and K₂CO₃ and EtOAc were added. The insoluble was filtered and the organic layer was extracted, dried over MgSO₄, filtered and evaporated to give 1 g. The residue was purified by prep. LC (40 g of irregular SiOH 35-40 µm GraceResolv™, mobile phase gradient from 100% DCM to 95% DCM 5% CH₃OH 0.1% NH₄OH). The pure fractions were collected and evaporated until dryness to give 510 mg which was crystallized from MeOH, filtered and dried to give 439 mg of Co. 216 (55%). m.p.: 200° C. (dsc).

Example A214

Preparation of Co 7 a—Synthesis of Int. 392:

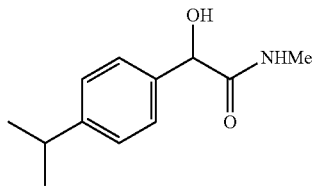

EDCI (1.2 g, 6.2 mmol) was added to a sol. of α-hydroxy-4-(1-methylethyl) benzene acetic acid (0.8 g, 4.1 mmol), HOBT (0.8 g, 6.2 mmol), DIPEA (1 mL, 6.2 mmol) methylamine (0.46 mL, 5.3 mmol) in DCM (25 mL). The mixture was stirred at r.t. for 8 h. Water and DCM were added, the mixture was extracted. The organic layer was separated, dried over MgSO$_4$, filtered and evaporated. The residue was purified by prep. LC (irregular SiOH 15-40 µm, 24 g, GraceResolv™, Mobile phase: 98/2 DCM/MeOH). The pure fractions were collected and evaporated until dryness to give yielding 500 mg of Int. 392 (59%).

b—Synthesis of Int. 393:

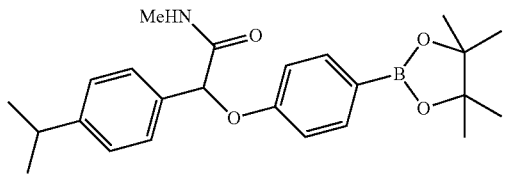 [SMILES: CNC(=O)C(Oc1ccc(B2OC(C)(C)C(C)(C)O2)cc1)c1ccc(C(C)C)cc1]

A sol. of 392 (500 mg, 2.40 mmol), 7 (690 mg, 3.12 mmol) and PPh$_3$ (759 mg, 2.89 mmol) in dry DCM (12 mL) was treated with DBAD (666 mg, 2.89 mmol) and stirred at r.t. for 19 h. Then, EtOAc and brine were added, and the organic layer was separated, dried over MgSO$_4$, filtered and evaporated in vacuo. The residue was purified by prep. LC (irregular SiOH 15-40 µm, 120 g, GraceResolv™, mobile phase gradient: from heptane 100% to heptane 70%, EtOAc 30%). The desired fractions were collected and solvent evaporated until dryness to give 320 mg of Int. 393 used as such for the next step.

c—Synthesis of Co. 217:

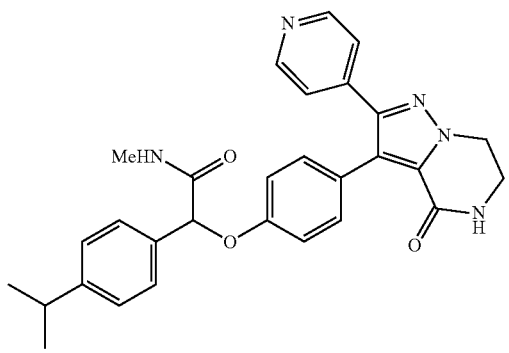 [SMILES: CNC(=O)C(Oc1ccc(-c2c(-c3ccncc3)nn3c2C(=O)NCC3)cc1)c1ccc(C(C)C)cc1]

A mixture of 4 (327 mg, 1.12 mmol), 393 (305 mg, 0.7 mmol) and K$_3$PO$_4$ (395 mg, 1.9 mmol) in 1,4-dioxane (3 mL) and H$_2$O (1.5 mL) was purged with N$_2$. PdCl$_2$(dppf) (71 mg, 86 mmol) was added. The mixture was purged with N$_2$ and stirred at 120° C. using one single mode microwave (Biotage Initiator EXP 60) with a power output ranging from 0 to 400 W for 20 min [fixed hold time]. Then a sol. of DCM/MeOH 95/5 and water were added. The organic layer was separated, washed (brine), separated, dried (MgSO$_4$), filtered and evaporated in vacuo. The residue was purified by prep. LC (Irregular SiOH 50 µm, 24 g Grace, mobile phase gradient: from DCM 100% to DCM 93%, MeOH 7%). The desired fractions were evaporated in vacuo to give 110 mg. The residue was crystallized from Et$_2$O and the precipitate was filtered off and dried to give 92 mg of Co. 217 (25%).

Example A215

Preparation of Co. 218 a—Synthesis of Int. 394:

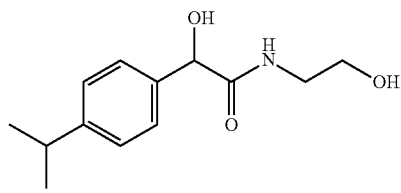 [SMILES: CC(C)c1ccc(C(O)C(=O)NCCO)cc1]

EDCI (1.2 g, 6.2 mmol) and HOBT (0.8 g, 6.2 mmol) were slowly added to a mixture of Hydroxy(4-isopropylphenyl)acetic acid (0.8 g, 4.1 mmol), DIPEA (1 mL, 6.2 mmol), ethanolamine (0.3 mL, 5.3 mmol) in DCM (25 mL). The mixture was stirred at r.t. for 24 h. Water and DCM were added. The mixture was extracted, the organic layer was separated, dried over MgSO$_4$, filtered and evaporated. The residue was purified by prep. LC (irregular SiOH 15-40 µm, 24 g, GraceResolv™, Mobile phase: 98/2 DCM/MeOH). The pure fractions were collected and evaporated until dryness to give 400 mg of Int. 394 (41%).

b—Synthesis of Int. 395:

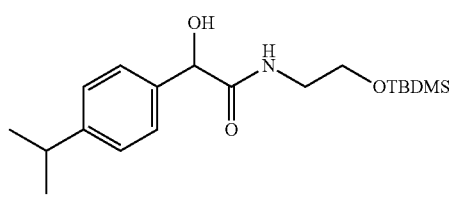 [SMILES: CC(C)c1ccc(C(O)C(=O)NCCO[Si](C)(C)C(C)(C)C)cc1]

Tert-butyldimethylsilyl chloride (0.28 g, 1.8 mmol) was added to a sol. 394 (400 mg, 1.7 mmol), imidazole (0.15 g, 2.2 mmol) in DCM (5 mL). The mixture was stirred at r.t. overnight. Water and DCM were added and the mixture was extracted. The organic layer was separated, dried over MgSO$_4$, filtered and evaporated. The residue was purified by prep. LC (irregular SiOH 15-40 µm, 24 g, GraceResolv™, Mobile phase: Heptane 70%, EtOAc 30%). The pure fractions were collected and evaporated until dryness to give 220 mg of Int. 395 (37%).

c—Synthesis of Int. 396:

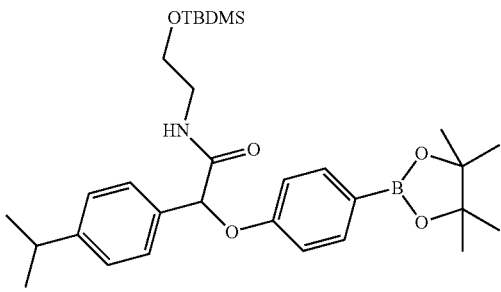 [SMILES: CC(C)c1ccc(C(Oc2ccc(B3OC(C)(C)C(C)(C)O3)cc2)C(=O)NCCO[Si](C)(C)C(C)(C)C)cc1]

A sol. of 395 (185 mg, 0.5 mmol), 7 (150 mg, 0.7 mmol) and PPh₃ (207 mg, 0.8 mmol) in dry THF (5 mL) was degassed under N₂ and, then, treated with DBAD (181 mg, 0.8 mmol) and stirred at r.t. for 19 h. DCM and brine were added, and the organic layer was separated, dried over MgSO₄, filtered and evaporated in vacuo. The residue was purified by prep. LC (irregular SiOH 15-40 nm, 12 g, GraceResolv™, mobile phase gradient: from heptane 100% to heptane 70%, EtOAc 30%). The desired fractions were collected and solvent evaporated until dryness to give 130 mg of Int. 396 (45%, purity 80%). The product was used as such for the next step.

d—Synthesis of Int. 397:

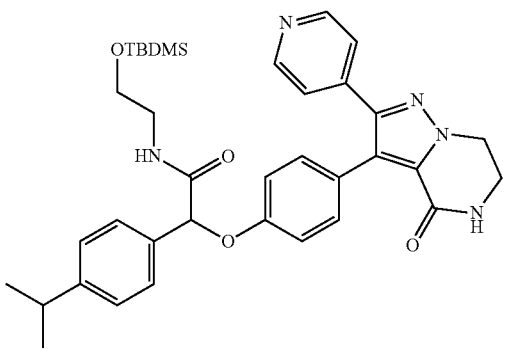 [SMILES: CC(C)c1ccc(C(Oc2ccc(-c3c(-c4ccncc4)nn4c3C(=O)NCC4)cc2)C(=O)NCCO[Si](C)(C)C(C)(C)C)cc1]

A mixture of 4 (103 mg, 0.3 mmol), 396 (130 mg, 0.23 mmol) and K₃PO₄ (124 mg, 0.6 mmol) in 1,4-dioxane (2 mL) and H₂O (0.6 mL) was purged with N₂. PdCl₂(dppf) (23 mg, 28 mmol) was then added. The mixture was purged again with N₂ and stirred at 110° C. overnight. Water and DCM were added and the mixture was extracted. The organic layer was separated, dried over MgSO₄, filtered and evaporated to give 81 mg. The residue was purified by prep. LC (Stationary phase: Spherical bare silica 5 μm 150×30.0 mm, Mobile phase gradient: from 70% Heptane, 2% MeOH (+10% NH₄OH), 28% EtOAc to 20% MeOH (+10% NH₄OH), 80% EtOAc). The pure fractions were collected and evaporated to give 21 mg of Int. 397 (14%).

e—Synthesis of Co. 218:

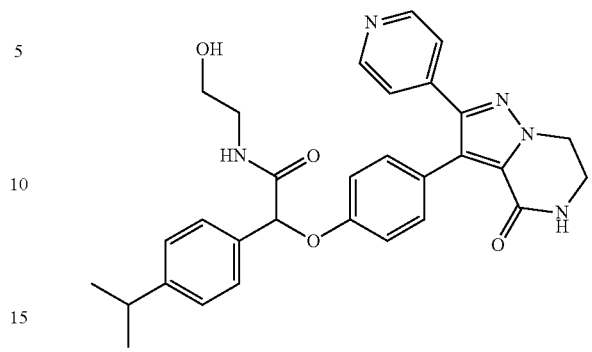

397 (21 mg, 0.033 mmol), TBAF (49 μl, 0.049 mmol) in THF (5 mL) was stirred at r.t. overnight. The mixture was evaporated till dryness and was purified by prep. LC (Stationary phase: Irregular SiOH 20-45 μm 24 g MATREX, Mobile phase: 95/5/0.1, DCM/MeOH/NH₄OH). The pure fractions were put together and evaporated till dryness to give 15 mg. The residue was purified by Reverse phase (Stationary phase: X-Bridge-C18 5 μm 30*150 mm, Mobile phase gradient: from 90% (NH₄HCO₃ 0.5% aq. sol.), 10% ACN to 100% ACN). The pure fractions were put together and evaporated till dryness. The residue was taken up in Et₂O and the precipitate was filtered off and dried to give 14 mg of Co. 218 (81%).

Example A216

Preparation of Co. 219a and Co. 219 a—Synthesis of Int. 398:

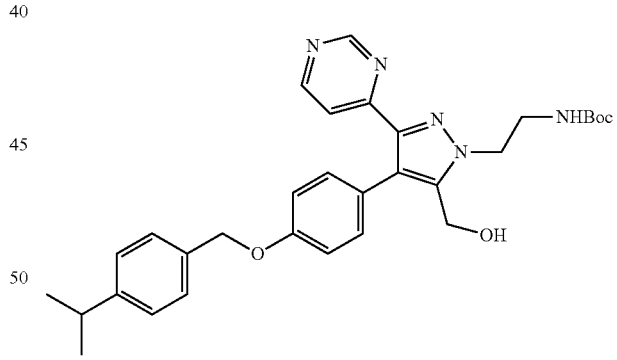

LAH bis(THF) in Toluene (15.9 mL, 15.9 mmol) was added to a stirred suspension of 320 (4.65 g, 7.94 mmol) in dry THF (70 mL) under N2 at −50° C. The r.m. was stirred at −50° C. for 20 min, and then quenched carefully with water (3 mL), a 3M sol. of NaOH (3 mL) and water (9 mL). EtOAc was added, and the crude mixture was filtered on glass frit, the cake was washed with EtOAc and the filtrate was evaporated in vacuo to afford 4.30 g of Int. 398, pale brown solid (100%).

b—Synthesis of Int. 399:

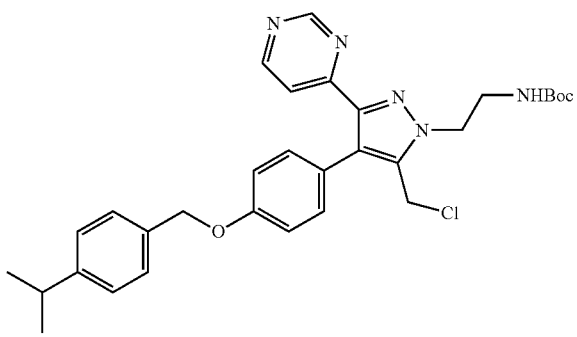 [SMILES: CC(C)c1ccc(COc2ccc(-c3c(-c4ccncn4)nn(CCNC(=O)OC(C)(C)C)c3CCl)cc2)cc1]

Et₃N (0.679 mL, 4.89 mmol) and methanesulfonyl chloride (0.354 mL, 4.58 mmol) were added to a stirred sol. of 398 (1.66 g, 3.05 mmol) in dry DCM (35 mL) at 0° C. The r.m. was stirred at r.t. for 18 h. Then, sat. sol. of NaHCO₃ and DCM were added, and the organic layer was washed with brine, separated, dried over MgSO₄, filtered and evaporated in vacuo to yield 1.76 g of Int. 399, brown solid (quant.).

c—Synthesis of Co. 219a

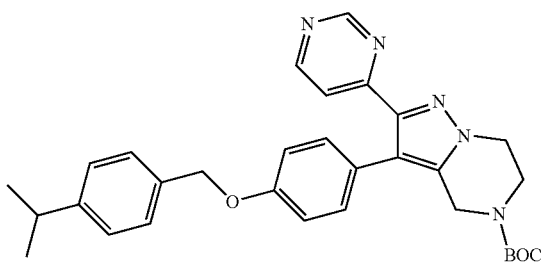 [SMILES: CC(C)c1ccc(COc2ccc(-c3c(-c4ccncn4)nn4c3CN(C(=O)OC(C)(C)C)CC4)cc2)cc1]

NaH 60% (250 mg, 6.26 mmol) was added to a stirred sol. of 399 (1.76 g, 3.13 mmol) in dry DMF (32 mL) at 0° C. under N₂. The r.m. was stirred at r.t. for 2 h. Then, water and EtOAc were added, and the organic layer was washed with brine, dried over MgSO₄, filtered and evaporated in vacuo to yield 1.59 g of Co. 219a, brown solid. The product was used as such for the next step.

d—Synthesis of Co. 219:

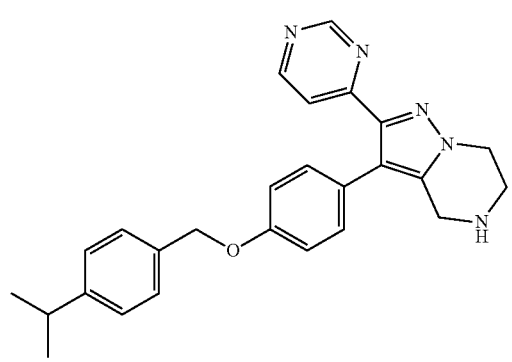 [SMILES: CC(C)c1ccc(COc2ccc(-c3c(-c4ccncn4)nn4c3CNCC4)cc2)cc1]

HCl 3N (4 mL) was added to a stirred sol. of Co. 219a (1.59 g, 2.57 mmol) in ACN (20 mL) at rt. The r.m. was stirred at 50° C. for 3 h. EtOAc and water were added, and the organic layer was washed with brine, dried over MgSO₄, filtered and evaporated in vacuo to yield 910 mg, brown solid. 310 mg of 910 mg were purified by prep. LC (Regular SiOH 50 µm, 12 g Grace, mobile phase: DCM 100% to DCM 88%, MeOH 12%). The fractions containing the desired Co. were evaporated in vacuo to yield 60 mg, sticky pale yellow solid. The solid was triturated in a mixture of pentane/Et₂O (1:1), and the solvents were removed to afford 48 mg of Co. 219 as a white solid. m.p.: 150° C. (DSC).

Example A217

Preparation of Co. 220

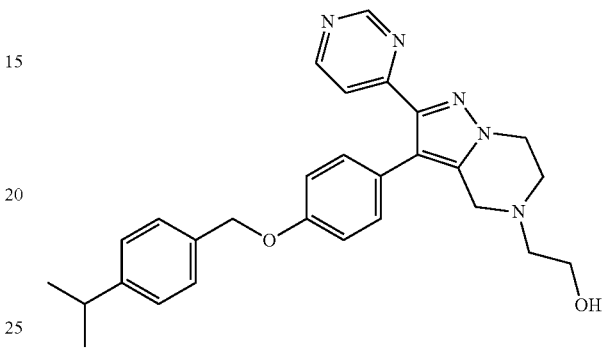

(2-bromoethoxy)-tert-butyldimethylsilane (0.214 mL, 0.987 mmol) was added to a stirred sol. of Co. 219 (280 mg, 0.658 mmol) and Et₃N (0.183 mL, 1.32 mmol) in DMF (4 mL) at r.t. The r.m. was stirred at 60° C. for 22 h. The crude material was dissolved in water and extracted with EtOAc. The organic phase was washed with brine, dried over MgSO₄, filtered and evaporated in vacuo to give 386 mg of an oil. The oil was dissolved in THF (4.5 mL), and TBAF (1.32 mL, 1.32 mmol) was added at r.t. The r.m. was stirred at r.t. for 16 h. The crude material was diluted in a mixture of DCM/MeOH (92/8) and water was added. The organic phase was separated, washed with brine (2×), dried (MgSO₄), filtered and evaporated in vacuo to give 260 mg of brown solid. The residue was purified by prep. LC (irregular SiOH 15-40 µm, 12 g Grace, Mobile phase gradient: from DCM 100% to DCM 92%, MeOH 8%). The desired fractions were combined and the solvent was removed in vacuo to give 18 mg of Co. 220 as a sticky solid (6%).

Example A218

Preparation of Co. 221 a—Synthesis of Int. 401:

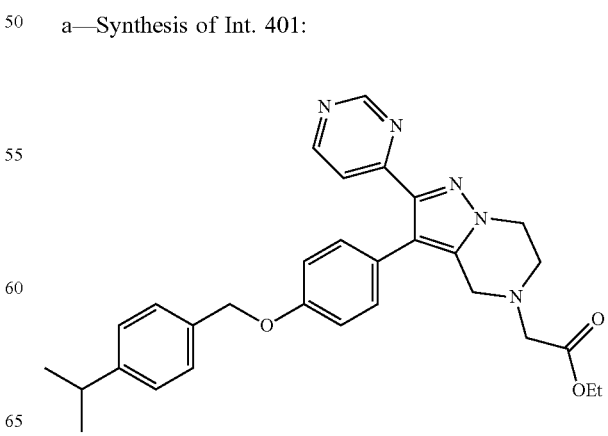

Ethylbromoacetate (0.117 mL, 1.06 mmol) was added to a sol. of Co. 219 (300 mg, 0.705 mmol) and K₂CO₃ (175 mg, 1.27 mmol) in DMF (4.5 mL) at r.t. The r.m. was then stirred at 55° C. for 4 h, then water and EtOAc were added. The organic layer was washed with brine, separated, dried over MgSO₄, filtered and concentrated in vacuo to afford 312 mg of Int. 401, red oil (74%, purity 85%). The product was used without further purification for the next step.

b—Synthesis of Co. 221:

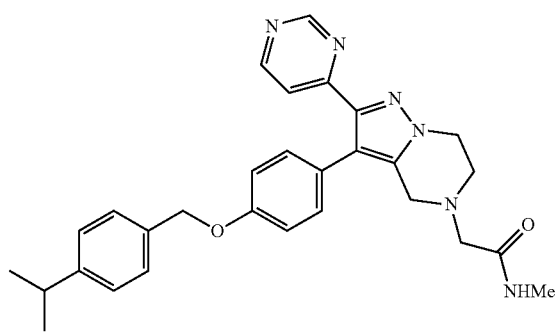 [SMILES: CNC(=O)CN1CCn2nc(-c3ccncn3)c(-c3ccc(OCc4ccc(C(C)C)cc4)cc3)c2C1]

Triazabicyclo[4.4.0]dec-5-ene (TBD) (51 mg, 0.357 mmol) and methylamine 2M in THF (0.668 mL, 1.34 mmol) were added to a stirred sol. of 401 (228 mg, 0.446 mmol) in dry toluene (8 mL) at r.t. The r.m. was stirred at 50° C. for 80 min, and then EtOAc and sat. NH₄Cl sol. were added. The organic layer was washed with brine, dried over MgSO₄, filtered and evaporated in vacuo to yield 198 mg of brown solid. The solid was purified by prep. LC (Regular SiOH 50 μm, 12 g Grace, liquid loading, mobile phase: DCM 100% to DCM 80%, MeOH 15%, aqueous NH₃ 5%). The desired fractions were evaporated in vacuo to yield 40 mg of sticky red solid. This solid was purified by achiral SFC (Stationary phase: Amino 6 μm 150×21.2 mm, Mobile phase: 80% CO₂, 20% MeOH (0.3% iPrNH₂)). The desired fractions were collected and evaporated in vacuo to yield 17 mg of Co. 221 as a viscous yellow solid (8%).

Example A219

Preparation of Co. 222 a—Synthesis of Int. 402:

A sol. of 4-methyl-7H-pyrrazolo[2,3-d]pyrimidine (3.11 g, 23.4 mmol) in DMF (40 mL) was cooled to 0° C. and treated with NaH 60% (1.40 g, 35.0 mmol). The r.m. was stirred at 0° C. for 2 h then 2-(trimethylsilyl)ethoxymethyl chloride (4.96 mL, 28.0 mmol) was added. The r.m. was stirred at r.t. for 2 h and diluted in EtOAc. The organic layer was washed with water and brine (twice), dried over MgSO₄ and evaporated in vacuo to give brown oil. The oil was purified by prep. LC (irregular SiOH 15-40 μm, 80 g, Grace, mobile phase gradient: from DCM 100% to DCM 96%, MeOH 4%). The desired fractions were collected and solvent evaporated until dryness to give 3.53 g. The residue was purified by prep. LC (irregular SiOH 15-40 μm, 80 g, Grace, mobile phase gradient: from DCM 100% to DCM 96%, MeOH 4%). The pure fractions were collected and solvent evaporated until dryness to give 1.56 g of Int. 402 as a brown oil (25%).

b—Synthesis of Int. 403:

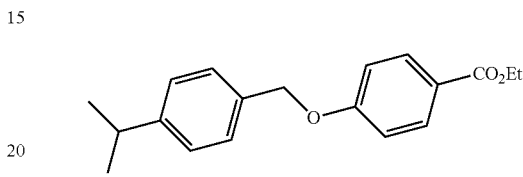

A sol. of ethyl-4-hydroxybenzoate (10 g, 60.2 mmol) in ACN (150 mL) and DMF (10 mL) was treated with K₂CO₃ (10.0 g, 72.2 mmol) and 8 (13.5 g, 63.2 mmol). The r.m. was stirred at 50° C. for 17 h. After concentration, the sol. was poured in EtOAc, washed with water (50 mL), brine (4×50 mL) and water (50 mL). The organic layer was dried over MgSO₄ and evaporated to give yellow oil. The oil was triturated in cold pentane to obtain a solid. After filtration on a glass frit, the solid was washed with cold pentane, collected and dried in vacuo to give 16.2 g of Int. 403 as a white solid (90%).

c—Synthesis of Int. 404:

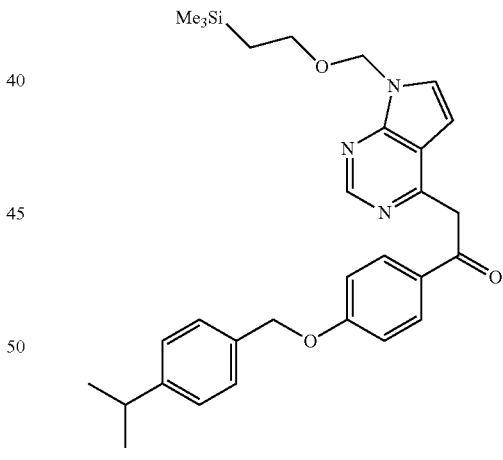

In a dry flask and under N₂ atmosphere, a sol. of 402 (1.56 g, 5.92 mmol) and 403 (1.77 g, 5.92 mmol) in dry THF (15 mL) was cooled to 0° C. and treated with LiHMDS (11.8 mL, 11.8 mmol) over 10 min. The r.m. was allowed to warm to r.t. and stirred for 17 h at this temperature. The r.m. was then poured in a 10% aq. sol. of NH₄Cl. The mixture was extracted with DCM, dried on MgSO₄ and concentrated in vacuo to give a beige solid. The solid was triturated in pentane, filtered and dried in vacuo to give 1.96 g of Int. 404 as a yellow solid (64%).

d—Synthesis of Int. 405:

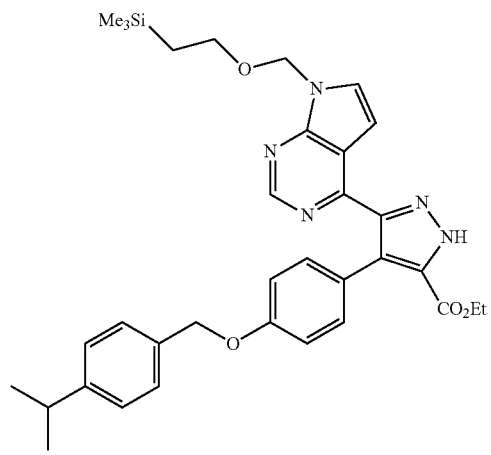 [SMILES: CCOC(=O)c1[nH]nc(-c2ncnc3c2ccn3COCC[Si](C)(C)C)c1-c1ccc(OCc2ccc(C(C)C)cc2)cc1]

A sol. of 404 (1.55 g, 3.01 mmol) and etyl diazoacetate (0.506 mL, 4.81 mmol) in ACN (25 mL) was treated with DBU (0.764 mL, 5.11 mmol) and stirred at r.t. for 17 h. The r.m. was diluted in EtOAc and a sat. sol. of NaHCO₃. The organic layer was separated, washed with brine, dried over MgSO₄ and evaporated in vacuo to give a brown residue. The residue was purified by prep. LC (irregular SiOH 15 µm, 80 g8, Interchim, mobile phase gradient: from DCM 100% to DCM 95%, MeOH 5%). The pure fractions were collected and solvent evaporated until dryness to give 1.13 g of Int. 405 as a reddish oil (61%).

e—Synthesis of Int. 406:

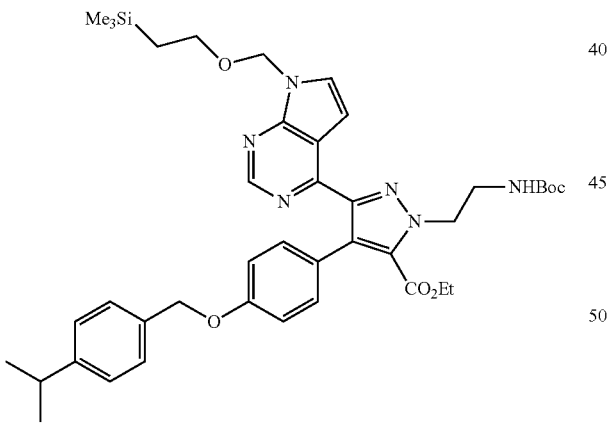

A mixture of 405 (1.13 g, 1.85 mmol), tert-butyl-N-(2-hydroxyethyl)carbamate (447 mg, 2.77 mmol) and PPh₃ supp. (0.866 mg, 2.77 mmol) in dry THF (40 mL) was treated with DBAD (638 mg, 2.77 mmol) and stirred at r.t. for 24 h. The r.m. was filtered through Celite® and the filtrate was evaporated in vacuo to give a red residue. The residue was purified by prep. LC (spheric SiOH 50 µm, 80 g, Grace, mobile phase gradient: from DCM 100% to DCM 95%, MeOH 5%). The pure fractions were collected and solvent evaporated until dryness to give 1.61 g of Int. 406 as a reddish oil (Quant.).

f—Synthesis of Int. 407:

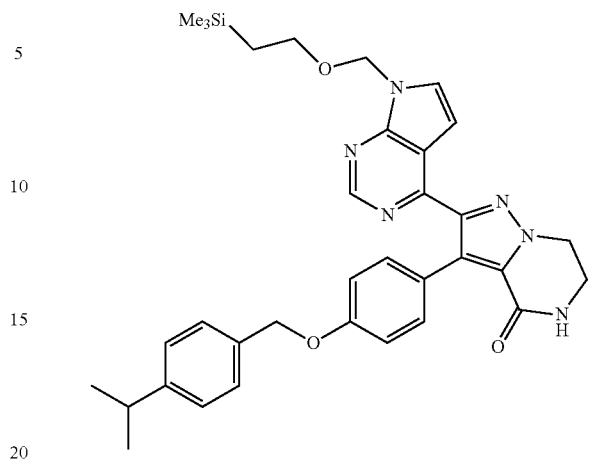

A sol. of 406 (1.61 g, 2.13 mmol) in ACN (35 mL) was treated with HCl 3N (3.55 mL, 10.7 mmol) and stirred at 90° C. for 4 h. The r.m. was diluted with DCM and washed with a sat. sol. of NaHCO₃. The organic layer was dried over MgSO₄ and evaporated in vacuo to give a yellow oil. The oil was dissolved in MeOH (40 mL), treated with Cs₂CO₃ (2.08 g, 6.40 mmol) and stirred at r.t. for 1 h. The r.m. was concentrated in vacuo and diluted with DCM. The organic layer was washed with water and directly evaporated in vacuo. The precipitate was washed with water and with Et₂O, collected and dried in vacuo to give 700 mg of Int. 407 as a grey solid (54%).

g—Synthesis of Co. 222:

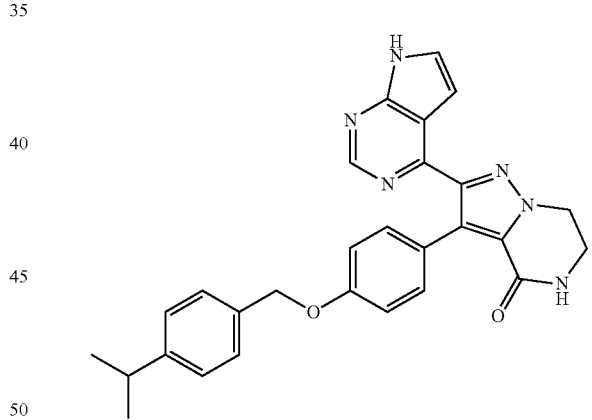

A sol. of 406 (300 mg, 493 µmol) in DCM (7.5 mL) was cooled to 0° C. and treated with boron trifluoride diethyl etherate (243 µL, 1.97 mmol). The r.m. was stirred at 0° C. for 2 h then at r.t. for 2 h. An extra amount of boron trifluoride diethyl etherate (122 µL, 0.986 mmol) was added to the mixture which was stirred at r.t. for one extra h. The r.m. was quenched with a sat. sol. of NaHCO₃ and DCM was evaporated in vacuo. MeOH was added and the mixture was stirred at r.t. for 24 h. The r.m. was diluted with water and extracted twice with DCM. The organic layers were combined, dried over MgSO₄ and evaporated in vacuo to give a white residue. The residue was purified by prep. LC (irregular SiOH 15-40 µm, 40 g, Merck, dry loading, mobile phase gradient: from DCM 100%, to DCM 90° C., MeOH 10%). The desired fractions were collected and solvent evaporated until dryness to give 141 mg, white solid. The solid was dissolved in THF (10 mL) and NaOH 1N (1 mL). The r.m. was stirred at r.t. for 17 h and diluted in water. The mixture was extracted twice with DCM/MeOH (95:5). The organic layers were combined, dried over MgSO$_4$ and evaporated in vacuo to give 75 mg of white solid. The solid was purified by prep. LC (irregular SiOH 15-40 µm, 12 g8, Grace, dry loading, mobile phase gradient: from DCM 100%, to DCM 90° C., MeOH 10%). The pure fractions were collected and solvent evaporated until dryness to give 64 mg of Co. 222, white solid (27%). m.p.: 238° C. (DSC).

Example A220

Preparation of Co. 223 a—Synthesis of Int. 408:

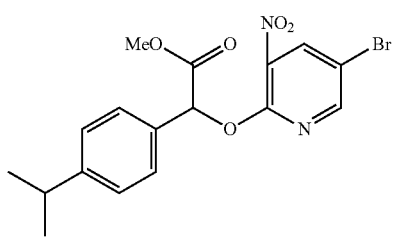 [SMILES: COC(=O)C(Oc1ncc(Br)cc1[N+](=O)[O-])c1ccc(C(C)C)cc1]

NaH 60% (0.272 g, 7.92 mmol) was added to a stirred sol. of methyl 2-hydroxy-2-[4-(propan-2-yl)phenyl]acetate (1.5 g, 7.2 mmol) in THF (75 mL) at 0° C. The mixture was stirred for 5 min and then 5-bromo-2-chloro-3-nitropyridine (1.71 g, 7.2 mmol) was added portionwise. The mixture was stirred at r.t. for 16 h. The mixture was treated with water and extracted with EtOAc. The organic layer was separated, dried (MgSO$_4$), filtered and the solvents were evaporated in vacuo to give 3 g which was crystallized from DIPE. The precipitate was filtered off and dried in vacuo to yield 1.29 g of Int. 408 (44%).

b—Synthesis of Int. 409:

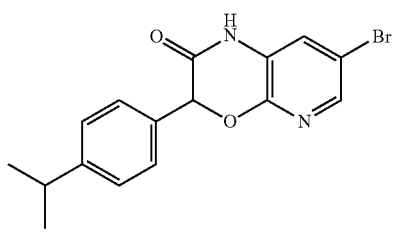 [SMILES: CC(C)c1ccc(C2Oc3ncc(Br)cc3NC2=O)cc1]

Fe (0.7 g, 12.56 mmol) was added to a stirred sol. of 408 (1.285 g, 3.14 mmol) in Acetic Acid (15 mL) in a sealed tube and under N$_2$. The mixture was stirred at 60° C. for 8 h. The mixture was diluted with EtOAc and filtered through a Celite® pad. The filtrate was concentrated, diluted with EtOAc and washed with sat NaHCO$_3$. The organic layer was separated, dried (MgSO4), filtered and the solvents evaporated in vacuo to yield 0.6 g of Int. 409 (55%).

c—Synthesis of Int. 410:

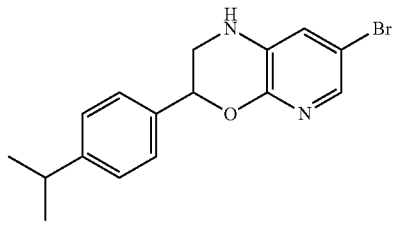 [SMILES: CC(C)c1ccc(C2CNc3cc(Br)cnc3O2)cc1]

LAH in 1M THF (4.9 mL, 4.896 mmol) was added to a sol. of 409 (0.85 g, 2.45 mmol) in THF (40 mL) at −78° C. under N$_2$. The reaction was stirred at −78° C. for 5 min and, then, was allowed to warm to r.t. slowly and stirred at r.t. for 4 h. EtOAc followed by Water were added dropwise to the mixture at −5° C. The suspension was filtered through a pad of Celite®. The organic layer was separated, dried over MgSO$_4$, filtered and the solvent was evaporated to give 0.4 g. The residue was purified by prep. LC (Irregular SiOH 15-40 µm 25 g Merck, mobile phase from: 100% DCM to 98% DCM 2% MeOH). The pure fractions were collected and the solvent was evaporated to give 0.19 g of Int. 410 (23%). The product was used as such for the next step.

d—Synthesis of Int. 411:

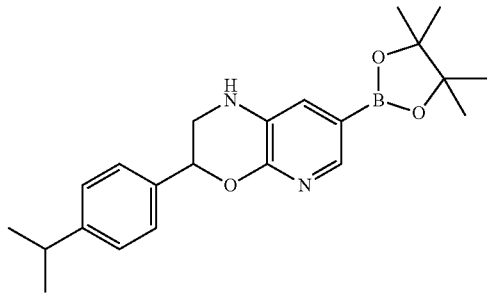 [SMILES: CC(C)c1ccc(C2CNc3cc(B4OC(C)(C)C(C)(C)O4)cnc3O2)cc1]

A mixture of 410 (0.16 g, 0.48 mmol), BisPin (0.183 g, 0.72 mmol) and KOAc (0.141 g, 1.44 mmol) in DME (3.6 mL) was carefully purged with N$_2$. PdCl$_2$(dppf) (31 mg, 0.038 mmol) was added and the r.m. was purged again with N$_2$. The r.m. was stirred at 100° C. for 4 h. The crude mixture was diluted with EtOAc and filtered over Celite®. The filtrate was washed with water and brine, and the organic layer was separated, dried over MgSO$_4$, filtered and evaporated in vacuo to yield 0.27 g of Int. 411 used in the next step without purification.

e—Synthesis of Co. 223:

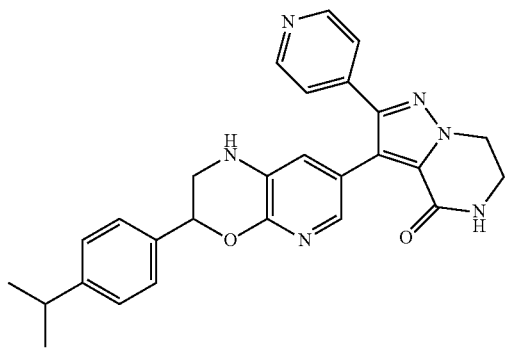 [SMILES: CC(C)c1ccc(C2CNc3cc(-c4c(-c5ccncc5)nn5c4C(=O)NCC5)cnc3O2)cc1]

A mixture of 411 (0.27 g, 0.71 mmol), 4 (0.138 g, 0.473 mmol) and K₃PO₄ (0251 g, 1.183 mmol) in 1,4-dioxane (2.75 mL) and H₂O (1.375 mL) was purged with N₂. PdCl₂(dppf) (31 mg, 37 μmol) was then added. The mixture was purged again with N₂ and stirred at 120° C. using one single mode microwave (Biotage Initiator EXP 60) with a power output ranging from 0 to 400 W for 20 min [fixed hold time]. The crude mixture was diluted with a sol. of DCM and water. The organic layer was separated, washed with brine, separated, dried over MgSO₄, filtered and evaporated in vacuo to yield 570 mg. The residue was purified by prep. LC (Irregular SiOH 15-40 μm 30 g Merck, mobile phase gradient: from 100% DCM to 98% DCM, 2% MeOH). The pure fractions were collected and the solvent was evaporated until dryness. The residue was crystallized from DIPE. The precipitate was filtered off and dried to give 15 mg of Co. 223 (7%).

Example A221

Preparation of Co. 224. Co. 225 and Co. 226 a—Synthesis of Int. 412:

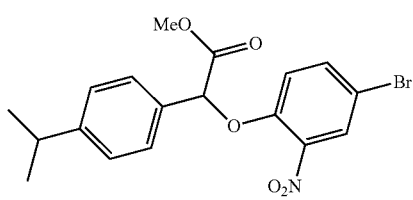 [SMILES: COC(=O)C(Oc1ccc(Br)cc1[N+](=O)[O-])c1ccc(C(C)C)cc1]

A sol. of methyl 2-hydroxy-2-[4-(propan-2-yl)phenyl] acetate (3.00 g, 14.4 mmol), 4-bromo-2-nitrophenol (4.08 g, 18.7 mmol) and PPh₃ (4.53 g, 17.3 mmol) in dry THF (77 mL) was treated with DBAD (3.98 g, 17.3 mmol) and stirred at r.t. for 18 h. Then, EtOAc and water were added. The organic layer was washed with brine, a 10% sol. of K₂CO₃ and brine, and then separated, dried (MgSO₄), filtered and evaporated in vacuo to yield 16.3 g of orange oil which was filtered over silica, eluting with a sol. of Heptane/EtOAc (70/30). The filtrate was evaporated in vacuo to yield 9.02 g of a yellow solid. The residue was purified by prep. LC (irregular SiOH 15-40 μm, 330 g, GraceResolv™, mobile phase gradient: heptane/EtOAc from 100/0 to 50/50). The pure fractions were collected and solvent evaporated to give 5.30 g of Int. 412 as pale yellow oil (85%).

b—Synthesis of Int. 413:

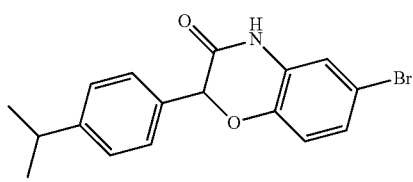 [SMILES: CC(C)c1ccc(C2Oc3ccc(Br)cc3NC2=O)cc1]

Fe (1.91 g, 34.2 mmol) was added to a stirred sol. of 412 (720 mg, 1.71 mmol) in acetic acid (15 mL) at r.t. The r.m. was stirred at 50° C. for 20 h. The crude mixture was diluted with EtOAc and filtered through Celite®. Water was added to the filtrate, and the organic layer was then treated with sat. NaHCO₃, washed with water, dried over MgSO₄, filtered and evaporated in vacuo to yield 520 mg of Int. 4, white solid (88%).

c—Synthesis of Int. 414:

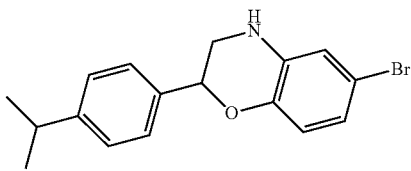 [SMILES: CC(C)c1ccc(C2CNc3cc(Br)ccc3O2)cc1]

LAH (658 mg, 17.3 mmol) was added to a stirred sol. of 413 (1.50 g, 4.33 mmol) in dry THF (40 mL) at r.t. under N₂. The r.m. was stirred at 50° C. for 2 h. The sol. was quenched with addition of water (660 μL, very slow addition), a 3N sol. of NaOH (660 μL) and water (1.98 mL). The crude mixture was filtered on glass frit, the cake was washed with EtOAc and the filtrate was evaporated in vacuo to afford 1.36 g of Int. 414 as pale brown solid (94%).

d—Synthesis of Int. 415:

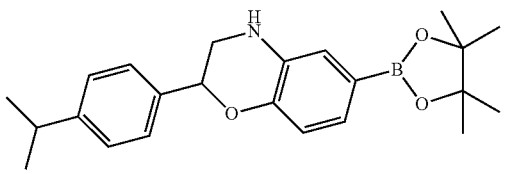 [SMILES: CC(C)c1ccc(C2CNc3cc(B4OC(C)(C)C(C)(C)O4)ccc3O2)cc1]

A mixture of 414 (1.68 g, 5.06 mmol), BisPin (1.93 g, 7.) and KOAc (1.49 g, 15.2 mmol) in DME (38 mL) was carefully purged with N₂. PdCl₂(dppf) (331 mg, 0.405 mmol) was added and the r.m. was purged again with N₂. The r.m. was stirred at 100° C. for 4 h. The crude mixture was diluted with EtOAc and filtered over Celite®. The filtrate was washed with water and brine, and the organic layer was separated, dried over MgSO₄, filtered and evaporated in vacuo to yield 3.34 g of black solid. The residue was purified by prep. LC (Irregular SiOH 50 μm, 120 g Grace, mobile phase gradient: from Heptane 100% to Heptane 65%, EtOAc 35%). The desired fractions were evaporated in vacuo to give 1.52 g of Int. 415, pale yellow solid (79%).

e—Synthesis of Co. 224, Co. 225 and Co. 226

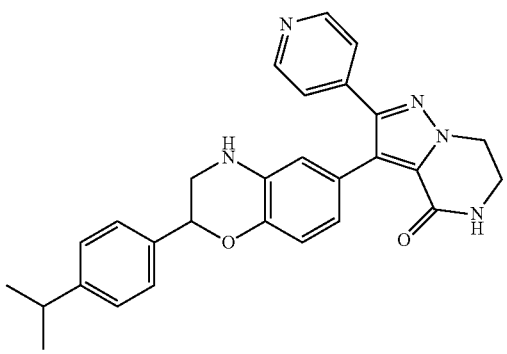 [SMILES: CC(C)c1ccc(C2CNc3cc(-c4c(-c5ccncc5)nn5c4C(=O)NCC5)ccc3O2)cc1]

Compound 224 (S or R)
Compound 225 (R or S)
Compound 226 (racemic mixture)

A mixture of 4 (0.2 g, 0.688 mmol), 415 (0.47 g, 1.239 mmol) and K₃PO₄ (0.365 g, 1.721 mmol) in 1,4-dioxane (4 mL) and H₂O (2 L) was purged with N₂. PdCl₂(dppf) (45 mg, 55 μmol) was then added. The mixture was purged again with N₂ and stirred at 120° C. using one single mode microwave (Biotage Initiator EXP 60) with a power output ranging from 0 to 400 W for 20 min [fixed hold time]. The crude mixture was diluted with a sol. of DCM and water. The organic layer was separated, washed with brine, separated, dried over MgSO₄, filtered and evaporated in vacuo to yield 0.96 g which was combined with another batch resulting of 50 mg of 4). The residue was purified by prep. LC (Stationary phase: Spherical bare silica 5 μm 150×30.0 mm, Mobile phase Gradient: from NH₄OH/DCM/MeOH 0.2/98/2 to 1.3/87/13. The pure fractions were collected and the solvent was evaporated to give 0.088 g of Co. 226 (22%) which was combined with another batch of Co. 226 (0.08 g) for enantiomeric separation. Co. 226 was purified by chiral SFC (Stationary phase: Chiralcel OJ-H 5 μm 250×20 mm, Mobile phase: 70% CO₂, 30% EtOH). The pure fractions were collected and the solvent was evaporated until dryness. The 1ˢᵗ residue (0.078 g) was crystallized from DIPE. The precipitate was filtered off and dried to give 0.068 g of Co. 224 (S or R; 8%). The 2ⁿᵈ residue (0.085 g) was crystallized from DIPE. The precipitate was filtered off and dried to give 0.068 g of Co. 225 (R or S; 8%). Co. 224: [α]_d: −28.35° (589 nm, c 0.254 w/v %, DMF, 20° C.); Co. 225: [α]_d: +27.23° (589 nm, c 0.235 w/v %, DMF, 20° C.).

Example A222

Preparation of Co. 227 a—Synthesis of Int. 416:

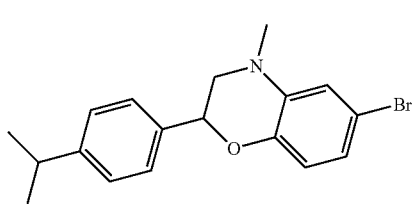 [SMILES: CC(C)c1ccc(C2CN(C)c3cc(Br)ccc3O2)cc1]

A mixture of 414 (0.38 g, 1.14 mmol), Iodomethane (0.752 mL, 1.72 mmol) and K₂CO₃ (0.474 g, 3.43 mmol) in DMF (10 mL) was heated at 80° C. overnight. The r.m. was cooled to r.t., poured into ice water and extracted with DCM. The organic layer was washed with brine, separated, dried over MgSO₄, filtered and the solvent was evaporated until dryness to give 0.45 g of Int. 416 which was used in the next step without purification.

b—Synthesis of Co. 227:

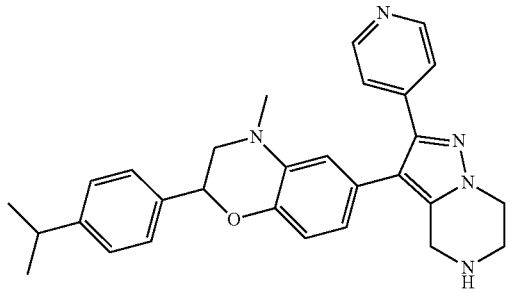 [SMILES: CC(C)c1ccc(C2CN(C)c3cc(-c4c(-c5ccncc5)nn5c4CNCC5)ccc3O2)cc1]

In a microwave vial, a mixture of 60 (0.35 g, 0.514 mmol), 416 (0.148 g, 0.429 mmol), K₃PO₄ (0.364 g, 1.715 mmol) in 1,4-dioxane (3.5 mL) and H₂O (1.05 mL) was carefully purged with N₂. PdCl₂(dppf) (35 mg, 0.043 mmol) was added and the r.m. was purged again with N₂. The r.m. was heated at 80° C. overnight. The r.m. was diluted with EtOAc, filtered off on a pad of Celite® and washed with EtOAc. The organic layer was washed with water (once) and with brine (3×). The organic phase was dried over MgSO₄, filtered and evaporated in vacuo to give 0.4 g. The residue was put together with another batch (0.1 g of reactant 60 in the same conditions) and purified by prep. LC (Irregular SiOH 15-40 μm, 40 g Merck, mobile phase gradient: from 100% DCM to 98% DCM, 2% MeOH, 0.1% NH₄Cl. The desired fractions were collected and the solvent was evaporated until dryness to give 0.09 g. The residue was purified by prep. LC (Stationary phase: Spherical bare silica 5 μm 150×30.0 mm, Mobile phase Gradient: from NH₄OH/DCM/MeOH 0.2/98/2 to NH₄OH/DCM/MeOH 0.8/92/8). The pure fractions were collected and the solvent was evaporated. The residue (0.04 g) was crystallized from DIPE. The precipitate was filtered off and dried to give 0.023 g of Co. 227 (global yield: 9%). m.p.: 291° C. (DSC).

Example A223

Preparation of Co. 228

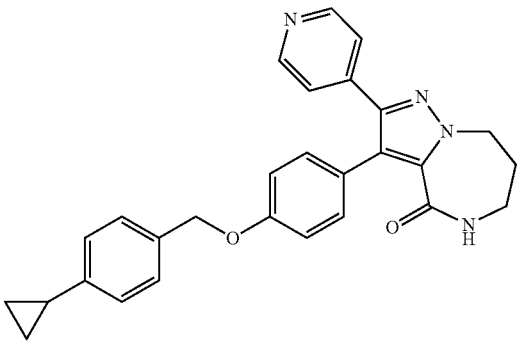 [SMILES: O=C1NCCCn2nc(-c3ccncc3)c(-c3ccc(OCc4ccc(C5CC5)cc4)cc3)c21]

Prepared by using an analogous reaction protocol as described for Co. 197 starting from Int. 36 using 3-(boc-amino)-1-propanol. Yield: 91%; m.p.: 235° C. (DSC).

Example A224

Preparation of Co. 229

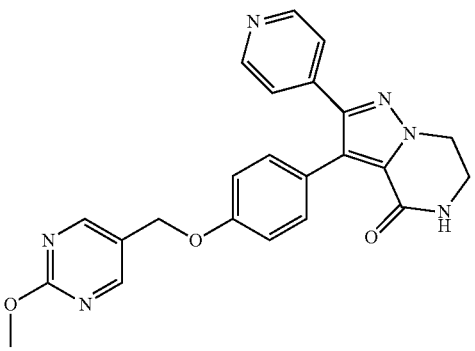 [SMILES: COc1ncc(COc2ccc(-c3c(-c4ccncc4)nn4c3C(=O)NCC4)cc2)cn1]

Prepared by using an analogous reaction protocol as described for Co. 3 starting from Int. 4 using

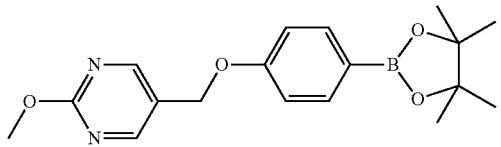

(prepared by using an analogous reaction protocol as described for Int. 32 starting from Int. 7 using 2-methoxy-5-pyrimidinemethanol). Yield: 53%; m.p.: 248° C. (DSC).

Example A225

Preparation of Co. 230

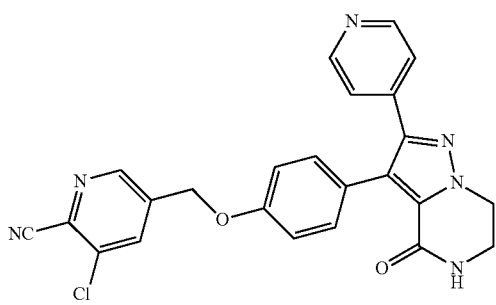 [SMILES: N#Cc1ncc(COc2ccc(-c3c(-c4ccncc4)nn4c3C(=O)NCC4)cc2)cc1Cl]

Prepared by using an analogous reaction protocol as described for Co. 3 starting from Int. 4 using

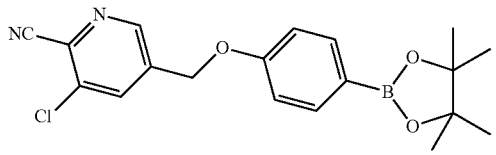 [SMILES: CC1(C)OB(c2ccc(OCc3cnc(C#N)c(Cl)c3)cc2)OC1(C)C]

(prepared by using an analogous reaction protocol as described for Int. 30 starting from Int. 7 using 3-chloro-5-(hydroxymethyl)-2-pyridinecarbonitrile). Yield: 18%; m.p.: 277° C. (DSC).

Example A226

Preparation of Co. 231

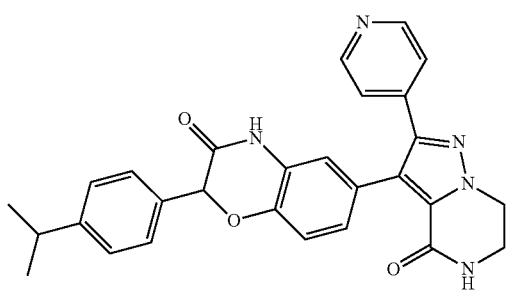 [SMILES: CC(C)c1ccc(C2Oc3ccc(-c4c(-c5ccncc5)nn5c4C(=O)NCC5)cc3NC2=O)cc1]

Prepared by using an analogous reaction protocol as described for Co. 226 starting from Int. 4 using

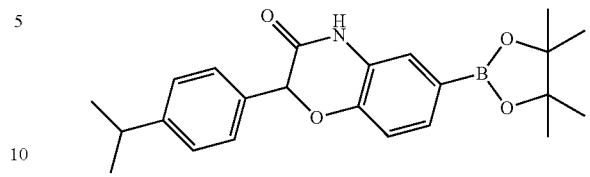

(prepared by using an analogous reaction protocol as described for Int. 415 starting from Int. 413). Yield: 53%; m.p.: 291° C. (DSC).

Example A227

Preparation of Co. 232

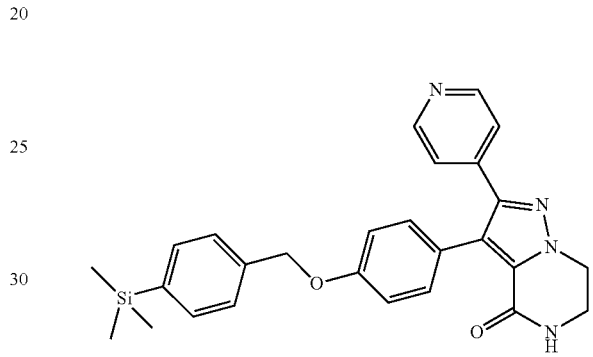

Prepared by using an analogous reaction protocol as described for Co. 6 starting from Int. 4 using

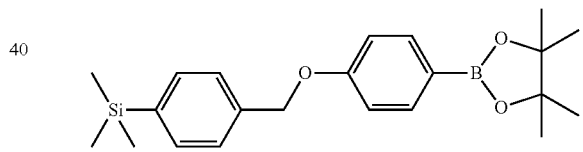

(prepared by using an analogous reaction protocol as described for Int. 32 starting from Int. 7 using 4-(trimethylsilyl)-benzenemethanol). Yield: 62%.

Example A228

Preparation of Co. 233 a—Synthesis of Int. 417:

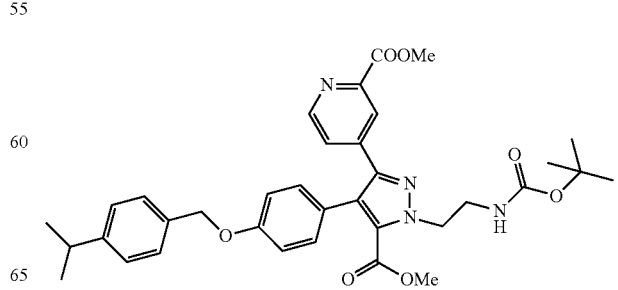

A mixture of 17 (300 mg, 0.511 mmol), methyl 4-(4,4,5,5-tetramethyl-1,3,2-dioxaborolan-2-yl)picolinate (202 mg, 0.767 mmol) and K₃PO₄ (434 mg, 2.05 mmol) in DME (10 mL) in a sealed tube was purged with N₂. Pd₂dba₃ (23.4 mg, 25.6 µmol) and PtBu₃.BF₄ (Tri-tert-butylphosphonium tetrafluoroborate) (14.8 mg, 51.2 µmol) were added, the mixture was purged again with N₂ and heated at 120° C. using one single mode microwave (Biotage Initiator EXP 60) with a power output ranging from 0 to 400 W for 45 min [fixed hold time]. The crude mixture was quenched with water and extracted with DCM. The organic layer was separated, dried over MgSO₄, filtered off and evaporated in vacuo to give a yellow oil. The residue (368 mg) was purified by prep. LC (Irregular SiOH 15-40 µm, 24 g Grace, DCM deposit, mobile phase: heptane 50%, EtOAc 50%). The pure fractions were collected and solvent evaporated to give 210 mg of Int. 417 as a white residue (60%).

b—Synthesis of Int. 418:

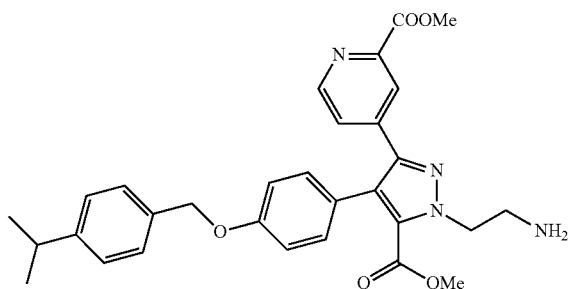 [SMILES: COC(=O)c1cc(-c2nn(CCN)c(C(=O)OC)c2-c2ccc(OCc3ccc(C(C)C)cc3)cc2)ccn1]

To a sol. of 417 (210 mg, 0.327 mmol) in ACN (2.50 mL) was added an aq. sol. of HCl 3N (545 µL, 1.63 mmol) and the sol. was heated at 60° C. for 1 h. After cooling down to r.t., a mixture of DCM and a sat. aq. sol. of NaHCO₃ was added. The organic layer was separated, dried over MgSO₄, filtered off and evaporated in vacuo to give 154 mg of Int. 418 as a white solid (87%).

c—Synthesis of Int. 419 and Int. 420

Int. 419

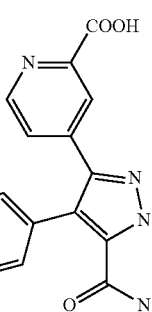

Int. 420

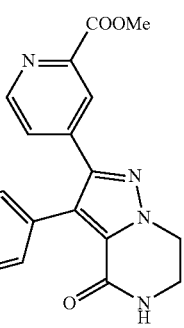

To a sol. of 418 (154 mg, 0.284 mmol) in MeOH (3 mL) was added Cs₂CO₃ (462 mg, 1.42 mmol) and the mixture was stirred at r.t. for 2 h. The solvent was removed in vacuo. The residue was taken up with water and DCM. The organic layer was separated, dried over MgSO₄, filtered off and evaporated in vacuo to give 33 mg of a first batch of Int. 420 as white solid (23%). The aq. layer was extracted again with a mixture of DCM/MeOH 90/10. The organic layer was dried over MgSO₄, filtered off and evaporated in vacuo to give 8 mg of a second batch of Int. 420 as white solid (6%). The aq. layer was acidified with a 1N aq. sol. of HCl until pH 6-7 and extracted again with DCM. The organic layer was dried over MgSO₄, filtered off and evaporated in vacuo to give 87 mg of Int. 419 as pale yellow solid (64%).

d—Synthesis of Co. 233:

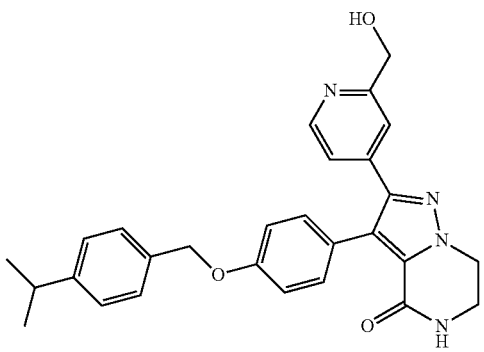 [SMILES: CC(C)c1ccc(COc2ccc(-c3c(-c4ccnc(CO)c4)nn4c3C(=O)NCC4)cc2)cc1]

A sol. of Int. 420 (33 mg, 66.5 µmol) in THF (2 mL) and MeOH (0.4 mL) was treated with NaBH₄ (15 mg, 399 µmol) and stirred at 60° C. for 17 h. The r.m. was poured in DCM and water. The organic layer was separated. The aq. layer was extracted twice with DCM/MeOH (95/5). The organic layers were combined, dried over MgSO₄ and evaporated in vacuo to give 27 mg of Co. 233 as a white solid (87%). M.p.: 232° C. (DSC).

Example A229

Preparation of Co. 234 a—Synthesis of Int. 421:

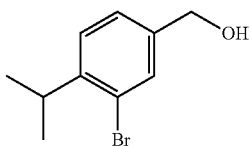

LiAlH₄ (5.52 g, 145 mmol) was added to a stirred sol. of methyl-3-bromo-4-isopropylbenzoate (34.0 g; 132 mmol) in THF (600 mL) at −20° C. The r.m. was stirred at −20° C. for 2 h. Then, the r.m. was quenched with 5.26 mL of H₂O, 5.52 mL of NaOH 3N and 16 mL of H₂O. The mixture was filtered and washed with DCM. The filtrate was evaporated in vacuo to give 20.0 g of Int. 421 as a yellow oil (66%).

b—Synthesis of Int. 422:

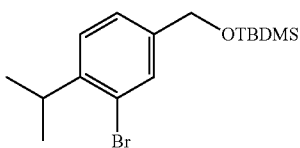 [SMILES: CC(C)c1ccc(CO[Si](C)(C)C(C)(C)C)cc1Br]

Tert-butyldimethylsilylchloride (15.8 g, 105 mmol) was added to a sol. of 421 (20.0 g, 87.3 mmol) and imidazole (8.91 g, 131 mmol) in DCM (400 mL) at r.t. The mixture was stirred at r.t. for 18 h. The mixture was quenched with water and extracted with DCM. The organic layer was decanted, washed with water then brine, dried over MgSO$_4$, filtered and evaporated in vacuo to give a yellow oil. This residue (29.85 g) was purified by prep. LC (Stationary phase: Irregular SiOH 20-45 µm 450 g MATREX, Mobile phase: 100% Heptane). The pure fractions were collected and solvent evaporated until dryness to give 15.0 g of Int. 422 as a white solid. The product was used without further purification for the next step.

c—Synthesis of Int. 423:

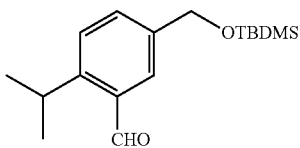 [SMILES: CC(C)c1ccc(CO[Si](C)(C)C(C)(C)C)cc1C=O]

and 424:

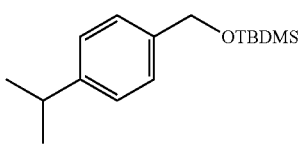 [SMILES: CC(C)c1ccc(CO[Si](C)(C)C(C)(C)C)cc1]

t-Butyl Lithium 1.6M in pentane (7 mL, 11.2 mmol) was added to a stirred sol. under N$_2$ of 422 (2.00 g; 3.50 mol) in dry THF (20 mL) at −78° C. The mixture was stirred at −78° C. for 30 min, and then DMF (3.8 mL, 51.7 mmol) was added at −78° C. The r.m. was stirred at −78° C. to r.t. for 18 h, and then quenched with water. DCM was added, and the organic layer was washed with brine, dried over MgSO$_4$, filtered and evaporated in vacuo to give 2.00 g of a mixture of Int. 423 and Int. 424 (423/424=2/1) as a yellow oil. This mixture was used without further purification for the next step.

d—Synthesis of Int. 425:

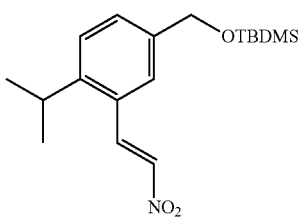 [SMILES: CC(C)c1ccc(CO[Si](C)(C)C(C)(C)C)cc1/C=C/[N+](=O)[O-]]

AcONH$_4$ (316 mg, 4.10 mmol) was added to a stirred sol. of a mixture of 423 and 424 (2.00 g, 6.84 mmol) in CH$_3$—NO$_2$ (517 mL). The mixture was stirred at 60° C. for 18 h. The r.m. was quenched with water and DCM was added. The organic layer was washed with brine, dried over MgSO$_4$, filtered and evaporated in vacuo to give an orange oil. This residue (1.8 g) was purified by prep. LC (irregular SiOH 15-40 µm, 50 g, MERCK, Mobile phase: from Heptane 100% to heptane 95%, EtOAc 5%). The pure fractions were collected and solvent evaporated until dryness to give 750 mg of Int. 425 as a yellow oil (33%).

e—Synthesis of Int 426:

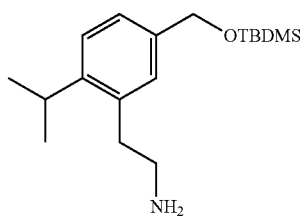 [SMILES: CC(C)c1ccc(CO[Si](C)(C)C(C)(C)C)cc1CCN]

LiAlH$_4$ (283 mg, 7.45 mmol) was added to a stirred sol. of 425 (1.0 g, 2.98 mmol) in Et$_2$O (30 mL) at 0° C. and the sol. was stirred at 0° C. for 1 h. To the sol. was added 280 µL of H$_2$O, 280 µL of an aq. sol. of NaOH 3N and 840 µL of H$_2$O. The precipitate was filtered and the filtrate was evaporated in vacuo to give a yellow oil. This residue (0.9 g) was purified by prep. LC (irregular SiOH 15-40 µm, 50 g, MERCK, Mobile phase: from DCM 100% to DCM 80%, MeOH(10% NH$_3$) 20%). The pure fractions were collected and solvent evaporated until dryness to give 250 mg of Int. 426 as a colorless oil.

f—Synthesis of Int. 427:

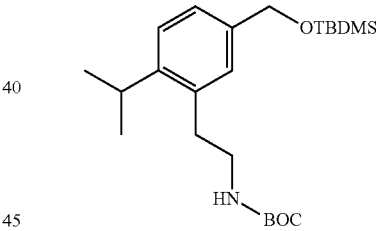

Boc$_2$O (266 mg, 1.22 mmol), Et$_3$N (0.169 mL, 1.219 mmol) and DMAP (10 mg, 81.3 µmol) were added to a stirred sol. of 426 (250 mg, 0.813 mmol) in ACN (4 mL) at r.t. The r.m. was stirred at r.t. for 72 h and the sol. was diluted in DCM. The organic layer was washed successively with an aq. sol. of HCl 1N and a sat. aq. sol. NaHCO$_3$. The organic phase was dried over MgSO$_4$, filtered and evaporated in vacuo to give 210 mg of Int. 427 (63%).

g—Synthesis of Int. 427 (Alternative):

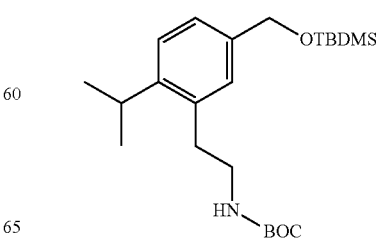

A suspension of Int. 422 (1.0 g, 2.91 mmol), potassium tert-butyl-2-N(2-trifluoroboranuidyl)ethylcarbamate (951 mg, 3.79 mmol), Cs$_2$CO$_3$ (2.85 g, 8.74 mmol) in toluene (15 mL) and H$_2$O (5 mL) was carefully purged with N$_2$. Pd(OAc)$_2$ (33 mg, 146 µmol) and S-Phos (136 mg, 291 µmol) were added to the mixture. The r.m. was purged again with N$_2$ and stirred at 110° C. for 17 h. After dilution in EtOAc, the organic layer was washed with water and brine, dried over MgSO$_4$ and evaporated in vacuo. The residue was purified by prep. LC (spherical SiOH 30 µm, 40 g, Interchim, dry loading, mobile phase gradient: from heptane 100% to heptane 80%, EtOAc 20%). The pure fractions were collected and solvent evaporated until dryness to give 650 mg of Int. 427 as a colorless oil (55%).

h—Synthesis of Int. 428:

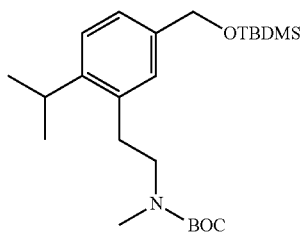 [SMILES: CC(C)c1ccc(CO[Si](C)(C)C(C)(C)C)cc1CCN(C)C(=O)OC(C)(C)C]

NaH (60% dispersion in mineral oil) (650 mg, 16.3 mmol) was added to a mixture of 427 (4.44 g, 10.9 mmol) in THF (40 mL) at 0° C. The r.m. was stirred at r.t. for 30 min. MeI (1.4 mL, 21.8 mmol) was then added to the sol. and the mixture was stirred at r.t. for 18 h. The sol. was diluted in DCM and washed with water. The organic phase was dried over MgSO$_4$, filtered and evaporated in vacuo to give 4.30 g of Int. 428 as a red oil (94%).

i—Synthesis of Int. 429:

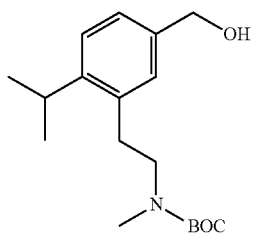 [SMILES: CC(C)c1ccc(CO)cc1CCN(C)C(=O)OC(C)(C)C]

A sol. of TBAF 1M in THF (20.4 mL, 20.4 mmol) was added to a mixture of 428 (4.30 g, 10.2 mmol) in THF (50 mL) and the r.m. was stirred for 17 h at r.t. The sol. was diluted in DCM and washed with water. The organic phase was dried over MgSO$_4$, filtered and evaporated in vacuo to give a red oil. This oil (4.71 g) was purified by prep. LC (irregular SiOH 15-40 µm, 50 g Merck, mobile phase gradient: from EtOAc 20%, Heptane 80% to EtOAc 50%, Heptane 50%). The pure fractions were collected and solvent evaporated to give 2.50 g of Int. 429 as a white gum.

j—Synthesis of Int. 430:

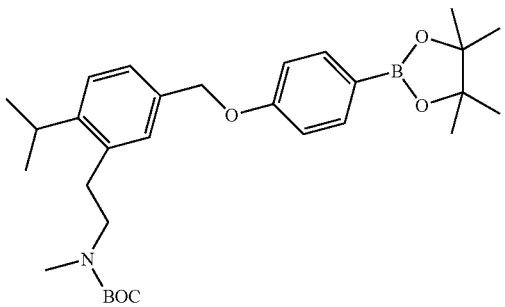 [SMILES: CC(C)c1ccc(COc2ccc(B3OC(C)(C)C(C)(C)O3)cc2)cc1CCN(C)C(=O)OC(C)(C)C]

Prepared by using an analogous reaction protocol as described for Int. 30 starting from Int. 7 using Int. 429 (60%).

k—Synthesis of Co. 234:

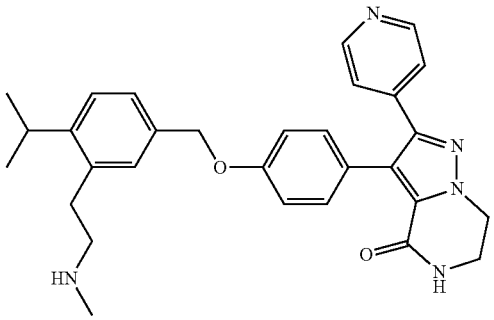 [SMILES: CNCCc1cc(COc2ccc(-c3c(-c4ccncc4)nn4c3C(=O)NCC4)cc2)ccc1C(C)C]

Prepared by using an analogous reaction protocol as described for Co. 31 starting from Int. 4 using Int. 430. Yield: 57%; m.p.: 166° C. and 200° C. (polymorph, DSC).

Example A230

Preparation of Co. 235

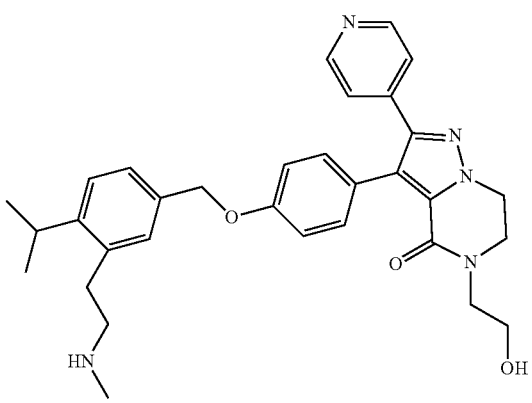 [SMILES: CNCCc1cc(COc2ccc(-c3c(-c4ccncc4)nn4c3C(=O)N(CCO)CC4)cc2)ccc1C(C)C]

Prepared by using an analogous reaction protocol as described for Co. 31 starting from Int. 28 using Int. 430. Yield: 56%.

Example A231

Preparation of Co. 236

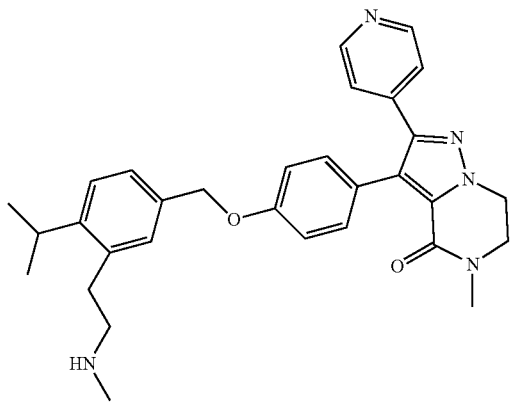 [SMILES: CNCCc1cc(COc2ccc(-c3c(-c4ccncc4)nn4c3C(=O)N(C)CC4)cc2)ccc1C(C)C]

Prepared by using an analogous reaction protocol as described for Co. 31, starting from Int. 98 using Int. 430. Yield: 62%.

Example A232

Preparation of Co. 237 a—Synthesis of Int. 431:

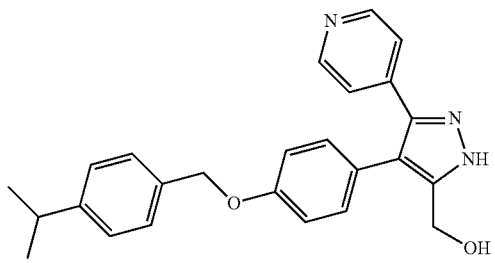 [SMILES: CC(C)c1ccc(COc2ccc(-c3c(-c4ccncc4)n[nH]c3CO)cc2)cc1]

LiAlH$_4$ (0.172 g, 1.36 mmol) was added portionwise to a sol. of 11 (1.00 g, 2.26 mmol) in THF (23 mL) at 0° C. under Ar. The resulting sol. was stirred at r.t. for 3 days. The r.m. was quenched by adding EtOAc followed by H$_2$O. The organic layer was washed with "rochelle salts" and brine, dried over Na$_2$SO$_4$, filtered off and concentrated to afford a yellow solid. This residue (0.803 g) was triturated in MeOH and filtered to give 0.755 g of a yellow solid. This second residue was co-evaporated with DCM and dried in vacuo to give 0.665 g of Int. 431 as an off-white solid (73%).

b—Synthesis of Int. 432:

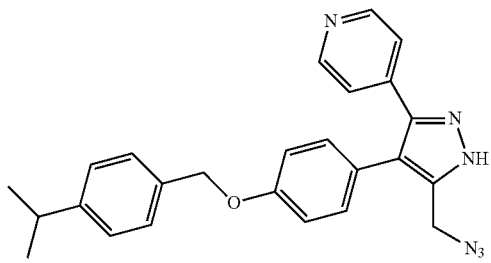 [SMILES: CC(C)c1ccc(COc2ccc(-c3c(-c4ccncc4)n[nH]c3CN=[N+]=[N-])cc2)cc1]

To a suspension of 431 (0.665 g, 1.66 mmol) in THF (10 mL) at r.t. under Ar was added diphenylphosphorylazide (0.400 mL, 1.83 mmol) and DBU (0.297 mL, 1.99 mmol). The resulting mixture was stirred at r.t. for 18 h. An additional amount of diphenylphosphorylazide (0.200 mL, 0.916 mmol) and DBU (0.150 mL, 1.00 mmol) were added and the mixture was stirred at r.t. for 3 h. The r.m. was quenched by adding an aq. sat. sol. of NaHCO$_3$ (30 mL). The aq. layer was extracted twice with EtOAc (2×30 mL) and the combined organic layers were dried over Na$_2$SO$_4$, filtered off and concentrated to dryness to a yellow gum. This residue (1.26 g) was purified by prep. LC (irregular SiOH 15-40 µmrn, mobile phase gradient: from DCM 98%, MeOH 2% to DCM 95%, MeOH 5%). The pure fractions were collected and solvent evaporated until dryness to give 0.370 g of Int. 432 as an off-white solid (52%).

c—Synthesis of Int. 433:

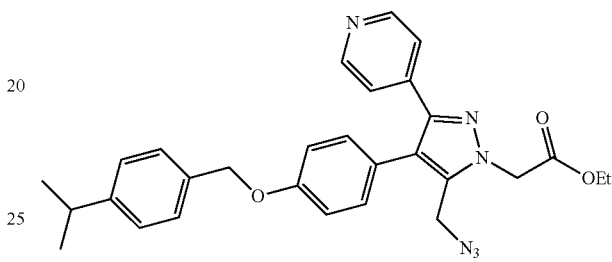

To a sol. of 432 (347 mg, 0.817 mmol) and K$_2$CO$_3$ (249 mg, 1.80 mmol) in DMF (6 mL) was added ethylbromoacetate (0.108 mL, 0.981 mmol) at r.t. The r.m. was stirred at r.t. for 18 h. Then, the crude mixture was diluted with EtOAc and water, and the organic layer was washed with brine, dried over MgSO$_4$, filtered and evaporated in vacuo to a viscous orange solid. This residue (0.43 g) was purified by prep. LC (Regular SiOH 50 µm, liquid loading, 24 g Grace, DCM 100% to DCM 30% EtOAc 70%) to give 247 mg of Int. 433 as a cream solid (66%)

d—Synthesis of Co. 237:

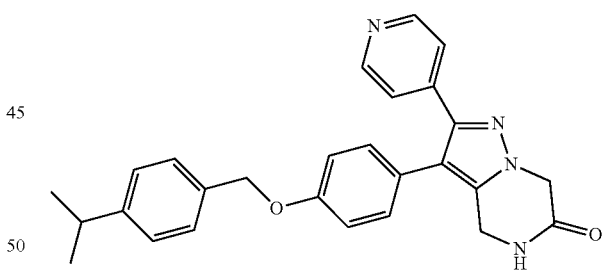

To a stirred sol. of 433 (254 mg, 0.497 mmol) in EtOH (8 mL) was added Raney Nickel (29 mg, 0.497 mmol) at r.t. The r.m. was hydrogenated at r.t. under atmospheric pressure for 1 h. The crude mixture was filtered off through a pad of Celite® which was washed with EtOH. The filtrate was evaporated in vacuo. The residue (0.185 g) was diluted in EtOH (3 mL) and EtOAc (3 mL), and an extra amount of Raney Nickel (555 mg, 9.45 mmol) was added. The r.m. was hydrogenated at r.t. under atmospheric pressure for 2 h. The crude mixture was filtered off through a pad of Celite® which was washed with DCM and EtOAc. The filtrate was evaporated in vacuo. The residue (0.130 g) was triturated in Et$_2$O, and the solvent was removed. The solid was dried in vacuo to yield 105 mg of Co. 237 as a white solid (48%). m.p.: 281° C. (DSC).

The compounds listed in Table 1 below have been prepared. The values of salt stoichiometry or acid content in the compounds as provided herein, are those obtained experimentally and may vary dependent on the analytical method used (for compound 210, $^1$H NMR was used; and for compound 59a, $^1$H NMR and elemental analysis was used).

In case no salt form is indicated, the compound was obtained as a free base. Salt forms of the free bases can easily be obtained by using typical procedures known to those skilled in the art. For example Compound 1 (free base) was converted into a HCl salt, a methanesulfonate salt and a sulfate salt.

TABLE 1

Compounds

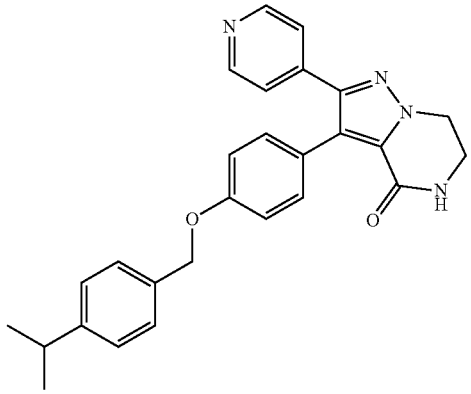 [SMILES: CC(C)c1ccc(COc2ccc(-c3c(-c4ccncc4)nn4c3C(=O)NCC4)cc2)cc1]

Compound 1; Method A1/A2/A3/A4/A5

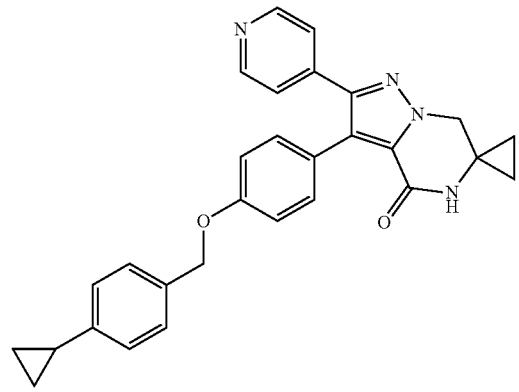 [SMILES: O=C1NC2(CC2)Cn2nc(-c3ccncc3)c(-c3ccc(OCc4ccc(C5CC5)cc4)cc3)c21]

Compound 5; Method A10

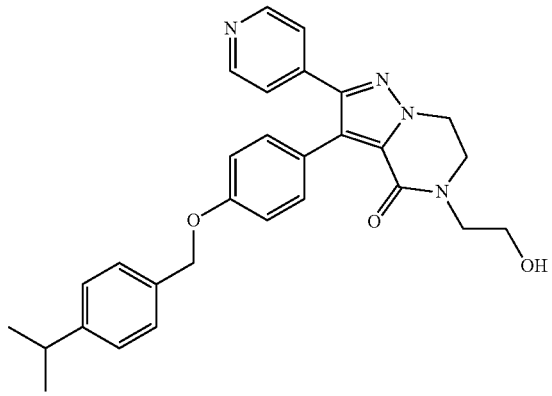 [SMILES: CC(C)c1ccc(COc2ccc(-c3c(-c4ccncc4)nn4c3C(=O)N(CCO)CC4)cc2)cc1]

Compound 2; Method A6/A7/A56

TABLE 1-continued
Compounds
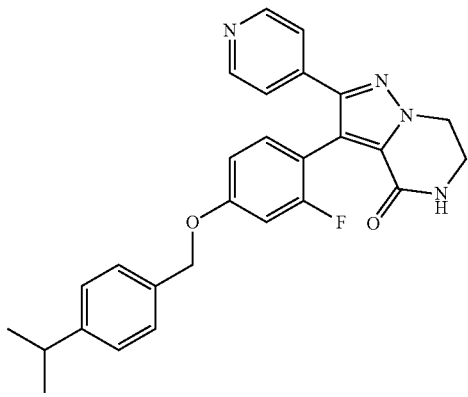 [SMILES: CC(C)c1ccc(COc2ccc(-c3c(-c4ccncc4)nn4c3C(=O)NCC4)c(F)c2)cc1]
Compound 6; Method A11
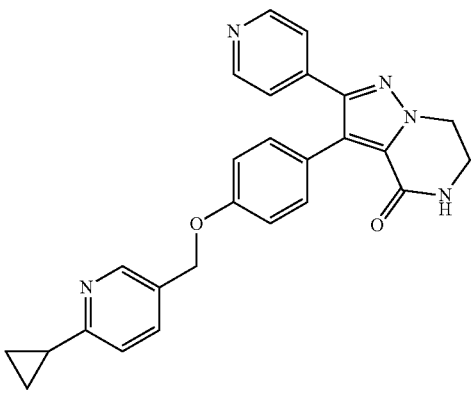 [SMILES: O=C1NCCn2nc(-c3ccncc3)c(-c3ccc(OCc4ccc(C5CC5)nc4)cc3)c21]
Compound 3; Method A8
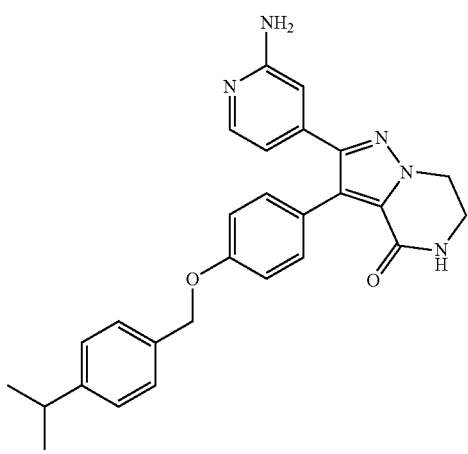 [SMILES: CC(C)c1ccc(COc2ccc(-c3c(-c4ccnc(N)c4)nn4c3C(=O)NCC4)cc2)cc1]
Compound 7; Method A12

TABLE 1-continued
Compounds
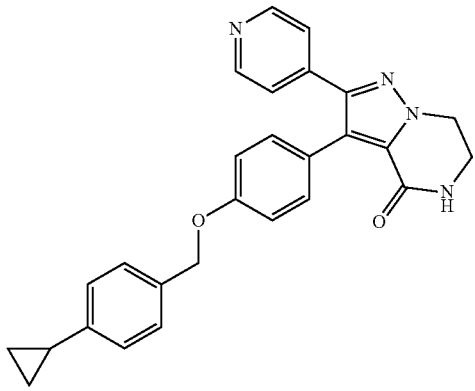
Compound 4; Method A9
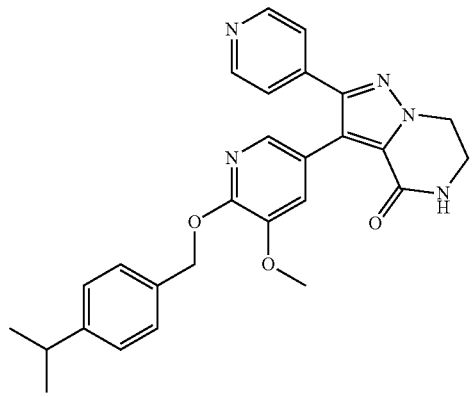 [SMILES: COc1cc(-c2c(-c3ccncc3)nn3c2C(=O)NCC3)cnc1OCc1ccc(C(C)C)cc1]
Compound 8; Method A13
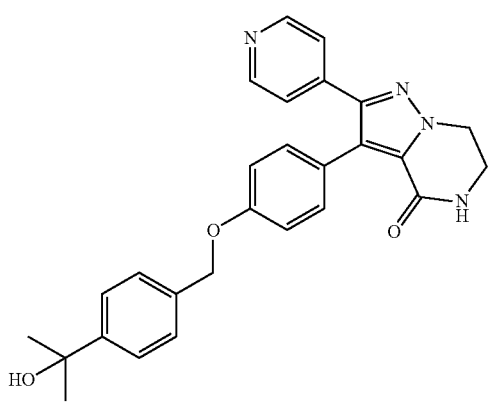 [SMILES: CC(C)(O)c1ccc(COc2ccc(-c3c(-c4ccncc4)nn4c3C(=O)NCC4)cc2)cc1]
Compound 9; Method A14

TABLE 1-continued
Compounds
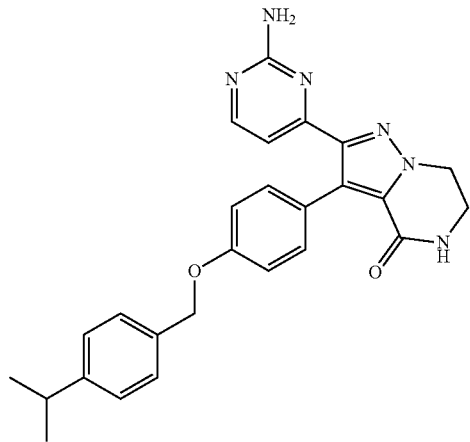 [SMILES: CC(C)c1ccc(COc2ccc(-c3c(-c4ccnc(N)n4)nn4c3C(=O)NCC4)cc2)cc1]
Compound 13; Method A18
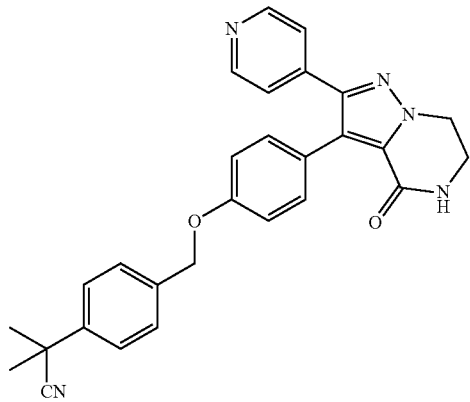 [SMILES: CC(C)(C#N)c1ccc(COc2ccc(-c3c(-c4ccncc4)nn4c3C(=O)NCC4)cc2)cc1]
Compound 10; Method A15
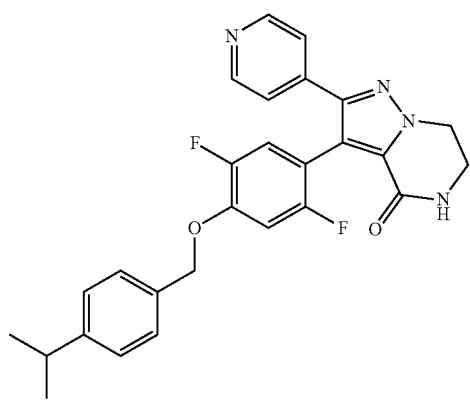 [SMILES: CC(C)c1ccc(COc2cc(F)c(-c3c(-c4ccncc4)nn4c3C(=O)NCC4)cc2F)cc1]
Compound 14; Method A19

TABLE 1-continued
Compounds
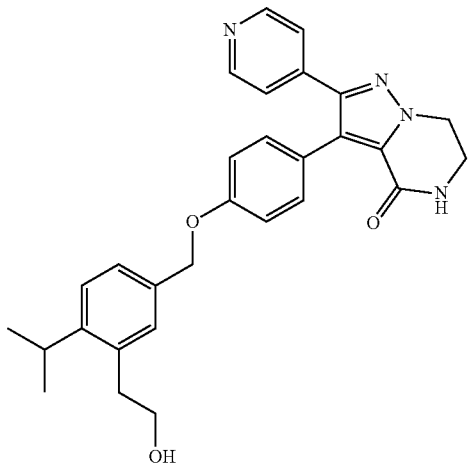 [SMILES: CC(C)c1ccc(COc2ccc(-c3c(-c4ccncc4)nn4c3C(=O)NCC4)cc2)cc1CCO]
Compound 11; Method A16
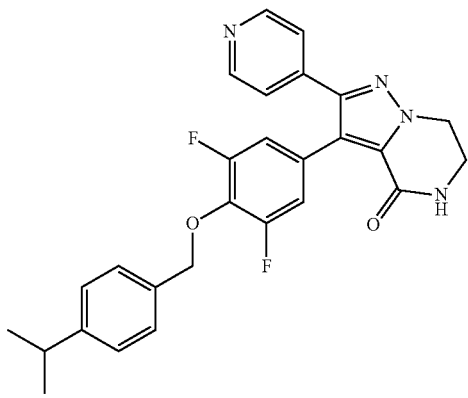 [SMILES: CC(C)c1ccc(COc2c(F)cc(-c3c(-c4ccncc4)nn4c3C(=O)NCC4)cc2F)cc1]
Compound 15; Method A20
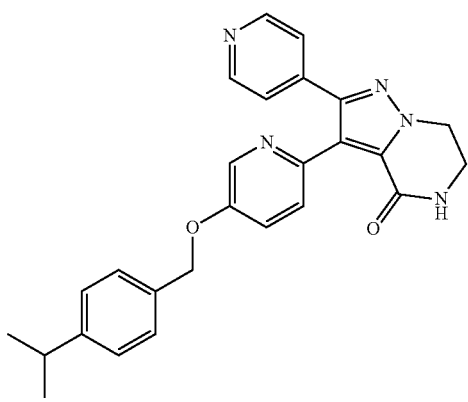 [SMILES: CC(C)c1ccc(COc2ccc(-c3c(-c4ccncc4)nn4c3C(=O)NCC4)nc2)cc1]
Compound 12; Method A17

TABLE 1-continued
Compounds
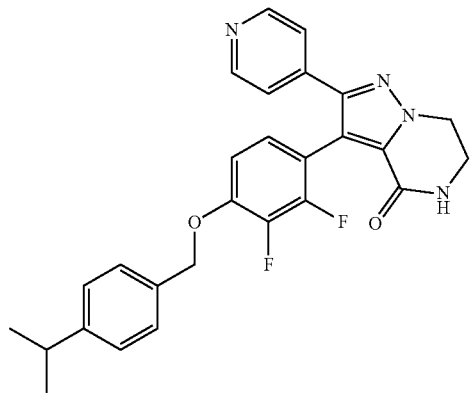 [SMILES: CC(C)c1ccc(COc2ccc(-c3c(-c4ccncc4)nn4c3C(=O)NCC4)c(F)c2F)cc1]
Compound 16; Method 21
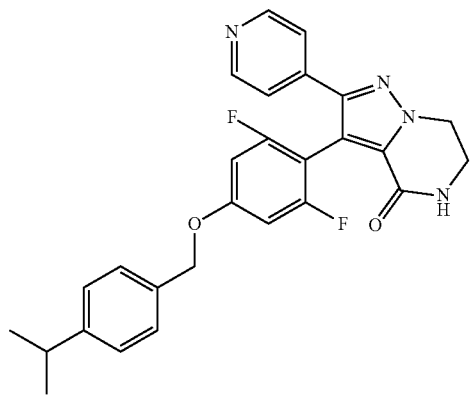 [SMILES: CC(C)c1ccc(COc2cc(F)c(-c3c(-c4ccncc4)nn4c3C(=O)NCC4)c(F)c2)cc1]
Compound 17; Method A22
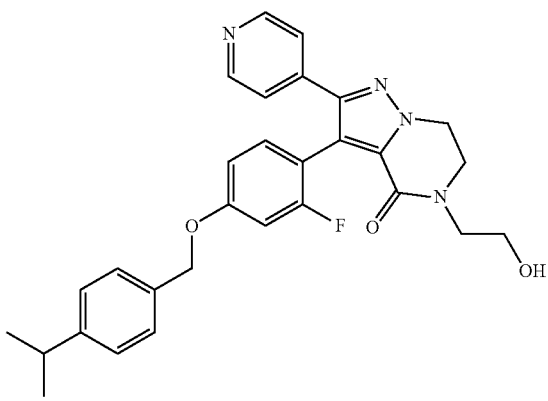 [SMILES: CC(C)c1ccc(COc2ccc(-c3c(-c4ccncc4)nn4c3C(=O)N(CCO)CC4)c(F)c2)cc1]
Compound 21; Method A26

TABLE 1-continued
Compounds
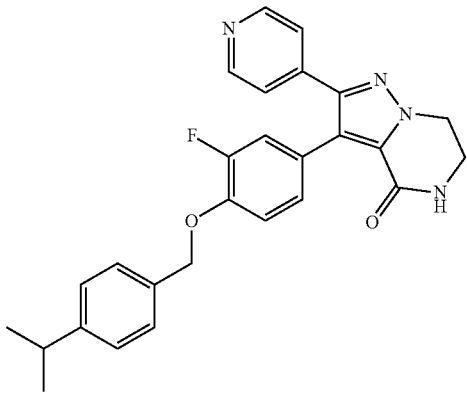 [SMILES: CC(C)c1ccc(COc2ccc(-c3c(-c4ccncc4)nn4c3C(=O)NCC4)cc2F)cc1]
Compound 18; Method A23
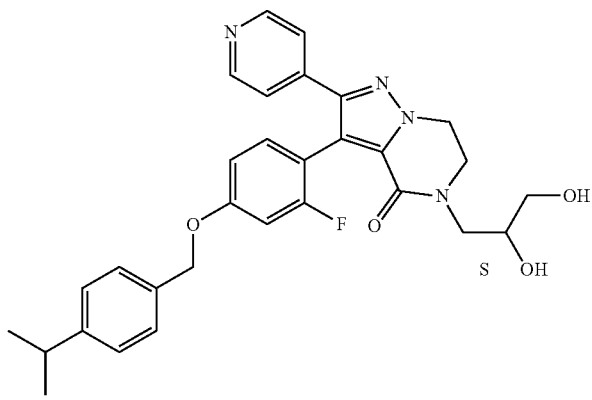
Compound 22; Method A27
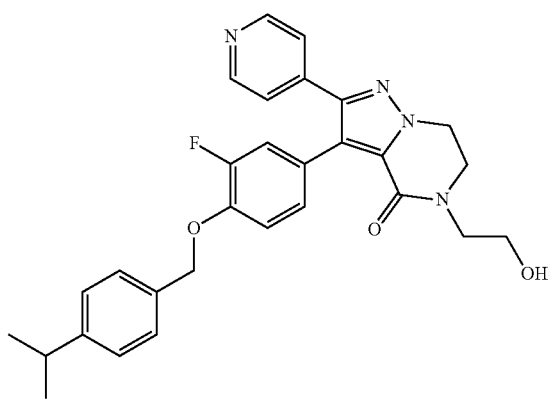 [SMILES: CC(C)c1ccc(COc2ccc(-c3c(-c4ccncc4)nn4c3C(=O)N(CCO)CC4)cc2F)cc1]
Compound 19; Method A24

TABLE 1-continued
Compounds
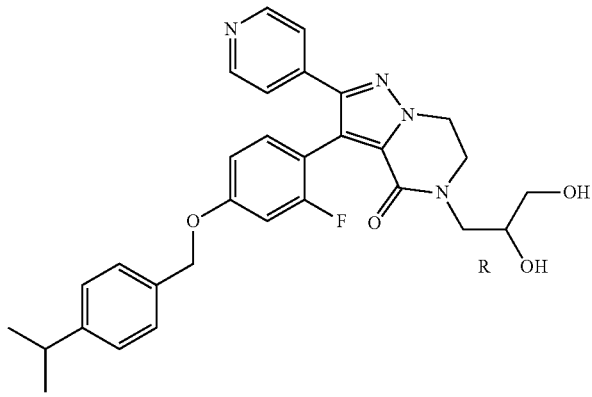
Compound 23; Method A28
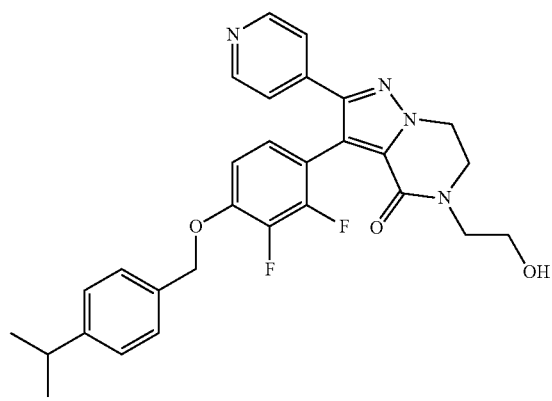 [SMILES: CC(C)c1ccc(COc2ccc(-c3c(-c4ccncc4)nn4c3C(=O)N(CCO)CC4)c(F)c2F)cc1]
Compound 20; Method A25
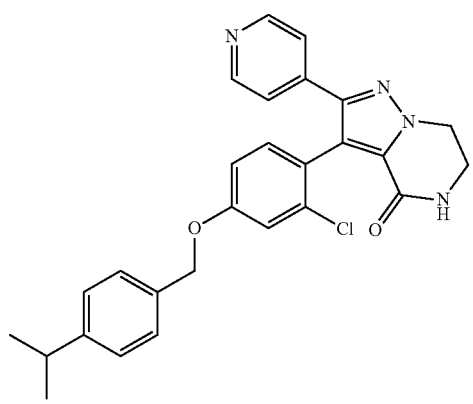
Compound 24; Method A29

TABLE 1-continued
Compounds
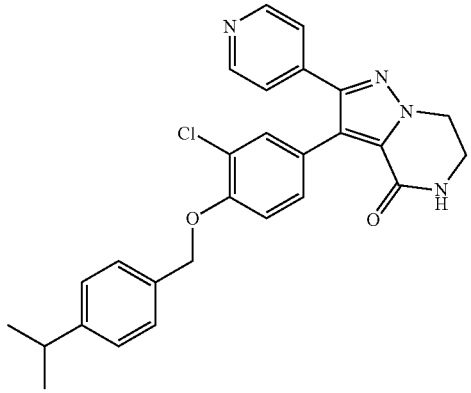 [SMILES: CC(C)c1ccc(COc2ccc(-c3c(-c4ccncc4)nn4c3C(=O)NCC4)cc2Cl)cc1]
Compound 25; Method A30
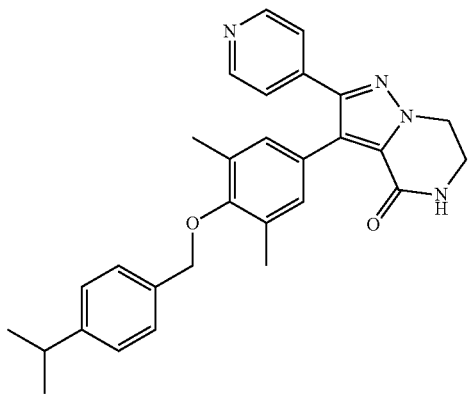
Compound 29; Method A34
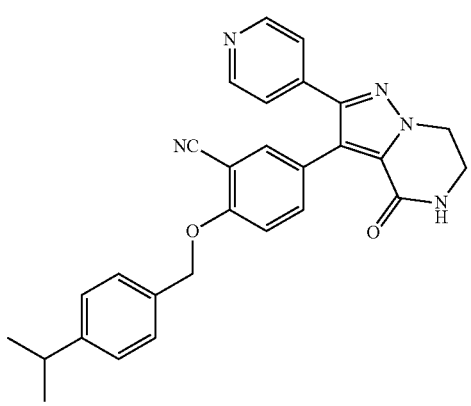 [SMILES: CC(C)c1ccc(COc2ccc(-c3c(-c4ccncc4)nn4c3C(=O)NCC4)cc2C#N)cc1]
Compound 26; Method A31

TABLE 1-continued
Compounds
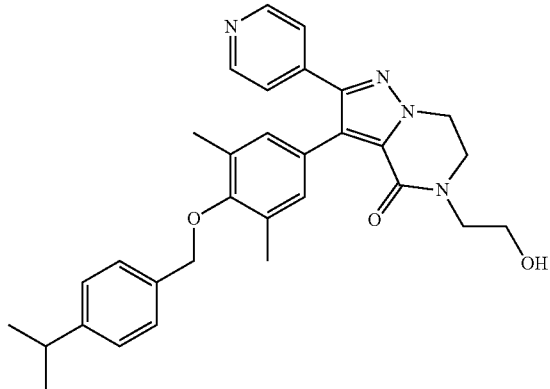 [SMILES: Cc1cc(-c2c(-c3ccncc3)nn3c2C(=O)N(CCO)CC3)cc(C)c1OCc1ccc(C(C)C)cc1]
Compound 30; Method A35
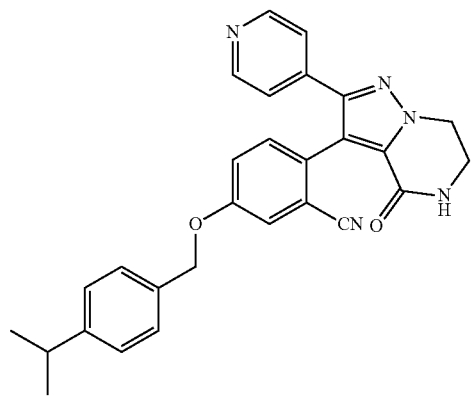 [SMILES: CC(C)c1ccc(COc2ccc(-c3c(-c4ccncc4)nn4c3C(=O)NCC4)c(C#N)c2)cc1]
Compound 27; Method A32
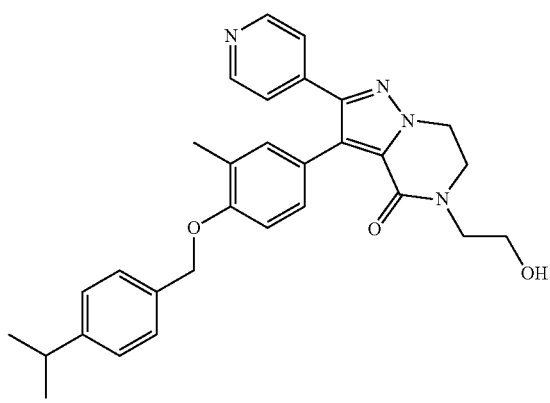 [SMILES: Cc1cc(-c2c(-c3ccncc3)nn3c2C(=O)N(CCO)CC3)ccc1OCc1ccc(C(C)C)cc1]
Compound 31; Method A36

TABLE 1-continued
Compounds
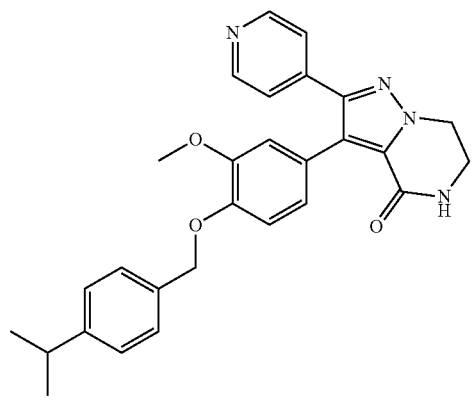 [SMILES: COc1cc(-c2c(-c3ccncc3)nn3c2C(=O)NCC3)ccc1OCc1ccc(C(C)C)cc1]
Compound 28; Method A33
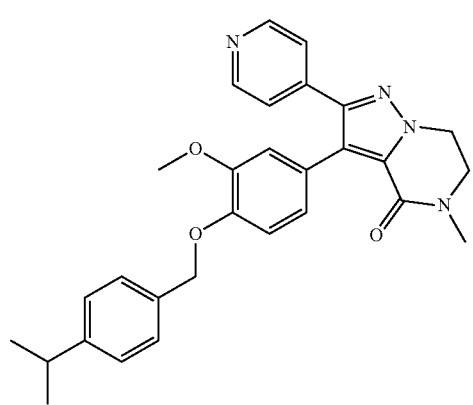 [SMILES: COc1cc(-c2c(-c3ccncc3)nn3c2C(=O)N(C)CC3)ccc1OCc1ccc(C(C)C)cc1]
Compound 32; Method A37
Compound 33; Method A38

TABLE 1-continued
Compounds
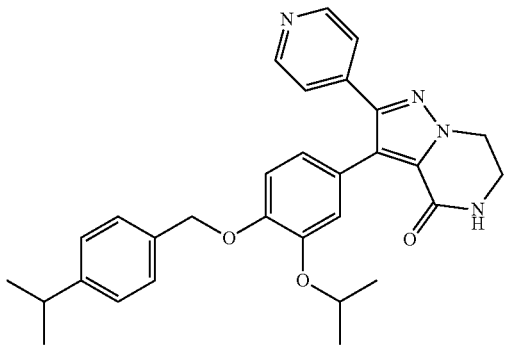 [SMILES: CC(C)Oc1cc(-c2c(-c3ccncc3)nn3c2C(=O)NCC3)ccc1OCc1ccc(C(C)C)cc1]
Compound 37; Method A42
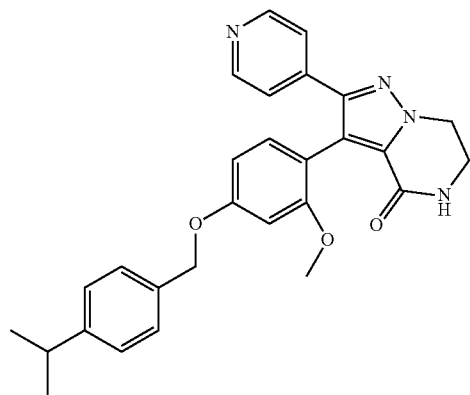 [SMILES: COc1cc(OCc2ccc(C(C)C)cc2)ccc1-c1c(-c2ccncc2)nn2c1C(=O)NCC2]
Compound 34; Method A39
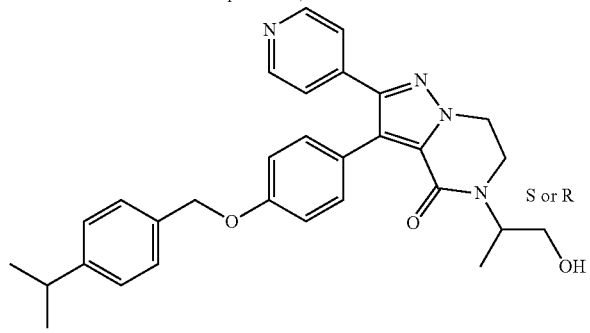
Compound 38; Method A43
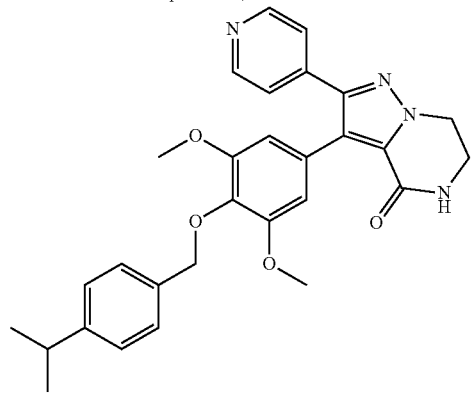
Compound 35; Method A40

TABLE 1-continued
Compounds
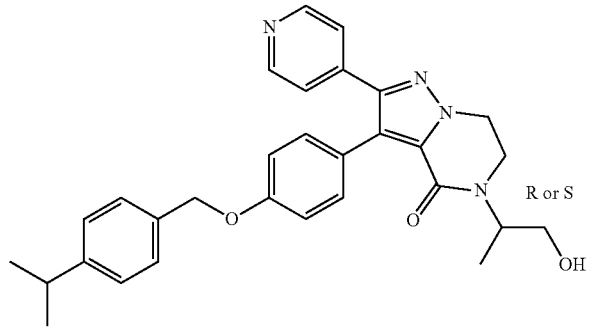 [SMILES: CC(C)c1ccc(COc2ccc(-c3c(-c4ccncc4)nn4c3C(=O)N(C(C)CO)CC4)cc2)cc1]
Compound 39; Method A43
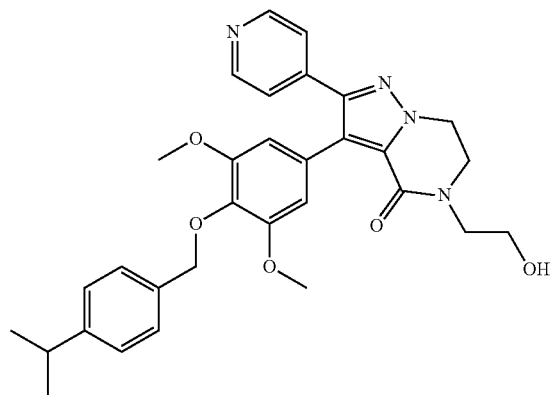 [SMILES: COc1cc(-c2c(-c3ccncc3)nn3c2C(=O)N(CCO)CC3)cc(OC)c1OCc1ccc(C(C)C)cc1]
Compound 36; Method 41
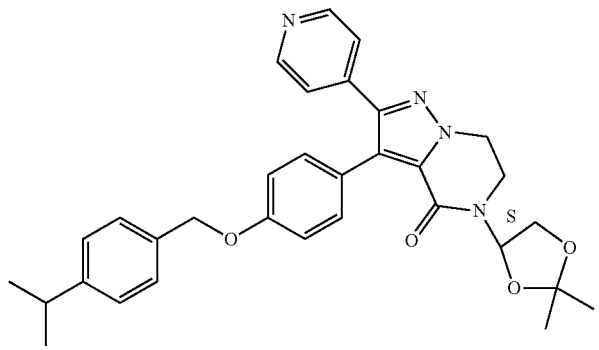
Compound 40; Method A44
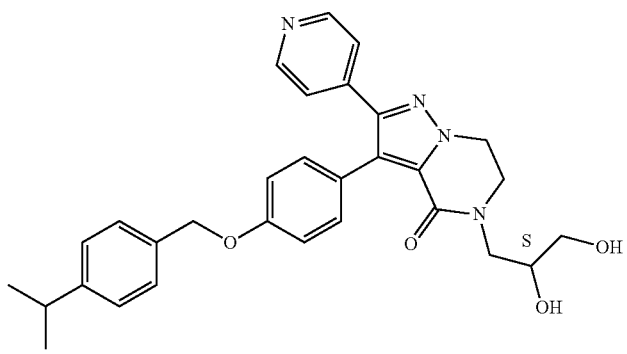
Compound 41; Method A45

TABLE 1-continued
Compounds
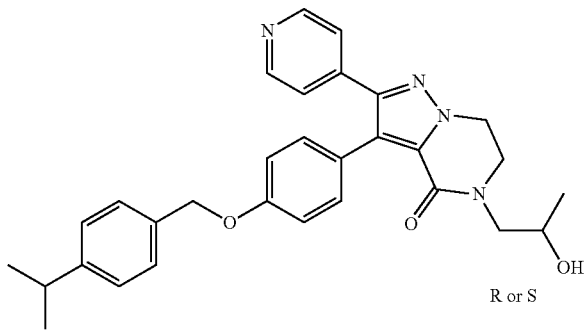 [SMILES: CC(O)CN1CCn2nc(-c3ccncc3)c(-c3ccc(OCc4ccc(C(C)C)cc4)cc3)c2C1=O]
Compound 46; Method A50
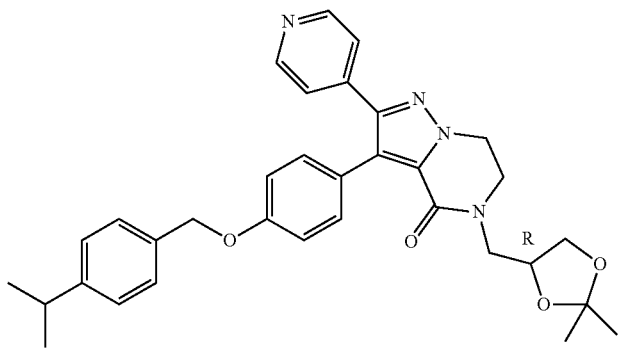
Compound 42; Method A46
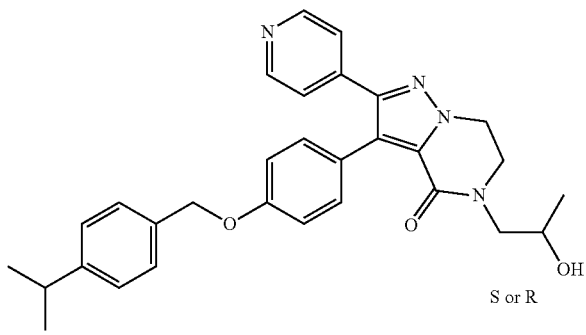 [SMILES: CC(O)CN1CCn2nc(-c3ccncc3)c(-c3ccc(OCc4ccc(C(C)C)cc4)cc3)c2C1=O]
Compound 47; Method A50
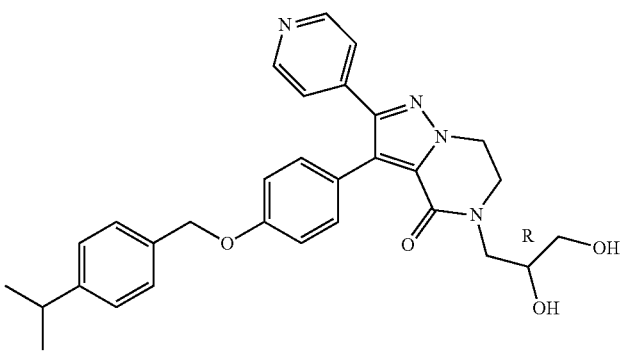
Compound 43; Method A47

TABLE 1-continued
Compounds
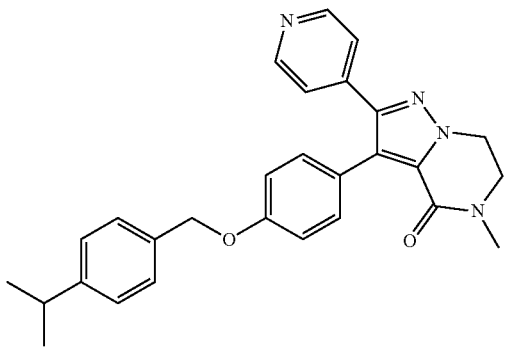 [SMILES: CC(C)c1ccc(COc2ccc(-c3c(-c4ccncc4)nn4c3C(=O)N(C)CC4)cc2)cc1]
Compound 48; Method A51
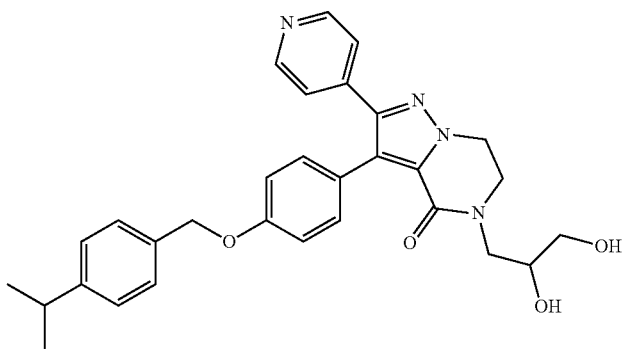 [SMILES: CC(C)c1ccc(COc2ccc(-c3c(-c4ccncc4)nn4c3C(=O)N(CC(O)CO)CC4)cc2)cc1]
Compound 44; Method A48
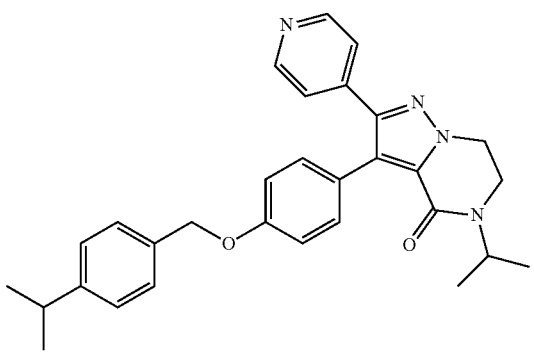 [SMILES: CC(C)c1ccc(COc2ccc(-c3c(-c4ccncc4)nn4c3C(=O)N(C(C)C)CC4)cc2)cc1]
Compound 49; Method A52
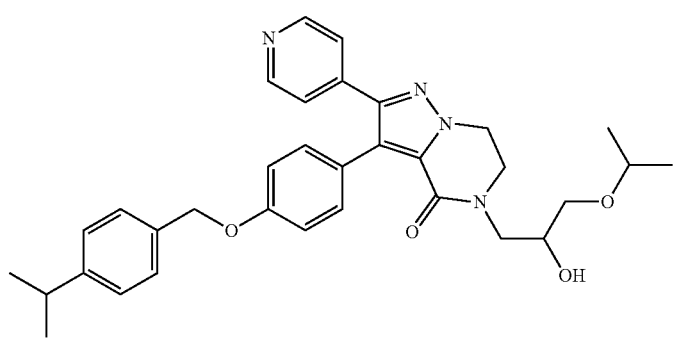 [SMILES: CC(C)OCC(O)CN1CCn2nc(-c3ccncc3)c(-c3ccc(OCc4ccc(C(C)C)cc4)cc3)c2C1=O]
Compound 45; Method A49

TABLE 1-continued
Compounds
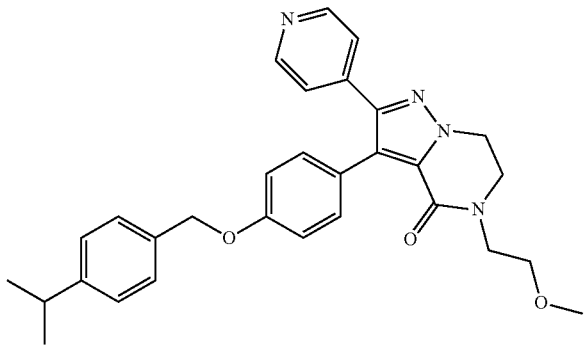 [SMILES: COCCN1CCn2nc(-c3ccncc3)c(-c3ccc(OCc4ccc(C(C)C)cc4)cc3)c2C1=O]
Compound 50; Method A53
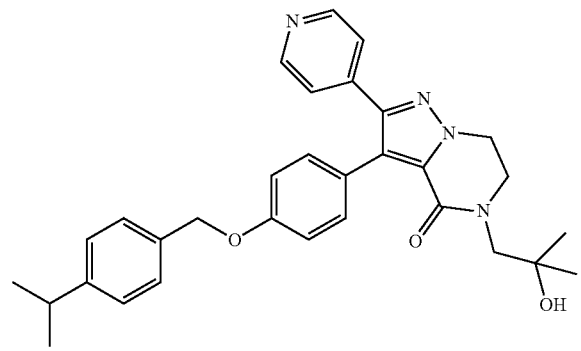
Compound 51; Method A54
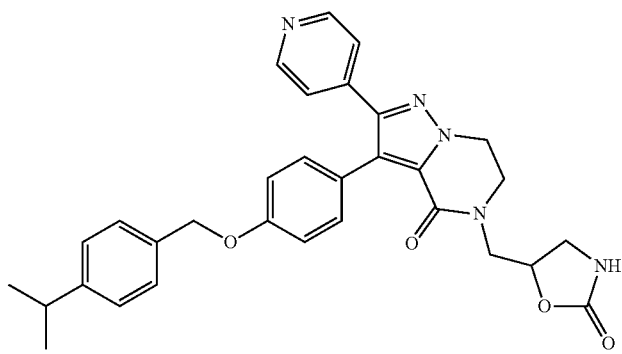 [SMILES: CC(C)c1ccc(COc2ccc(-c3c(-c4ccncc4)nn4c3C(=O)N(CC3CNC(=O)O3)CC4)cc2)cc1]
Compound 56; Method A59
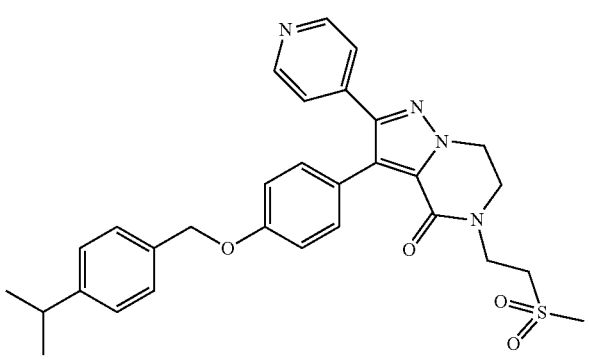 [SMILES: CC(C)c1ccc(COc2ccc(-c3c(-c4ccncc4)nn4c3C(=O)N(CCS(C)(=O)=O)CC4)cc2)cc1]
Compound 52; Method A55

TABLE 1-continued
Compounds
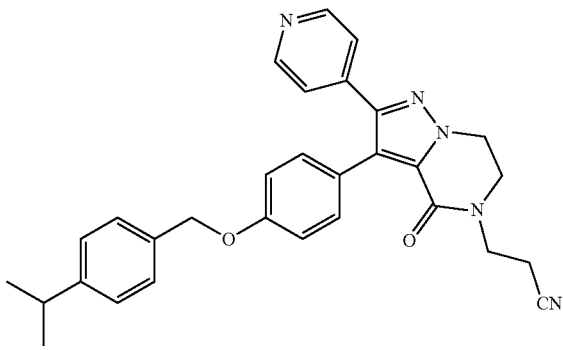
Compound 57; Method A60
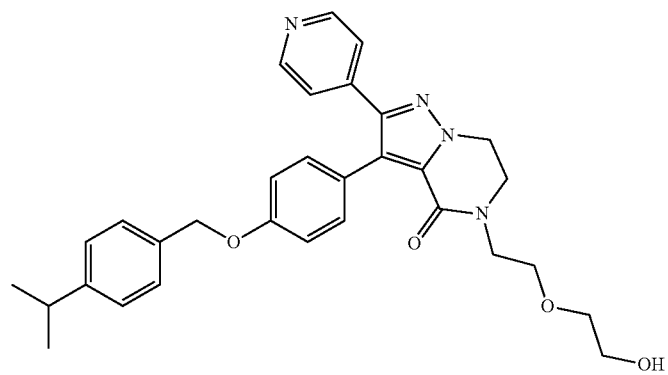 [SMILES: CC(C)c1ccc(COc2ccc(-c3c(-c4ccncc4)nn4c3C(=O)N(CCOCCO)CC4)cc2)cc1]
Compound 53; Method A56
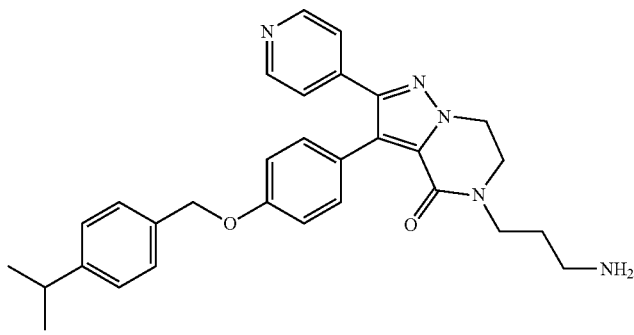 [SMILES: CC(C)c1ccc(COc2ccc(-c3c(-c4ccncc4)nn4c3C(=O)N(CCCN)CC4)cc2)cc1]
Compound 58; Method A61
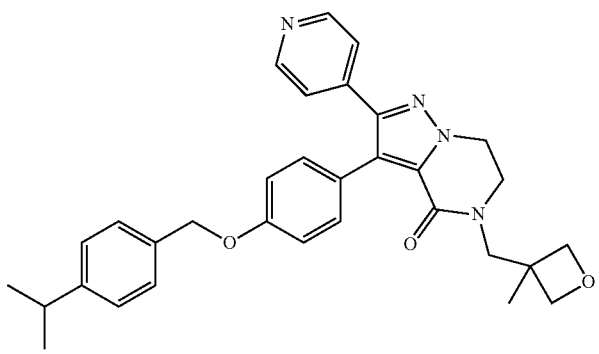 [SMILES: CC(C)c1ccc(COc2ccc(-c3c(-c4ccncc4)nn4c3C(=O)N(CC3(C)COC3)CC4)cc2)cc1]
Compound 54; Method A57

TABLE 1-continued
Compounds
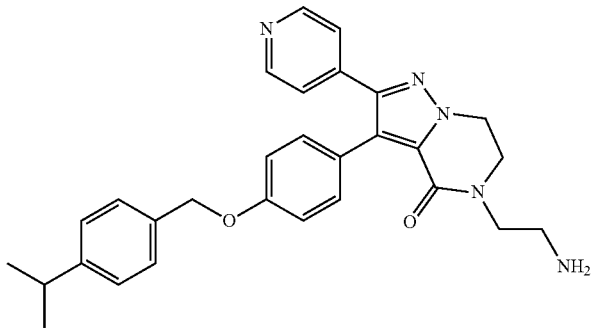 [SMILES: CC(C)c1ccc(COc2ccc(-c3c(-c4ccncc4)nn4c3C(=O)N(CCN)CC4)cc2)cc1]
Compound 59; Method A62
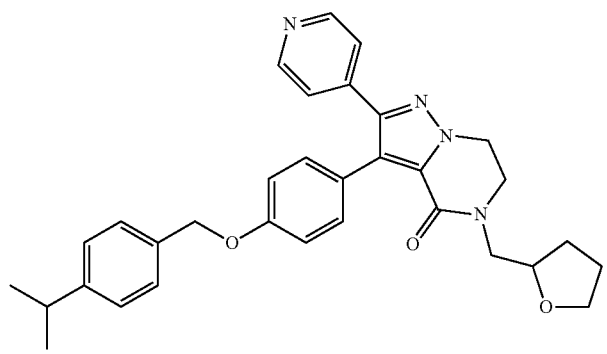
Compound 55; Method A58
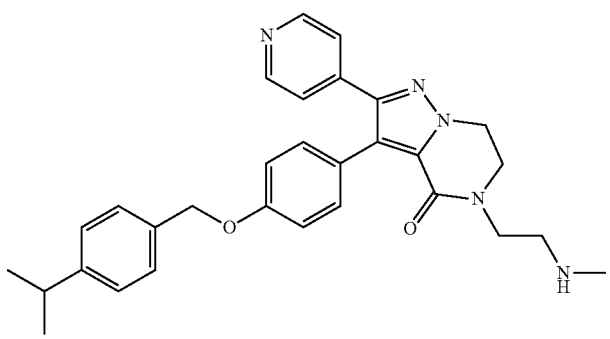 [SMILES: CNCCN1CCn2nc(-c3ccncc3)c(-c3ccc(OCc4ccc(C(C)C)cc4)cc3)c2C1=O]
Compound 60; Method A63
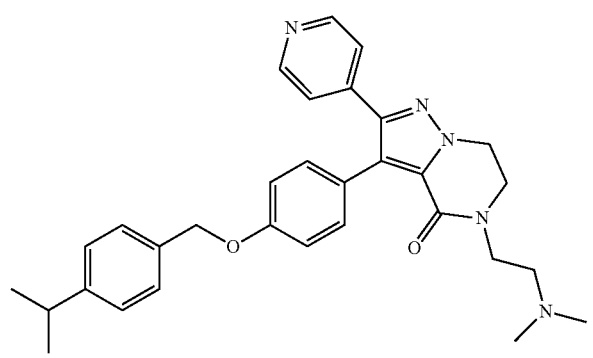 [SMILES: CC(C)c1ccc(COc2ccc(-c3c(-c4ccncc4)nn4c3C(=O)N(CCN(C)C)CC4)cc2)cc1]
Compound 61; Method A64

TABLE 1-continued
Compounds
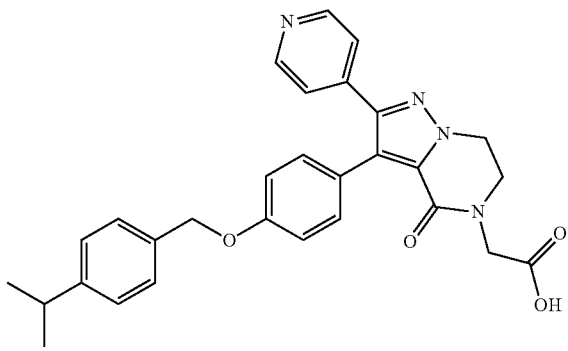 [SMILES: CC(C)c1ccc(COc2ccc(-c3c(-c4ccncc4)nn4c3C(=O)N(CC(=O)O)CC4)cc2)cc1]
Compound 66; Method A69
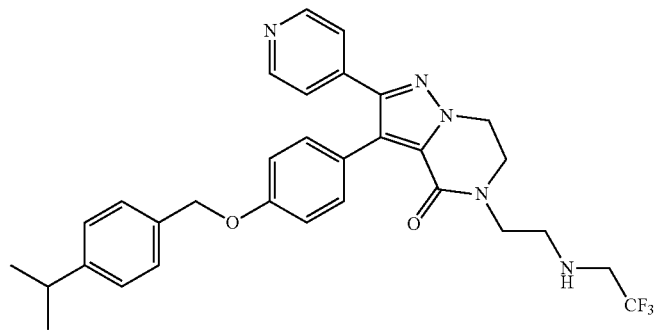 [SMILES: CC(C)c1ccc(COc2ccc(-c3c(-c4ccncc4)nn4c3C(=O)N(CCNCC(F)(F)F)CC4)cc2)cc1]
Compound 62; Method A65
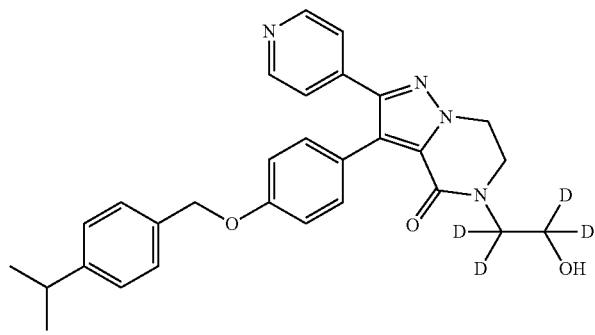 [SMILES: [2H]C([2H])(O)C([2H])([2H])N1CCn2nc(-c3ccncc3)c(-c3ccc(OCc4ccc(C(C)C)cc4)cc3)c2C1=O]
Compound 67; Method A70
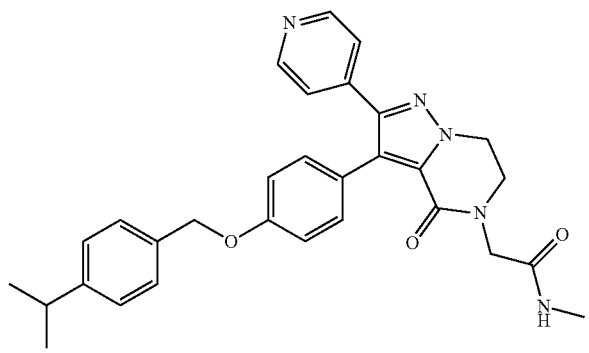 [SMILES: CNC(=O)CN1CCn2nc(-c3ccncc3)c(-c3ccc(OCc4ccc(C(C)C)cc4)cc3)c2C1=O]
Compound 63; Method A66

TABLE 1-continued

Compounds

Compound 68; Method A71

Compound 64; Method A67

Compound 69; Method A72

Compound 65; Method A68

419  420
TABLE 1-continued
Compounds
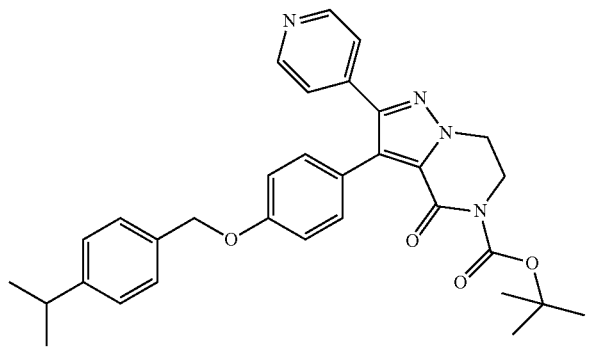 [SMILES: CC(C)c1ccc(COc2ccc(-c3c(-c4ccncc4)nn4c3C(=O)N(C(=O)OC(C)(C)C)CC4)cc2)cc1]
Compound 70; Method A5.b
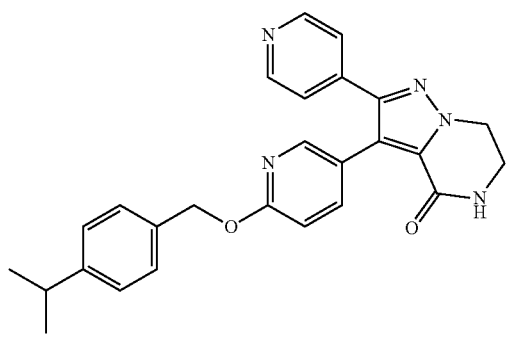 [SMILES: CC(C)c1ccc(COc2ccc(-c3c(-c4ccncc4)nn4c3C(=O)NCC4)cn2)cc1]
Compound 71; Method A73
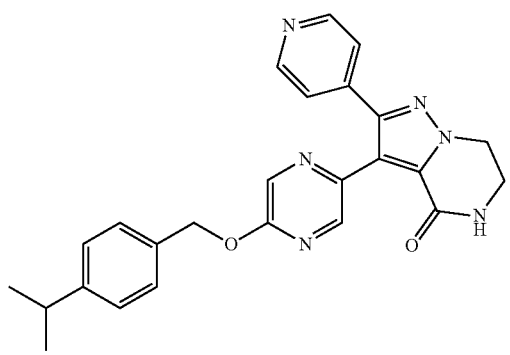 [SMILES: CC(C)c1ccc(COc2cnc(-c3c(-c4ccncc4)nn4c3C(=O)NCC4)cn2)cc1]
Compound 76; Method A78
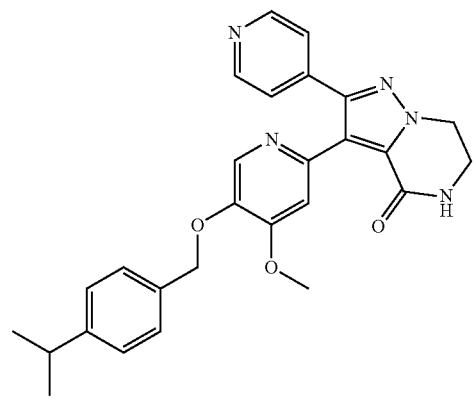 [SMILES: COc1cc(-c2c(-c3ccncc3)nn3c2C(=O)NCC3)ncc1OCc1ccc(C(C)C)cc1]
Compound 72; Method A74

TABLE 1-continued
Compounds
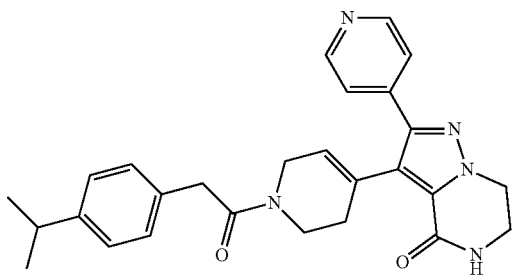 [SMILES: CC(C)c1ccc(CC(=O)N2CC=C(c3c(-c4ccncc4)nn4c3C(=O)NCC4)CC2)cc1]
Compound 77; Method A79
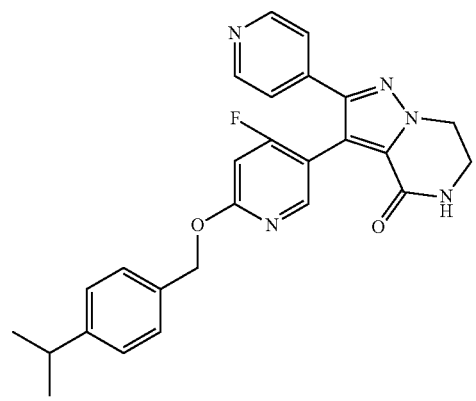 [SMILES: CC(C)c1ccc(COc2cc(F)c(-c3c(-c4ccncc4)nn4c3C(=O)NCC4)cn2)cc1]
Compound 73; Method A75
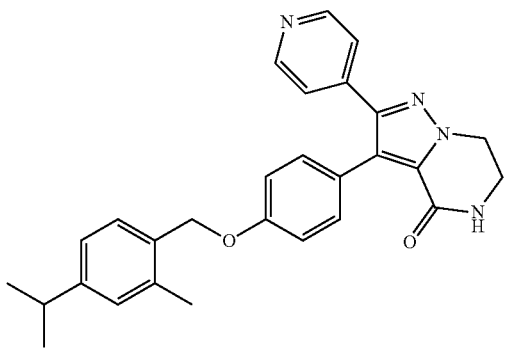 [SMILES: Cc1cc(C(C)C)ccc1COc1ccc(-c2c(-c3ccncc3)nn3c2C(=O)NCC3)cc1]
Compound 78; Method A80
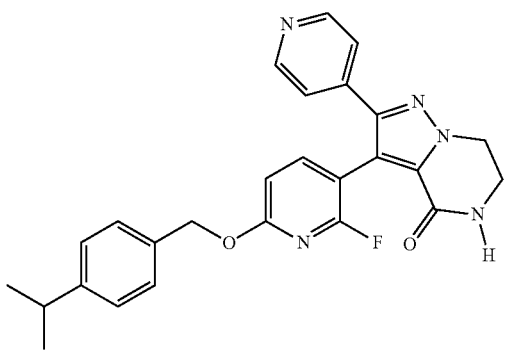 [SMILES: CC(C)c1ccc(COc2ccc(-c3c(-c4ccncc4)nn4c3C(=O)NCC4)c(F)n2)cc1]
Compound 74; Method A76

TABLE 1-continued
Compounds
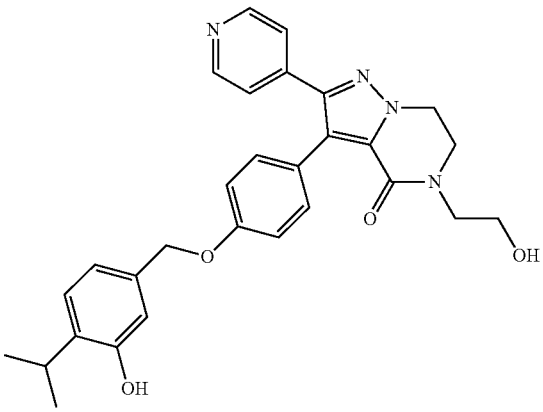 [SMILES: CC(C)c1ccc(COc2ccc(-c3c(-c4ccncc4)nn4c3C(=O)N(CCO)CC4)cc2)cc1O]
Compound 79; Method A81
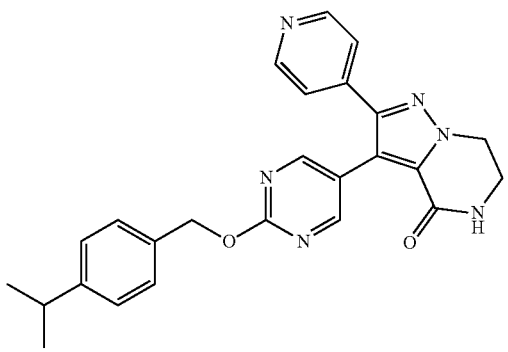 [SMILES: CC(C)c1ccc(COc2ncc(-c3c(-c4ccncc4)nn4c3C(=O)NCC4)cn2)cc1]
Compound 75; Method A77
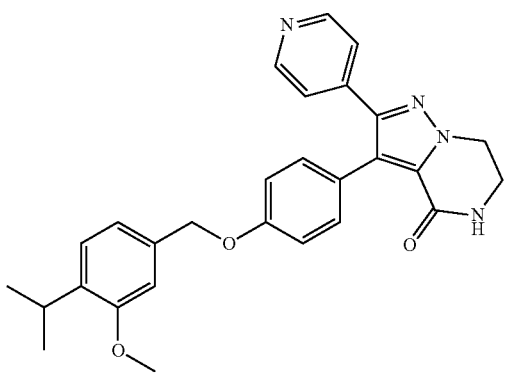 [SMILES: COc1cc(COc2ccc(-c3c(-c4ccncc4)nn4c3C(=O)NCC4)cc2)ccc1C(C)C]
Compound 80; Method A82

TABLE 1-continued
Compounds
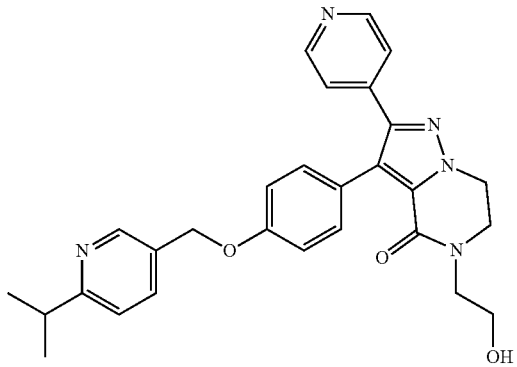 [SMILES: CC(C)c1ccc(COc2ccc(-c3c(-c4ccncc4)nn4c3C(=O)N(CCO)CC4)cc2)cn1]
Compound 81; Method A83
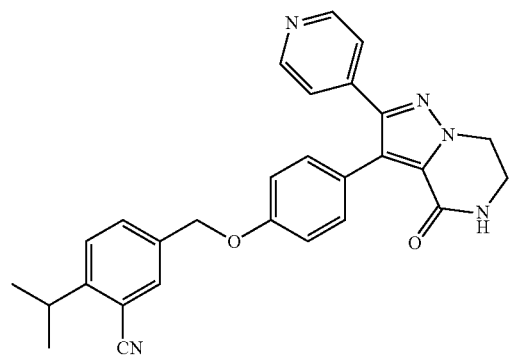 [SMILES: CC(C)c1ccc(COc2ccc(-c3c(-c4ccncc4)nn4c3C(=O)NCC4)cc2)cc1C#N]
Compound 85; Method A87
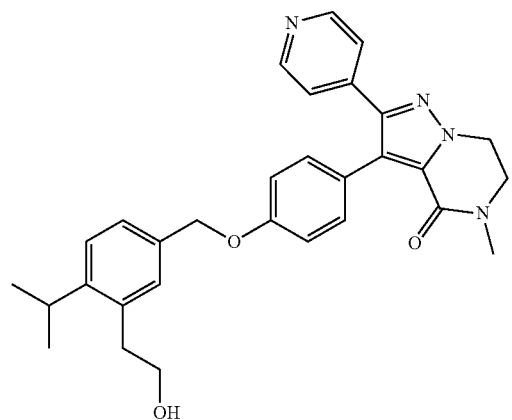 [SMILES: CC(C)c1ccc(COc2ccc(-c3c(-c4ccncc4)nn4c3C(=O)N(C)CC4)cc2)cc1CCO]
Compound 82; Method A84

TABLE 1-continued
Compounds
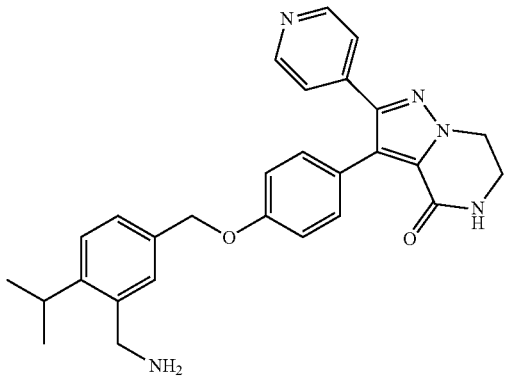 [SMILES: CC(C)c1ccc(COc2ccc(-c3c(-c4ccncc4)nn4c3C(=O)NCC4)cc2)cc1CN]
Compound 86; Method A87
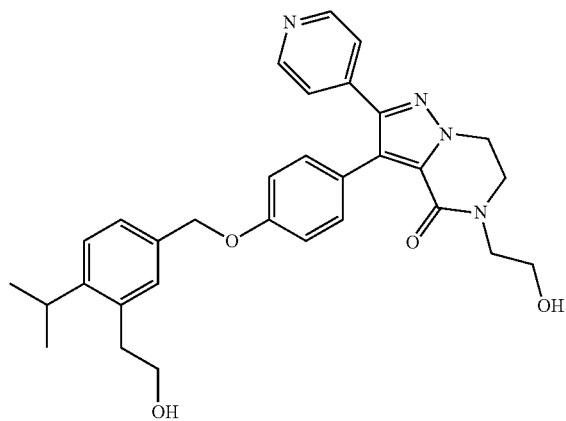 [SMILES: CC(C)c1ccc(COc2ccc(-c3c(-c4ccncc4)nn4c3C(=O)N(CCO)CC4)cc2)cc1CCO]
Compound 83; Method A85
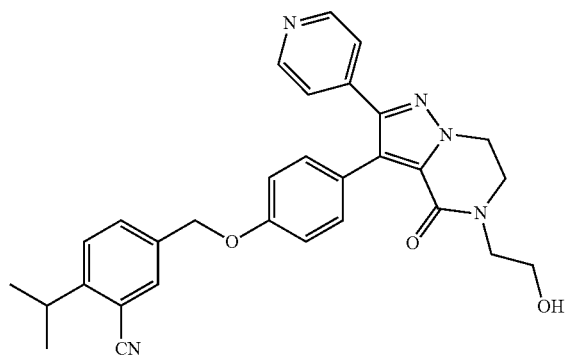 [SMILES: CC(C)c1ccc(COc2ccc(-c3c(-c4ccncc4)nn4c3C(=O)N(CCO)CC4)cc2)cc1C#N]
Compound 87; Method A88

TABLE 1-continued
Compounds
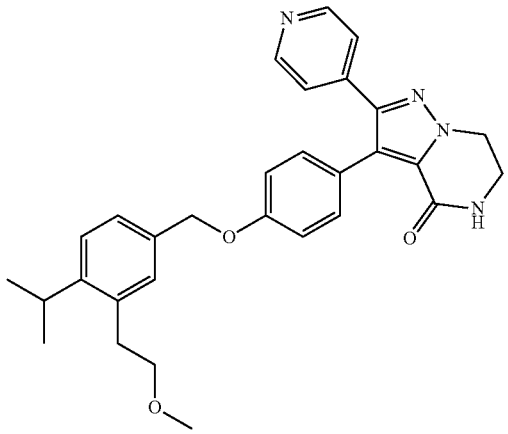 [SMILES: COCCc1cc(COc2ccc(-c3c(-c4ccncc4)nn4c3C(=O)NCC4)cc2)ccc1C(C)C]
Compound 84; Method A86
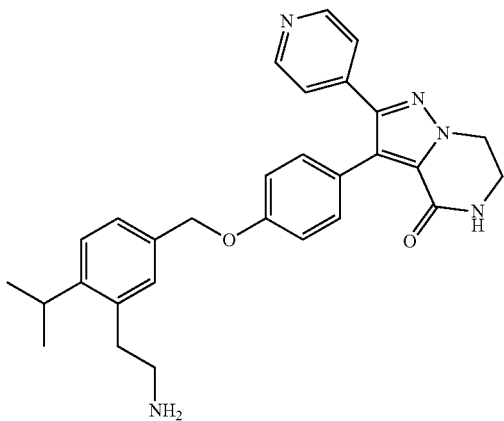 [SMILES: CC(C)c1ccc(COc2ccc(-c3c(-c4ccncc4)nn4c3C(=O)NCC4)cc2)cc1CCN]
Compound 88; Method A89
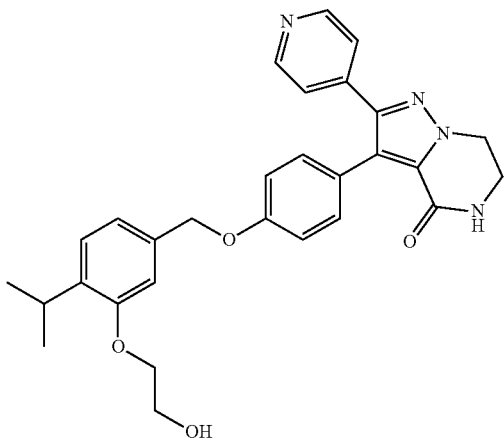 [SMILES: CC(C)c1ccc(COc2ccc(-c3c(-c4ccncc4)nn4c3C(=O)NCC4)cc2)cc1OCCO]
Compound 89; Method A90

TABLE 1-continued
Compounds
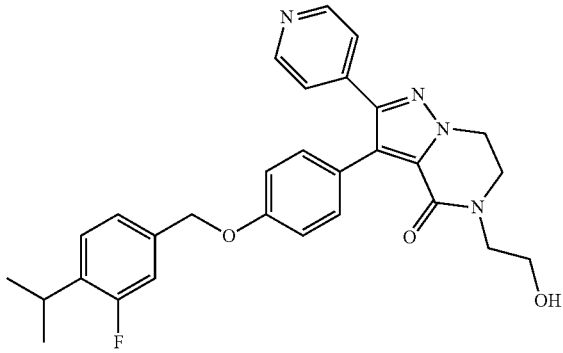 [SMILES: CC(C)c1ccc(COc2ccc(-c3c(-c4ccncc4)nn4c3C(=O)N(CCO)CC4)cc2)cc1F]
Compound 93; Method A94
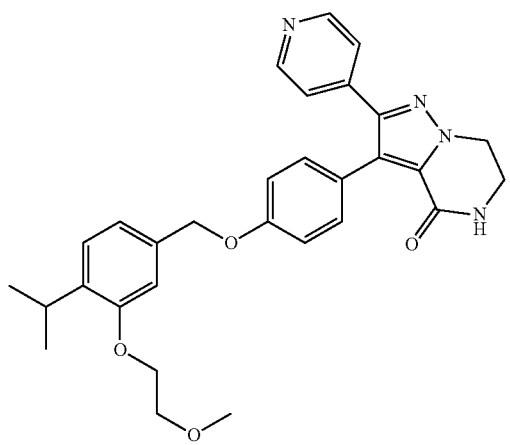 [SMILES: COCCOc1cc(COc2ccc(-c3c(-c4ccncc4)nn4c3C(=O)NCC4)cc2)ccc1C(C)C]
Compound 90; 90; Method A91
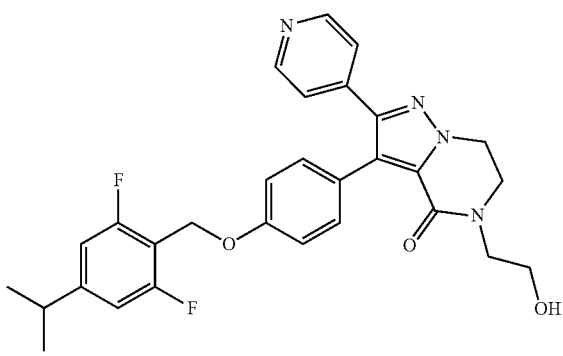 [SMILES: CC(C)c1cc(F)c(COc2ccc(-c3c(-c4ccncc4)nn4c3C(=O)N(CCO)CC4)cc2)c(F)c1]
Compound 94; Method A95

TABLE 1-continued
Compounds
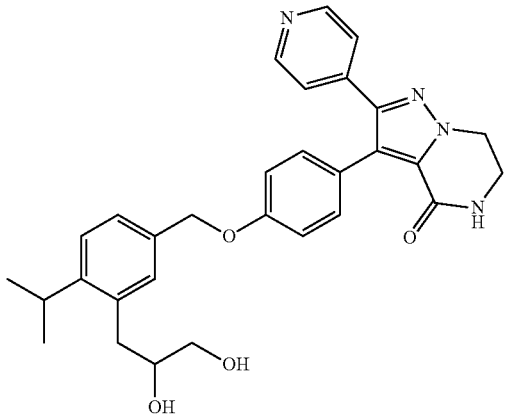 [SMILES: CC(C)c1ccc(COc2ccc(-c3c(-c4ccncc4)nn4c3C(=O)NCC4)cc2)cc1CC(O)CO]
Compound 91; Method A92
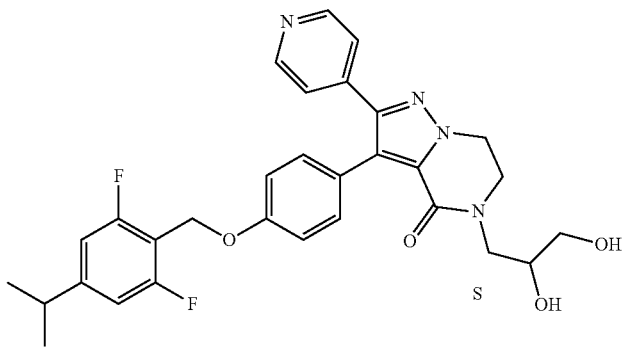
Compound 95; Method A96
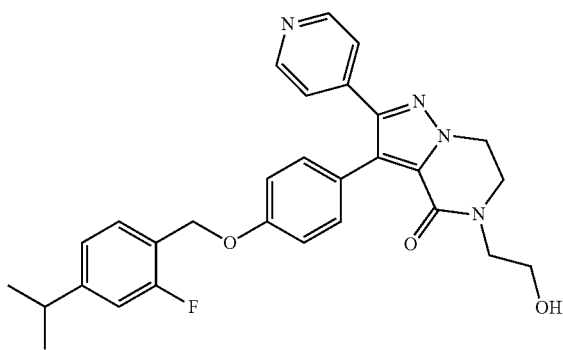 [SMILES: CC(C)c1ccc(COc2ccc(-c3c(-c4ccncc4)nn4c3C(=O)N(CCO)CC4)cc2)c(F)c1]
Compound 92; Method A93
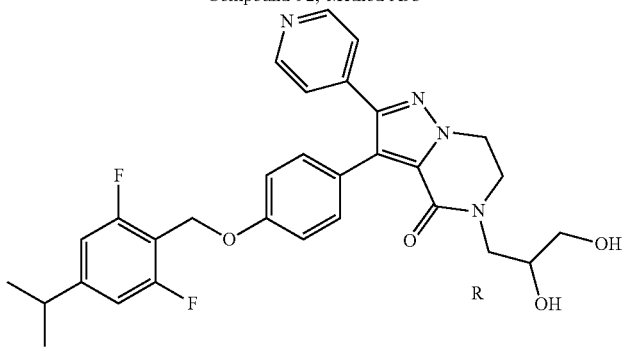
Compound 96; Method A97

TABLE 1-continued
Compounds
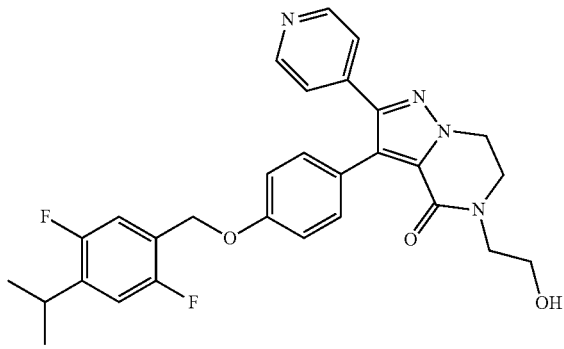 [SMILES: CC(C)c1cc(F)c(COc2ccc(-c3c(-c4ccncc4)nn4c3C(=O)N(CCO)CC4)cc2)cc1F]
Compound 97; Method A98
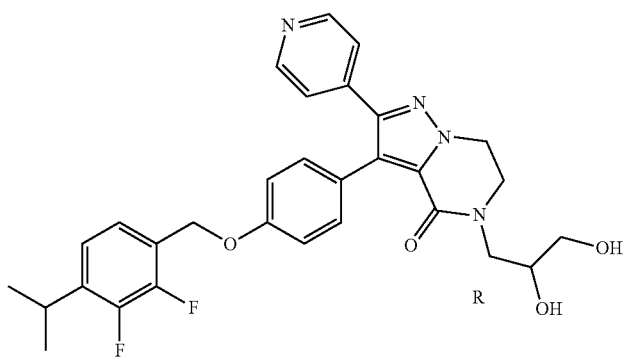
Compound 102; Method A103
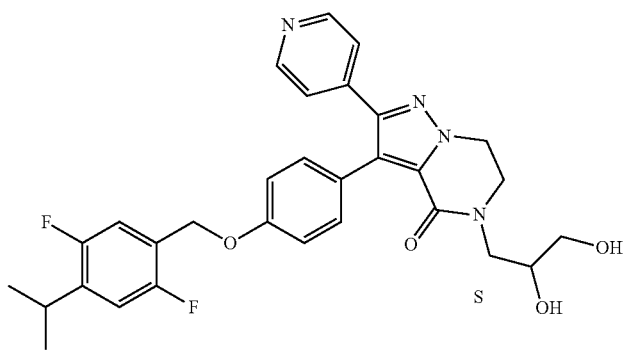
Compound 98; Method A99
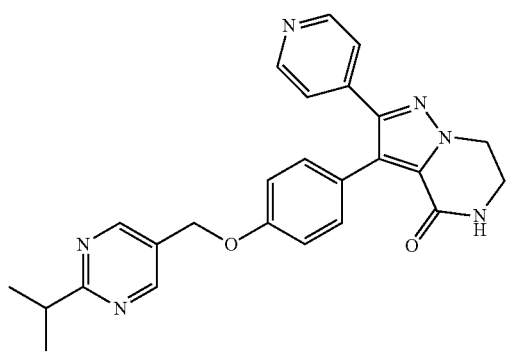 [SMILES: CC(C)c1ncc(COc2ccc(-c3c(-c4ccncc4)nn4c3C(=O)NCC4)cc2)cn1]
Compound 103; Method A104

TABLE 1-continued
Compounds
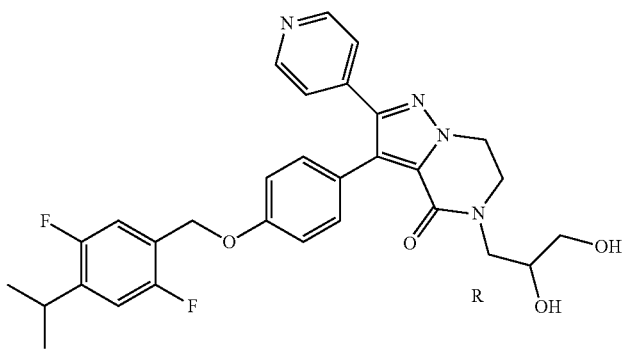
Compound 99; Method A100
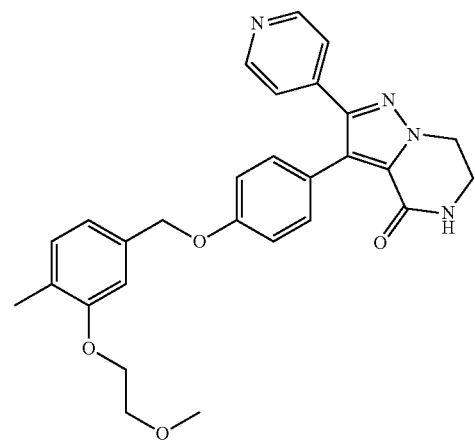 [SMILES: COCCOc1cc(COc2ccc(-c3c(-c4ccncc4)nn4c3C(=O)NCC4)cc2)ccc1C]
Compound 104; Method A105
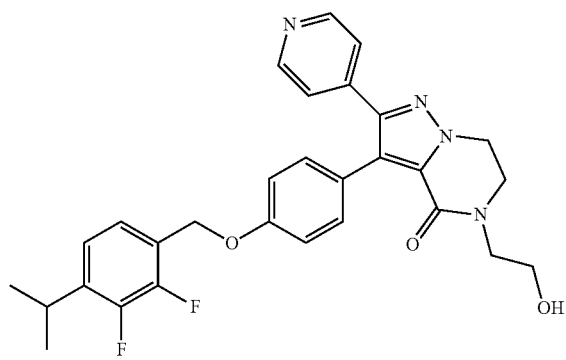 [SMILES: CC(C)c1ccc(COc2ccc(-c3c(-c4ccncc4)nn4c3C(=O)N(CCO)CC4)cc2)c(F)c1F]
Compound 100; Method A101
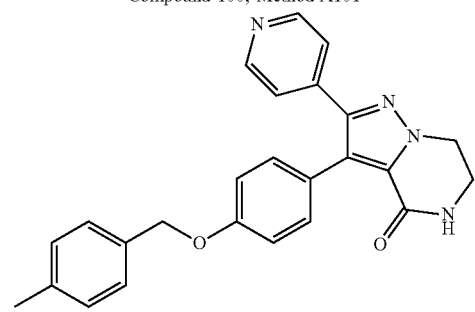
Compound 105; Method A106

TABLE 1-continued
Compounds
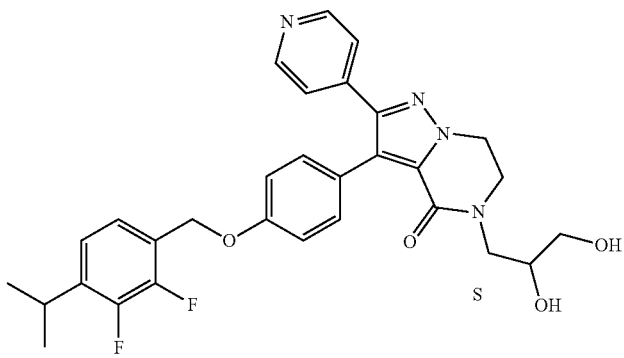
Compound 101; Method A102
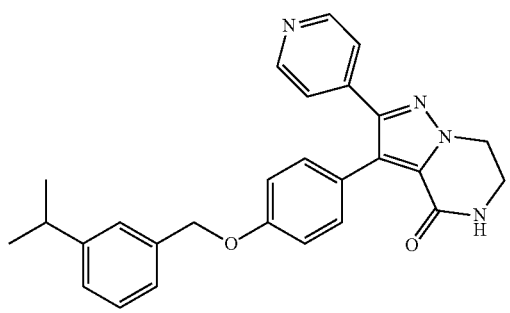 [SMILES: CC(C)c1cccc(COc2ccc(-c3c(-c4ccncc4)nn4c3C(=O)NCC4)cc2)c1]
Compound 110; Method A111
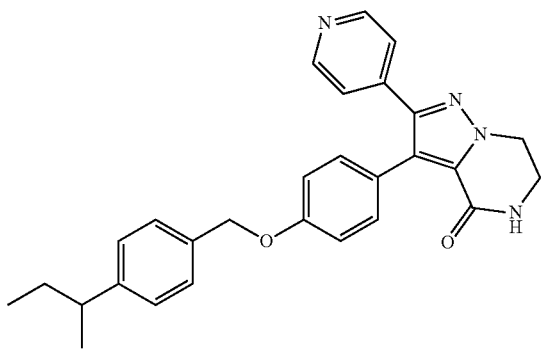 [SMILES: CCC(C)c1ccc(COc2ccc(-c3c(-c4ccncc4)nn4c3C(=O)NCC4)cc2)cc1]
Compound 106; Method A107
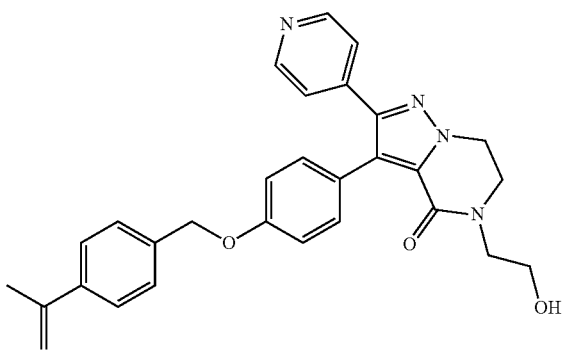
Compound 111; Method A112

TABLE 1-continued
Compounds
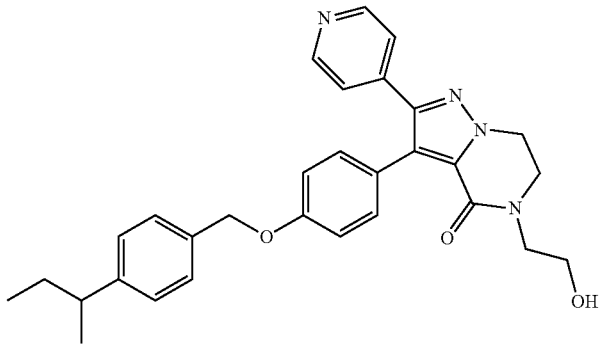 [SMILES: CCC(C)c1ccc(COc2ccc(-c3c(-c4ccncc4)nn4c3C(=O)N(CCO)CC4)cc2)cc1]
Compound 107; Method A108
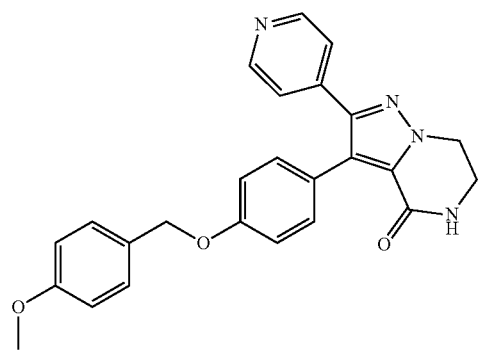 [SMILES: COc1ccc(COc2ccc(-c3c(-c4ccncc4)nn4c3C(=O)NCC4)cc2)cc1]
Compound 112; Method A113
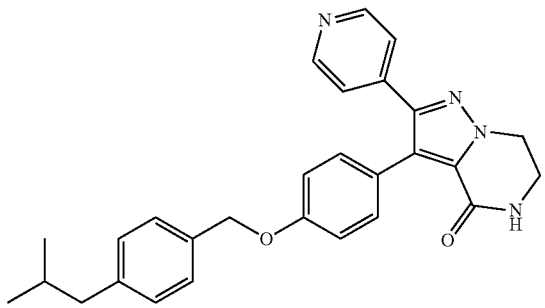 [SMILES: CC(C)Cc1ccc(COc2ccc(-c3c(-c4ccncc4)nn4c3C(=O)NCC4)cc2)cc1]
Compound 108; Method A109
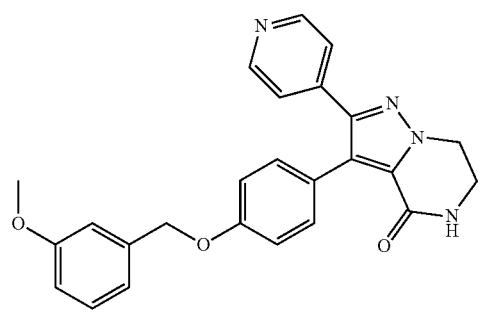 [SMILES: COc1cccc(COc2ccc(-c3c(-c4ccncc4)nn4c3C(=O)NCC4)cc2)c1]
Compound 113; Method A114

TABLE 1-continued
Compounds
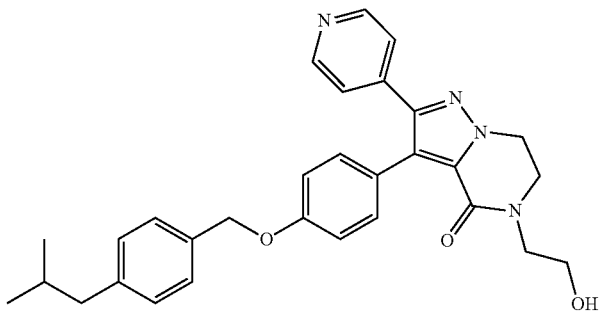 [SMILES: CC(C)Cc1ccc(COc2ccc(-c3c(-c4ccncc4)nn4c3C(=O)N(CCO)CC4)cc2)cc1]
Compound 109; Method A110
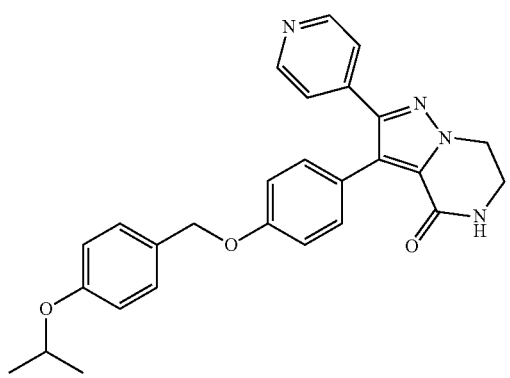 [SMILES: CC(C)Oc1ccc(COc2ccc(-c3c(-c4ccncc4)nn4c3C(=O)NCC4)cc2)cc1]
Compound 114; Method A115
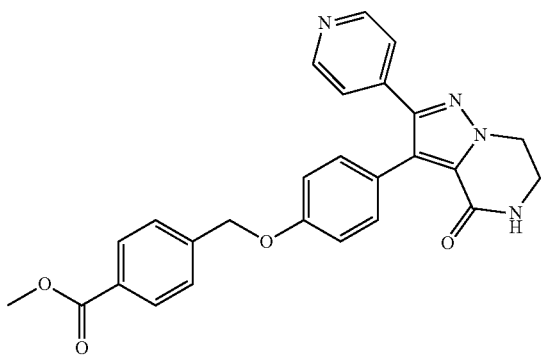 [SMILES: COC(=O)c1ccc(COc2ccc(-c3c(-c4ccncc4)nn4c3C(=O)NCC4)cc2)cc1]
Compound 9a; Method A14
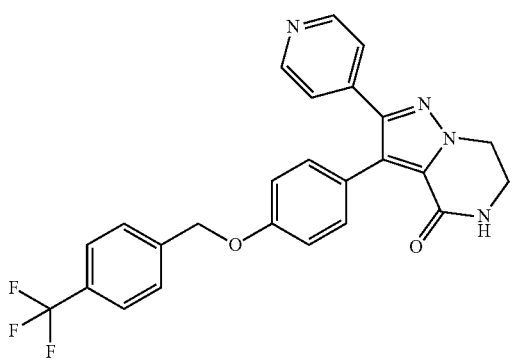 [SMILES: O=C1NCCn2nc(-c3ccncc3)c(-c3ccc(OCc4ccc(C(F)(F)F)cc4)cc3)c21]
Compound 119; Method A120

TABLE 1-continued
Compounds
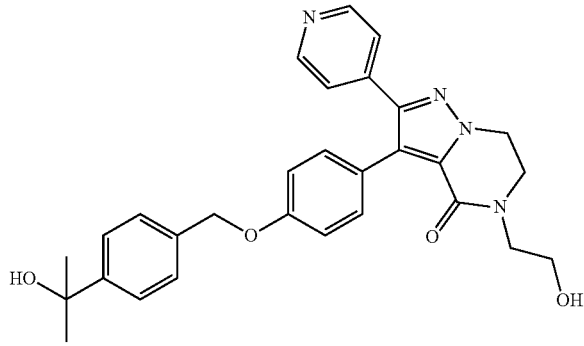 [SMILES: CC(C)(O)c1ccc(COc2ccc(-c3c(-c4ccncc4)nn4c3C(=O)N(CCO)CC4)cc2)cc1]
Compound 115; Method A116
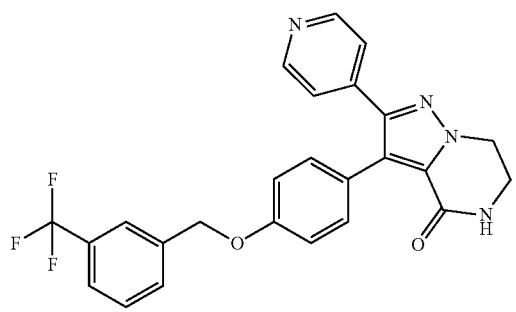 [SMILES: O=C1NCCn2nc(-c3ccncc3)c(-c3ccc(OCc4cccc(C(F)(F)F)c4)cc3)c21]
Compound 120; Method A121
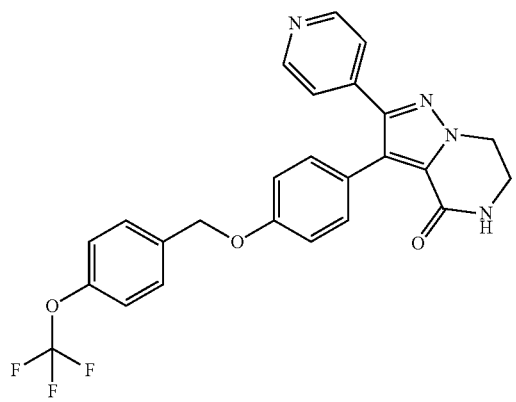 [SMILES: O=C1NCCn2nc(-c3ccncc3)c(-c3ccc(OCc4ccc(OC(F)(F)F)cc4)cc3)c21]
Compound 116; Method A117
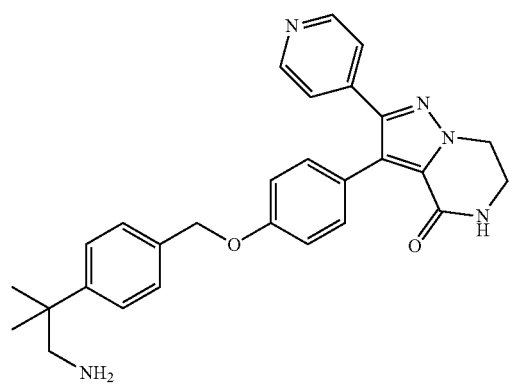 [SMILES: CC(C)(CN)c1ccc(COc2ccc(-c3c(-c4ccncc4)nn4c3C(=O)NCC4)cc2)cc1]
Compound 121; Method A122

TABLE 1-continued
Compounds
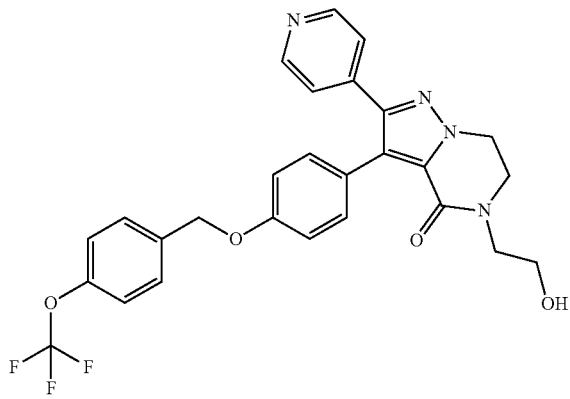 [SMILES: O=C1c2c(-c3ccc(OCc4ccc(OC(F)(F)F)cc4)cc3)c(-c3ccncc3)nn2CCN1CCO]
Compound 117; Method A118
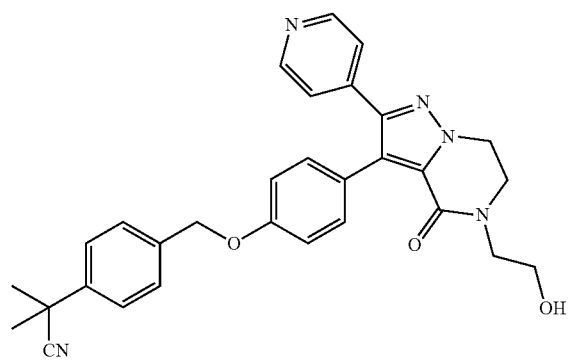 [SMILES: CC(C)(C#N)c1ccc(COc2ccc(-c3c(-c4ccncc4)nn4c3C(=O)N(CCO)CC4)cc2)cc1]
Compound 122; Method A123
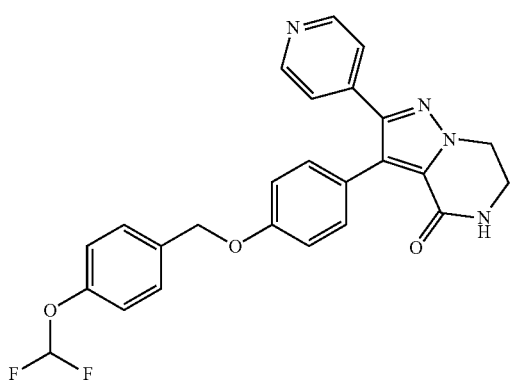 [SMILES: O=C1NCCn2nc(-c3ccncc3)c(-c3ccc(OCc4ccc(OC(F)F)cc4)cc3)c21]
Compound 118; Method A119

TABLE 1-continued
Compounds
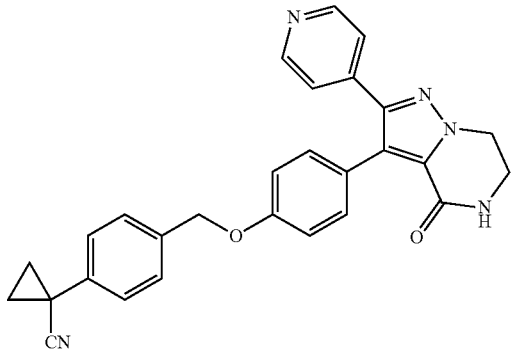 [SMILES: N#CC1(c2ccc(COc3ccc(-c4c(-c5ccncc5)nn5c4C(=O)NCC5)cc3)cc2)CC1]
Compound 123; Method A124
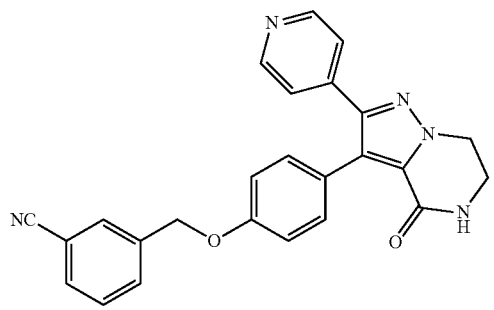 [SMILES: N#Cc1cccc(COc2ccc(-c3c(-c4ccncc4)nn4c3C(=O)NCC4)cc2)c1]
Compound 124; Method A125
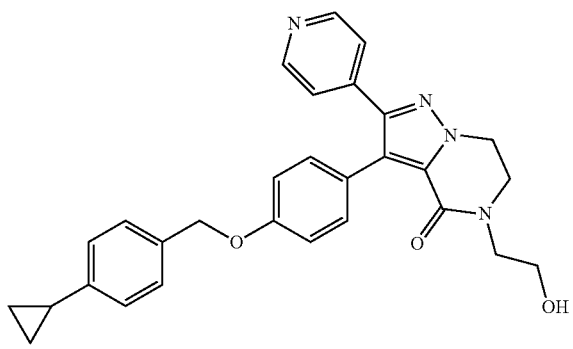
Compound 129 ; Method A130
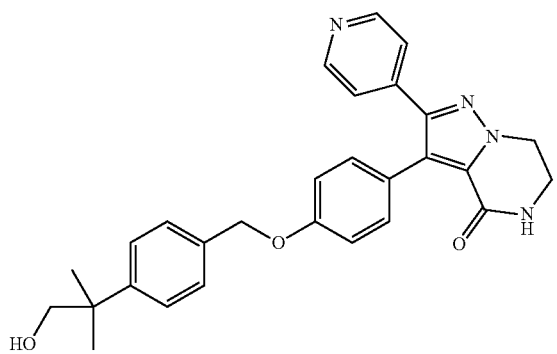 [SMILES: CC(C)(CO)c1ccc(COc2ccc(-c3c(-c4ccncc4)nn4c3C(=O)NCC4)cc2)cc1]
Compound 125; Method A126

TABLE 1-continued
Compounds
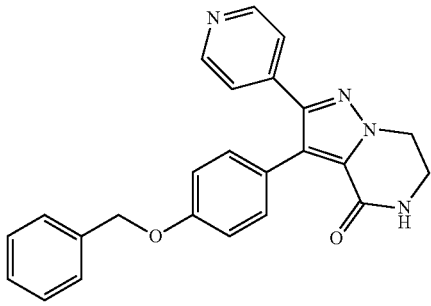 [SMILES: O=C1NCCn2nc(-c3ccncc3)c(-c3ccc(OCc4ccccc4)cc3)c21]
Compound 130; Method A131
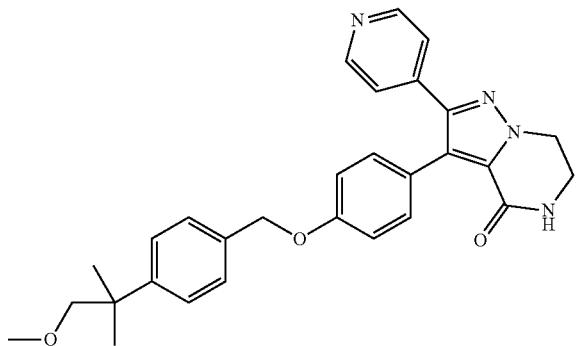 [SMILES: COCC(C)(C)c1ccc(COc2ccc(-c3c(-c4ccncc4)nn4c3C(=O)NCC4)cc2)cc1]
Compound 126; Method A127
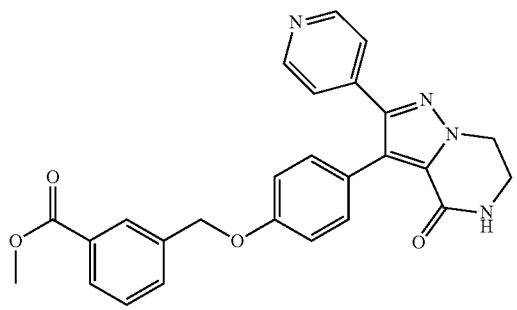 [SMILES: COC(=O)c1cccc(COc2ccc(-c3c(-c4ccncc4)nn4c3C(=O)NCC4)cc2)c1]
Compound 131; Method A132
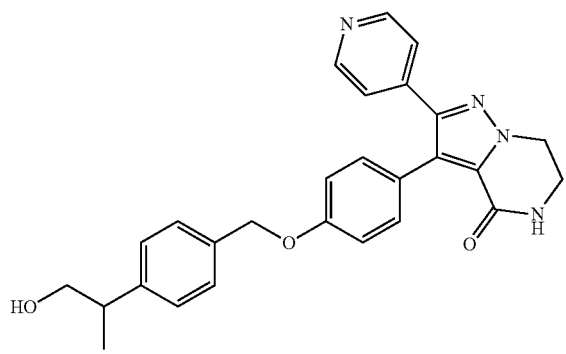 [SMILES: CC(CO)c1ccc(COc2ccc(-c3c(-c4ccncc4)nn4c3C(=O)NCC4)cc2)cc1]
Compound 127; Method A128

US 10,280,170 B2
453
454
TABLE 1-continued
Compounds
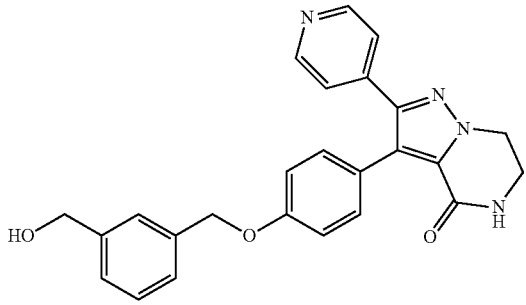 [SMILES: O=C1NCCn2nc(-c3ccncc3)c(-c3ccc(OCc4cccc(CO)c4)cc3)c21]
Compound 132; Method A133
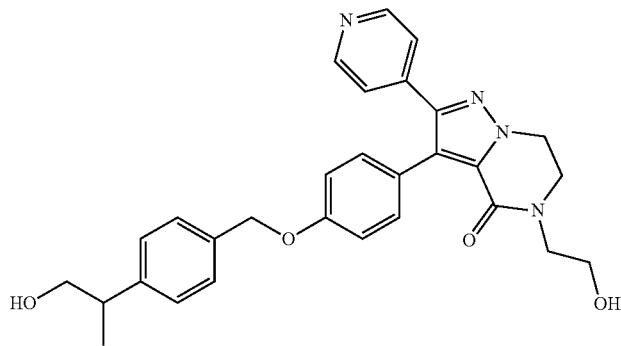 [SMILES: CC(CO)c1ccc(COc2ccc(-c3c(-c4ccncc4)nn4c3C(=O)N(CCO)CC4)cc2)cc1]
Compound 128; Method A129
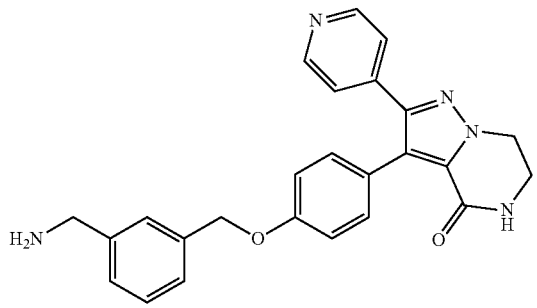 [SMILES: NCc1cccc(COc2ccc(-c3c(-c4ccncc4)nn4c3C(=O)NCC4)cc2)c1]
Compound 133; Method A133
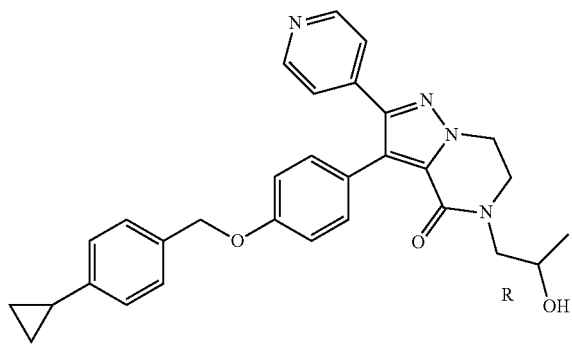
Compound 134; Method A134

TABLE 1-continued
Compounds
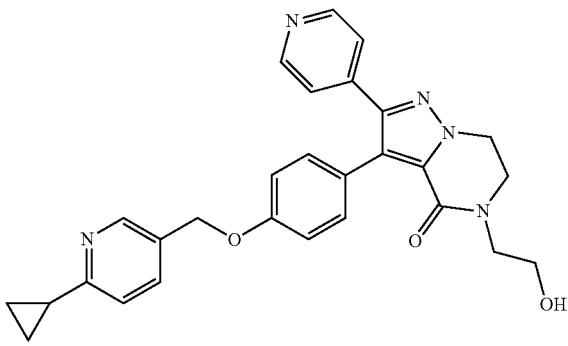 [SMILES: O=C1c2c(-c3ccc(OCc4ccc(C5CC5)nc4)cc3)c(-c3ccncc3)nn2CCN1CCO]
Compound 139; Method A139
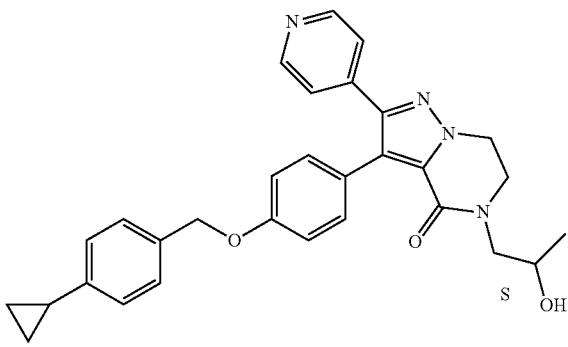
Compound 135; Method A135
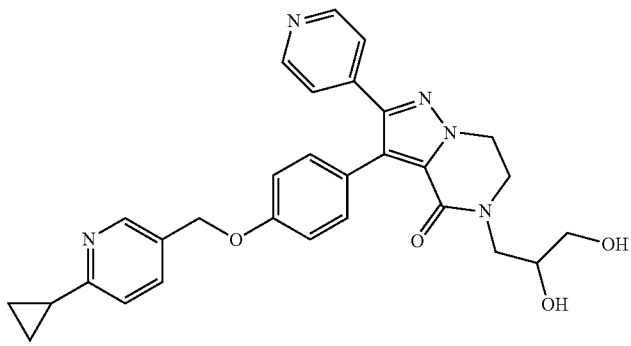 [SMILES: O=C1c2c(-c3ccc(OCc4ccc(C5CC5)nc4)cc3)c(-c3ccncc3)nn2CCN1CC(O)CO]
Compound 140; Method A140
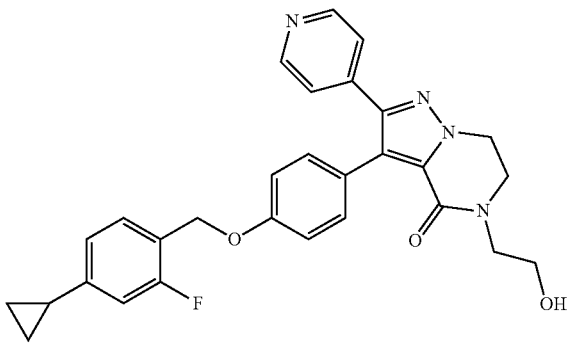 [SMILES: O=C1c2c(-c3ccc(OCc4ccc(C5CC5)cc4F)cc3)c(-c3ccncc3)nn2CCN1CCO]
Compound 136; Method A136

TABLE 1-continued

Compounds

Compound 141; Method A141

Compound 137; Method A137

Compound 142; Method A142

Compound 138; Method A138

TABLE 1-continued
Compounds
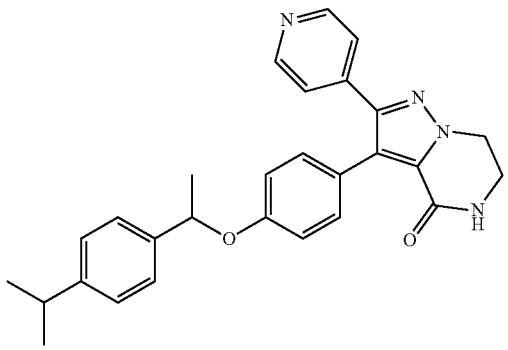 [SMILES: CC(C)c1ccc(C(C)Oc2ccc(-c3c(-c4ccncc4)nn4c3C(=O)NCC4)cc2)cc1]
Compound 143; Method A143
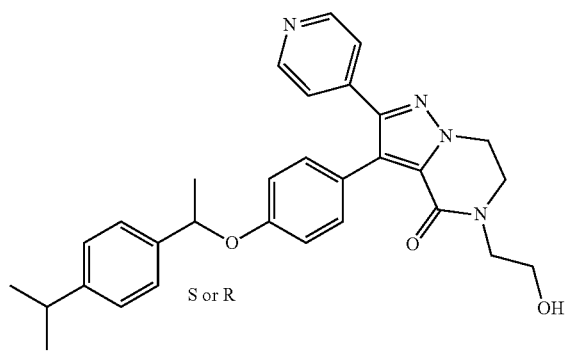 [SMILES: CC(C)c1ccc(C(C)Oc2ccc(-c3c(-c4ccncc4)nn4c3C(=O)N(CCO)CC4)cc2)cc1]
S or R
Compound 144; Method A144
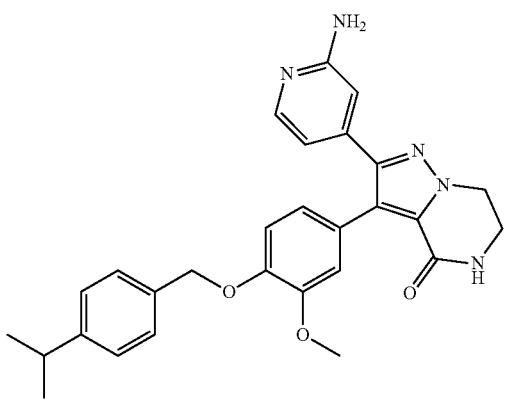 [SMILES: COc1cc(-c2c(-c3ccnc(N)c3)nn3c2C(=O)NCC3)ccc1OCc1ccc(C(C)C)cc1]
Compound 149; Method A148
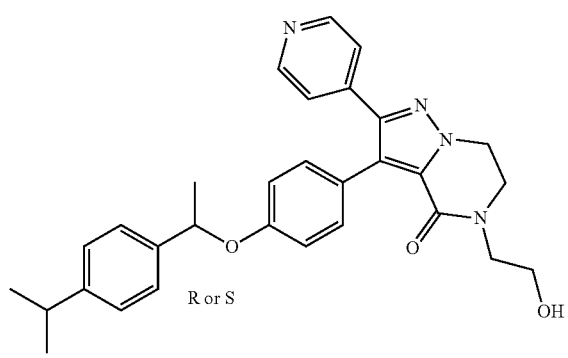 [SMILES: CC(C)c1ccc(C(C)Oc2ccc(-c3c(-c4ccncc4)nn4c3C(=O)N(CCO)CC4)cc2)cc1]
R or S
Compound 145; Method A144

TABLE 1-continued
Compounds
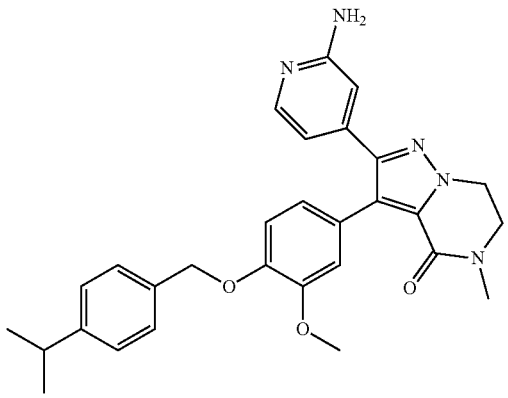 [SMILES: COc1cc(-c2c(-c3ccnc(N)c3)nn3c2C(=O)N(C)CC3)ccc1OCc1ccc(C(C)C)cc1]
Compound 150; Method A149
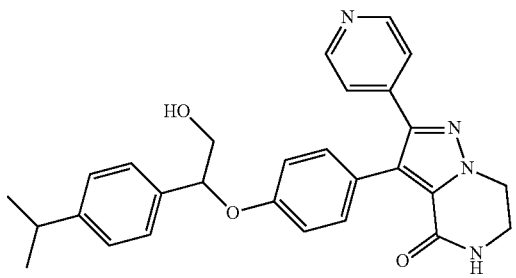 [SMILES: CC(C)c1ccc(C(CO)Oc2ccc(-c3c(-c4ccncc4)nn4c3C(=O)NCC4)cc2)cc1]
Compound 146; Method A145
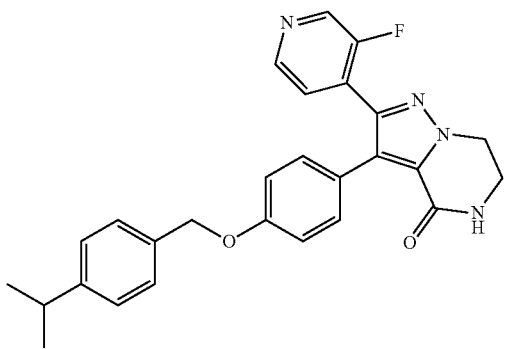 [SMILES: CC(C)c1ccc(COc2ccc(-c3c(-c4ccncc4F)nn4c3C(=O)NCC4)cc2)cc1]
Compound 151; Method A150
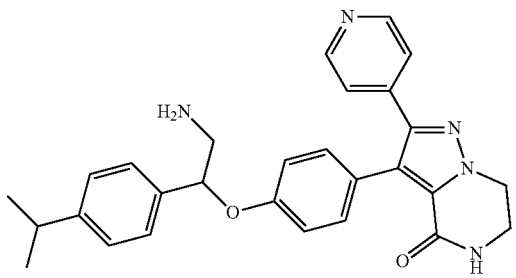 [SMILES: CC(C)c1ccc(C(CN)Oc2ccc(-c3c(-c4ccncc4)nn4c3C(=O)NCC4)cc2)cc1]
Compound 147; Method A146

TABLE 1-continued
Compounds
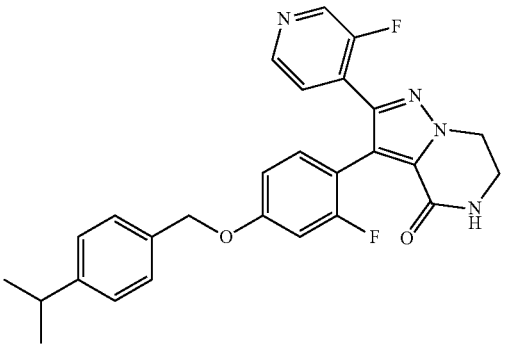 [SMILES: CC(C)c1ccc(COc2ccc(-c3c(-c4ccncc4F)nn4c3C(=O)NCC4)c(F)c2)cc1]
Compound 152; Method A151
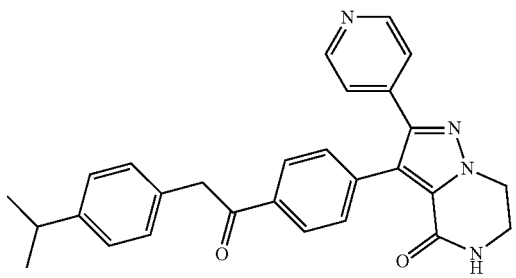 [SMILES: CC(C)c1ccc(CC(=O)c2ccc(-c3c(-c4ccncc4)nn4c3C(=O)NCC4)cc2)cc1]
Compound 148; Method A147
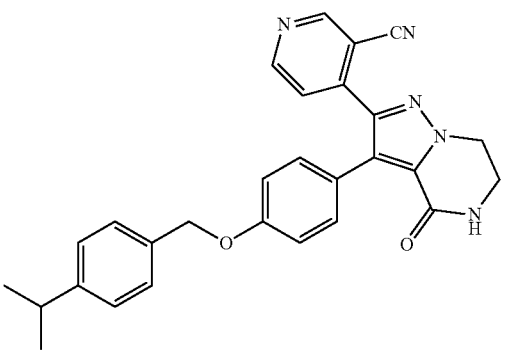 [SMILES: CC(C)c1ccc(COc2ccc(-c3c(-c4ccncc4C#N)nn4c3C(=O)NCC4)cc2)cc1]
Compound 153; Method A152
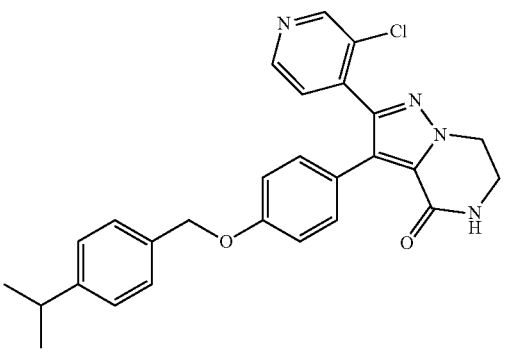
Compound 154; Method A153

TABLE 1-continued
Compounds
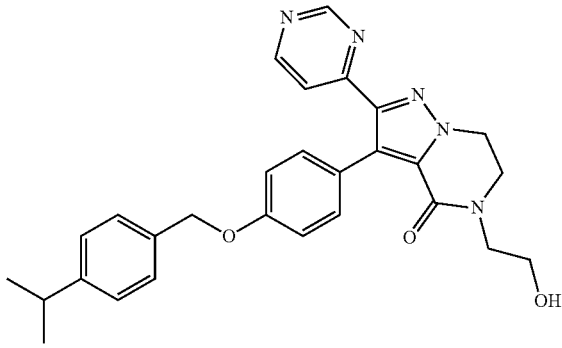 [SMILES: CC(C)c1ccc(COc2ccc(-c3c(-c4ccncn4)nn4c3C(=O)N(CCO)CC4)cc2)cc1]
Compound 159; Method A158
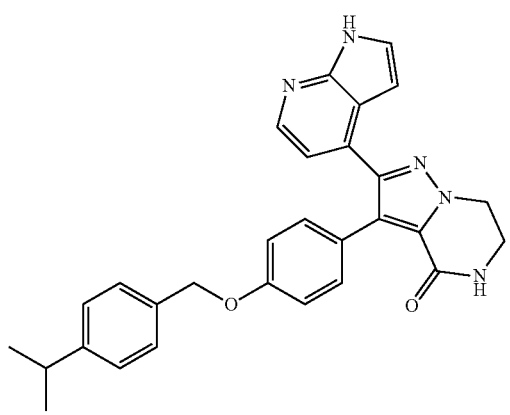 [SMILES: CC(C)c1ccc(COc2ccc(-c3c(-c4ccnc5[nH]ccc45)nn4c3C(=O)NCC4)cc2)cc1]
Compound 155; Method A154
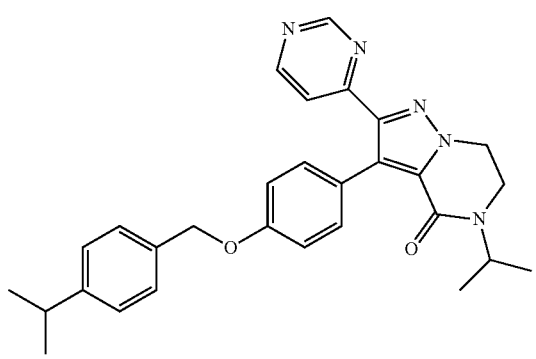 [SMILES: CC(C)c1ccc(COc2ccc(-c3c(-c4ccncn4)nn4c3C(=O)N(C(C)C)CC4)cc2)cc1]
Compound 160; Method A159

467
468
TABLE 1-continued
Compounds
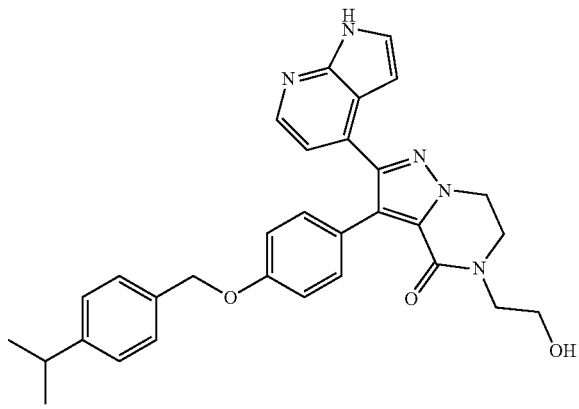 [SMILES: CC(C)c1ccc(COc2ccc(-c3c(-c4ccnc5[nH]ccc45)nn4c3C(=O)N(CCO)CC4)cc2)cc1]
Compound 156; Method A155
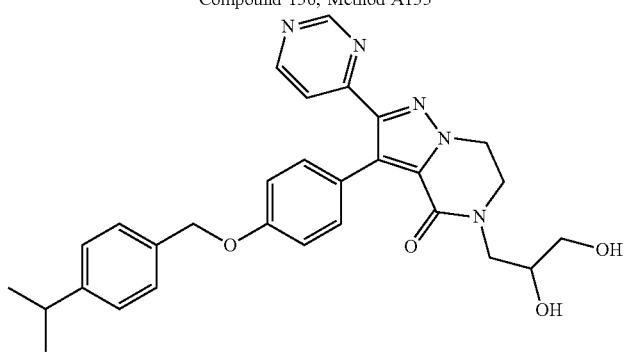
Compound 161; Method A160
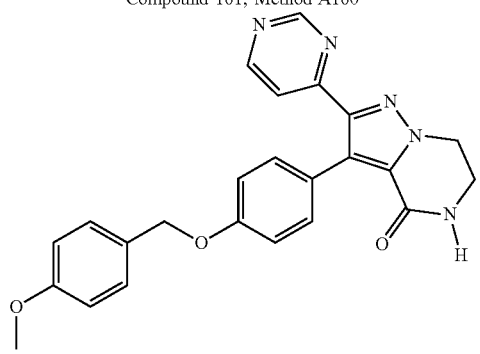
Compound 157; Method A156
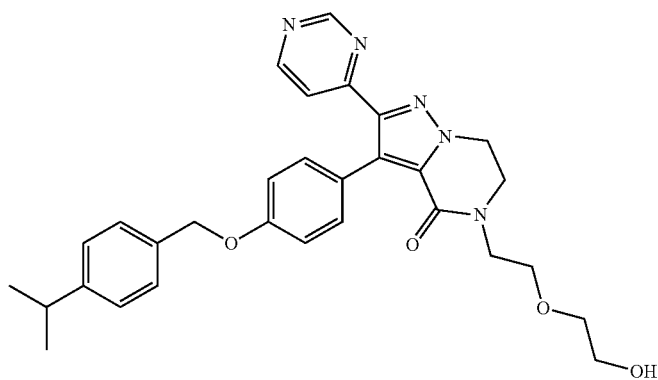 [SMILES: CC(C)c1ccc(COc2ccc(-c3c(-c4ccncn4)nn4c3C(=O)N(CCOCCO)CC4)cc2)cc1]
Compound 162; Method A161

TABLE 1-continued
Compounds
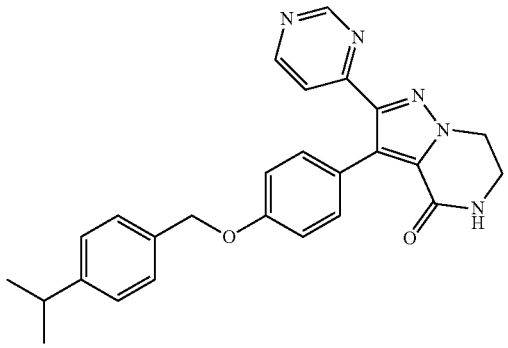 [SMILES: CC(C)c1ccc(COc2ccc(-c3c(-c4ccncn4)nn4c3C(=O)NCC4)cc2)cc1]
Compound 158; Method A157
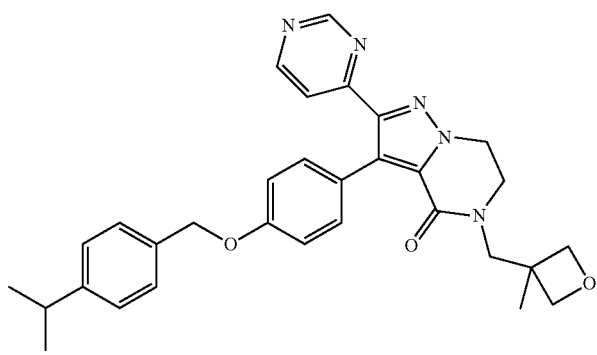 [SMILES: CC(C)c1ccc(COc2ccc(-c3c(-c4ccncn4)nn4c3C(=O)N(CC3(C)COC3)CC4)cc2)cc1]
Compound 163; Method A162
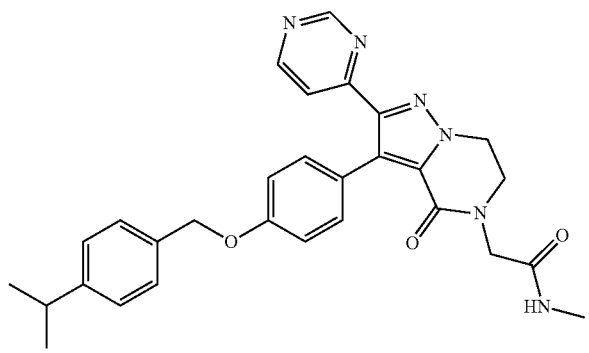 [SMILES: CNC(=O)CN1CCn2nc(-c3ccncn3)c(-c3ccc(OCc4ccc(C(C)C)cc4)cc3)c2C1=O]
Compound 164; Method A163
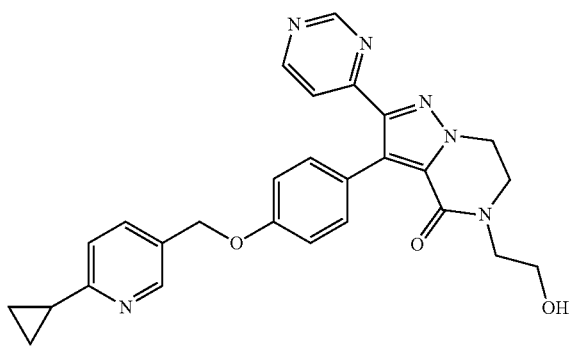 [SMILES: O=C1c2c(-c3ccc(OCc4ccc(C5CC5)nc4)cc3)c(-c3ccncn3)nn2CCN1CCO]
Compound 169; Method A168

TABLE 1-continued
Compounds
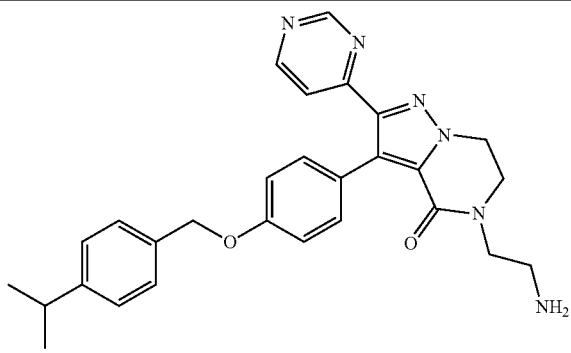
Compound 165; Method A164
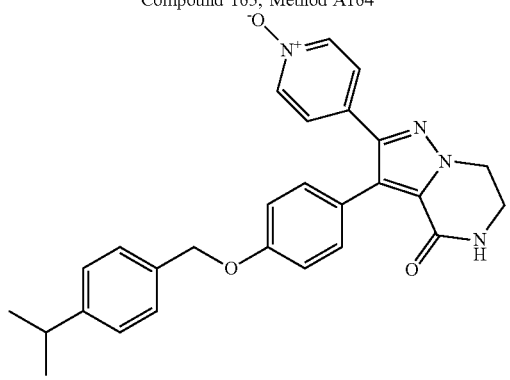
Compound 170; Method A169
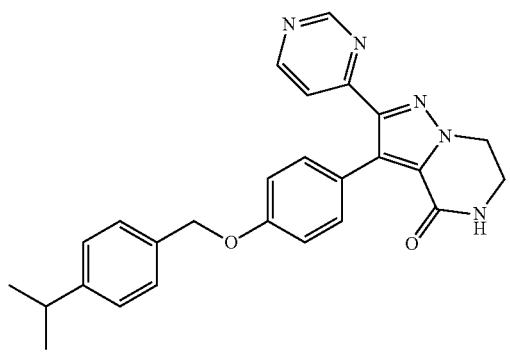 [SMILES: CC(C)c1ccc(COc2ccc(-c3c(-c4ccncn4)nn4c3C(=O)NCC4)cc2)cc1]
Compound 166; Method A165
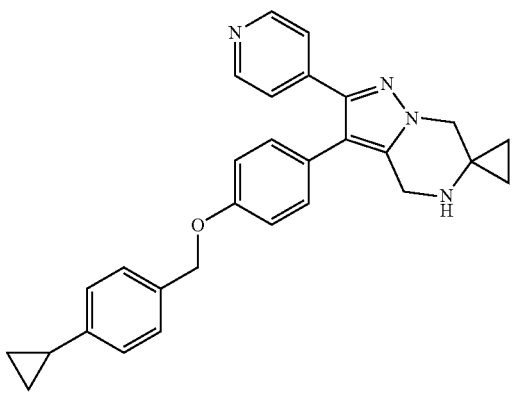 [SMILES: c1cc(-c2nn3c(c2-c2ccc(OCc4ccc(C5CC5)cc4)cc2)CNC2(CC2)C3)ccn1]
Compound 171; Method A170

473
TABLE 1-continued
Compounds
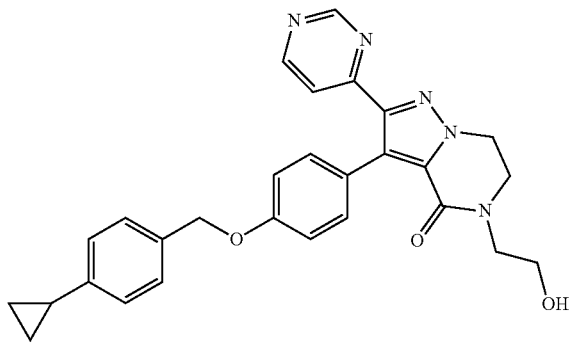
Compound 167; Method A166
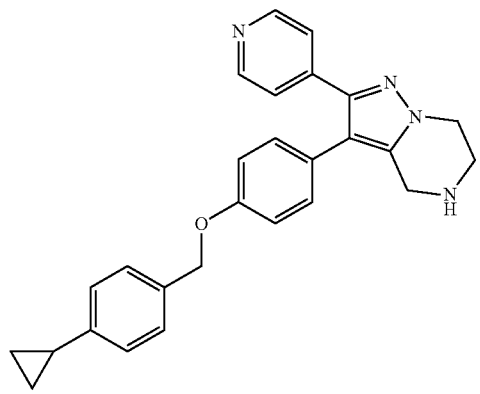 [SMILES: c1cc(-c2nn3c(c2-c2ccc(OCc4ccc(C5CC5)cc4)cc2)CNCC3)ccn1]
Compound 172; Method A171
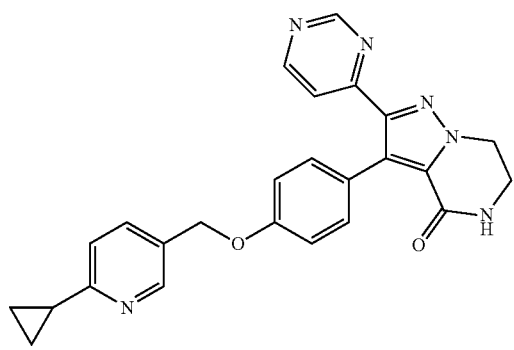 [SMILES: O=C1NCCn2nc(-c3ccncn3)c(-c3ccc(OCc4ccc(C5CC5)nc4)cc3)c21]
Compound 168; Method A167

TABLE 1-continued
Compounds
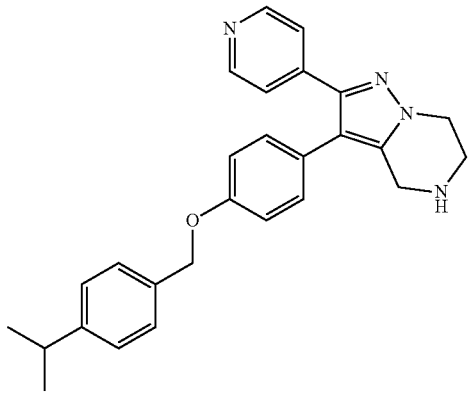 [SMILES: CC(C)c1ccc(COc2ccc(-c3c(-c4ccncc4)nn4c3CNCC4)cc2)cc1]
Compound 173; Method A172
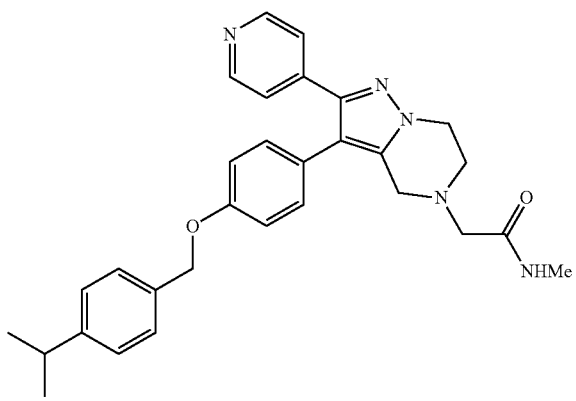 [SMILES: CNC(=O)CN1CCn2nc(-c3ccncc3)c(-c3ccc(OCc4ccc(C(C)C)cc4)cc3)c2C1]
Compound 174; Method A173
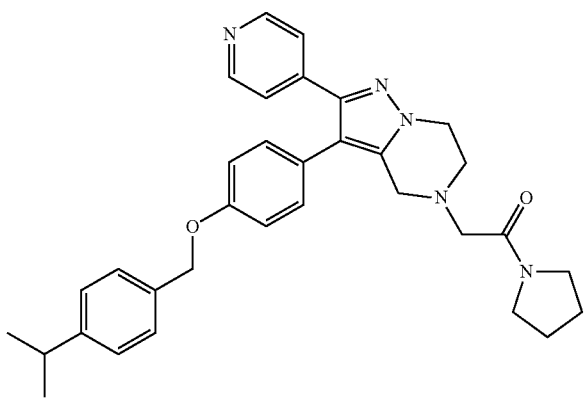 [SMILES: CC(C)c1ccc(COc2ccc(-c3c(-c4ccncc4)nn4c3CN(CC(=O)N3CCCC3)CC4)cc2)cc1]
Compound 179; Method A178

477
TABLE 1-continued
Compounds
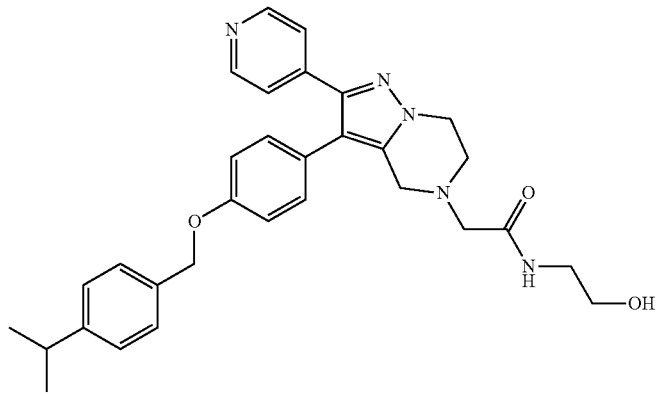 [SMILES: CC(C)c1ccc(COc2ccc(-c3c(-c4ccncc4)nn4c3CN(CC(=O)NCCO)CC4)cc2)cc1]
Compound 175; Method A174
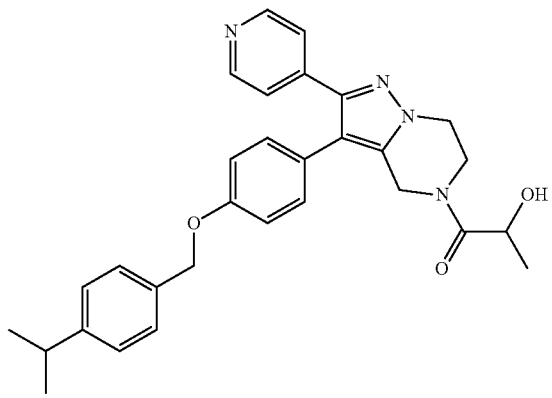 [SMILES: CC(O)C(=O)N1CCn2nc(-c3ccncc3)c(-c3ccc(OCc4ccc(C(C)C)cc4)cc3)c2C1]
Compound 180; Method A179
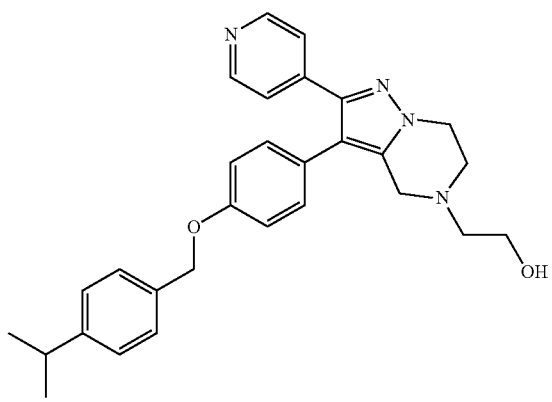 [SMILES: CC(C)c1ccc(COc2ccc(-c3c(-c4ccncc4)nn4c3CN(CCO)CC4)cc2)cc1]
Compound 176; Method A175

TABLE 1-continued
Compounds
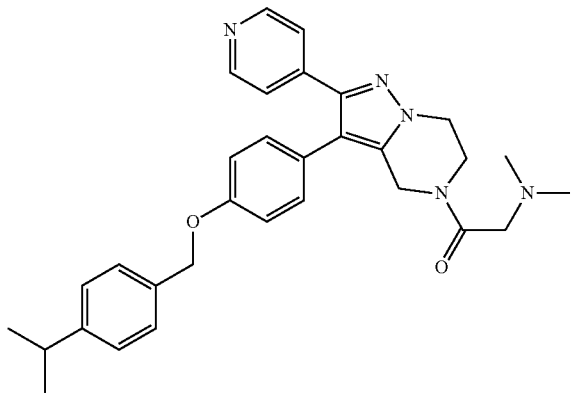 [SMILES: CC(C)c1ccc(COc2ccc(-c3c(-c4ccncc4)nn4c3CN(C(=O)CN(C)C)CC4)cc2)cc1]
Compound 181; Method A180
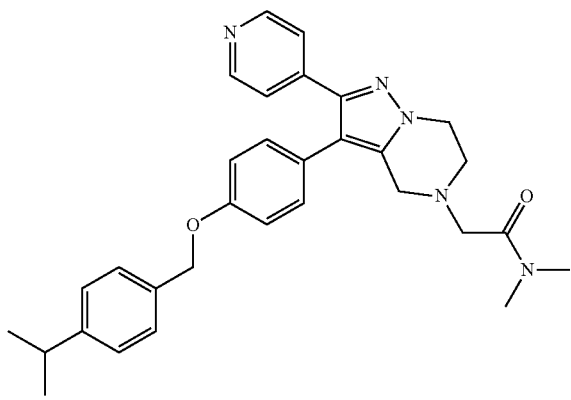 [SMILES: CC(C)c1ccc(COc2ccc(-c3c(-c4ccncc4)nn4c3CN(CC(=O)N(C)C)CC4)cc2)cc1]
Compound 177; Method A176
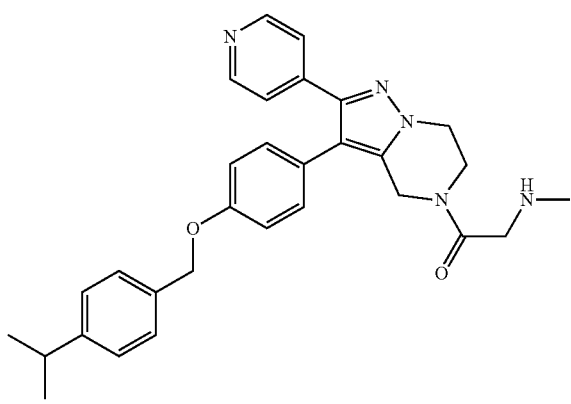 [SMILES: CNCC(=O)N1CCn2nc(-c3ccncc3)c(-c3ccc(OCc4ccc(C(C)C)cc4)cc3)c2C1]
Compound 182; Method A181

TABLE 1-continued
Compounds
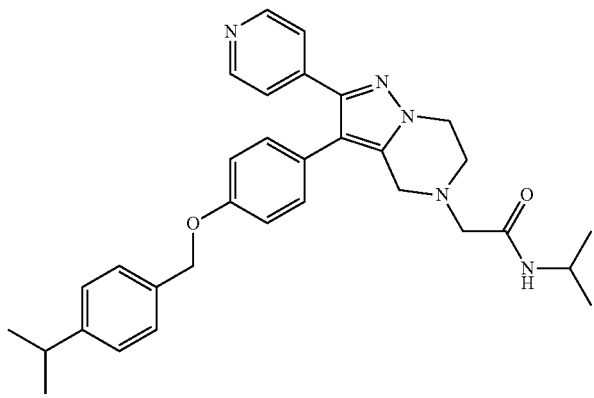 [SMILES: CC(C)NC(=O)CN1CCn2nc(-c3ccncc3)c(-c3ccc(OCc4ccc(C(C)C)cc4)cc3)c2C1]
Compound 178; Method A177
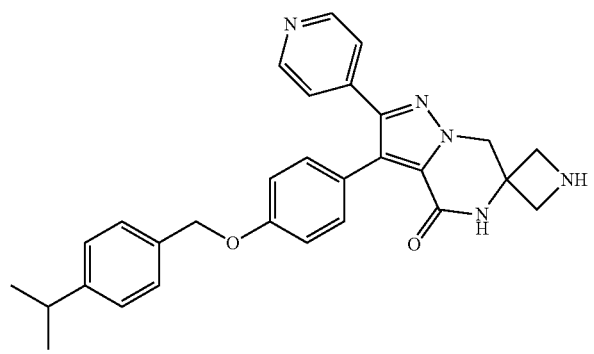 [SMILES: CC(C)c1ccc(COc2ccc(-c3c(-c4ccncc4)nn4c3C(=O)NC3(CNC3)C4)cc2)cc1]
Compound 183; Method A182
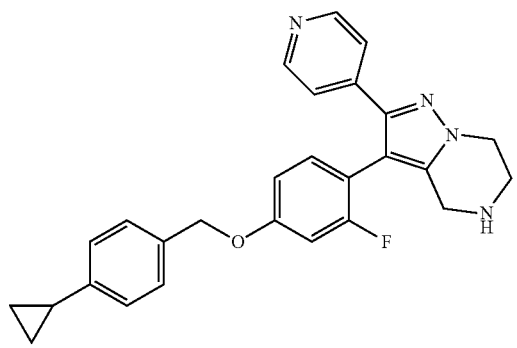 [SMILES: Fc1cc(OCc2ccc(C3CC3)cc2)ccc1-c1c(-c2ccncc2)nn2c1CNCC2]
Compound 184; Method A183
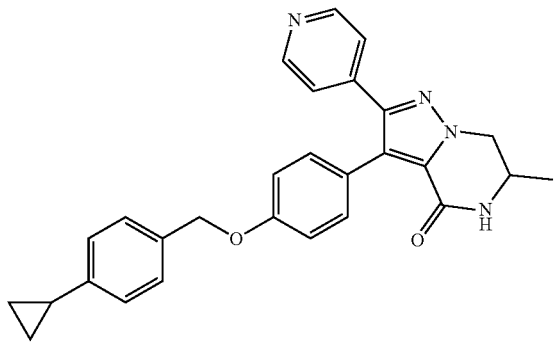 [SMILES: CC1Cn2nc(-c3ccncc3)c(-c3ccc(OCc4ccc(C5CC5)cc4)cc3)c2C(=O)N1]
Compound 189; Method A188

TABLE 1-continued
Compounds
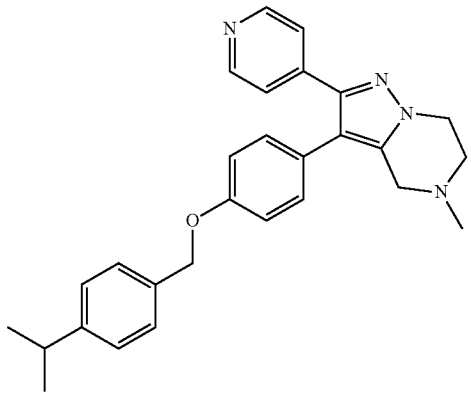 [SMILES: CC(C)c1ccc(COc2ccc(-c3c(-c4ccncc4)nn4c3CN(C)CC4)cc2)cc1]
Compound 185; Method A184
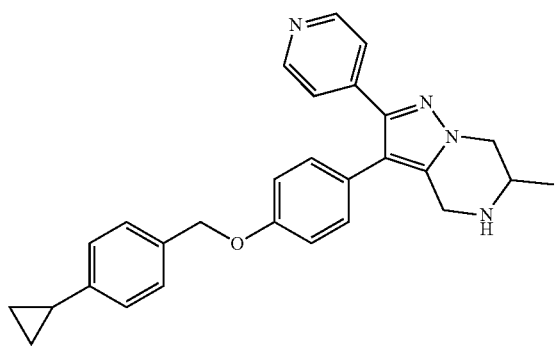 [SMILES: CC1Cn2nc(-c3ccncc3)c(-c3ccc(OCc4ccc(C5CC5)cc4)cc3)c2CN1]
Compound 190; Method A189
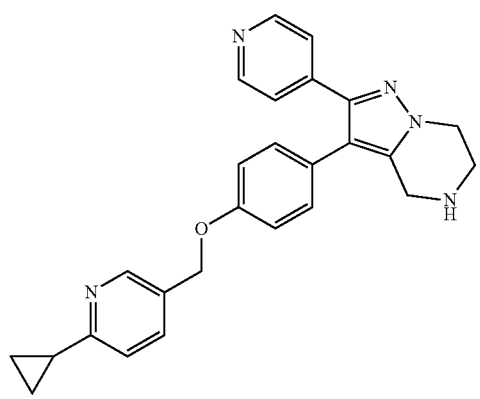 [SMILES: c1cc(-c2nn3c(c2-c2ccc(OCc4ccc(C5CC5)nc4)cc2)CNCC3)ccn1]
Compound 186; Method A185

TABLE 1-continued
Compounds
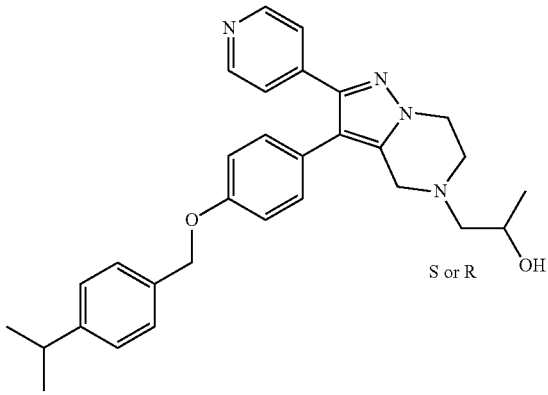 [SMILES: CC(O)CN1CCn2nc(-c3ccncc3)c(-c3ccc(OCc4ccc(C(C)C)cc4)cc3)c2C1]
Compound 191; Method A190
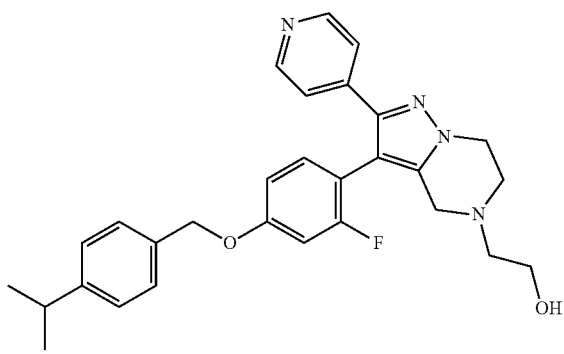 [SMILES: CC(C)c1ccc(COc2ccc(-c3c(-c4ccncc4)nn4c3CN(CCO)CC4)c(F)c2)cc1]
Compound 187; Method A186
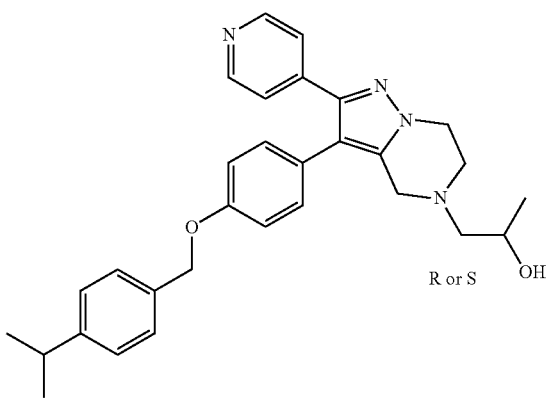 [SMILES: CC(O)CN1CCn2nc(-c3ccncc3)c(-c3ccc(OCc4ccc(C(C)C)cc4)cc3)c2C1]
Compound 192; Method A190

TABLE 1-continued
Compounds
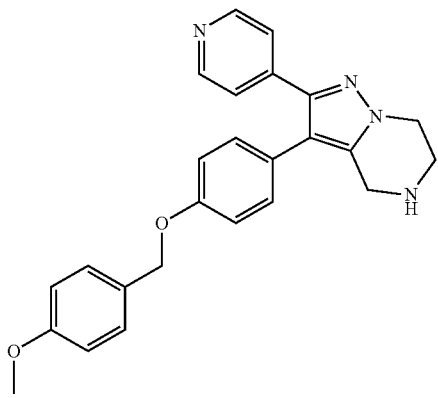 [SMILES: COc1ccc(COc2ccc(-c3c(-c4ccncc4)nn4c3CNCC4)cc2)cc1]
Compound 188; Method A187
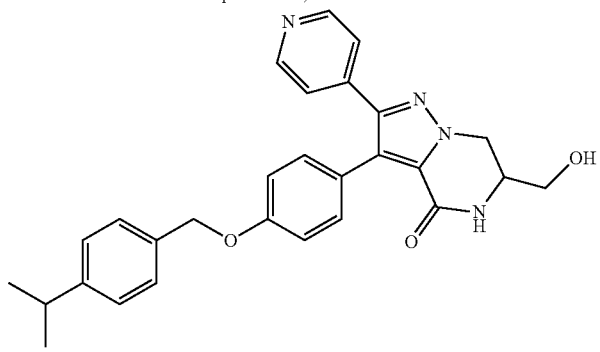
Compound 193; Method A191
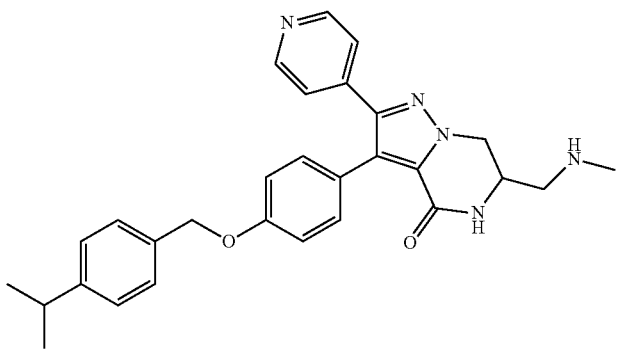 [SMILES: CNCC1Cn2nc(-c3ccncc3)c(-c3ccc(OCc4ccc(C(C)C)cc4)cc3)c2C(=O)N1]
Compound 194; Method A192
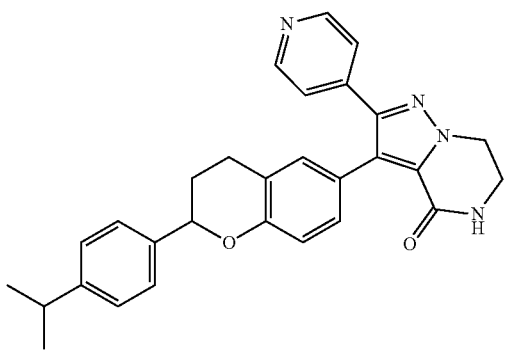
Compound 199; Method A197

TABLE 1-continued
Compounds
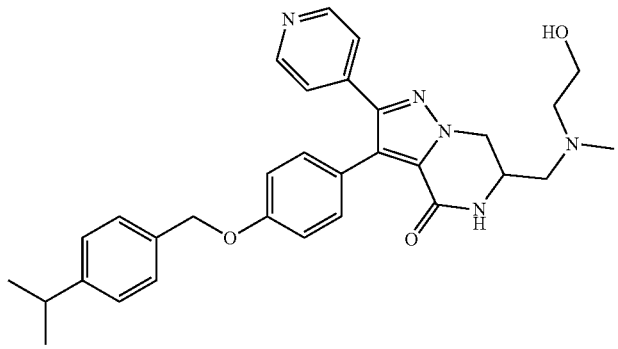 [SMILES: CC(C)c1ccc(COc2ccc(-c3c(-c4ccncc4)nn4c3C(=O)NC(CN(C)CCO)C4)cc2)cc1]
Compound 195; Method A193
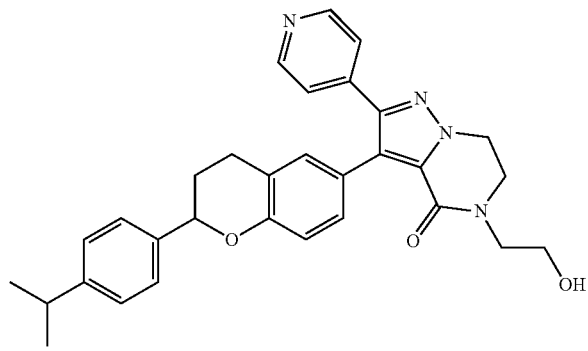 [SMILES: CC(C)c1ccc(C2CCc3cc(-c4c(-c5ccncc5)nn5c4C(=O)N(CCO)CC5)ccc3O2)cc1]
Compound 200; Method A198
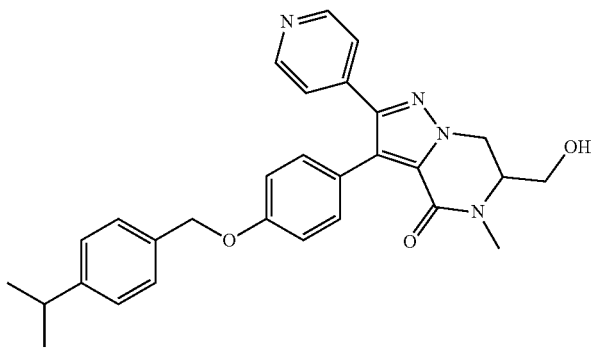 [SMILES: CC(C)c1ccc(COc2ccc(-c3c(-c4ccncc4)nn4c3C(=O)N(C)C(CO)C4)cc2)cc1]
Compound 196; Method A194
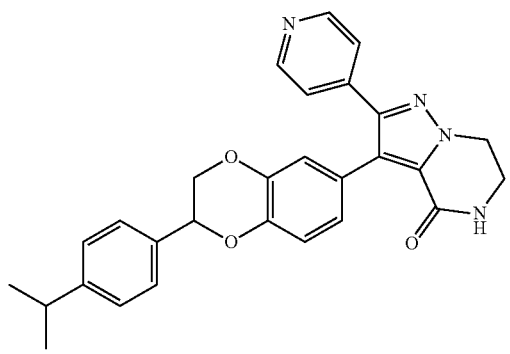
Compound 201; Method A199

TABLE 1-continued
Compounds
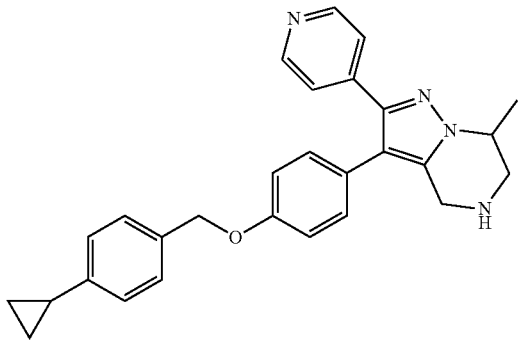 [SMILES: CC1CNCc2c(-c3ccc(OCc4ccc(C5CC5)cc4)cc3)c(-c3ccncc3)nn21]
Compound 197; Method A195
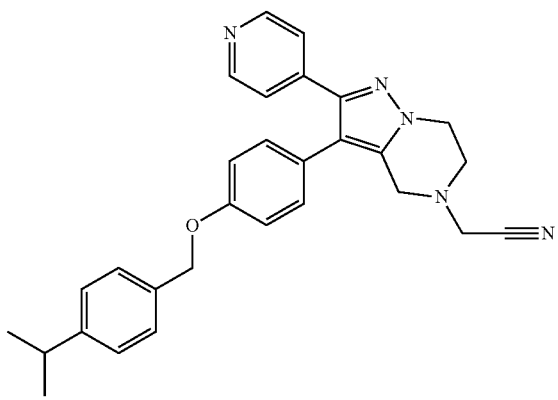 [SMILES: CC(C)c1ccc(COc2ccc(-c3c(-c4ccncc4)nn4c3CN(CC#N)CC4)cc2)cc1]
Compound 210a; Method A207
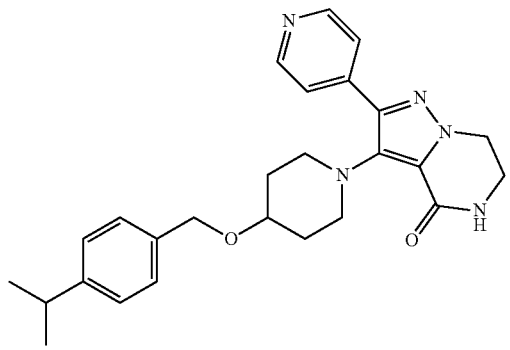 [SMILES: CC(C)c1ccc(COC2CCN(c3c(-c4ccncc4)nn4c3C(=O)NCC4)CC2)cc1]
Compound 198; Method A196
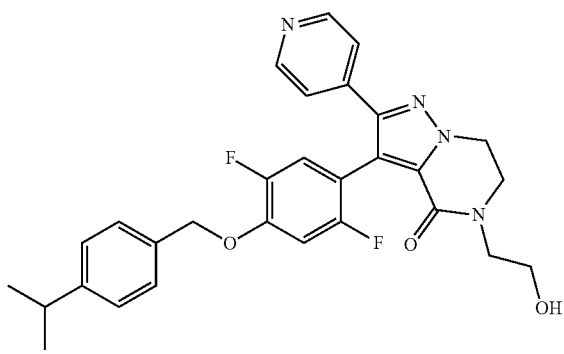 [SMILES: CC(C)c1ccc(COc2cc(F)c(-c3c(-c4ccncc4)nn4c3C(=O)N(CCO)CC4)cc2F)cc1]
Compound 203; Method A200

TABLE 1-continued
Compounds
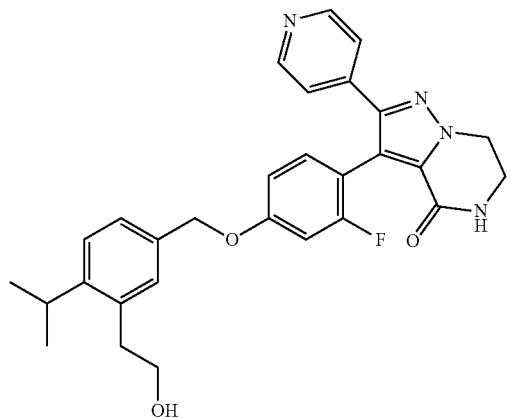 [SMILES: CC(C)c1ccc(COc2ccc(-c3c(-c4ccncc4)nn4c3C(=O)NCC4)c(F)c2)cc1CCO]
Compound 204; Method A201
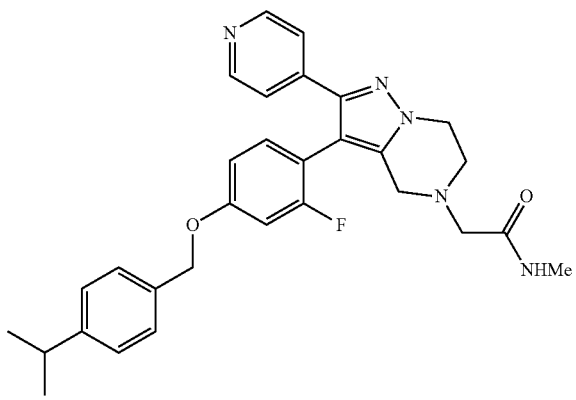 [SMILES: CNC(=O)CN1CCn2nc(-c3ccncc3)c(-c3ccc(OCc4ccc(C(C)C)cc4)cc3F)c2C1]
Compound 209; Method A206
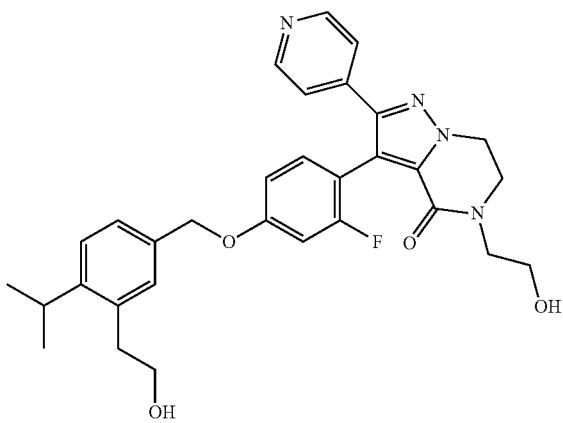 [SMILES: CC(C)c1ccc(COc2ccc(-c3c(-c4ccncc4)nn4c3C(=O)N(CCO)CC4)c(F)c2)cc1CCO]
Compound 205; Method A202

TABLE 1-continued
Compounds
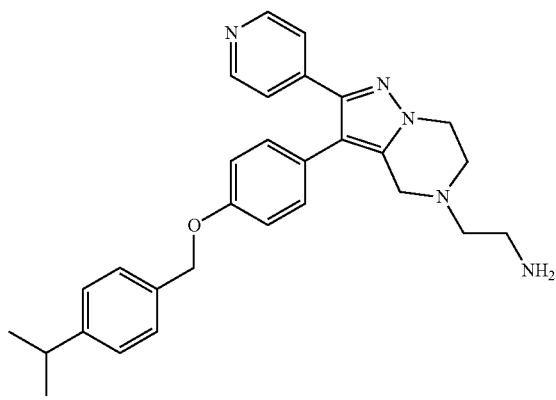
fumarate salt (0.79 eq. fumarate)
Compound 210; Method A207
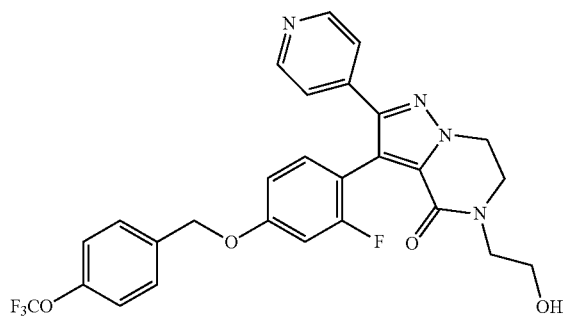 [SMILES: O=C1c2c(-c3ccc(OCc4ccc(OC(F)(F)F)cc4)cc3F)c(-c3ccncc3)nn2CCN1CCO]
Compound 206; Method A203
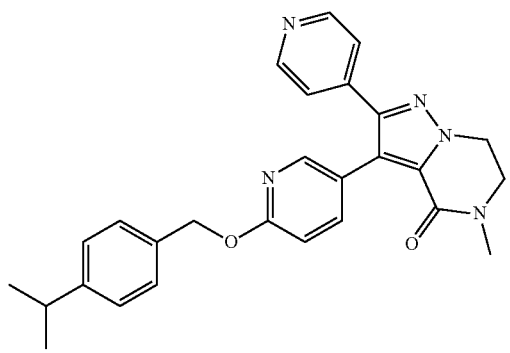 [SMILES: CC(C)c1ccc(COc2ccc(-c3c(-c4ccncc4)nn4c3C(=O)N(C)CC4)cn2)cc1]
Compound 211; Method A208
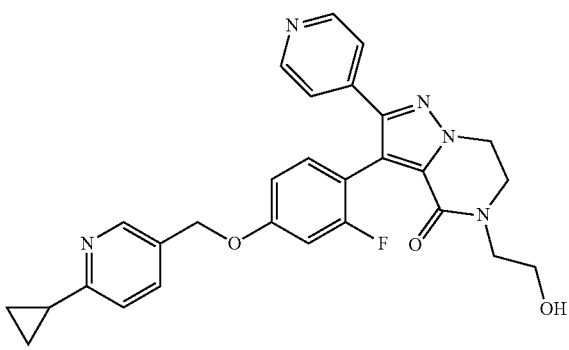 [SMILES: O=C1c2c(-c3ccc(OCc4ccc(C5CC5)nc4)cc3F)c(-c3ccncc3)nn2CCN1CCO]
Compound 207; Method A204

TABLE 1-continued
Compounds
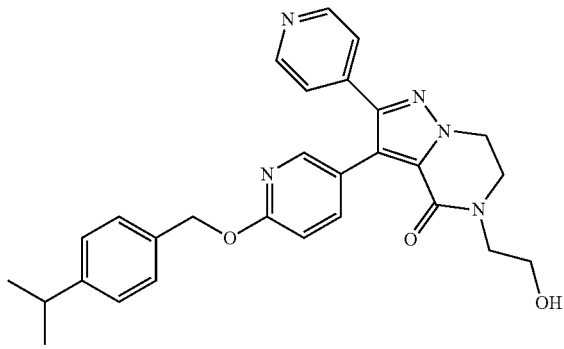
Compound 212; Method A209
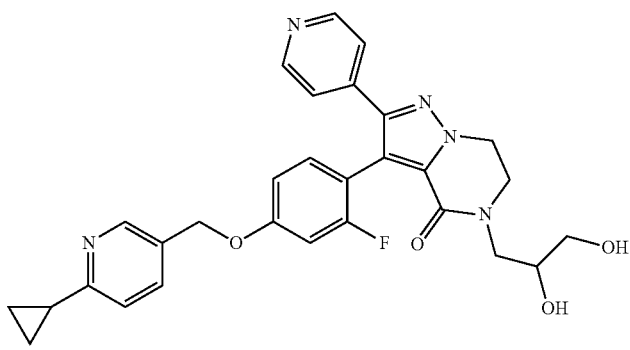 [SMILES: O=C1c2c(-c3ccc(OCc4ccc(C5CC5)nc4)cc3F)c(-c3ccncc3)nn2CCN1CC(O)CO]
Compound 208; Method A205
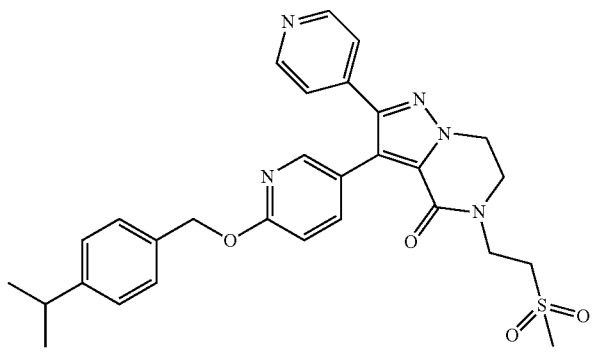 [SMILES: CC(C)c1ccc(COc2ccc(-c3c(-c4ccncc4)nn4c3C(=O)N(CCS(C)(=O)=O)CC4)cn2)cc1]
Compound 213; Method A210
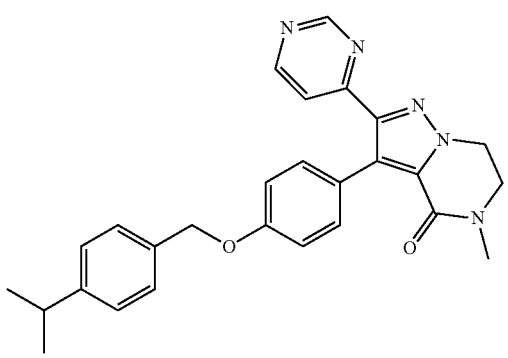 [SMILES: CC(C)c1ccc(COc2ccc(-c3c(-c4ccncn4)nn4c3C(=O)N(C)CC4)cc2)cc1]
Compound 214; Method A211

TABLE 1-continued
Compounds
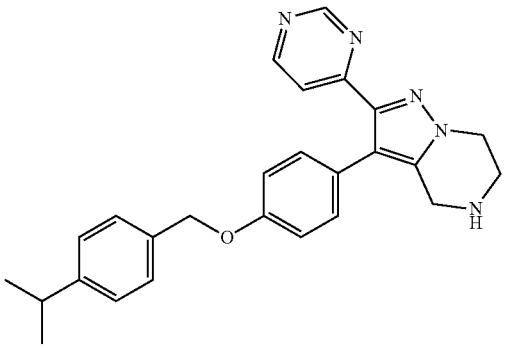 [SMILES: CC(C)c1ccc(COc2ccc(-c3c(-c4ccncn4)nn4c3CNCC4)cc2)cc1]
Compound 219; Method A216
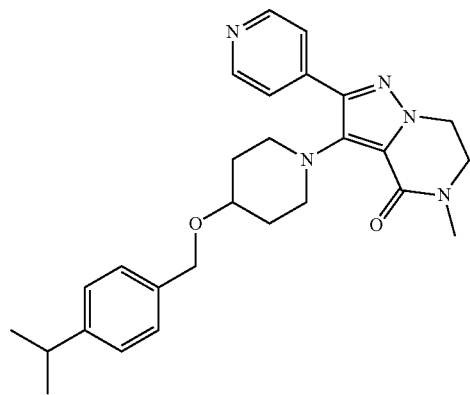 [SMILES: CC(C)c1ccc(COC2CCN(c3c(-c4ccncc4)nn4c3C(=O)N(C)CC4)CC2)cc1]
Compound 215; Method A212
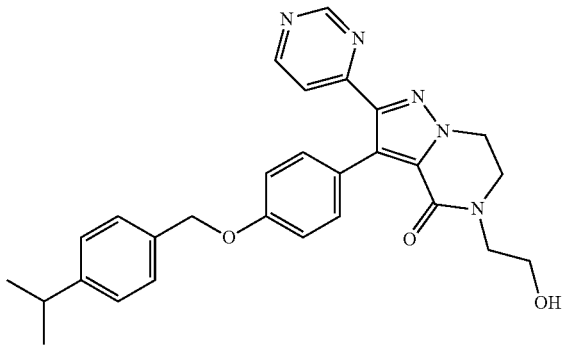 [SMILES: CC(C)c1ccc(COc2ccc(-c3c(-c4ccncn4)nn4c3C(=O)N(CCO)CC4)cc2)cc1]
Compound 220; Method A217
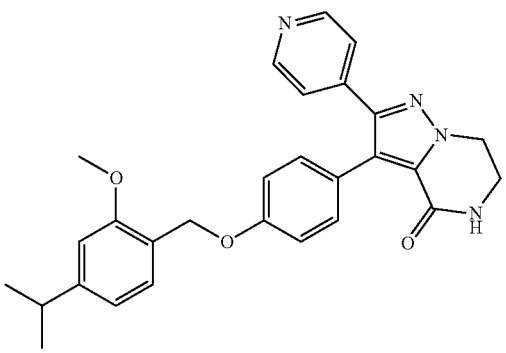 [SMILES: COc1cc(C(C)C)ccc1COc1ccc(-c2c(-c3ccncc3)nn3c2C(=O)NCC3)cc1]
Compound 216; Method A213

TABLE 1-continued
Compounds
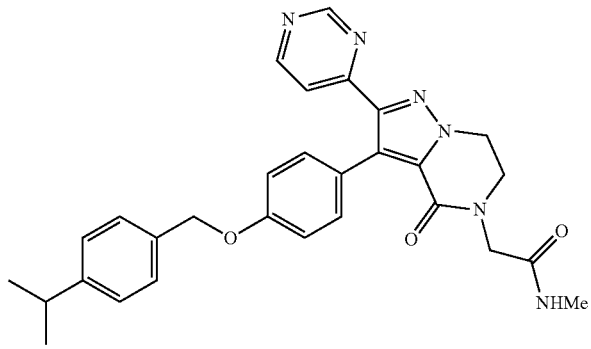 [SMILES: CNC(=O)CN1CCn2nc(-c3ccncn3)c(-c3ccc(OCc4ccc(C(C)C)cc4)cc3)c2C1=O]
Compound 221; Method A218
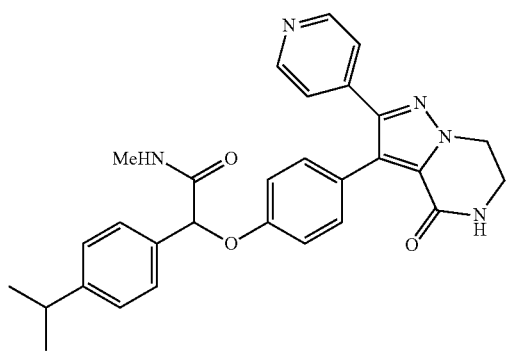 [SMILES: CNC(=O)C(Oc1ccc(-c2c(-c3ccncc3)nn3c2C(=O)NCC3)cc1)c1ccc(C(C)C)cc1]
Compound 217; Method A214
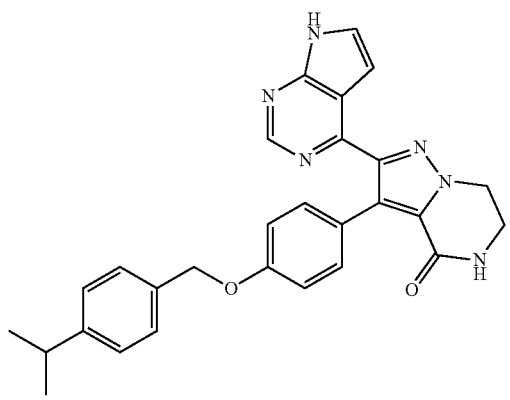 [SMILES: CC(C)c1ccc(COc2ccc(-c3c(-c4ncnc5[nH]ccc45)nn4c3C(=O)NCC4)cc2)cc1]
Compound 222; Method A219
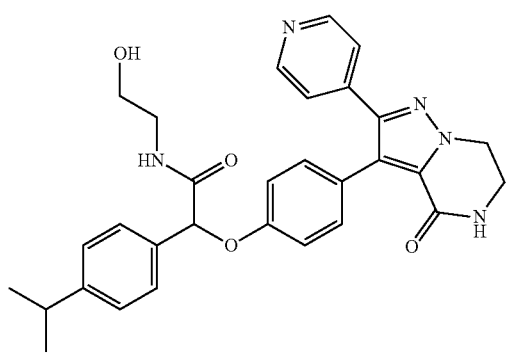 [SMILES: CC(C)c1ccc(C(Oc2ccc(-c3c(-c4ccncc4)nn4c3C(=O)NCC4)cc2)C(=O)NCCO)cc1]
Compound 218; Method A215

TABLE 1-continued
Compounds
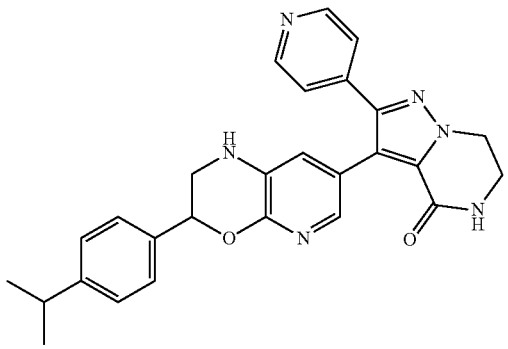 [SMILES: CC(C)c1ccc(C2CNc3cc(-c4c(-c5ccncc5)nn5c4C(=O)NCC5)cnc3O2)cc1]
Compound 223; Method A220
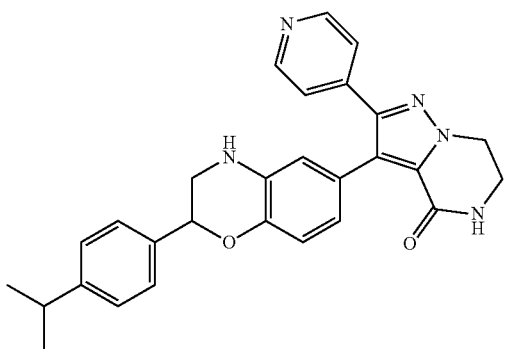 [SMILES: CC(C)c1ccc(C2CNc3cc(-c4c(-c5ccncc5)nn5c4C(=O)NCC5)ccc3O2)cc1]
Compound 226; Method A221
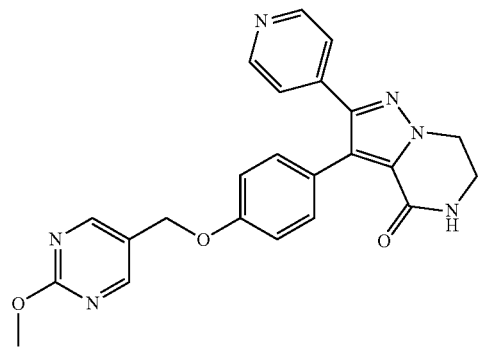
Compound 229; Method A224
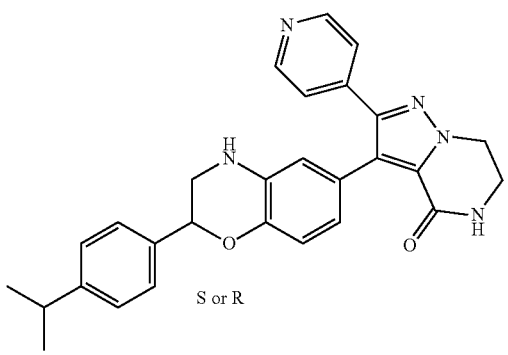 [SMILES: CC(C)c1ccc(C2CNc3cc(-c4c(-c5ccncc5)nn5c4C(=O)NCC5)ccc3O2)cc1]
S or R
Compound 224; Method A221

TABLE 1-continued
Compounds
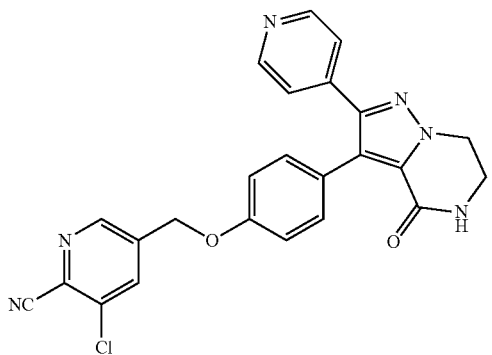 [SMILES: N#Cc1ncc(COc2ccc(-c3c(-c4ccncc4)nn4c3C(=O)NCC4)cc2)cc1Cl]
Compound 230; Method A225
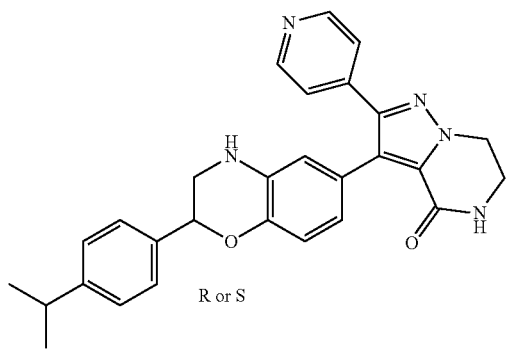 [SMILES: CC(C)c1ccc(C2CNc3cc(-c4c(-c5ccncc5)nn5c4C(=O)NCC5)ccc3O2)cc1]
R or S
Compound 225; Method A221
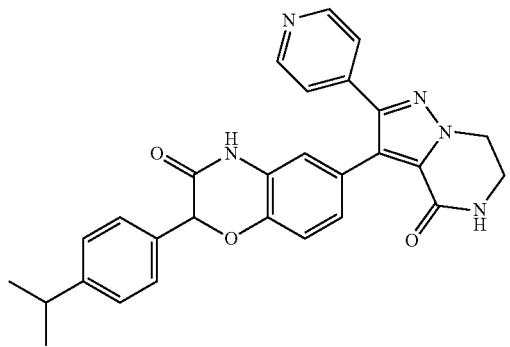 [SMILES: CC(C)c1ccc(C2Oc3ccc(-c4c(-c5ccncc5)nn5c4C(=O)NCC5)cc3NC2=O)cc1]
Compound 231; Method A226
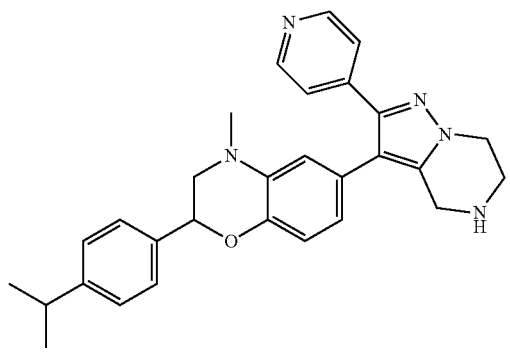 [SMILES: CC(C)c1ccc(C2CN(C)c3cc(-c4c(-c5ccncc5)nn5c4CNCC5)ccc3O2)cc1]
Compound 227; Method A222

TABLE 1-continued
Compounds
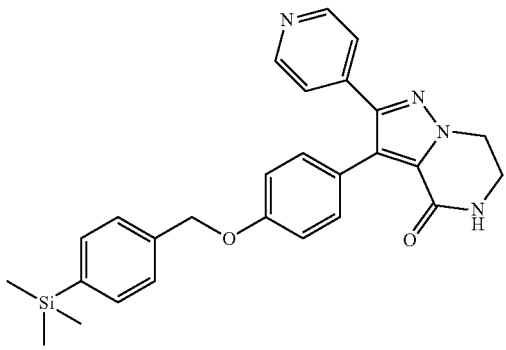 [SMILES: C[Si](C)(C)c1ccc(COc2ccc(-c3c(-c4ccncc4)nn4c3C(=O)NCC4)cc2)cc1]
Compound 232; Method A227
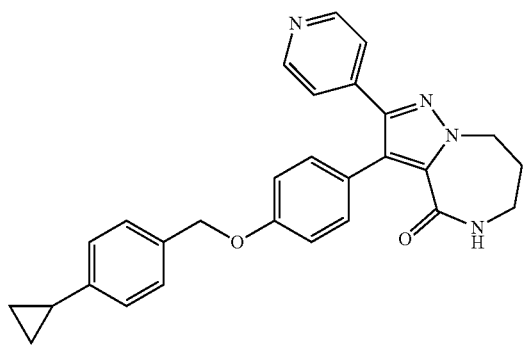 [SMILES: O=C1NCCCn2nc(-c3ccncc3)c(-c3ccc(OCc4ccc(C5CC5)cc4)cc3)c21]
Compound 228; Method A223
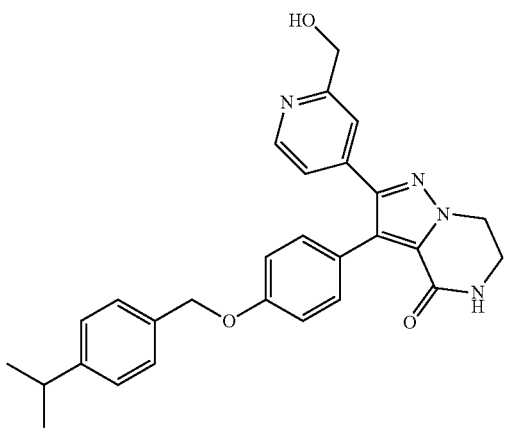 [SMILES: CC(C)c1ccc(COc2ccc(-c3c(-c4ccnc(CO)c4)nn4c3C(=O)NCC4)cc2)cc1]
Compound 233; Method A228

TABLE 1-continued
Compounds
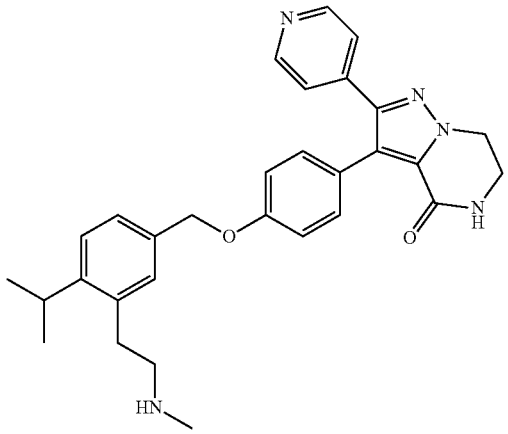 [SMILES: CNCCc1cc(COc2ccc(-c3c(-c4ccncc4)nn4c3C(=O)NCC4)cc2)ccc1C(C)C]
Compound 234; Method A229
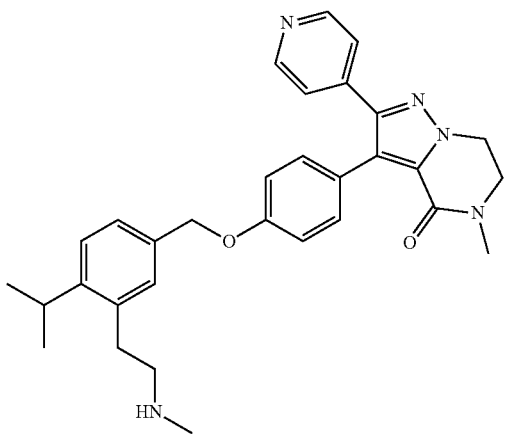 [SMILES: CNCCc1cc(COc2ccc(-c3c(-c4ccncc4)nn4c3C(=O)N(C)CC4)cc2)ccc1C(C)C]
Compound 236; Method A231
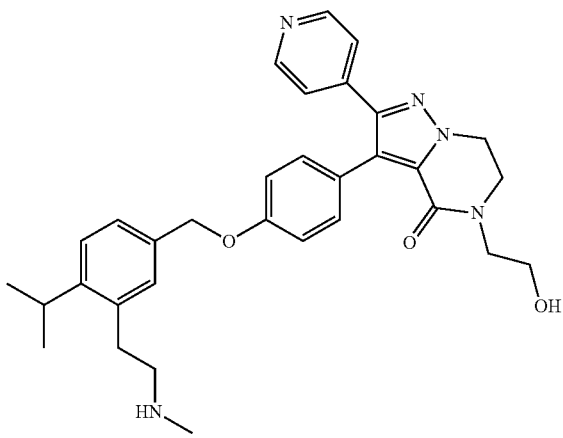 [SMILES: CNCCc1cc(COc2ccc(-c3c(-c4ccncc4)nn4c3C(=O)N(CCO)CC4)cc2)ccc1C(C)C]
Compound 235; Method A230

511
TABLE 1-continued
Compounds
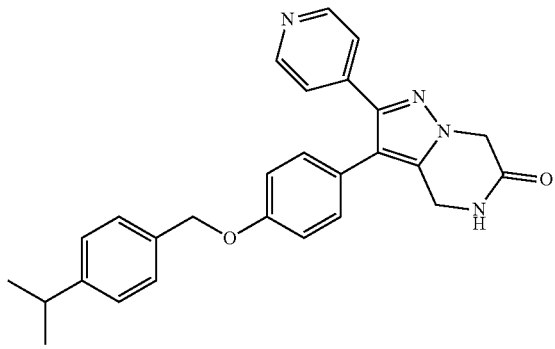 [SMILES: CC(C)c1ccc(COc2ccc(-c3c(-c4ccncc4)nn4c3CNC(=O)C4)cc2)cc1]
Compound 237; Method A232
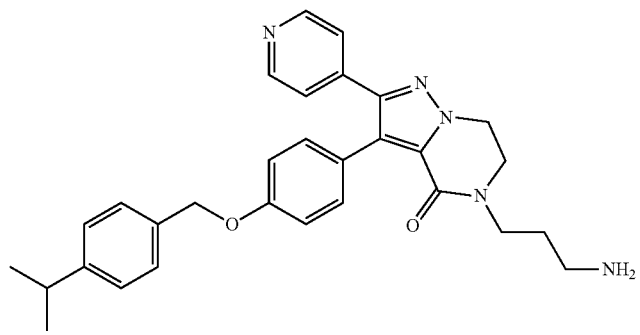
HCl salt (•2 HCl •1.78 H₂O)
Compound 59a; Method A61
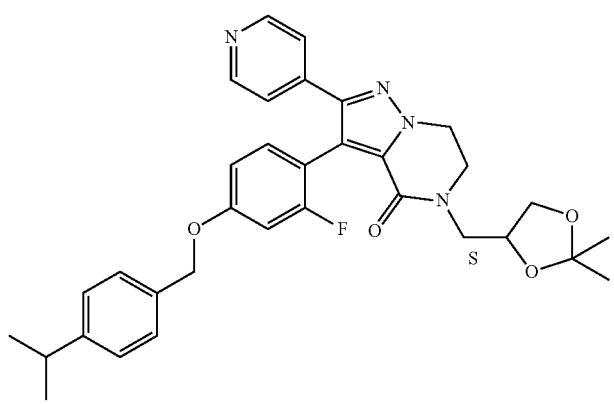
Compound 22a; Method A27

TABLE 1-continued
Compounds
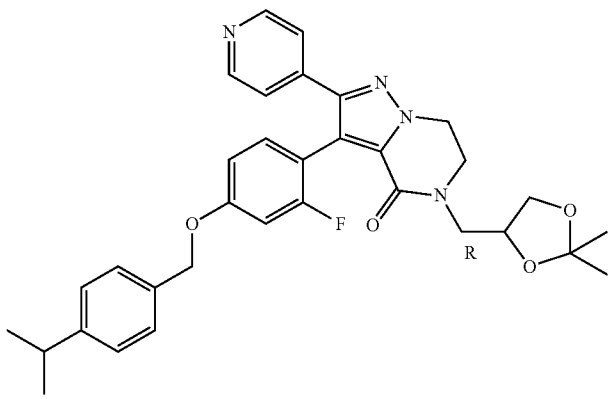
Compound 23a; Method A28
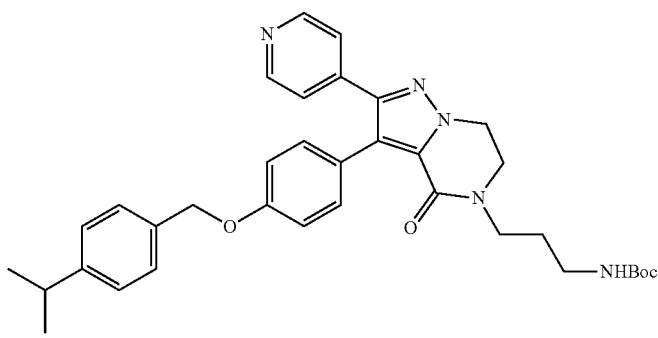 [SMILES: CC(C)c1ccc(COc2ccc(-c3c(-c4ccncc4)nn4c3C(=O)N(CCCNC(=O)OC(C)(C)C)CC4)cc2)cc1]
Compound 58a; Method A61
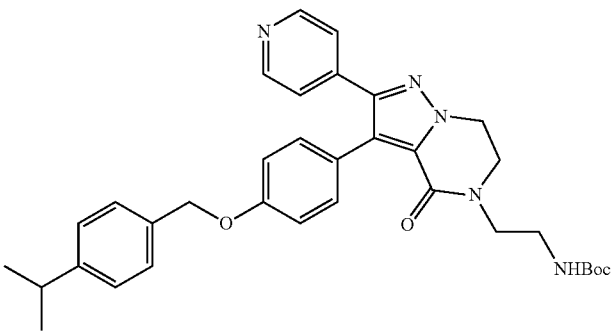 [SMILES: CC(C)c1ccc(COc2ccc(-c3c(-c4ccncc4)nn4c3C(=O)N(CCNC(=O)OC(C)(C)C)CC4)cc2)cc1]
Compound 238; Method A62
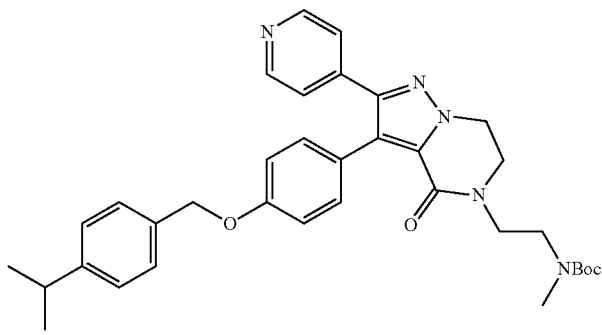 [SMILES: CC(C)c1ccc(COc2ccc(-c3c(-c4ccncc4)nn4c3C(=O)N(CCN(C)C(=O)OC(C)(C)C)CC4)cc2)cc1]
Compound 60a; Method A63

TABLE 1-continued
Compounds
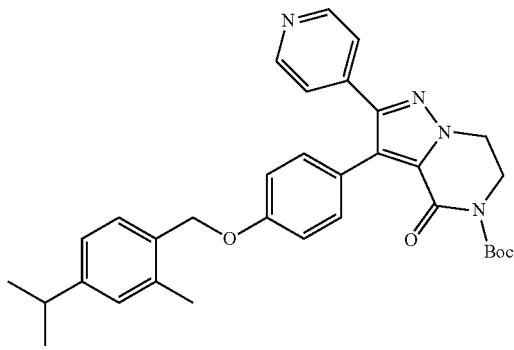 [SMILES: Cc1cc(C(C)C)ccc1COc1ccc(-c2c(-c3ccncc3)nn3c2C(=O)N(C(=O)OC(C)(C)C)CC3)cc1]
Compound 78a; Method A80
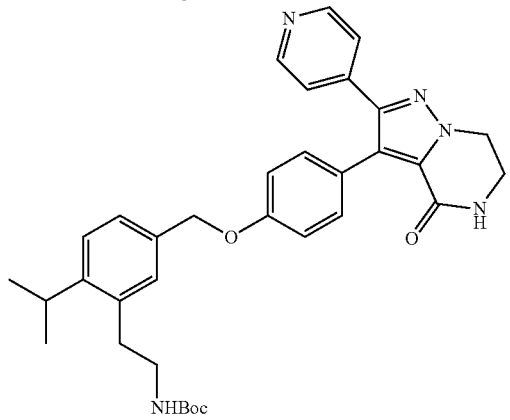 [SMILES: CC(C)c1ccc(COc2ccc(-c3c(-c4ccncc4)nn4c3C(=O)NCC4)cc2)cc1CCNC(=O)OC(C)(C)C]
Compound 88a; Method A89
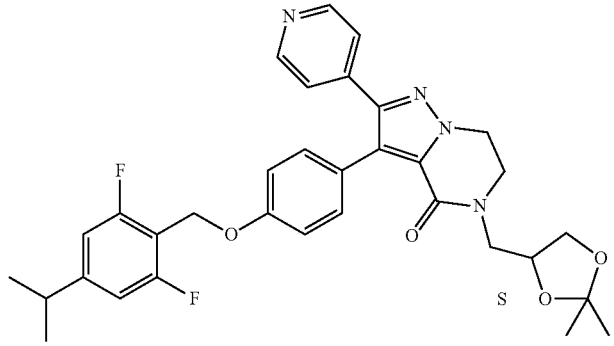
Compound 95a; Method A96
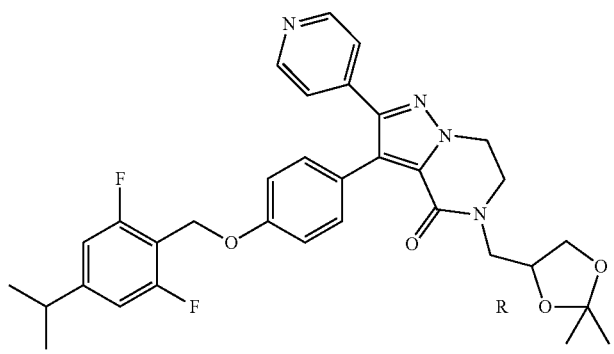
Compound 96a; Method A97

TABLE 1-continued
Compounds
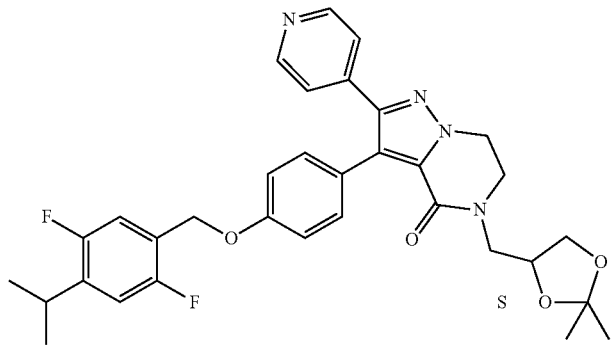
Compound 98a; Method A99
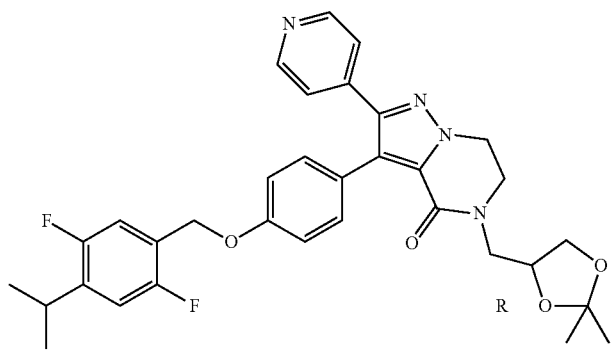
Compound 99a; Method A100
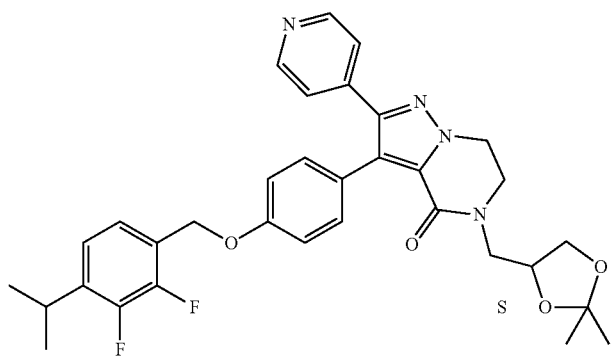
Compound 101a; Method A102
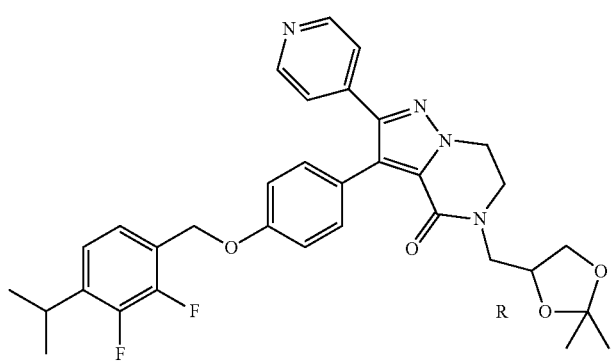
Compound 102a; Method A103

TABLE 1-continued
Compounds
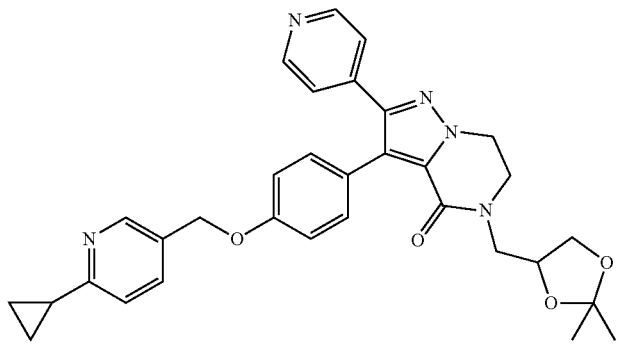 [SMILES: CC1(C)OCC(CN2CCn3nc(-c4ccncc4)c(-c4ccc(OCc5ccc(C6CC6)nc5)cc4)c3C2=O)O1]
Compound 140a; Method A140
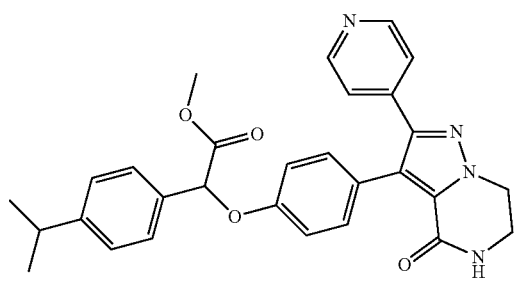 [SMILES: COC(=O)C(Oc1ccc(-c2c(-c3ccncc3)nn3c2C(=O)NCC3)cc1)c1ccc(C(C)C)cc1]
Compound 146a; Method A145
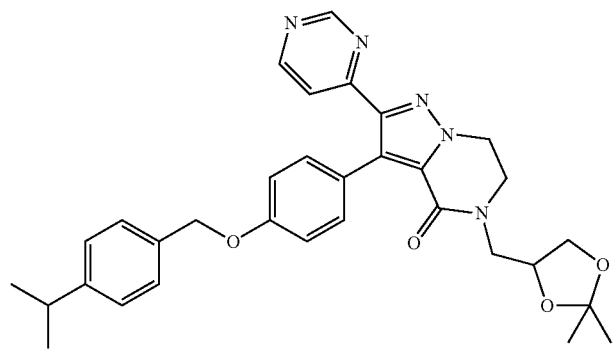 [SMILES: CC(C)c1ccc(COc2ccc(-c3c(-c4ccncn4)nn4c3C(=O)N(CC3COC(C)(C)O3)CC4)cc2)cc1]
Compound 161a; Method A160
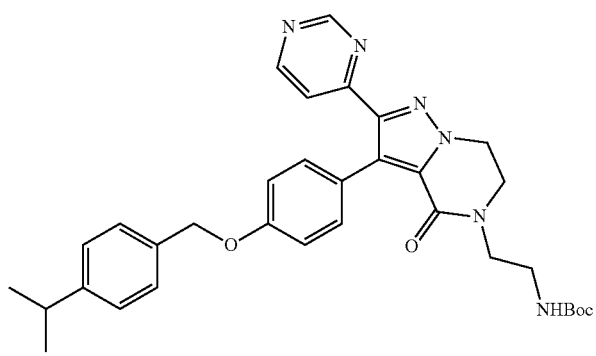 [SMILES: CC(C)c1ccc(COc2ccc(-c3c(-c4ccncn4)nn4c3C(=O)N(CCNC(=O)OC(C)(C)C)CC4)cc2)cc1]
Compound 165a; Method A164

TABLE 1-continued

Compounds

Compound 184a; Method A183

Compound 197a; Method A195

Compound 208a; Method A205

Compound 219a; Method A216

Analytical Part

LCMS (Liquid Chromatography/Mass Spectrometry)

LCMS General Procedure

The High Performance Liquid Chromatography (HPLC) measurement was performed using a LC pump, a diode-array (DAD) or a UV detector and a column as specified in the respective methods. If necessary, additional detectors were included (see table of methods below).

Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software.

Compounds are described by their experimental retention times (Re) and ions. If not specified differently in the table of data, the reported molecular ion corresponds to the [M+H]⁺ (protonated molecule) and/or [M−H]⁻ (deprotonated molecule). In case the compound was not directly ionizable the type of adduct is specified (i.e. [M+NH₄]⁺, [M+HCOO]⁻, etc. . . . ). For molecules with multiple isotopic patterns (Br, Cl . . . ), the reported value is the one obtained for the lowest isotope mass. All results were obtained with experimental uncertainties that are commonly associated with the method used.

Hereinafter, "SQD" means Single Quadrupole Detector, "RT" room temperature, "BEH" bridged ethylsiloxane/silica hybrid, "HSS" High Strength Silica, "DAD" Diode Array Detector.

TABLE 2

LCMS Method codes (Flow expressed in mL/min; column temperature (T) in ° C.; Run time in minutes).

| LCMS Method | Instrument | Column | Mobile phase | gradient | Flow Column T | Run time |
|---|---|---|---|---|---|---|
| (1) | Waters: Acquity UPLC ®- DAD and Quattro Micro ™ | Waters: BEH C18 (1.7 μm, 2.1 × 100 mm) | A: 95% CH₃COONH₄ 7 mM/5% CH₃CN, B: CH₃CN | 84.2% A for 0.49 min, to 10.5% A in 2.18 min, held for 1.94 min, back to 84.2% A in 0.73 min, held for 0.73 min. | 0.343 40 | 6.2 |
| (2) | Waters: Acquity UPLC ® H-Class - DAD and SQD 2 | Waters: BEH C18 (1.7 μm, 2.1 × 100 mm) | A: 95% CH₃COONH₄ 7 mM/5% CH₃CN, B: CH₃CN | 84.2% A for 0.49 min, to 10.5% A in 1.81 min, held for 2.31 min, back to 84.2% A in 0..73 min, held for 0.73 min. | 0.343 40 | 6.1 |
| (3) | Agilent: 1100/1200 - DAD and MSD | Agilent: Eclipse ® C18 (5 μm, 4.6 × 150 mm) | A: CF₃COOH 0.1% in water, B: CH₃CN | 98% A for 3 min, to 100% B in 12 min, held for 5 min, back to 98% A in 2 min, held for 6 min. | 1 RT | 28 |
| (4) | Waters: Acquity UPLC ® H-Class - DAD and SQD 2 | Macherey Nagel: Nucleoshell ® RP18 (2.7 μm, 3 × 50 mm) | A: 95% CH₃COONH₄ 7 mM/5% CH₃CN, B: CH₃CN | 95% A for 0.25 min, to 5% A in 0.75 min, held for 1.9 min, back to 95% A in 0.3 min, held for 0.3 min. | 0.6 40 | 3.5 |
| (5) | Waters: Alliance ® - DAD and ZQ ™ | Waters: XBridge ™ C18 (3.5 μm, 4.6 × 100 mm) | A: CH₃COONH₄ 7 mM, B: CH₃CN | 80% A for 0.5 min, to 10% A in 4.5 min, held for 4 min, back to 80% A in 1.5 min, held for 1.5 min. | 0.8 30 | 12 |
| (6) | Waters: Acquity UPLC ® H-Class - DAD and SQD 2 | Thermo Scientific ™: Accucore ®RP MS C18 (2.6 μm, 3 × 50 mm) | A: 95% CH₃COONH₄ 7 mM/5% CH₃CN, B: CH₃CN | 95% A for 0.25 min, to 5% A in 0.75 min, held for 1.9 min, back to 95% A in 0.3 min, held for 0.3 min. | 0.6 40 | 3.5 |

Melting Points

For a number of compounds, melting points (m.p.) were determined with a DSC 1 STAR$^e$ System from Mettler Toledo. Melting points were measured with a temperature gradient of 10° C./minute up to 350° C. Melting points are given by peak values.

The melting points for compounds 1, 151, 158, 172, 203 and 204 are reported in the experimental part ('exp').

The results of the analytical measurements are shown in table 3.

TABLE 3

Retention time ($R_t$) in min., [M + H]⁺ peak (protonated molecule), LCMS method and m.p. (melting point in ° C.) (n.d. means not determined).

| Co. No. | $R_t$ | [M + H]⁺ | LCMS Method | m.p. (° C.) |
|---|---|---|---|---|
| 1 | 3.01 | 439 | 1 | exp |
| 2 | 2.96 | 483 | 1 | 181 |
| 3 | 2.43 | 438 | 1 | 276 |
| 4 | 2.87 | 437 | 1 | 262 |
| 5 | 3.04 | 463 | 1 | 239 |
| 6 | 3.04 | 457 | 1 | 271 |
| 7 | 2.83 | 454 | 1 | 267 |
| 8 | 2.89 | 470 | 1 | 135 |
| 9 | 2.34 | 455 | 1 | 290 |
| 10 | 2.63 | 464 | 1 | 280 |

TABLE 3-continued

Retention time ($R_t$) in min., [M + H]⁺ peak (protonated molecule), LCMS method and m.p. (melting point in ° C.) (n.d. means not determined).

| Co. No. | $R_t$ | [M + H]⁺ | LCMS Method | m.p. (° C.) |
|---|---|---|---|---|
| 11 | 2.56 | 483 | 1 | 195 |
| 12 | 2.73 | 440 | 1 | 84 |

TABLE 3-continued

Retention time ($R_t$) in min., $[M + H]^+$ peak (protonated molecule), LCMS method and m.p. (melting point in ° C.) (n.d. means not determined).

| Co. No. | $R_t$ | $[M + H]^+$ | LCMS Method | m.p. (° C.) |
|---|---|---|---|---|
| 13 | 2.8 | 455 | 1 | n.d. |
| 14 | 3.03 | 475 | 1 | 226/231 |
| 15 | 3.11 | 475 | 1 | n.d. |
| 16 | 3.04 | 475 | 1 | 214 |
| 17 | 3.1 | 475 | 1 | 235 |
| 18 | 3.02 | 457 | 1 | 241 |
| 19 | 2.96 | 501 | 1 | 172 |
| 20 | 2.98 | 519 | 1 | 138 |
| 21 | 2.97 | 501 | 1 | 141 |
| 22 | 2.84 | 531 | 1 | 188 |
| 23 | 2.84 | 531 | 1 | 192 |
| 24 | 3.13 | 473 | 1 | 267 |
| 25 | 3.13 | 473 | 1 | 251 |
| 26 | 2.91 | 464 | 1 | 235 |
| 27 | 2.94 | 464 | 1 | 268 |
| 28 | 2.89 | 508 | 1 | 185 |
| 29 | 3.21 | 467 | 1 | 260 |
| 30 | 3.14 | 511 | 1 | 170 |
| 31 | 3.1 | 497 | 1 | n.d. |
| 32 | 2.93 | 469 | 1 | 187 |
| 33 | 3.1 | 483 | 1 | 151 |
| 34 | 3 | 469 | 1 | 276 |
| 35 | 2.91 | 499 | 1 | 192 |
| 36 | 2.85 | 543 | 1 | 176 |
| 37 | 3.18 | 497 | 1 | 206 |
| 38 | 3.05 | 497 | 1 | 144 |
| 39 | 3.05 | 497 | 1 | 144 |
| 40 | 3.44 | 553 | 1 | 113 |
| 41 | 2.82 | 513 | 1 | 191 |
| 42 | 3.44 | 553 | 1 | 114 |
| 43 | 2.82 | 513 | 1 | 190 |
| 44 | 2.85 | 513 | 1 | 192 |
| 45 | 3.29 | 555 | 1 | 148 |
| 46 | 3.59 | 497 | 2 | 177 |
| 47 | 3.09 | 497 | 1 | 177 |
| 48 | 3.22 | 453 | 1 | 155 |
| 49 | 3.47 | 481 | 1 | 168 |
| 50 | 3.32 | 497 | 1 | 167 |
| 51 | 3.18 | 511 | 1 | 211 |
| 52 | 3.08 | 545 | 1 | 219 |
| 53 | 2.98 | 527 | 1 | 121 |
| 54 | 3.23 | 523 | 1 | 204 |
| 55 | 3.4 | 523 | 1 | 165 |
| 56 | 2.93 | 538 | 1 | n.d. |
| 57 | 3.18 | 492 | 1 | 158 |
| 58 | 2.69 | 496 | 1 | n.d. |
| 59 | 3.28 | 482 | 2 | n.d. |
| 60 | 2.78 | 496 | 1 | n.d. |
| 61 | 3 | 510 | 1 | n.d. |
| 62 | 3.36 | 564 | 1 | n.d. |
| 63 | 2.95 | 510 | 1 | 161 |
| 64 | 3.06 | 524 | 1 | 199 |
| 65 | 3.12 | 538 | 1 | 159 |
| 66 | 2.97 | 497 | 2 | n.d. |
| 67 | 2.94 | 487 | 1 | 179 |
| 68 | 3.18 | 603 | 1 | 90 |
| 69 | 3.34 | 539 | 1 | n.d. |
| 70 | 3.64 | 539 | 1 | 147 |
| 71 | 2.95 | 440 | 1 | 199 |
| 72 | 2.62 | 470 | 1 | 231 |
| 73 | 2.97 | 458 | 1 | 207 |
| 74 | 2.98 | 458 | 1 | 275 |
| 75 | 2.7 | 441 | 1 | 126 |
| 76 | 2.81 | 441 | 1 | 225 |
| 77 | 3.08 | 456 | 1 | n.d. |
| 78 | 3.13 | 453 | 1 | 247 |
| 79 | 2.62 | 499 | 1 | 236 |
| 80 | 3.1 | 469 | 1 | 232 |
| 81 | 2.4 | 484 | 1 | 93 |
| 82 | 2.72 | 497 | 1 | n.d. |
| 83 | 2.51 | 527 | 1 | 176 |
| 84 | 3.02 | 497 | 1 | 208 |
| 85 | 2.81 | 464 | 1 | 240 |
| 86 | 2.15 | 468 | 1 | n.d. |
| 87 | 2.75 | 508 | 1 | 160 |
| 88 | 2.83 | 482 | 2 | 181 |
| 89 | 2.65 | 499 | 1 | n.d. |
| 90 | 3.03 | 513 | 1 | 209 |
| 91 | 2.37 | 513 | 1 | 199/220 |
| 92 | 2.96 | 501 | 1 | 132 |
| 93 | 2.99 | 501 | 1 | 183 |
| 94 | 2.95 | 519 | 1 | 194 |
| 95 | 2.81 | 549 | 1 | 227 |
| 96 | 2.82 | 549 | 1 | 228 |
| 97 | 3.02 | 519 | 1 | 147 |
| 98 | 2.88 | 549 | 1 | 184 |
| 99 | 2.88 | 549 | 1 | 183 |
| 100 | 3.01 | 519 | 1 | 172 |
| 101 | 2.87 | 549 | 1 | 192 |
| 102 | 2.88 | 549 | 1 | 191 |
| 103 | 2.32 | 441 | 1 | 235 |
| 104 | 2.7 | 485 | 1 | 190 |
| 105 | 2.74 | 411 | 1 | 259 |
| 106 | 3.18 | 453 | 1 | 229 |
| 107 | 3.12 | 497 | 1 | 163 |
| 108 | 3.21 | 453 | 1 | 233 |
| 109 | 3.15 | 497 | 1 | 155 |
| 110 | 3.01 | 439 | 1 | 268 |
| 111 | 2.85 | 465 | 1 | 165 |
| 112 | 2.55 | 427 | 1 | 260 |
| 113 | 2.56 | 427 | 1 | 242 |
| 114 | 2.84 | 455 | 1 | 252 |
| 115 | 2.25 | 499 | 1 | 193 |
| 116 | 2.91 | 481 | 1 | 260 |
| 117 | 2.81 | 525 | 1 | 134 |
| 118 | 2.67 | 463 | 1 | 250 |
| 119 | 2.85 | 465 | 1 | 280 |
| 120 | 9.52 | 465 | 3 | 293 |
| 121 | 2.04 | 468 | 1 | 233 |
| 122 | 2.59 | 508 | 1 | 199 |
| 123 | 2.53 | 462 | 1 | 260 |
| 124 | 2.43 | 422 | 1 | 238 |
| 125 | 2.43 | 469 | 1 | 280 |
| 126 | 2.91 | 483 | 1 | 212 |
| 127 | 2.19 | 455 | 1 | 259 |
| 128 | 2.24 | 499 | 1 | n.d. |
| 129 | 2.78 | 481 | 1 | 194 |
| 130 | 2.57 | 397 | 1 | 260 |
| 131 | 2.54 | 455 | 1 | 222 |
| 132 | 2.71 | 526 | 1 | 186/194 |
| 133 | 1.83 | 426 | 1 | 154/238 |
| 134 | 2.89 | 495 | 1 | 196 |
| 135 | 2.89 | 495 | 1 | 197 |
| 136 | 2.81 | 499 | 1 | 183 |
| 137 | 2.84 | 499 | 1 | 185 |
| 138 | 2.59 | 452 | 1 | 175 |
| 139 | 2.34 | 482 | 1 | 97 |
| 140 | 2.24 | 512 | 1 | n.d. |
| 141 | 2.57 | 456 | 1 | 257 |
| 142 | 2.69 | 421 | 1 | 245 |
| 143 | 3.11 | 453 | 1 | 217 |
| 144 | 3.03 | 497 | 1 | 148 |
| 145 | 3.03 | 497 | 1 | 148/162 |
| 146 | 2.54 | 469 | 1 | 228/238 |
| 147 | 2.23 | 468 | 1 | 178 |
| 148 | 2.86 | 451 | 1 | 259 |
| 149 | 2.74 | 484 | 1 | 179 |
| 150 | 2.91 | 498 | 1 | n.d. |
| 151 | 3.09 | 457 | 1 | exp |
| 152 | 3.14 | 475 | 1 | 262 |
| 153 | 3.09 | 464 | 1 | 225 |
| 154 | 3.2 | 473 | 1 | 207 |
| 155 | 2.89 | 478 | 1 | 266 |
| 156 | 2.84 | 522 | 1 | 219 |
| 157 | 2.46 | 428 | 1 | 264 |
| 158 | 2.95 | 440 | 1 | exp |

TABLE 3-continued

Retention time ($R_t$) in min., $[M + H]^+$ peak (protonated molecule), LCMS method and m.p. (melting point in ° C.) (n.d. means not determined).

| Co. No. | $R_t$ | $[M + H]^+$ | LCMS Method | m.p. (° C.) |
|---|---|---|---|---|
| 159 | 2.87 | 484 | 1 | 160 |
| 160 | 3.35 | 482 | 1 | 166 |
| 161 | 2.74 | 514 | 1 | 209 |
| 162 | 2.84 | 528 | 1 | n.d. |
| 163 | 3.14 | 524 | 1 | 164/180 |
| 164 | 2.84 | 511 | 1 | 97/157 |
| 165 | 2.63 | 483 | 1 | 154 |
| 166 | 2.79 | 438 | 1 | 268 |
| 167 | 2.71 | 482 | 1 | 170 |
| 168 | 2.28 | 439 | 1 | 254 |
| 169 | 2.24 | 483 | 1 | 143 |
| 170 | 2.61 | 455 | 1 | 227 |
| 171 | 3.19 | 449 | 1 | 152 |
| 172 | 2.93 | 423 | 1 | exp |
| 173 | 3.1 | 425 | 1 | 194 |
| 174 | 3.05 | 496 | 1 | 185 |
| 175 | 2.85 | 526 | 1 | 189 |
| 176 | 3.6 | 469 | 2 | 150 |
| 177 | 3.14 | 510 | 1 | 95 |
| 178 | 3.26 | 524 | 1 | 188 |
| 179 | 3.29 | 536 | 1 | n.d. |
| 180 | 3.09 | 497 | 1 | n.d. |
| 181 | 3.14 | 510 | 1 | n.d. |
| 182 | 2.8 | 496 | 1 | n.d. |
| 183 | 2.66 | 478 | 1 | 173 |
| 184 | 2.92 | 441 | 1 | 195/339 |
| 185 | 3.47 | 439 | 1 | 120 |
| 186 | 2.43 | 424 | 1 | 195 |
| 187 | 3.61 | 487 | 2 | n.d. |
| 188 | 2.58 | 413 | 1 | 192/342 |
| 189 | 2.98 | 451 | 1 | 249 |
| 190 | 3.06 | 437 | 1 | 166/177 |
| 191 | 3.28 | 483 | 1 | 148 |
| 192 | 3.28 | 483 | 1 | 151 |
| 193 | 2.91 | 469 | 1 | 254 |
| 194 | 2.86 | 482 | 1 | 230 |
| 195 | 2.99 | 526 | 1 | 193 |
| 196 | 2.99 | 483 | 1 | n.d. |
| 197 | 3.09 | 437 | 1 | 153 |
| 198 | 3.09 | 446 | 1 | n.d. |
| 199 | 3.12 | 465 | 1 | 262 |
| 200 | 3.06 | 509 | 1 | 118/203 |
| 201 | 3 | 467 | 1 | 290 |
| 203 | 2.97 | 519 | 1 | exp |
| 204 | 2.59 | 501 | 1 | exp |
| 205 | 2.54 | 545 | 1 | 151 |
| 206 | 2.83 | 543 | 1 | 140 |
| 207 | 2.37 | 500 | 1 | n.d. |
| 208 | 2.27 | 530 | 1 | 116/126 |
| 209 | 3.03 | 514 | 1 | 175/159 |
| 210 | 2.76 | 468 | 1 | 197 |
| 210a | 8.30 | 464 | 5 | n.d. |
| 211 | 3.12 | 454 | 1 | 57 |
| 212 | 2.85 | 484 | 1 | 138/161 |
| 213 | 2.95 | 546 | 1 | 200 |
| 214 | 3.11 | 454 | 1 | 160 |
| 215 | 3.38 | 460 | 1 | 140 |
| 216 | 3.01 | 469 | 1 | 200 |
| 217 | 2.47 | 496 | 1 | n.d. |
| 218 | 2.36 | 526 | 1 | n.d. |
| 219 | 3.02 | 426 | 1 | 150 |
| 220 | 3.01 | 470 | 1 | n.d. |
| 221 | 2.98 | 497 | 1 | n.d. |
| 222 | 2.78 | 479 | 1 | 238 |
| 223 | 2.55 | 467 | 1 | n.d. |
| 224 | 2.91 | 466 | 1 | n.d. |
| 225 | 2.91 | 466 | 1 | n.d. |
| 226 | 2.87 | 466 | 1 | 252 |
| 227 | 3.1 | 480 | 1 | 291 |
| 228 | 2.91 | 451 | 1 | 235 |
| 229 | 2.07 | 429 | 1 | 248 |
| 230 | 2.48 | 457 | 1 | 277 |
| 231 | 2.58 | 480 | 1 | 291 |
| 232 | 3.25 | 469 | 1 | n.d. |
| 233 | 2.77 | 469 | 1 | 232 |
| 234 | 2.23 | 496 | 1 | 166/200 |
| 235 | 2.21 | 540 | 1 | n.d. |
| 236 | 2.36 | 510 | 1 | n.d. |
| 237 | 3.01 | 439 | 1 | 281 |
| 238 | n.d. | n.d. | n.d. | n.d. |
| 9a | 2.54 | 455 | 1 | 254 |
| 22a | n.d. | n.d. | n.d. | n.d. |
| 23a | n.d. | n.d. | n.d. | n.d. |
| 58a | 1.91 | 596 | 4 | n.d. |
| 59a | 3.28 | 482 | 2 | n.d. |
| 60a | n.d. | n.d. | n.d. | n.d. |
| 78a | 1.95 | 553 | 6 | n.d. |
| 88a | 1.74 | 582 | 4 | n.d. |
| 95a | n.d. | n.d. | n.d. | n.d. |
| 96a | n.d. | n.d. | n.d. | n.d. |
| 98a | 1.92 | 589 | 4 | n.d. |
| 99a | 1.92 | 589 | 4 | n.d. |
| 101a | 1.92 | 589 | 4 | n.d. |
| 102a | 1.91 | 589 | 4 | n.d. |
| 140a | n.d. | n.d. | n.d. | n.d. |
| 146a | 2.86 | 497 | 1 | n.d. |
| 161a | n.d. | n.d. | n.d. | n.d. |
| 165a | 1.8 | 583 | 4 | n.d. |
| 184a | n.d. | n.d. | n.d. | n.d. |
| 197a | 6.38 | 451 | 5 | n.d. |
| 208a | n.d. | n.d. | n.d. | n.d. |
| 219a | 1.93 | 526 | 6 | n.d. |

NMR

NMR experiment was carried out using a Bruker Avance 500 spectrometer equipped with a reverse triple-resonance ($^1$H, $^{13}$C, $^{15}$N TXI) probe head with z gradients and operating at 500 MHz for the proton and 125 MHz for carbon, or using using a Bruker 400 spectrometer equipped with a reverse resonance ($^1$H, $^{13}$C, SEI) probe head with z gradients and operating at 400 MHz for the proton.

TABLE 4

$^1$H NMR results

| Co. No. | $^1$H NMR result |
|---|---|
| 1 | (500 MHz, DMSO-$d_6$) δ ppm 8.46 (d, J = 6.0 Hz, 2H), 8.22 (br. s., 1H), 7.39 (d, J = 8.5 Hz, 2H), 7.23-7.31 (m, 4H), 7.19 (d, J = 8.5 Hz, 2H), 6.99 (d, J = 8.5 Hz, 2H), 5.07 (s, 2H), 4.43 (t, J = 6.0 Hz, 2H), 3.61-3.70 (m, 2H), 2.90 (spt, J = 6.9 Hz, 1H), 1.21 (d, J = 6.9 Hz, 6H) |

TABLE 4-continued

<sup>1</sup>H NMR results

| Co. No. | <sup>1</sup>H NMR result |
|---|---|
| 2 | (500 MHz, DMSO-$d_6$) δ ppm 8.46 (d, J = 5.7 Hz, 2H), 7.39 (d, J = 8.5 Hz, 2H), 7.22-7.31 (m, 4H), 7.18 (d, J = 8.5 Hz, 2H), 6.99 (d, J = 8.5 Hz, 2H), 5.07 (s, 2H), 4.80 (br. s., 1H), 4.48 (t, J = 5.8 Hz, 2H), 3.90 (t, J = 5.8 Hz, 2H), 3.51-3.59 (m, 2H), 3.44-3.52 (m, 2H), 2.90 (spt, J = 6.6 Hz, 1H), 1.21 (d, J = 6.6 Hz, 6H) |
| 3 | (400 MHz, DMSO-$d_6$) δ ppm 8.50 (d, J = 2.0 Hz, 1H), 8.46 (d, J = 6.1 Hz, 2H), 8.22 (br. s., 1H), 7.74 (dd, J = 2.0, 7.8 Hz, 1H), 7.33 (d, J = 7.8 Hz, 1H), 7.25 (d, J = 6.1 Hz, 2H), 7.20 (d, J = 8.6 Hz, 2H), 7.00 (d, J = 8.6 Hz, 2H), 5.09 (s, 2H), 4.43 (t, J = 6.1 Hz, 2H), 3.61-3.69 (m, 2H), 2.07-2.17 (m, 1H), 0.89-1.00 (m, 4H) |
| 4 | (500 MHz, DMSO-$d_6$) δ ppm 8.46 (d, J = 6.0 Hz, 2H), 8.23 (br. s., 1H), 7.34 (d, J = 7.9 Hz, 2H), 7.25 (d, J = 6.0 Hz, 2H), 7.18 (d, J = 8.5 Hz, 2H), 7.10 (d, J = 8.5 Hz, 2H), 6.98 (d, J = 7.9 Hz, 2H), 5.05 (s, 2H), 4.43 (t, J = 6.0 Hz, 2H), 3.62-3.68 (m, 2H), 1.89-1.97 (m, 1H), 0.92-0.98 (m, 2H), 0.65-0.70 (m, 2H) |
| 5 | (400 MHz, DMSO-$d_6$) δ ppm 8.37-8.55 (m, 3H), 7.35 (d, J = 8.1 Hz, 2H), 7.26 (d, J = 5.6 Hz, 2H), 7.21 (d, J = 8.6 Hz, 2H), 7.10 (d, J = 8.1 Hz, 2H), 6.98 (d, J = 8.6 Hz, 2H), 5.06 (s, 2H), 4.41 (s, 2H), 1.87-1.99 (m, 1H), 0.87-1.03 (m, 6H), 0.63-0.72 (m, 2H) |
| 6 | (500 MHz, DMSO-$d_6$) δ ppm 8.49 (d, J = 6.0 Hz, 2H), 8.28 (br. s., 1H), 7.40 (d, J = 7.9 Hz, 2H), 7.26-7.32 (m, 4H), 7.23 (t, J = 8.6 Hz, 1H), 6.95 (dd, J = 2.2, 11.7 Hz, 1H), 6.88 (dd, J = 2.2, 8.6 Hz, 1H), 5.10 (s, 2H), 4.45 (t, J = 6.0 Hz, 2H), 3.62-3.70 (m, 2H), 2.91 (spt, J = 6.8 Hz, 1H), 1.21 (d, J = 6.8 Hz, 6H) |
| 7 | (500 MHz, DMSO-$d_6$) δ ppm 8.18 (br. s., 1H), 7.73 (d, J = 5.4 Hz, 1H), 7.39 (d, J = 7.9 Hz, 2H), 7.27 (d, J = 7.9 Hz, 2H), 7.17 (d, J = 8.5 Hz, 2H), 6.96 (d, J = 8.5 Hz, 2H), 6.57 (d, J = 1.4 Hz, 1H), 6.20 (dd, J = 1.4, 5.4 Hz, 1H), 5.87 (s, 2H), 5.06 (s, 2H), 4.38 (t, J = 6.2 Hz, 2H), 3.60-3.66 (m, 2H), 2.90 (spt, J = 6.8 Hz, 1H), 1.21 (d, J = 6.8 Hz, 6H) |
| 10 | (500 MHz, DMSO-$d_6$) δ ppm 8.46 (d, J = 6.3 Hz, 2H), 8.24 (br. s., 1H), 7.51-7.59 (m, 4H), 7.25 (d, J = 6.3 Hz, 2H), 7.20 (d, J = 8.5 Hz, 2H), 7.00 (d, J = 8.5 Hz, 2H), 5.14 (s, 2H), 4.43 (t, J = 6.0 Hz, 2H), 3.62-3.68 (m, 2H), 1.70 (s, 6H) |
| 18 | (500 MHz, DMSO-$d_6$) δ ppm 8.48 (d, J = 6.0 Hz, 2H), 8.28 (br. s., 1H), 7.40 (d, J = 8.2 Hz, 2H), 7.29 (d, J = 8.2 Hz, 2H), 7.26 (d, J = 6.0 Hz, 2H), 7.22 (t, J = 8.8 Hz, 1H), 7.19 (dd, J = 1.7, 12.4 Hz, 1H), 6.96 (d, J = 8.8 Hz, 1H), 5.15 (s, 2H), 4.43 (t, J = 5.8 Hz, 2H), 3.63-3.68 (m, 2H), 2.91 (spt, J = 6.9 Hz, 1H), 1.21 (d, J = 6.9 Hz, 6H) |
| 19 | (500 MHz, DMSO-$d_6$) δ ppm 8.48 (d, J = 5.7 Hz, 2H), 7.40 (d, J = 7.9 Hz, 2H), 7.29 (d, J = 7.9 Hz, 2H), 7.26 (d, J = 5.7 Hz, 2H), 7.15-7.25 (m, 2H), 6.95 (d, J = 8.2 Hz, 1H), 5.15 (s, 2H), 4.80 (t, J = 5.2 Hz, 1H), 4.49 (t, J = 5.8 Hz, 2H), 3.90 (t, J = 5.8 Hz, 2H), 3.52-3.58 (m, 2H), 3.46-3.51 (m, 2H), 2.91 (spt, J = 6.8 Hz, 1H), 1.21 (d, J = 6.8 Hz, 6H) |
| 20 | (500 MHz, DMSO-$d_6$) δ ppm 8.49 (d, J = 6.0 Hz, 2H), 7.40 (d, J = 7.9 Hz, 2H), 7.27-7.32 (m, 4H), 7.23 (t, J = 8.6 Hz, 1H), 6.94 (dd, J = 2.2, 11.7 Hz, 1H), 6.88 (dd, J = 2.2, 8.6 Hz, 1H), 5.10 (s, 2H), 4.81 (t, J = 4.7 Hz, 1H), 4.51 (t, J = 5.9 Hz, 2H), 3.91 (t, J = 5.9 Hz, 2H), 3.52-3.58 (m, 2H), 3.45-3.50 (m, 2H), 2.91 (spt, J = 6.9 Hz, 1H), 1.21 (d, J = 6.9 Hz, 6H) |
| 21 | (500 MHz, DMSO-$d_6$) δ ppm 8.24-8.61 (m, 2H), 7.40 (d, J = 8.2 Hz, 2H), 7.26-7.32 (m, 4H), 7.23 (t, J = 8.6 Hz, 1H), 6.94 (dd, J = 2.2, 11.7 Hz, 1H), 6.88 (dd, J = 2.2, 8.6 Hz, 1H), 5.10 (s, 2H), 4.80 (t, J = 5.5 Hz, 1H), 4.51 (t, J = 6.0 Hz, 2H), 3.92 (t, J = 6.0 Hz, 2H), 3.55 (q, J = 5.5 Hz, 2H), 3.45-3.50 (m, 2H), 2.91 (spt, J = 6.9 Hz, 1H), 1.21 (d, J = 6.9 Hz, 6H) |
| 28 | (500 MHz, DMSO-$d_6$) δ ppm 8.49 (d, J = 6.3 Hz, 2H), 7.57 (d, J = 2.5 Hz, 1H), 7.41 (d, J = 8.2 Hz, 2H), 7.34-7.39 (m, 2H), 7.30 (d, J = 8.2 Hz, 2H), 7.22 (d, J = 6.3 Hz, 2H), 5.16 (s, 2H), 4.82 (t, J = 5.2 Hz, 1H), 4.49-4.61 (m, 2H), 3.91-3.96 (m, 2H), 3.55 (q, J = 5.2 Hz, 2H), 3.46-3.51 (m, 2H), 2.91 (spt, J = 6.9 Hz, 1H), 1.21 (d, J = 6.9 Hz, 6H) |
| 32 | (500 MHz, DMSO-$d_6$) δ ppm 8.47 (d, J = 6.0 Hz, 2H), 8.23 (t, J = 2.7 Hz, 1H), 7.39 (d, J = 8.2 Hz, 2H), 7.24-7.32 (m, 4H), 7.02 (d, J = 8.2 Hz, 2H), 6.91 (d, J = 1.9 Hz, 1H), 6.75 (dd, J = 1.9, 8.2 Hz, 1H), 5.04 (s, 2H), 4.39-4.47 (m, 2H), 3.61-3.69 (m, 5H), 2.90 (spt, J = 6.9 Hz, 1H), 1.21 (d, J = 6.9 Hz, 6H) |
| 44 | (500 MHz, DMSO-$d_6$) δ ppm 8.46 (d, J = 6.0 Hz, 2H), 7.39 (d, J = 8.2 Hz, 2H), 7.23-7.31 (m, 4H), 7.18 (d, J = 8.8 Hz, 2H), 6.99 (d, J = 8.8 Hz, 2H), 5.07 (s, 2H), 4.89 (d, J = 5.0 Hz, 1H), 4.58 (t, J = 5.7 Hz, 1H), 4.49 (t, J = 6.0 Hz, 2H), 3.84-4.01 (m, 2H), 3.66-3.75 (m, 1H), 3.61 (dd, J = 4.0, 13.7 Hz, 1H), 3.21-3.40 (m, 3H), 2.90 (spt, J = 6.9 Hz, 1H), 1.21 (d, J = 6.9 Hz, 6H) |
| 46 | (500 MHz, DMSO-$d_6$) δ ppm 8.46 (d, J = 6.0 Hz, 2H), 7.39 (d, J = 8.2 Hz, 2H), 7.23-7.31 (m, 4H), 7.18 (d, J = 8.8 Hz, 2H), 6.99 (d, J = 8.8 Hz, 2H), 5.07 (s, 2H), 4.82 (d, J = 4.7 Hz, 1H), 4.49 (t, J = 6.0 Hz, 2H), 3.82-3.98 (m, 3H), 3.45 (dd, J = 4.3, 13.5 Hz, 1H), 3.22 (dd, J = 7.6, 13.5 Hz, 1H), 2.90 (spt, J = 6.9 Hz, 1H), 1.21 (d, J = 6.9 Hz, 6H), 1.04 (d, J = 6.0 Hz, 3H) |
| 47 | (500 MHz, DMSO-$d_6$) δ ppm 8.46 (d, J = 6.0 Hz, 2H), 7.39 (d, J = 8.2 Hz, 2H), 7.23-7.32 (m, 4H), 7.18 (d, J = 8.8 Hz, 2H), 6.99 (d, J = 8.8 Hz, 2H), 5.07 (s, 2H), 4.82 (d, J = 5.0 Hz, 1H), 4.49 (t, J = 6.0 Hz, 2H), 3.80-3.98 (m, 3H), 3.45 (dd, J = 4.1, 13.6 Hz, 1H), 3.22 (dd, J = 7.6, 13.6 Hz, 1H), 2.90 (spt, J = 6.9 Hz, 1H), 1.21 (d, J = 6.9 Hz, 6H), 1.04 (d, J = 6.0 Hz, 3H) |

TABLE 4-continued

<sup>1</sup>H NMR results

| Co. No. | <sup>1</sup>H NMR result |
|---|---|
| 49 | (500 MHz, DMSO-d<sub>6</sub>) δ ppm 8.46 (d, J = 6.3 Hz, 2H), 7.39 (d, J = 8.2 Hz, 2H), 7.22-7.31 (m, 4H), 7.18 (d, J = 8.8 Hz, 2H), 6.99 (d, J = 8.8 Hz, 2H), 5.08 (s, 2H), 4.68 (spt, J = 6.7 Hz, 1H), 4.42-4.51 (m, 2H), 3.68-3.79 (m, 2H), 2.90 (spt, J = 6.9 Hz, 1H), 1.21 (d, J = 6.9 Hz, 6H), 1.13 (d, J = 6.7 Hz, 6H) |
| 51 | (500 MHz, DMSO-d<sub>6</sub>) δ ppm 8.46 (d, J = 6.0 Hz, 2H), 7.39 (d, J = 8.2 Hz, 2H), 7.23-7.31 (m, 4H), 7.17 (d, J = 8.5 Hz, 2H), 6.98 (d, J = 8.5 Hz, 2H), 5.07 (s, 2H), 4.61 (s, 1H), 4.46-4.54 (m, 2H), 3.94-4.03 (m, 2H), 3.37 (s, 2H), 2.90 (spt, J = 6.9 Hz, 1H), 1.21 (d, J = 6.9 Hz, 6H), 1.09 (s, 6H) |
| 53 | (500 MHz, DMSO-d<sub>6</sub>) δ ppm 8.46 (d, J = 6.0 Hz, 2H), 7.39 (d, J = 8.2 Hz, 2H), 7.28 (d, J = 8.2 Hz, 2H), 7.26 (d, J = 6.0 Hz, 2H), 7.18 (d, J = 8.5 Hz, 2H), 6.99 (d, J = 8.5 Hz, 2H), 5.07 (s, 2H), 4.59 (t, J = 5.5 Hz, 1H), 4.48 (t, J = 6.0 Hz, 2H), 3.91 (t, J = 6.0 Hz, 2H), 3.54-3.62 (m, 4H), 3.46-3.51 (m, 2H), 3.41-3.45 (m, 2H), 2.90 (spt, J = 6.9 Hz, 1H), 1.21 (d, J = 6.9 Hz, 6H) |
| 54 | (500 MHz, DMSO-d<sub>6</sub>) δ ppm 8.47 (d, J = 5.7 Hz, 2H), 7.39 (d, J = 8.2 Hz, 2H), 7.28 (d, J = 8.2 Hz, 2H), 7.25 (d, J = 5.7 Hz, 2H), 7.17 (d, J = 8.5 Hz, 2H), 6.99 (d, J = 8.5 Hz, 2H), 5.07 (s, 2H), 4.47-4.55 (m, 4H), 4.17 (d, J = 5.7 Hz, 2H), 3.86 (t, J = 5.8 Hz, 2H), 3.63 (s, 2H), 2.90 (spt, J = 6.9 Hz, 1H), 1.29 (s, 3H), 1.21 (d, J = 6.9 Hz, 6H) |
| 63 | (500 MHz, DMSO-d<sub>6</sub>) δ ppm 8.47 (d, J = 4.7 Hz, 2H), 7.87-7.99 (m, 1H), 7.39 (d, J = 7.6 Hz, 2H), 7.23-7.32 (m, 4H), 7.18 (d, J = 8.2 Hz, 2H), 6.99 (d, J = 8.2 Hz, 2H), 5.07 (s, 2H), 4.47-4.59 (m, 2H), 4.04 (s, 2H), 3.83-3.93 (m, 2H), 2.90 (spt, J = 6.9 Hz, 1H), 2.59 (d, J = 4.1 Hz, 3H), 1.21 (d, J = 6.9 Hz, 6H) |
| 70 | (500 MHz, DMSO-d<sub>6</sub>) δ 8.47 (d, J = 6 Hz, 2H), 7.40 (d, J = 7.9 Hz, 2H), 7.28 (d, J = 7.9 Hz, 2H), 7.25 (d, J = 6 Hz, 2H), 7.20 (d, J = 8.5 Hz, 2H), 7.03 (d, J = 8.5 Hz, 2H), 5.08 (s, 2H), 4.51-4.58 (m, 2H), 4.20-4.25 (m, 2H), 2.90 (spt, J = 6.9 Hz, 1H), 1.46 (s, 9H), 1.21 (d, J = 6.9 Hz, 6H) |
| 71 | (500 MHz, DMSO-d<sub>6</sub>) δ ppm 8.51 (d, J = 6.0 Hz, 2H), 8.32 (br. s., 1H), 8.06 (d, J = 2.5 Hz, 1H), 7.62 (dd, J = 2.5, 8.5 Hz, 1H), 7.39 (d, J = 8.2 Hz, 2H), 7.29 (d, J = 6.0 Hz, 2H), 7.26 (d, J = 8.2 Hz, 2H), 6.87 (d, J = 8.5 Hz, 1H), 5.31 (s, 2H), 4.45 (t, J = 6.0 Hz, 2H), 3.63-3.70 (m, 2H), 2.89 (spt, J = 6.9 Hz, 1H), 1.21 (d, J = 6.9 Hz, 6H) |
| 84 | (500 MHz, DMSO-d<sub>6</sub>) δ ppm 8.46 (d, J = 6.3 Hz, 2H), 8.24 (br. s., 1H), 7.24-7.32 (m, 5H), 7.19 (d, J = 8.8 Hz, 2H), 6.99 (d, J = 8.8 Hz, 2H), 5.03 (s, 2H), 4.43 (t, J = 6.0 Hz, 2H), 3.62-6.68 (m, 2H), 3.49 (t, J = 7.1 Hz, 2H), 3.25 (s, 3H), 3.16 (spt, J = 6.9 Hz, 1H), 2.88 (t, J = 7.1 Hz, 2H), 1.19 (d, J = 6.9 Hz, 6H) |
| 111 | (500 MHz, DMSO-d<sub>6</sub>) δ ppm 8.46 (d, J = 5.0 Hz, 2H), 7.54 (d, J = 7.9 Hz, 2H), 7.45 (d, J = 7.9 Hz, 2H), 7.25 (d, J = 5.0 Hz, 2H), 7.18 (d, J = 8.2 Hz, 2H), 7.00 (d, J = 8.2 Hz, 2H), 5.45 (s, 1H), 5.09-5.17 (m, 3H), 4.79 (t, J = 5.0 Hz, 1H), 4.48 (t, J = 5.4 Hz, 2H), 3.90 (t, J = 5.4 Hz, 2H), 3.45-3.59 (m, 4H), 2.12 (s, 3H) |
| 112 | (500 MHz, DMSO-d<sub>6</sub>) δ ppm 8.47 (d, J = 4.7 Hz, 2H), 8.23 (br. s., 1H), 7.41 (d, J = 8.2 Hz, 2H), 7.26 (d, J = 4.7 Hz, 2H), 7.18 (d, J = 8.2 Hz, 2H), 6.92-7.02 (m, 4H), 5.03 (s, 2H), 4.43 (t, J = 5.2 Hz, 2H), 3.77 (s, 3H), 3.61-3.69 (m, 2H) |
| 116 | (400 MHz, DMSO-d<sub>6</sub>) δ ppm 8.46 (d, J = 6.1 Hz, 2H), 8.23 (br. s., 1H), 7.62 (d, J = 8.6 Hz, 2H), 7.41 (d, J = 8.6 Hz, 2H), 7.25 (d, J = 6.1 Hz, 2H), 7.20 (d, J = 8.6 Hz, 2H), 7.01 (d, J = 8.6 Hz, 2H), 5.17 (s, 2H), 4.43 (t, J = 6.1 Hz, 2H), 3.61-3.69 (m, 2H) |
| 138 | (500 MHz, DMSO-d<sub>6</sub>) δ ppm 8.50 (d, J = 2.2 Hz, 1H), 8.46 (d, J = 6.3 Hz, 2H), 7.74 (dd, J = 2.2, 8.2 Hz, 1H), 7.33 (d, J = 8.2 Hz, 1H), 7.25 (d, J = 6.3 Hz, 2H), 7.18 (d, J = 8.8 Hz, 2H), 7.00 (d, J = 8.8 Hz, 2H), 5.09 (s, 2H), 4.50 (t, J = 6.0 Hz, 2H), 3.83 (t, J = 6.0 Hz, 2H), 2.97 (s, 3H), 2.07-2.16 (m, 1H), 0.89-0.99 (m, 4H) |
| 158 | (500 MHz, DMSO-d<sub>6</sub>) δ ppm 9.01 (s, 1H), 8.74 (d, J = 5.4 Hz, 1H), 8.26 (br. s., 1H), 7.58 (d, J = 5.4 Hz, 1H), 7.39 (d, J = 8.2 Hz, 2H), 7.27 (d, J = 8.2 Hz, 2H), 7.22 (d, J = 8.8 Hz, 2H), 6.93 (d, J = 8.8 Hz, 2H), 5.06 (s, 2H), 4.45 (t, J = 5.8 Hz, 2H), 3.62-3.69 (m, 2H), 2.90 (spt, J = 6.9 Hz, 1H), 1.21 (d, J = 6.9 Hz, 6H) |
| 159 | (500 MHz, DMSO-d<sub>6</sub>) δ ppm 9.01 (s, 1H), 8.74 (d, J = 5.0 Hz, 1H), 7.58 (d, J = 5.0 Hz, 1H), 7.39 (d, J = 7.9 Hz, 2H), 7.28 (d, J = 7.9 Hz, 2H), 7.22 (d, J = 8.5 Hz, 2H), 6.93 (d, J = 8.5 Hz, 2H), 5.06 (s, 2H), 4.80 (t, J = 5.2 Hz, 1H), 4.51 (t, J = 5.7 Hz, 2H), 3.91 (t, J = 5.7 Hz, 2H), 3.44-3.62 (m, 4H), 2.90 (spt, J = 6.7 Hz, 1H), 1.21 (d, J = 6.7 Hz, 6H) |
| 171 | (400 MHz, DMSO-d<sub>6</sub>) δ ppm 8.45 (d, J = 6.1 Hz, 2H), 7.30-7.38 (m, 4H), 7.07-7.16 (m, 4H), 7.02 (d, J = 8.6 Hz, 2H), 5.04 (s, 2H), 4.04 (s, 2H), 3.82 (d, J = 7.2 Hz, 2H), 2.96 (t, J = 7.2 Hz, 2H), 1.87-1.99 (m, 1H), 0.91-0.99 (m, 2H), 0.63-0.76 (m, 6H) |
| 172 | (400 MHz, DMSO-d<sub>6</sub>) δ ppm 8.45 (d, J = 6.1 Hz, 2H), 7.28-7.37 (m, 4H), 7.07-7.16 (m, 4H), 7.02 (d, J = 8.6 Hz, 2H), 5.04 (s, 2H), 4.08 (t, J = 5.3 Hz, 2H), 3.82 (d, J = 4.4 Hz, 2H), 3.12-3.19 (m, 2H), 2.59-2.67 (m, 1H), 1.86-1.99 (m, 1H), 0.91-0.99 (m, 2H), 0.63-0.71 (m, 2H) |
| 174 | (500 MHz, DMSO-d<sub>6</sub>) δ ppm 8.46 (d, J = 6.0 Hz, 2H), 7.86 (q, J = 4.3 Hz, 1H), 7.39 (d, J = 8.2 Hz, 2H), 7.32 (d, J = 6.0 Hz, 2H), 7.28 (d, J = 8.2 Hz, 2H), 7.11 (d, J = 8.8 Hz, 2H), 7.07 (d, J = 8.8 Hz, 2H), 5.06 (s, 2H), 4.26 (t, J = 5.4 Hz, |

TABLE 4-continued

¹H NMR results

| Co. No. | ¹H NMR result |
|---|---|
| | 2H), 3.67 (s, 2H), 3.18 (s, 2H), 3.01 (t, J = 5.4 Hz, 2H), 2.90 (spt, J = 6.9 Hz, 1H), 2.58 (d, J = 4.3 Hz, 3H), 1.21 (d, J = 6.9 Hz, 6H) |
| 183 | (400 MHz, DMSO-d₆) δ ppm 8.92 (s, 1H), 8.47 (d, J = 6.1 Hz, 2H), 7.34 (d, J = 8.1 Hz, 2H), 7.26 (d, J = 6.1 Hz, 2H), 7.18 (d, J = 8.6 Hz, 2H), 7.10 (d, J = 8.1 Hz, 2H), 6.98 (d, J = 8.6 Hz, 2H), 5.06 (s, 2H), 4.68 (s, 2H), 3.63 (d, J = 8.6 Hz, 2H), 3.37 (d, J = 8.6 Hz, 2H), 2.7 (br. s, 1H), 1.86-1.99 (m, 1H), 0.91-1.00 (m, 2H), 0.63-0.72 (m, 2H) |
| 200 | (400 MHz, DMSO-d₆) δ ppm 8.48 (d, J = 5.6 Hz, 2H), 7.38 (d, J = 8.1 Hz, 2H), 7.26-7.33 (m, 4H), 7.06 (d, J = 2.0 Hz, 1H), 6.95 (dd, J = 2.0, 8.1 Hz, 1H), 6.78 (d, J = 8.1 Hz, 1H), 5.08-5.15 (m, 1H), 4.79 (t, J = 5.3 Hz, 1H), 4.48 (t, J = 6.1 Hz, 2H), 3.90 (t, J = 6.1 Hz, 2H), 3.53-3.59 (m, 2H), 3.47-3.52 (m, 2H), 2.86-3.00 (m, 2H), 2.61-2.72 (m, 1H), 2.10-2.20 (m, 1H), 1.94-2.09 (m, 1H), 1.22 (d, J = 7.1 Hz, 6H) |
| 22a | (400 MHz, DMSO-d₆) δ ppm 8.49 (d, J = 5.56 Hz, 2H), 7.40 (d, J = 8.08 Hz, 2H), 7.26-7.34 (m, 4H), 7.22 (s, 1H), 6.80-6.98 (m, 2H), 5.10 (s, 2H), 4.52 (br. s., 2H), 4.19-4.32 (m, 1H), 3.90-4.25 (m, 3H), 3.55-3.69 (m, 2H), 3.42-3.55 (m, 1H), 2.87-2.97 (m, 1H), 1.36 (s, 3H), 1.27 (s, 3H), 1.22 (d, J = 7.07 Hz, 6H) |
| 238 | (400 MHz, DMSO-d₆) δ ppm 8.46 (d, J = 6.06 Hz, 2H), 7.39 (d, J = 8.08 Hz, 2H), 7.23-7.32 (m, 4H), 7.18 (d, J = 8.59 Hz, 2H), 6.98 (d, J = 8.59 Hz, 2H), 6.84-6.93 (m, 1H), 5.08 (s, 2H), 4.50 (t, J = 6.06 Hz, 2H), 3.78-3.92 (m, 2H), 3.46 (t, J = 5.81 Hz, 2H), 3.13 (d, J = 6.06 Hz, 2H), 2.90 (td, J = 6.69, 13.89 Hz, 1H), 1.32 (s, 9H), 1.21 (d, J = 6.69 Hz, 6H) |
| 60a | (500 MHz, DMSO-d₆) δ ppm 8.34-8.52 (m, 2H), 7.39 (d, J = 8.20 Hz, 2H), 7.28 (d, J = 8.20 Hz, 2H), 7.24 (d, J = 5.67 Hz, 2H), 7.17 (d, J = 8.83 Hz, 2H), 6.99 (d, J = 8.83 Hz, 2H), 5.07 (s, 2H), 4.44-4.54 (m, 2H), 3.83-3.90 (m., 2H), 3.53-3.59 (m., 2H), 3.35-3.42 (m, 2H), 2.84-2.95 (m, 1H), 2.79 (s, 3H), 1.27 (s, 9H), 1.21 (d, J = 6.94 Hz, 6H) |
| 95a | (400 MHz, DMSO-d₆) δ ppm 8.43-8.52 (m, 2H), 7.27 (d, J = 6.06 Hz, 2H), 7.21 (d, J = 8.59 Hz, 2H), 7.10 (d, J = 9.09 Hz, 2H), 7.02 (d, J = 8.59 Hz, 2H), 5.09 (s, 2H), 4.44-4.54 (m, 2H), 4.21-4.33 (m, 1H), 3.91-4.04 (m, 3H), 3.42-3.70 (m, 3H), 2.85-3.02 (m, 1H), 1.36 (s, 3H), 1.27 (s, 3H), 1.22 (d, J = 7.07 Hz, 6H) |
| 96a | (400 MHz, DMSO-d₆) δ ppm 8.43-8.51 (m, 2H), 7.25-7.30 (m, 2H), 7.18-7.23 (m, 2H), 7.07-7.12 (m, 2H), 6.95-7.04 (m, 2H), 5.01-5.12 (m, 2H), 4.41-4.54 (m, 2H), 4.20-4.32 (m, 1H), 3.87-4.03 (m, 3H), 3.57-3.69 (m, 2H), 3.43-3.55 (m, 1H), 2.88-3.02 (m, 1H), 1.32-1.38 (m, 3H), 1.24-1.28 (m, 3H), 1.18-1.24 (m, 6H) |
| 161a | (400 MHz, DMSO-d₆) δ ppm 9.01 (d, J = 1.52 Hz, 1H), 8.74 (d, J = 5.56 Hz, 1H), 7.58 (dd, J = 1.52, 5.56 Hz, 1H), 7.39 (d, J = 8.08 Hz, 2H), 7.27 (d, J = 8.08 Hz, 2H), 7.22 (d, J = 9.09 Hz, 2H), 6.93 (d, J = 9.09 Hz, 2H), 5.06 (s, 2H), 4.43-4.55 (m, 2H), 4.20-4.32 (m, 1H), 3.86-4.02 (m, 3H), 3.42-3.70 (m, 3H), 2.85-2.95 (m, 1H), 1.36 (s, 3H), 1.27 (s, 3H), 1.21 (d, J = 7.07 Hz, 6H) |
| 184a | (400 MHz, DMSO-d₆) δ ppm 8.47 (d, J = 6.06 Hz, 2H), 7.35 (d, J = 8.08 Hz, 2H), 7.31 (d, J = 6.06 Hz, 2H), 7.22 (t, J = 8.59 Hz, 1H), 7.11 (d, J = 8.08 Hz, 2H), 7.03 (dd, J = 2.27, 11.87 Hz, 1H), 6.93 (dd, J = 2.27, 8.59 Hz, 1H), 5.09 (s, 2H), 4.47 (s, 2H), 4.24 (t, J = 5.31 Hz, 2H), 3.84-3.91 (m, 2H), 1.87-1.97 (m, 1H), 1.42 (s, 9H), 0.87-1.00 (m, 2H), 0.61-0.72 (m, 2H) |

Pharmacology

A) In Vitro Tests

Ros1 Enzymatic Assay

Compounds were spotted onto white 384-well Proxiplate plus plates (Perkin Elmer) to which 5 µl of enzyme mix (0.5 µg/ml Ros1 enzyme, 50 mM Tris-HCl pH7.5, 1 mM EGTA, 10 mM MgCl2, 0.01% Tween-20) and 5 µl of substrate mix (6 µg/ml IRS-Tide [American Peptide Company], 20 µM ATP, 13.33 µCi/ml ATP (adenosine 5'-triphosphate) P³³, 50 mM Tris-HCl pH7.5, 1 mM EGTA (ethylene glycol-bis(2-aminoethylether)-N,N,N',N'-tetraacetic acid), 10 mM MgCl$_2$, 0.01% Tween-20) were added. After incubation for 120 minutes at room temperature, 10 µl of stop reaction buffer (5 mM EDTA, 50 µM ATP, 0.1% BSA (bovine serum albumin), 0.1% Triton X-100, 50 mM Tris-HCl pH7.5, 1 mM EGTA, 10 mM MgCl$_2$, 0.01% Tween-20) containing 2 mg/ml streptavidin coupled polystyrene imaging beads (Amersham Biosciences) was added and incubated for 15 minutes at room temperature. Plates were centrifuged for 3 minutes at 1500 rpm and signals detected in a LEADseeker imaging system (GE).

In this assay, the inhibitory effects of different compound concentrations (ranging from 10 µM to 0.3 nM) were determined and used to calculate an $IC_{50}$ (M) and $pIC_{50}$ (−log $IC_{50}$) value.

Ba/F3-Ros1 Cell Proliferation Assay

This assay was carried out with Ba/F3 cells containing three different versions of Ros1: the wild-type protein, protein with a mutation at the gatekeeper residue (L2026M), and protein with a mutation identified in a tumor from a patient that became resistant to crizotinib (Xalkori®) treatment (G2032R). Compounds were solubilized in 100% DMSO (dimethyl sulfoxide) and sprayed into polystyrene, tissue culture treated 384-well plates. A 50 µl volume of cell culture medium (phenol red free RPMI-1640, 10% FBS (fetal bovine serum), 2 mM L-Glutamine) containing 20000 Ba/F3-Ros1 cells was added to each well and the plates were placed in an incubator at 37° C. and 5% CO$_2$. After 24 hours, 10 µl of Alamar Blue solution (0.5 mM K$_3$Fe(CN)$_6$, 0.5 mM K$_4$Fe(CN)$_6$, 0.15 mM Resazurin and 100 mM Phosphate Buffer) was added to the wells, incubated for 4 hours at 37° C. and 5% CO$_2$ before RFU's (Relative Fluorescence Units) (ex. 540 nm., em. 590 nm.) were measured in a fluorescence plate reader.

In this assay, the inhibitory effects of different compound concentrations (ranging from 10 µM to 0.3 nM) were determined and used to calculate an $IC_{50}$ (M) and $pIC_{50}$ (−log $IC_{50}$) value.

As a counter-screen the same experiment was performed for the wild-type protein in the presence of 10 ng/ml murine IL-3.

HCC78 Cell Proliferation Assay

Approximately 1000 HCC78 non-small cell lung cancer cells in 180 µl of cell culture medium (RPMI-1640, 10% FBS, 2 mM L-Glutamine, 10 mM Hepes, 1 mM sodium pyruvate, 4.5 g/L glucose, 1.5 g/L sodium bicarbonate, 25 µg/ml Gentamycin) were seeded in each well of a 96-well polystyrene, tissue-culture treated plate and incubated at 37° C. and 5% $CO_2$. After 24 hours, compounds were diluted in cell culture medium from which 20 µl was added to the wells containing cells and incubated for 4 days at 37° C. and 5% $CO_2$. A 5 mg/ml solution of the tetrazolium dye MTT was prepared in PBS (phosphate-buffered saline) and 25 µl was added to each well. After 2 hours the medium was removed and replaced by 125 µL of 4/1 DMSO/glycine buffer (0.1M glycine, 0.1M NaCl, pH 10.5) before absorbance was determined at 538 nm. In this assay, the inhibitory effects of different compound concentrations (ranging from 10 µM to 30 nM) were determined and used to calculate an $EC_{50}$ (M) and $pEC_{50}$ (−log $EC_{50}$) value.

pROS1 Immunofluorescence Assay in HCC78 Cells

Approximately 20000 HCC78 non-small cell lung cancer cells in 180 µl of cell culture medium (RPMI-1640, 10% FBS, 2 mM L-Glutamine, 10 mM Hepes, 1 mM sodium pyruvate, 4.5 g/L glucose, 1.5 g/L sodium bicarbonate, 25 µg/ml Gentamycin) were seeded in each well of a 96-well polystyrene, poly-D-lysine coated plate and incubated at 37° C. and 5% $CO_2$. After 24 hours, compounds were diluted in cell culture medium from which 20 µl was added to the wells containing cells and incubated for 4 hours at 37° C. and 5% $CO_2$. The medium was removed and the cells were fixed by adding 100 µl of 5% formaldehyde in TBS (tris-buffered saline) (50 mM Tris.HCl, pH 7.4, 150 mM NaCl) and incubating for 15 minutes at room temperature. The formaldehyde was removed and replaced with methanol for 10 minutes at room temperature, after which the cells were washed 3 times with TBS containing 1% Triton X-100 and incubated in Odyssee (Li-Cor) blocking buffer for 1 hour at room temperature. The cells were then incubated with the primary rabbit antibody directed against Ros pY2274 (cst-3078) diluted 1/200 in blocking buffer for 24 hours at room temperature. The cells were washed three times with TBS containing 0.1% Triton X-100 and incubated with a secondary anti-rabbit antibody conjugated to the fluorescent dye Alexafluor 680 in blocking buffer for 1 hour at room temperature. The cells were washed three times with TBS containing 0.1% Triton X-100 and left to dry before measuring RFUs (Relative Fluorescence Units) at 700 nm using a fluorescence imager.

The same experiment was performed using total Ros1 antibody (sc-6347) diluted 1/1000 instead of Ros1 pY2274 antibody and an anti-goat antibody conjugated to IRDye800cw as a secondary antibody. RFUs were measured at 800 nM. The signals from total Ros1 detection were used to normalize the Ros1 pY2274 values.

In this assay, the inhibitory effects of different compound concentrations (ranging from 10 µM to 3 nM) were determined and used to calculate an $IC_{50}$ (M) and $pIC_{50}$ (−log $IC_{50}$) value.

The results of the above in vitro test are shown in table 5:

| Co. | ROS1 pIC50 | BaF3-ROS1-IL3 pIC50 | BaF3-ROS1 + IL3 pIC50 | Ba/F3 Ros1 L2026M (-IL-3) pIC50 | Ba/3 Ros1 G2032R (-IL-3) pIC50 | HCC-78 PROL pEC50 | HCC78-pRos1 pIC50 |
|---|---|---|---|---|---|---|---|
| Co. 112 | 6.8 | 6.8 | <5 | | 5.8 | 6.0 | 6.5 |
| Co. 1 | 7.6 | 7.6 | <5 | 7.3 | 7.0 | 6.9 | 7.6 |
| Co. 3 | 7.1 | 7.3 | <5 | 7.0 | | 6.1 | 7.1 |
| Co. 4 | 7.4 | 7.6 | <5 | 7.4 | 6.8 | 6.7 | 7.1 |
| Co. 172 | 6.2 | 6.4 | <5 | 6.3 | 5.2 | 5.4 | 6.5 |
| Co. 188 | 5.4 | 5.5 | <5 | | | | |
| Co. 228 | 6.4 | 6.3 | <5 | | | 5.7 | 6.3 |
| Co. 48 | 7.5 | 7.1 | <5 | | | 6.4 | 7.2 |
| Co. 32 | 8.2 | 8.0 | <5 | 8.0 | 7.3 | 7.3 | 7.8 |
| Co. 189 | 7.5 | 7.1 | <5 | | | 6.7 | 7.4 |
| Co. 5 | 7.6 | 7.6 | <5 | 7.5 | | 6.5 | 7.3 |
| Co. 138 | 7.0 | 6.9 | <5 | 6.8 | 6.0 | 6.3 | 6.5 |
| Co. 185 | 6.9 | 6.3 | <5 | | | 6.1 | 6.8 |
| Co. 71 | 7.6 | 7.7 | <5 | 7.6 | 7.0 | 7.0 | 7.4 |
| Co. 119 | 6.7 | 7.2 | <5 | 6.9 | | 6.4 | 6.5 |
| Co. 197 | 6.1 | 5.8 | <5 | | | | |
| Co. 190 | 6.2 | 6.1 | <5 | | | | |
| Co. 171 | 6.4 | 6.2 | <5 | | 6.0 | 5.8 | 6.3 |
| Co. 116 | 6.9 | 7.3 | <5 | 7.3 | 6.6 | 6.6 | 6.8 |
| Co. 173 | 6.4 | 6.1 | <5 | | | 5.8 | 6.5 |
| Co. 157 | 6.0 | 6.1 | <5 | | | | |
| Co. 143 | 6.0 | 6.4 | 5.3 | 6.0 | | | |
| Co. 229 | <5 | <5 | <5 | | | | |
| Co. 114 | 6.3 | 6.4 | <5 | | | | |
| Co. 6 | 8.0 | 7.9 | <5 | 7.7 | 7.4 | 7.2 | 7.8 |
| Co. 183 | 6.7 | 6.0 | <5 | | 5.6 | 5.8 | 6.4 |
| Co. 103 | 5.9 | 6.0 | <5 | | | 5.7 | 5.4 |
| Co. 7 | 7.4 | 7.4 | <5 | 7.4 | 6.8 | 6.6 | 7.0 |
| Co. 8 | 8.2 | 7.9 | <5 | 7.8 | | 7.4 | 7.6 |
| Co. 158 | 7.3 | 7.4 | <5 | 7.4 | 6.5 | 6.5 | 6.9 |
| Co. 181 | 6.1 | 5.7 | 5.3 | | | 5.7 | 5.9 |
| Co. 9 | 6.2 | 6.4 | <5 | 6.2 | | 5.7 | 5.6 |
| Co. 120 | 6.6 | 6.6 | <5 | | | | |
| Co. 124 | 5.7 | 5.7 | <5 | | | | |

-continued

| Co. | ROS1 pIC50 | BaF3-ROS1-IL3 pIC50 | BaF3-ROS1 + IL3 pIC50 | Ba/F3 Ros1 L2026M (-IL-3) pIC50 | Ba/3 Ros1 G2032R (-IL-3) pIC50 | HCC-78 PROL pEC50 | HCC78-pRos1 pIC50 |
|---|---|---|---|---|---|---|---|
| Co. 33 | 8.0 | 7.7 | <5 | 7.4 | | >7.5 | 7.9 |
| Co. 142 | 6.9 | 6.9 | <5 | 6.4 | | 6.4 | 6.9 |
| Co. 182 | 5.9 | 5.7 | 5.3 | | | | |
| Co. 149 | 8.1 | 7.6 | <5 | 7.4 | | >7.5 | 7.9 |
| Co. 150 | 8.1 | 7.6 | <5 | 7.4 | | 7.4 | 8.0 |
| Co. 110 | 6.9 | 6.9 | <5 | | | | |
| Co. 113 | 6.1 | 6.0 | <5 | | | | |
| Co. 211 | 7.5 | 7.3 | <5 | 7.3 | | | |
| Co. 49 | 7.4 | 7.3 | <5 | 7.2 | 6.9 | 7.0 | 7.5 |
| Co. 10 | 7.1 | 7.1 | <5 | 6.9 | 6.6 | 6.8 | 7.6 |
| Co. 2 | 7.7 | 7.6 | <5 | 7.4 | 7.1 | 6.9 | 7.6 |
| Co. 12 | 6.5 | 6.5 | <5 | 6.7 | | 6.1 | 6.3 |
| Co. 151 | 7.5 | 7.4 | <5 | 7.1 | | 7.2 | 7.7 |
| Co. 130 | 5.5 | 5.8 | <5 | | | | |
| Co. 198 | 6.6 | 6.6 | <5 | | | | |
| Co. 174 | 6.7 | 6.8 | <5 | 6.8 | 6.4 | 6.1 | 6.6 |
| Co. 54 | 7.1 | 7.3 | <5 | 7.2 | 6.6 | 7.1 | 7.7 |
| Co. 214 | 7.5 | 7.4 | <5 | 7.3 | | 7.0 | 7.5 |
| Co. 160 | 7.4 | 7.3 | <5 | 7.3 | | 7.0 | 7.5 |
| Co. 165 | 6.7 | 6.7 | <5 | 6.5 | | 5.9 | 6.2 |
| Co. 186 | 6.0 | 6.2 | <5 | | | | |
| Co. 210 | 7.2 | 6.3 | 5.2 | | | | |
| Co. 26 | 6.4 | 6.6 | <5 | 6.5 | | 6.1 | 6.2 |
| Co. 163 | 6.9 | 7.1 | <5 | 7.1 | | 6.9 | 6.5 |
| Co. 176 | 6.8 | 6.9 | <5 | 7.1 | | 7.1 | |
| Co. 18 | 8.0 | 7.7 | <5 | 7.7 | 7.3 | 7.4 | |
| Co. 25 | 6.9 | 6.8 | <5 | 6.5 | | 6.3 | |
| Co. 59 | 7.2 | 6.4 | 5.3 | ~6.1 | | 6.3 | |
| Co. 59a | 7.2 | 6.6 | 5.2 | | | | |
| Co. 104 | 5.9 | 6.1 | <5 | | | | |
| Co. 179 | 6.3 | 6.4 | <5 | | | | |
| Co. 50 | 7.3 | 7.1 | <5 | 7.2 | | 6.8 | |
| Co. 166 | 7.2 | 6.9 | <5 | | | | |
| Co. 105 | 6.9 | 7.0 | <5 | 6.6 | | 6.8 | |
| Co. 37 | 5.6 | 5.4 | <5 | | | | |
| Co. 121 | 5.0 | 6.3 | <5 | 5.9 | | 6.0 | |
| Co. 170 | 5.2 | 5.2 | <5 | | | | |
| Co. 9a | 5.6 | <5 | <5 | | | | |
| Co. 122 | 6.9 | 6.9 | <5 | 7.1 | | 7.2 | |
| Co. 159 | 7.3 | 7.3 | <5 | 7.2 | 6.4 | 7.2 | |
| Co. 15 | 7.4 | 7.5 | <5 | 7.5 | | 7.3 | |
| Co. 132 | 5.4 | 5.7 | <5 | | | | |
| Co. 154 | 7.0 | 6.9 | <5 | 7.1 | | 6.5 | |
| Co. 133 | <5 | 5.6 | <5 | | | | |
| Co. 21 | 8.0 | 7.8 | <5 | 7.6 | 7.4 | 7.4 | |
| Co. 180 | 6.3 | 6.5 | <5 | | | | |
| Co. 131 | 6.2 | 6.2 | <5 | | | | |
| Co. 90 | 7.1 | 7.2 | <5 | 7.4 | | 6.8 | |
| Co. 13 | 7.7 | 7.5 | <5 | | | | |
| Co. 17 | 6.3 | 6.8 | <5 | | | | |
| Co. 34 | 6.5 | 6.6 | <5 | | | | |
| Co. 153 | 7.4 | 7.5 | <5 | 6.8 | | 6.5 | |
| Co. 63 | 7.0 | 7.1 | <5 | 7.3 | 6.7 | 6.4 | |
| Co. 80 | 6.9 | 6.9 | <5 | | | | |
| Co. 118 | 6.8 | 7.1 | <5 | | | | |
| Co. 152 | 8.0 | 8.0 | <5 | 8.1 | | 7.2 | |
| Co. 11 | 8.0 | 7.7 | <5 | 7.8 | | 7.5 | |
| Co. 24 | 8.1 | 7.8 | <5 | 8.2 | | 8.8 | |
| Co. 84 | 7.6 | 7.7 | <5 | 7.2 | 7.0 | 7.5 | |
| Co. 44 | 7.3 | 7.4 | <5 | 6.9 | 6.8 | 6.6 | |
| Co. 230 | <5 | 5.2 | <5 | | | | |
| Co. 215 | 6.9 | 7.0 | <5 | 7.2 | | 6.6 | |
| Co. 187 | 7.1 | 7.2 | <5 | 6.4 | | 7.0 | |
| Co. 89 | 7.5 | 7.6 | <5 | 7.1 | | 6.7 | |
| Co. 52 | 7.3 | 7.6 | <5 | 6.9 | | 6.6 | |
| Co. 51 | 7.1 | 7.2 | <5 | 7.3 | 6.6 | 7.0 | |
| Co. 193 | 7.1 | 7.3 | <5 | 6.3 | | 6.7 | |
| Co. 77 | 6.5 | 6.3 | <5 | 6.3 | | 5.7 | |
| Co. 53 | 7.4 | 7.4 | <5 | 6.9 | 7.0 | 7.0 | |
| Co. 47 | 7.3 | 7.3 | <5 | 7.5 | 6.9 | 7.1 | |
| Co. 46 | 7.3 | 7.5 | <5 | 7.1 | 6.9 | 7.0 | |
| Co. 66 | 6.6 | 5.1 | <5 | | | | |
| Co. 88 | 7.9 | 7.1 | <5 | 6.8 | | 7.1 | |
| Co. 14 | 8.2 | 7.8 | <5 | 8.2 | | >7.5 | |

-continued

| Co. | ROS1 pIC50 | BaF3-ROS1-IL3 pIC50 | BaF3-ROS1 + IL3 pIC50 | Ba/F3 Ros1 L2026M (-IL-3) pIC50 | Ba/3 Ros1 G2032R (-IL-3) pIC50 | HCC-78 PROL pEC50 | HCC78-pRos1 pIC50 |
|---|---|---|---|---|---|---|---|
| Co. 184 | 7.0 | 7.3 | <5 | 6.6 | | 6.6 | |
| Co. 19 | 7.9 | 8.2 | <5 | 8.0 | 7.5 | >7.5 | |
| Co. 194 | 7.1 | 6.6 | 5.2 | 6.2 | | 6.3 | |
| Co. 62 | 6.7 | 7.0 | <5 | 6.6 | | 6.3 | |
| Co. 123 | 7.4 | 7.4 | <5 | 7.1 | | 6.4 | |
| Co. 16 | 7.0 | 7.4 | <5 | 7.1 | | 6.4 | |
| Co. 203 | 8.4 | 8.2 | <5 | 8.0 | | 8.0 | |
| Co. 85 | 7.4 | 7.4 | <5 | 7.1 | | 6.5 | |
| Co. 61 | | 6.3 | <5 | 5.9 | | 6.2 | |
| Co. 195 | 6.9 | 6.7 | <5 | 7.0 | | 6.1 | |
| Co. 191 | 6.8 | 6.9 | <5 | 7.0 | | 6.3 | |
| Co. 192 | 6.8 | 6.9 | <5 | 6.9 | | 6.2 | |
| Co. 60 | 7.2 | 6.6 | 5.4 | 6.2 | | 6.2 | |
| Co. 86 | 8.0 | 7.2 | <5 | 6.9 | | 6.3 | |
| Co. 39 | 7.1 | 7.3 | <5 | 7.0 | | 6.8 | |
| Co. 38 | 7.9 | 7.9 | <5 | 7.5 | | 7.3 | |
| Co. 106 | 7.6 | 7.5 | <5 | | | | |
| Co. 20 | 7.0 | 6.9 | <5 | 7.0 | | 5.8 | |
| Co. 125 | 6.5 | 6.7 | <5 | | | | |
| Co. 127 | 6.4 | 6.6 | <5 | | | | |
| Co. 57 | 7.6 | 7.7 | <5 | | | | |
| Co. 178 | 6.7 | 6.6 | <5 | | | | |
| Co. 141 | 6.2 | 6.4 | <5 | | | | |
| Co. 108 | 6.9 | 7.0 | <5 | | | | |
| Co. 43 | 7.3 | 7.4 | <5 | 7.3 | | 6.9 | |
| Co. 126 | 6.7 | 6.9 | <5 | 6.6 | | 5.9 | |
| Co. 55 | 6.9 | 7.0 | <5 | 6.8 | | 6.1 | |
| Co. 40 | 7.0 | 6.9 | <5 | 6.4 | | 5.4 | |
| Co. 42 | 6.4 | 6.7 | <5 | 6.3 | | 5.9 | |
| Co. 41 | 7.5 | 7.4 | <5 | 6.6 | | 7.1 | |
| Co. 23 | 7.9 | 7.7 | <5 | 7.2 | | 7.2 | |
| Co. 22 | 7.9 | 7.8 | <5 | 7.4 | | 7.7 | |
| Co. 91 | 7.5 | 7.3 | <5 | 6.6 | | 7.2 | |
| Co. 129 | 7.2 | 7.4 | <5 | 7.0 | | 7.0 | |
| Co. 87 | 7.4 | 7.3 | <5 | 7.2 | | 6.7 | |
| Co. 107 | 7.7 | 7.7 | <5 | 7.4 | | 7.1 | |
| Co. 109 | 7.0 | 7.1 | <5 | 7.2 | | 6.4 | |
| Co. 65 | 7.0 | 7.2 | <5 | 6.7 | | 6.5 | |
| Co. 136 | 7.2 | 7.1 | <5 | 6.6 | | 6.5 | |
| Co. 64 | 7.1 | 7.1 | <5 | 6.6 | | 6.2 | |
| Co. 81 | 7.2 | 7.3 | <5 | 6.5 | | 6.8 | |
| Co. 196 | 6.8 | 6.9 | <5 | 6.4 | | 6.2 | |
| Co. 175 | 7.0 | 6.9 | 5.3 | 6.8 | | 6.4 | |
| Co. 27 | 7.8 | 7.7 | <5 | 7.1 | | 7.7 | |
| Co. 137 | 6.9 | 6.8 | <5 | 6.4 | | 6.4 | |
| Co. 56 | 7.4 | 7.5 | <5 | 7.0 | | 6.9 | |
| Co. 139 | 6.9 | 6.8 | <5 | 6.0 | | 7.0 | |
| Co. 207 | 7.7 | 7.1 | <5 | 6.5 | | 6.3 | |
| Co. 94 | 7.0 | 7.0 | <5 | 6.6 | | 6.4 | |
| Co. 29 | <5 | <5 | <5 | <5 | | <5 | |
| Co. 95 | 6.8 | 6.8 | <5 | | | 6.4 | |
| Co. 92 | 7.3 | 7.2 | <5 | 6.7 | | 6.7 | |
| Co. 155 | 7.5 | 7.8 | <5 | 7.5 | | 7.1 | |
| Co. 209 | 7.2 | 7.5 | 5.3 | 7.5 | | 6.3 | |
| Co. 30 | <5 | <5 | <5 | <5 | | <5 | |
| Co. 93 | 7.1 | 7.2 | <5 | 7.0 | | 6.4 | |
| Co. 161 | 7.3 | 7.1 | <5 | 6.7 | | 6.5 | |
| Co. 45 | 6.8 | 6.7 | <5 | 6.6 | | 5.9 | |
| Co. 68 | 6.5 | 6.7 | 5.6 | 6.5 | | 5.6 | |
| Co. 96 | 6.8 | 6.9 | <5 | 6.6 | | 5.9 | |
| Co. 177 | 6.7 | 6.9 | <5 | 6.6 | | 6.4 | |
| Co. 164 | 6.8 | 7.0 | <5 | 6.7 | | 6.1 | |
| Co. 208 | 7.2 | 6.8 | <5 | 6.3 | | 6.4 | |
| Co. 167 | 6.9 | 7.2 | <5 | 6.2 | | 6.3 | |
| Co. 98 | 6.6 | 6.8 | <5 | 6.6 | | 6.5 | |
| Co. 35 | 5.3 | 5.7 | <5 | 5.8 | | <5 | |
| Co. 111 | 6.9 | 7.1 | <5 | 6.7 | 6.6 | 6.2 | |
| Co. 36 | 5.3 | 5.8 | <5 | 5.7 | | <5 | |
| Co. 97 | 6.8 | 6.9 | <5 | 6.3 | <5 | 5.5 | |
| Co. 99 | 6.3 | 6.6 | <5 | 6.0 | | 5.7 | |
| Co. 140 | 6.6 | 6.4 | <5 | 5.8 | | 5.7 | |
| Co. 148 | 5.2 | 5.5 | <5 | 5.9 | | 5.8 | |
| Co. 144 | 5.9 | 6.3 | <5 | 5.7 | | 5.0 | |
| Co. 145 | 5.5 | 5.8 | <5 | 5.1 | | <5.5 | |

-continued

| Co. | ROS1 pIC50 | BaF3-ROS1-IL3 pIC50 | BaF3-ROS1 + IL3 pIC50 | Ba/F3 Ros1 L2026M (-IL-3) pIC50 | Ba/3 Ros1 G2032R (-IL-3) pIC50 | HCC-78 PROL pEC50 | HCC78-pRos1 pIC50 |
|---|---|---|---|---|---|---|---|
| Co. 79 | 7.6 | 7.8 | <5 | 7.3 | | 5.6 | |
| Co. 205 | 8.1 | 7.8 | <5 | 7.5 | | | |
| Co. 100 | 6.7 | 6.9 | <5 | 6.3 | | | |
| Co. 101 | 6.4 | 6.7 | <5 | 6.4 | | | |
| Co. 102 | 6.1 | 6.7 | <5 | 6.4 | | | |
| Co. 213 | 7.0 | 7.0 | <5 | 6.4 | | | |
| Co. 212 | 7.4 | 7.3 | <5 | 6.8 | | | |
| Co. 204 | 8.2 | 7.9 | <5 | 7.8 | | | |
| Co. 169 | 6.0 | 6.2 | <5 | 5.6 | | | |
| Co. 168 | 6.4 | 6.5 | <5 | 6.2 | | | |
| Co. 70 | 5.5 | 6.4 | <5 | 6.1 | | | |
| Co. 83 | 7.7 | 7.6 | <5 | 7.2 | | | |
| Co. 82 | 8.0 | 7.6 | <5 | 7.3 | | | |
| Co. 75 | 7.9 | 7.9 | <5 | 7.5 | | | 7.2 |
| Co. 117 | 6.9 | 7.0 | <5 | 6.9 | | | 6.6 |
| Co. 31 | 5.8 | 6.3 | <5 | 5.9 | | | 5.2 |
| Co. 162 | 7.1 | 7.2 | <5 | 7.1 | | | 6.4 |
| Co. 28 | 7.8 | 7.8 | <5 | 7.7 | 7.3 | | 7.2 |
| Co. 206 | 7.4 | 7.5 | <5 | ~7.4 | | | 7.0 |
| Co. 199 | 6.7 | 7.1 | <5 | 7.5 | | | 5.9 |
| Co. 74 | 7.8 | 8.1 | <5 | 7.5 | | | 7.9 |
| Co. 73 | 7.8 | 7.9 | <5 | 7.4 | | | 6.9 |
| Co. 146 | 5.7 | 6.2 | <5 | 7.6 | | | 5.4 |
| Co. 200 | 6.9 | 7.3 | <5 | 6.3 | 6.6 | | 6.5 |
| Co. 147 | 5.4 | 5.4 | 5.4 | 6.7 | | | 5.4 |
| Co. 115 | 5.9 | 6.3 | <5 | <5 | | | 5.8 |
| Co. 69 | 7.2 | 7.4 | <5 | <5 | | | 6.7 |
| Co. 76 | 6.6 | 6.8 | <5 | 7.0 | | | 6.1 |
| Co. 72 | 7.2 | 7.2 | <5 | 6.0 | | | 6.6 |
| Co. 201 | 7.6 | 7.8 | <5 | 7.4 | | | 7.4 |
| Co. 156 | 7.2 | 8.0 | <5 | 7.0 | | | 7.7 |
| Co. 58 | 7.7 | 7.3 | 5.2 | 7.0 | | | 6.0 |
| Co. 134 | 7.1 | 7.3 | <5 | 7.0 | | | 6.7 |
| Co. 135 | 6.8 | 7.3 | <5 | 7.0 | | | 6.5 |
| Co. 128 | 5.9 | 6.6 | <5 | 6.2 | | | 6.0 |
| Co. 226 | 6.2 | 7.1 | <5 | 6.8 | | | 6.3 |
| Co. 67 | 7.6 | 7.9 | <5 | 7.1 | | | |
| Co. 231 | 6.1 | 6.4 | <5 | 5.7 | | | |
| Co. 232 | 5.7 | 6.7 | <5 | 6.5 | | | 5.6 |
| Co. 233 | 6.1 | 6.5 | <5 | 5.9 | | | 5.6 |
| Co. 234 | 7.7 | 7.1 | <5 | 6.7 | | | 6.9 |
| Co. 78 | 6.6 | 7.1 | <5 | 6.9 | | | 6.1 |
| Co. 235 | 7.6 | 6.7 | <5 | 6.5 | | | 6.5 |
| Co. 236 | 7.8 | 7.6 | 5.4 | 7.4 | | | 6.9 |
| Co. 216 | 7.2 | 7.3 | <5 | 6.9 | | | 6.2 |
| Co. 217 | 6.4 | 6.3 | <5 | 6.0 | | | 5.5 |
| Co. 223 | 6.4 | 6.5 | <5 | | | | |
| Co. 219 | 5.9 | 6.0 | <5 | | | | |
| Co. 224 | 6.4 | 6.7 | <5 | | | | |
| Co. 225 | 6.5 | 6.7 | <5 | | | | |
| Co. 218 | 6.7 | 6.3 | <5 | | | | |
| Co. 222 | 6.7 | 7.0 | <5 | | | | |
| Co. 220 | 6.3 | 6.5 | <5 | | | | |
| Co. 227 | 6.1 | 6.3 | <5 | | | | |
| Co. 221 | 6.3 | 6.5 | <5 | | | | |
| Co. 237 | 6.1 | 6.8 | <5 | | | | |

B) In Vivo Test

Efficacy Studies in Mice Bearing Ba/F3-Ros1 Tumors

Approximately $2 \times 10^6$ Ba/F3 cells containing either wild-type, L2026M or G2032R mutant Ros1 were inoculated into the inguinal region of NMRI nude mice. When the resulting tumors reached a size of 250 to 350 mm$^3$, mice were randomly assigned to the different treatment groups (8 to 12 mice per group). Compounds formulated in 20% cyclodextrin were administered to the mice by oral gavage at various doses for 10-days once (QD) or twice (BID) a day. Tumor sizes were determined by caliper measurement on day 1 prior to treatment and then twice weekly for the duration of the study using the commonly following formula: tumor volume (mm$^3$)=(a×b$^2$/2); where 'a' represents the length, and 'b' the width of the tumor. Treatment/control (T/C) ratios were calculated at the end of the study based on the change in final relative tumor volumes.

| Tumor model | Co. | Dose (mg/kg) | administration frequency | T/C (%) | number of mice per group |
|---|---|---|---|---|---|
| Ba/F3-Ros1 wild-type | Co. 1 | 1.56 | QD | 88 | 12 |
| Ba/F3-Ros1 wild-type | Co. 1 | 3.125 | QD | 75 | 12 |
| Ba/F3-Ros1 wild-type | Co. 1 | 6.25 | QD | 35 | 12 |
| Ba/F3-Ros1 wild-type | Co. 1 | 12.5 | QD | 12 | 12 |
| Ba/F3-Ros1 wild-type | Co. 1 | 25 | QD | −27 | 12 |

| Tumor model | Co. | Dose (mg/kg) | administration frequency | T/C (%) | number of mice per group |
|---|---|---|---|---|---|
| Ba/F3-Ros1 wild-type | Co. 1 | 6.25 | BID | 50 | 8 |
| Ba/F3-Ros1 wild-type | Co. 1 | 12.5 | BID | 20 | 8 |
| Ba/F3-Ros1 wild-type | Co. 1 | 25 | BID | −13 | 8 |
| Ba/F3-Ros1 wild-type | Co. 2 | 12.5 | QD | 61 | 12 |
| Ba/F3-Ros1 wild-type | Co. 2 | 25 | QD | 46 | 12 |
| Ba/F3-Ros1 wild-type | Co. 2 | 50 | QD | 20 | 12 |
| Ba/F3-Ros1 wild-type | Co. 2 | 3.125 | BID | 91 | 12 |
| Ba/F3-Ros1 wild-type | Co. 2 | 6.25 | BID | 67 | 12 |
| Ba/F3-Ros1 wild-type | Co. 2 | 12.5 | BID | 47 | 12 |
| Ba/F3-Ros1 wild-type | Co. 2 | 25 | BID | 5 | 12 |
| Ba/F3-Ros1 wild-type | Co. 2 | 50 | BID | −15 | 12 |
| Ba/F3-Ros1 wild-type | Co. 2 | 12.5 | BID | 51 | 8 |
| Ba/F3-Ros1 wild-type | Co. 2 | 25 | BID | 41 | 8 |
| Ba/F3-Ros1 wild-type | Co. 2 | 50 | BID | 32 | 8 |
| Ba/F3-Ros1 wild-type | Co. 2 | 100 | BID | −22 | 8 |
| Ba/F3-Ros1 L2026M | Co. 1 | 25 | QD | 42 | 8 |
| Ba/F3-Ros1 L2026M | Co. 1 | 25 | BID | −11 | 8 |
| Ba/F3-Ros1 L2026M | Co. 1 | 6.25 | BID | 94 | 8 |
| Ba/F3-Ros1 L2026M | Co. 1 | 12.5 | BID | 23 | 8 |
| Ba/F3-Ros1 L2026M | Co. 1 | 25 | BID | 24 | 8 |
| Ba/F3-Ros1 L2026M | Co. 2 | 12.5 | BID | 82 | 8 |
| Ba/F3-Ros1 L2026M | Co. 2 | 25 | BID | 50 | 8 |
| Ba/F3-Ros1 L2026M | Co. 2 | 50 | BID | 28 | 8 |
| Ba/F3-Ros1 L2026M | Co. 2 | 100 | BID | −32 | 8 |
| Ba/F3-Ros1 G2032R | Co. 1 | 6.25 | BID | 79 | 8 |
| Ba/F3-Ros1 G2032R | Co. 1 | 12.5 | BID | 43 | 8 |
| Ba/F3-Ros1 G2032R | Co. 1 | 25 | BID | 7 | 8 |
| Ba/F3-Ros1 G2032R | Co. 2 | 12.5 | BID | 89 | 8 |
| Ba/F3-Ros1 G2032R | Co. 2 | 25 | BID | 55 | 8 |
| Ba/F3-Ros1 G2032R | Co. 2 | 50 | BID | 18 | 8 |
| Ba/F3-Ros1 G2032R | Co. 2 | 100 | BID | −16 | 8 |

Composition Examples

"Active ingredient" (a.i.) as used throughout these examples relates to a compound of Formula (I), including any tautomer or stereoisomeric form thereof, or a N-oxide, a pharmaceutically acceptable addition salt or a solvate thereof; in particular to any one of the exemplified compounds.

Typical examples of recipes for the formulation of the invention are as follows:

1. Tablets

| Active ingredient | 5 to 50 mg |
|---|---|
| Di-calcium phosphate | 20 mg |
| Lactose | 30 mg |
| Talcum | 10 mg |
| Magnesium stearate | 5 mg |
| Potato starch | ad 200 mg |

2. Suspension

An aqueous suspension is prepared for oral administration so that each milliliter contains 1 to 5 mg of active ingredient, 50 mg of sodium carboxymethyl cellulose, 1 mg of sodium benzoate, 500 mg of sorbitol and water ad 1 ml.

3. Injectable

A parenteral composition is prepared by stirring 1.5% (weight/volume) of active ingredient in 0.9% NaCl solution or in 10% by volume propylene glycol in water.

4. Ointment

| Active ingredient | 5 to 1000 mg |
|---|---|
| Stearyl alcohol | 3 g |
| Lanoline | 5 g |
| White petroleum | 15 g |
| Water | ad 100 g |

In this Example, active ingredient can be replaced with the same amount of any of the compounds according to the present invention, in particular by the same amount of any of the exemplified compounds.

The invention claimed is:

1. A compound of Formula (I)

a tautomer or a stereoisomeric form thereof, wherein
$y_1$ is $CR_{7a}$ or N;
$y_2$ is CH or N;
$R_{7a}$ is hydrogen, halo, trifluoromethyl or cyano;
$R_7$ is hydrogen, —NH$_2$, —NHCH$_3$, —NH(CH$_2$CH$_3$), methyl, —CH$_2$OH, halo or cyano;
or when $y_1$ represents $CR_{7a}$, this $R_{7a}$ can be taken together with a $R_7$ on an adjacent carbon atom to form —CH=CH—NH— or —N=CH—NH—;
X is —CR$_1$R$_{1a}$—, —CH$_2$—CHR$_1$—;
$R_1$ is hydrogen or $C_{1-6}$alkyl;
$R_{1a}$ is hydrogen; $C_{1-6}$alkyl; mono- or polyhalo$C_{1-6}$alkyl; $C_{1-6}$alkyl substituted with one or two hydroxyl groups; $C_{1-6}$alkyl substituted with one —NR$_{9a}$R$_{9b}$; or —C(=O)—NR$_{9a}$R$_{9b}$;
$R_{2a}$ is hydrogen; $C_{1-6}$alkyl; mono- or polyhalo$C_{1-6}$alkyl; $C_{1-6}$alkyl substituted with one or two hydroxyl groups; or $C_{1-6}$alkyl substituted with one substituent selected from the group consisting of —NR$_{9a}$R$_{9b}$, cyano and $C_{1-4}$alkyloxy;
$R_{2b}$ is hydrogen or $C_{1-6}$alkyl; or
$R_{2a}$ and $R_{2b}$ are taken together to form —CH$_2$—CH$_2$—, —CH$_2$—NR$_{2c}$—CH$_2$—, —CH$_2$—CH$_2$—CH$_2$—, —CH$_2$—O—CH$_2$—, —CH$_2$—CH$_2$—CH$_2$—CH$_2$—, —CH$_2$—CH$_2$—NR$_{2c}$—CH$_2$— or =O;
$R_{2c}$ is hydrogen; $C_{1-4}$alkyl optionally substituted with one or two hydroxyl groups; mono- or polyhalo$C_{1-6}$alkyl; $C_{1-6}$alkyloxy; $C_{1-6}$alkyl substituted with one cyano group; or $C_{1-6}$alkyl substituted with one —NR$_{9a}$R$_{9b}$;
$R_3$ is hydrogen; $C_{1-6}$alkyl; mono- or polyhalo$C_{1-6}$alkyl; $C_{1-6}$alkyl substituted with one or two hydroxyl groups; $C_{1-6}$alkyl substituted with one or two hydroxyl groups and one $C_{1-6}$alkyloxy; $C_{1-6}$alkylcarbonyl- optionally substituted with one or two hydroxyl groups; mono- or polyhalo$C_{1-6}$alkylcarbonyl-; $R_{10a}R_{10b}$N—$C_{1-6}$alkylcarbonyl-; $C_{1-6}$alkyl-O-carbonyl-; $C_{1-6}$alkylcarbonyloxy-; C$_{1-6}$alkyl substituted with one R$_{11}$; C$_{1-6}$alkyloxy optionally substituted with one —NR$_{10a}$R$_{10b}$; C$_{2-6}$alkenyl; C$_{2-6}$alkynyl;

hydroxyC$_{2-6}$alkenyl; hydroxyC$_{2-6}$alkynyl; C$_{1-6}$alkyloxyC$_{2-6}$alkenyl;

C$_{1-6}$alkyloxyC$_{2-6}$alkynyl; C$_{2-6}$alkenyl substituted with one —NR$_{10a}$R$_{10b}$; C$_{2-6}$alkynyl substituted with one —NR$_{10a}$R$_{10b}$; C$_{1-6}$alkyl substituted with one or two hydroxyl groups and one —NR$_{10a}$R$_{10b}$; —C$_{1-6}$alkyl-C(R$_{13}$)=N—O—R$_{13}$; —S(=O)$_2$—C$_{1-6}$alkyl; —S(=O)$_2$—NR$_{9a}$R$_{9b}$; C$_{1-6}$alkyl substituted with one —(C=O)—R$_{14}$; C$_{1-6}$alkyl substituted with one or two hydroxyl groups and one R$_{14}$; C$_{1-6}$alkyl substituted with one R$_{14}$; C$_{2-6}$alkenyl substituted with one R$_{14}$; C$_{2-6}$alkynyl substituted with one R$_{14}$; or R$_{14}$, R$_{4a}$ is hydrogen;
R$_{4b}$ is hydrogen; or
R$_{4a}$ and R$_{4b}$ are taken together to form =O;
Y is —O— or —C(=O)—;
Z is —CHR$_6$— or —CH$_2$—C≡C—;
R$_6$ is hydrogen; C$_{1-4}$alkyl-O-carbonyl-; C$_{1-4}$alkyl; C$_{1-4}$alkyl substituted with one or two hydroxyl groups; C$_{1-4}$alkyl substituted with one —NR$_{9a}$R$_{9b}$; or —C(=O)—NR$_{9a}$R$_{9b}$;
Ring A is phenyl or a 6-membered saturated, partially saturated or aromatic heterocyclyl, said heterocyclyl containing one or two nitrogen atoms; wherein the phenyl or the heterocyclyl is optionally substituted with one or two R$_8$ substituents;
each R$_8$ is independently hydrogen; C$_{1-4}$alkyloxy; hydroxyl; cyano; C$_{1-4}$alkyl or halo;
or a R$_8$ substituent on an atom adjacent to the atom carrying the Y—Z substituent may be taken together with the R$_6$ substituent of Z, by which ring A together with Y—Z forms a bicycle of formula (a-1), (a-2), (a-3) or (a-4):

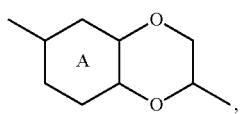

(a-1)

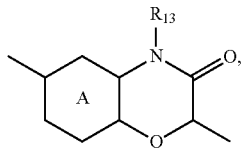

(a-2)

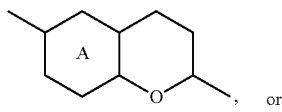

(a-3)

or

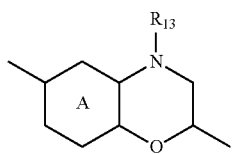

(a-4)

R$_{9a}$ and R$_{9b}$ each independently represent hydrogen; mono- or polyhaloC$_{1-4}$alkyl; C$_{1-4}$alkylcarbonyl-; C$_{1-4}$alkyl-O-carbonyl-; C$_{1-4}$alkyl substituted with one or two hydroxyl groups; or C$_{1-4}$alkyl optionally substituted with one substituent selected from the group consisting of C$_{1-4}$alkyloxy, cyano, amino and mono- or di(C$_{1-4}$alkyl) amino;

R$_{10a}$ and R$_{10b}$ each independently represent hydrogen; C$_{1-4}$alkyl; cyanoC$_{1-6}$alkyl;

C$_{1-6}$alkyl substituted with one NR$_{9a}$R$_{9b}$; C$_{1-6}$alkyl substituted with one —C(=O)—NR$_{9a}$R$_{9b}$; C$_{1-6}$alkyloxy optionally substituted with one or two hydroxyl groups;

C$_{1-6}$alkyloxyC$_{1-6}$alkyl wherein each C$_{1-6}$alkyl is optionally substituted with one or two hydroxyl groups; R$_{14}$; C$_{1-6}$alkyl substituted with one R$_{14}$; —(C=O)—R$_{14}$;

C$_{1-6}$alkylcarbonyl-; C$_{1-6}$alkyl-O-carbonyl-; mono- or polyhaloC$_{1-6}$alkylcarbonyl- substituted with one or two hydroxyl groups; mono- or polyhaloC$_{1-6}$alkyl substituted with one or two hydroxyl groups; mono- or polyhaloC$_{1-6}$alkylcarbonyl-; C$_{1-6}$alkyl substituted with one —Si(CH$_3$)$_3$; —S(=O)$_2$—C$_{1-6}$alkyl optionally substituted with one or more halo substituents; —S(=O)$_2$—NR$_{9a}$R$_{9b}$;

C$_{1-6}$alkyl substituted with one —S(=O)$_2$—C$_{1-6}$alkyl wherein —S(=O)$_2$—C$_{1-6}$alkyl is optionally substituted with one or more halo substituents;

C$_{1-6}$alkyl substituted with one —S(=O)$_2$—NR$_{9a}$R$_{9b}$;

C$_{1-6}$alkyl substituted with one —NH—S(=O)$_2$—C$_{1-6}$alkyl wherein —NH—S(=O)$_2$—C$_{1-6}$alkyl is optionally substituted on a carbon atom with one or more halo substituents;

C$_{1-6}$alkyl substituted with one 13 NH—S(=O)$_2$—NR$_{9a}$R$_{9b}$;

mono- or polyhaloC$_{1-4}$alkyl; or C$_{1-4}$alkyl substituted with one or two hydroxyl groups;

R$_{11}$ is cyano; —NR$_{10a}$R$_{10b}$; C$_{1-6}$alkyloxy optionally substituted with one or two hydroxyl groups; —S(=O)$_2$—C$_{1-6}$alkyl; —S(=O)$_2$—NR$_{9a}$R$_{9b}$; —NR$_{13}$—S(=O)$_2$—C$_{1-6}$alkyl; —NR$_{13}$—S(=O)$_2$—NR$_{9a}$R$_{9b}$; C$_{1-6}$alkylcarbonyloxy-; —C(=O)—NR$_{10a}$R$_{10b}$; —O—C(=O)—NR$_{10a}$R$_{10b}$; —COOH; —P(=O)(OH)$_2$; or —P(=O)(O—C$_{1-4}$alkyl)$_2$;

R$_{12}$ is —NR$_{9a}$R$_{9b}$, C$_{1-6}$alkyloxy, or cyano;
R$_{13}$ is hydrogen or C$_{1-4}$alkyl;
R$_{14}$ is a C$_{3-8}$cycloalkyl; or a 4, 5 or 6 membered saturated heterocyclyl which is optionally substituted with one, two or three substituents selected from the group consisting of oxo, C$_{1-4}$alkyl, halogen, cyano, hydroxyl, C$_{1-6}$alkyloxy and NR$_{9a}$R$_{9b}$;

x$_1$ is CR$_{5a}$ or N;
x$_2$ is CR$_{5b}$ or N;
x$_3$ is CR$_{5c}$ or N;

each R$_{15}$ is independently selected from the group consisting of hydrogen, methyl, halo, C$_{1-4}$alkyloxy and hydroxyl;

R$_{5a}$ and R$_{5c}$ each independently are selected from the group consisting of hydrogen; hydroxyl; cyano; halo; C$_{1-6}$alkyl; C$_{1-6}$alkyl substituted with one or two hydroxyl groups; mono- or polyhaloC$_{1-6}$alkyl; mono- or polyhaloC$_{1-6}$alkyloxy; C$_{1-6}$alkyl substituted with one —NR$_{9a}$R$_{9b}$; C$_{1-6}$alkyl substituted with one cyano; C$_{1-6}$alkyloxyC$_{1-6}$alkyl wherein each of the C$_{1-6}$alkyl groups are optionally substituted with one or two hydroxyl groups; C$_{2-6}$alkenyl; C$_{1-6}$alkyl-O-carbonyl-; C$_{1-6}$alkyloxy; C$_{1-6}$alkyloxy substituted with one or two hydroxyl groups; C$_{1-6}$alkyloxyC$_{1-6}$alkyloxy wherein each of the C$_{1-6}$alkyl groups are optionally substituted with one or two hydroxyl groups; C$_{1-6}$alkyloxy substituted with one cyano; and C$_{1-6}$alkyloxy substituted with one —NR$_{9a}$R$_{9b}$;

R$_{5b}$ is hydrogen; C$_{1-6}$alkyl; C$_{3-6}$cycloalkyl optionally substituted with one cyano; hydroxyl; cyano; mono- or polyhaloC$_{1-6}$alkyloxy; mono- or polyhaloC$_{1-6}$alkyl; C$_{1-4}$alkyl substituted with one or two hydroxyl groups; C$_{2-6}$alkenyl; C$_{1-4}$alkyloxy; —Si(CH$_3$)$_3$; C$_{1-6}$alkyl substituted with one R$_{12}$; C$_{1-6}$alkyl-O-carbonyl-; or C$_{1-6}$alkyloxy substituted with one R$_{12}$; or an N-oxide formed at the nitrogen the ring

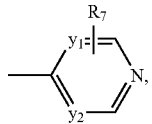

when y$_1$ is CR$_{7a}$ and y$_2$ is CH, or a pharmaceutically acceptable addition salt or a solvate thereof.

2. The compound according to claim 1, wherein
y$_1$ is CR$_{7a}$ or N;
y$_2$ is CH;
R$_{7a}$ is hydrogen;
R$_7$ is hydrogen, —NH$_2$, —NHCH$_3$, —NH(CH$_2$CH$_3$), methyl, —CH$_2$OH, halo or cyano;
or when y$_1$ represents CR$_{7a}$, this R$_{7a}$ can be taken together with a R$_7$ on an adjacent carbon atom to form —CH=CH—NH— or —N=CH—NH—;
X is —CR$_1$R$_{1a}$—, —CH$_2$—CHR$_1$—;
R$_1$ is hydrogen or C$_{1-6}$alkyl;
R$_{1a}$ is hydrogen;
R$_{2a}$ is hydrogen; C$_{1-6}$alkyl; mono- or polyhaloC$_{1-6}$alkyl; C$_{1-6}$alkyl substituted with one or two hydroxyl groups; or C$_{1-6}$alkyl substituted with one substituent selected from the group consisting of —NR$_{9a}$R$_{9b}$, cyano and C$_{1-4}$alkyloxy;
R$_{2b}$ is hydrogen; or
R$_{2a}$ and R$_{2b}$ are taken together to form —CH$_2$—CH$_2$—, —CH$_2$—NR$_{2c}$—CH$_2$—, —CH$_2$—CH$_2$—CH$_2$—, —CH$_2$—O—CH$_2$—, —CH$_2$—CH$_2$—CH$_2$—CH$_2$—, —CH$_2$—CH$_2$—NR$_{2c}$—CH$_2$— or =O;
R$_2$c is hydrogen; C$_{1-4}$alkyl optionally substituted with one or two hydroxyl groups; mono- or polyhaloC$_{1-6}$alkyl; C$_{1-6}$alkyloxy; C$_{1-6}$alkyl substituted with one cyano group; or C$_{1-6}$alkyl substituted with one —NR$_{9a}$R$_{9b}$;
R$_3$ is hydrogen; C$_{1-6}$alkyl; mono- or polyhaloC$_{1-6}$alkyl; C$_{1-6}$alkyl substituted with one or two hydroxyl groups; C$_{1-6}$alkyl substituted with one or two hydroxyl groups and one C$_{1-6}$alkyloxy; C$_{1-6}$alkylcarbonyl- optionally substituted with one or two hydroxyl groups; mono- or polyhaloC$_{1-6}$alkylcarbonyl-; R$_{10a}$R$_{10b}$N—C$_{1-6}$alkylcarbonyl-; C$_{1-6}$alkyl-O-carbonyl-; C$_{1-6}$alkylcarbonyloxy-; C$_{1-6}$alkyl substituted with one R$_{11}$; C$_{1-6}$alkyloxy optionally substituted with one —NR$_{10a}$R$_{10b}$; C$_{1-6}$alkyl substituted with one or two hydroxyl groups and one —NR$_{10a}$R$_{10b}$; —S(=O)$_2$—C$_{1-6}$alkyl; —S(=O)$_2$—NR$_{9a}$R$_{9b}$; C$_{1-6}$alkyl substituted with one —(C=O)—R$_{14}$; C$_{1-6}$alkyl substituted with one or two hydroxyl groups and one R$_{14}$; C$_{1-6}$alkyl substituted with one R$_{14}$; or R$_{14}$,
R$_{4a}$ is hydrogen;
R$_{4b}$ is hydrogen; or
R$_{4a}$ and R$_{4b}$ are taken together to form =O;
Y is —O— or —C(=O)—;
Z is —CHR$_6$— or —CH$_2$—C≡C—;
R$_6$ is hydrogen; C$_{1-4}$alkyl-O-carbonyl-; C$_{1-4}$alkyl; C$_{1-4}$alkyl substituted with one or two hydroxyl groups; C$_{1-4}$alkyl substituted with one —NR$_{9a}$R$_{9b}$; or —C(=O)—NR$_{9a}$R$_{9b}$;

Ring A is phenyl or a 6-membered saturated, partially saturated or aromatic heterocyclyl, said heterocyclyl containing one or two nitrogen atoms; wherein the phenyl or the heterocyclyl is optionally substituted with one or two R$_8$ substituents;
each R$_8$ is independently hydrogen; C$_{1-4}$alkyloxy; hydroxyl; cyano; C$_{1-4}$alkyl or halo;
or a R$_8$ substituent on an atom adjacent to the atom carrying the Y—Z substituent may be taken together with the R$_6$ substituent of Z, by which ring A together with Y—Z forms a bicycle of formula (a-1), (a-2), (a-3) or (a-4);
R$_{9a}$ and R$_{9b}$ each independently represent hydrogen; mono- or polyhaloC$_{1-4}$alkyl; C$_{1-4}$alkylcarbonyl-; C$_{1-4}$alkyl-O-carbonyl-; C$_{1-4}$alkyl substituted with one or two hydroxyl groups; or C$_{1-4}$alkyl optionally substituted with one substituent selected from the group consisting of C$_{1-4}$alkyloxy, cyano, amino and mono- or di(C$_{1-4}$alkyl)amino;
R$_{10a}$ and R$_{10b}$ each independently represent hydrogen; C$_{1-4}$alkyl; cyanoC$_{1-6}$alkyl; C$_{1-6}$alkyl substituted with one NR$_{9a}$R$_{9b}$; C$_{1-6}$alkyl substituted with one —C(=O)—NR$_{9a}$R$_{9b}$; C$_{1-6}$alkyloxy optionally substituted with one or two hydroxyl groups;
C$_{1-6}$alkyloxyC$_{1-6}$alkyl wherein each C$_{1-6}$alkyl is optionally substituted with one or two hydroxyl groups;
C$_{1-6}$alkylcarbonyl-; C$_{1-6}$alkyl-O-carbonyl-;
mono- or polyhaloC$_{1-6}$alkylcarbonyl- substituted with one or two hydroxyl groups; mono- or polyhalo C$_{1-6}$alkyl substituted with one or two hydroxyl groups; mono- or polyhaloC$_{1-6}$alkylcarbonyl-; mono- or polyhaloC$_{1-4}$alkyl; or C$_{1-4}$alkyl substituted with one or two hydroxyl groups;
R$_{11}$ is cyano; —NR$_{10a}$R$_{10b}$; C$_{1-6}$alkyloxy optionally substituted with one or two hydroxyl groups; —S(=O)$_2$—C$_{1-6}$alkyl; —S(=O)$_2$—NR$_{9a}$R$_{9b}$; —NR$_{13}$—S(=O)$_2$—C$_{1-6}$alkyl; —NR$_{13}$—S(=O)$_2$—NR$_{9a}$R$_{9b}$; C$_{1-6}$alkylcarbonyloxy-; —C(=O)—NR$_{10a}$R$_{10b}$; —O—C(=O)—NR$_{10a}$R$_{10b}$; —COOH; —P(=O)(OH)$_2$; or —P(=O)(O—C$_{1-4}$alkyl)$_2$;
R$_{12}$ is —NR$_{9a}$R$_{9b}$, C$_{1-6}$alkyloxy, or cyano;
R$_{13}$ is hydrogen or C$_{1-4}$alkyl;
R$_{14}$ is a 4, 5 or 6 membered saturated heterocyclyl which is optionally substituted with one, two or three substituents selected from the group consisting of oxo, C$_{1-4}$alkyl, halogen, cyano, hydroxyl, C$_{1-6}$alkyloxy and NR$_{9a}$R$_{9b}$;
x$_1$ is CR$_{5a}$ or N;
x$_2$ is CR$_{5b}$;
x$_3$ is CR$_{5c}$ or N;
each R$_{15}$ is independently selected from the group consisting of hydrogen, methyl, halo, C$_{1-4}$alkyloxy and hydroxyl;
R$_{5a}$ and R$_{5c}$ each independently are selected from the group consisting of hydrogen; hydroxyl; cyano; halo; C$_{1-6}$alkyl; C$_{1-6}$alkyl substituted with one or two hydroxyl groups; mono- or polyhaloC$_{1-6}$alkyl; mono- or polyhaloC$_{1-6}$alkyloxy; C$_{1-6}$alkyl substituted with one —NR$_{9a}$R$_{9b}$; C$_{1-6}$alkyl substituted with one cyano; C$_{1-6}$alkyloxyC$_{1-6}$alkyl wherein each of the C$_{1-6}$alkyl groups are optionally substituted with one or two hydroxyl groups; C$_{2-6}$alkenyl; C$_{1-6}$alkyl-O-carbonyl-; C$_{1-6}$alkyloxy; C$_{1-6}$alkyloxy substituted with one or two hydroxyl groups; C$_{1-6}$alkyloxyC$_{1-6}$alkyloxy wherein each of the C$_{1-6}$alkyl groups are optionally substituted with one or two hydroxyl groups; $C_{1-6}$alkyloxy substituted with one cyano; and $C_{1-6}$alkyloxy substituted with one —$NR_{9a}R_{9b}$;

$R_{5b}$ is hydrogen; $C_{1-6}$alkyl; $C_{3-6}$cycloalkyl optionally substituted with one cyano; hydroxyl; cyano; mono- or polyhalo$C_{1-6}$alkyloxy; mono- or polyhalo$C_{1-6}$alkyl; $C_{1-4}$alkyl substituted with one or two hydroxyl groups; $C_{2-6}$alkenyl; $C_{1-4}$alkyloxy; —$Si(CH_3)_3$; $C_{1-6}$alkyl substituted with one $R_{12}$; $C_{1-6}$alkyl-O-carbonyl-; or $C_{1-6}$alkyloxy substituted with one $R_{12}$.

3. The compound according to claim 1, wherein
$y_1$ is $CR_{7a}$ or N;
$y_2$ is CH;
$R_{7a}$ is hydrogen;
$R_7$ is hydrogen, —$NH_2$, —$CH_2OH$, halo or cyano;
or when $y_1$ represents $CR_{7a}$, this $R_{7a}$ can be taken together with a $R_7$ on an adjacent carbon atom to form —CH=CH—NH—;
X is —$CR_1R_{1a}$—, —$CH_2$—$CHR_1$—;
$R_1$ is hydrogen or $C_{1-6}$alkyl;
$R_{1a}$ is hydrogen;
$R_{2a}$ is hydrogen; $C_{1-6}$alkyl; $C_{1-6}$alkyl substituted with one hydroxyl group; or $C_{1-6}$alkyl substituted with one —$NR_{9a}R_{9b}$substituent;
$R_{2b}$ is hydrogen; or
$R_{2a}$ and $R_{2b}$ are taken together to form —$CH_2$—$CH_2$—, —$CH_2$—$NR_{2c}$—$CH_2$— or =O;
$R_{2c}$ is hydrogen; or $C_{1-6}$alkyl substituted with one —$NR_{9a}R_{9b}$;
$R_3$ is hydrogen; $C_{1-6}$alkyl; $C_{1-6}$alkyl substituted with one or two hydroxyl groups; $C_{1-6}$alkyl substituted with one or two hydroxyl groups and one $C_{1-6}$alkyloxy; $R_{10a}R_{10b}N$—$C_{1-6}$alkylcarbonyl-; $C_{1-6}$alkyl-O-carbonyl-; $C_{1-6}$alkyl substituted with one $R_{11}$; $C_{1-6}$alkyl substituted with one —(C=O)—$R_{14}$; or $C_{1-6}$alkyl substituted with one $R_{14}$;
$R_{4a}$ is hydrogen;
$R_{4b}$ is hydrogen; or
$R_{4a}$ and $R_{4b}$ are taken together to form =O;
Y is —O— or —C(=O)—;
Z is —$CHR_6$— or —$CH_2$—C≡C—;
$R_6$ is hydrogen; $C_{1-4}$alkyl-O-carbonyl-; $C_{1-4}$alkyl; $C_{1-4}$alkyl substituted with one hydroxyl group; $C_{1-4}$alkyl substituted with one —$NR_{9a}R_{9b}$; or —C(=O)—$NR_{9a}R_{9b}$;
Ring A is phenyl or a 6-membered saturated, partially saturated or aromatic heterocyclyl, said heterocyclyl containing one or two nitrogen atoms; wherein the phenyl or the heterocyclyl is optionally substituted with one or two $R_8$ substituents;
each $R_8$ is independently hydrogen; $C_{1-6}$alkyloxy; cyano; $C_{1-4}$alkyl or halo;
or a $R_8$ substituent on an atom adjacent to the atom carrying the Y—Z substituent may be taken together with the $R_6$ substituent of Z, by which ring A together with Y—Z forms a bicycle of formula (a-1a), (a-2a), (a-3a), (a-4a) or (a-4b):

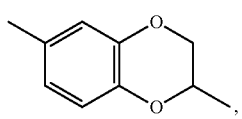

(a-1a)

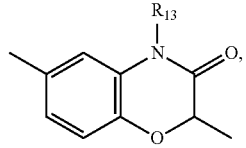

(a-2a)

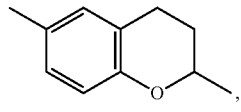

(a-3a)

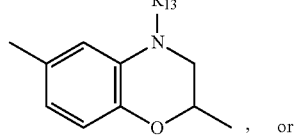

, or (a-4a)

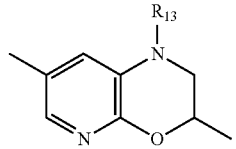

(a-4b)

$R_{9a}$ and $R_{9b}$ each independently represent hydrogen; $C_{1-4}$alkyl substituted with one hydroxyl group; or $C_{1-4}$alkyl;
$R_{10a}$ and $R_{10b}$ each independently represent hydrogen; $C_{1-4}$alkyl; $C_{1-6}$alkyl-O-carbonyl-; mono- or polyhalo$C_{1-4}$alkyl; or $C_{1-4}$alkyl substituted with one hydroxyl group;
$R_{11}$ is cyano; —$NR_{10a}R_{10b}$; $C_{1-6}$alkyloxy optionally substituted with one hydroxyl group; —S(=O)$_2$—$C_{1-6}$alkyl; $C_{1-6}$alkylcarbonyloxy-; —C(=O)—$NR_{10a}R_{10b}$; —COOH; or —P(=O)(O—$C_{1-4}$alkyl)$_2$;
$R_{12}$ is —$NR_{9a}R_{9b}$, $C_{1-6}$alkyloxy, or cyano;
$R_{13}$ is hydrogen or $C_{1-4}$alkyl;
$R_{14}$ is a 5 membered saturated heterocyclyl which is optionally substituted with one, two or three substituents selected from the group consisting of oxo and $C_{1-4}$alkyl;
$x_1$ is $CR_{5a}$ or N;
$x_2$ is $CR_{5b}$;
$x_3$ is $CR_{5c}$ or N;
each $R_{15}$ is independently selected from the group consisting of hydrogen, methyl, halo, and $C_{1-4}$alkyloxy;
$R_{5a}$ and $R_{5c}$ each independently are selected from the group consisting of hydrogen; hydroxyl; cyano; halo; $C_{1-6}$alkyl substituted with one or two hydroxyl groups; $C_{1-6}$alkyl substituted with one —$NR_{9a}R_{9b}$; $C_{1-6}$alkyloxy$C_{1-6}$alkyl; $C_{1-6}$alkyloxy; $C_{1-6}$alkyloxy substituted with one hydroxyl group; $C_{1-6}$alkyloxy$C_{1-6}$alkyloxy;
$R_{5b}$ is hydrogen; $C_{1-6}$alkyl; $C_{3-6}$cycloalkyl optionally substituted with one cyano; cyano; mono- or polyhalo $C_{1-6}$alkyloxy; mono- or polyhalo$C_{1-6}$alkyl; $C_{1-4}$alkyl substituted with one hydroxyl group; $C_{2-6}$alkenyl; $C_{1-4}$alkyloxy; —$Si(CH_3)_3$; $C_{1-6}$alkyl substituted with one $R_{12}$; or $C_{1-6}$alkyl-O-carbonyl-.

4. The compound according to claim 1, wherein
$y_1$ is CH or N;
$y_2$ is CH;
$R_7$ is hydrogen or —$NH_2$;
X is $CH_2$;
$R_{2a}$ is hydrogen;

R$_{2b}$ is hydrogen; or

R$_{2a}$ and R$_{2b}$ are taken together to form —CH$_2$—CH$_2$— or —CH$_2$—NH—CH$_2$—;

R$_3$ is hydrogen; C$_{1-6}$alkyl; C$_{1-6}$alkyl substituted with one or two hydroxyl groups;

C$_{1-6}$alkyl substituted with one R$_{11}$; or C$_{1-6}$alkyl substituted with one R$_{14}$.

R$_{4a}$ is hydrogen;

R$_{4b}$ is hydrogen; or

R$_{4a}$ and R$_{4b}$ are taken together to form =O;

Y is —O—;

Z is —CHR$_6$—;

R$_6$ is hydrogen;

Ring A is phenyl or pyridinyl; wherein the phenyl or pyridinyl is optionally substituted with one or two R$_8$ substituents;

each R$_8$ is independently hydrogen; C$_{1-4}$alkyloxy; cyano; or halo;

or a R$_8$ substituent on an atom adjacent to the atom carrying the Y—Z substituent may be taken together with the R$_6$ substituent of Z, by which ring A together with Y—Z forms a bicycle of formula (a-3a);

R$_{11}$ is C$_{1-6}$alkyloxy optionally substituted with one hydroxyl group; or —C(=O)—NR$_{10a}$R$_{10b}$;

R$_{10a}$ and R$_{10b}$ each independently represent hydrogen or C$_{1-4}$alkyl;

R$_{14}$ is a 5 membered saturated heterocyclyl which is optionally substituted with one, two or three substituents selected from the group consisting of C$_{1-4}$alkyl;

x$_1$ is CR$_{5a}$ or N;

x$_2$ is CR$_{5b}$;

x$_3$ is CR$_{5c}$;

each R$_{15}$ is hydrogen;

R$_{5a}$ is hydrogen or C$_{1-6}$alkyloxyC$_{1-6}$alkyl;

R$_{5b}$ is C$_{1-6}$alkyl; C$_{3-6}$cycloalkyl; mono- or polyhalo C$_{1-6}$alkyloxy; C$_{2-6}$alkenyl; C$_{1-6}$alkyl substituted with one cyano; C$_{1-4}$alkyloxy; or C$_{1-6}$alkyl-O-carbonyl-;

R$_{5c}$ is hydrogen.

5. The compound according to claim 1, wherein y$_1$ is CH;

y$_2$ is CH;

R$_7$ is hydrogen;

X is CH$_2$;

R$_{2a}$ is hydrogen;

R$_{2b}$ is hydrogen;

R$_3$ is hydrogen; C$_{1-6}$alkyl substituted with one or two hydroxyl groups;

R$_{4a}$ and R$_{4b}$ are taken together to form =O;

Y is —O—;

Z is —CH$_2$—;

Ring A is phenyl optionally substituted with one or two R$_8$ substituents;

each R$_8$ is independently hydrogen; C$_{1-4}$alkyloxy; cyano; or F;

x$_1$ is CH;

x$_2$ is CR$_{5b}$;

x$_3$ is CH;

each R$_{15}$ is hydrogen;

R$_{5b}$ is isopropyl or cyclopropyl.

6. The compound according to claim 1, wherein ring A is phenyl or a 6-membered saturated, partially saturated or aromatic heterocyclyl, said heterocyclyl containing one or two nitrogen atoms; wherein the phenyl or the heterocyclyl is optionally substituted with one or two R$_8$ substituents;

each R$_8$ is independently hydrogen; C$_{1-4}$alkyloxy; hydroxyl; cyano; or halo.

7. The compound according to claim 6, wherein ring A is phenyl or a 6-membered aromatic heterocyclyl, said heterocyclyl containing one or two nitrogen atoms; wherein the phenyl or the heterocyclyl is optionally substituted with one or two R$_8$ substituents;

each R$_8$ is independently hydrogen; C$_{1-4}$alkyloxy; hydroxyl; cyano; or halo.

8. The compound according to claim 1, wherein ring A is phenyl or a 6-membered saturated, partially saturated or aromatic heterocyclyl, said heterocyclyl containing one or two nitrogen atoms; wherein the phenyl or the heterocyclyl is substituted with one R$_8$ substituent on an atom adjacent to the atom carrying the Y—Z substituent, and said R$_8$ substituent is taken together with the R$_6$ substituent of Z, by which ring A together with Y—Z forms a bicycle of formula (a-1), (a-2), (a-3) or (a-4).

9. The compound according to claim 1, wherein x$_1$ and x$_3$ are CH; x$_2$ is CR$_{5b}$; R$_{5b}$ is isopropyl.

10. The compound according to claim 1, wherein y$_1$ and y$_2$ are CH.

11. The compound according to claim 1 wherein the compound is selected from the group consisting of

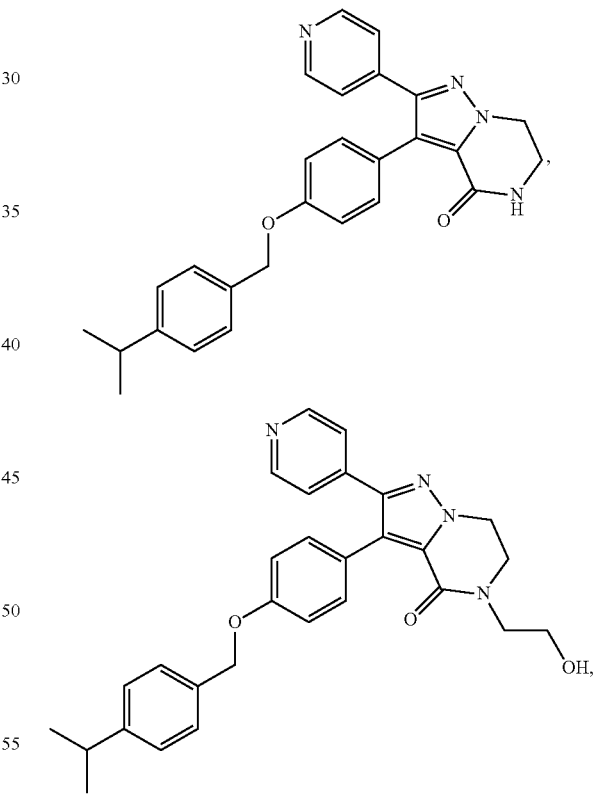

tautomers and stereoisomeric forms thereof, or an N-oxide formed at the nitrogen the pyridinyl ring, or pharmaceutically acceptable addition salts, and solvates thereof.

12. A pharmaceutical composition comprising a pharmaceutically acceptable carrier and, as active ingredient, a therapeutically effective amount of a compound according to claim 1.

13. A method of treating a patient suffering from non-small cell lung cancer comprising administering to said patient a compound according to claim 1, tautomers and stereoisomeric forms thereof, or N-oxides, pharmaceutically acceptable addition salts, and solvates thereof.

* * * * *